US009889205B2

(12) United States Patent
Lin et al.

(10) Patent No.: US 9,889,205 B2

(45) Date of Patent: Feb. 13, 2018

(54) GLUCOSE-RESPONSIVE INSULIN CONJUGATES

(71) Applicant: Merck Sharp & Dohme Corp., Rahway, NJ (US)

(72) Inventors: Songnian Lin, Monroe, NJ (US); Lin Yan, East Brunswick, NJ (US); Pei Huo, Millburn, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/191,584

(22) Filed: Jun. 24, 2016

(65) Prior Publication Data

US 2016/0303244 A1 Oct. 20, 2016

Related U.S. Application Data

(62) Division of application No. 14/504,476, filed on Oct. 2, 2014, now Pat. No. 9,427,475.

(60) Provisional application No. 61/886,717, filed on Oct. 4, 2013.

(51) Int. Cl.

| | |
|---|---|
| ***A61K 38/00*** | (2006.01) |
| ***A61K 47/48*** | (2006.01) |
| ***A61K 38/28*** | (2006.01) |
| ***C07K 14/62*** | (2006.01) |

(52) U.S. Cl.

CPC .......... *A61K 47/4823* (2013.01); *A61K 38/28* (2013.01); *A61K 47/48092* (2013.01); *C07K 14/62* (2013.01)

(58) Field of Classification Search

CPC .............. A61K 38/28; A61K 47/48092; A61K 47/4823; B06B 1/18; C07K 14/62; E01B 27/16

See application file for complete search history.

(56) References Cited

U.S. PATENT DOCUMENTS

| | | | |
|---|---|---|---|
| 3,591,574 | A | 7/1971 | Fenichel et al. |
| 3,684,791 | A | 8/1972 | Geiger et al. |
| 3,847,890 | A | 11/1974 | Green et al. |
| 4,348,387 | A | 9/1982 | Brownlee et al. |
| 4,372,948 | A | 2/1983 | Yoshikumi et al. |
| 4,377,567 | A | 3/1983 | Geho |
| 4,444,683 | A | 4/1984 | Kim et al. |
| 4,603,044 | A | 7/1986 | Geho et al. |
| 4,863,896 | A | 9/1989 | Geho et al. |
| 5,239,062 | A | 8/1993 | Blattler et al. |
| 5,395,924 | A | 3/1995 | Blattler et al. |
| 5,461,031 | A | 10/1995 | De Felippis |
| 5,478,575 | A | 12/1995 | Miyazaki et al. |
| 5,527,524 | A | 6/1996 | Tomalia et al. |
| 5,563,056 | A | 10/1996 | Swan et al. |
| 5,723,589 | A | 3/1998 | Miljkovic et al. |
| 5,830,506 | A | 11/1998 | Taylor |
| 5,843,886 | A | 12/1998 | Weiner et al. |
| 5,854,208 | A | 12/1998 | Jones et al. |
| 5,866,538 | A | 2/1999 | Norup et al. |
| 5,902,607 | A | 5/1999 | Taylor |
| 5,905,140 | A | 5/1999 | Hansen |
| 5,922,675 | A | 7/1999 | Baker et al. |
| 5,948,751 | A | 9/1999 | Kimer et al. |
| 5,994,517 | A | 11/1999 | Ts'o et al. |
| 6,034,054 | A | 3/2000 | DeFelippis et al. |
| 6,180,757 | B1 | 1/2001 | Bogsnes |
| 6,214,547 | B1 | 4/2001 | Kjeldsen et al. |
| 6,323,311 | B1 | 11/2001 | Liu et al. |
| 6,342,225 | B1 | 1/2002 | Jones et al. |
| 6,410,053 | B1 | 6/2002 | Taylor |
| 6,500,645 | B1 | 12/2002 | Kjeldsen et al. |
| 6,521,738 | B2 | 2/2003 | Kjeldsen et al. |
| 6,551,992 | B1 | 4/2003 | DeFelippis et al. |
| 6,777,207 | B2 | 8/2004 | Kjeldsen et al. |
| 6,844,166 | B1 | 1/2005 | Wolf |
| 6,869,930 | B1 | 3/2005 | Havelund et al. |
| RE39,055 | E | 4/2006 | Jones et al. |
| 7,063,863 | B2 | 6/2006 | Taylor |
| 7,087,408 | B2 | 8/2006 | Kjeldsen et al. |
| 7,105,314 | B2 | 9/2006 | Kjeldsen |

(Continued)

FOREIGN PATENT DOCUMENTS

| | | |
|---|---|---|
| CN | 101273961 | 10/2008 |
| EP | 009842 | 4/1980 |

(Continued)

OTHER PUBLICATIONS

Baudys, J Pharma Sci, Physical Stabilization of Insulin by Glycosylation, 1995, 28-33, 64.

Brownlee et al., Glycosylated Insulin Complexed to Concanavalin A, Biochem. Basis for a closed loop insulin delivery system, 1983, pp. 498-504, 32.

Brownlee, Science, Glycosylated Insulin Complexed to Concanavalin A, 1979, 1190-1191, 206.

Dea, Albumin Binding of Acylated Insulin (NN304) Does Not Deter Action to Stimulate Glucose Uptake, Diabetes, 2002, pp. 762-769, 51.

Eggert, A New Glucose Selective Fluorescent Bisboronic Acid, J. Org. Chem., 1999, pp. 3846-3852, 64.

Heinnemann, Time action profile of the soluble fatty acid acylated long acting insulin analogue NN304, Diabetic Med, 1999, pp. 332-338, 16.

Jansen et al., Synthetic 6B Di-, Tri- and Tetrasaccharide-Protein Conjugates Contain Pneumococcal Type 6A and 6B Common and 6B-Specific Epitopes that Elicit Protective Antibodies in Mice, Infect Immun, 2001, pp. 787-793, 69.

(Continued)

*Primary Examiner* — Marcela M Cordero Garcia

(74) *Attorney, Agent, or Firm* — Julie M. Lake; John C. Todaro

(57) ABSTRACT

Insulin conjugates comprising an insulin molecule covalently attached to at least one bi-dentate linker having two arms, each arm independently attached to a ligand comprising a saccharide and wherein the saccharide for at least one ligand of the linker is fucose are disclosed. The insulin conjugates display a pharmacokinetic (PK) and/or pharmacodynamic (PD) profile that is responsive to the systemic concentrations of a saccharide such as glucose or alpha-methylmannose even when administered to a subject in need thereof in the absence of an exogenous multivalent saccharide-binding molecule such as Con A.

2 Claims, 22 Drawing Sheets

(56) References Cited

U.S. PATENT DOCUMENTS

| | | | |
|---|---|---|---|
| 7,138,371 B2 | 11/2006 | DeFrees et al. | |
| 7,316,999 B2 | 1/2008 | Hoeg-Jensen et al. | |
| 7,317,000 B2 | 1/2008 | Hoeg-Jensen et al. | |
| 7,416,858 B2 | 8/2008 | DeFrees et al. | |
| 7,423,014 B2 | 9/2008 | Ekwuribe et al. | |
| 7,473,680 B2 | 1/2009 | DeFrees et al. | |
| 7,531,191 B2 | 5/2009 | Zion et al. | |
| 7,687,608 B2 | 3/2010 | Lancaster et al. | |
| 8,906,850 B2 * | 12/2014 | Zion | A61K 38/28 514/5.9 |
| 9,050,370 B2 * | 6/2015 | Zion | A61K 47/48092 |
| 9,427,475 B2 * | 8/2016 | Lin | A61K 47/48092 |
| 9,463,249 B2 * | 10/2016 | Lancaster | A61K 38/28 |
| 2002/0068295 A1 | 6/2002 | Madou et al. | |
| 2006/0019874 A1 | 1/2006 | Radhakrishnan et al. | |
| 2006/0216265 A1 | 9/2006 | Goodman et al. | |
| 2006/0247154 A1 | 11/2006 | Palmieri et al. | |
| 2007/0099820 A1 | 5/2007 | Lancaster et al. | |
| 2007/0110811 A1 | 5/2007 | Lancaster et al. | |
| 2007/0207498 A1 | 9/2007 | Palmieri et al. | |
| 2009/0053167 A1 | 2/2009 | DeFrees | |
| 2009/0137454 A1 | 5/2009 | Fynbo et al. | |
| 2010/0130726 A1 | 5/2010 | Lancaster et al. | |
| 2011/0281791 A1 | 11/2011 | Zion et al. | |
| 2011/0281939 A1 | 11/2011 | Zion et al. | |
| 2011/0301083 A1 | 12/2011 | Zion et al. | |
| 2012/0010134 A1 | 1/2012 | Zion et al. | |
| 2012/0014908 A1 | 1/2012 | Zion et al. | |
| 2012/0046223 A1 | 2/2012 | Zion et al. | |
| 2012/0135919 A1 | 5/2012 | Lancaster et al. | |
| 2012/0324702 A1 | 12/2012 | Phillips et al. | |
| 2013/0131310 A1 | 5/2013 | Kane et al. | |
| 2013/0190475 A1 | 7/2013 | Chen et al. | |
| 2014/0274888 A1 | 9/2014 | Zion et al. | |
| 2015/0105317 A1 * | 4/2015 | Lin | A61K 47/48092 514/5.9 |
| 2016/0251407 A1 * | 9/2016 | Lin | A61K 47/48092 514/6.2 |
| 2016/0303244 A1 * | 10/2016 | Lin | A61K 47/48092 |

FOREIGN PATENT DOCUMENTS

| | | |
|---|---|---|
| EP | 0119650 | 9/1984 |
| EP | 0725648 | 8/1996 |
| RU | 2381238 | 8/2009 |
| WO | 198100354 | 2/1981 |
| WO | 198401896 | 5/1984 |
| WO | 199010645 | 9/1990 |
| WO | 199952934 | 10/1999 |
| WO | 200192334 | 12/2001 |
| WO | WO2003035011 | 5/2003 |
| WO | WO2003047462 | 6/2003 |
| WO | WO2003048915 | 6/2003 |
| WO | WO2003074087 | 9/2003 |
| WO | 2004101619 | 5/2004 |
| WO | WO2004057002 | 7/2004 |
| WO | WO2006008238 | 1/2006 |
| WO | 2006062685 | 6/2006 |
| WO | WO2006082184 A2 | 8/2006 |
| WO | WO2006088473 | 8/2006 |
| WO | WO2007043050 | 4/2007 |
| WO | WO2007047922 | 4/2007 |
| WO | WO2007047997 A2 | 4/2007 |
| WO | WO2008012440 | 1/2008 |
| WO | WO2008012528 | 1/2008 |
| WO | WO2008036147 | 3/2008 |
| WO | WO2009033588 | 3/2009 |
| WO | WO2009059450 | 5/2009 |
| WO | WO2009089396 | 7/2009 |
| WO | WO2009104199 | 8/2009 |
| WO | WO2010088261 | 8/2010 |
| WO | WO2010088276 A2 | 8/2010 |
| WO | WO2010088286 | 8/2010 |
| WO | WO2010088294 | 8/2010 |
| WO | WO2011000823 | 1/2011 |
| WO | 2012015681 | 2/2012 |
| WO | 2012015687 | 2/2012 |
| WO | 2012015691 | 2/2012 |
| WO | WO2012050822 A1 | 4/2012 |
| WO | WO2013022721 A1 | 2/2013 |

OTHER PUBLICATIONS

Jeong, Self Regulating Insulin Delivery Systems I, Synthesis and Characterization of Glycosylated Insulin, J of Controlled Release, 1984, pp. 57-66, 1.
Kanbe et al., Novel Synthesized Trimannose Conjugate induces endocytosis and expression of immunostimulatory molecules in monocytic leukemia cells, Int. J. Hematol., 2001, pp. 309-315, 74.
Lee, Biochemistry of carbohydrate protein interaction, FASEB J, 1992, pp. 3193, 1.
Lindhorst et al., Trivalent alpha-D-mannoside clusters as inhibitors of type-1 fimbriae-mediated adhesion of *Escherichia coli*: structural variation and biotinylation, J. Chem, Soc. Perkin Trans 1, 2001, pp. 823-831, 1.
Monsigny, Endogenous Lectins and Drug Targeting, Annals NY Acad Sci, 1988, pp. 399-414, 551.
International Search Report for PCTUS1022225 dated Mar. 9, 2010.
Written Opinion for PCTUS1022225 dated Mar. 9, 2010.
Nishimura et al., Machine Translation—English, WO2004101619, translated Mar. 11, 2014, Nishimura et al., WO2004101619 published on Nov. 25, 2004, translated to English Mar. 11, 2014, NA.
Ruziak, Basal activity profiles of NPH and [Ne-palmitoyl Lys (B29) human insulins in subjects with IDDM, Diabetologia, 1998, 116-120, 41.
Shojaee-Moradie, Novel Hepatoselective Insulin Analog, Diabetes Care, 2000, pp. 1124-1129, 23.
Takata et al., L-Fucose, D-Mannose, L-Galactose and their BSA Conjugates Stimulate Macrophage Migration, Journal of Leukocyte Biology, 1987, pp. 248-256, 41.
Vanbever, Sustained Release of Insulin From Insoluble Inhaled Particles, Drug Development Research, 1999, pp. 178-185, 48.
Yamazaki, Endogenous Lectins as Targets for Drug Delivery, Adv Drug Delivery Rev, 2000, pp. 225-244, 43.

* cited by examiner

GLUCOSE-RESPONSIVE INSULIN CONJUGATES

CROSS REFERENCE TO RELATED APPLICATIONS

This application is a division of U.S. application Ser. No. 14/504,476, filed Oct. 2, 2014, now pending, which claims the benefit under 35 U.S.C. 119(e) of U.S. Provisional Application No. 61/886,717, filed Oct. 4, 2013, now expired.

REFERENCE TO SEQUENCE LISTING SUBMITTED ELECTRONICALLY

The sequence listing of the present application is submitted electronically via EFS-Web as an ASCII formatted sequence listing with a file name "23616_US_DIV_SEQLIST_23JUNE2016", creation date of Jun. 23, 2016, and a size of 6 KB. This sequence listing submitted via EFS-Web is part of the specification and is herein incorporated by reference in its entirety.

BACKGROUND OF THE INVENTION (1) Field of the Invention

The present invention relates to insulin conjugates comprising fucose that display a pharmacokinetic (PK) and/or pharmacodynamic (PD) profile that is responsive to the systemic concentrations of a saccharide such as glucose or alpha-methylmannose even when administered to a subject in need thereof in the absence of an exogenous multivalent saccharide-binding molecule such as Con A. In particular, the present invention relates to insulin conjugates that comprise an insulin molecule covalently attached to at least one bi-dentate linker wherein each arm of the linker is independently attached to a ligand comprising a saccharide and wherein the saccharide for at least one ligand is fucose.

(2) Description of Related Art

The majority of "controlled-release" drug delivery systems known in the prior art (e.g., U.S. Pat. No. 4,145,410 to Sears which describes drug release from capsules which are enzymatically labile) are incapable of providing drugs to a patient at intervals and concentrations which are in direct proportion to the amount of a molecular indicator (e.g., a metabolite) present in the human body. The drugs in these prior art systems are thus not literally "controlled," but simply provided in a slow release format which is independent of external or internal factors. The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

Each of these systems relies on the combination of a multivalent glucose binding molecule (e.g., the lectin Con A) and a sugar based component that is reversibly bound by the multivalent glucose binding molecule. Unfortunately, Con A and many of the other readily available lectins have the potential to stimulate lymphocyte proliferation. By binding to carbohydrate receptors on the surfaces of particular types of lymphocytes, these so-called "mitogenic" lectins can potentially induce the mitosis of lymphocytes and thereby cause them to proliferate. Most mitogenic lectins including Con A are selective T-cell mitogens. A few lectins are less selective and stimulate both T-cells and B-cells. Local or systemic in vivo exposure to mitogenic lectins can result in inflammation, cytotoxicity, macrophage digestion, and allergic reactions including anaphylaxis. In addition, plant lectins are known to be particularly immunogenic, giving rise to the production of high titers of anti-lectin specific antibodies. It will be appreciated that mitogenic lectins cannot therefore be used in their native form for in vivo methods and devices unless great care is taken to prevent their release. For example, in U.S. Pat. No. 5,830,506, Taylor highlights the toxic risks that are involved in using Con A and emphasizes the importance and difficulty of containing Con A within a drug delivery device that also requires glucose and insulin molecules to diffuse freely in and out of the device.

The risks and difficulties that are involved with these and other in vivo uses of lectins could be significantly diminished if an alternative controlled drug delivery system could be provided that did not require lectins.

BRIEF SUMMARY OF THE INVENTION

The present invention provides insulin conjugates comprising fucose that display a pharmacokinetic (PK) and/or pharmacodynamic (PD) profile that is responsive to the systemic concentrations of a saccharide such as glucose or alpha-methylmannose when administered to a subject in need thereof in the absence of an exogenous multivalent saccharide-binding molecule such as Con A. In general, the conjugates comprise an insulin or insulin analog molecule covalently attached to at least one branched linker having two arms (bi-dentate linker), each arm independently attached to a ligand comprising a saccharide wherein at least one ligand of the linker is fucose. In particular embodiments, the linker is non-polymeric. In particular embodiments, a conjugate may have a polydispersity index of one and a MW of less than about 20,000 Da. In particular embodiments, the conjugate is long acting (i.e., exhibits a PK profile that is more sustained than soluble recombinant human insulin (RHI)).

The conjugates disclosed herein display a pharmacodynamic (PD) or pharmacokinetic (PK) profile that is sensitive to the serum concentration of a serum saccharide when administered to a subject in need thereof in the absence of an exogenous saccharide binding molecule. In particular aspects, the serum saccharide is glucose or alpha-methylmannose. In further aspects, the conjugate binds an endogenous saccharide binding molecule at a serum glucose concentration of 60 or 70 mg/dL or less when administered to a subject in need thereof. The binding of the conjugate to the endogenous saccharide binding molecule is sensitive to the serum concentration of the serum saccharide. In a further aspect, the conjugate is capable of binding the insulin receptor at a serum saccharide concentration great than 60, 70, 80, 90, or 100 mg/dL. At serum saccharide concentration at 60 or 70 mg/dL the conjugate preferentially binds the endogenous saccharide binding molecule over the insulin receptor and as the serum concentration of the serum saccharide increases from 60 or 70 mg/dL, the binding of the conjugate to the endogenous saccharide binding molecule decreases and the binding of the conjugate to the insulin receptor increases.

Therefore, the present invention provides a conjugate comprising an insulin or insulin analog molecule covalently attached to at least one branched linker having a first and second arm, wherein the first arm is linked to a first ligand that includes or consists of a first saccharide and the second arm is linked to a second ligand that includes or consists of a second saccharide, wherein the first saccharide for at least one branched linker is fucose. Further provided is a composition comprising said conjugate and a pharmaceutically acceptable carrier, and optionally one or more pharmaceutically acceptable incipients, preservatives, zinc salt, and/or surfactants.

In particular aspects of the conjugate, the second saccharide is fucose, mannose, glucosamine, or glucose. In other aspects, the second ligand comprises a bisaccharide, trisaccharide, tetrasaccharide, or branched trisaccharide. In a further aspect, the second ligand comprises a bimannose, trimannose, tetramannose, or branched trimannose. In particular aspects, both the first saccharide and the second saccharide are fucose. In particular aspects, the first saccharide is fucose and the second saccharide is a branched trimannose. In particular aspects, the first saccharide is fucose and the second saccharide is a trimannose. In particular aspects, the first saccharide is fucose and the second saccharide is glucose. In particular aspects, the first saccharide is fucose and the second saccharide is a mannose. In particular aspects, the first saccharide is fucose and the second saccharide is a bimannose. In particular aspects, the first saccharide is fucose and the second saccharide is a trimannose. In particular aspects, the first saccharide is fucose and the second saccharide is a tetramannose.

In particular aspects, the at least one branched linker is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule.

In a further aspect of the conjugate, the insulin or insulin analog is further covalently linked to a linear or branched linker comprising a ligand that includes or consists of a saccharide. In particular aspects, the saccharide is fucose, mannose, glucosamine, or glucose. In other aspects, the ligand comprises a bisaccharide, trisaccharide, tetrasaccharide, or branched trisaccharide. In a further aspect, the ligand comprises a bimannose, trimannose, tetramannose, or branched trimannose.

In a further aspect of the conjugate, the conjugate has the general formula (I):

I

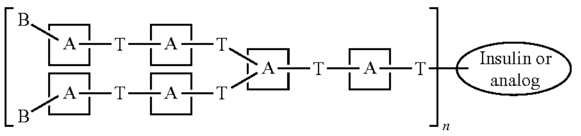

wherein:

(i) each occurrence of

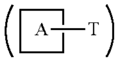

represents a potential repeat within a branch of the conjugate;

(ii) each occurrence of 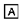 is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —$N(R)SO_2$—, —$SO_2N(R)$—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) —B is -T-$L^B$-X, wherein each occurrence of X is independently a ligand comprising a saccharide and each occurrence of $L^B$ is independently a covalent bond or a group derived from the covalent conjugation of a T with an X; and, (vi) n is 1, 2, or 3, with the proviso that the insulin or insulin analog is conjugated to at least one linker in which one of the ligands X comprises a saccharide, which is fucose.

In particular aspects of the conjugate, at least one saccharide for at least one linker is fucose and the other saccharide or saccharides are fucose, mannose, glucosamine, or glucose. In other aspects, at least one saccharide for at least one linker is fucose and the other saccharide or saccharides are a bisaccharide, trisaccharide, tetrasaccharide, or branched trisaccharide. In a further aspect, at least one saccharide for at least one linker is fucose and the other saccharide or saccharides are a bimannose, trimannose, tetramannose, or branched trimannose. Further provided is a composition comprising said conjugate and a pharmaceutically acceptable carrier, and optionally one or more pharmaceutically acceptable incipients, preservatives, zinc salt, and/or surfactants.

In a particular aspect of the conjugate, n is 1 and the sacchride for the first occurrence of X is fucose and the saccharide for the second occurrence of X is fucose, mannose, glucosamine, or glucose. In other aspects, the sacchride for the first occurrence of X is fucose and the saccharide for the second occurrence of X is a bisaccharide, trisaccharide, tetrasaccharide, or branched trisaccharide. In a further aspect, the sacchride for the first occurrence of X is fucose and the saccharide for the second occurrence of X is a bimannose, trimannose, tetramannose, or branched trimannose. Further provided is a composition comprising said conjugate and a pharmaceutically acceptable carrier, and optionally one or more pharmaceutically acceptable incipients, preservatives, zinc salt, and/or surfactants.

In a particular aspect of the conjugate, n is 2 and the sacchride for the first occurrence of X is fucose and the saccharide for the second, third, and fourth occurrences of X are independently fucose, mannose, glucosamine, glucose, bisaccharide, trisaccharide, tetrasaccharide, or branched trisaccharide, bimannose, trimannose, tetramannose, or branched trimannose. Further provided is a composition comprising said conjugate and a pharmaceutically acceptable carrier, and optionally one or more pharmaceutically acceptable incipients, preservatives, zinc salt, and/or surfactants.

In a particular aspect of the conjugate, n is 3 and the sacchride for the first occurrence of X is fucose and the saccharide for the second, third, fourth, fifth, and sixth occurrences of X are independently fucose, mannose, glucosamine, glucose, bisaccharide, trisaccharide, tetrasaccharide, branched trisaccharide, bimannose, trimannose, tetramannose, or branched trimannose. Further provided is a composition comprising said conjugate and a pharmaceutically acceptable carrier, and optionally one or more pharmaceutically acceptable incipients, preservatives, zinc salt, and/or surfactants.

In a further aspect of the conjugate, the conjugate comprises the general formula (II):

II

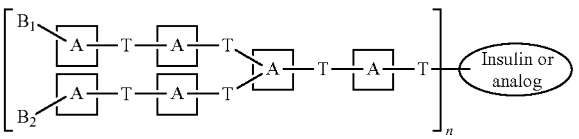

wherein:

(i) each occurrence of

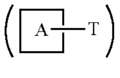

represents a potential repeat within a branch of the conjugate;

(ii) each occurrence of  is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —$N(R)SO_2$—, —$SO_2N(R)$—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) —$B_1$ is -T-$L^{B_1}$-$X_1$, wherein $X_1$ is a ligand comprising fucose, wherein $L^{B_1}$ is a covalent bond or a group derived from the covalent conjugation of a T with $X_1$;

(vi) —$B_2$ is -T-$L^{B_2}$-$X_2$, wherein $X_2$ is a ligand comprising a saccharide, which may be fucose, mannose, or glucose; and $L^{B_2}$ is a covalent bond or a group derived from the covalent conjugation of a T with an $X_2$; and, (vii) n is 1, 2, or 3.

In particular aspects of the conjugate, $X_2$ is fucose, mannose, glucosamine, glucose, bisaccharide, trisaccharide, tetrasaccharide, or branched trisaccharide, bimannose, trimannose, tetramannose, or branched trimannose. Further provided is a composition comprising said conjugate and a pharmaceutically acceptable carrier, and optionally one or more pharmaceutically acceptable incipients, preservatives, zinc salt, and/or surfactants.

In a further aspect of the conjugate, the bi-dentate linker has the formula

A

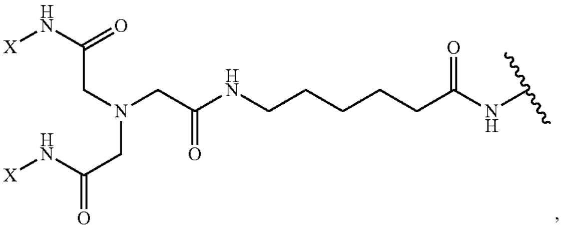

,

B

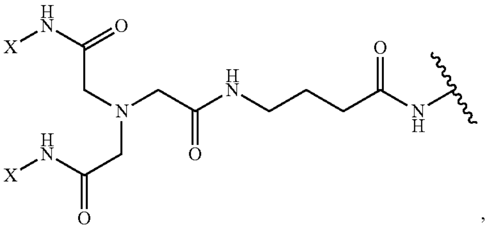

,

C

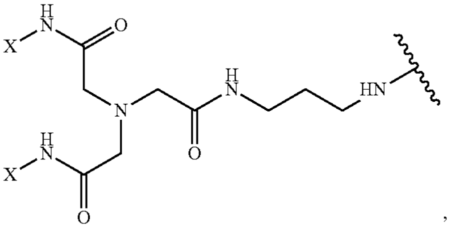

,

D

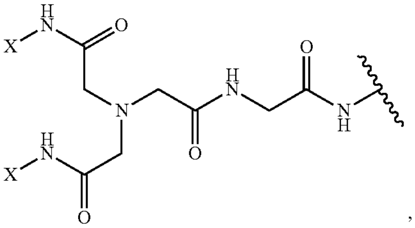

,

E

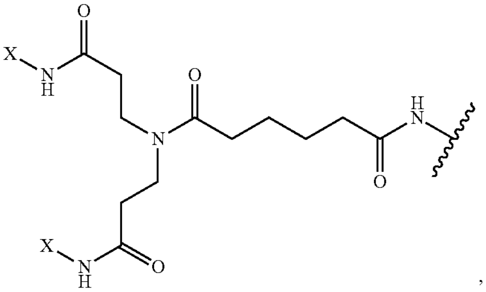

,

F

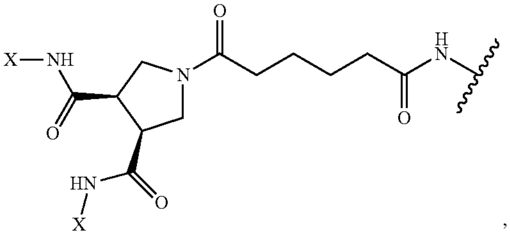

,

-continued
G
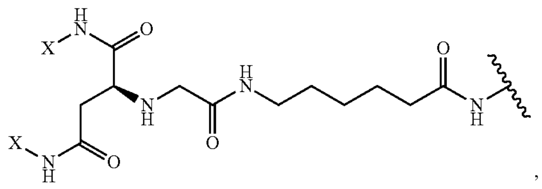
,
H
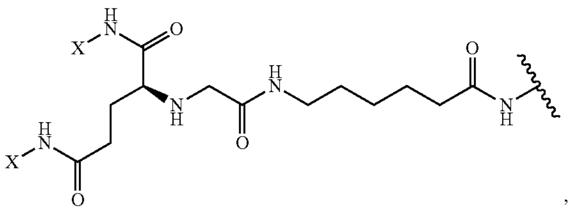
,
I
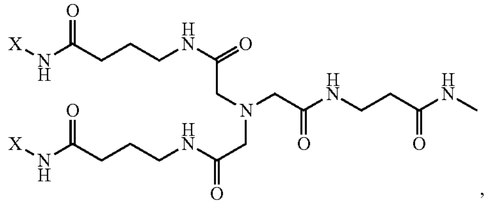
,
J
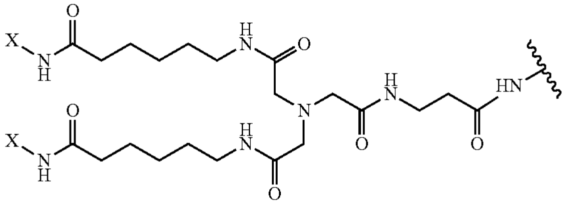
,
K
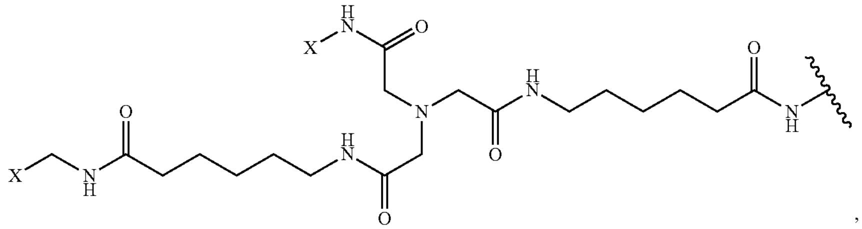
,
L
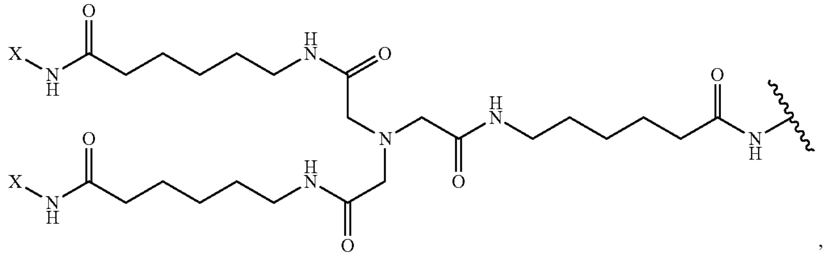
,
M
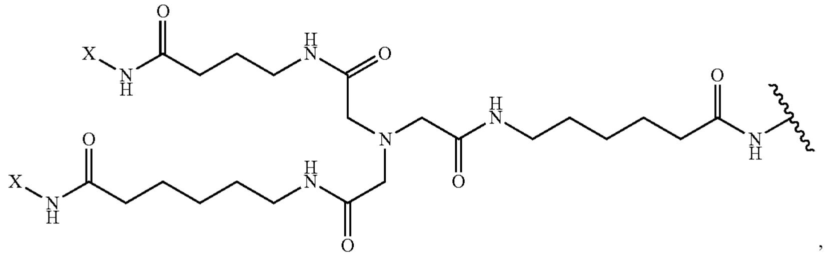
,
N
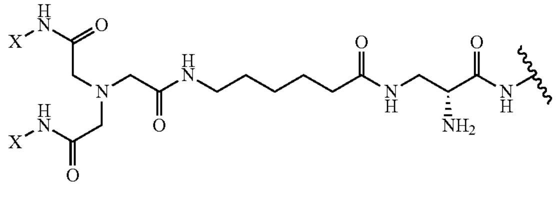
,
O
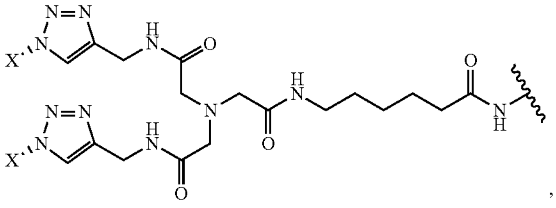
, -continued
P
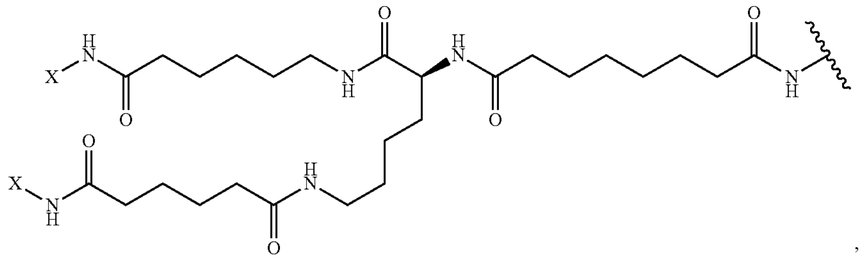
,
Q
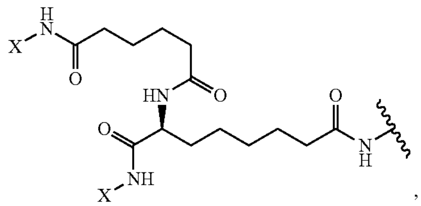
,
R
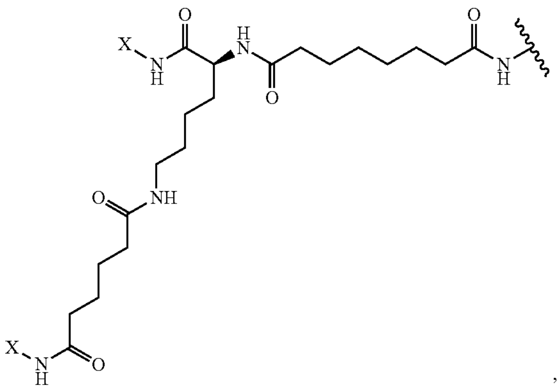
,
S
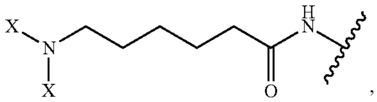
,
T
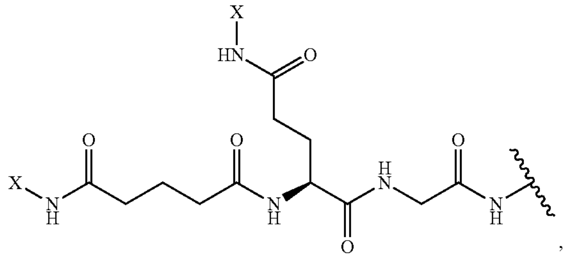
,
U
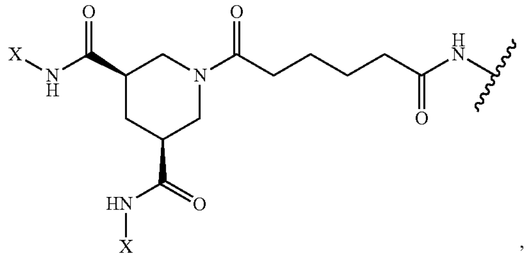
,
V
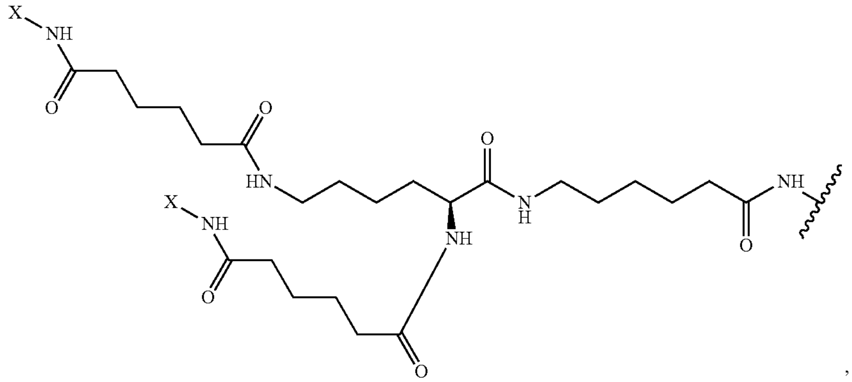
, -continued
W
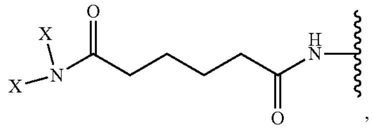
,
X
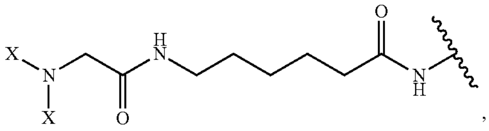
,
Y
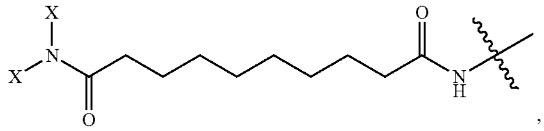
,
Z
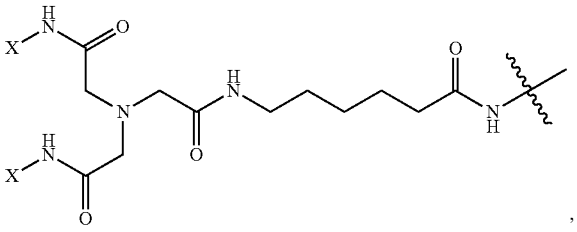
,
AA
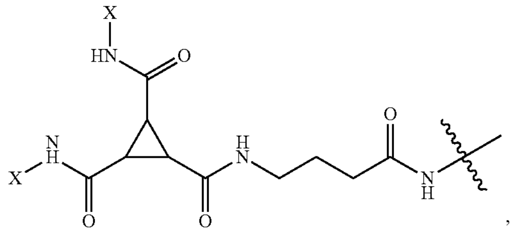
,
AB
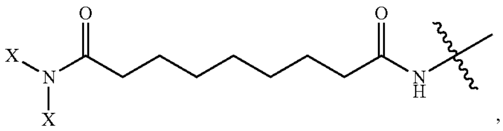
,
AC
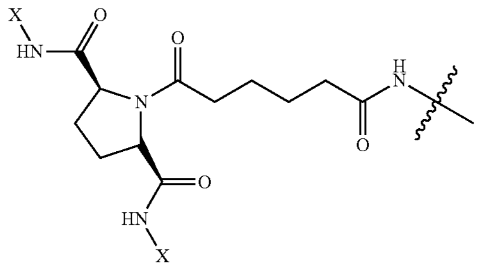
,
AD
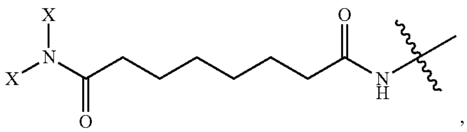
,
AE
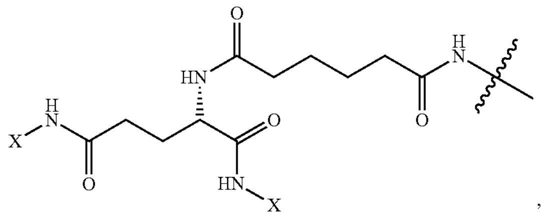
,
AF
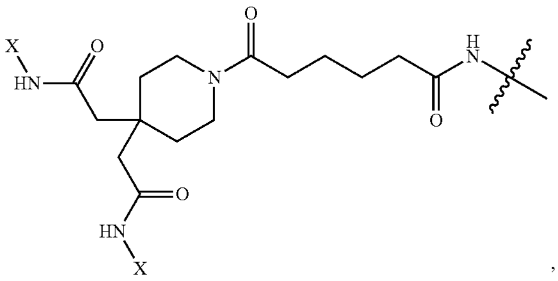
,
AG
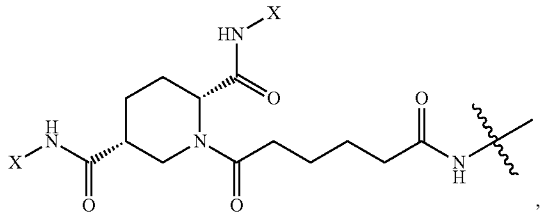
,
AH
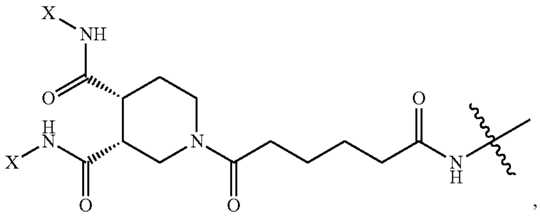
, -continued

AI

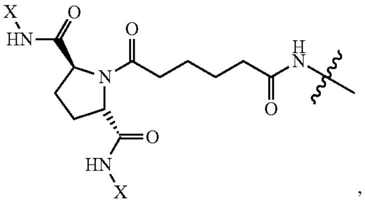

,

AJ

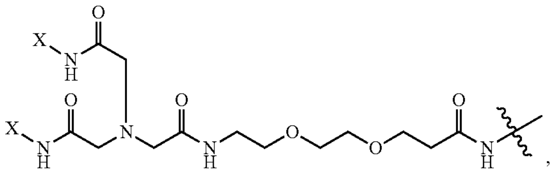

, or

AK

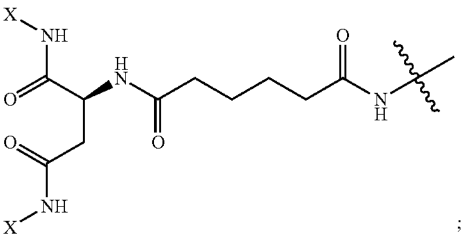

;

wherein each X is independently a ligand comprising a saccharide with the proviso that at least one bi-dentate linker conjugated to the insulin or insulin analog comprises a ligand X comprising fucose on at least one arm of the bi-dentate linker. Further provided is a composition comprising said conjugate having said bidentate linker and a pharmaceutically acceptable carrier, and optionally one or more pharmaceutically acceptable incipients, preservatives, zinc salt, and/or surfactants.

In a further aspect of the conjugate, each X may independently have formula

EG

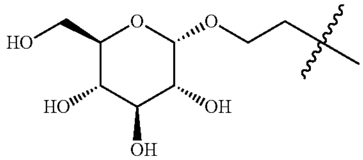

,

EM

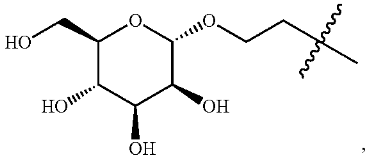

,

EBM

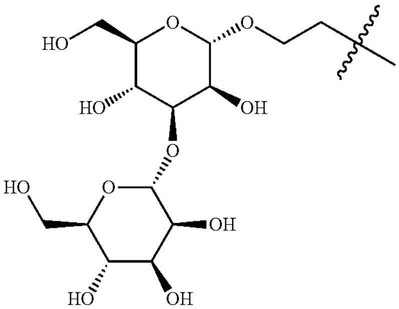

,

-continued

EGA

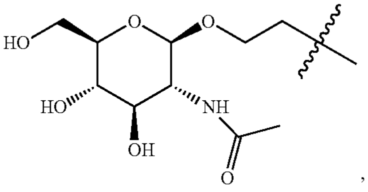

,

EF

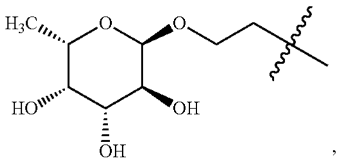

,

EFβ

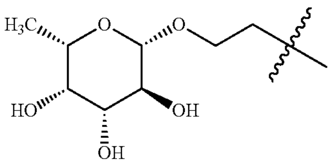

EBM'

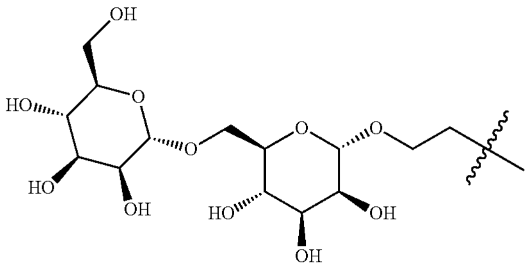

,

-continued

ETM

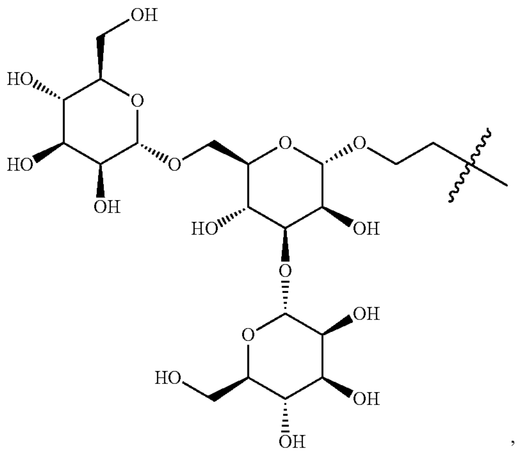

,

EDG

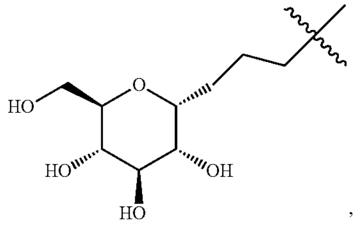

,

EDF

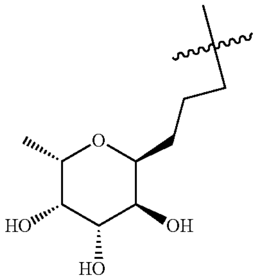

, or

EDM

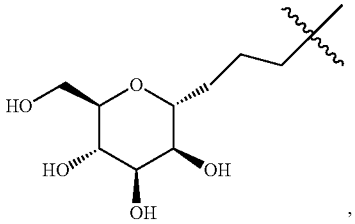

, wherein the wavy line indicates the bond is linked to an atom comprising the bi-dentate linker with the proviso that at least one bi-dentate linker conjugated to the insulin or insulin analog comprises EDF on at least one arm of the bi-dentate linker. Further provided is a composition comprising said conjugate and a pharmaceutically acceptable carrier, and optionally one or more pharmaceutically acceptable incipients, preservatives, zinc salt, and/or surfactants.

In a further aspect of the conjugate, the conjugate comprises an insulin or insulin analog molecule covalently attached to at least two branched linkers, each having a first and second arm, wherein the first arm is linked to a first ligand that includes a first saccharide and the second arm is linked to a second ligand that includes a second saccharide, wherein the first saccharide is fucose. In particular aspects of the conjugate, the second saccharide is independently a fucose, mannose, glucosamine, or glucose. In other aspects, the second saccharide is independently a bisaccharide, trisaccharide, tetrasaccharide, or branched trisaccharide. In a further aspect, the second saccharide is independently a bimannose, trimannose, tetramannose, or branched trimannose. In particular aspects, both the first saccharide and the second saccharide are fucose. In particular aspects, the first saccharide is fucose and the second saccharide is a branched trimannose. In particular aspects, the first saccharide is fucose and the second saccharide is a trimannose. In particular aspects, the first saccharide is fucose and the second saccharide is glucose. In particular aspects, the first saccharide is fucose and the second saccharide is a mannose. In particular aspects, the first saccharide is fucose and the second saccharide is a bimannose. In particular aspects, the first saccharide is fucose and the second saccharide is a trimannose. In particular aspects, the first saccharide is fucose and the second saccharide is a tetramannose.

In a further aspect of the above conjugate, two amino acid positions selected from A1, B1, B29, B28, and B3 of the insulin or insulin analog molecule are covalently linked to the two linkers.

In a further aspect of the conjugate, the conjugate comprises an insulin or insulin analog molecule covalently attached to at least three branched linkers, each having a first and second arm, wherein the first arm is linked to a first ligand that includes a first saccharide and the second arm is linked to a second ligand that includes a second saccharide, wherein the first saccharide is fucose. In particular aspects of the conjugate, the second saccharide is independently a fucose, mannose, glucosamine, or glucose. In other aspects, the second saccharide is independently a bisaccharide, trisaccharide, tetrasaccharide, or branched trisaccharide. In a further aspect, the second saccharide is independently a bimannose, trimannose, tetramannose, or branched trimannose. In particular aspects, both the first saccharide and the second saccharide are fucose. In particular aspects, the first saccharide is fucose and the second saccharide is a branched trimannose. In particular aspects, the first saccharide is fucose and the second saccharide is a trimannose. In particular aspects, the first saccharide is fucose and the second saccharide is glucose. In particular aspects, the first saccharide is fucose and the second saccharide is a mannose. In particular aspects, the first saccharide is fucose and the second saccharide is a bimannose. In particular aspects, the first saccharide is fucose and the second saccharide is a trimannose. In particular aspects, the first saccharide is fucose and the second saccharide is a tetramannose.

In a further aspect of the above conjugate, three amino acid positions selected from A1, B1, B29, B28, and B3 of the insulin or insulin analog molecule are covalently linked to the three linkers.

In a further aspect of the conjugate, the conjugate comprises an insulin or insulin analog molecule covalently attached to at least two branched linkers, each having a first and second arm, wherein the first arm is linked to a first ligand that includes a first saccharide and the second arm is linked to a second ligand that includes a second saccharide, wherein the first saccharide of one of the two linkers is fucose.

In particular aspects of the conjugate, the remaining first saccharide and second saccharide are independently fucose, mannose, glucosamine, or glucose. In other aspects, the remaining first saccharide and second saccharide are independently a bisaccharide, trisaccharide, tetrasaccharide, or branched trisaccharide. In a further aspect, the remaining first saccharide and second saccharide are independently a bimannose, trimannose, tetramannose, or branched trimannose.

In particular aspects, both the first saccharide and the second saccharide for each of the two linkers are fucose. In particular aspects, for each of the two linkers the first saccharide is fucose and the second saccharide is a branched trimannose. In particular aspects, for each of the two linkers the first saccharide is fucose and the second saccharide is a trimannose. In particular aspects, for each of the two linkers the first saccharide is fucose and the second saccharide is glucose. In particular aspects, for each of the two linkers the first saccharide for each of the two linkers is fucose and the second saccharide is a mannose. In particular aspects, for each of the two linkers the first saccharide is fucose and the second saccharide is a bimannose. In particular aspects, for each of the two linkers the first saccharide is fucose and the second saccharide is a trimannose. In particular aspects, for each of the two linkers the first saccharide is fucose and the second saccharide is a tetramannose.

In particular aspects, both the first saccharide and the second saccharide for one of the two linkers are fucose and for the second linker the first saccharide and second saccharide are independently fucose, mannose, glucosamine, glucose bisaccharide, trisaccharide, tetrasaccharide, or branched trisaccharide bimannose, trimannose, tetramannose, or branched trimannose. In particular aspects, for one of the two linkers the first saccharide is fucose and the second saccharide is a branched trimannose and for the second linker the first saccharide and second saccharide are independently fucose, mannose, glucosamine, glucose bisaccharide, trisaccharide, tetrasaccharide, or branched trisaccharide bimannose, trimannose, tetramannose, or branched trimannose. In particular aspects, for one of the two linkers the first saccharide is fucose and the second saccharide is a trimannose and for the second linker the first saccharide and second saccharide are independently fucose, mannose, glucosamine, glucose bisaccharide, trisaccharide, tetrasaccharide, or branched trisaccharide bimannose, trimannose, tetramannose, or branched trimannose. In particular aspects, for one of the two linkers the first saccharide is fucose and the second saccharide is glucose and for the second linker the first saccharide and second saccharide are independently fucose, mannose, glucosamine, glucose bisaccharide, trisaccharide, tetrasaccharide, or branched trisaccharide bimannose, trimannose, tetramannose, or branched trimannose. In particular aspects, for one of the two linkers the first saccharide for each of the two linkers is fucose and the second saccharide is a mannose and for the second linker the first saccharide and second saccharide are independently fucose, mannose, glucosamine, glucose bisaccharide, trisaccharide, tetrasaccharide, or branched trisaccharide bimannose, trimannose, tetramannose, or branched trimannose. In particular aspects, for one of the two linkers the first saccharide is fucose and the second saccharide is a bimannose and for the second linker the first saccharide and second saccharide are independently fucose, mannose, glucosamine, glucose bisaccharide, trisaccharide, tetrasaccharide, or branched trisaccharide bimannose, trimannose, tetramannose, or branched trimannose. In particular aspects, for one of the two linkers the first saccharide is fucose and the second saccharide is a trimannose and for the second linker the first saccharide and second saccharide are independently fucose, mannose, glucosamine, glucose bisaccharide, trisaccharide, tetrasaccharide, or branched trisaccharide bimannose, trimannose, tetramannose, or branched trimannose. In particular aspects, for one of the two linkers the first saccharide is fucose and for the second linker the second saccharide is a tetramannose and the first saccharide and second saccharide are independently fucose, mannose, glucosamine, glucose bisaccharide, trisaccharide, tetrasaccharide, or branched trisaccharide bimannose, trimannose, tetramannose, or branched trimannose.

In a further aspect of the above conjugate, two amino acid positions selected from A1, B1, B29, B28, and B3 of the insulin or insulin analog molecule are covalently linked to the two linkers.

In a further aspect of the conjugate, the conjugate comprises an insulin or insulin analog molecule covalently attached to at least three branched linkers, each having a first and second arm, wherein the first arm is linked to a first ligand that includes a first saccharide and the second arm is linked to a second ligand that includes a second saccharide, wherein the first saccharide of at least one of the three linkers is fucose and the remaining first saccharides and second saccharide are independently fucose, mannose, glucosamine, or glucose. In other aspects, the remaining first saccharides and second saccharide are independently a bisaccharide, trisaccharide, tetrasaccharide, or branched trisaccharide. In a further aspect, the remaining first saccharides and second saccharide are a bimannose, trimannose, tetramannose, or branched trimannose.

In a further aspect of the above conjugate, three amino acid positions selected from A1, B1, B29, B28, and B3 of the insulin or insulin analog molecule are covalently linked to the three linkers.

Further provided is conjugate or a composition comprising a conjugate having the formula as set forth for IOC-1, IOC-2, IOC-3, IOC-4, IOC-5, IOC-6, IOC-7, IOC-8, IOC-9, IOC-10, IOC-11, IOC-12, IOC-13, IOC-14, IOC-15, IOC-16, IOC-17, IOC-18, IOC-19, IOC-20, IOC-21, IOC-22, IOC-23, IOC-24, IOC-25, IOC-26, IOC-27, IOC-28, IOC-29, IOC-30, IOC-31, IOC-32, IOC-33, IOC-34, IOC-35, IOC-36, IOC-37, IOC-38, IOC-39, IOC-41, IOC-42, IOC-43, IOC-44, IOC-45, IOC-46, IOC-47, IOC-49, IOC-50, IOC-51, IOC-52, IOC-53, IOC-54, IOC-55, IOC-56, IOC-57, IOC-58, IOC-59, IOC-60, IOC-61, IOC-62, IOC-63, IOC-64, IOC-65, IOC-66, IOC-67, IOC-68, IOC-69, IOC-70, IOC-71, IOC-72, IOC-73, IOC-74, IOC-75, IOC-76, IOC-77, IOC-78, IOC-79, IOC-80, IOC-81, IOC-82, IOC-83, IOC-84, IOC-85, IOC-86, IOC-87, IOC-88, IOC-89, IOC-90, IOC-91, IOC-92, IOC-93, IOC-94, IOC-95, IOC-96, IOC-97, IOC-98, IOC-99, or IOC-100.

Further provided is conjugate or a composition comprising a conjugate having the formula as set forth for IOC-101, IOC-102, IOC-103, IOC-104, IOC-105, IOC-106, IOC-107, IOC-108, IOC-109, IOC-110, IOC-111, IOC-112, IOC-113, IOC-114, IOC-115, IOC-116, IOC-117, IOC-118, IOC-119, IOC-120, IOC-121, IOC-122, IOC-123, IOC-124, IOC-125, IOC-126, IOC-127, IOC-128, IOC-129, IOC-130, IOC-131, IOC-132, IOC-133, IOC-134, IOC-135, IOC-136, IOC-137, IOC-138, IOC-139, IOC-140, IOC-141, IOC-142, IOC-143, IOC-144, IOC-145, IOC-146, IOC-147, IOC-149, IOC-150, IOC-151, IOC-152, IOC-153, IOC-154, IOC-155, IOC-156, IOC-157, IOC-158, IOC-159, IOC-160, IOC-161, IOC-162, IOC-163, IOC-164, IOC-165, IOC-166, IOC-167, IOC-168, IOC-169, IOC-170, IOC-171, IOC-172, IOC-173, IOC-174, IOC-175, IOC-176, IOC-177, IOC-178, IOC-179, IOC-180, IOC-181, IOC-182, IOC-183, IOC-184, IOC-185, IOC-186, IOC-187, IOC-188, IOC-189, IOC-190, IOC-191, or IOC-192.

Further provided is conjugate or a composition comprising a conjugate having the formula as set forth for IOC-193, IOC-194, IOC-195, IOC-196, IOC-197, IOC-198, IOC-199, IOC-200, IOC-201, IOC-202, IOC-203, IOC-204, IOC-205, IOC-206, IOC-207, IOC-208, IOC-210, IOC-211, IOC-212, IOC-213, IOC-214, IOC-215, IOC-216, IOC-217, IOC-218, IOC-219, IOC-220, IOC-221, IOC-222, IOC-223, IOC-224, IOC-225, IOC-226, IOC-227, IOC-228, IOC-229, IOC-230, IOC-231, IOC-232, IOC-233, IOC-234, IOC-235, IOC-236, IOC-237, IOC-238, IOC-239, IOC-240, IOC-241, IOC-242, IOC-243, IOC-244, IOC-245, IOC-246, IOC-247, IOC-248, IOC-249, IOC-250, IOC-251, IOC-252, IOC-253, IOC-254, IOC-255, IOC-256, IOC-257, IOC-258, IOC-259, IOC-260, IOC-261, IOC-262, IOC-263, IOC-264, IOC-265, IOC-266, IOC-267, IOC-268, IOC-269, IOC-270, IOC-271, or IOC-272.

The above conjugates may further be provided in a pharmaceutical formula comprising a pharmaceutically acceptable carrier and optionally one or more pharmaceutically acceptable excipients, preservatives, and/or surfactants. In further aspects the conjugates may further include zinc and/or a protamine. The conjugates may be provided as crystalline form.

Thus, the present invention further provides a composition comprising one or more of the conjugates as generically or specifically disclosed herein and a pharmaceutically acceptable carrier, and optionally one or more pharmaceutically acceptable incipients, preservatives, zinc salt, and/or surfactants. Further provided is a composition comprising one or more of the conjugates as generically or specifically disclosed herein in a crystalline form and a pharmaceutically acceptable carrier, and optionally one or more pharmaceutically acceptable incipients, preservatives, zinc salt, protamine, and/or surfactants.

In further aspects of the conjugates, the insulin molecule is a mammalian insulin, which in particular embodiments, may be a human insulin, bovine insulin, dog insulin, cat insulin, goat insulin, horse insulin, pig insulin or an analog thereof. In particular embodiments, the insulin analog is insulin lispro or insulin glulisine. In further embodiments, the insulin or insulin analog is modified to comprise a polyethylene glycol or fatty acid covalently linked to an amino acid of the insulin or insulin analog. In particular embodiments, the insulin analog is insulin lispro, insulin glargine, insulin aspart, insulin detemir, or insulin glulisine.

The present invention further provides methods for treating diabetes comprising administering the conjugates disclosed herein or a pharmaceutical formulation comprising the conjugates disclosed herein to an subject who is diabetic. The present invention further provides for the use of the conjugates disclosed herein for the manufacture of a medicament for the treatment of diabetes.

The present invention further provides a composition or pharmaceutical composition comprising: an insulin or insulin analog molecule covalently attached to at least one branched linker having a first arm and second arm, wherein the first arm is linked to a first ligand that includes a first saccharide and the second arm is linked to a second ligand that includes a second saccharide and wherein the first saccharide is fucose, to provide a conjugate, and a pharmaceutically acceptable carrier.

In general, the second saccharide is a fucose, mannose, glucosamine, glucose, bisaccharide, trisaccharide, tetrasaccharide, branched trisaccharide, bimannose, trimannose, tetramannose, or branched trimannose.

In particular aspects, the branched linker is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule.

In a further embodiment, the insulin or insulin analog is covalently attached to a second branched linker having a first arm and second arm, wherein the first arm is linked to a third ligand that includes a third saccharide and the second arm is linked to a fourth ligand that includes a fourth saccharide. In particular aspects, the second branched linker is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule and which is not occupied by the first branched linker.

In a further embodiment, the insulin or insulin analog is covalently attached to a third branched linker having a first arm and second arm, wherein the first arm is linked to a fifth ligand that includes a fifth saccharide and the second arm is linked to a sixth ligand that includes a sixth saccharide. In particular aspects, the third branched linker is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule and which is not occupied by the first branched linker and the second branched linker.

In any embodiment of the above conjugate, the third, fourth, fifth, and sixth saccharides are each independently a fucose, mannose, glucosamine, glucose, bisaccharide, trisaccharide, tetrasaccharide, branched trisaccharide, bimannose, trimannose, tetramannose, or branched trimannose.

In a further aspect, the insulin or insulin analog molecule is further covalently linked to a linear linker comprising a ligand that includes a saccharide and the saccharide may be a fucose, mannose, glucosamine, glucose, bisaccharide, trisaccharide, tetrasaccharide, branched trisaccharide, bimannose, trimannose, tetramannose, or branched trimannose.

In particular aspects, the insulin analog molecule is insulin lispro, insulin glargine, insulin aspart, insulin detemir, or insulin glulisine.

In any one of the above aspects or embodiments, the conjugate displays a pharmacodynamic (PD) or pharmacokinetic (PK) profile that is sensitive to the serum concentration of a serum saccharide when administered to a subject in need thereof in the absence of an exogenous saccharide binding molecule. In particular aspects, the serum saccharide is glucose or alpha-methylmannose. In particular aspects, the conjugate binds an endogenous saccharide binding molecule at a serum glucose concentration of 60 mg/dL or less when administered to a subject in need thereof. The endogenous saccharide binding molecule may be the human mannose receptor 1.

In particular aspects of the composition, the conjugate has the general formula (I):

I

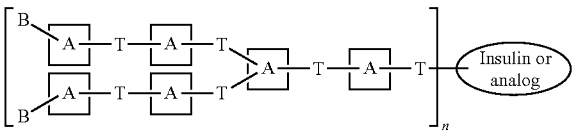

wherein:

(i) each occurrence of

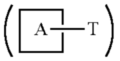

represents a potential repeat within a branch of the conjugate;

(ii) each occurrence of A is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —N(R)$SO_2$—, —$SO_2$N(R)—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) —B is -T-$L^B$-X, wherein each occurrence of X is independently a ligand comprising a saccharide and each occurrence of $L^B$ is independently a covalent bond or a group derived from the covalent conjugation of a T with an X; and, (vi) n is 1, 2, or 3, with the proviso that at least one X is fucose.

In particular aspects of the composition, the conjugate comprises the general formula (II):

II

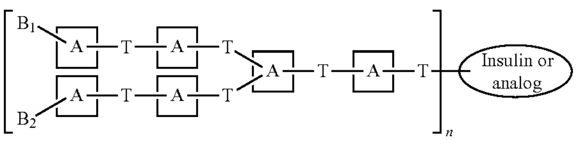

wherein:

(i) each occurrence of

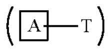

represents a potential repeat within a branch of the conjugate;

(ii) each occurrence of A is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —N(R)$SO_2$—, —$SO_2$N(R)—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) —$B_1$ is -T-$L^{B_1}$-Fucose, wherein $L^{B_1}$ is a covalent bond or a group derived from the covalent conjugation of a T with an X;

(vi) —$B_2$ is -T-$L^{B_2}$-X, wherein X is a ligand comprising a saccharide, which may be fucose, mannose, or glucose; and $L^{B_2}$ is a covalent bond or a group derived from the covalent conjugation of a T with an X; and, (vii) n is 1, 2, or 3.

In particular aspects of the composition, the bi-dentate linker has formula A, B, C, D, E, F, G, H, I, J, K, L, M, N, O, P, Q, R, S, T, U, V, W, X, Y, Z, AA, AB, AC, AD, AE, AF, AG, AH, AI, AJ, or AK as shown supra wherein each X is independently a ligand comprising a saccharide with the proviso that at least one bi-dentate linker conjugated to the insulin or insulin analog comprises a fucose on at least one arm of the bi-dentate linker. In particular aspects, each X may independently have formular EG, EM, EBM, EGA, EF, EFβ, EBM, ETM, EDG, EDF, or EDM as shown supra.

Further provided is a composition comprising a conjugate having the formula as set forth for IOC-1, IOC-2, IOC-3, IOC-4, IOC-5, IOC-6, IOC-7, IOC-8, IOC-9, IOC-10, IOC-11, IOC-12, IOC-13, IOC-14, IOC-15, IOC-16, IOC-17, IOC-18, IOC-19, IOC-20, IOC-21, IOC-22, IOC-23, IOC-24, IOC-25, IOC-26, IOC-27, IOC-28, IOC-29, IOC-30, IOC-31, IOC-32, IOC-33, IOC-34, IOC-35, IOC-36, IOC-37, IOC-38, IOC-39, IOC-41, IOC-42, IOC-43, IOC-44, IOC-45, IOC-46, IOC-47, IOC-49, IOC-50, IOC-51, IOC-52, IOC-53, IOC-54, IOC-55, IOC-56, IOC-57, IOC-58, IOC-59, IOC-60, IOC-61, IOC-62, IOC-63, IOC-64, IOC-65, IOC-66, IOC-67, IOC-68, IOC-69, IOC-70, IOC-71, IOC-72, IOC-73, IOC-74, IOC-75, IOC-76, IOC-77, IOC-78, IOC-79, IOC-80, IOC-81, IOC-82, IOC-83, IOC-84, IOC-85, IOC-86, IOC-87, IOC-88, IOC-89, IOC-90, IOC-91, IOC-92, IOC-93, IOC-94, IOC-95, IOC-96, IOC-97, IOC-98, IOC-99, or IOC-100, and a pharmaceutically acceptable carrier; a composition comprising a conjugate having the formula as set forth for IOC-101, IOC-102, IOC-103, IOC-104, IOC-105, IOC-106, IOC-107, IOC-108, IOC-109, IOC-110, IOC-111, IOC-112, IOC-113, IOC-114, IOC-115, IOC-116, IOC-117, IOC-118, IOC-119, IOC-120, IOC-121, IOC-122, IOC-123, IOC-124, IOC-125, IOC-126, IOC-127, IOC-128, IOC-129, IOC-130, IOC-131, IOC-132, IOC-133, IOC-134, IOC-135, IOC-136, IOC-137, IOC-138, IOC-139, IOC-140, IOC-141, IOC-142, IOC-143, IOC-144, IOC-145, IOC-146, IOC-147, IOC-149, IOC-150, IOC-151, IOC-152, IOC-153, IOC-154, IOC-155, IOC-156, IOC-157, IOC-158, IOC-159, IOC-160, IOC-161, IOC-162, IOC-163, IOC-164, IOC-165, IOC-166, IOC-167, IOC-168, IOC-169, IOC-170, IOC-171, IOC-172, IOC-173, IOC-174, IOC-175, IOC-176, IOC-177, IOC-178, IOC-179, IOC-180, IOC-181, IOC-182, IOC-183, IOC-184, IOC-185, IOC-186, IOC-187, IOC-188, IOC-189, IOC-190, IOC-191, or IOC-192, and a pharmaceutically acceptable carrier; and a composition comprising a conjugate having the formula as set forth for IOC-193, IOC-194, IOC-195, IOC-196, IOC-197, IOC-198, IOC-199, IOC-200, IOC-201, IOC-202, IOC-203, IOC-204, IOC-205, IOC-206, IOC-207, IOC-208, IOC-210, IOC-211, IOC-212, IOC-213, IOC-214, IOC-215, IOC-216, IOC-217, IOC-218, IOC-219, IOC-220, IOC-221, IOC-222, IOC-223, IOC-224, IOC-225, IOC-226, IOC-227, IOC-228, IOC-229, IOC-230, IOC-231, IOC-232, IOC-233, IOC-234, IOC-235, IOC-236, IOC-237, IOC-238, IOC-239, IOC-240, IOC-241, IOC-242, IOC-243, IOC-244, IOC-245, IOC-246, IOC-247, IOC-248, IOC-249, IOC-250, IOC-251, IOC-252, IOC-253, IOC-254, IOC-255, IOC-256, IOC-257, IOC-258, IOC-259, IOC-260, IOC-261, IOC-262, IOC-263, IOC-264, IOC-265, IOC-266, IOC-267, IOC-268, IOC-269, IOC-270, IOC-271, or IOC-272, and a pharmaceutically acceptable carrier.

The present invention further provides for the use of the compositions disclosed herein for the treatment of diabetes. In particular aspects, the diabetes is type I diabetes, type II diabetes, or gestational diabetes.

The present invention further provides a method for treating a subject who has diabetes comprising: administering to the subject an amount of a composition for treating the diabetes, wherein the composition comprises an insulin or insulin analog molecule covalently attached to at least one branched linker having a first arm and second arm, wherein the first arm is linked to a first ligand that includes a first saccharide and the second arm is linked to a second ligand that includes a second saccharide and wherein the first saccharide is fucose, to provide a conjugate, and a pharmaceutically acceptable carrier to treat the diabetes; wherein said administering treats the diabetes. In particular aspects, the amount of composition administered is an effective amount or therapeutically effective amount.

In general, the second saccharide is a fucose, mannose, glucosamine, glucose, bisaccharide, trisaccharide, tetrasaccharide, branched trisaccharide, bimannose, trimannose, tetramannose, or branched trimannose.

In particular aspects, the branched linker is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule.

In a further embodiment, the insulin or insulin analog is covalently attached to a second branched linker having a first arm and second arm, wherein the first arm is linked to a third ligand that includes a third saccharide and the second arm is linked to a fourth ligand that includes a fourth saccharide. In particular aspects, the second branched linker is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule and which is not occupied by the first branched linker.

In a further embodiment, the insulin or insulin analog is covalently attached to a third branched linker having a first arm and second arm, wherein the first arm is linked to a fifth ligand that includes a fifth saccharide and the second arm is linked to a sixth ligand that includes a sixth saccharide. In particular aspects, the third branched linker is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule and which is not occupied by the first branched linker and the second branched linker.

In any embodiment of the above conjugate, the third, fourth, fifth, and sixth saccharides are each independently a fucose, mannose, glucosamine, glucose, bisaccharide, trisaccharide, tetrasaccharide, branched trisaccharide, bimannose, trimannose, tetramannose, or branched trimannose.

In a further aspect, the insulin or insulin analog molecule is further covalently linked to a linear linker comprising a ligand that includes a saccharide and the saccharide may be a fucose, mannose, glucosamine, glucose, bisaccharide, trisaccharide, tetrasaccharide, branched trisaccharide, bimannose, trimannose, tetramannose, or branched trimannose.

In particular aspects, the insulin analog molecule is insulin lispro, insulin glargine, insulin aspart, insulin detemir, or insulin glulisine.

In any one of the above aspects or embodiments, the conjugate displays a pharmacodynamic (PD) or pharmacokinetic (PK) profile that is sensitive to the serum concentration of a serum saccharide when administered to a subject in need thereof in the absence of an exogenous saccharide binding molecule. In particular aspects, the serum saccharide is glucose or alpha-methylmannose. In particular aspects, the conjugate binds an endogenous saccharide binding molecule at a serum glucose concentration of 60 mg/dL or less when administered to a subject in need thereof. The endogenous saccharide binding molecule may be the human mannose receptor 1.

In particular aspects of the composition, the conjugate has the general formula (I):

I

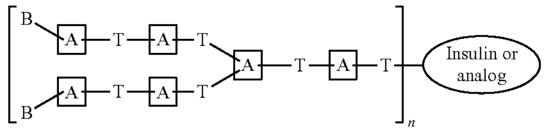

wherein:

(i) each occurrence of

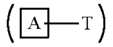

represents a potential repeat within a branch of the conjugate;

(ii) each occurrence of A is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —$N(R)SO_2$—, —$SO_2N(R)$—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) —B is -T-$L^B$-X, wherein each occurrence of X is independently a ligand comprising a saccharide and each occurrence of $L^B$ is independently a covalent bond or a group derived from the covalent conjugation of a T with an X; and, (vi) n is 1, 2, or 3, with the proviso that at least one X is fucose.

In particular aspects of the composition, the conjugate comprises the general formula (II):

II

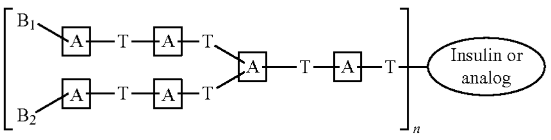

wherein:

(i) each occurrence of

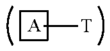

represents a potential repeat within a branch of the conjugate;

(ii) each occurrence of A is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —N(R)$SO_2$—, —$SO_2$N(R)—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) —$B_1$ is -T-$L^{B1}$-Fucose, wherein $L^{B1}$ is a covalent bond or a group derived from the covalent conjugation of a T with an X;

(vi) —$B_2$ is -T-$L^{B2}$-X, wherein X is a ligand comprising a saccharide, which may be fucose, mannose, or glucose; and $L^{B2}$ is a covalent bond or a group derived from the covalent conjugation of a T with an X; and, (vii) n is 1, 2, or 3.

In particular aspects of the composition, the bi-dentate linker has formula A, B, C, D, E, F, G, H, I, J, K, L, M, N, O, P, Q, R, S, T, U, V, W, X, Y, Z, AA, AB, AC, AD, AE, AF, AG, AH, AI, AJ, or AK as shown supra wherein each X is independently a ligand comprising a saccharide with the proviso that at least one bi-dentate linker conjugated to the insulin or insulin analog comprises a fucose on at least one arm of the bi-dentate linker. In particular aspects, each X may independently have formular EG, EM, EBM, EGA, EF, EFβ, EBM, ETM, EDG, EDF, or EDM as shown supra.

The present invention further provides a method for treating a subject who has diabetes, comprising: administering to the subject a composition comprising a conjugate having the formula as set forth for IOC-1, IOC-2, IOC-3, IOC-4, IOC-5, IOC-6, IOC-7, IOC-8, IOC-9, IOC-10, IOC-11, IOC-12, IOC-13, IOC-14, IOC-15, IOC-16, IOC-17, IOC-18, IOC-19, IOC-20, IOC-21, IOC-22, IOC-23, IOC-24, IOC-25, IOC-26, IOC-27, IOC-28, IOC-29, IOC-30, IOC-31, IOC-32, IOC-33, IOC-34, IOC-35, IOC-36, IOC-37, IOC-38, IOC-39, IOC-41, IOC-42, IOC-43, IOC-44, IOC-45, IOC-46, IOC-47, IOC-49, IOC-50, IOC-51, IOC-52, IOC-53, IOC-54, IOC-55, IOC-56, IOC-57, IOC-58, IOC-59, IOC-60, IOC-61, IOC-62, IOC-63, IOC-64, IOC-65, IOC-66, IOC-67, IOC-68, IOC-69, IOC-70, IOC-71, IOC-72, IOC-73, IOC-74, IOC-75, IOC-76, IOC-77, IOC-78, IOC-79, IOC-80, IOC-81, IOC-82, IOC-83, IOC-84, IOC-85, IOC-86, IOC-87, IOC-88, IOC-89, IOC-90, IOC-91, IOC-92, IOC-93, IOC-94, IOC-95, IOC-96, IOC-97, IOC-98, IOC-99, or IOC-100 and a pharmaceutically acceptable carrier to treat the diabetes in the subject; a method for treating a subject who has diabetes, comprising: administering to the subject a composition comprising a conjugate having the formula as set forth for IOC-101, IOC-102, IOC-103, IOC-104, IOC-105, IOC-106, IOC-107, IOC-108, IOC-109, IOC-110, IOC-111, IOC-112, IOC-113, IOC-114, IOC-115, IOC-116, IOC-117, IOC-118, IOC-119, IOC-120, IOC-121, IOC-122, IOC-123, IOC-124, IOC-125, IOC-126, IOC-127, IOC-128, IOC-129, IOC-130, IOC-131, IOC-132, IOC-133, IOC-134, IOC-135, IOC-136, IOC-137, IOC-138, IOC-139, IOC-140, IOC-141, IOC-142, IOC-143, IOC-144, IOC-145, IOC-146, IOC-147, IOC-149, IOC-150, IOC-151, IOC-152, IOC-153, IOC-154, IOC-155, IOC-156, IOC-157, IOC-158, IOC-159, IOC-160, IOC-161, IOC-162, IOC-163, IOC-164, IOC-165, IOC-166, IOC-167, IOC-168, IOC-169, IOC-170, IOC-171, IOC-172, IOC-173, IOC-174, IOC-175, IOC-176, IOC-177, IOC-178, IOC-179, IOC-180, IOC-181, IOC-182, IOC-183, IOC-184, IOC-185, IOC-186, IOC-187, IOC-188, IOC-189, IOC-190, IOC-191, or IOC-192 and a pharmaceutically acceptable carrier to treat the diabetes in the subject; and a method for treating a subject who has diabetes, comprising: administering to the subject a composition comprising a conjugate having the formula as set forth for IOC-193, IOC-194, IOC-195, IOC-196, IOC-197, IOC-198, IOC-199, IOC-200, IOC-201, IOC-202, IOC-203, IOC-204, IOC-205, IOC-206, IOC-207, IOC-208, IOC-210, IOC-211, IOC-212, IOC-213, IOC-214, IOC-215, IOC-216, IOC-217, IOC-218, IOC-219, IOC-220, IOC-221, IOC-222, IOC-223, IOC-224, IOC-225, IOC-226, IOC-227, IOC-228, IOC-229, IOC-230, IOC-231, IOC-232, IOC-233, IOC-234, IOC-235, IOC-236, IOC-237, IOC-238, IOC-239, IOC-240, IOC-241, IOC-242, IOC-243, IOC-244, IOC-245, IOC-246, IOC-247, IOC-248, IOC-249, IOC-250, IOC-251, IOC-252, IOC-253, IOC-254, IOC-255, IOC-256, IOC-257, IOC-258, IOC-259, IOC-260, IOC-261, IOC-262, IOC-263, IOC-264, IOC-265, IOC-266, IOC-267, IOC-268, IOC-269, IOC-270, IOC-271, or IOC-272, and a pharmaceutically acceptable carrier to treat the diabetes in the subject.

In anyone of the aforementioned aspects or embodiments of the method, the diabetes is type I diabetes, type II diabetes, or gestational diabetes.

The present invention further provides a composition comprising an insulin and insulin analog conjugate wherein the conjugate comprises at least one fucose molecule and the conjugate is characterized as having a ratio of $EC_{50}$ or IP as determined by a functional insulin receptor phosphorylation assay to the $IC_{50}$ or IP as determined by a competition binding assay at the macrophage mannose receptor that is about 0.5:1 to about 1:100; about 1:1 to about 1:50; about 1:1 to about 1:20; or about 1:1 to about 1:10; and a pharmaceutically acceptable carrier.

In particular aspects, wherein the conjugate comprises an insulin or insulin analog molecule covalently attached to at least one branched linker having a first arm and second arm, wherein the first arm is linked to a first ligand that includes a first saccharide and the second arm is linked to a second ligand that includes a second saccharide and wherein the first saccharide is fucose. In further aspects, the second saccharide is a fucose, mannose, glucosamine, glucose, bisaccharide, trisaccharide, tetrasaccharide, branched trisaccharide, bimannose, trimannose, tetramannose, or branched trimannose.

In particular embodiments, the conjugate may be a conjugate as disclosed herein.

The present invention further provides a method for treating a subject who has diabetes, comprising administering to the subject a composition comprising a conjugate comprising fucose and characterized as having a ratio of $EC_{50}$ or IP as determined by a functional insulin receptor phosphorylation assay to the $IC_{50}$ or IP as determined by a competition binding assay at the macrophage mannose receptor that is about 0.5:1 to about 1:100; about 1:1 to about 1:50; about 1:1 to about 1:20; or about 1:1 to about 1:10; and a pharmaceutically acceptable carrier to treat the diabetes.

In particular embodiments, the conjugate comprises an insulin or insulin analog molecule covalently attached to at least one branched linker having a first arm and second arm, wherein the first arm is linked to a first ligand that includes a first saccharide and the second arm is linked to a second ligand that includes a second saccharide and wherein the first saccharide is fucose. In further aspects, the second saccharide is a fucose, mannose, glucosamine, glucose, bisaccharide, trisaccharide, tetrasaccharide, branched trisaccharide, bimannose, trimannose, tetramannose, or branched trimannose.

In particular embodiments, the conjugate may be a conjugate as disclosed herein.

In particular aspects. the diabetes is type I diabetes, type II diabetes, or gestational diabetes.

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

Acyl—As used herein, the term "acyl," refers to a group having the general formula $—C(═O)R^{X1}$, $—C(═O)OR^{X1}$, $—C(═O)—O—C(═O)R^{X1}$, $—C(═O)SR^{X1}$, $—C(═O)N(R^{X1})_2$, $—C(═S)R^{X1}$, $—C(═S)N(R^{X1})_2$, and $—C(═S)S(R^{X1})$, $—C(═NR^{X1})R^{X1}$, $—C(═NR^{X1})OR^{X1}$, $—C(═NR^{X1})SR^{X1}$, and $C(═NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids ($—CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In particular embodiments, the alkenyl group employed in the invention contains 2-6 carbon atoms. In particular embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In particular embodiments, the alkynyl group employed in the invention contains 2-6 carbon atoms. In particular embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In particular embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bidentate—a molecule formed from two or more molecules covalently bound together as a single unit molecule.

Bivalent hydrocarbon chain—As used herein, the term "bivalent hydrocarbon chain" (also referred to as a "bivalent alkylene group") is a polymethylene group, i.e., $—(CH_2)_z—$, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Fucose—refers to the D or L form of fucose and may refer to an oxygen or carbon linked glycoside.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in particular embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH═CHPh, which may be substituted with $R^\circ$; $—NO_2$; —CN; $—N_3$; $—(CH_2)_{0-4}N(R^\circ)_2$; $—(CH_2)_{0-4}N(R^\circ)C(O) R^\circ$; $—N(R^\circ)C(S) R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O) R^\circ_2$; $—OP(O)R^\circ)_2$; $—OP(O)(OR^\circ)_2$; $SiR^\circ_3$; $—(C_{1-4}$ straight or branched)alkylene)$O—N(R^\circ)_2$; or $—(C_{1-4}$ straight or branched)alkylene) $C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OR^\bullet$, $—(CH_2)_{0-2}CH(OR^\bullet)_2$; —O(halo$R^\bullet$), —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O, ═S, $═NNR^*_2$, $═NNHC(O)R^*$, $═NNHC(O)OR^*$, $═NNHS(O)_2R^*$, $═NR^*$, $═NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, -(halo$R^\bullet$), —OH, $—OR^\bullet$, —O(halo$R^\bullet$), —CN, —C(O)OH, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NO^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NO^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $—R^\bullet$, -(halo$R^\bullet$), —OH, $—OR^\bullet$, —O(halo$R^\bullet$), —CN, —C(O)OH, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, —$CH_2$Ph, —O($CH_2$)$_{0-1}$Ph, or a 5-6-membered saturated, partially unsaturated, or aryl ring having 0-4 heteroatoms independently selected from nitrogen, oxygen, or sulfur.

Suitable protecting group —As used herein, the term “suitable protecting group,” refers to amino protecting groups or hydroxyl protecting groups depending on its location within the compound and includes those described in detail in *Protecting Groups in Organic Synthesis*, T. W. Greene and P. G. M. Wuts, 3rd edition, John Wiley & Sons, 1999.

Suitable amino—protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1, 1-dimethyl-2-haloethyl carbamate, 1, 1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-34N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In any case where a chemical variable (e.g., an R group) is shown attached to a bond that crosses a bond of the ring, this means that one or more such variables are optionally attached to the ring having the crossed bond. Each R group on such a ring can be attached at any suitable position on the ring, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Biodegradable—As used herein, the term "biodegradable" refers to molecules that degrade (i.e., lose at least some of their covalent structure) under physiological or endosomal conditions. Biodegradable molecules are not necessarily hydrolytically degradable and may require enzymatic action to degrade.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/ National Formulary-20, published by the United States Pharmcopeial Convention, Inc., Rockville Md., 2001.

Exogenous—As used herein, an "exogenous" molecule is one which is not present at significant levels in a patient unless administered to the patient. In particular embodiments the patient is a mammal, e.g., a human, a dog, a cat, a rat, a minipig, etc. As used herein, a molecule is not present at significant levels in a patient if normal serum for that type of patient includes less than 0.1 mM of the molecule. In particular embodiments, normal serum for the patient may include less than 0.08 mM, less than 0.06 mM, or less than 0.04 mM of the molecule.

Hyperbranched—As used herein, a "hyperbranched" structure is a covalent structure that includes at least one branched branch (e.g., a dendrimeric structure). A hyperbranched structure may include polymeric and/or non-polymeric substructures.

Normal serum—As used herein, "normal serum" is serum obtained by pooling approximately equal amounts of the liquid portion of coagulated whole blood from five or more non-diabetic patients. A non-diabetic human patient is a randomly selected 18-30 year old who presents with no diabetic symptoms at the time blood is drawn.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide—As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide—As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 Da. Preferred small molecules are biologically active in that they produce a local or systemic effect in animals, preferably mammals, more preferably humans. In particular preferred embodiments, the small molecule is a drug. Preferably, though not necessarily, the drug is one that has already been deemed safe and effective for use by the appropriate governmental agency or body. For example, drugs for human use listed by the FDA under 21 C.F.R. § § 330.5, 331 through 361, and 440 through 460; drugs for veterinary use listed by the FDA under 21 C.F.R. § § 500 through 589, are all considered acceptable for use in accordance with the present invention.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition. For example, as used herein the term "treating diabetes" will refer in general to maintaining glucose blood levels near normal levels and may include increasing or decreasing blood glucose levels depending on a given situation.

Pharmaceutically acceptable carrier—as used herein, the term includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

Pharmaceutically acceptable salt—as used herein, the term refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Effective or therapeutically effective amount—as used herein refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

Parenteral—as used herein, the term means not through the alimentary canal but by some other route such as intranasal, inhalation, subcutaneous, intramuscular, intraspinal, or intravenous.

Insulin—as used herein, the term means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

Insulin or insulin molecule—the term is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

Insulin analog or analogue—the term as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; or conjugating directly or by a polymeric or non-polymeric linker one or more acyl, polyethylglycine (PEG), or saccharide moiety (moieties); or any combination thereof. As exemplified by the N-linked glycosylated insulin analogues disclosed herein, the term further includes any insulin heterodimer and single-chain analogue that has been modified to have at least one N-linked glycosylation site and in particular, embodiments in which the N-linked glycosylation site is linked to or occupied by an N-glycan. Examples of insulin analogues include but are not limited to the heterodimer and single-chain analogues disclosed in published international application WO20100080606, WO2009/099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., Biochem. J. 305: 981-986 (1995), the disclosures of which are each incorporated herein by reference.

The term further includes single-chain and heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin and which further includes at least one N-linked glycosylation site. In particular aspects, the insulin analogue is a partial agonist that has from 2× to 100× less activity at the insulin receptor as does native insulin. In other aspects, the insulin analogue has enhanced activity at the insulin receptor, for example, the $IGF^{B16B17}$ derivative peptides disclosed in published international application WO2010080607 (which is incorporated herein by reference). These insulin analogues, which have reduced activity at the insulin growth hormone receptor and enhanced activity at the insulin receptor, include both heterodimers and single-chain analogues.

Single-chain insulin or single-chain insulin analog—as used herein, the term encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

Connecting peptide or C-peptide—as used herein, the term refers to the connection moiety "C" of the B-C-A polypeptide sequence of a single chain preproinsulin-like molecule. Specifically, in the natural insulin chain, the C-peptide connects the amino acid at position 30 of the B-chain and the amino acid at position 1 of the A-chain. The term can refer to both the native insulin C-peptide (SEQ ID NO:30), the monkey C-peptide, and any other peptide from 3 to 35 amino acids that connects the B-chain to the A-chain thus is meant to encompass any peptide linking the B-chain peptide to the A-chain peptide in a single-chain insulin analogue (See for example, U.S. Published application Nos. 20090170750 and 20080057004 and WO9634882) and in insulin precursor molecules such as disclosed in WO9516708 and U.S. Pat. No. 7,105,314.

Amino acid modification—as used herein, the term refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

Amino acid substitution—as used herein refers to the replacement of one amino acid residue by a different amino acid residue.

Conservative amino acid substitution—as used herein, the term is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine

DETAILED DESCRIPTION OF THE INVENTION

Figure 1:
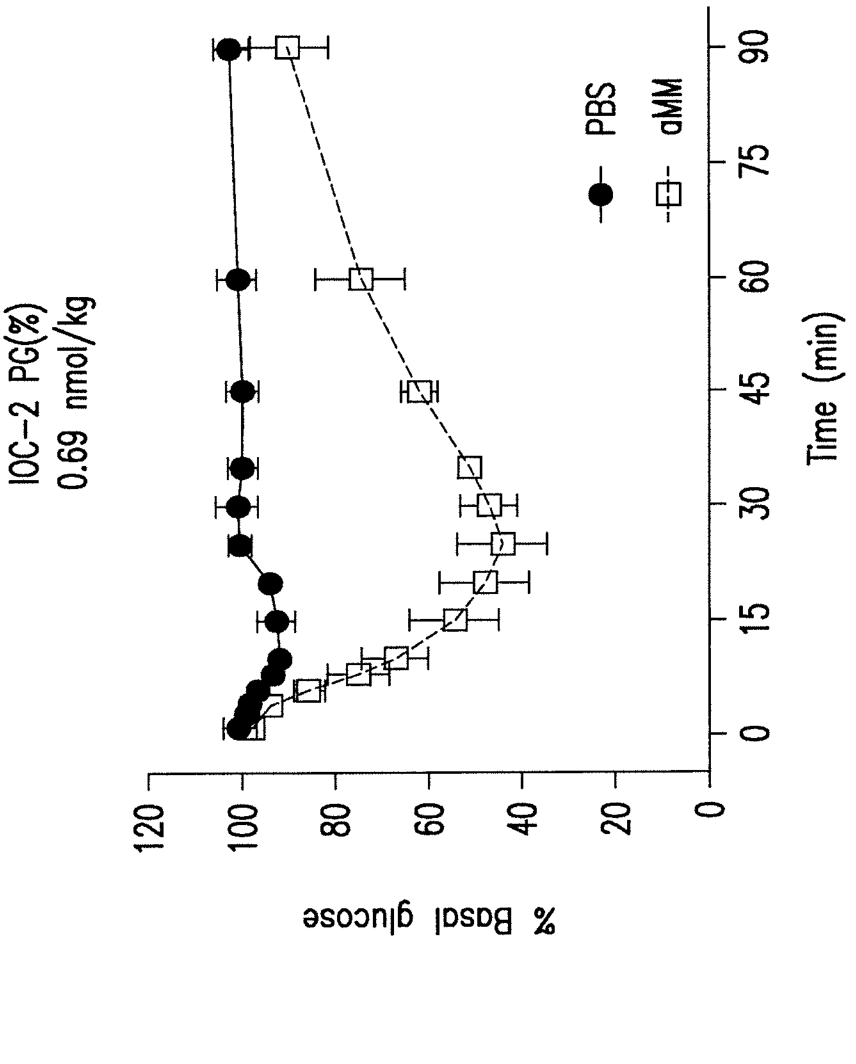
FIG. 1: Plots of serum concentrations of IOC-2 following a 0.69 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

The present invention provides methods for controlling the pharmacokinetic (PK) and/or pharmacodynamic (PD) profiles of insulin in a manner that is responsive to the systemic concentrations of a saccharide such as glucose. The methods are based in part on the discovery disclosed in U.S. Published Application No. 2011/0301083 that when particular insulin conjugates are modified to include high affinity saccharide ligands such as branched trimannose, they could be made to exhibit PK/PD profiles that responded to saccharide concentration changes even in the absence of an exogenous multivalent saccharide-binding molecule such as the lectin Concanavalin A (Con A).

In general, the insulin conjugates of the present invention comprise an insulin or insulin analog molecule covalently attached to at least one branched linker having or consisting of two arms, each arm independently covalently attached to a ligand comprising or consisting of a saccharide wherein at least one ligand of the linker includes the saccharide fucose. In particular embodiments, the ligands are capable of competing with a saccharide (e.g., glucose or alpha-methylmannose) for binding to an endogenous saccharide-binding molecule. In particular embodiments, the ligands are capable of competing with glucose or alpha-methylmannose for binding to Con A. In particular embodiments, the linker is non-polymeric. In particular embodiments, the conjugate may have a polydispersity index of one and a MW of less than about 20,000 Da. In particular embodiments, the conjugate is of formula (I) or (II) as defined and described herein. In particular embodiments, the conjugate is long acting (i.e., exhibits a PK profile that is more sustained than soluble recombinant human insulin (RHI)).

As used herein, the term "insulin conjugate" includes (i) insulin conjugates comprising an insulin molecule have the native or wild-type amino acid sequence of insulin and (ii) insulin conjugates comprising an insulin analog molecule wherein the insulin analog comprises an amino acid sequence that differs from the native or wild-type insulin amino acid sequence by at least one amino acid substitution, deletion, rearrangement, or addition. The term further includes insulin or insulin analog molecules that are conjugated to a polyethylene glycol or fatty acid molecule. The insulin molecule may be human insulin, porcine insulin, bovine insulin, rabbit insulin, sheep insulin, etc. or analog thereof. A number of these insulin molecules are available commercially, e.g., from Sigma-Aldrich (St. Louis, Mo.). A variety of modified forms of insulin are known in the art (e.g., see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids).

Insulin Conjugates

In one aspect, the present invention provides insulin conjugates that comprise an insulin or insulin analog molecule covalently attached to at least one branched linker having two arms (bi-dentate linker) wherein each arm of the bi-dentate linker is independently covalently linked to a ligand comprising or consisting of a saccharide and wherein the first ligand of the bi-dentate linker comprises or consists of a first saccharide, which is fucose. The second ligand of the bi-dentate linker comprises or consists of a second saccharide, which may be fucose, mannose, glucosamine, or glucose. In particular aspects, the second ligand comprises or consists of a bisaccharide, trisaccharide, tetrasaccharide, or branched trisaccharide. In particular aspects, the second ligand comprises a bimannose, trimannose, tetramannose, or branched trimannose.

In particular aspects, the insulin or insulin analog molecule is conjugated to one, two, three, or four bi-dentate linkers wherein each arm of each bi-dentate linker is independently covalently linked to a ligand comprising or consisting of a saccharide and wherein the first ligand of the bi-dentate linker comprises or consists of a first saccharide, which is fucose, and the second ligand of the bi-dentate linker comprises or consists of a second saccharide, which may be fucose, mannose, or glucose. In particular aspects, the second ligand comprises or consists of a bisaccharide, trisaccharide, tetrasaccharide, or branched trisaccharide. In particular aspects, the second ligand comprises or consists of a bimannose, trimannose, tetramannose, or branched trimannose.

In particular aspects, the insulin or insulin analog molecule is conjugated to one, two, three, or four bi-dentate linkers wherein each arm of each bi-dentate linker is independently covalently linked to a ligand comprising or consisting of a saccharide and wherein for at least one of the bi-dentate linkers the first ligand of the bi-dentate linker comprises or consists of a first saccharide, which is fucose, and the second ligand of the bi-dentate linker comprises or consists of a second saccharide, which may be fucose, mannose, or glucose. In particular aspects, the second ligand comprises or consists of a bisaccharide, trisaccharide, tetrasaccharide, or branched trisaccharide. In particular aspects, the second ligand comprises or consists of a bimannose, trimannose, tetramannose, or branched trimannose. For the second, third, and fourth bi-dentate linkers, the first and second saccharides may independently be fucose, mannose, glucose, bisaccharide, trisaccharide, tetrasaccharide, branched trisaccharide, bimannose, trimannose, tetramannose, or branched trimannose.

In particular aspects, the insulin or insulin analog molecule is conjugated to (i) one bi-dentate linker wherein each arm of each bi-dentate linker is independently covalently linked to a ligand comprising or consisting of a saccharide wherein the first ligand of the bi-dentate linker comprises or consists of a first saccharide, which is fucose, and the second ligand of the bi-dentate linker comprises or consists of a second saccharide, which may be fucose, mannose, glucose, bisaccharide, trisaccharide, tetrasaccharide, branched trisaccharide, bimannose, trimannose, tetramannose, or branched trimannose.

In particular aspects, the insulin or insulin analog molecule of the insulin conjugate disclosed herein is further covalently attached to at least one linear linker having one ligand comprising or consisting of a saccharide, which may be fucose, mannose, glucosamine, or glucose. In particular aspects, the ligand comprises or consisting of a bisaccharide, trisaccharide, tetrasaccharide, or branched trisaccharide. In particular aspects, the ligand comprises or consisting of a bimannose, trimannose, tetramannose, or branched trimannose.

In particular aspects, the insulin or insulin analog molecule conjugate disclosed herein is further covalently attached to at least one tri-dentate linker wherein each arm of the tri-dentate linker is independently covalently linked to a ligand comprising or consisting of a saccharide, which may be fucose, mannose, glucosamine, or glucose. In particular aspects, the ligand comprises or consisting of a bisaccharide, trisaccharide, tetrasaccharide, or branched trisaccharide. In particular aspects, the ligand comprises or consisting of a bimannose, trimannose, tetramannose, or branched trimannose.

When the insulin conjugate is administered to a mammal at least one pharmacokinetic or pharmacodynamic property of the conjugate is sensitive to the serum concentration of a saccharide. In particular embodiments, the PK and/or PD properties of the conjugate are sensitive to the serum concentration of an endogenous saccharide such as glucose. In particular embodiments, the PK and/or PD properties of the conjugate are sensitive to the serum concentration of an exogenous saccharide, e.g., without limitation, mannose, L-fucose, N-acetyl glucosamine and/or alpha-methyl mannose.

PK and PD Properties

In various embodiments, the pharmacokinetic and/or pharmacodynamic behavior of the insulin conjugate may be modified by variations in the serum concentration of a saccharide. For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In particular embodiments, the serum concentration curve of a conjugate is substantially different when administered to the mammal under fasted and hyperglycemic conditions. As used herein, the term "substantially different" means that the two curves are statistically different as determined by a student t-test ($p<0.05$). As used herein, the term "fasted conditions" means that the serum concentration curve was obtained by combining data from five or more fasted non-diabetic individuals. In particular embodiments, a fasted non-diabetic individual is a randomly selected 18-30 year old human who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose $C_{max}$ at least 100 mg/dL above the mean glucose concentration observed under fasted conditions) were induced by concurrent administration of conjugate and glucose. Concurrent administration of conjugate and glucose simply requires that the glucose $C_{max}$ occur during the period when the conjugate is present at a detectable level in the serum. For example, a glucose injection (or ingestion) could be timed to occur shortly before, at the same time or shortly after the conjugate is administered. In particular embodiments, the conjugate and glucose are administered by different routes or at different locations. For example, in particular embodiments, the conjugate is administered subcutaneously while glucose is administered orally or intravenously.

In particular embodiments, the serum $C_{max}$ of the conjugate is higher under hyperglycemic conditions as compared to fasted conditions. Additionally or alternatively, in particular embodiments, the serum area under the curve (AUC) of the conjugate is higher under hyperglycemic conditions as compared to fasted conditions. In various embodiments, the serum elimination rate of the conjugate is slower under hyperglycemic conditions as compared to fasted conditions. In particular embodiments, the serum concentration curve of the conjugates can be fit using a two-compartment bi-exponential model with one short and one long half-life. The long half-life appears to be particularly sensitive to glucose concentration. Thus, in particular embodiments, the long half-life is longer under hyperglycemic conditions as compared to fasted conditions. In particular embodiments, the fasted conditions involve a glucose $C_{max}$ of less than 100 mg/dL (e.g., 80 mg/dL, 70 mg/dL, 60 mg/dL, 50 mg/dL, etc.). In particular embodiments, the hyperglycemic conditions involve a glucose $C_{max}$ in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/dl). Glucose concentrations below 60 mg/dL are considered hypoglycemic. Glucose concentrations above 200 mg/dL are considered hyperglycemic. In particular embodiments, the PK properties of the conjugate may be tested using a glucose clamp method (see Examples) and the serum concentration curve of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum $T_{max}$, serum $C_{max}$, mean serum residence time (MRT), mean serum absorption time (MAT) and/or serum half-life may be substantially different at the two glucose concentrations. As discussed below, in particular embodiments, 100 mg/dL and 300 mg/dL may be used as comparative glucose concentrations. It is to be understood however that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc.

Thus, in particular embodiments, the $C_{max}$ of the conjugate is higher when administered to the mammal at the higher of the two glucose concentrations (e.g., 300 vs. 100 mg/dL glucose). In particular embodiments, the $C_{max}$ of the conjugate is at least 50% (e.g., at least 100%, at least 200% or at least 400%) higher when administered to the mammal at the higher of the two glucose concentrations (e.g., 300 vs. 100 mg/dL glucose).

In particular embodiments, the AUC of the conjugate is higher when administered to the mammal at the higher of the two glucose concentrations (e.g., 300 vs. 100 mg/dL glucose). In particular embodiments, the AUC of the conjugate is at least 50% (e.g., at least e.g., at least 100%, at least 200% or at least 400%) higher when administered to the mammal at the higher of the two glucose concentrations (e.g., 300 vs. 100 mg/dL glucose).

In particular embodiments, the serum elimination rate of the conjugate is slower when administered to the mammal at the higher of the two glucose concentrations (e.g., 300 vs. 100 mg/dL glucose). In particular embodiments, the serum elimination rate of the conjugate is at least 25% (e.g., at least 50%, at least 100%, at least 200%, or at least 400%) faster when administered to the mammal at the lower of the two glucose concentrations (e.g., 100 vs. 300 mg/dL glucose).

In particular embodiments the serum concentration curve of conjugates may be fit using a two-compartment bi-exponential model with one short and one long half-life. The long half-life appears to be particularly sensitive to glucose concentration. Thus, in particular embodiments, the long half-life is longer when administered to the mammal at the higher of the two glucose concentrations (e.g., 300 vs. 100 mg/dL glucose). In particular embodiments, the long half-life is at least 50% (e.g., at least 100%, at least 200% or at least 400%) longer when administered to the mammal at the higher of the two glucose concentrations (e.g., 300 vs. 100 mg/dL glucose).

In particular embodiments, the present disclosure provides a method in which the serum concentration curve of a conjugate is obtained at two different glucose concentrations (e.g., 300 vs. 100 mg/dL glucose); the two curves are fit using a two-compartment bi-exponential model with one short and one long half-life; and the long half-lives obtained under the two glucose concentrations are compared. In particular embodiments, this method may be used as an assay for testing or comparing the glucose sensitivity of one or more conjugates.

In particular embodiments, the present disclosure provides a method in which the serum concentration curves of a conjugated drug (e.g., an insulin conjugate of the present disclosure) and an unconjugated version of the drug (e.g., RHI) are obtained under the same conditions (e.g., fasted conditions); the two curves are fit using a two-compartment bi-exponential model with one short and one long half-life; and the long half-lives obtained for the conjugated and unconjugated drug are compared. In particular embodiments, this method may be used as an assay for identifying conjugates that are cleared more rapidly than the unconjugated drug.

In particular embodiments, the serum concentration curve of a conjugate is substantially the same as the serum concentration curve of an unconjugated version of the drug when administered to the mammal under hyperglycemic conditions. As used herein, the term "substantially the same" means that there is no statistical difference between the two curves as determined by a student t-test ($p>0.05$). In particular embodiments, the serum concentration curve of the conjugate is substantially different from the serum concentration curve of an unconjugated version of the drug when administered under fasted conditions. In particular embodiments, the serum concentration curve of the conjugate is substantially the same as the serum concentration curve of an unconjugated version of the drug when administered under hyperglycemic conditions and substantially different when administered under fasted conditions.

In particular embodiments, the hyperglycemic conditions involve a glucose $C_{max}$ in excess of 200 mg/dL (e.g., 300 mg/dL, 400 mg/dL, 500 mg/dL, 600 mg/dL, etc.). In particular embodiments, the fasted conditions involve a glucose $C_{max}$ of less than 100 mg/dL (e.g., 80 mg/dL, 70 mg/dL, 60 mg/dL, 50 mg/dL, etc.). It will be appreciated that any of the aforementioned PK parameters such as serum $T_{max}$, serum $C_{max}$, AUC, mean serum residence time (MRT), mean serum absorption time (MAT) and/or serum half-life could be compared.

From a pharmacodynamic (PD) perspective, the bioactivity of the conjugate may increase when the glucose concentration increases or when the glucose concentration crosses a threshold, e.g., is higher than normal glucose levels. In particular embodiments, the bioactivity of a conjugate is lower when administered under fasted conditions as compared to hyperglycemic conditions. In particular embodiments, the fasted conditions involve a glucose $C_{max}$ of less than 100 mg/dL (e.g., 80 mg/dL, 70 mg/dL, 60 mg/dL, 50 mg/dL, etc.). In particular embodiments, the hyperglycemic conditions involve a glucose $C_{max}$ in excess of 200 mg/dL (e.g., 300 mg/dL, 400 mg/dL, 500 mg/dL, 600 mg/dL, etc.).

In particular embodiments, the PD properties of the conjugate may be tested by measuring the glucose infusion rate (GIR) required to maintain a steady glucose concentration. According to such embodiments, the bioactivity of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in particular embodiments, the bioactivity of the conjugate is higher when administered to the mammal at the higher of the two glucose concentrations (e.g., 300 vs. 100 mg/dL glucose). In particular embodiments, the bioactivity of the conjugate is at least 25% (e.g., at least 50% or at least 100%) higher when administered to the mammal at the higher of the two glucose concentrations (e.g., 300 vs. 100 mg/dL glucose).

In particular embodiments, the conjugate includes an insulin molecule as the drug. According to such embodiments, the PD behavior for insulin can be observed by comparing the time to reach minimum blood glucose concentration ($T_{nadir}$), the duration over which the blood glucose level remains below a particular percentage of the initial value (e.g., 70% of initial value or $T_{70\%\ BGL}$), etc.

In general, it will be appreciated that any of the PK and PD characteristics discussed in this section can be determined according to any of a variety of published pharmacokinetic and pharmacodynamic methods (e.g., see Baudys et al., *Bioconjugate Chem.* 9:176-183, 1998 for methods suitable for subcutaneous delivery). It is also to be understood that the PK and/or PD properties may be measured in any mammal (e.g., a human, a rat, a cat, a minipig, a dog, etc.). In particular embodiments, PK and/or PD properties are measured in a human. In particular embodiments, PK and/or PD properties are measured in a rat. In particular embodiments, PK and/or PD properties are measured in a minipig. In particular embodiments, PK and/or PD properties are measured in a dog.

It will also be appreciated that while the foregoing was described in the context of glucose-responsive conjugates, the same properties and assays apply to conjugates that are responsive to other saccharides including exogenous saccharides, e.g., mannose, L-fucose, N-acetyl glucosamine, alpha-methyl mannose, etc. As discussed in more detail below and in the Examples, instead of comparing PK and/or PD properties under fasted and hyperglycemic conditions, the PK and/or PD properties may be compared under fasted conditions with and without administration of the exogenous saccharide. It is to be understood that conjugates can be designed that respond to different $C_{max}$ values of a given exogenous saccharide.

Ligand(s)

In general, the insulin conjugates comprise an insulin or insulin analog molecule covalently attached to at least one bi-dentate linker having two ligands wherein at least one of the ligands (the first ligand) comprises or consists of a saccharide, which is fucose, and the other ligand (the second ligand) comprises or consists of one or more saccharides. In particular embodiments, the insulin conjugates may further include one or more linear linkers, each comprising a single ligand, which comprises or consist of one or more saccharides. In particular embodiments, the insulin conjugates may further include one or more branched linkers that each includes at least two, three, four, five, or more ligands, where each ligand independently comprises or consists of one or more saccharides. When more than one ligand is present the ligands may have the same or different chemical structures.

In particular embodiments, the ligands are capable of competing with a saccharide (e.g., glucose, alpha-methylmannose, or mannose) for binding to an endogenous saccharide-binding molecule (e.g., without limitation surfactant proteins A and D or members of the selectin family). In particular embodiments, the ligands are capable of competing with a saccharide (e.g., glucose, alpha-methylmannose, or mannose) for binding to cell-surface sugar receptor (e.g., without limitation macrophage mannose receptor, glucose transporter ligands, endothelial cell sugar receptors, or hepatocyte sugar receptors). In particular embodiments, the ligands are capable of competing with glucose for binding to an endogenous glucose-binding molecule (e.g., without limitation surfactant proteins A and D or members of the selectin family). In particular embodiments, the ligands are capable of competing with glucose or alpha-mewthylmannose for binding to the human macrophage mannose receptor 1 (MRC1). In particular embodiments, the ligands are capable of competing with a saccharide for binding to a non-human lectin (e.g., Con A). In particular embodiments, the ligands are capable of competing with glucose, alpha-methylmannose, or mannose for binding to a non-human lectin (e.g., Con A). Exemplary glucose-binding lectins include calnexin, calreticulin, N-acetylglucosamine receptor, selectin, asialoglycoprotein receptor, collectin (mannose-binding lectin), mannose receptor, aggrecan, versican, pisum sativum agglutinin (PSA), vicia faba lectin, lens culinaris lectin, soybean lectin, peanut lectin, lathyrus ochrus lectin, sainfoin lectin, sophora japonica lectin, bowringia milbraedii lectin, concanavalin A (Con A), and pokeweed mitogen.

In particular embodiments, the ligand(s) other than the first ligand comprising or consisting of the saccharide fucose may have the same chemical structure as glucose or may be a chemically related species of glucose, e.g., glucosamine. In various embodiments, it may be advantageous for the ligand(s) to have a different chemical structure from glucose, e.g., in order to fine tune the glucose response of the conjugate. For example, in particular embodiments, one might use a ligand that includes glucose, mannose, L-fucose or derivatives of these (e.g., alpha-L-fucopyranoside, mannosamine, beta-linked N-acetyl mannosamine, methylglucose, methylmannose, ethylglucose, ethylmannose, propylglucose, propylmannose, etc.) and/or higher order combinations of these (e.g., a bimannose, linear and/or branched trimannose, etc.).

In particular embodiments, the ligand(s) include(s) a monosaccharide. In particular embodiments, the ligand(s) include(s) a disaccharide. In particular embodiments, the ligand(s) include(s) a trisaccharide. In some embodiments, the ligand(s) comprise a saccharide and one or more amine groups. In some embodiments, the ligand(s) comprise a saccharide and ethyl group. In particular embodiments, the saccharide and amine group are separated by a $C_1$-$C_6$ alkyl group, e.g., a $C_1$-$C_3$ alkyl group. In some embodiments, the ligand is aminoethylglucose (AEG). In some embodiments, the ligand is aminoethylmannose (AEM). In some embodiments, the ligand is aminoethylbimannose (AEBM). In some embodiments, the ligand is aminoethyltrimannose (AETM). In some embodiments, the ligand is β-aminoethyl-N-acetylglucosamine (AEGA). In some embodiments, the ligand is aminoethylfucose (AEF). In particular embodiments, the saccharide is of the "D" configuration and in other embodiments, the saccharide is of the "L" configuration. Below are the structures of exemplary saccharides having an amine group separated from the saccharide by a $C_2$ ethyl group wherein R may be hydrogen or a carbonyl group of the linker. Other exemplary ligands will be recognized by those skilled in the art.

AEG

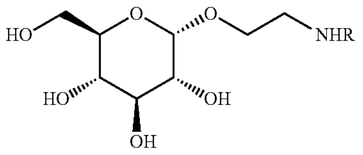

AEM

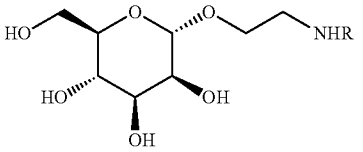

AEBM

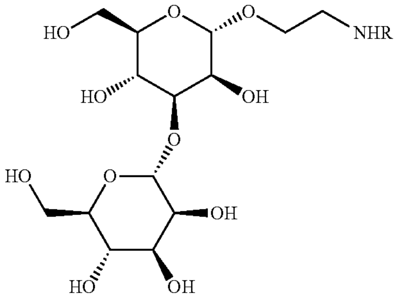

AETM

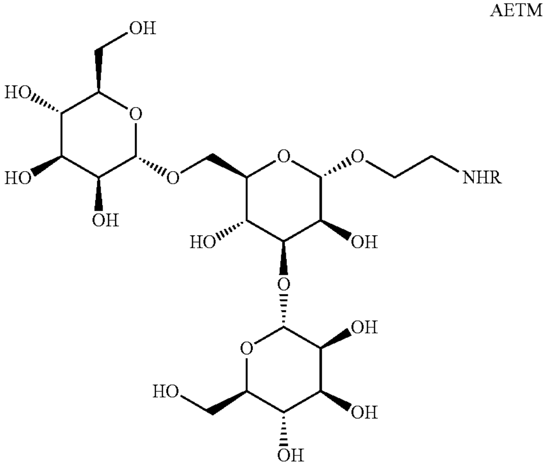

AEGA

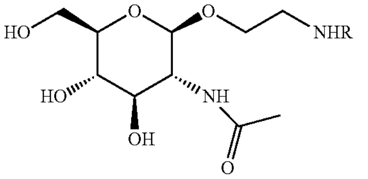

AEF

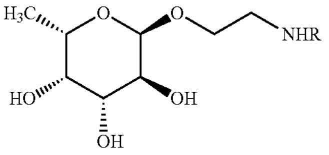

-continued

AEBM'

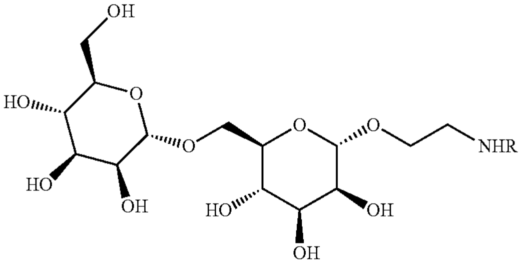

Insulin

As used herein, the term "insulin" or "insulin molecule" encompasses all salt and non-salt forms of the insulin molecule. It will be appreciated that the salt form may be anionic or cationic depending on the insulin molecule. By "insulin" or "an insulin molecule" we intend to encompass both wild-type insulin and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, *Pediatr. Emerg. Care.* 23:903-905, 2007 and Gerich, Am. J. Med. 113:308-16, 2002 and references cited therein). Modified forms of insulin (insulin analogs) may be chemically modified (e.g., by addition of a chemical moiety such as a PEG group or a fatty acyl chain as described below) and/or mutated (i.e., by addition, deletion or substitution of one or more amino acids).

In particular embodiments, an insulin molecule of the present disclosure will differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7- 8, 8-9, 9, 8, 7, 6, 5, 4, 3, 2 or 1) amino acid substitutions, additions and/or deletions. In particular embodiments, an insulin molecule of the present disclosure will differ from a wild-type insulin by amino acid substitutions only. In particular embodiments, an insulin molecule of the present disclosure will differ from a wild-type insulin by amino acid additions only. In particular embodiments, an insulin molecule of the present disclosure will differ from wild-type insulin by both amino acid substitutions and additions. In particular embodiments, an insulin molecule of the present disclosure will differ from a wild-type insulin by both amino acid substitutions and deletions.

In particular embodiments, amino acid substitutions may be made on the basis of similarity in polarity, charge, solubility, hydrophobicity, hydrophilicity, and/or the amphipathic nature of the residues involved. In particular embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In particular embodiments, the hydrophobic index of amino acids may be considered in choosing suitable mutations. The importance of the hydrophobic amino acid index in conferring interactive biological function on a polypeptide is generally understood in the art. Alternatively, the substitution of like amino acids can be made effectively on the basis of hydrophilicity. The importance of hydrophilicity in conferring interactive biological function of a polypeptide is generally understood in the art. The use of the hydrophobic index or hydrophilicity in designing polypeptides is further discussed in U.S. Pat. No. 5,691,198.

The wild-type sequence of human insulin (A-chain and B-chain) is shown below.

```
A-Chain (SEQ ID NO: 1):
GIVEQCCTSICSLYQLENYCN

B-Chain (SEQ ID NO: 2):
FVNQHLCGSHLVEALYLVCGERGFFYTPKT
```

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin) (SEQ ID NO:3). This modification blocks the formation of insulin multimers. Insulin aspart (NOVOLOG®) is another rapid acting insulin mutant in which proline at position B28 has been substituted with aspartic acid ($Asp^{B28}$-human insulin) (SEQ ID NO:4). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin) (SEQ ID NO:5).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine (SEQ ID NO:6), and two arginine residues have been added to the C-terminus of the B-peptide (SEQ ID NO:7). The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 and B32 are Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, an insulin molecule of the present disclosure is truncated. For example, in particular embodiments, a B-peptide sequence of an insulin polypeptide of the present disclosure is missing B1, B2, B3, B26, B27, B28, B29 and/or B30. In particular embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des(B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In particular embodiments, an insulin molecule does not include any additional amino acid residues at positions A0, A21, B0 or B31.

In particular embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$, or $Asn^{B3}$, or any combination of those residues, may be replaced by aspartic acid or glutamic acid. $Gln^{A15}$ or $Gln^{B4}$, or both, may be replaced by aspartic acid or glutamic acid. In particular embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid ($His^{B10} \rightarrow Asp^{B10}$); replacement of the phenylalanine residue at position B1 with aspartic acid ($Phe^{B1} \rightarrow Asp^{B1}$); replacement of the threonine residue at position B30 with alanine ($Thr^{B30} \rightarrow Ala^{B30}$); replacement of the tyrosine residue at position B26 with alanine ($Tyr^{B26}$-$Ala^{B26}$); and replacement of the serine residue at position B9 with aspartic acid ($Ser^{B9} \rightarrow Asp^{B9}$).

In various embodiments, an insulin molecule of the present disclosure has a protracted profile of action. Thus, in particular embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type human insulin or may be acylated on lysine residue that has been introduced into the wild-type human insulin sequence. In particular embodiments, an insulin molecule may be acylated at position B1. In particular embodiments, an insulin molecule may be acylated at position B29. In particular embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which $Thr^{B30}$ has been deleted, and a C14 fatty acid chain (myristic acid) has been attached to $Lys^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

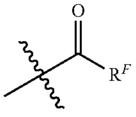

wherein $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In particular embodiments, the insulin polypeptide is conjugated to the moiety at the A1 position. In particular embodiments, the insulin polypeptide is conjugated to the moiety at the B1 position. In particular embodiments, the insulin polypeptide is conjugated to the moiety at the epsilon-amino group of Lys at position B29. In particular embodiments, position B28 of the insulin molecule is Lys and the epsilon-amino group of $Lys^{B28}$ is conjugated to the fatty acid moiety. In particular embodiments, position B3 of the insulin molecule is Lys and the epsilon-amino group of $Lys^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In particular embodiments, the fatty acid is myristic acid (C14), pentadecanoic acid (C15), palmitic acid (C16), heptadecanoic acid (C17), stearic acid (C18), nonadecanoic acid (C19), or arachidic acid (C20).

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain). In particular embodiments, an insulin molecule is mutated such that the site of mutation is used as a conjugation point, and conjugation at the mutated site reduces binding to the insulin receptor (e.g., $Lys^{A3}$). In particular other embodiments, conjugation at an existing wild-type amino acid or terminus reduces binding to the insulin receptor (e.g., $Gly^{A1}$). In some embodiments, an insulin molecule is conjugated at position A4, A5, A8, A9, or B30. In particular embodiments, the conjugation at position A4, A5, A8, A9, or B30 takes place via a wild-type amino acid side chain (e.g., $Glu^{A4}$). In particular other embodiments, an insulin molecule is mutated at position A4, A5, A8, A9, or B30 to provide a site for conjugation (e.g., $Lys^{A4}$, $Lys^{A5}$, $Lys^{A8}$, $Lys^{A9}$, or $Lys^{B30}$).

Methods for conjugating insulin molecules are described below. In particular embodiments an insulin molecule is conjugated to a linker via the A1 amino acid residue. In particular embodiments the A1 amino acid residue is glycine. It is to be understood however, that the present disclosure is not limited to N-terminal conjugation and that in particular embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In particular embodiments, an insulin molecule is conjugated to the linker via the B1 amino acid residue. In particular embodiments the B1 amino acid residue is phenylalanine. It is to be understood however, that the present disclosure is not limited to N-terminal conjugation and that in particular embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in particular embodiments an insulin molecule may be conjugated via the B29 lysine residue. In the case of insulin glulisine, conjugation to the at least one ligand via the B3 lysine residue may be employed. It will be appreciated that different conjugation positions on the B-chain may lead to different reductions in insulin activity.

In particular embodiments, the ligands are conjugated to more than one conjugation point on the insulin molecule. For example, an insulin molecule can be conjugated at both the A1 N-terminus and the B29 lysine. In some embodiments, amide conjugation takes place in carbonate buffer to conjugate at the B29 and A1 positions, but not at the B1 position. In other embodiments, an insulin molecule can be conjugated at the A1 N-terminus, the B1 N-terminus, and the B29 lysine. In yet other embodiments, protecting groups are used such that conjugation takes place at the B1 and B29 or B1 and A1 positions. It will be appreciated that any combination of conjugation points on an insulin molecule may be employed. In some embodiments, at least one of the conjugation points is a mutated lysine residue, e.g., $Lys^{A3}$.

Exemplary Insulin Conjugates

In various embodiments, the insulin conjugate of the present disclosure comprises an insulin or insulin analog molecule conjugated to at least one bi-dentate linker wherein at least one arm of the bi-dentate linker is attached to the ligand aminoethylfucose (AEF). The other arm of the bi-dentate linker may be conjugated to the ligand AEF and/or one or more ligands that are independently selected from the group consisting of aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF). In particular embodiments, the insulin molecule is conjugated via the A1 amino acid residue. In particular embodiments, the insulin molecule is conjugated via the B1 amino acid residue. In particular embodiments, the insulin molecule is conjugated via the epsilon-amino group of $Lys^{B29}$. In particular embodiments, the insulin molecule is an analog that comprises a lysine at position B28 ($Lys^{B28}$) and the insulin molecule is conjugated via the epsilon-amino group of $Lys^{B28}$, for example, insulin lispro conjugated via the epsilon-amino group of $Lys^{B28}$. In particular embodiments, the insulin molecule is an analog that comprises a lysine at position B3 ($Lys^{B3}$) and the insulin molecule is conjugated via the epsilon-amino group of $Lys^{B3}$, for example, insulin glulisine conjugated via the epsilon-amino group of $Lys^{B3}$.

In particular embodiments, the insulin or insulin molecule of the above insulin conjugate may be conjugated to one or more additional linkers attached to one or more ligands, each ligand independently selected from aminoethylglucose (AEG), aminoethylmannose (AEM), aminoethylbimannose (AEBM) ligands, aminoethyltrimannose (AETM) ligands, β-aminoethyl-N-acetylglucosamine (AEGA), and aminoethylfucose (AEF). The additional linkers may be linear, bi-dentate, tri-dentate, quadri-dentate, etc. wherein each arm of the linker comprises a ligand which may independently be selected from aminoethylglucose (AEG), aminoethylmannose (AEM), aminoethylbimannose (AEBM) ligands, aminoethyltrimannose (AETM) ligands, β-aminoethyl-N-acetylglucosamine (AEGA), and aminoethylfucose (AEF).

Thus, in particular embodiments, the insulin conjugate may comprise or consist of a bi-dentate linker wherein at least one arm of the bi-dentate linker is attached to the ligand aminoethylfucose (AEF) conjugated to the amino group at position A1 of the insulin or insulin analog; or the amino group at position B1 of the insulin or insulin analog; or the amino group at position B3 of the insulin analog; or the amino group at position B28 of the insulin analog; or the amino group at position B29 of the insulin or insulin analog.

In particular embodiments, the insulin conjugate may comprise or consist of two bi-dentate linkers wherein a first bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, is conjugated to the amino group at position A1 and a second bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1, B3, B28, or B29.

In particular embodiments, the insulin conjugate may comprise or consist of two bi-dentate linkers wherein a first bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, is conjugated to the amino group at position B1 and a second bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position A1, B3, B28, or B29.

In particular embodiments, the insulin conjugate may comprise or consist of two bi-dentate linkers wherein a first bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, is conjugated to the amino group at position B3 and a second bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1, A1, B28, or B29.

In particular embodiments, the insulin conjugate may comprise or consist of two bi-dentate linkers wherein a first bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, is conjugated to the amino group at position B28 and a second bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1, B3, A1, or B29.

In particular embodiments, the insulin conjugate may comprise or consist of two bi-dentate linkers wherein a first bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, is conjugated to the amino group at position B29 and a second bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1, B3, B28, or A1.

In particular embodiments, the insulin conjugate may comprise or consist of three bi-dentate linkers wherein a first bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, is conjugated to the amino group at position A1; a second bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1; and, a third bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B3, B28, or B29.

In particular embodiments, the insulin conjugate may comprise or consist of four bi-dentate linkers wherein a first bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, is conjugated to the amino group at position A1; a second bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1; a third bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B3; and a fourth bi-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B28 or B29.

In particular embodiments, the insulin conjugate may comprise or consist of (a) a bi-dentate linker wherein at least one arm of the bi-dentate linker is attached to the ligand aminoethylfucose (AEF) conjugated to the amino group at position A1; or the amino group at position B1; or the amino group at position B3; or the amino group at position B28; or the amino group at position B29 and (b) a linear or tri-dentate linker attached to one or more ligands, each ligand independently selected from aminoethylglucose (AEG), aminoethylmannose (AEM), aminoethylbimannose (AEBM), aminoethyltrimannose (AETM), 3-aminoethyl-N-acetylglucosamine (AEGA), and aminoethylfucose (AEF) conjugated to the amino group at position A1; or the amino group at position B1; or the amino group at position B3; or the amino group at position B28; or the amino group at position B29, whichever position is not occupied by the bi-dentate linker.

In particular embodiments, the insulin conjugate may comprise or consist of (a) a bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, conjugated to the amino group at position A1 and (b) a linear or tri-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) conjugated to the amino group at position B1, B3, B28, or B29.

In particular embodiments, the insulin conjugate may comprise or consist of (a) a bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, conjugated to the amino group at position B1 and (b) a linear or tri-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) conjugated to the amino group at position A1, B3, B28, or B29.

In particular embodiments, the insulin conjugate may comprise or consist of (a) a bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, conjugated to the amino group at position B3 and (b) a linear or tri-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) conjugated to the amino group at position B1, A1, B28, or B29.

In particular embodiments, the insulin conjugate may comprise or consist of (a) a bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), 3-aminoethyl-N-acetylglucosamine (AEGA), and aminoethylfucose (AEF) attached to the other arm of the bi-dentate linker, conjugated to the amino group at position B28 and (b) a linear or tri-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) conjugated to the amino group at position B1, B3, A1, or B29.

In particular embodiments, the insulin conjugate may comprise or consist of (a) a bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker, conjugated to the amino group at position B29 and (b) a linear or tri-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) conjugated to the amino group at position B1, B3, B28, or A1.

In particular embodiments, the insulin conjugate may comprise or consist of (a) a bi-dentate linker, which has the ligand aminoethylfucose (AEF) attached to one arm of the first bi-dentate linker and a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) attached to the other arm of the bi-dentate linker; (b) a first linear or tri-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF); and (c) a second linear or tri-dentate linker attached to one or more ligands, each ligand independently selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF), wherein each linker is each conjugated to a amino group at position A1, B1, B3, B28, or B29 with the proviso that each occupies a separate position such that three sites in total are occupied.

Insulin Conjugates

This section describes some exemplary insulin or insulin analog conjugates.

In particular embodiments, provided are insulin and insulin analog conjugates comprising at least one fucose wherein the conjugate is characterized as having a ratio of $EC_{50}$ or IP as determined by a functional insulin receptor phosphorylation assay verses the $IC_{50}$ or IP as determined by a competition binding assay at the macrophage mannose receptor is about 0.5:1 to about 1:100; about 1:1 to about 1:50; about 1:1 to about 1:20; or about 1:1 to about 1:10. In further aspects, the above conjugate comprises an insulin or insulin analog molecule covalently attached to at least one branched linker having a first arm and second arm, wherein the first arm is linked to a first ligand that includes a first saccharide and the second arm is linked to a second ligand that includes a second saccharide and wherein the first saccharide is fucose and wherein the conjugate is characterized as having a ratio of $EC_{50}$ or IP as determined by a functional insulin receptor phosphorylation assay verses the $IC_{50}$ or IP as determined by a competition binding assay at the macrophage mannose receptor is about 0.5:1 to about 1:100; about 1:1 to about 1:50; about 1:1 to about 1:20; or about 1:1 to about 1:10. In particular aspects, the second saccharide is a fucose, mannose, glucosamine, glucose, bisaccharide, trisaccharide, tetrasaccharide, branched trisaccharide, bimannose, trimannose, tetramannose, or branched trimannose.

The term “IP” refers to the inflection point, which is a point on a curve at which the curvature or concavity changes sign from plus to minus or from minus to plus. In general, IP is usually equivalent to the $EC_{50}$ or $IC_{50}$.

In particular aspects, the $IC_{50}$ or IP as determined by a competition binding assay at the macrophage mannose receptor may be less than about 100 nM and greater than about 0.5 nM. In particular aspects, the $IC_{50}$ or IP is less than about 50 nM and greater than about 1 nM; less than about 25 nM and greater than about 1 nM; or less than about 20 nM and greater than about 1 nM. In particular aspects, the $IC_{50}$ or IP as determined by a functional insulin receptor phosphorylation assay may be less than about 100 nM and greater than about 0.5 nM. In particular aspects, the $IC_{50}$ or IP is less than about 50 nM and greater than about 1 nM; less than about 25 nM and greater than about 1 nM; or less than about 20 nM and greater than about 1 nM.

In various embodiments, the conjugates may have the general formula (I):

I

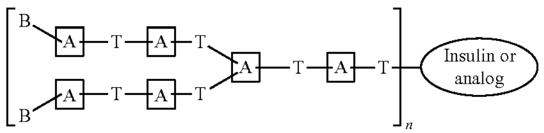

wherein:

each occurrence of

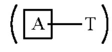

represents a potential repeat within a branch of the conjugate;

each occurrence of A is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—B is -T-$L^B$-X;

each occurrence of X is independently a ligand;

each occurrence of $L^B$ is independently a covalent bond or a group derived from the covalent conjugation of a T with an X; and, wherein n is 1, 2, or 3, with the proviso that the insulin is conjugated to at least one linker in which one of the ligands is Fucose.

In particular aspects, the aforementioned conjugate may be characterized as having a ratio of $EC_{50}$ or IP as determined by a functional insulin receptor phosphorylation assay verses the $IC_{50}$ or IP as determined by a competition binding assay at the macrophage mannose receptor is about 0.5:1 to about 1:100; about 1:1 to about 1:50; about 1:1 to about 1:20; or about 1:1 to about 1:10.

In particular embodiments, the insulin or insulin analog conjugate may have the general formula (II):

II

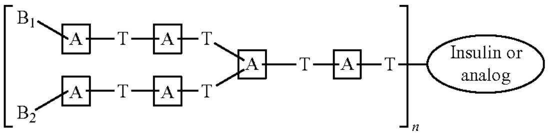

wherein:

each occurrence of

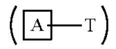

represents a potential repeat within a branch of the conjugate;

each occurrence of A is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—$B_1$ is -T-$L^{B_1}$-Fucose wherein $L^{B_1}$ is a covalent bond or a group derived from the covalent conjugation of a T with an X;

—$B_2$ is -T-$L^{B_2}$-X wherein X is a ligand comprising a saccharide, which may be fucose, mannose, or glucose; and $L^{B_2}$ is a covalent bond or a group derived from the covalent conjugation of a T with an X; and, wherein n is 1, 2, or 3.

In particular aspects, the aforementioned conjugate may be characterized as having a ratio of $EC_{50}$ or IP as determined by a functional insulin receptor phosphorylation assay verses the $IC_{50}$ or IP as determined by a competition binding assay at the macrophage mannose receptor is about 0.5:1 to about 1:100; about 1:1 to about 1:50; about 1:1 to about 1:20; or about 1:1 to about 1:10.

Description of Exemplary Groups

🄰 (node)

In particular embodiments, each occurrence of 🄰 is independently an optionally substituted group selected from the group consisting of acyl, aliphatic, heteroaliphatic, aryl, heteroaryl, and heterocyclic. In some embodiments, each occurrence of 🄰 is the same. In some embodiments, the central 🄰 is different from all other occurrences of 🄰. In particular embodiments, all occurrences of 🄰 are the same except for the central In some embodiments, 🄰 is an optionally substituted aryl or heteroaryl group. In some embodiments, 🄰 is a 2-, 3, 4, 6, or 8-membered aryl or heteroaryl group. In some embodiments, 🄰 is a 5- or 6-membered heterocyclic group. In particular embodiments, 🄰 is a heteroatom selected from N, O, or S. In some embodiments, 🄰 is nitrogen atom. In some embodiments, 🄰 is an oxygen atom. In some embodiments, 🄰 is sulfur atom. In some embodiments, 🄰 is a carbon atom. In some embodiments, 🄰 is the structure

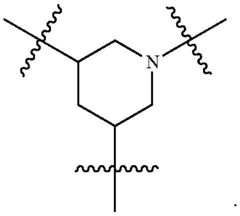 [SMILES: *C1CC(*)CN(*)C1]

.

(Spacer)

In particular embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —$N(R)SO_2$—, —$SO_2N(R)$—, a heterocyclic group, an aryl group, or a heteroaryl group. In particular embodiments, one, two, three, four, or five methylene units of T are optionally and independently replaced. In particular embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —$S(O)_2$—, —$N(R)SO_2$—, —$SO_2N(R)$—, a heterocyclic group, an aryl group, or a heteroaryl group. In some embodiments, one or more methylene units of T is replaced by a heterocyclic group. In some embodiments, one or more methylene units of T is replaced by a triazole moiety. In particular embodiments, one or more methylene units of T is replaced by —C(O)—. In particular embodiments, one or more methylene units of T is replaced by —C(O)N(R)—. In particular embodiments, one or more methylene units of T is replaced by —O—.

In particular embodiments, T may be structure

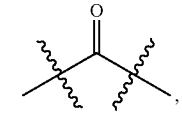

,

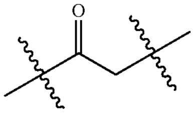

,

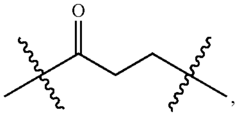

,

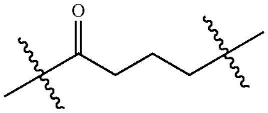

,

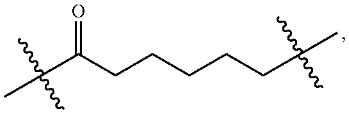

,

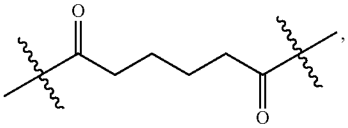

,

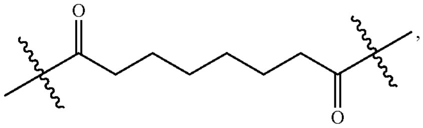

,

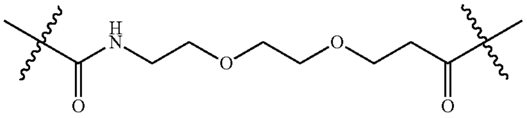

,

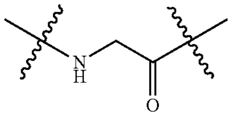

,

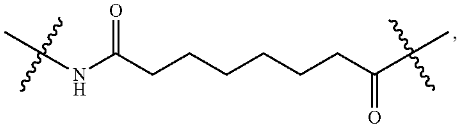

,

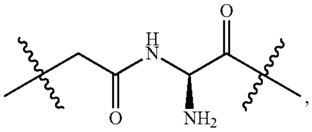

,

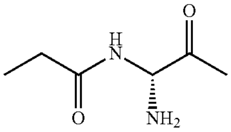

,

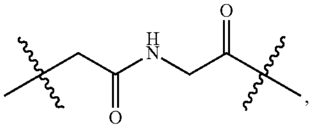

,

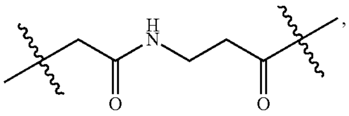

,

-continued
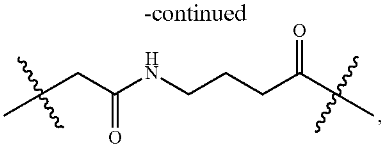,
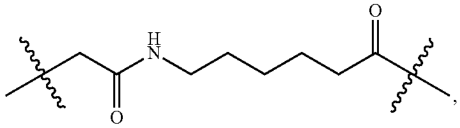,
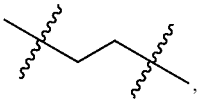, 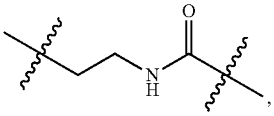,
-continued
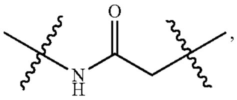, 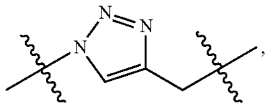, or
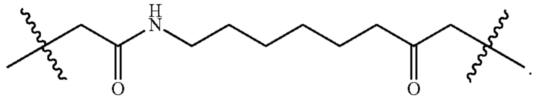.
In particular embodiments, the present disclosure provides insulin or insulin analog conjugates comprising 1, 2, or 3 bi-dentate linkers, each independently selected from the group consisting of
A
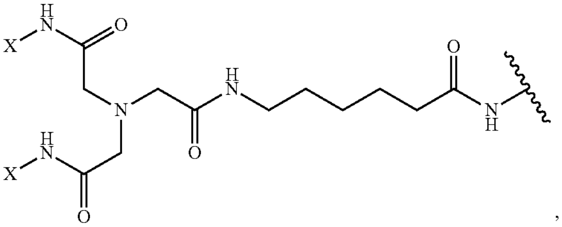,
B
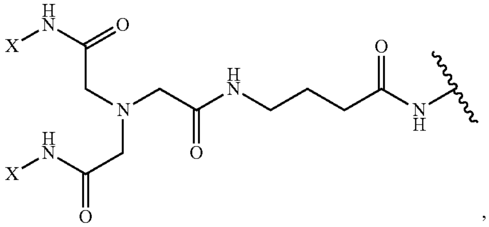,
C
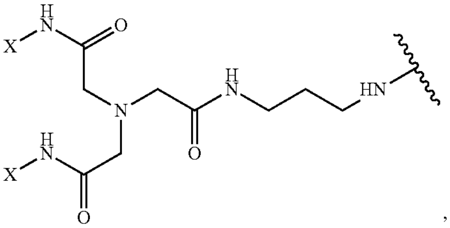,
D
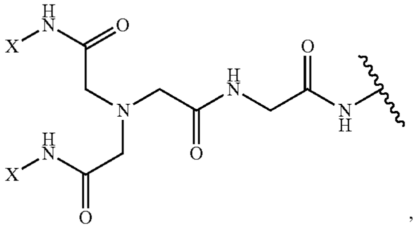,
E
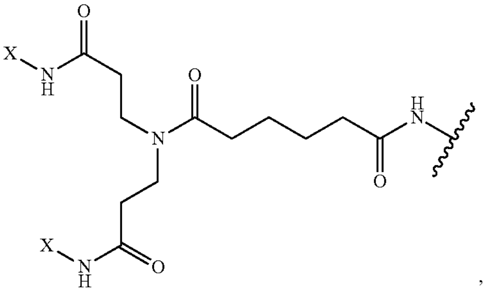,
F
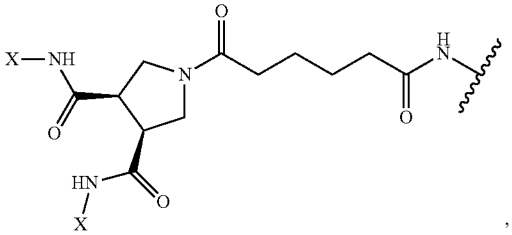,
G
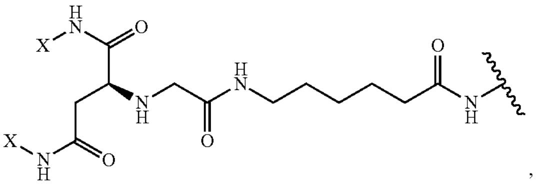,
H
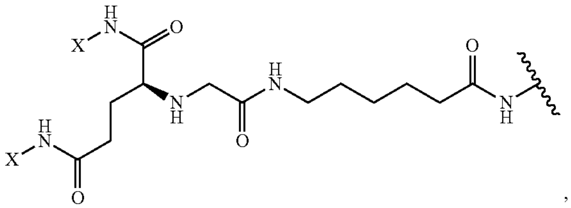, -continued
I
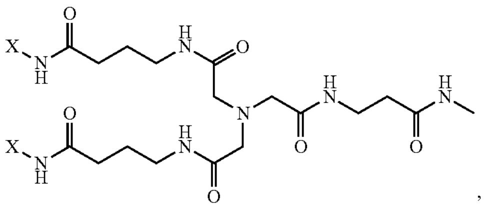
,
J
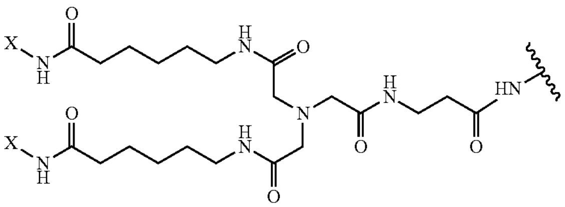
,
K
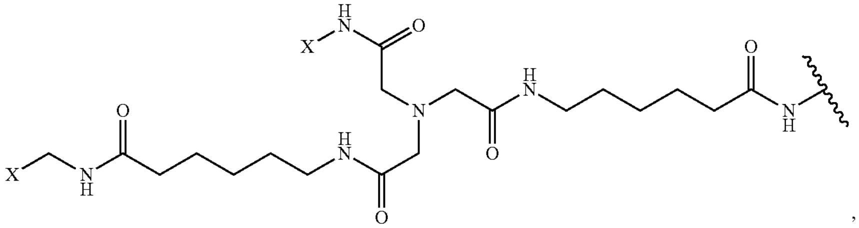
,
L
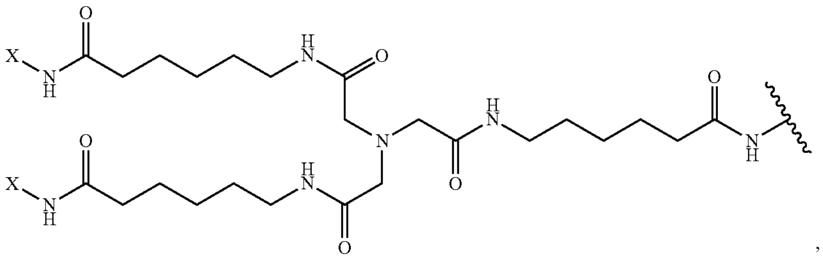
,
M
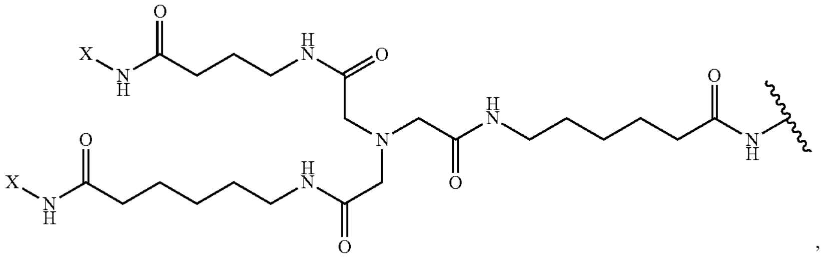
,
N
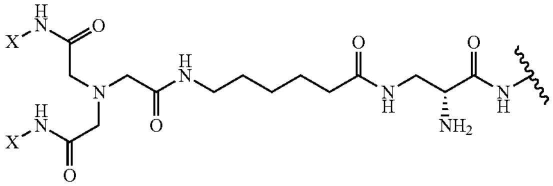
,
O
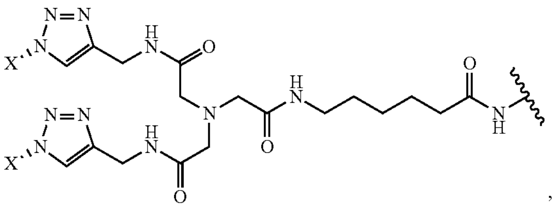
,
P
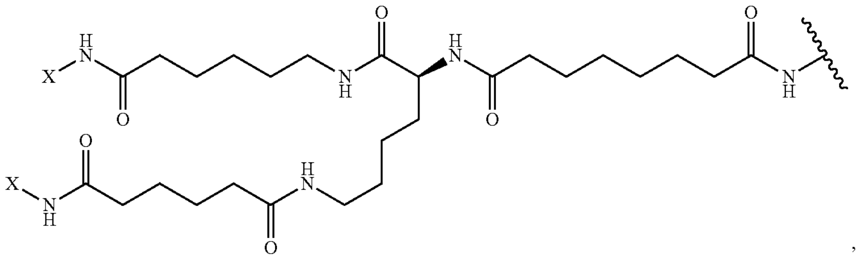
, -continued
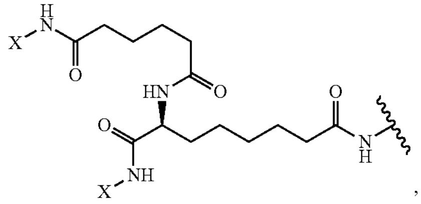
,
Q
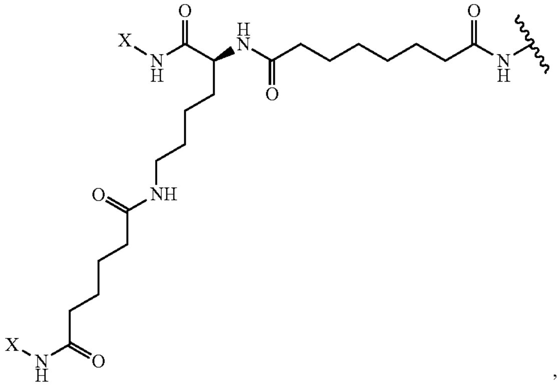
,
R
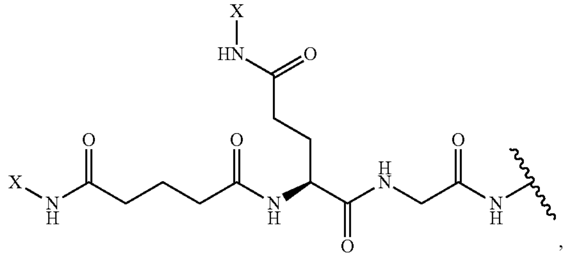
,
S
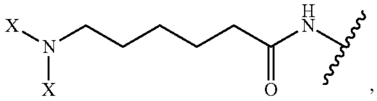
,
T
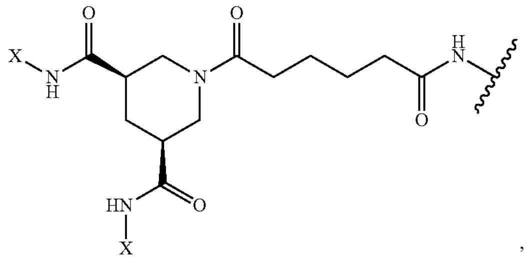
,
U
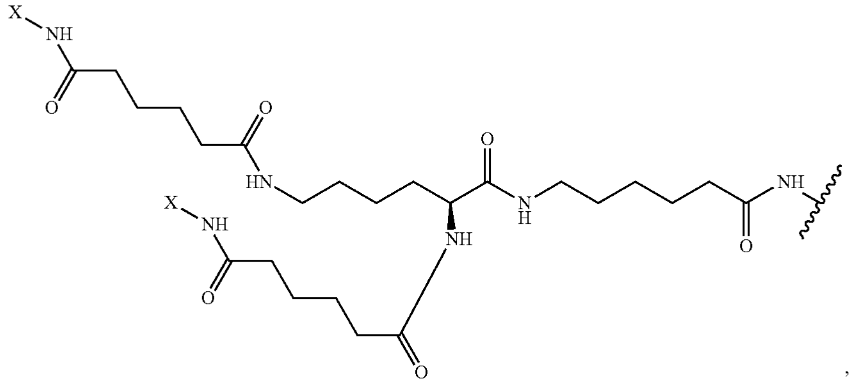
, and
V
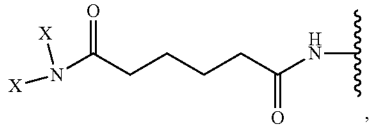
,
W
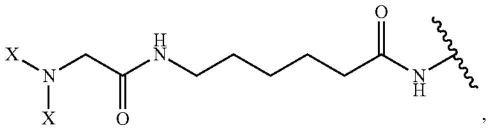
,
X -continued
Y
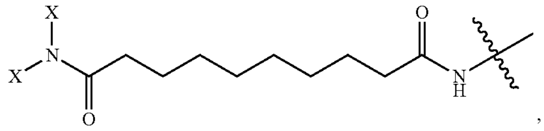
,
Z
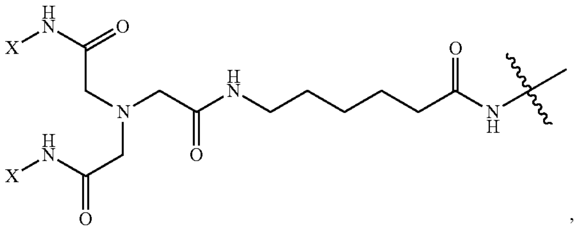
,
AA
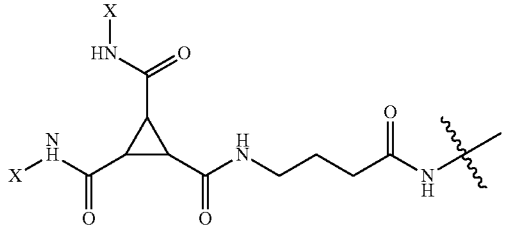
,
AB
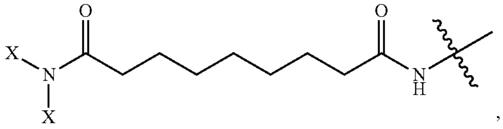
,
AC
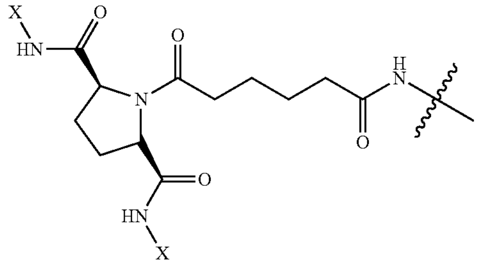
,
AD
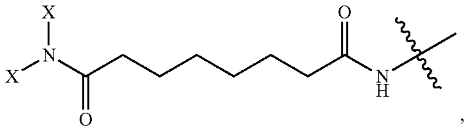
,
AE
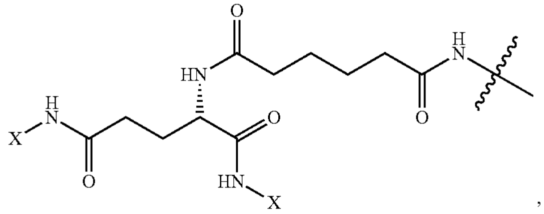
,
AF
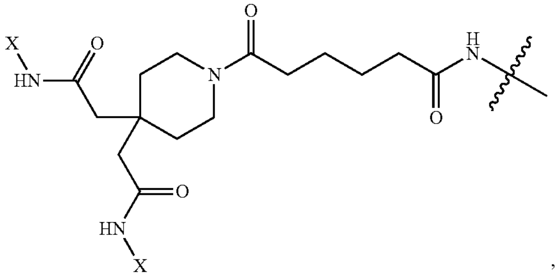
,
AG
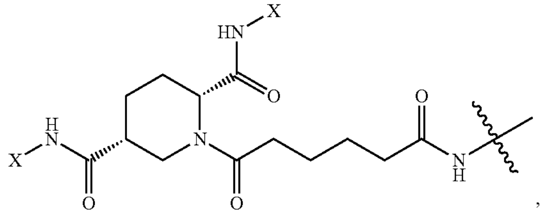
,
AH
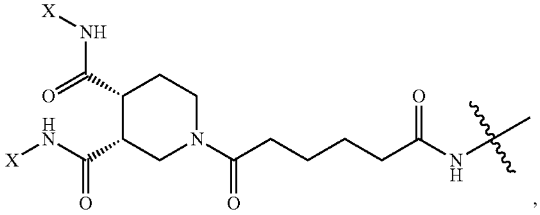
,
AI
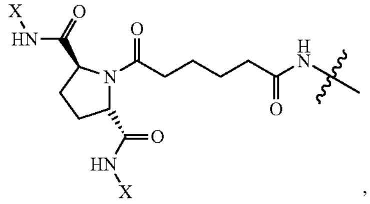
,
AJ
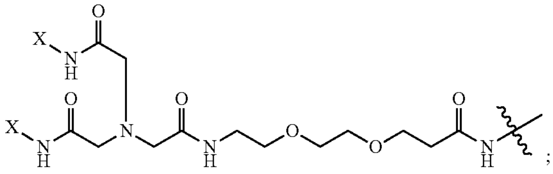
; or -continued
AK
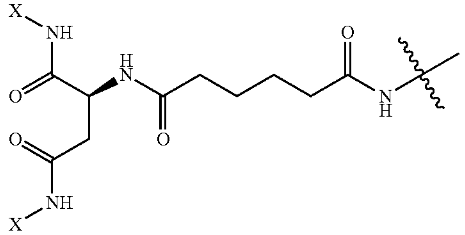
wherein each X is independently a ligand comprising a saccharide with the proviso that at least one bi-dentate linker conjugated to the insulin or insulin analog comprises a fucose on at least one arm of the bi-dentate linker. In particular embodiments, each X may independently be
EG
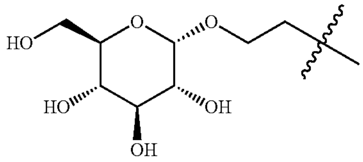
,
EM
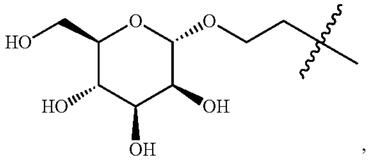
,
EBM
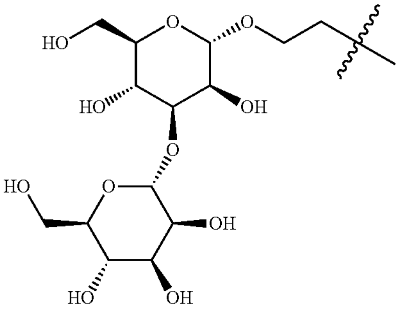
,
EGA
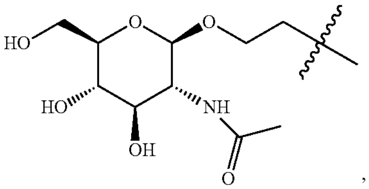
,
EF
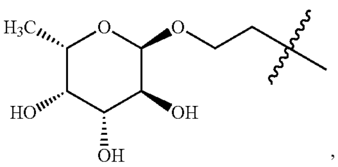
,
-continued
EFβ
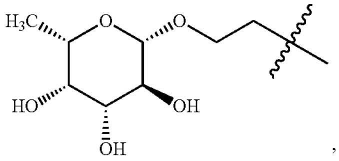
,
EBM′
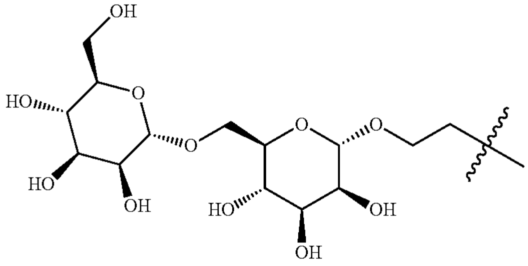
,
ETM
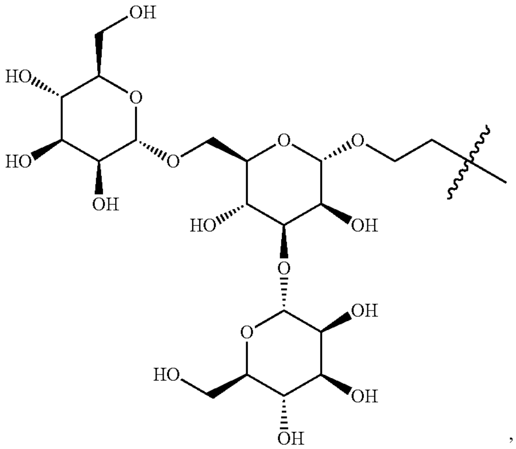
,
EDG
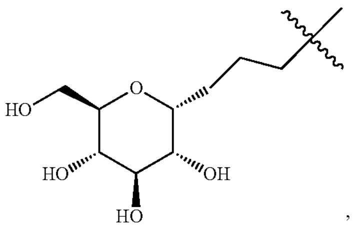
, -continued

EDF

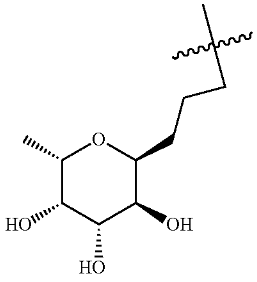

, or

EDM

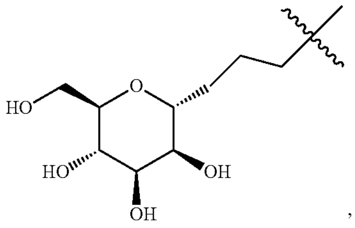

, wherein the wavy line indicates the bond is linked to an atom comprising the bi-dentate linker. EG is ethylglucose, EM is ethylmannose, EF is ethylfucose, ETM is ethyltrimannose, EBM is ethyldimannose, EGA is ethylgluccosamine, EDG is ethyldeoxyglucose, EDF is ethyldeoxyfucose, and EDM is ethyldeoxymannose.

One of ordinary skill will appreciate that a variety of conjugation chemistries may be used to covalently conjugate an X with a T and/or a W with a T (generally "components"). Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between the conjugated element and the remainder of the linker). It is to be understood that components may be covalently bound to a linker through any number of chemical bonds, including but not limited to amide, amine, ester, ether, thioether, isourea, imine, etc. bonds.

In various embodiments, components may be covalently bound to a linker using "click chemistry" reactions as is known in the art. These include, for example, cycloaddition reactions, nucleophilic ring-opening reactions, and additions to carbon-carbon multiple bonds (e.g., see Kolb and Sharpless, *Drug Discovery Today* 8:1128-1137, 2003 and references cited therein as well as Dondoni, *Chem. Asian J.* 2:700-708, 2007 and references cited therein). As discussed above, in various embodiments, the components may be bound to a linker via natural or chemically added pendant groups. In general, it will be appreciated that the first and second members of a pair of reactive groups (e.g., a carboxyl group and an amine group which react to produce an amide bond) can be present on either one of the component and linker (i.e., the relative location of the two members is irrelevant as long as they react to produce a conjugate). Exemplary linkages are discussed in more detail below.

Particular components may naturally possess more than one of the same chemically reactive moiety. In some examples, it is possible to choose the chemical reaction type and conditions to selectively react the component at only one of those sites. For example, in the case where insulin is conjugated through reactive amines, in particular embodiments, the N-terminal α-Phe-B1 may be more desirable as a site of attachment over the N-terminal α-Gly-A1 and ϵ-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in particular embodiments it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., Biochem. J. 109: 312-314, 1968; and Schuettler et al., *D. Brandenburg Hoppe Seyler's Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THF are added slowly and the solution allowed to mix for 30 to 60 minutes. After reaction, the crude solution is poured in an excess of acetone followed by dropwise addition of dilute HCl to precipitate the reacted insulin. The precipitated material is centrifuged, washed with acetone and dried completely under vacuum.

The desired di-BOC protected product may be separated from unreacted insulin, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, the acetonitrile removed and lyophilized to obtain the product.

In particular embodiments, the insulin oligosaccharide conjugates may comprise an insulin or insulin analog and at least one bi-dentate linker having a first arm and second arm, wherein the first arm is linked to a first ligand that includes a first saccharide and the second arm is linked to a second ligand that includes a second saccharide and wherein for at least one bi-dentate linker the first saccharide is fucose, and wherein the at least one bi-dentate linker is conjugated to the alpha amino group of the N-terminal amino acid of the A-chain or B-chain of the insulin or insulin analog or to the epsilon amino group of a lysine residue of the A-chain or the B-chain of the insulin or insulin analog. In particular embodiments the conjugate may include at least two linkers wherein at least one linker is a bidentate linker comprising a fucose. In particular embodiments the conjugate may include at least three linkers wherein at least one linker is a bidentate linker comprising a fucose.

In particular embodiments, the at least one bi-dentate linker may have formula A, B, C, D, E, F, G, H, I, J, K, L, M, N, O, P, Q, R, S, T, U, V, W, X, Y, Z, AA, AB, AC, AD, AE, AF, AG, AH, AI, AJ, or AK as shown supra wherein X is a saccharide; with the proviso that for at least one bi-dentate linker the X on at least one arm of the at least one bi-dentate linker is fucose. In particular embodiments, X has the formula EG, EM, EBM, EGA, EF, EFβ, EBM, ETM, EDG, EDF, or EDM as shown supra.

In particular embodiments, the insulin analog may comprise an A chain sequence comprising a sequence of GIVEQCC$X_1$SICSLYQLENYC$X_2$ (SEQ ID NO: 8); and a B chain sequence comprising a sequence of $X_3$LCG$X_4$$X_5$LVEALYLVCG ERGFF (SEQ ID NO: 9) or $X_8$VNQ$X_3$LCG$X_4$$X_5$LVEALYLVCGERGFFYT$X_6$$X_7$ (SEQ ID NO: 10) wherein $X_1$ is selected from the group consisting of threonine and histidine;

$X_2$ is asparagine or glycine;

$X_3$ is selected from the group consisting of histidine and threonine;

$X_4$ is selected from the group consisting of alanine, glycine and serine;

$X_5$ is selected from the group consisting of histidine, aspartic acid, glutamic acid, homocysteic acid and cysteic acid;

$X_6$ is aspartate-lysine dipeptide, a lysine-proline dipeptide, or a proline-lysine dipeptide;

$X_7$ is threonine, alanine, or a threonine-arginine-arginine tripeptide; and $X_8$ is selected from the group consisting of phenylalanine and desamino-phenylalanine In particular embodiments, the A-chain may have the amino acid sequence set forth in SEQ ID NO:1 or SEQ ID NO:6 and the B-chain may have the amino acid sequence set forth in SEQ ID NO:2, SEQ ID NO:3, SEQ ID NO:4, or SEQ ID NO:5. In particular embodiments, the insulin analog is a desB30 insulin analog, a des B29-B30 insulin analog, a des B28-B30 insulin analog, a des B27-B30 insulin analog or a des B26-B30 insulin analog.

In particular embodiments, the insulin oligosaccharide conjugate of the present invention may have the formula Conjugate A
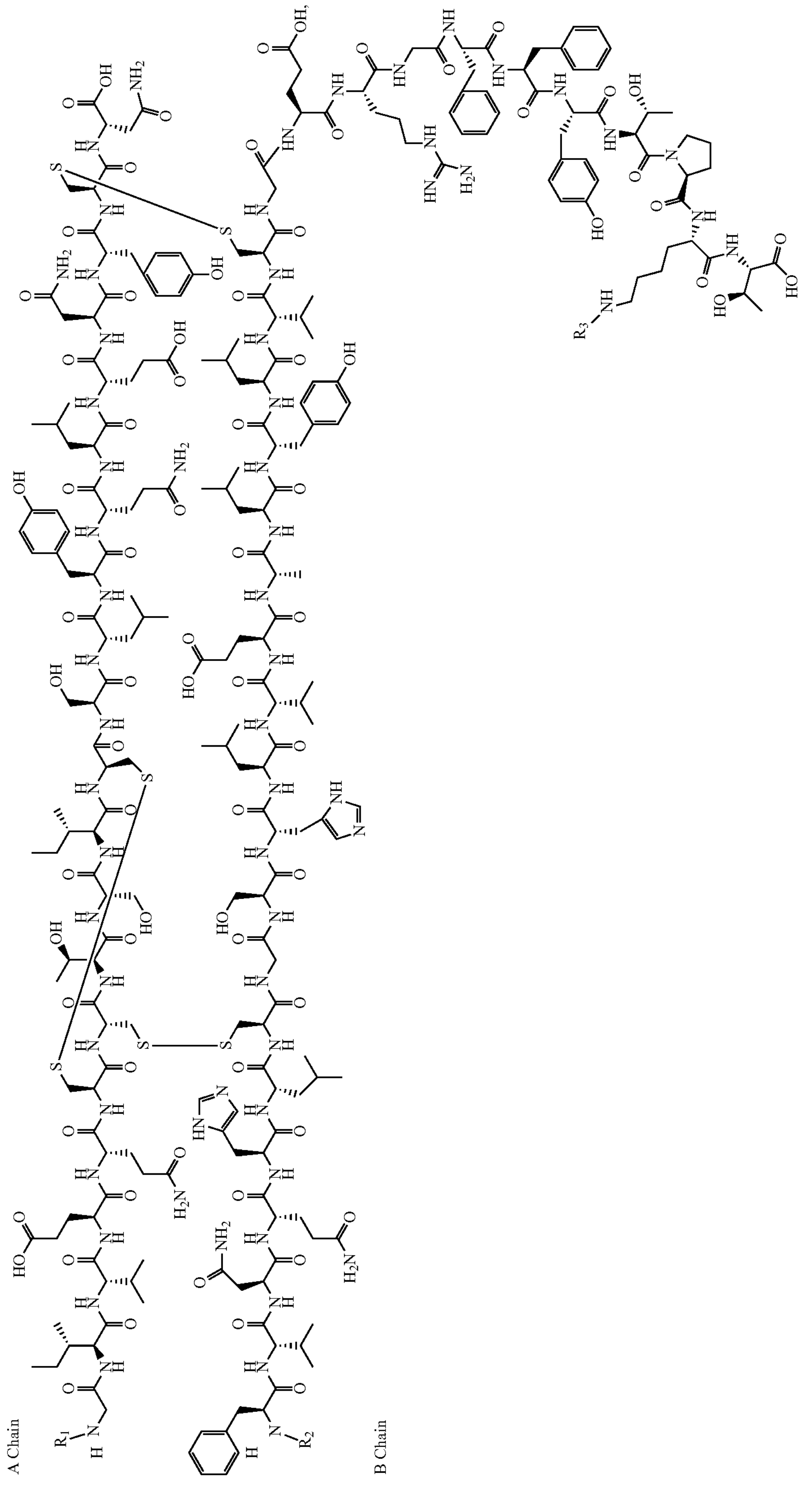

-continued
Conjugate B
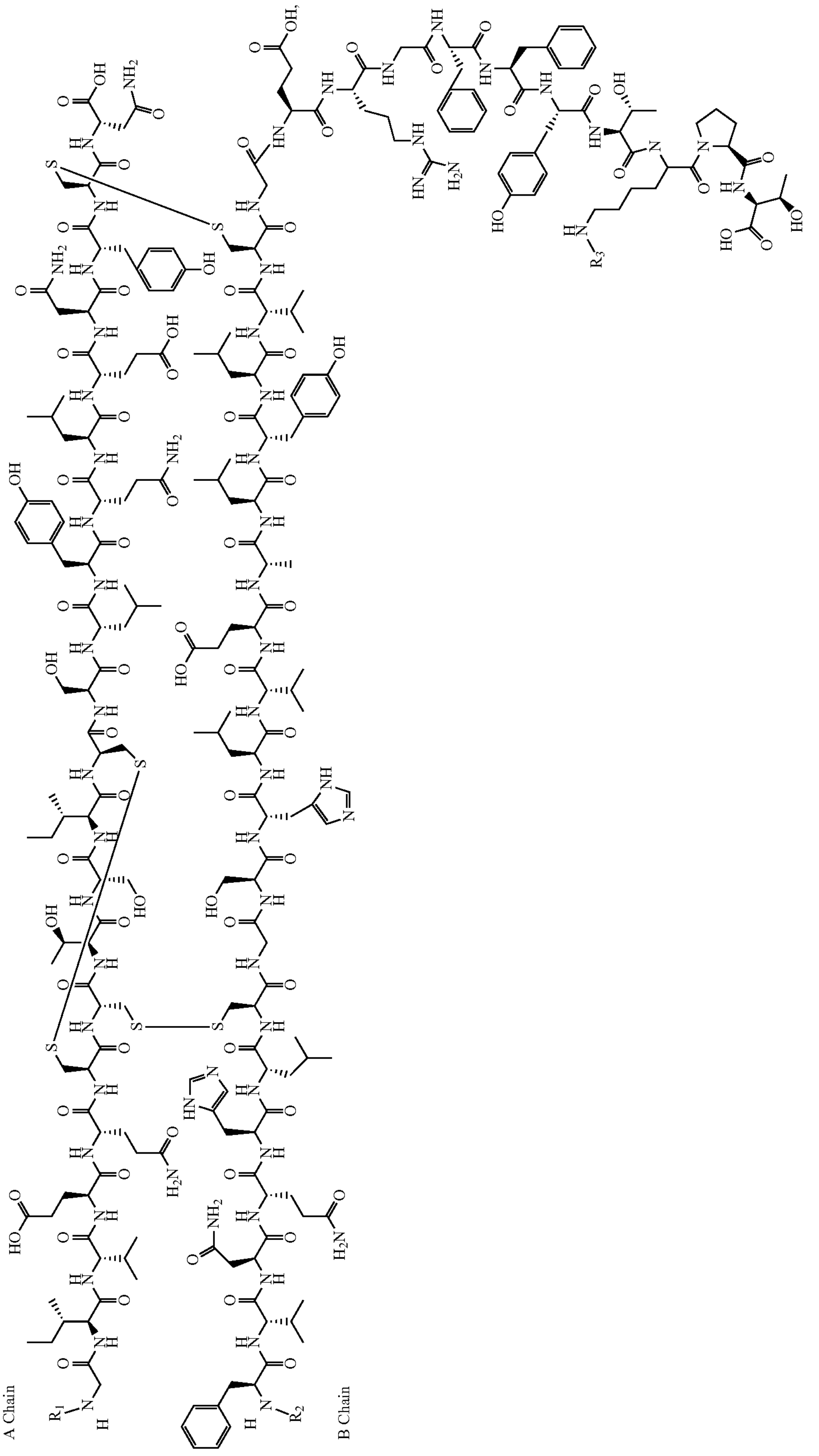

-continued
Conjugate C
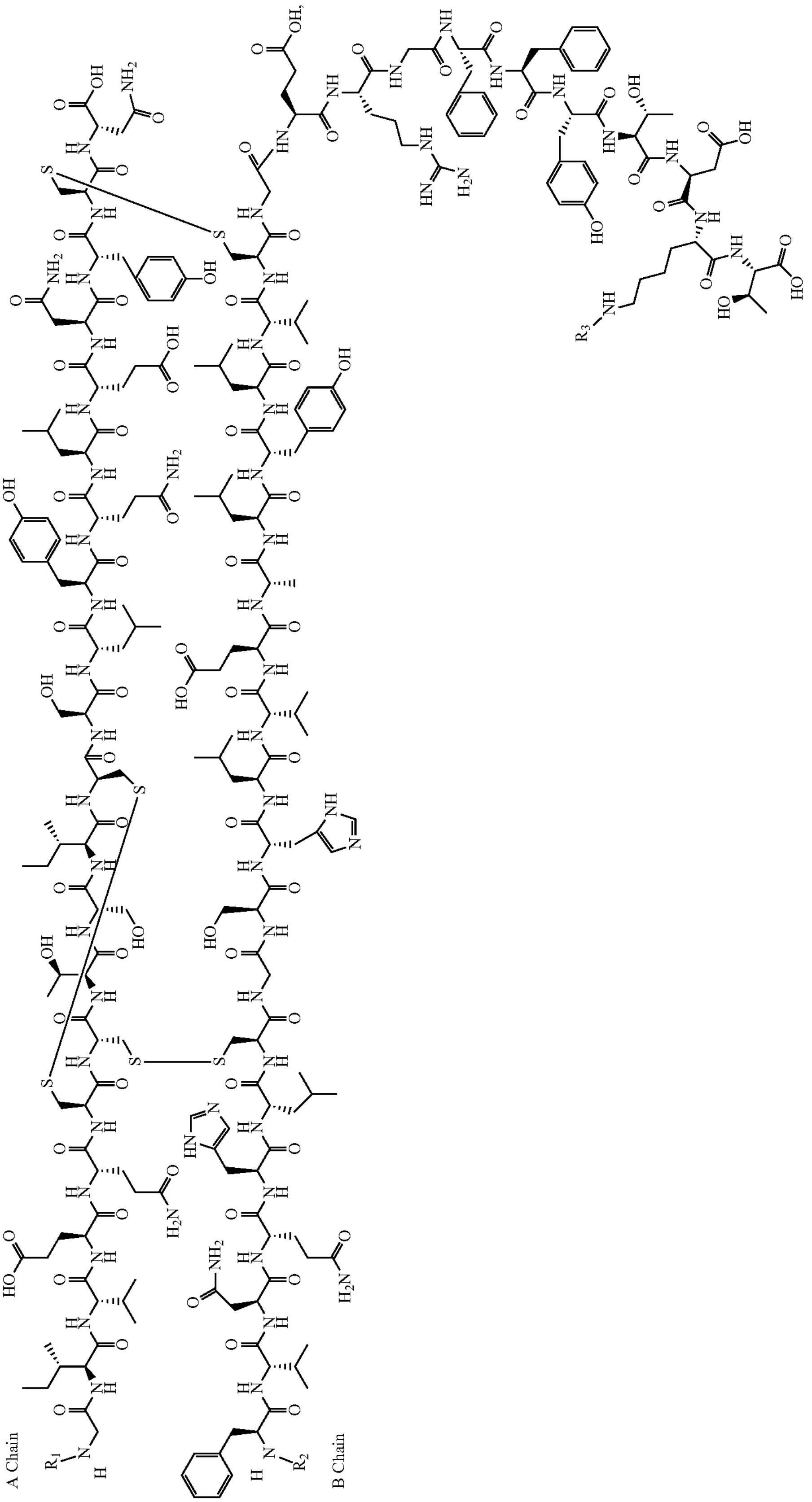

-continued
Conjugate D
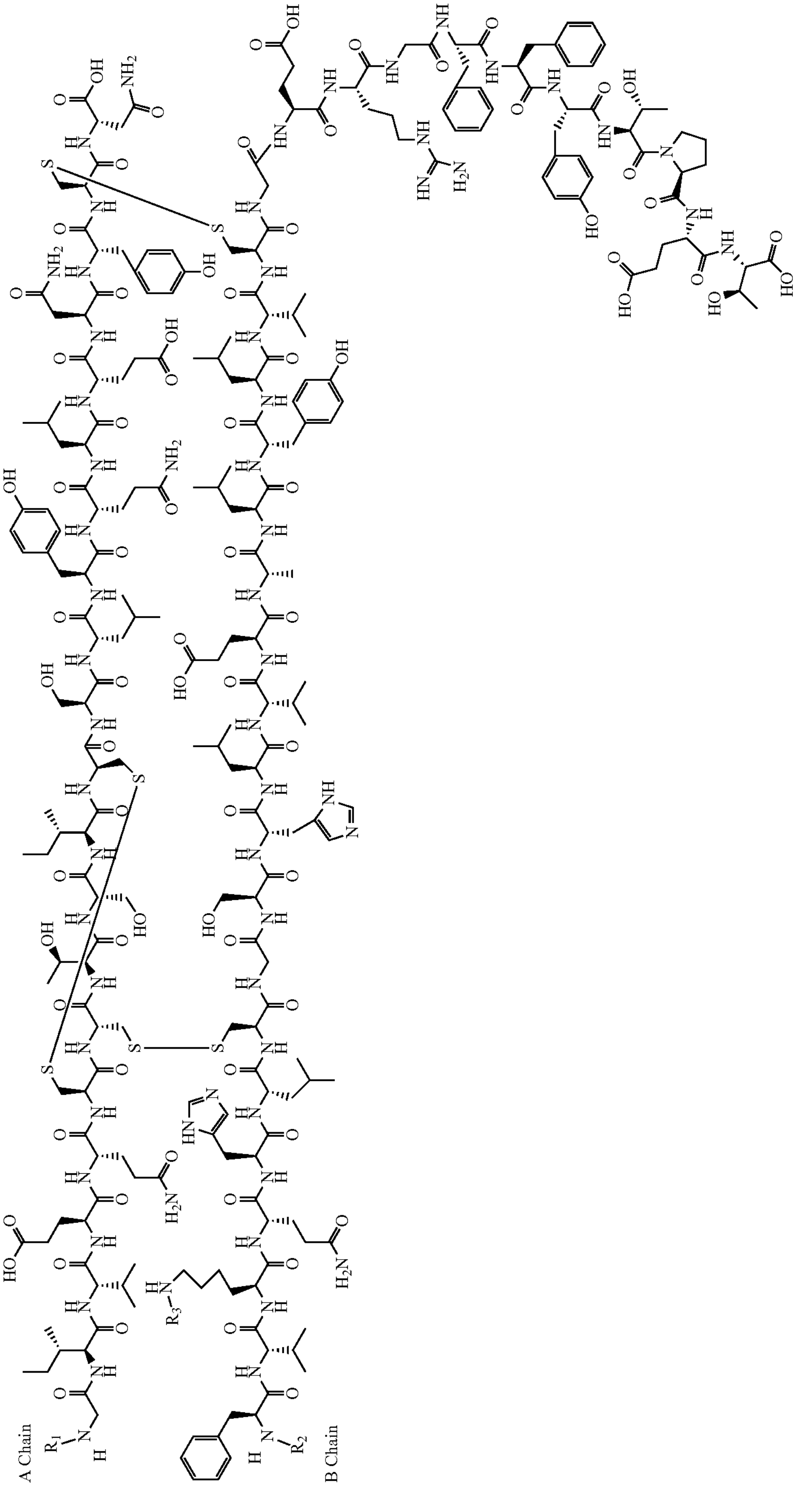
, or

-continued
Conjugate E
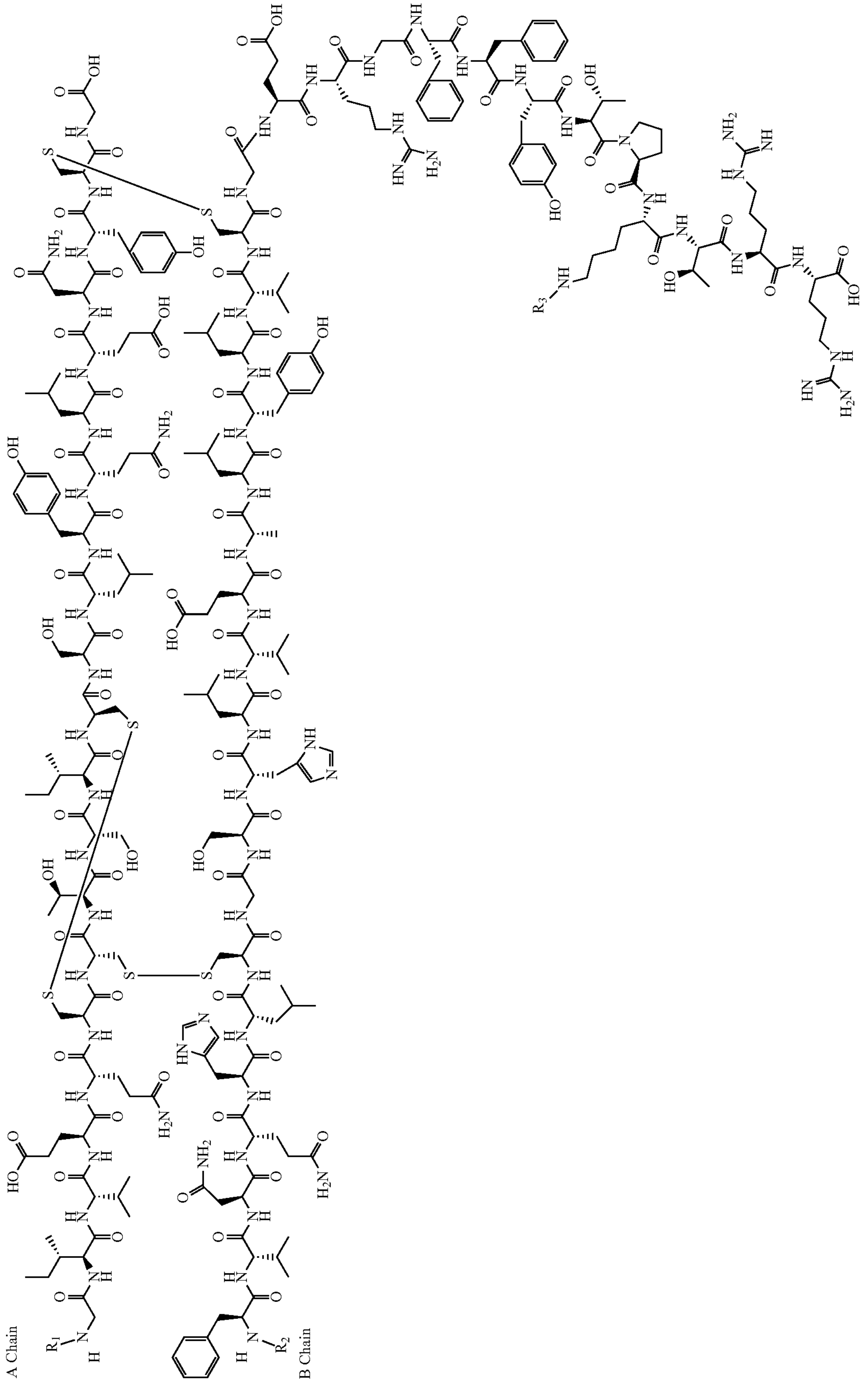

Wherein $R_1$, $R_2$, and $R_3$, are each independently either H (hydrogen) or a linear linker having a ligand thereon that includes a saccharide or a bi-dentate linker having a first arm and second arm, wherein the first arm is linked to a first ligand that includes a first saccharide and the second arm is linked to a second ligand that includes a second saccharide with the proviso that at least one of $R_1$, $R_2$, or $R_3$ is a bi-dentate linker wherein the first saccharide is fucose. In a particular embodiment, $R_1$, $R_2$, or $R_3$ are each independently either H (hydrogen) or a bi-dentate linker having formula A, B, C, D, E, F, G, H, I, J, K, L, M, N, O, P, Q, R, S, T, U, V, W, X, Y, Z, AA, AB, AC, AD, AE, AF, AG, AH, AI, AJ, or AK as shown supra wherein X is a saccharide; with the proviso that at least one of $R_1$, $R_2$, or $R_3$ is a bi-dentate linker and the X on at least one arm of at least one bi-dentate linker is fucose. In particular embodiments, X has the formula EG, EM, EBM, EGA, EF, EFβ, EBM, ETM, EDG, EDF, or EDM as shown supra.

Exemplary human insulin oligosaccharide conjugates (IOCs) of the present invention include the IOCs having the following structures.

IOC-1

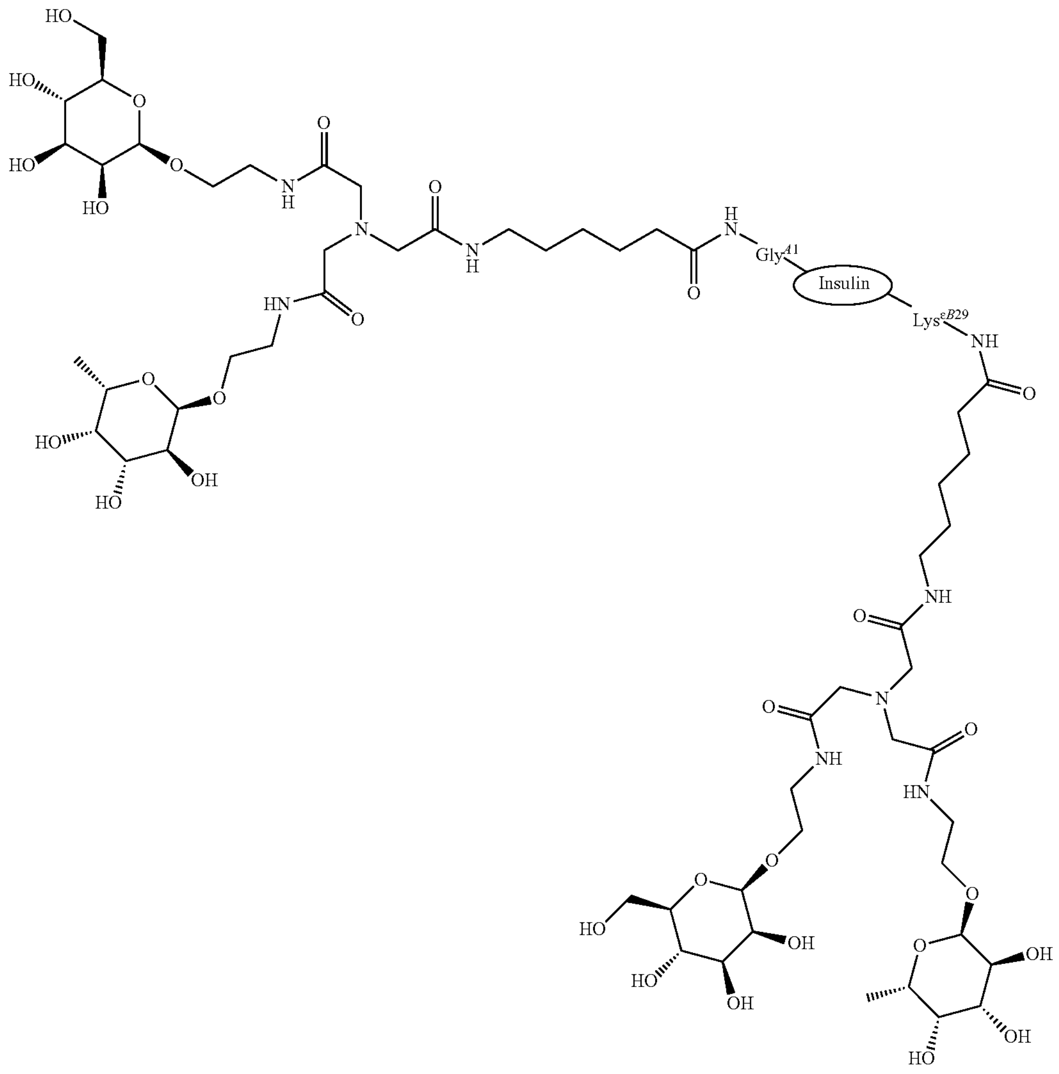

-continued
IOC-2
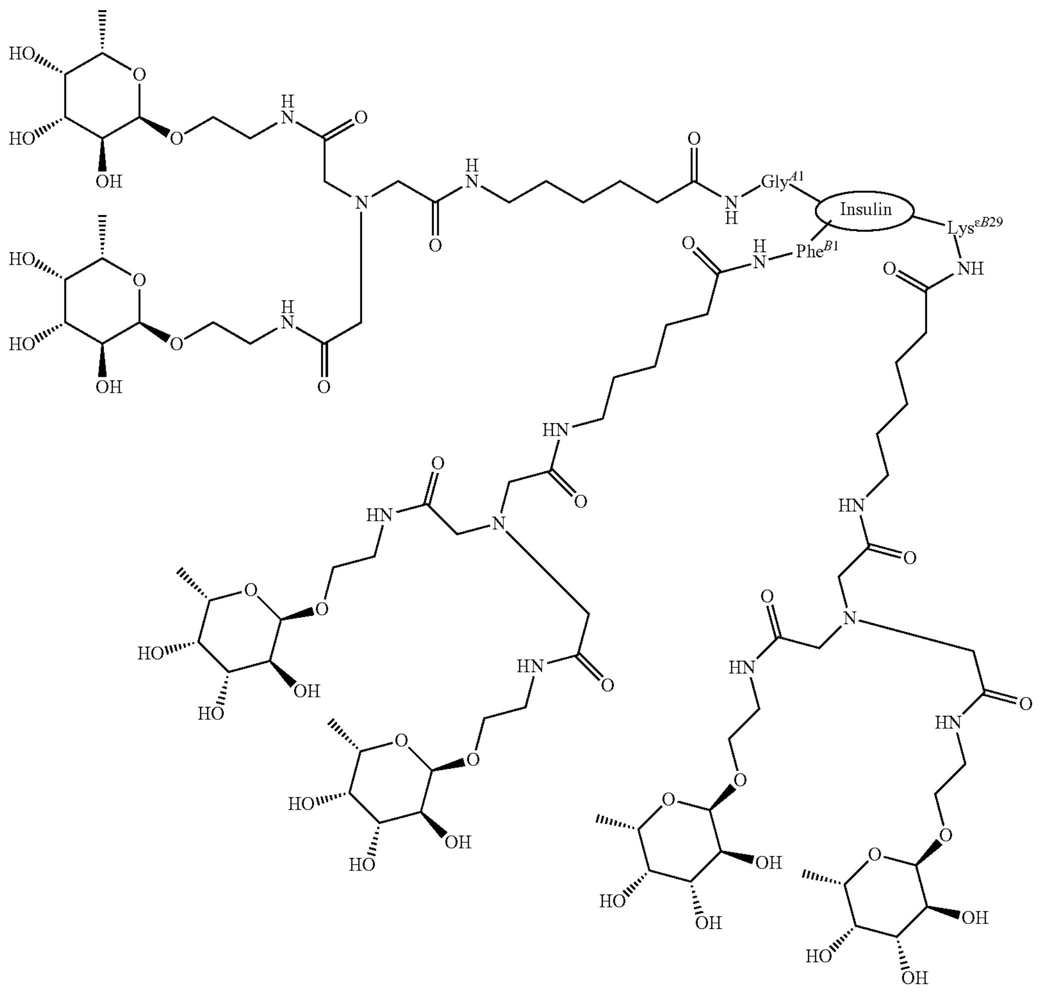

-continued
IOC-3
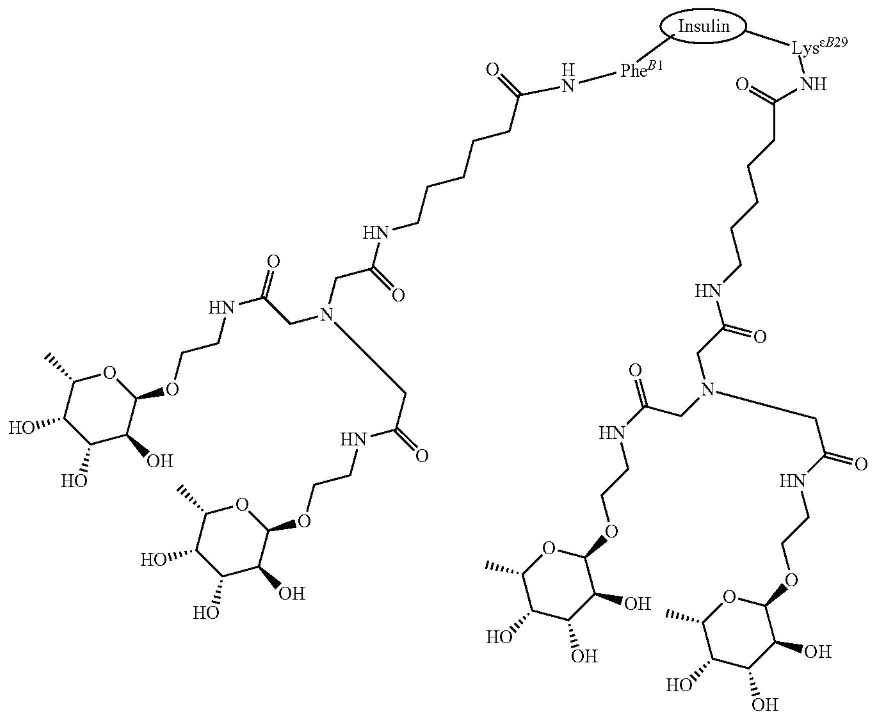
IOC-4
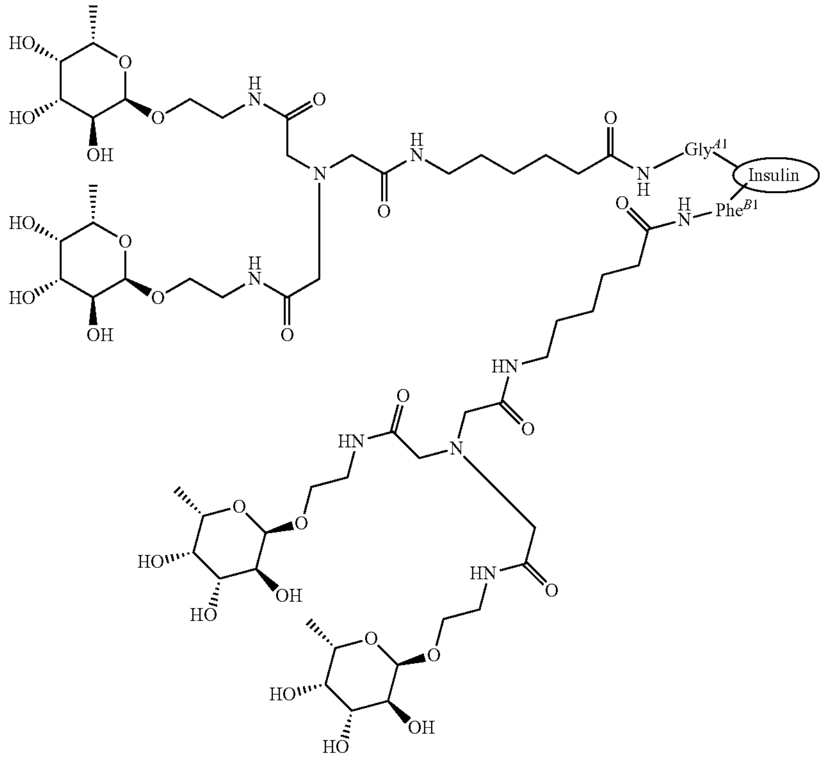

-continued
IOC-5
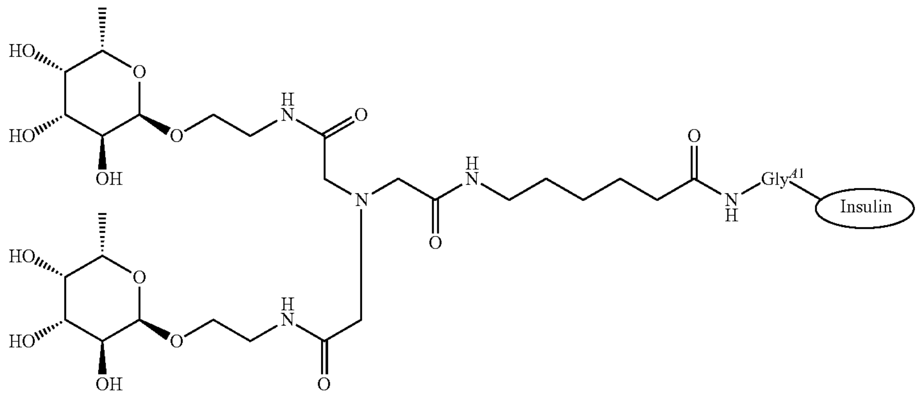
IOC-6
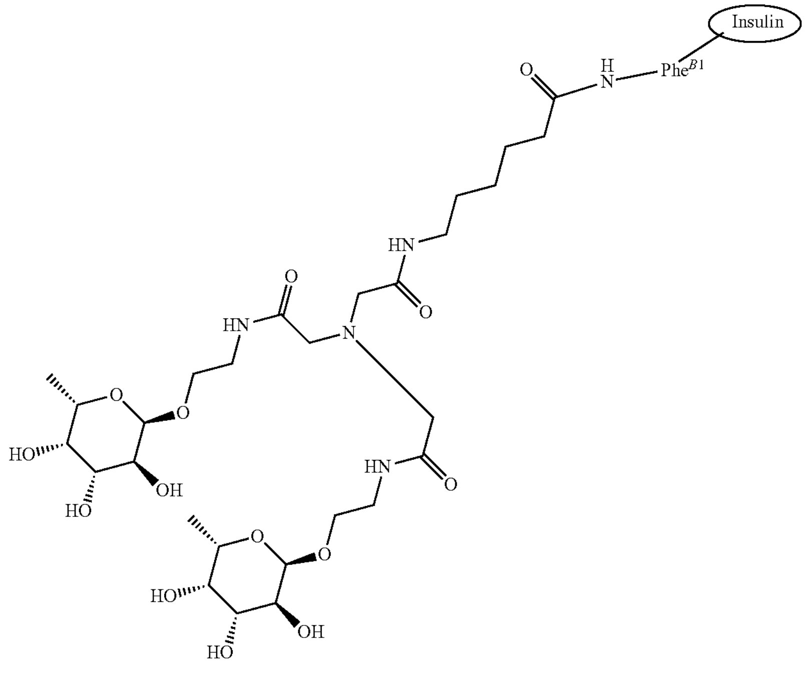

-continued
IOC-7
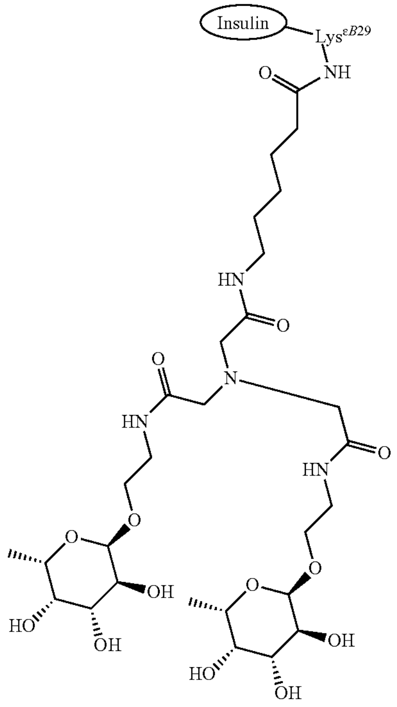
IOC-8
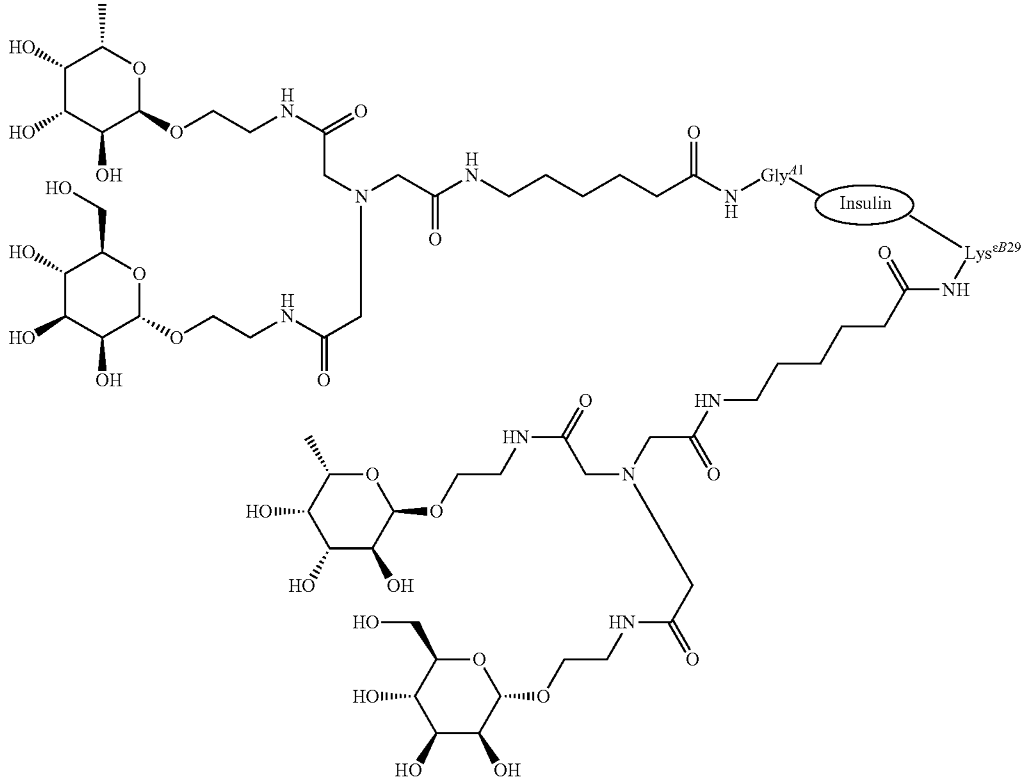

-continued
IOC-9
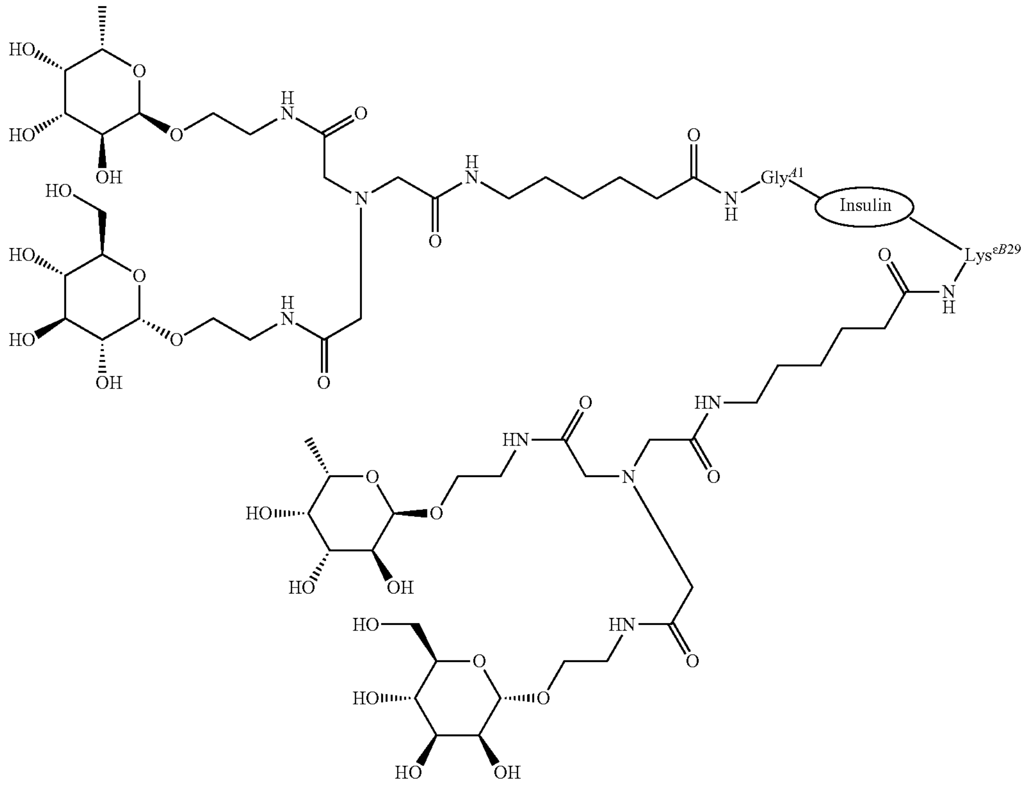
IOC-10
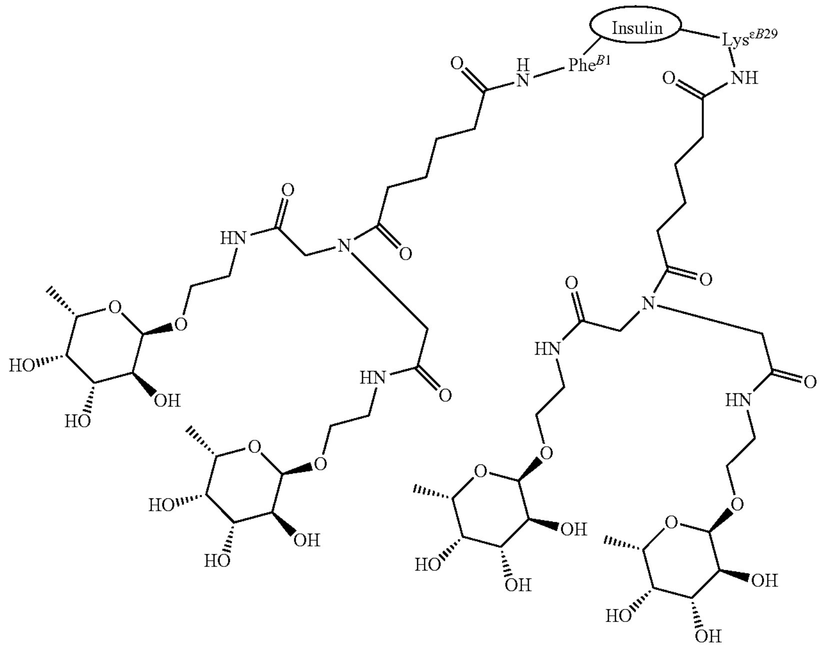

-continued
IOC-11
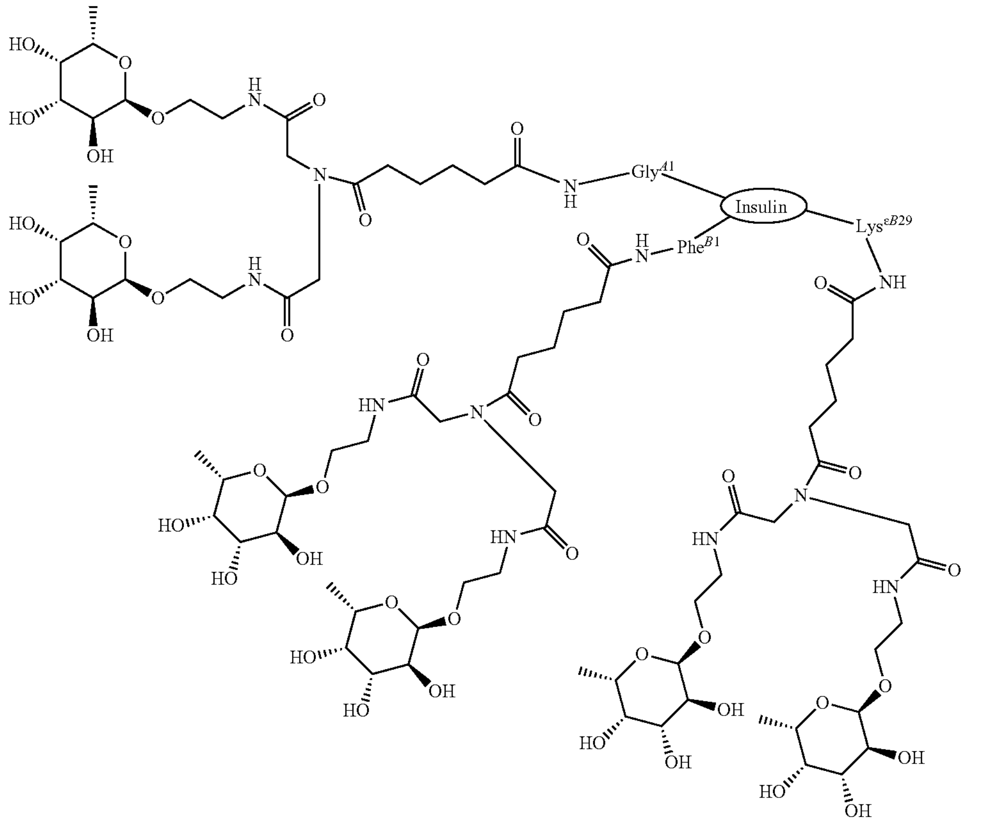
IOC-12
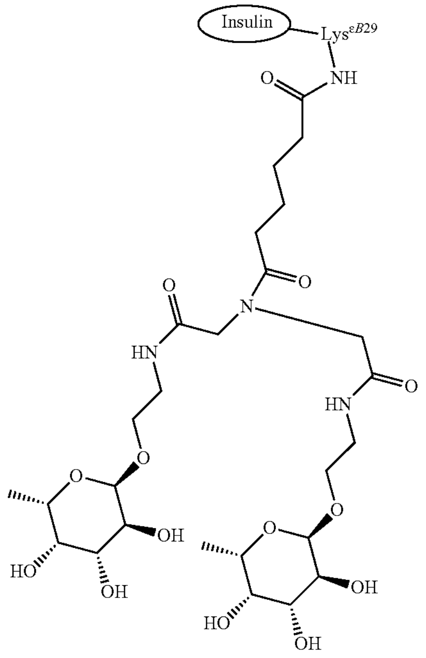

-continued
IOC-13
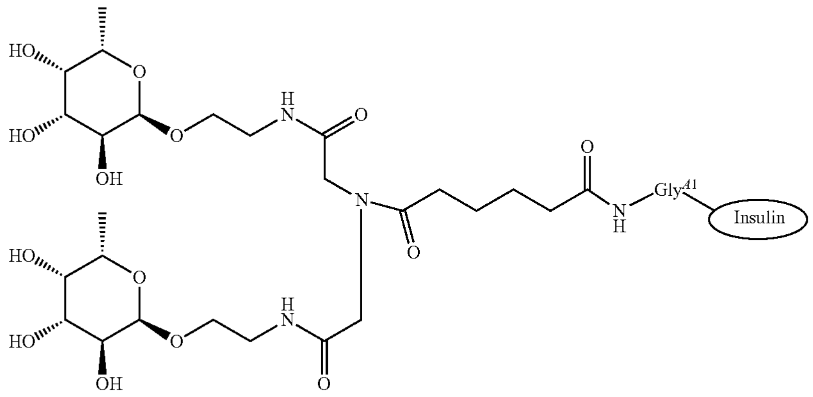
IOC-14
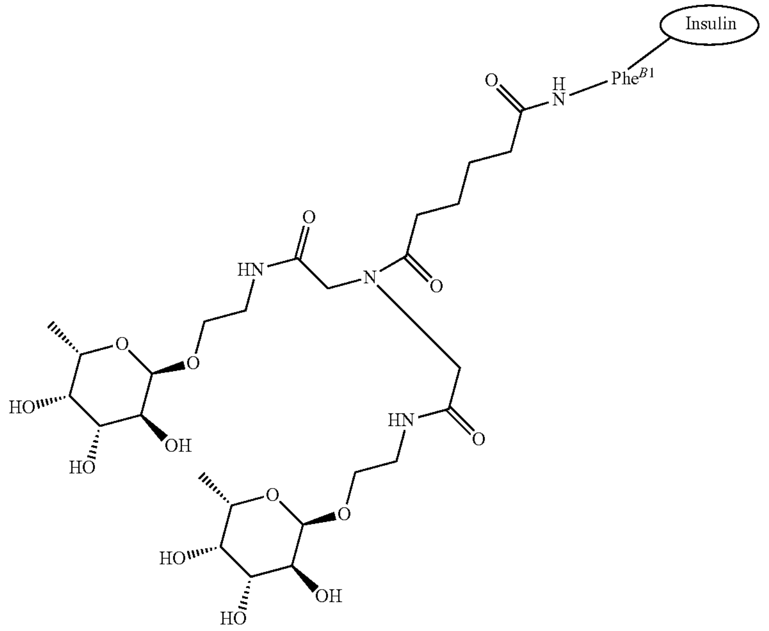

-continued
IOC-15
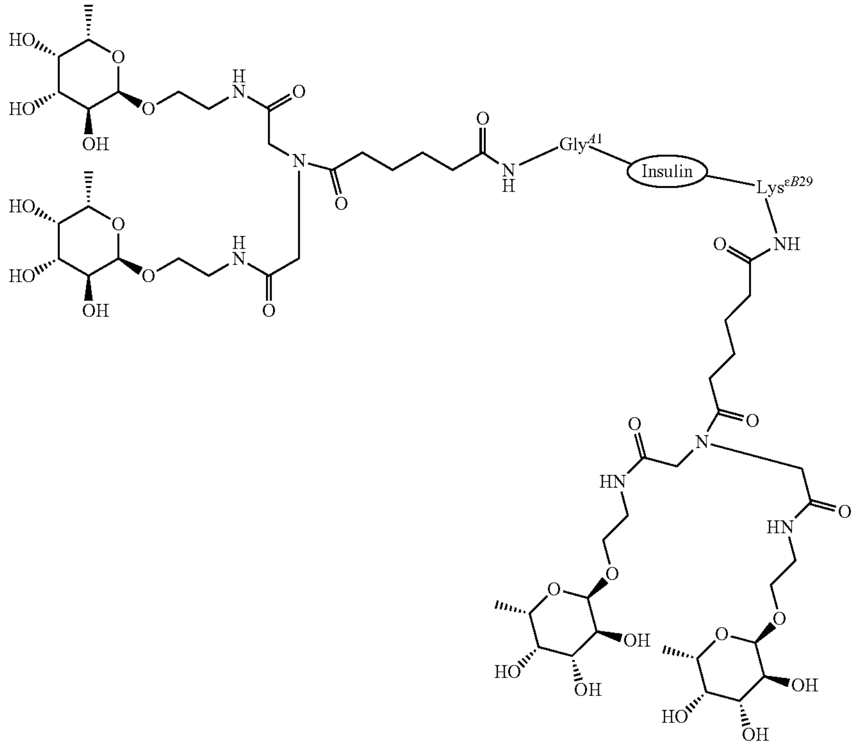
IOC-16
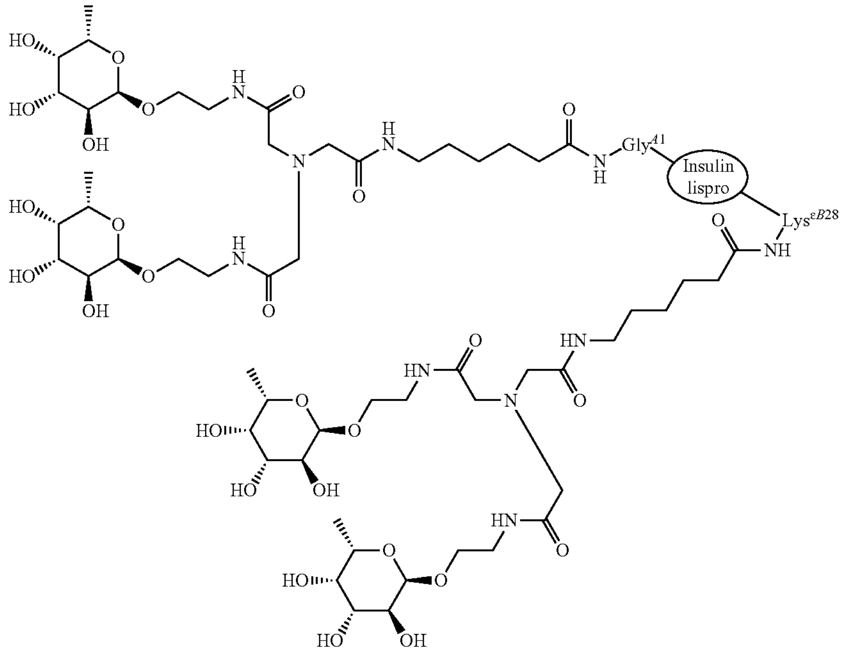

-continued
IOC-17
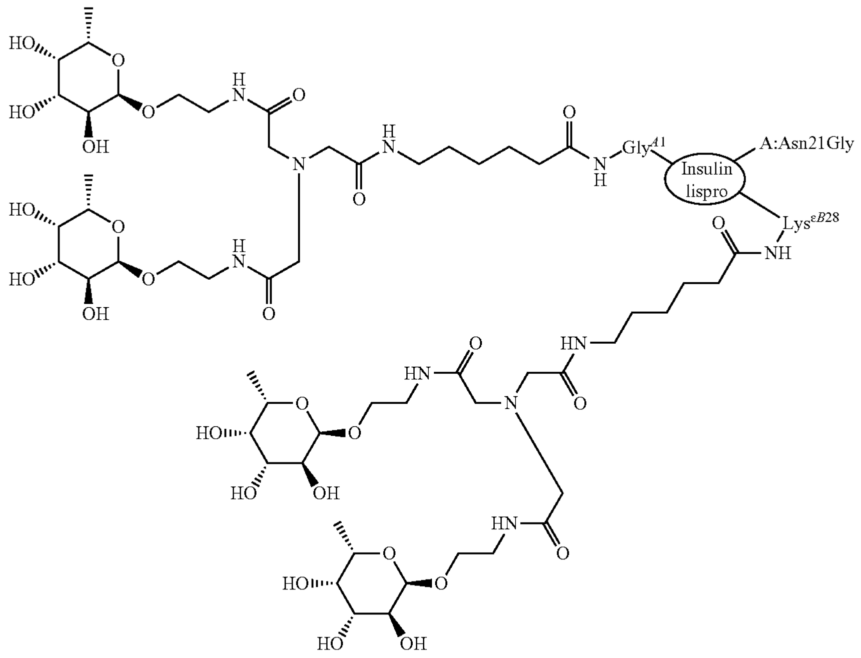
IOC-18
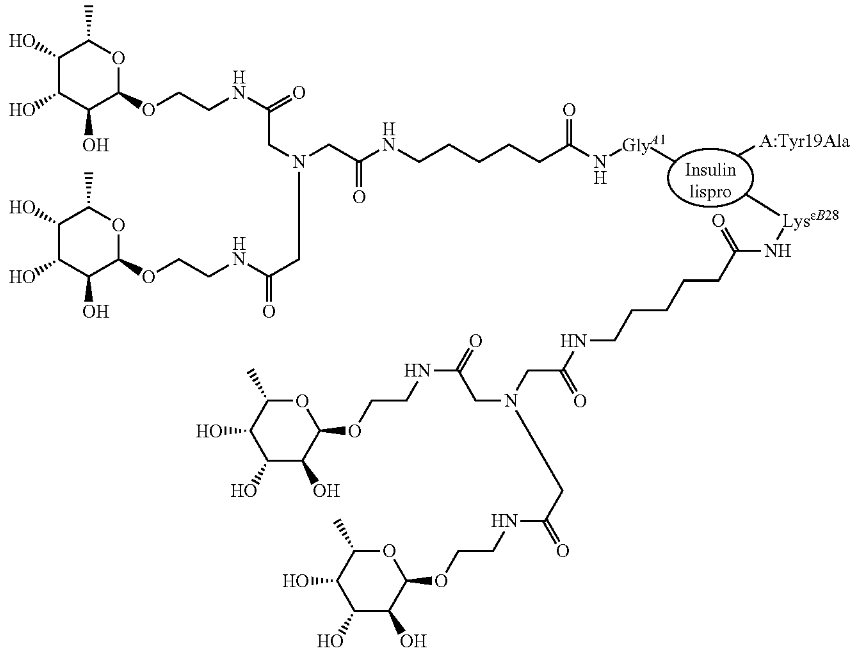

-continued
IOC-19
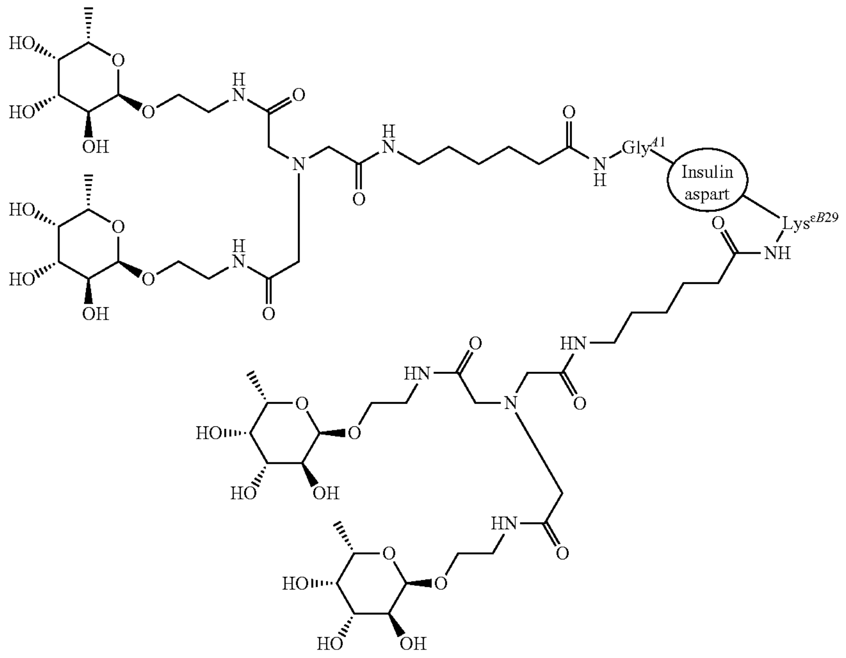
IOC-20
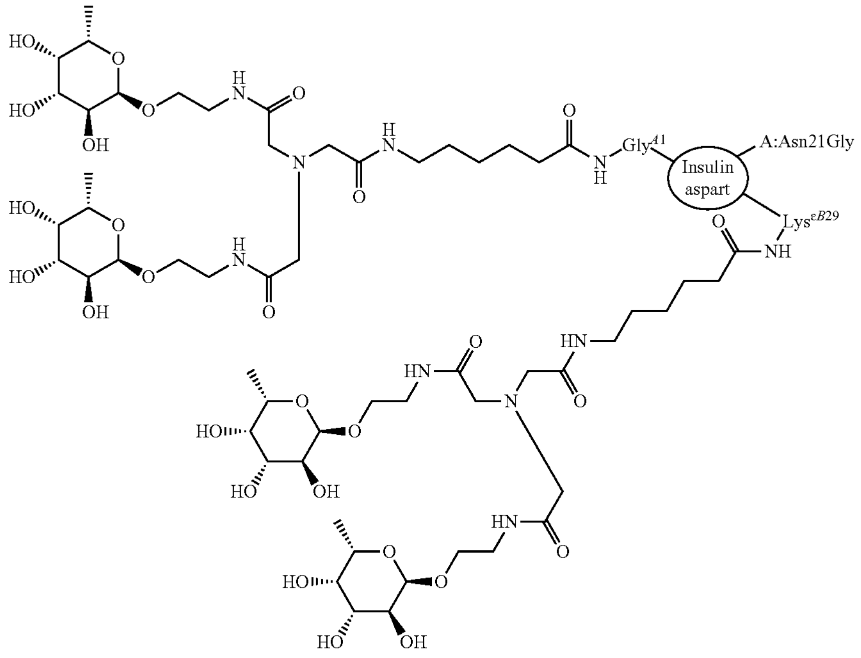

-continued
IOC-21
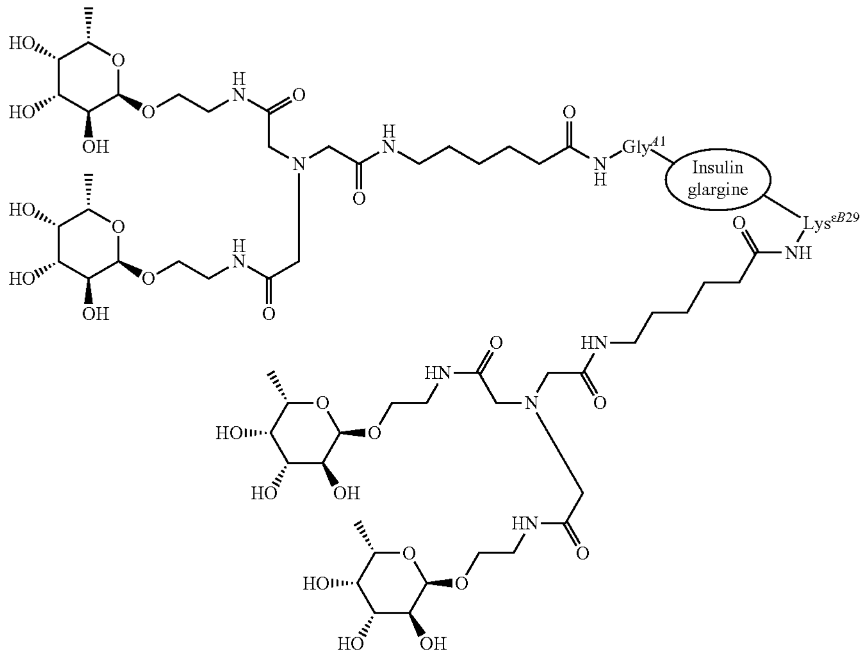
IOC-22
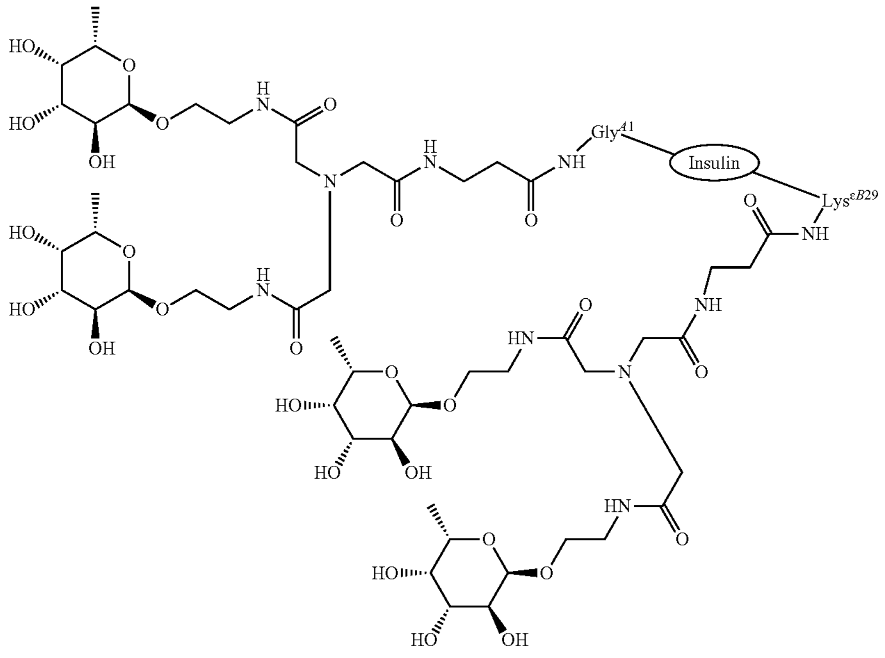

-continued
IOC-23
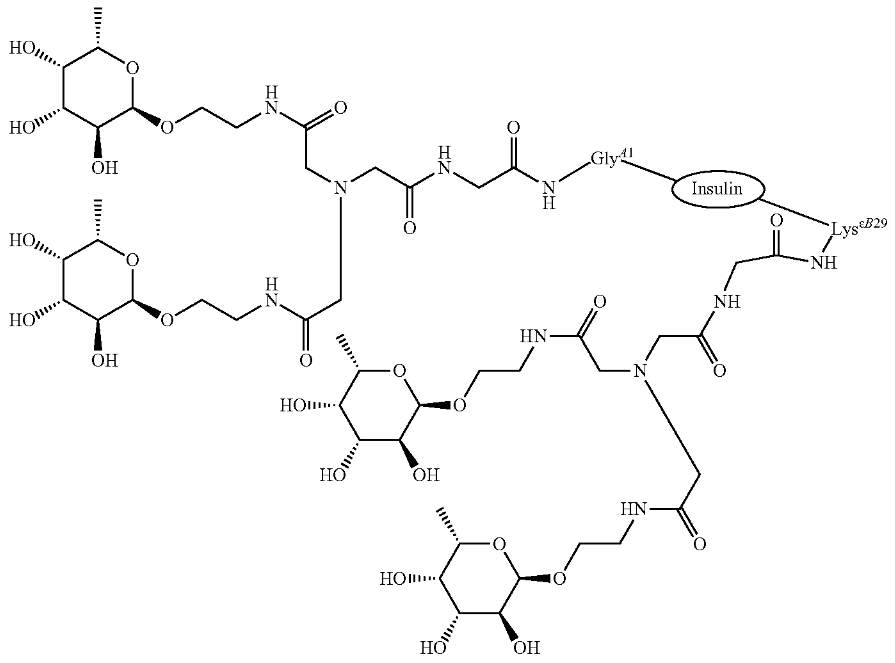
IOC-24
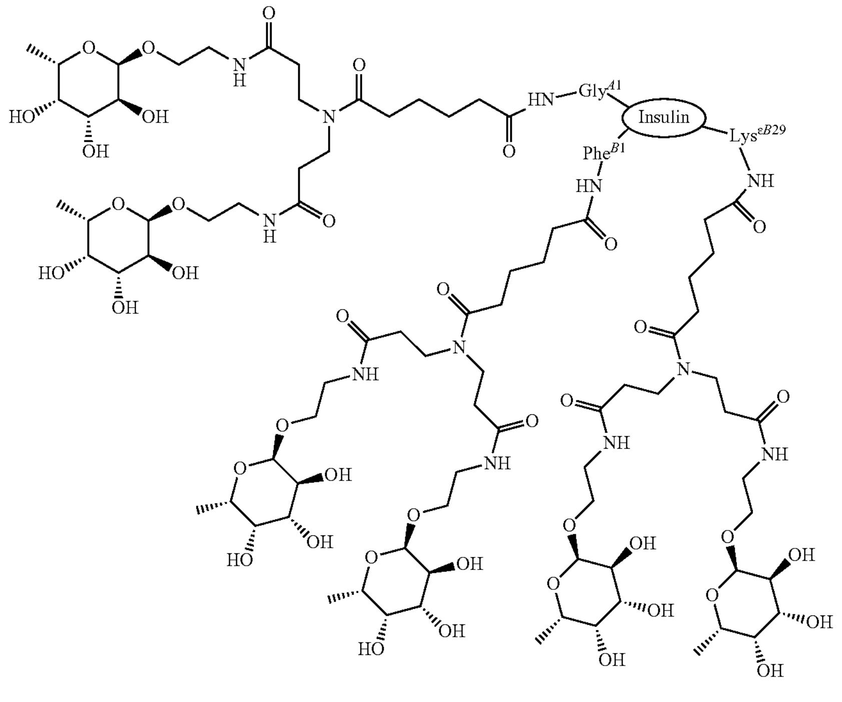

-continued
IOC-25
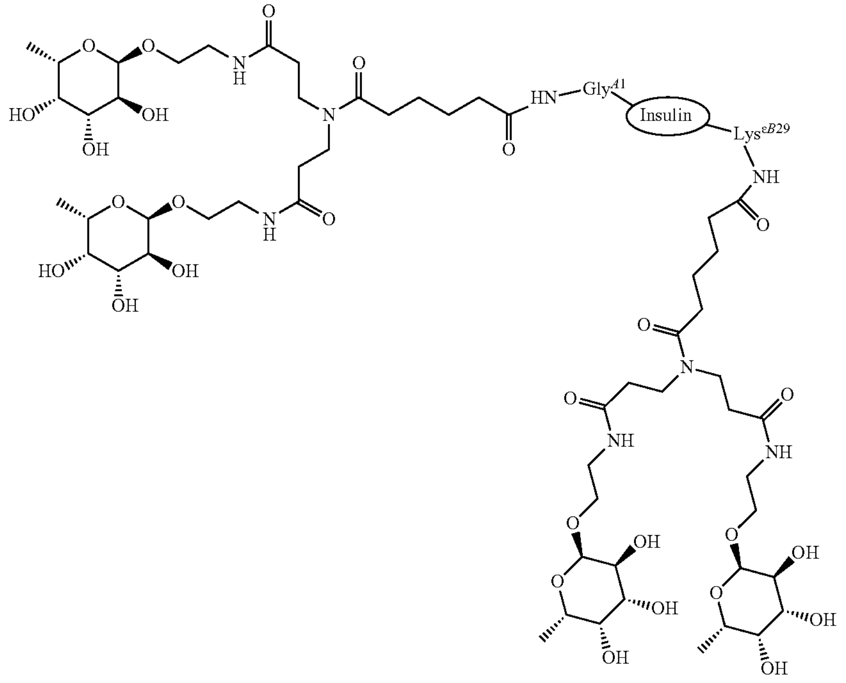
IOC-26
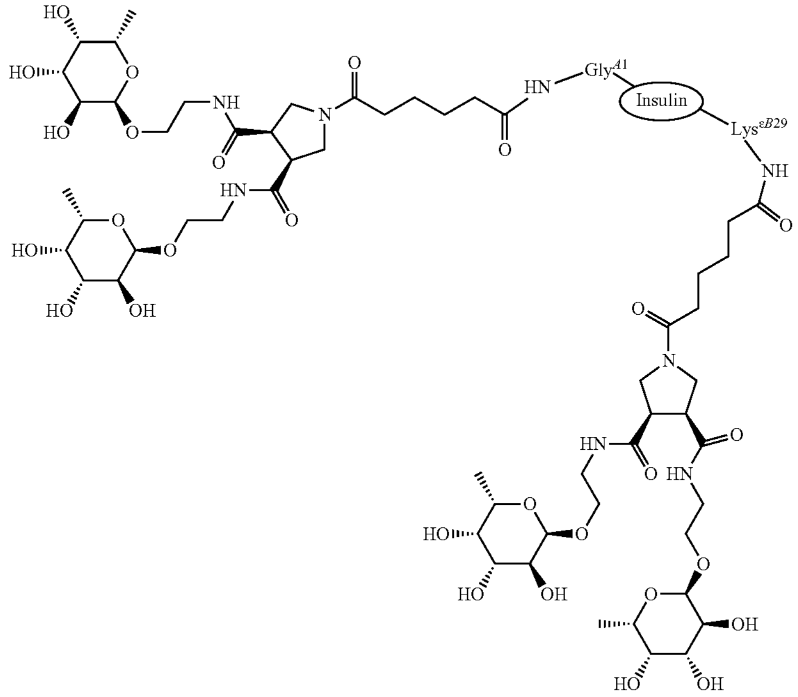

-continued
IOC-27
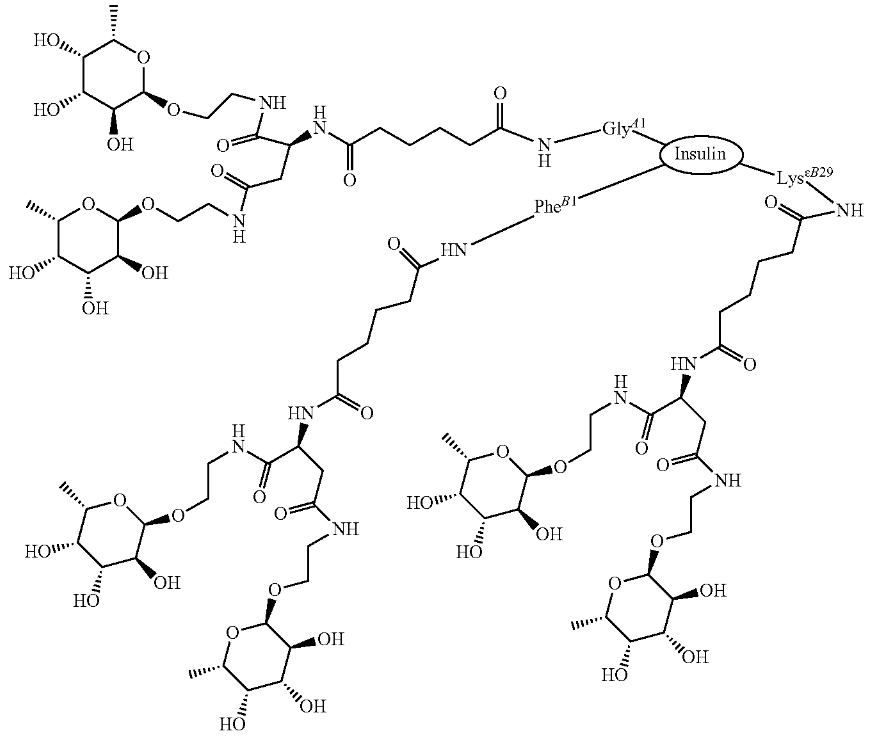
IOC-28
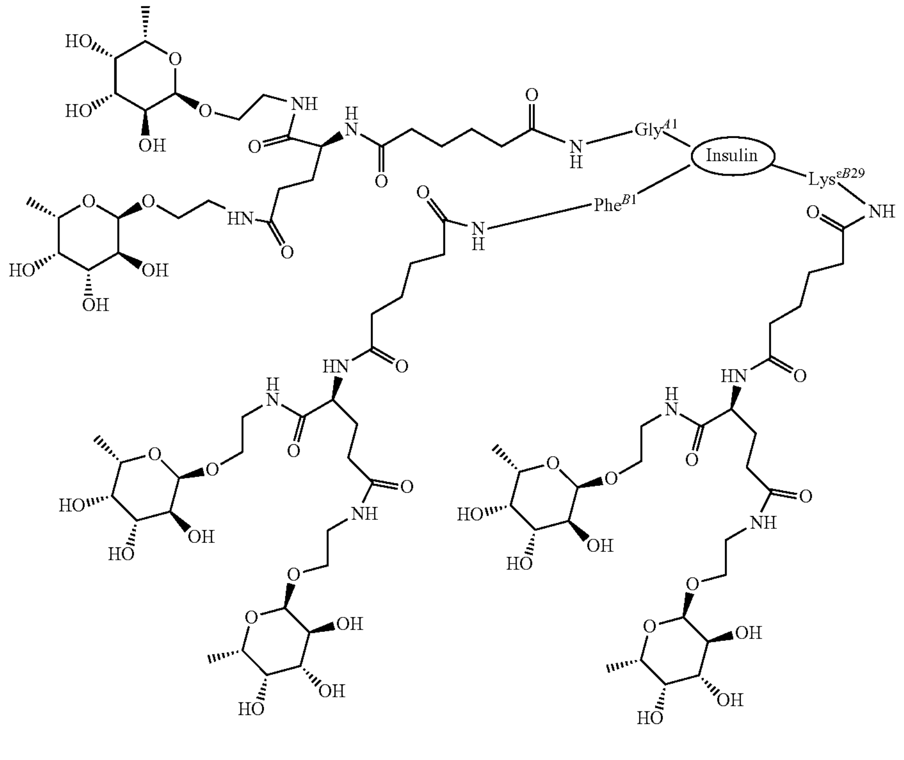

-continued
IOC-29
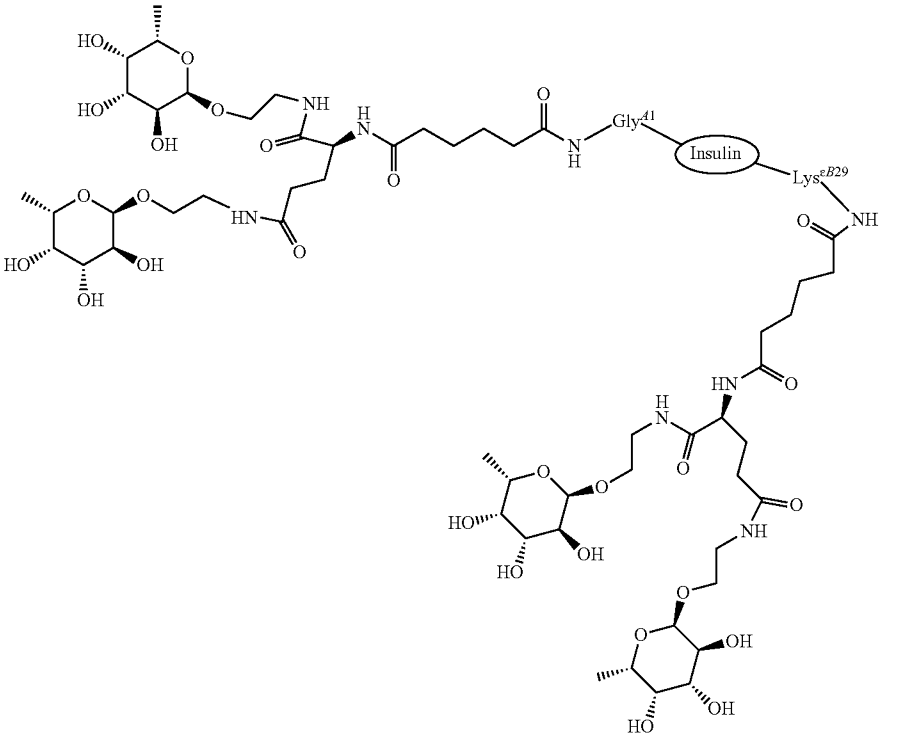
IOC-30
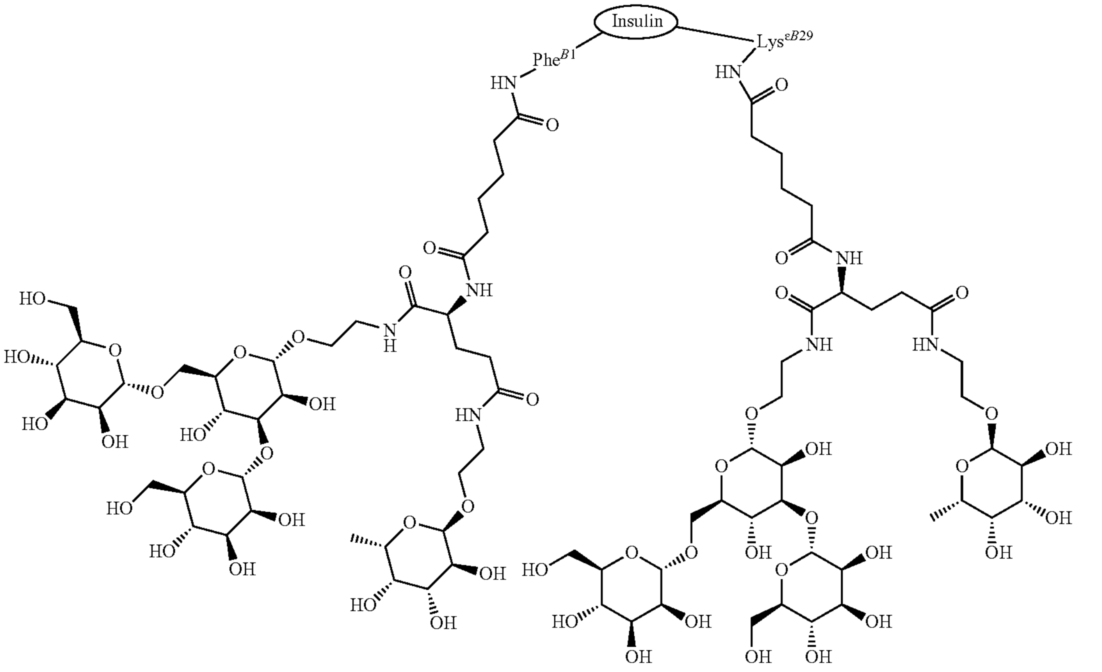

-continued
IOC-31
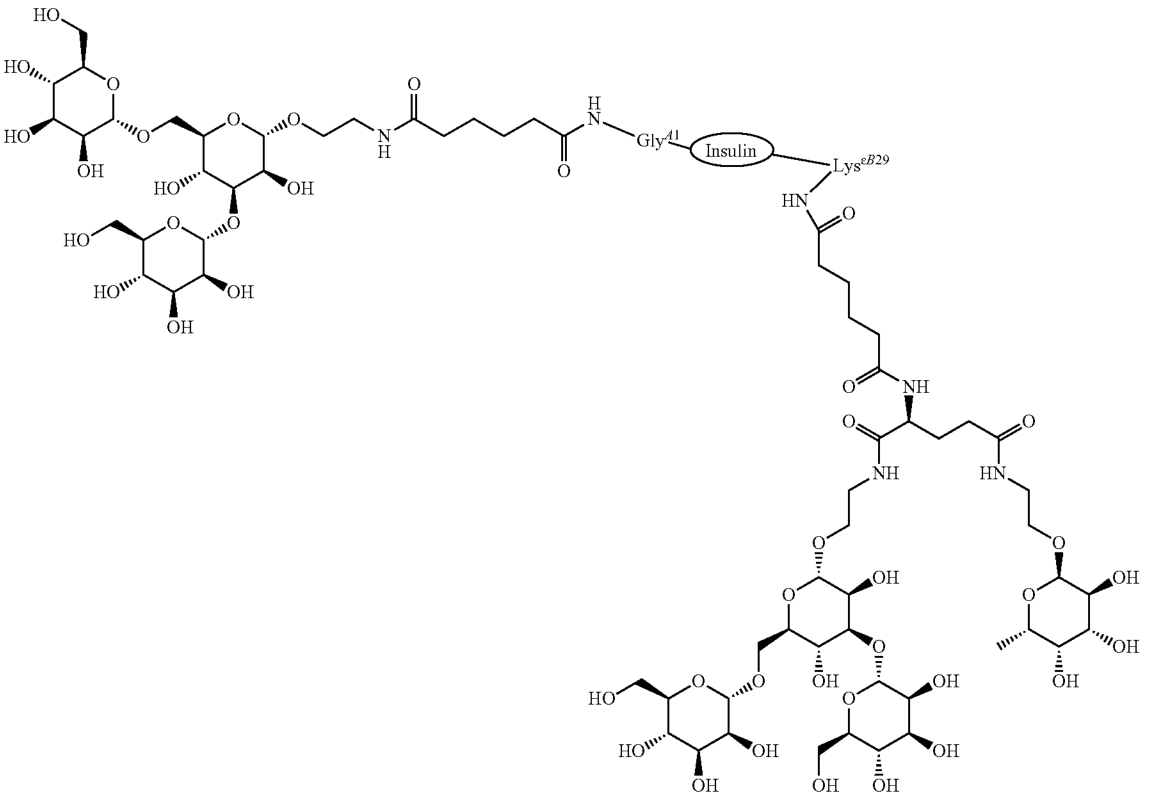
IOC-32
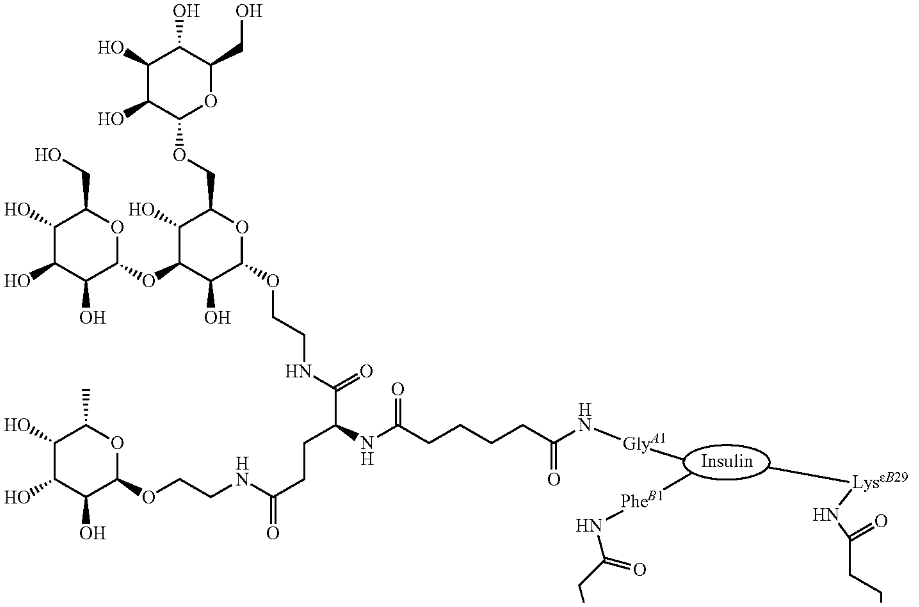

-continued
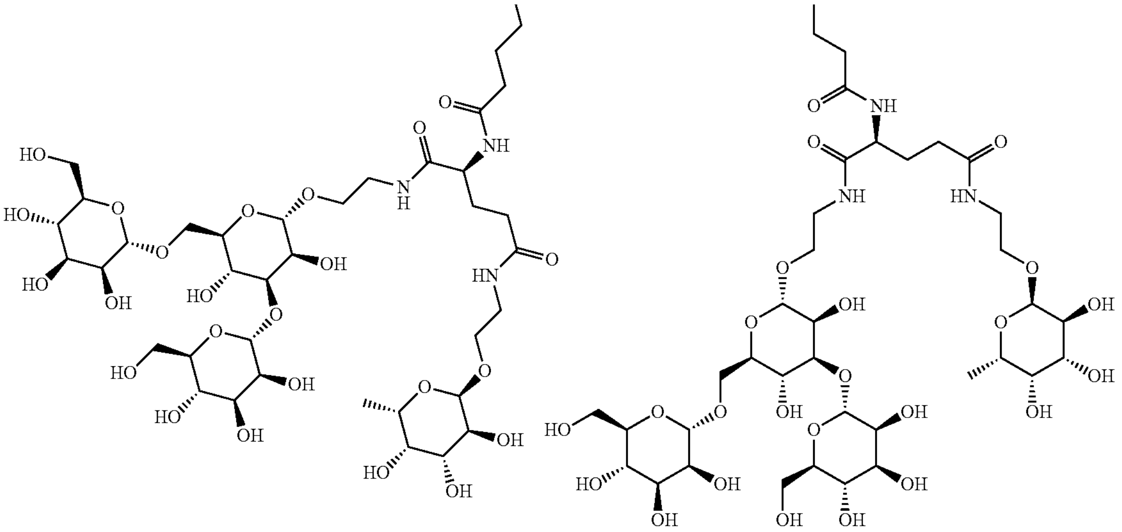
IOC-33
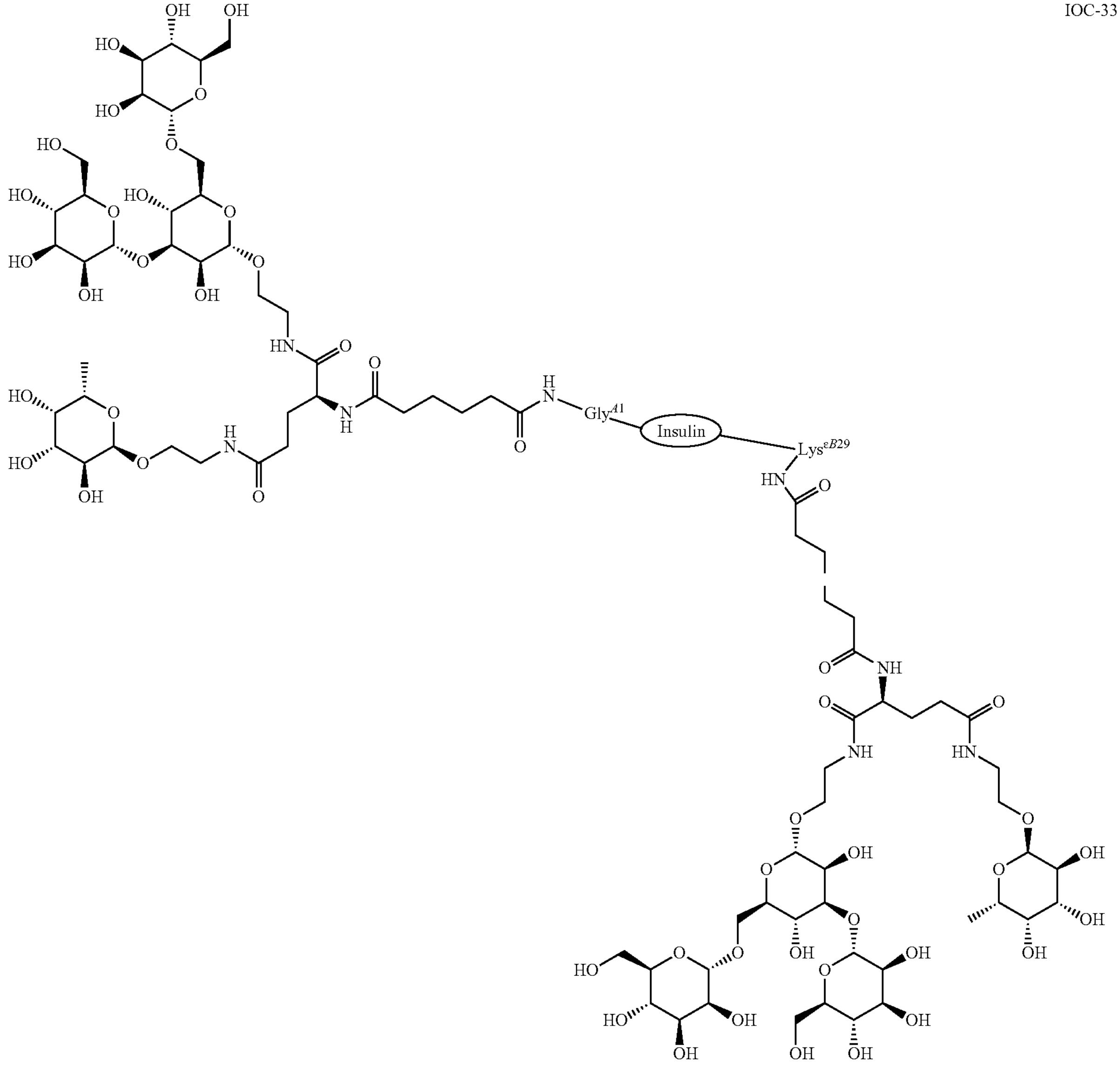

IOC-34
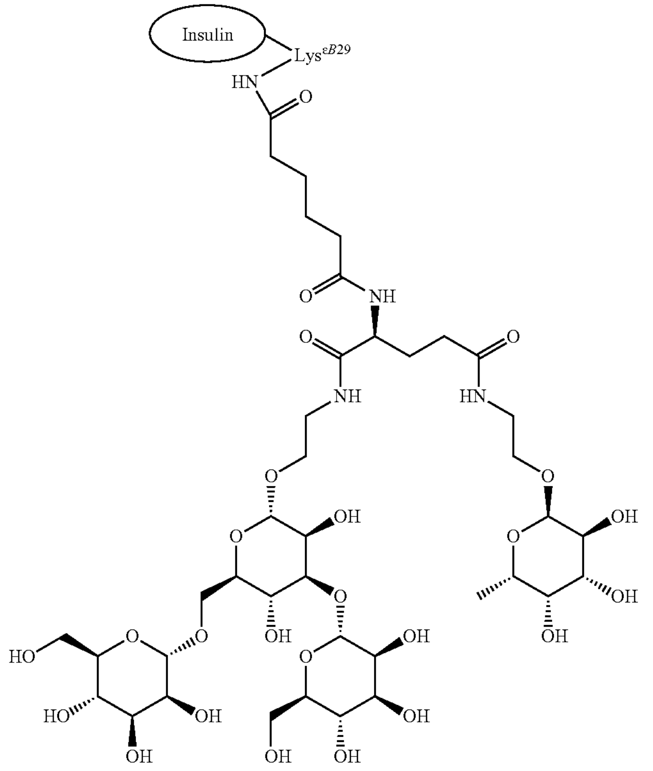
IOC-35
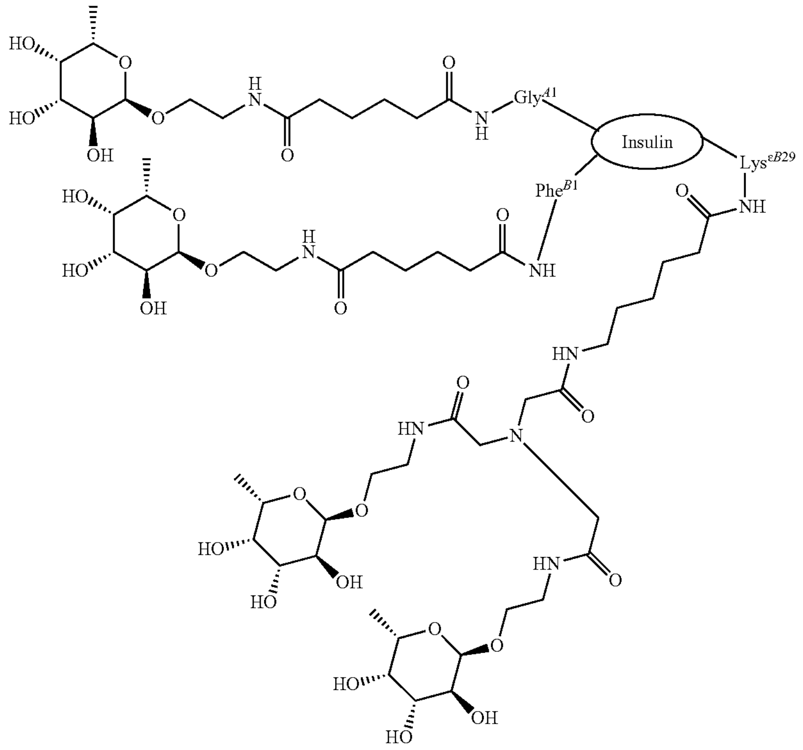

-continued
IOC-36
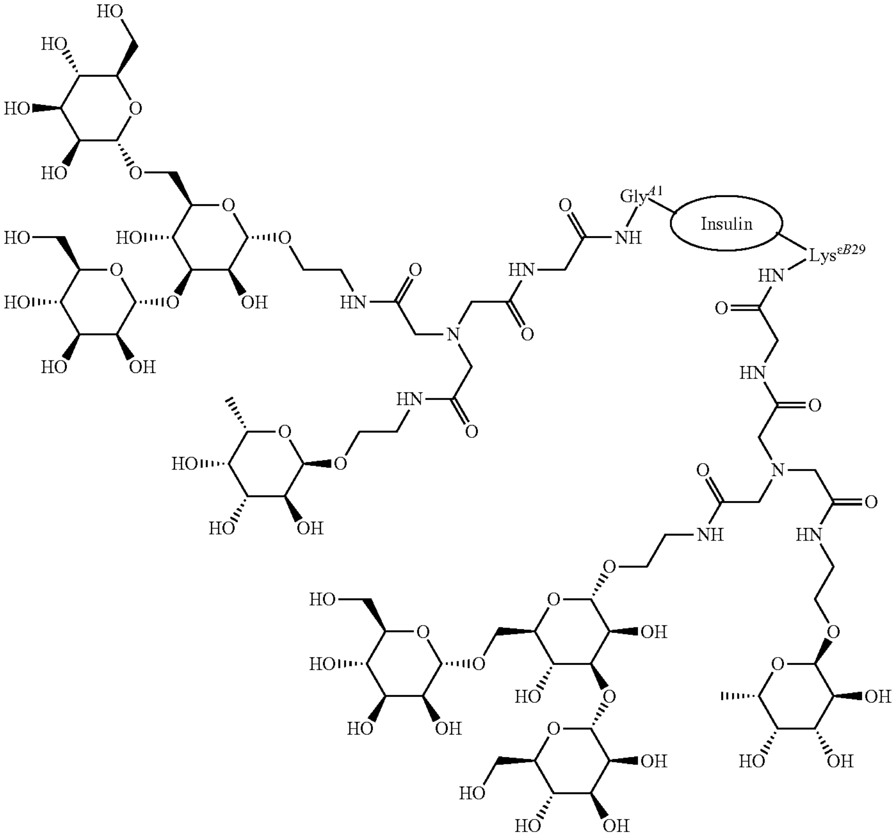
IOC-37
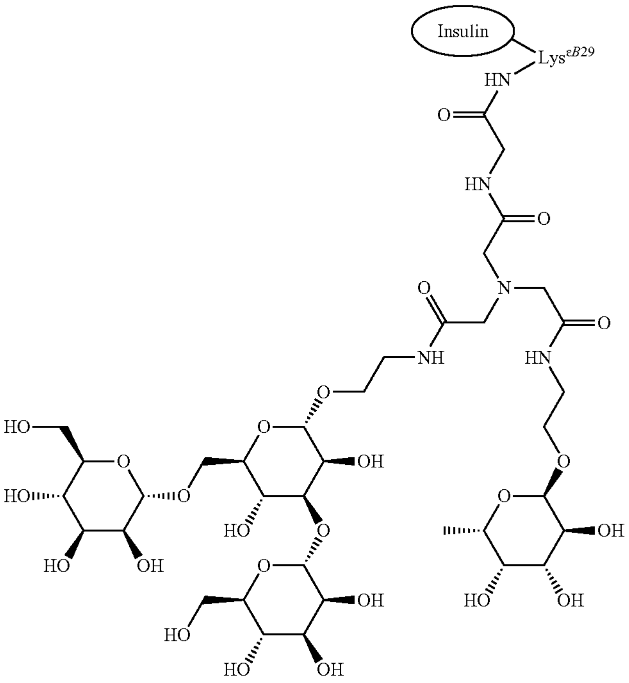

-continued
IOC-38
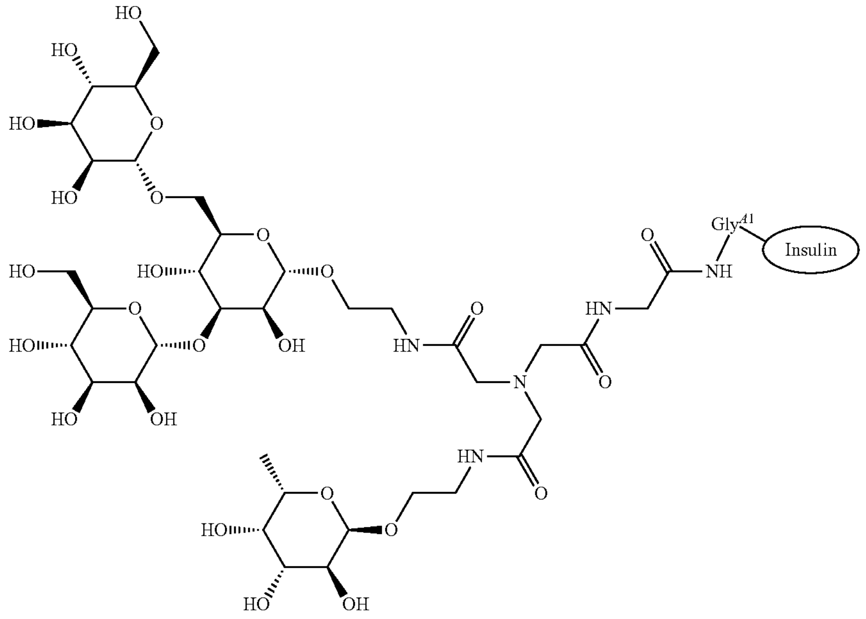
IOC-39
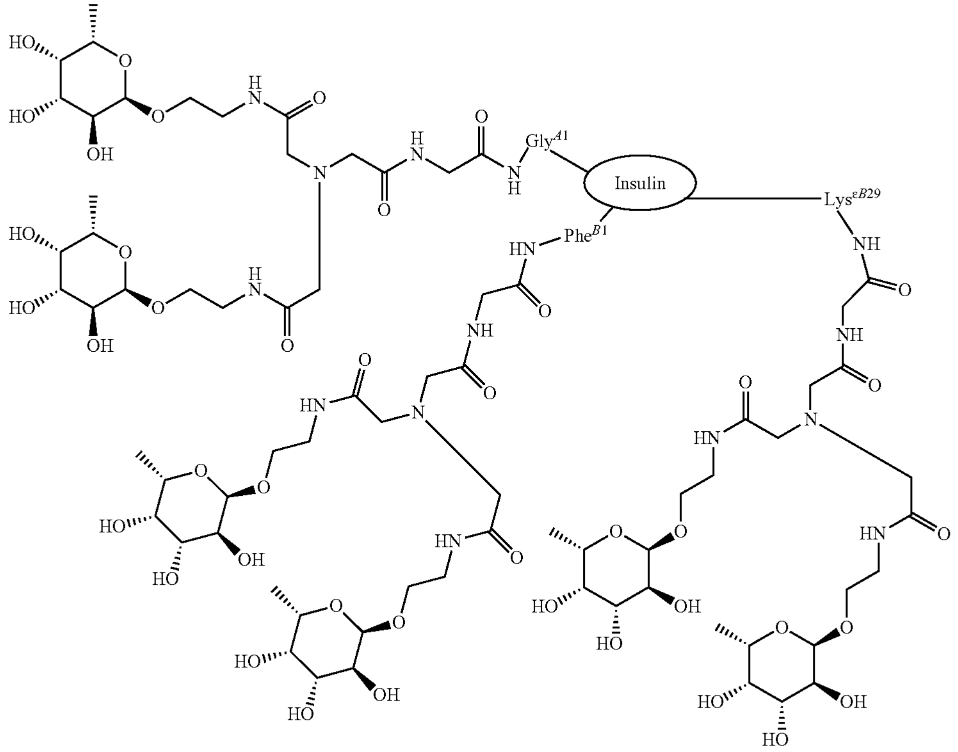

-continued
IOC-41
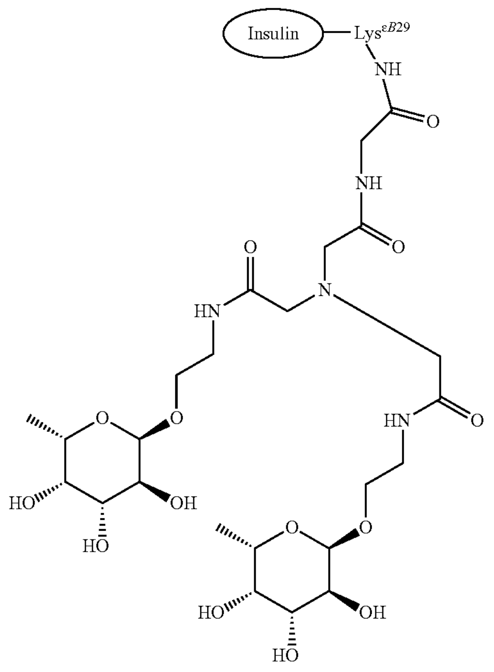
IOC-42
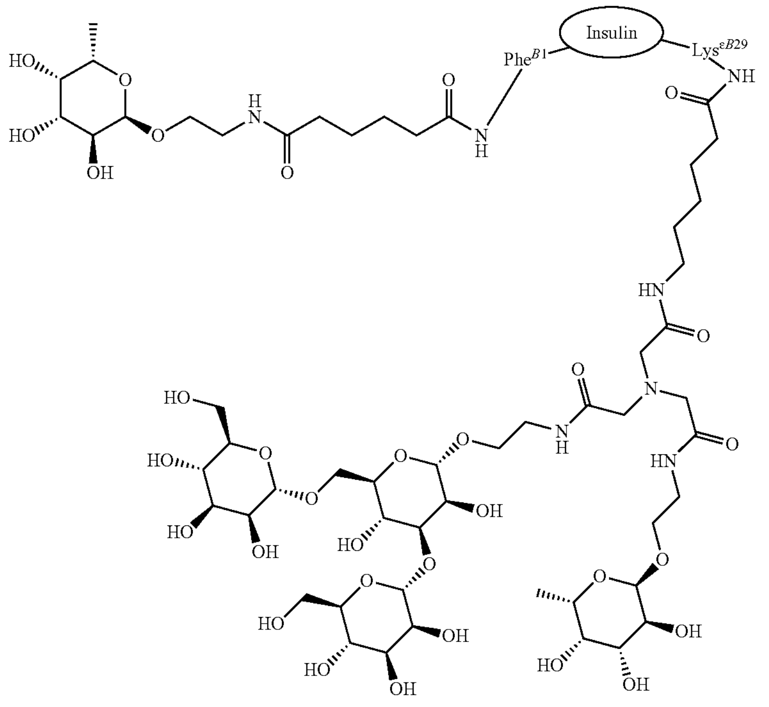

-continued
IOC-43
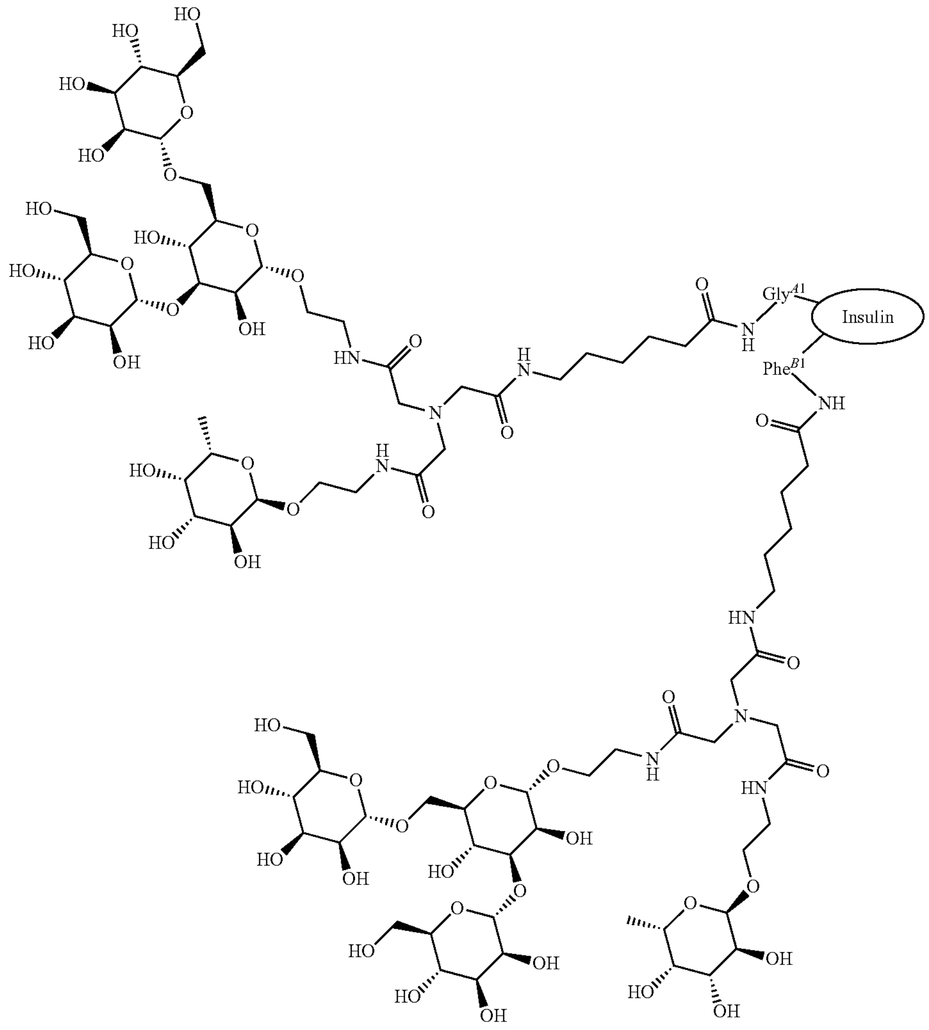

-continued
IOC-44
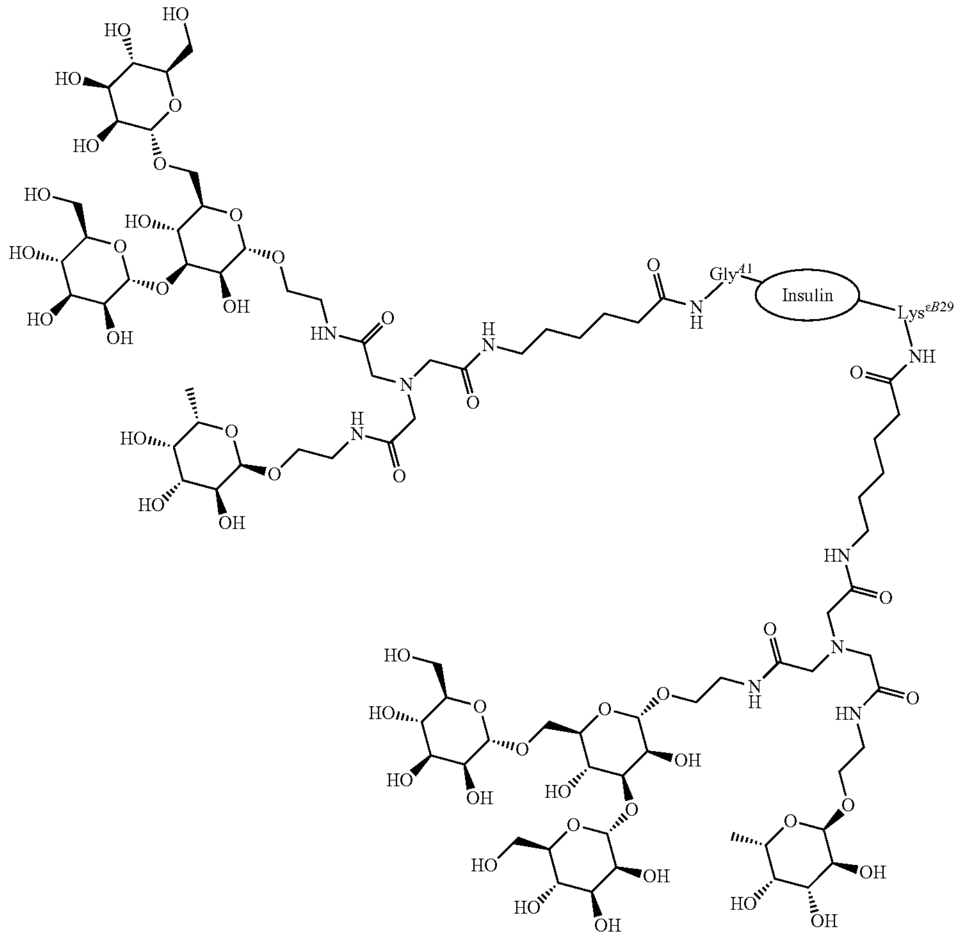
IOC-45
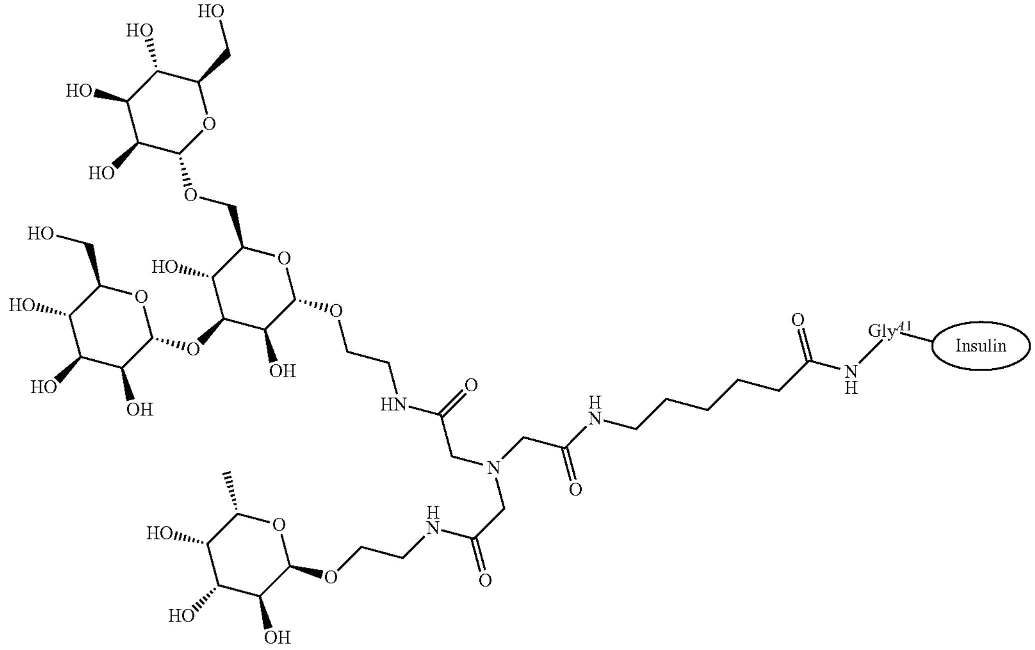

-continued
IOC-46
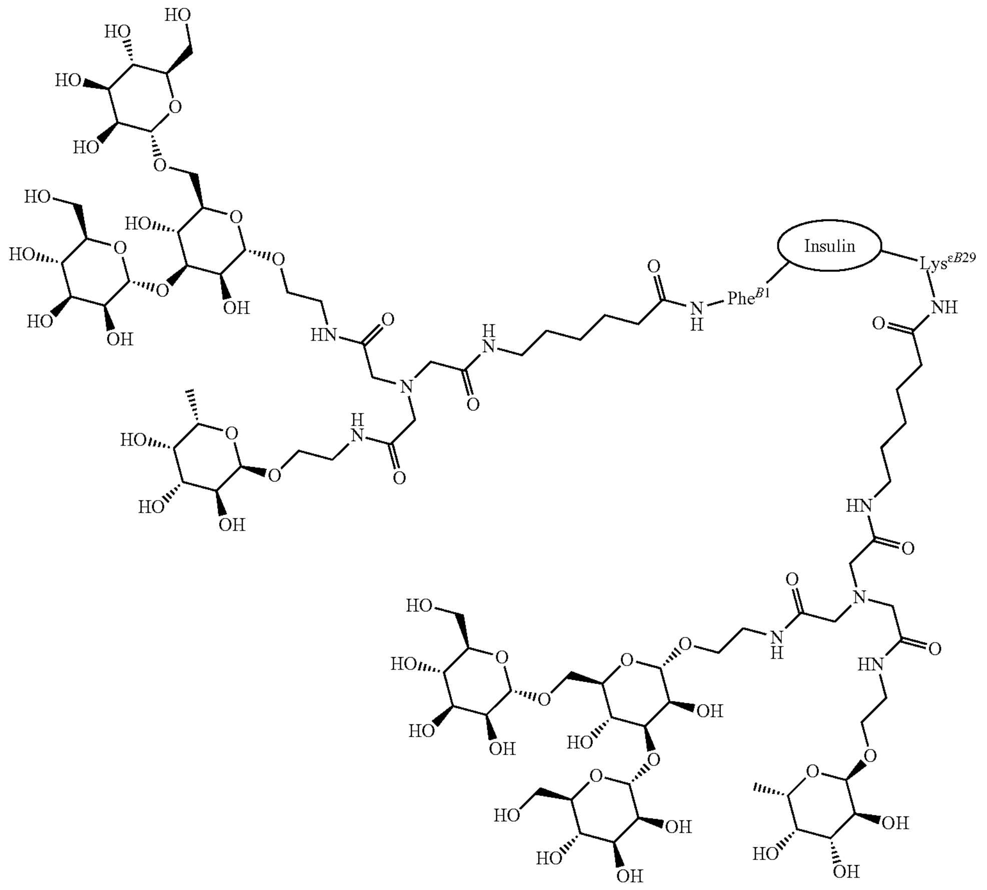
IOC-47
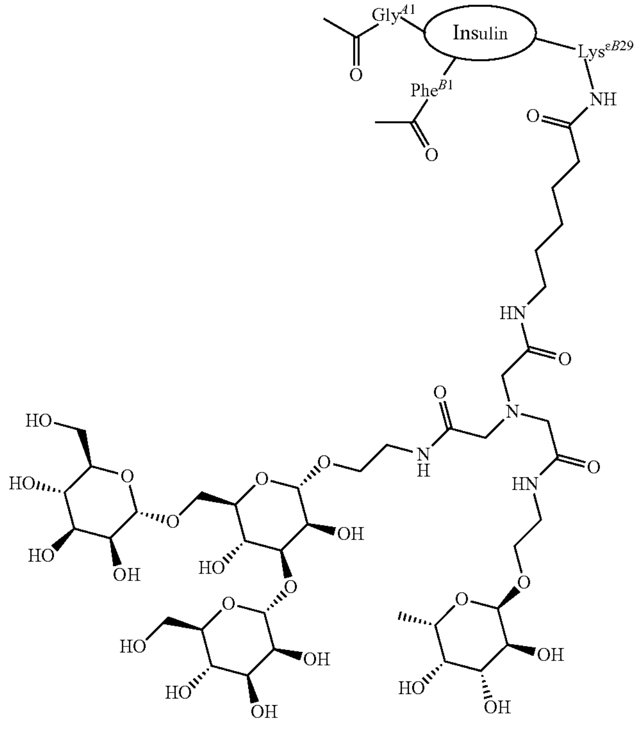

-continued
IOC-48
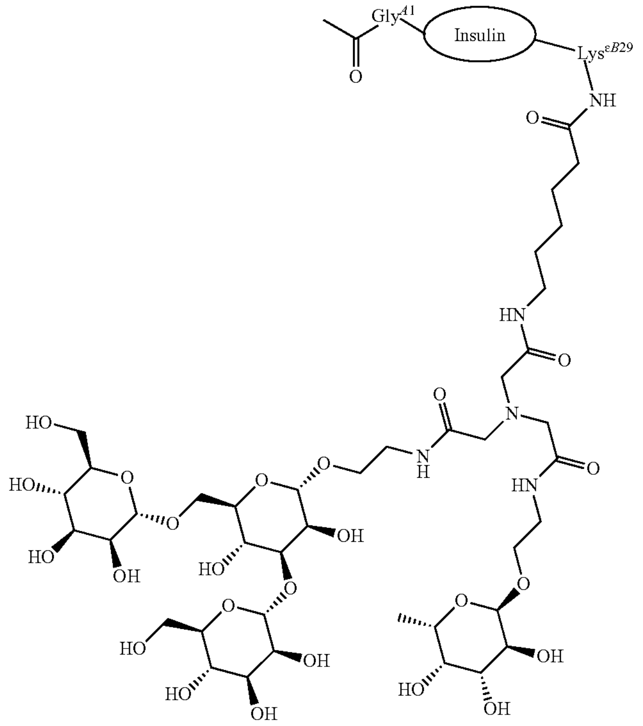
IOC-49
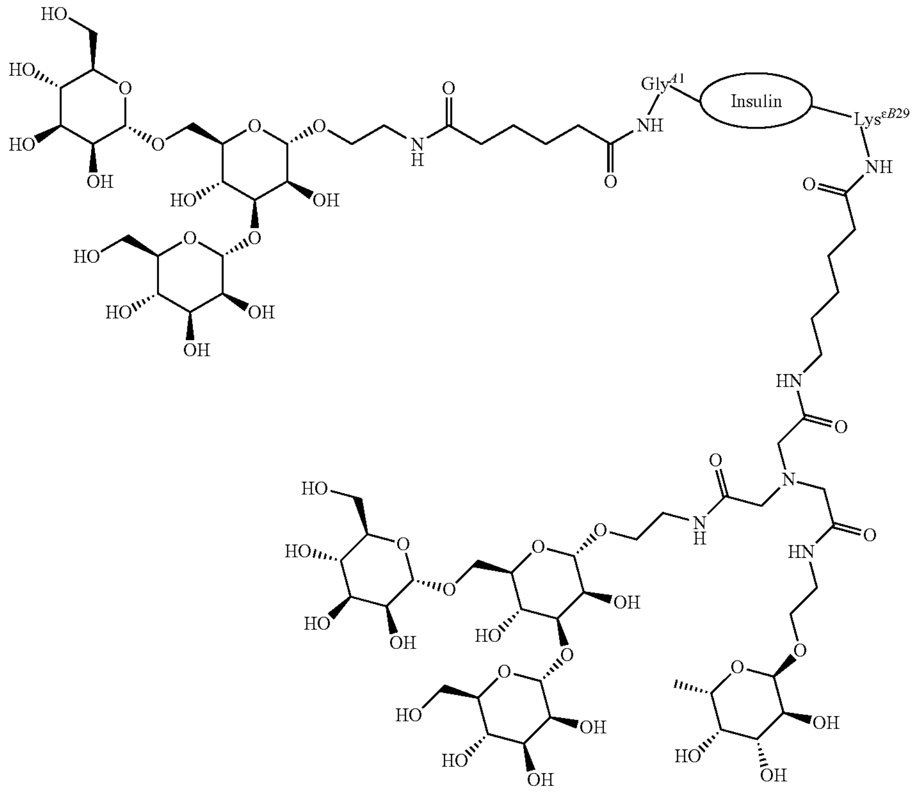

-continued
IOC-50
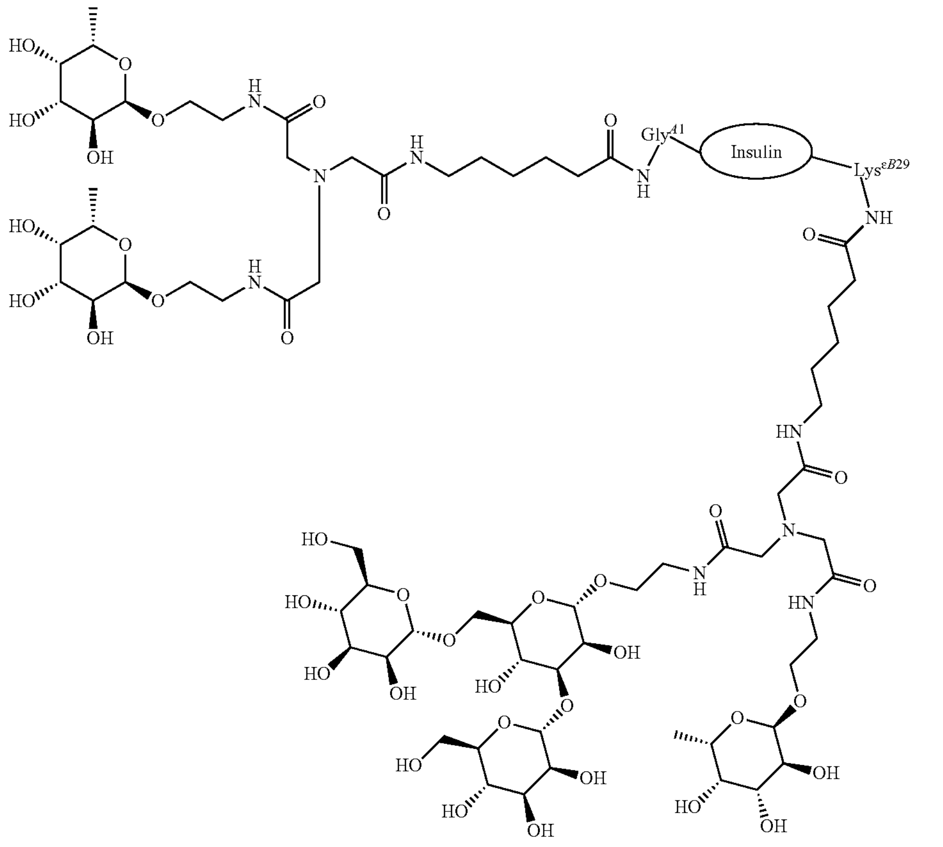
IOC-51
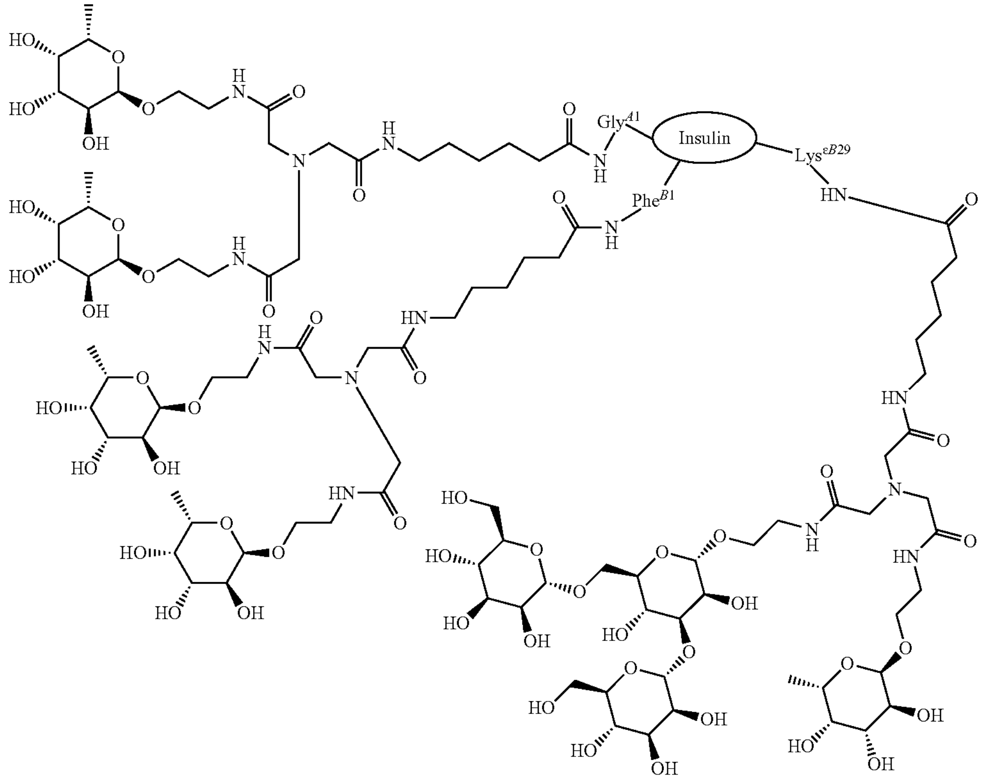

-continued
IOC-52
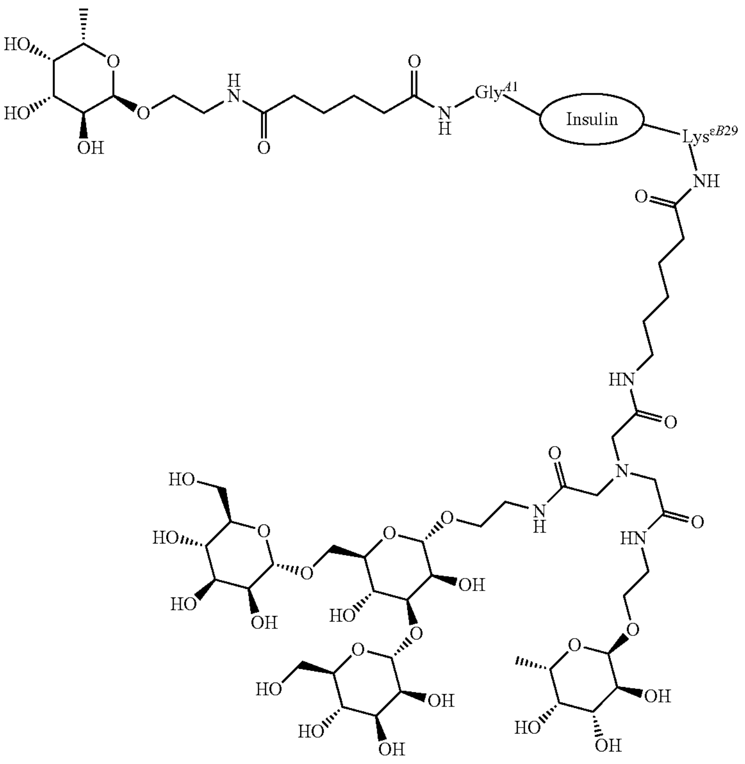
IOC-53
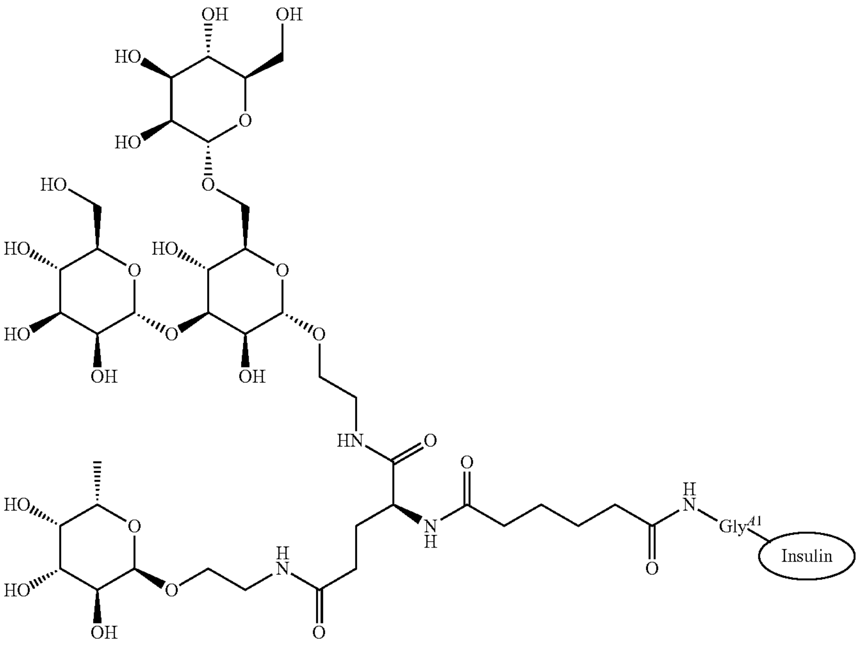

-continued
IOC-54
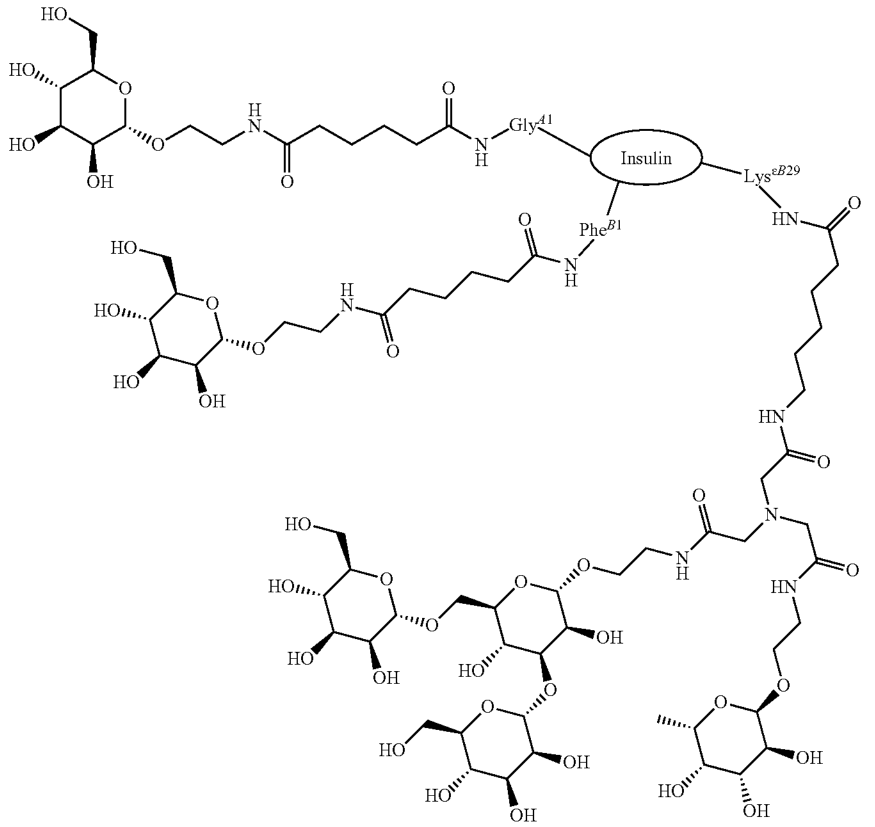
IOC-55
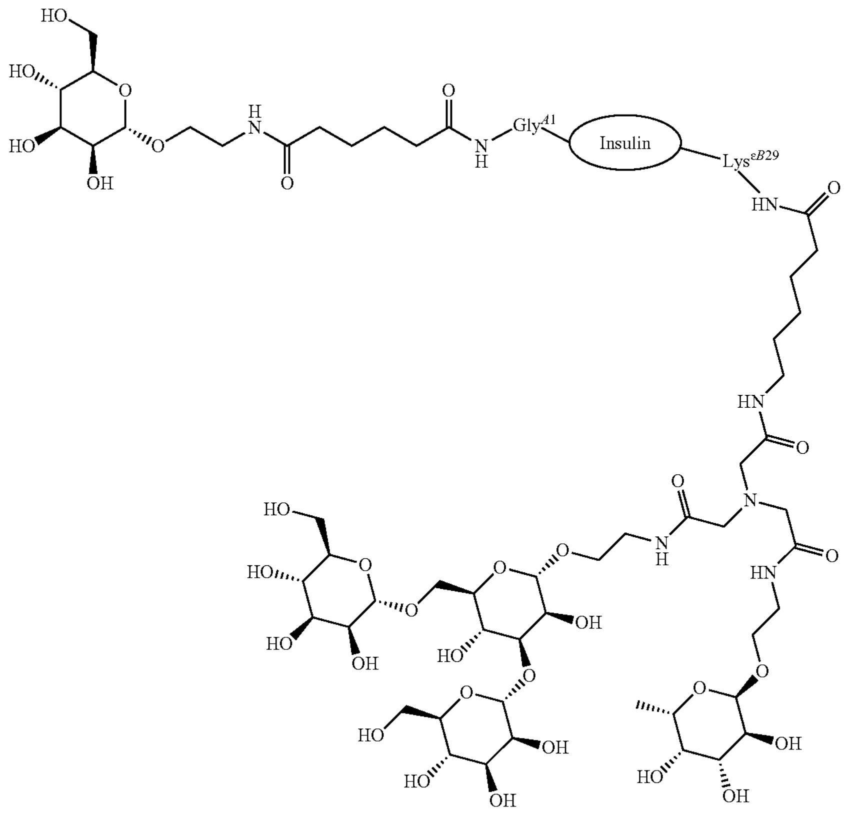

-continued
IOC-56
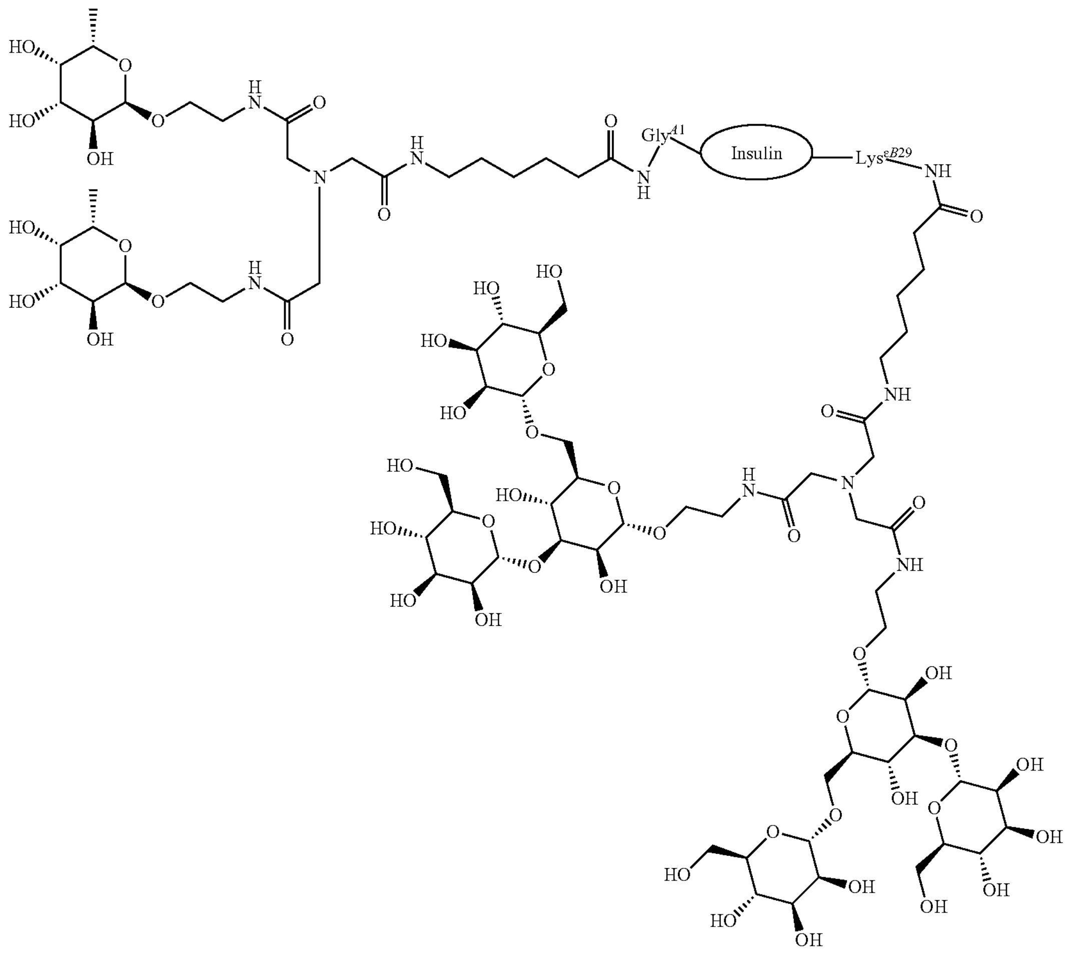

-continued
IOC-57
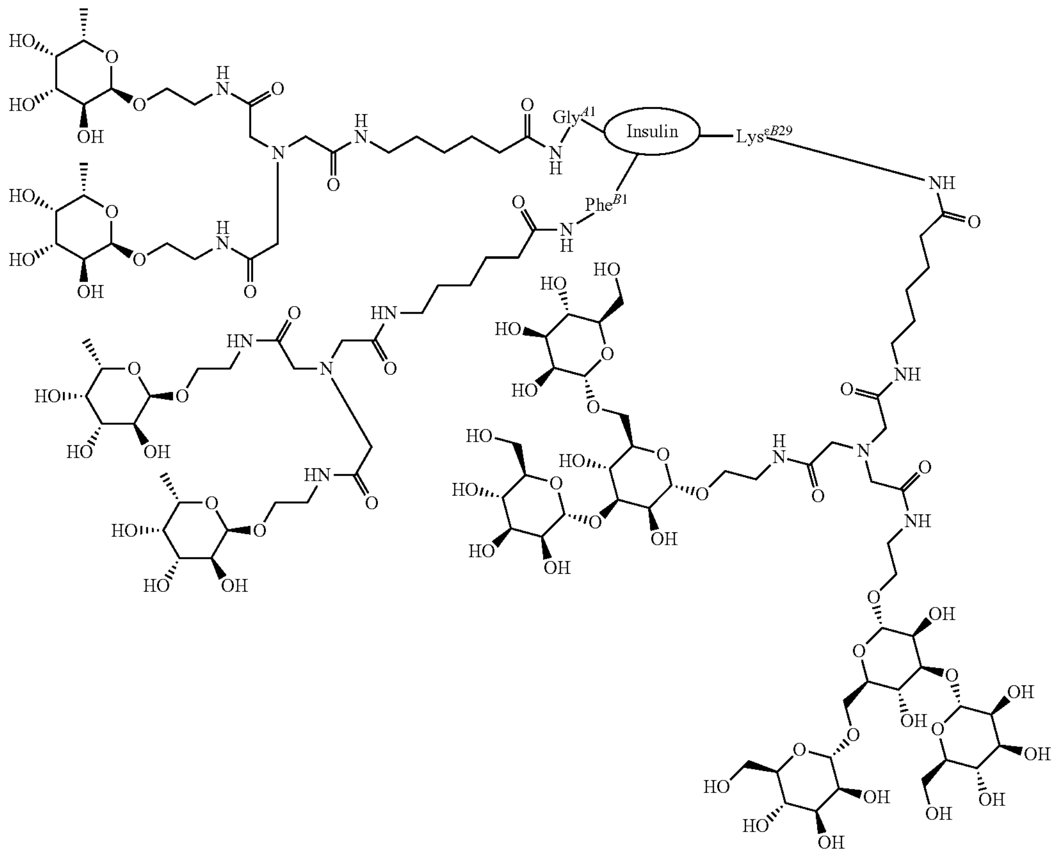
IOC-58
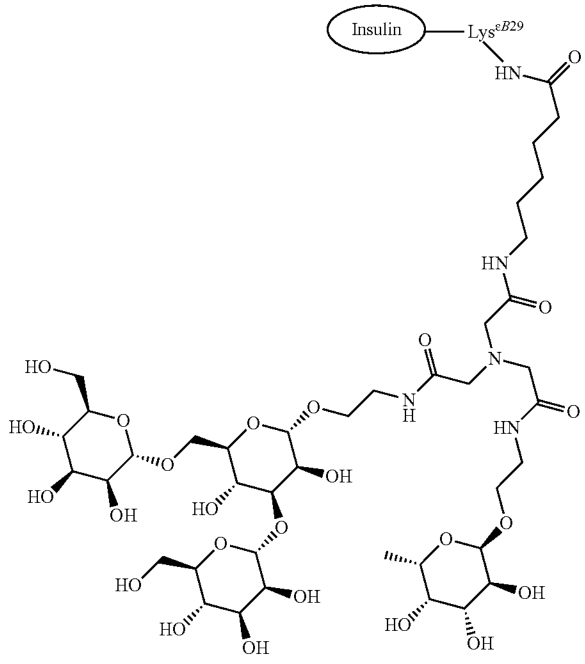

-continued
IOC-59
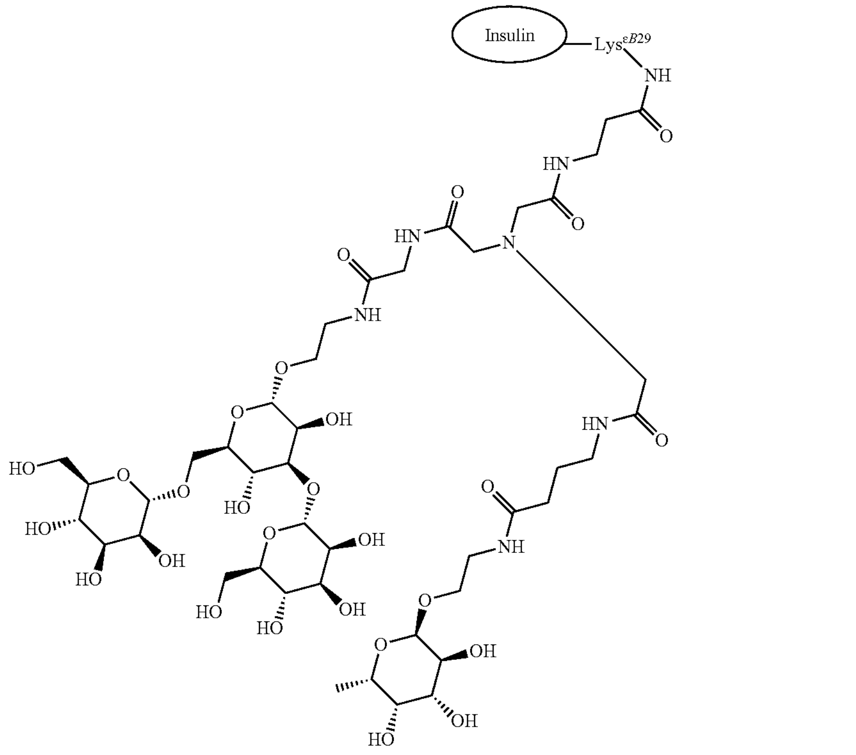
IOC-60
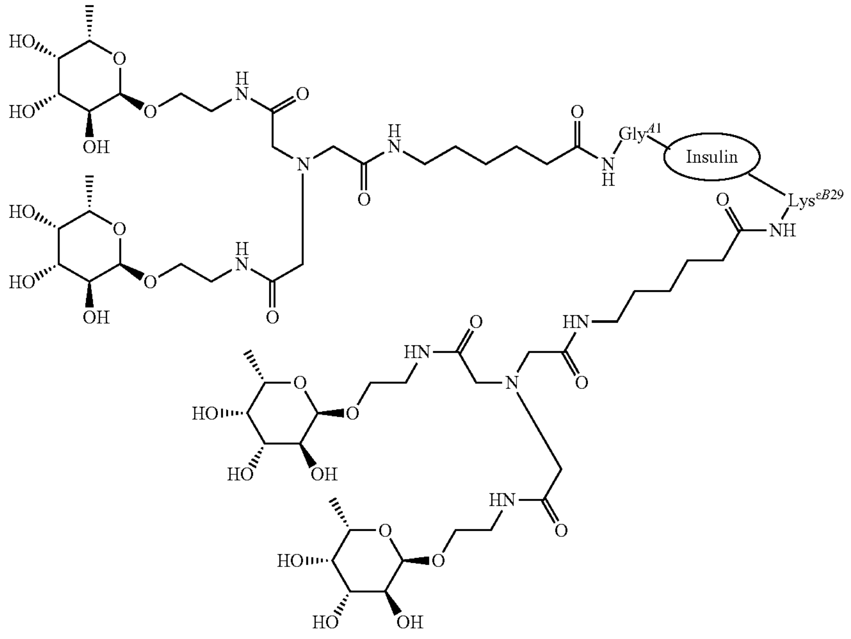

-continued
IOC-61
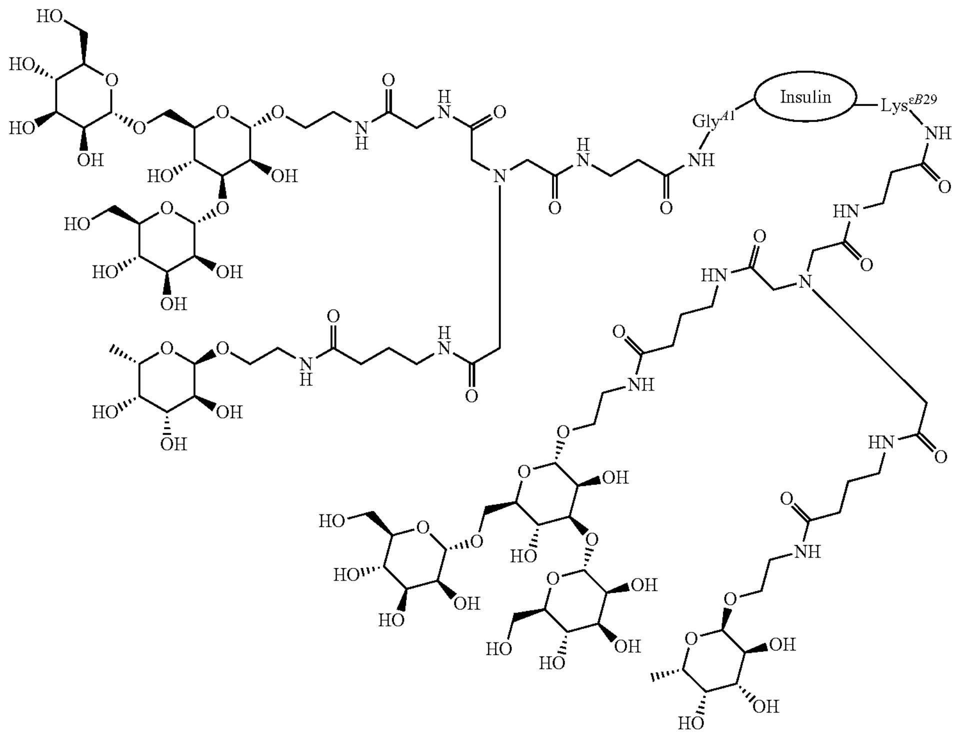
IOC-62
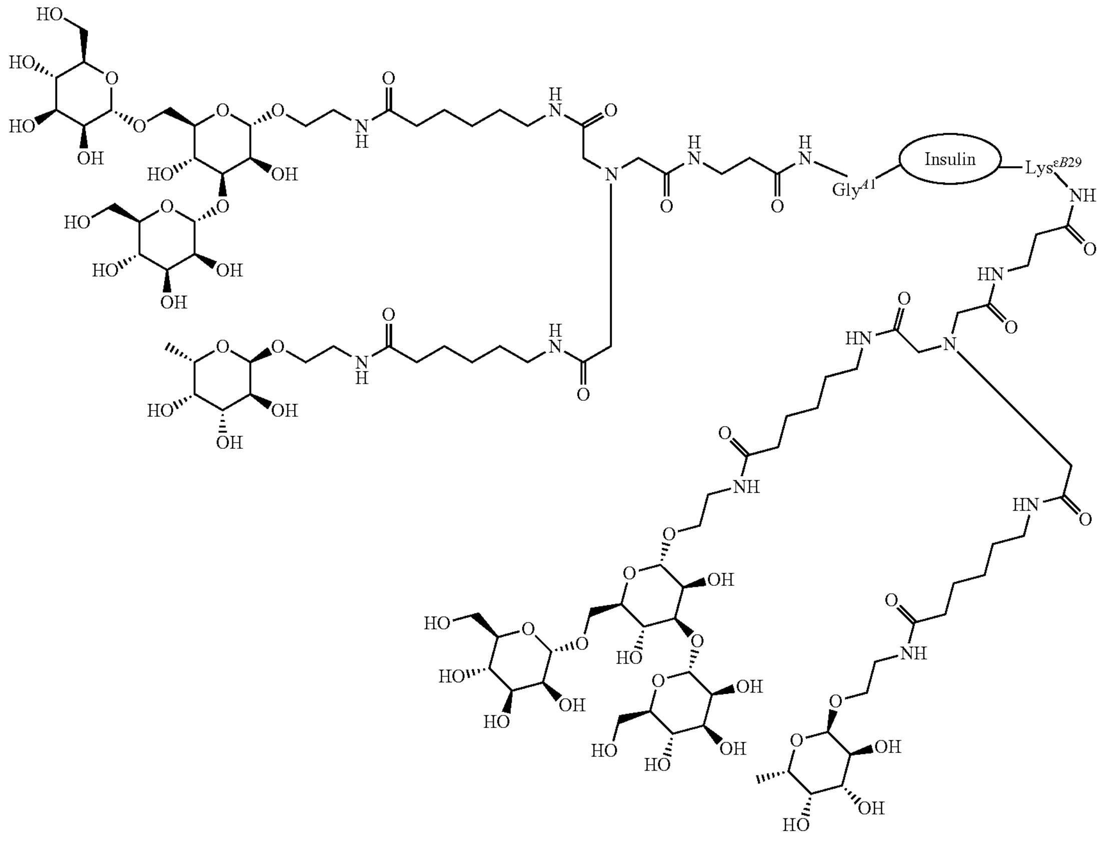

-continued
IOC-63
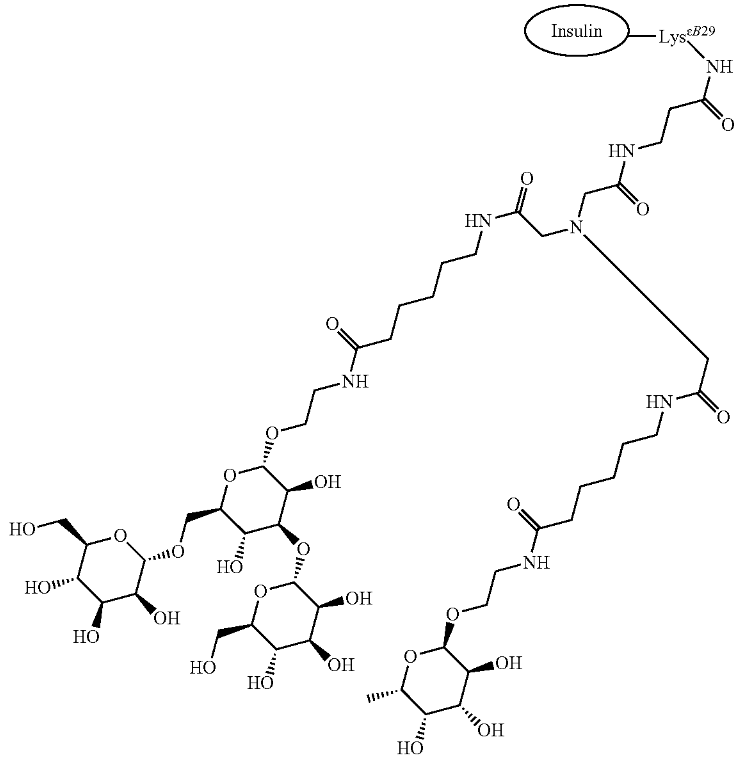
IOC-64
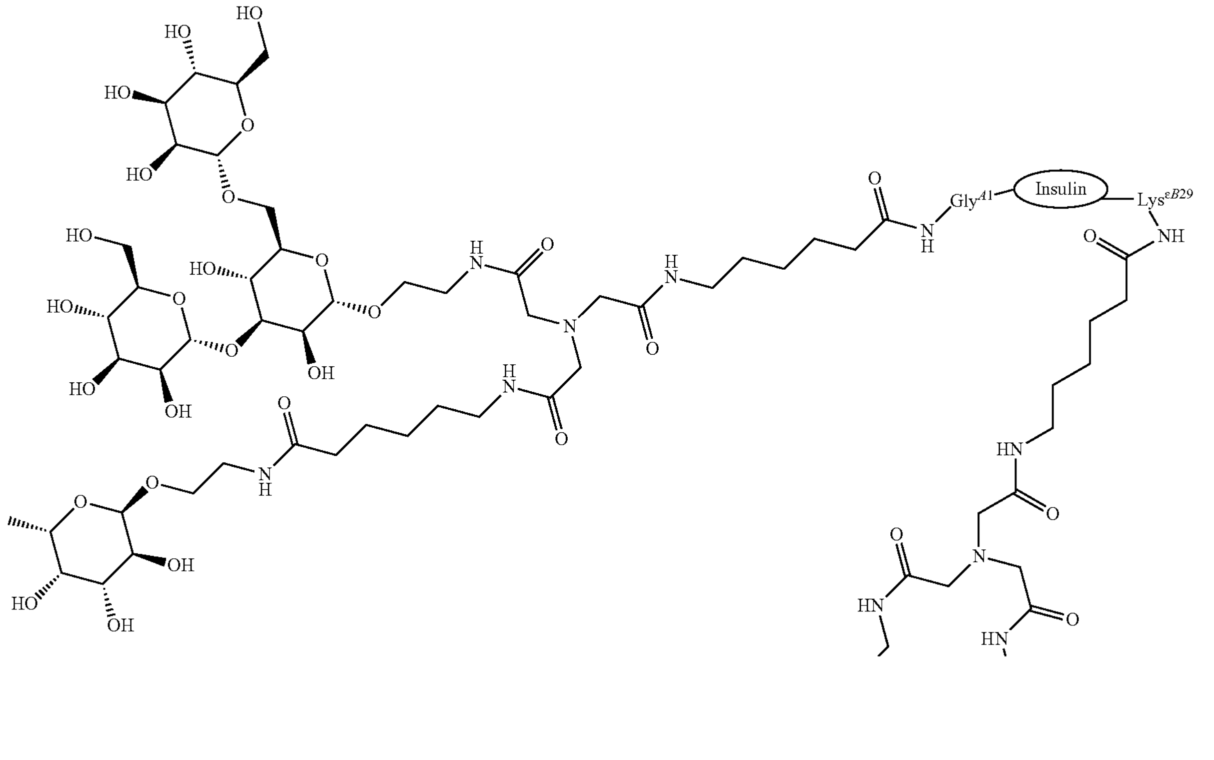

-continued
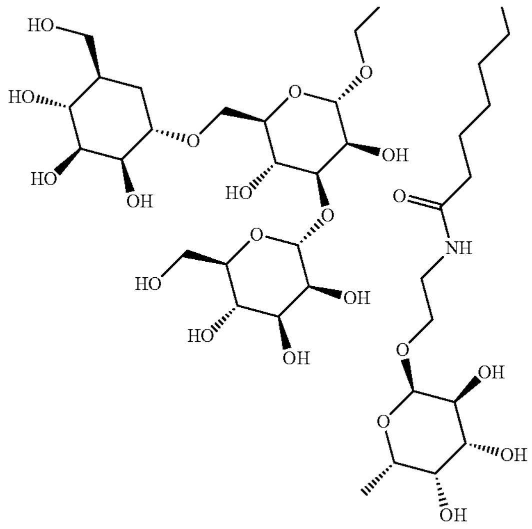
IOC-65
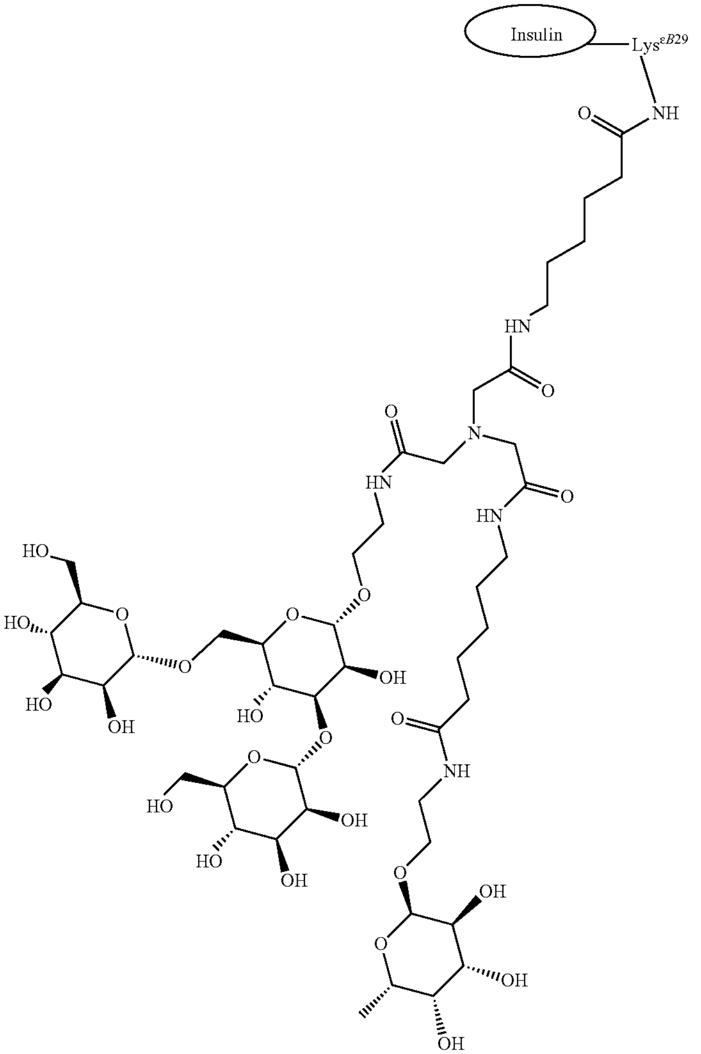

-continued
IOC-66
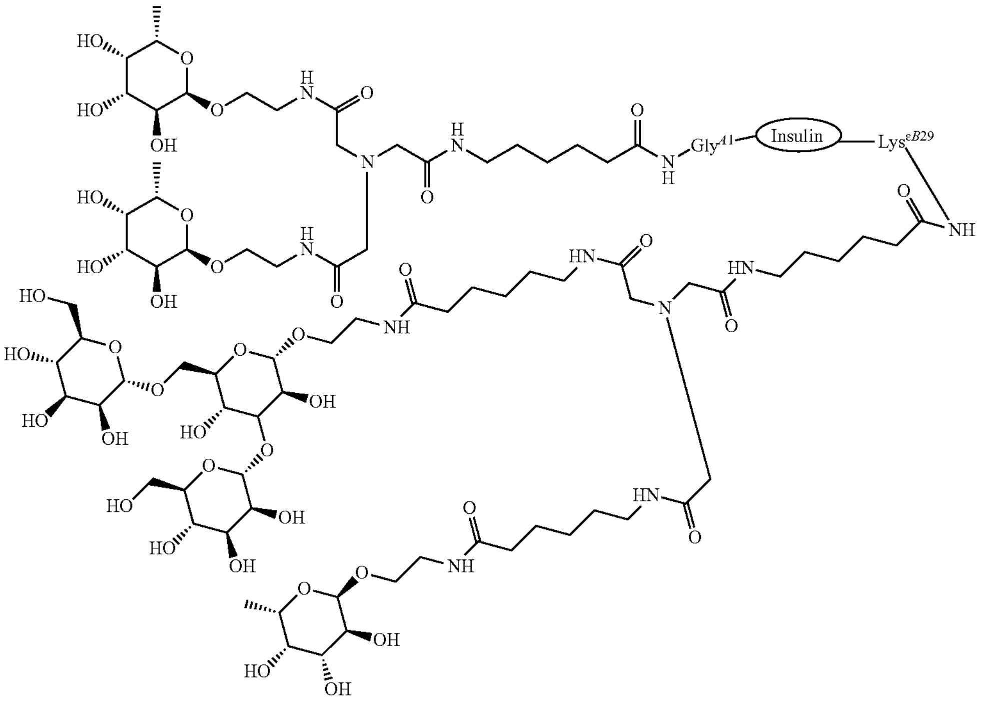
IOC-67
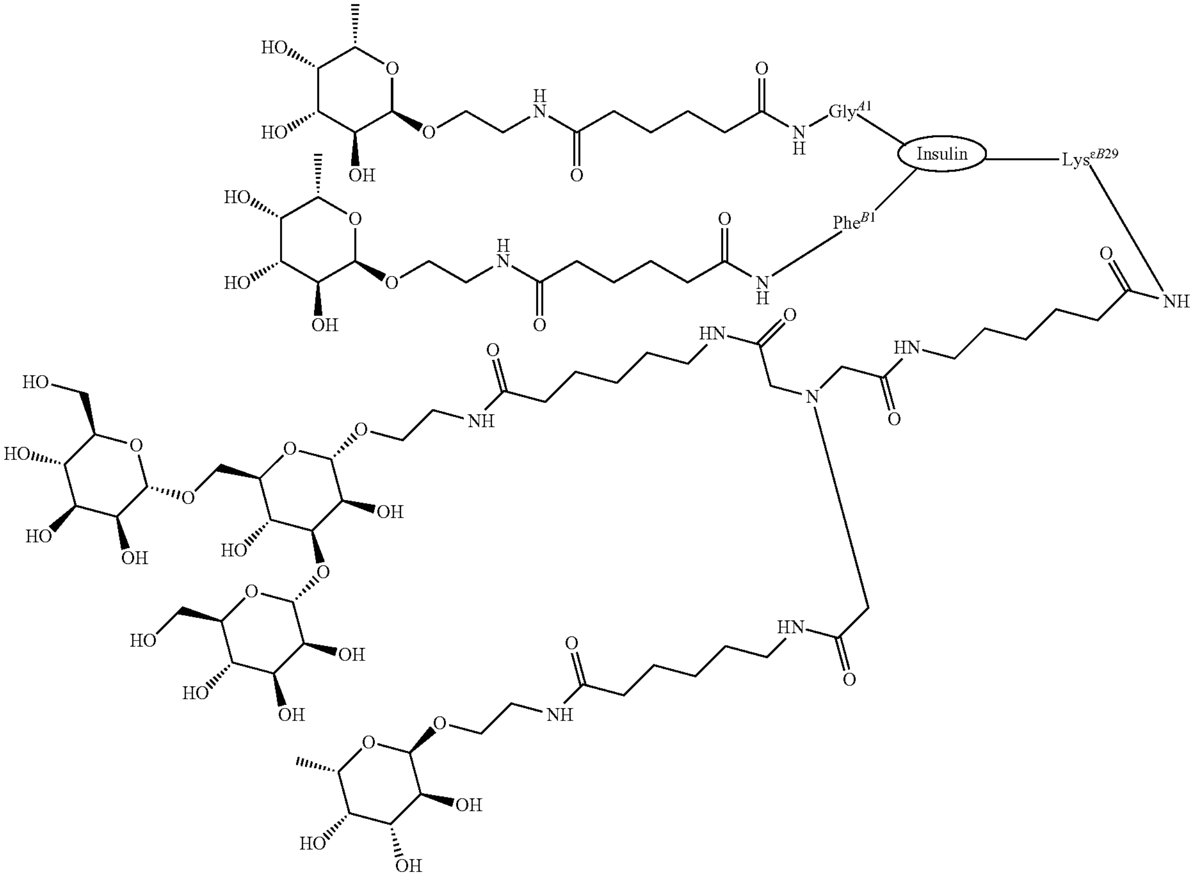

-continued
IOC-68
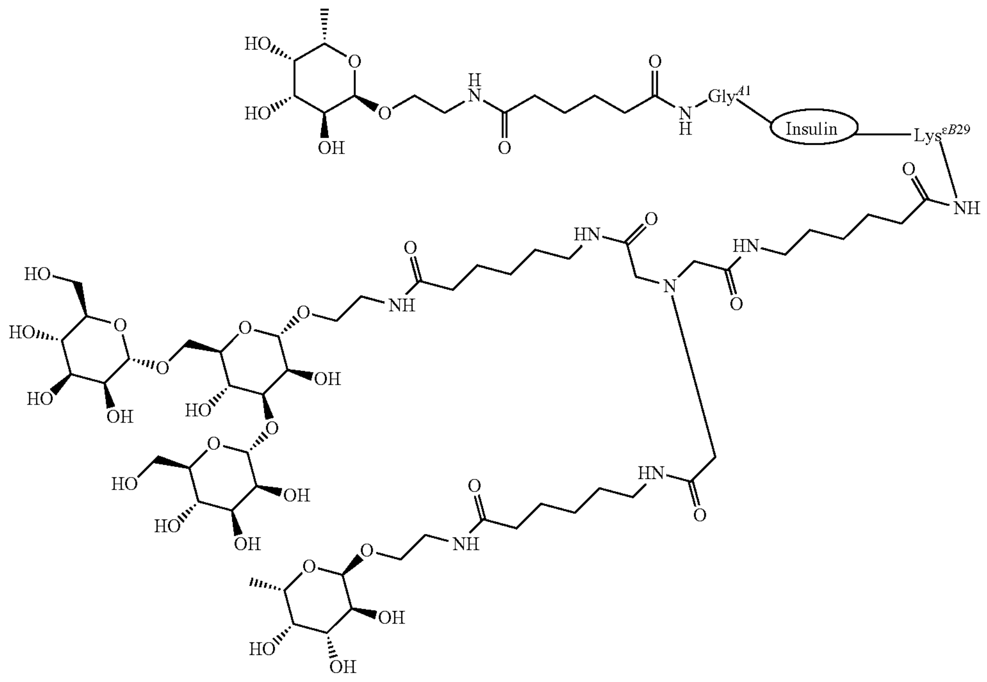
IOC-69
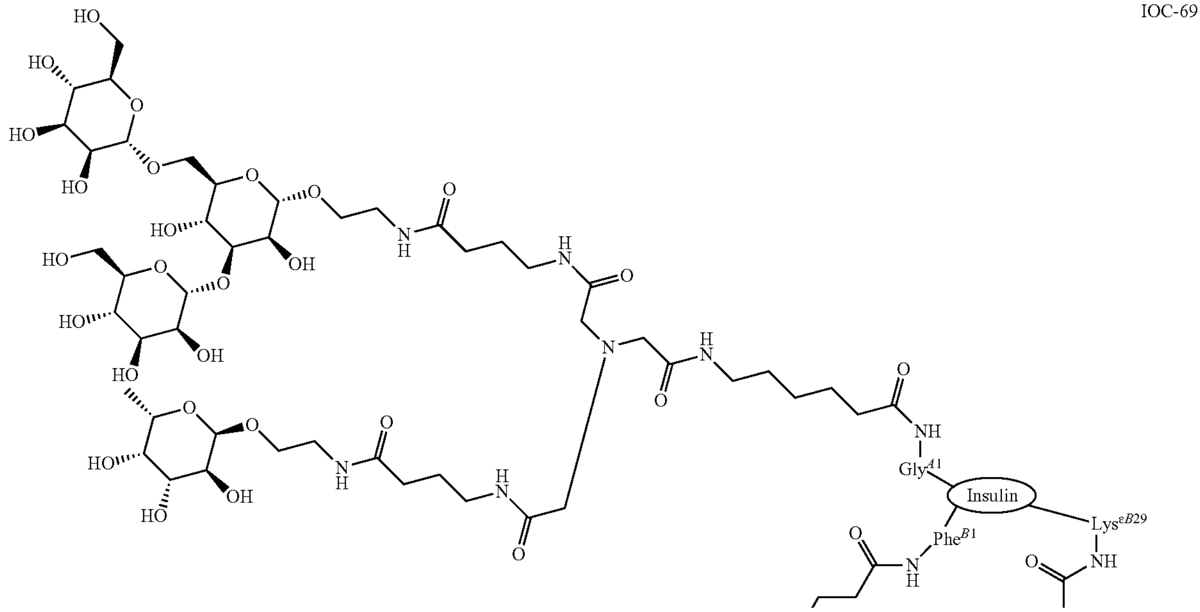

-continued
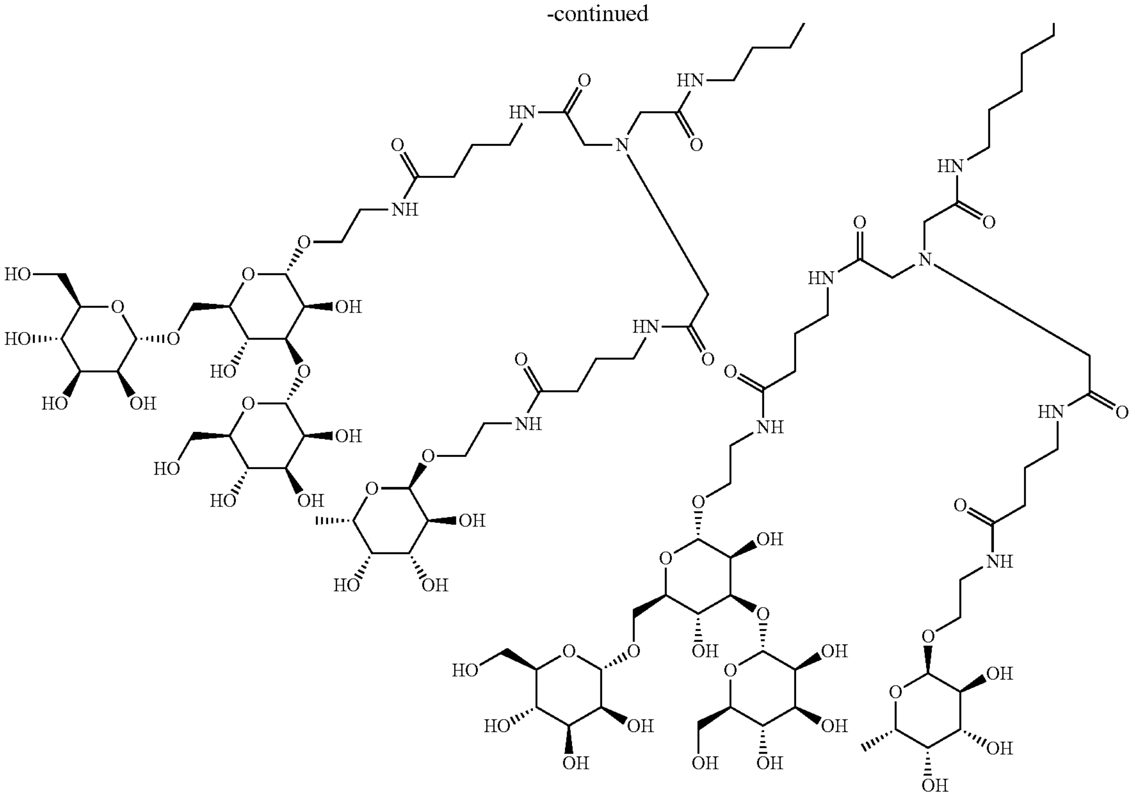
IOC-70
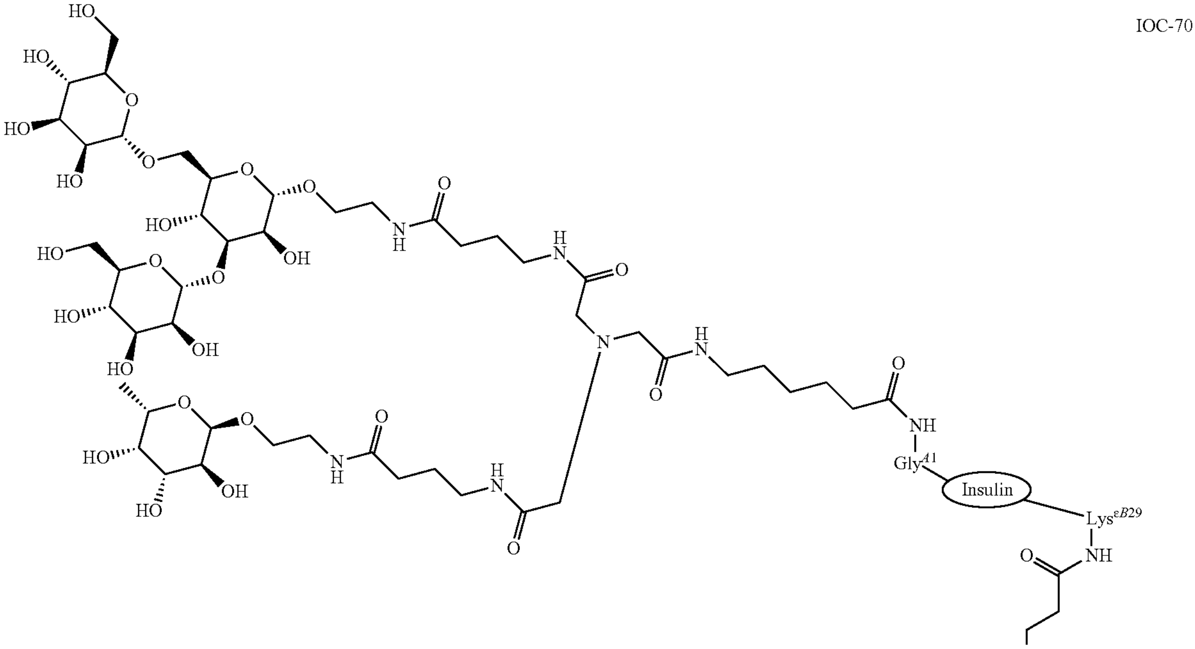

-continued
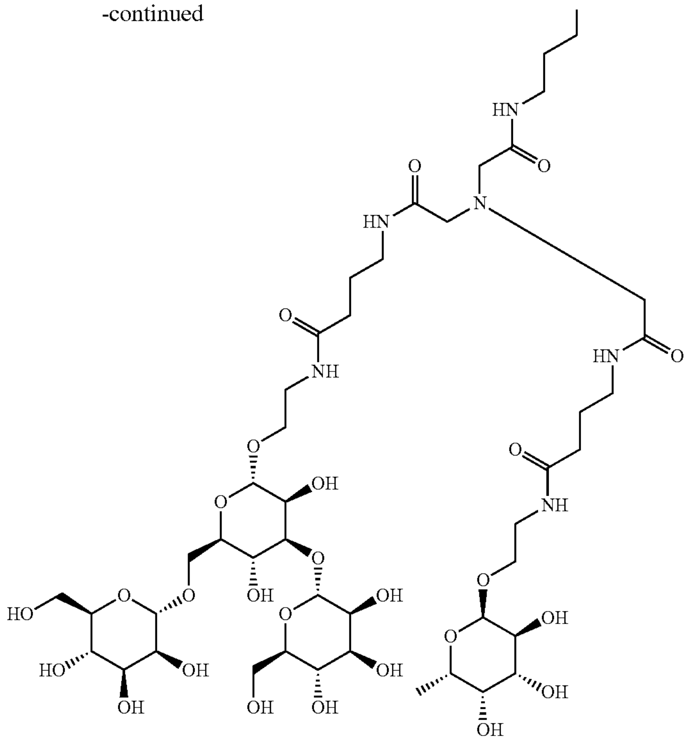
IOC-71
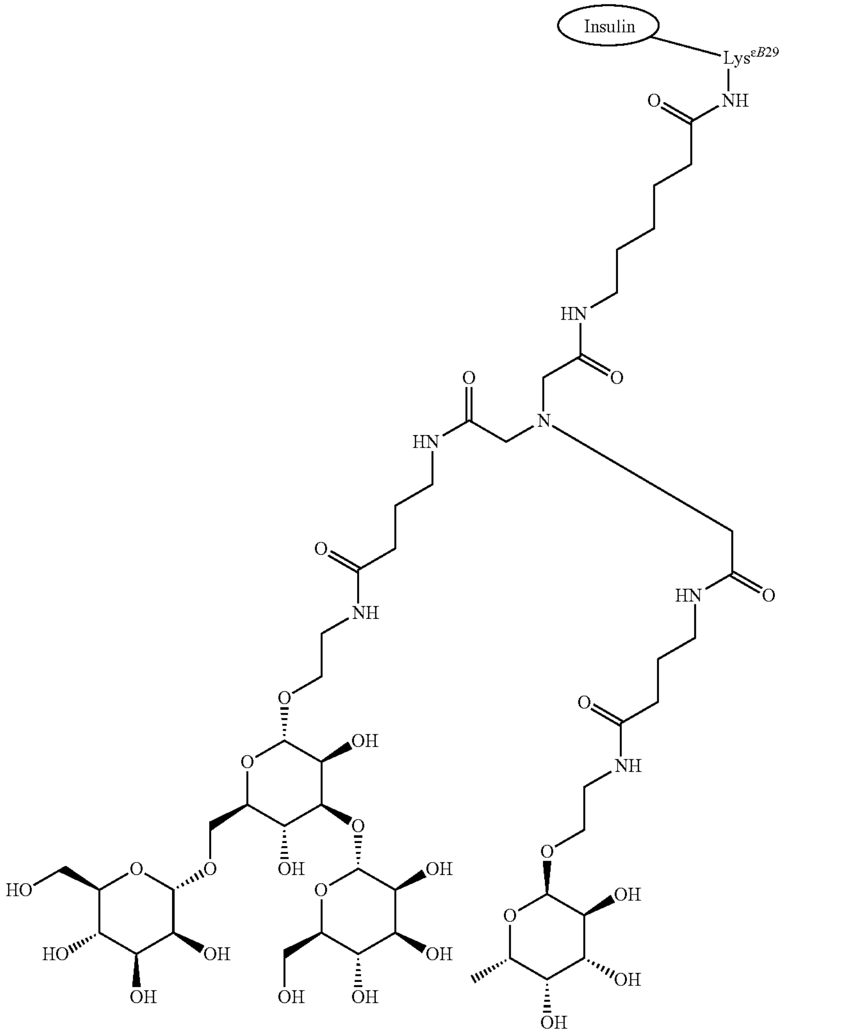

-continued
IOC-72
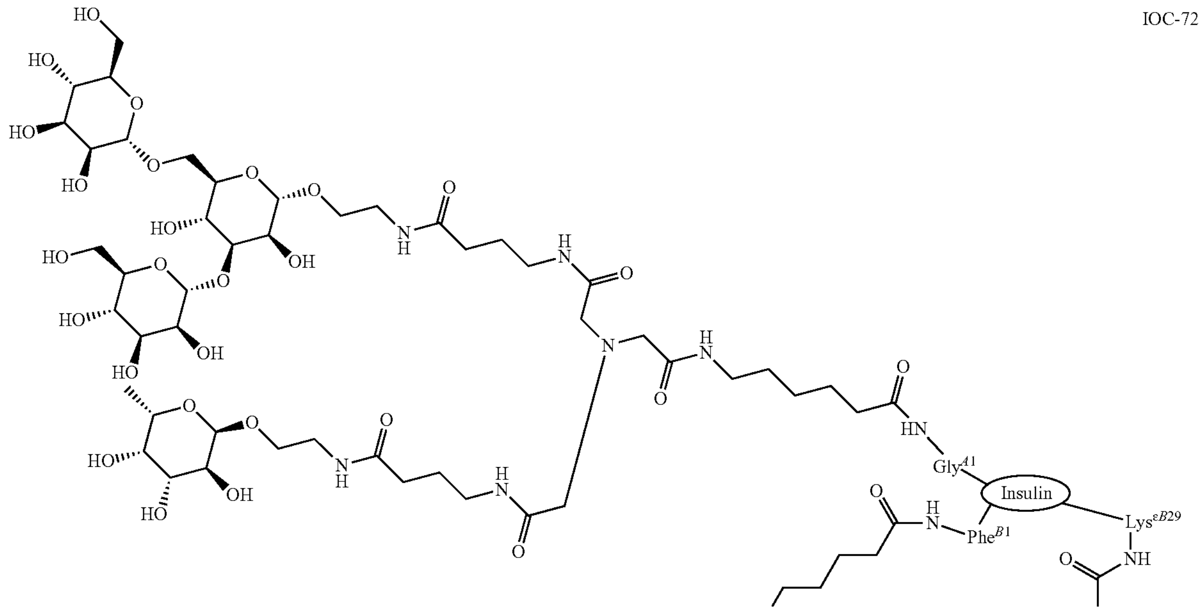
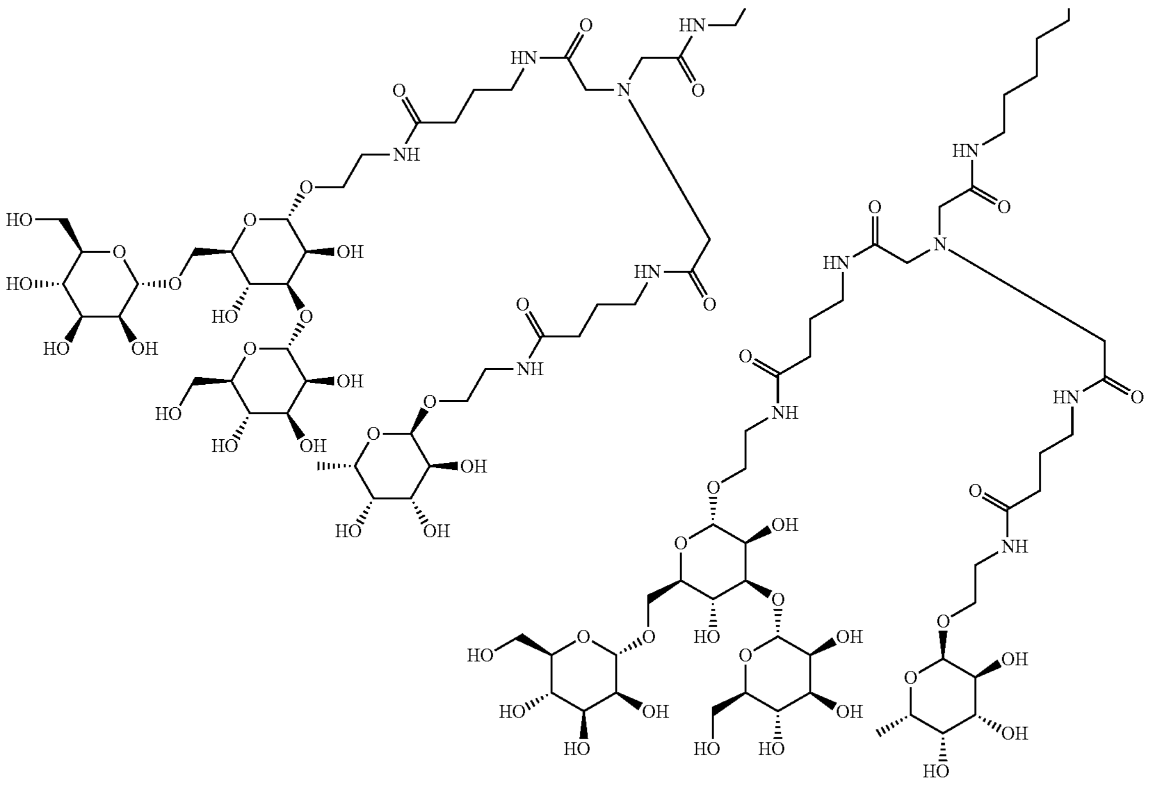

-continued
IOC-73
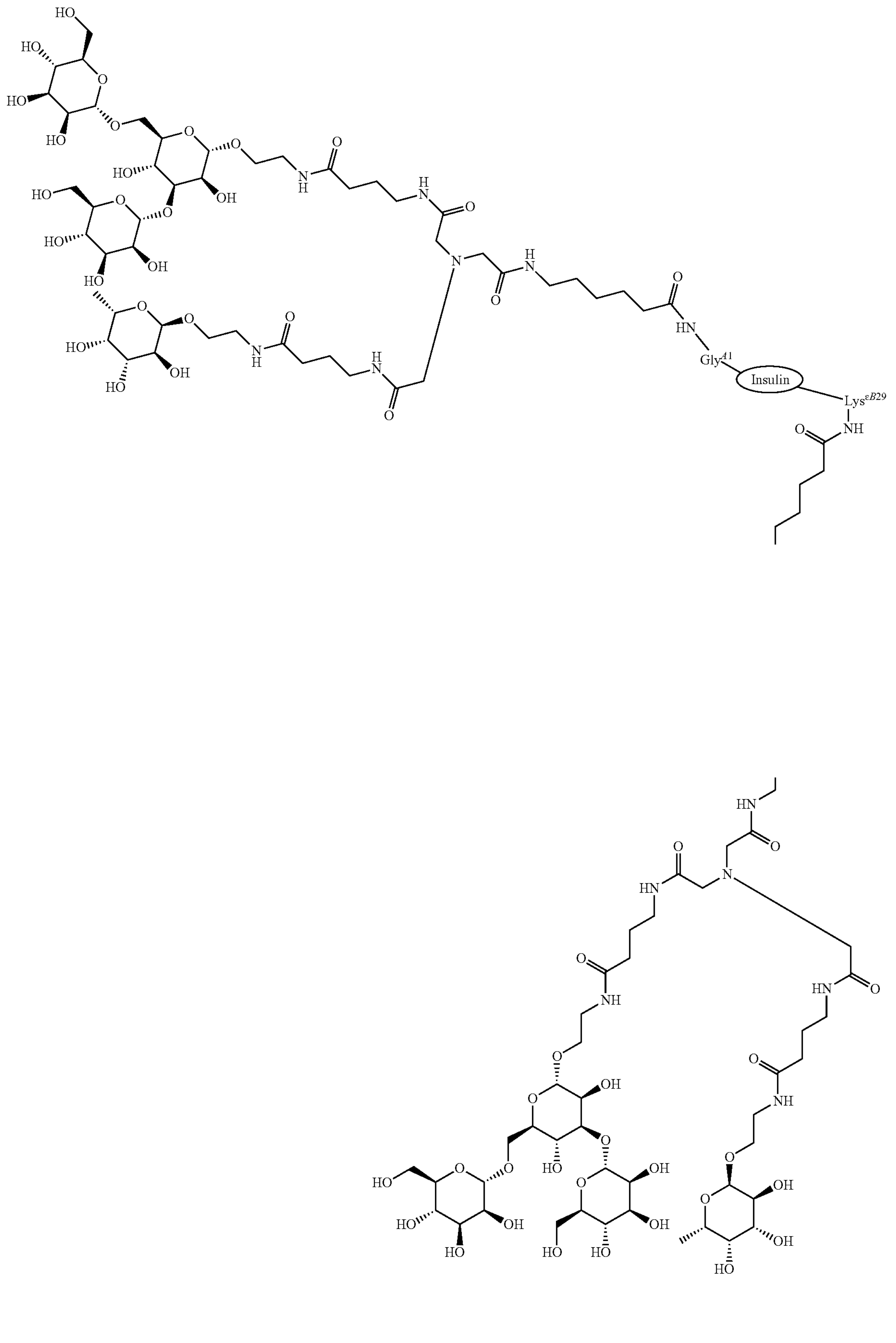

-continued
IOC-74
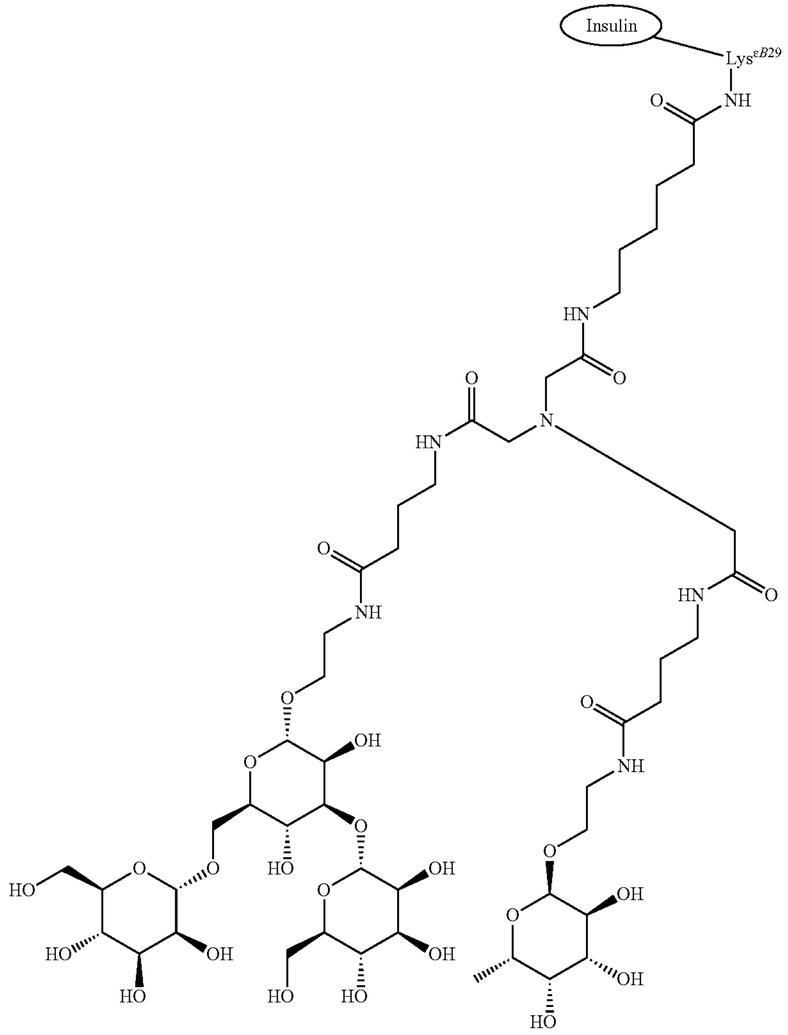
IOC-75
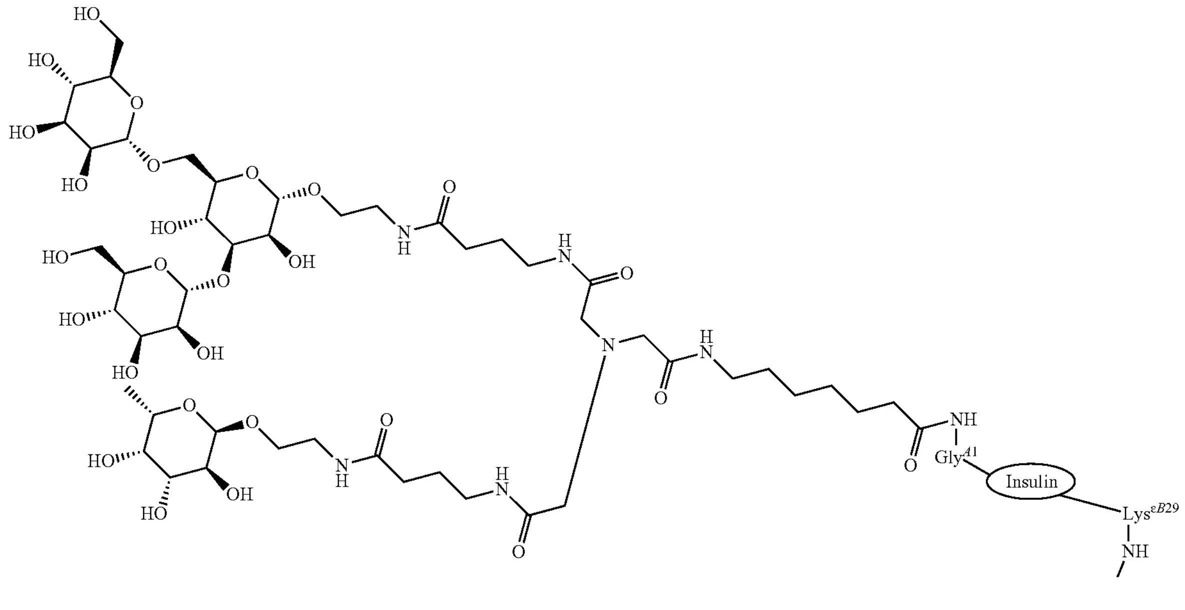

-continued
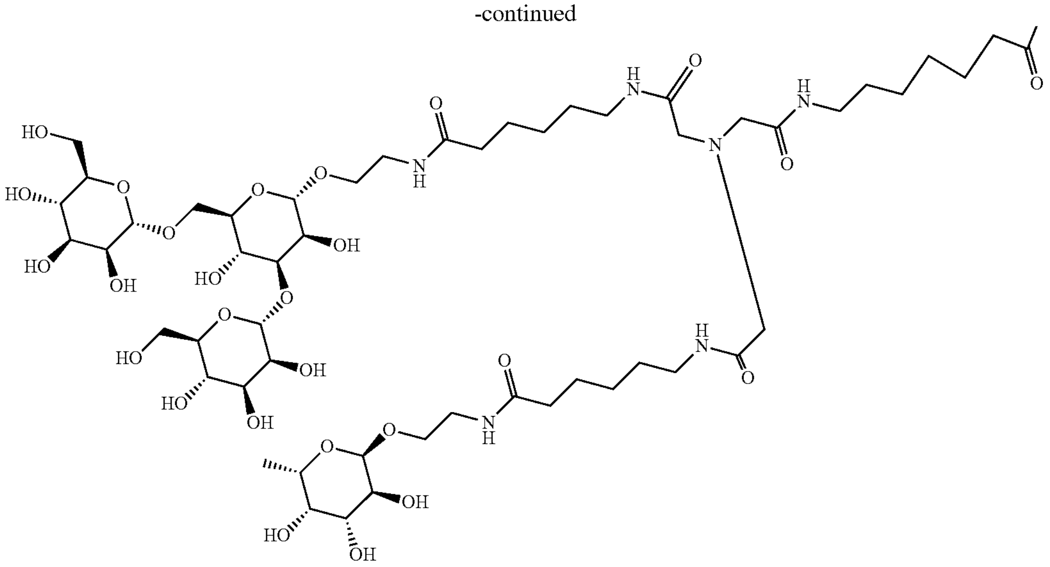
IOC-76
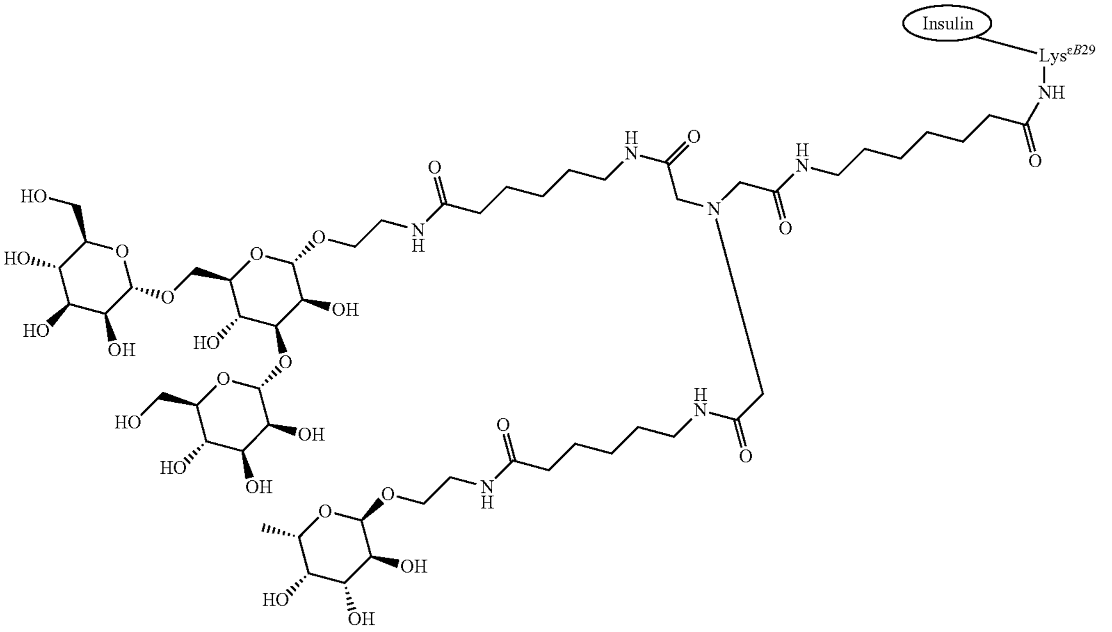

-continued
IOC-77
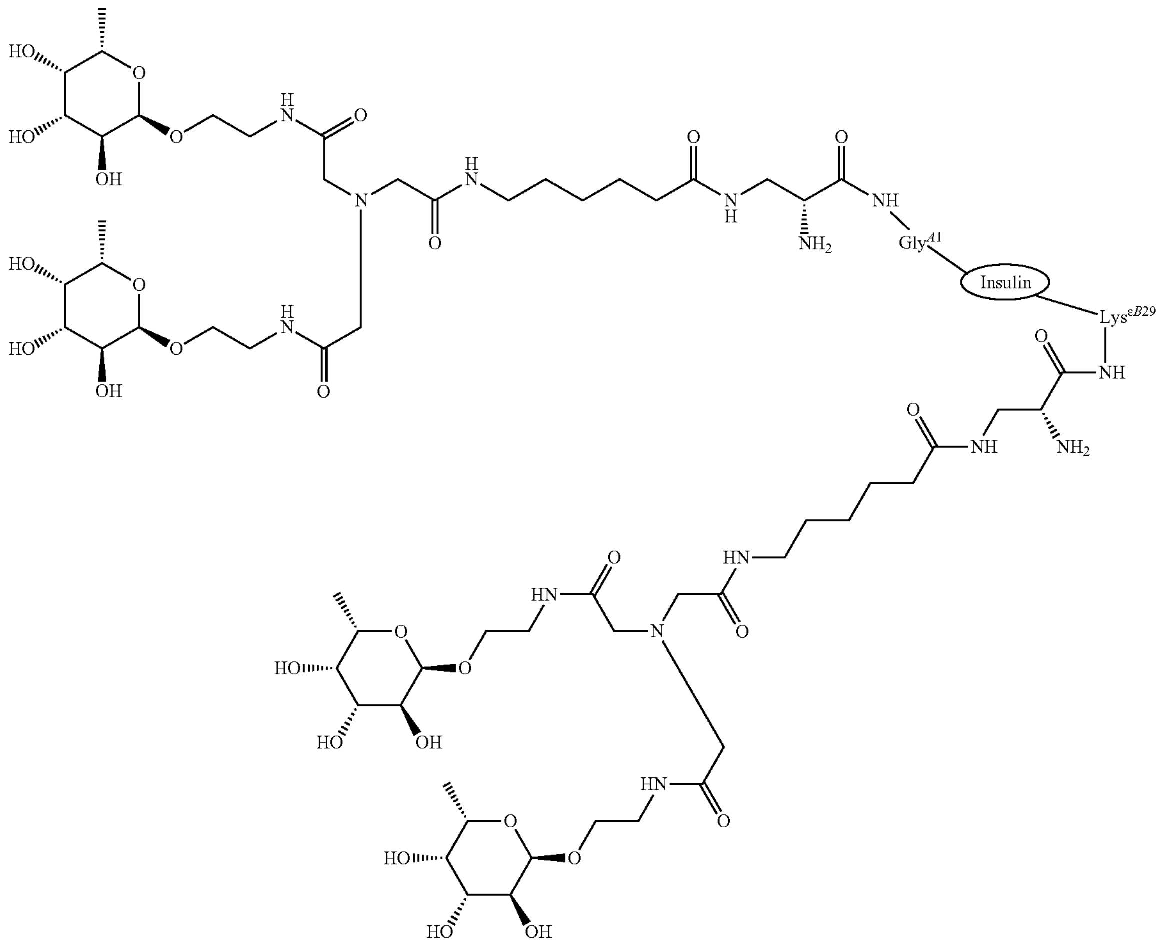

-continued
IOC-78
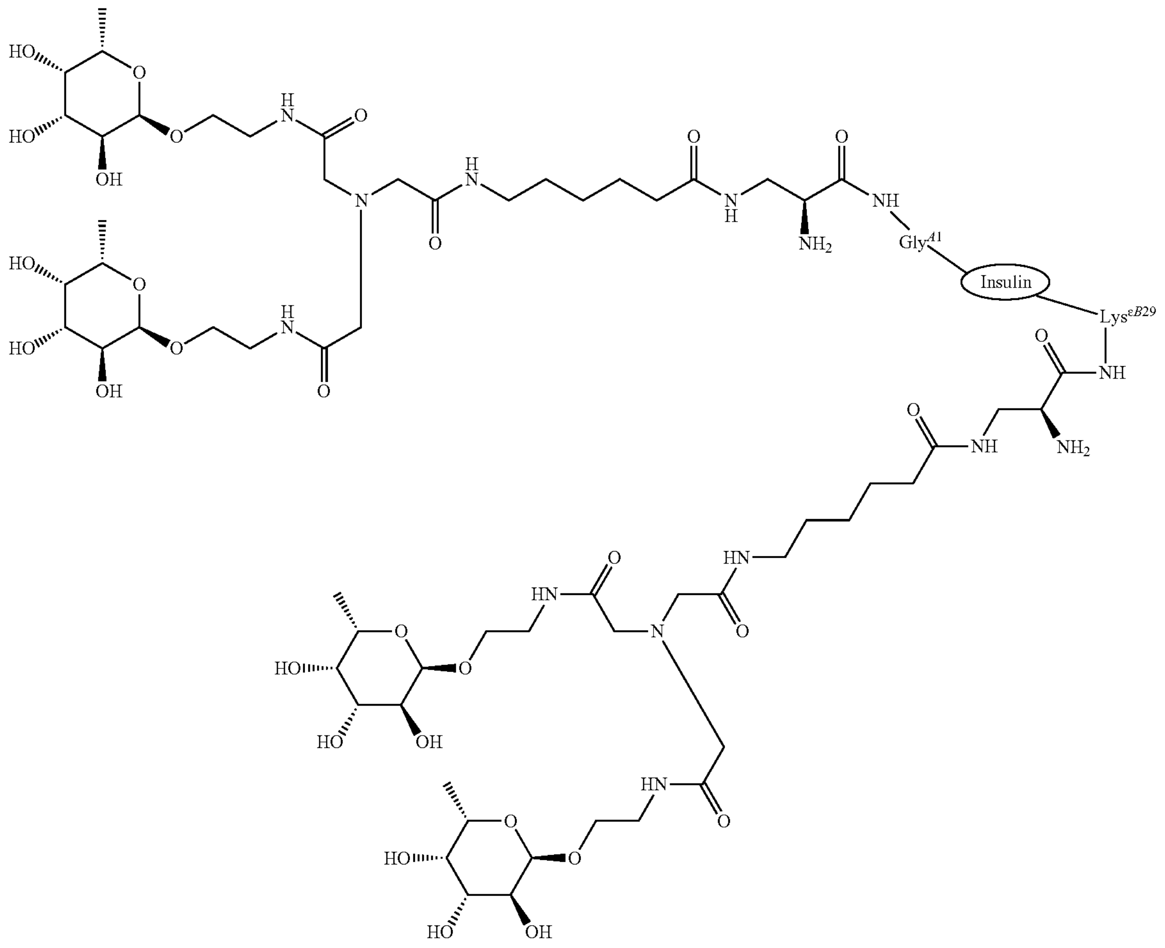

-continued
IOC-79
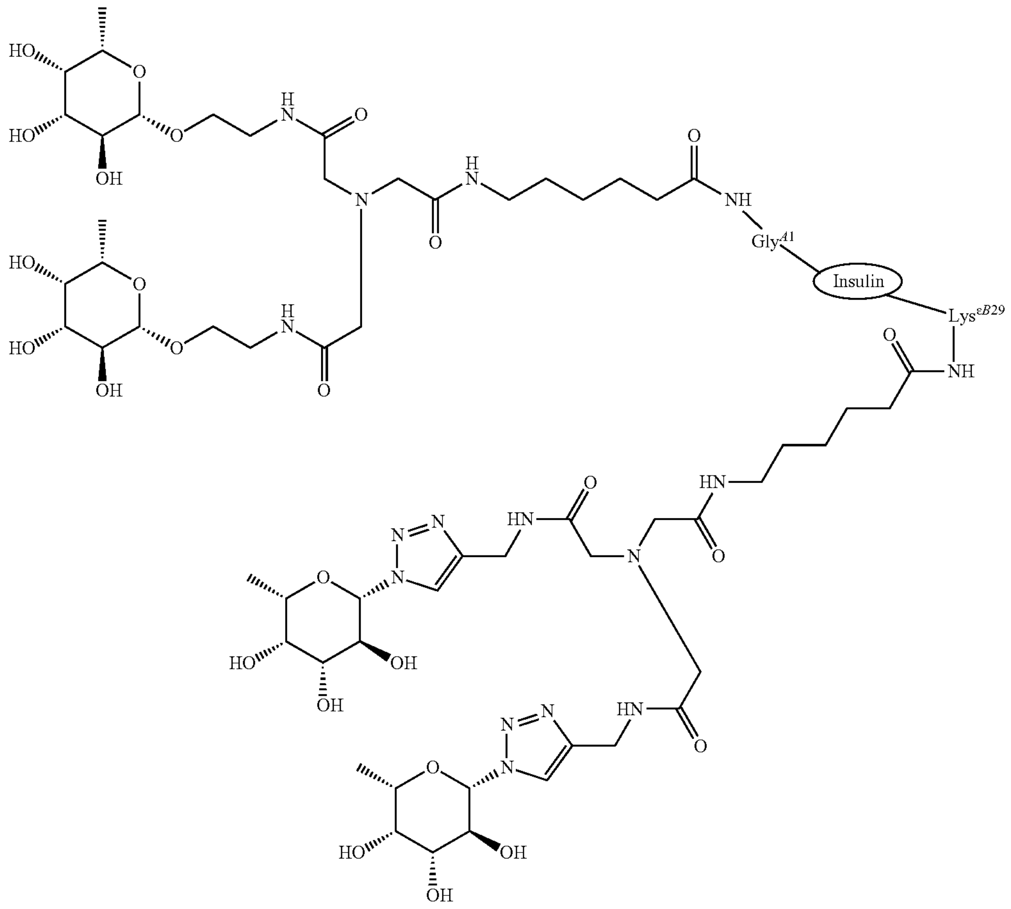

-continued
IOC-80
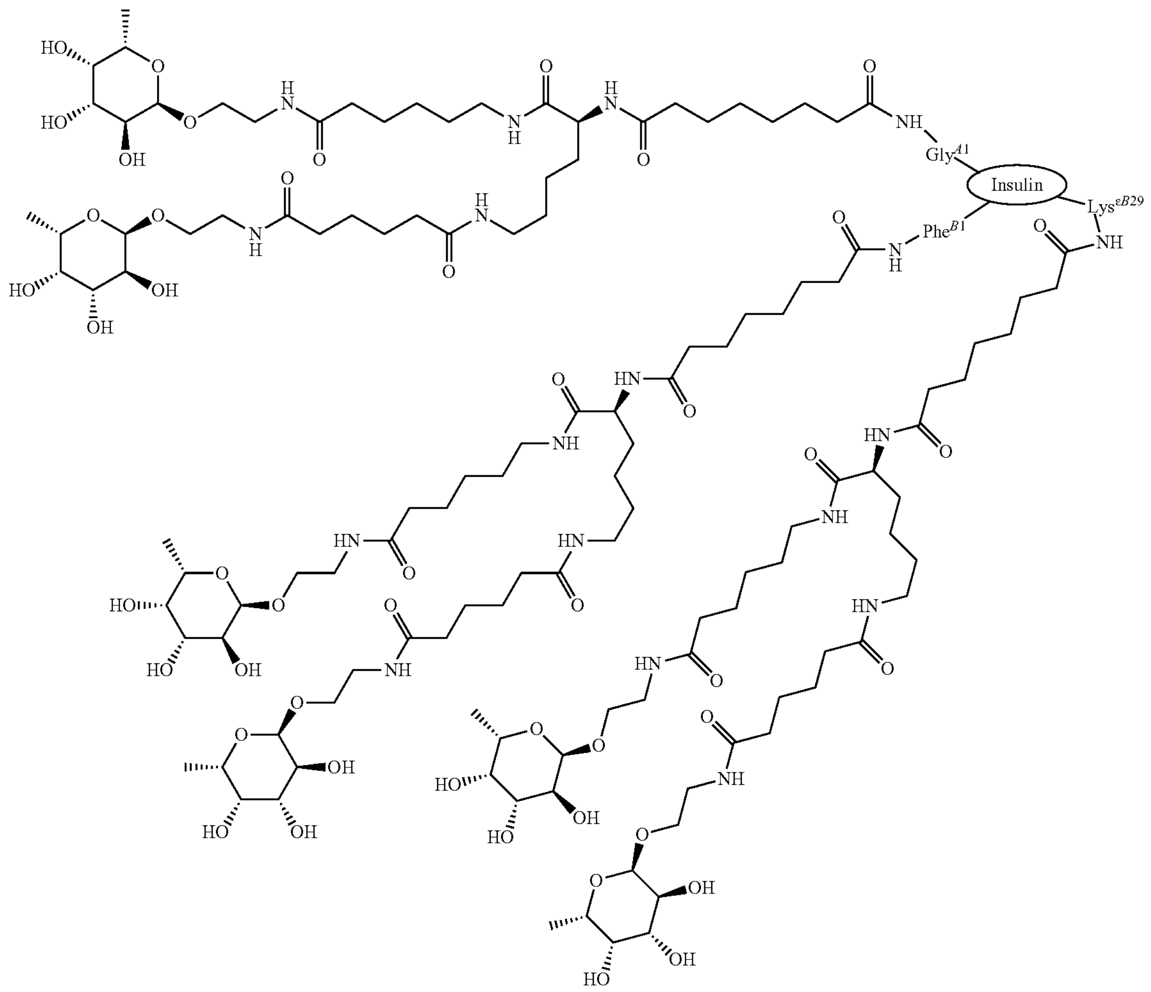

-continued
IOC-81
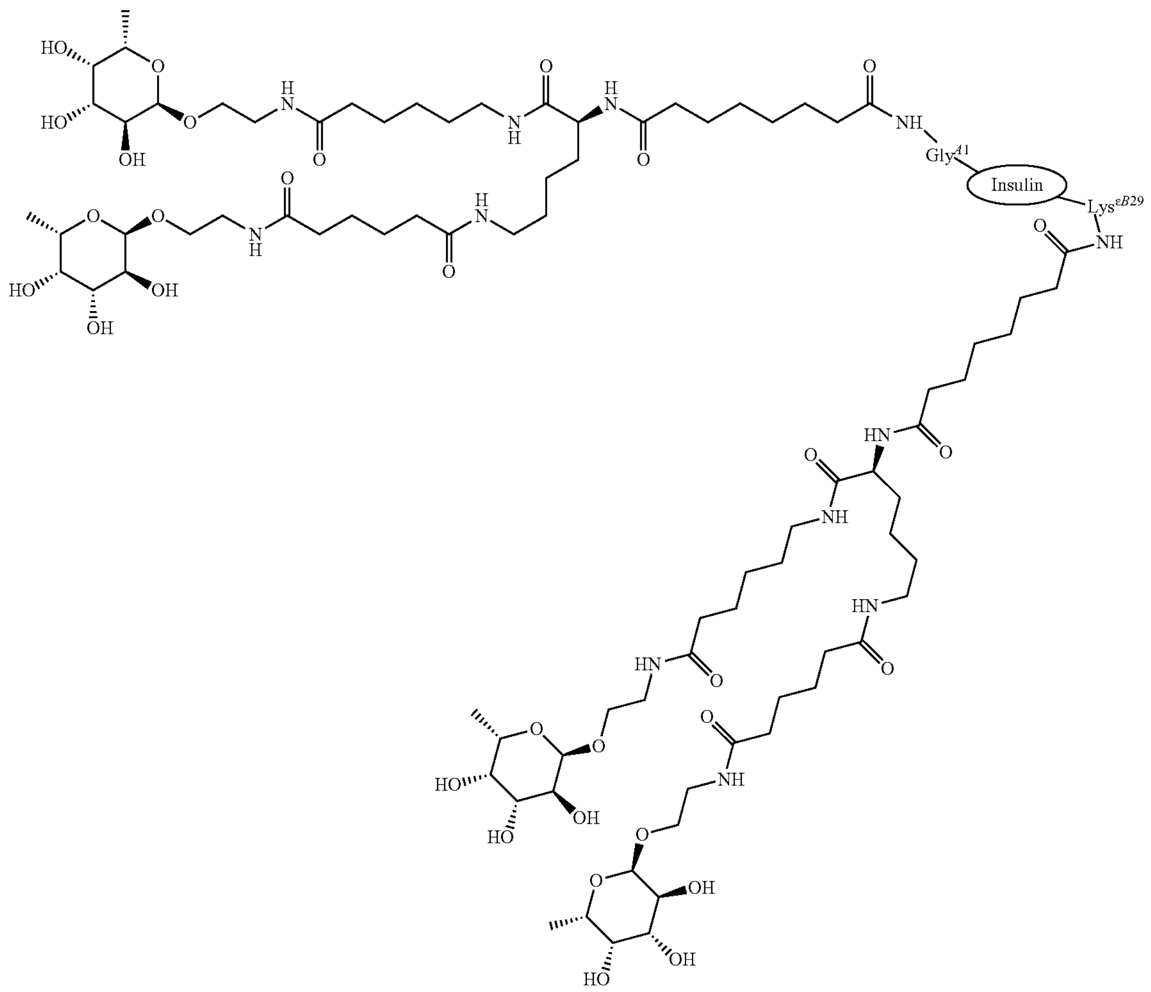

-continued
IOC-82
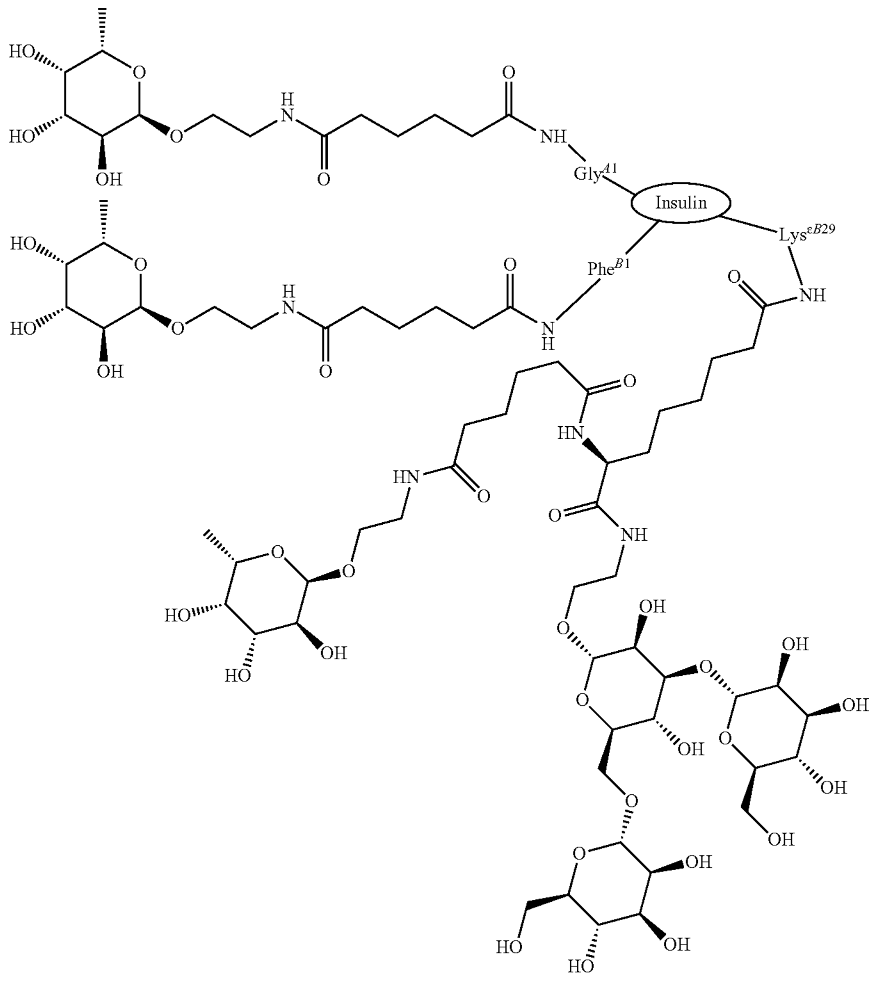

-continued
IOC-83
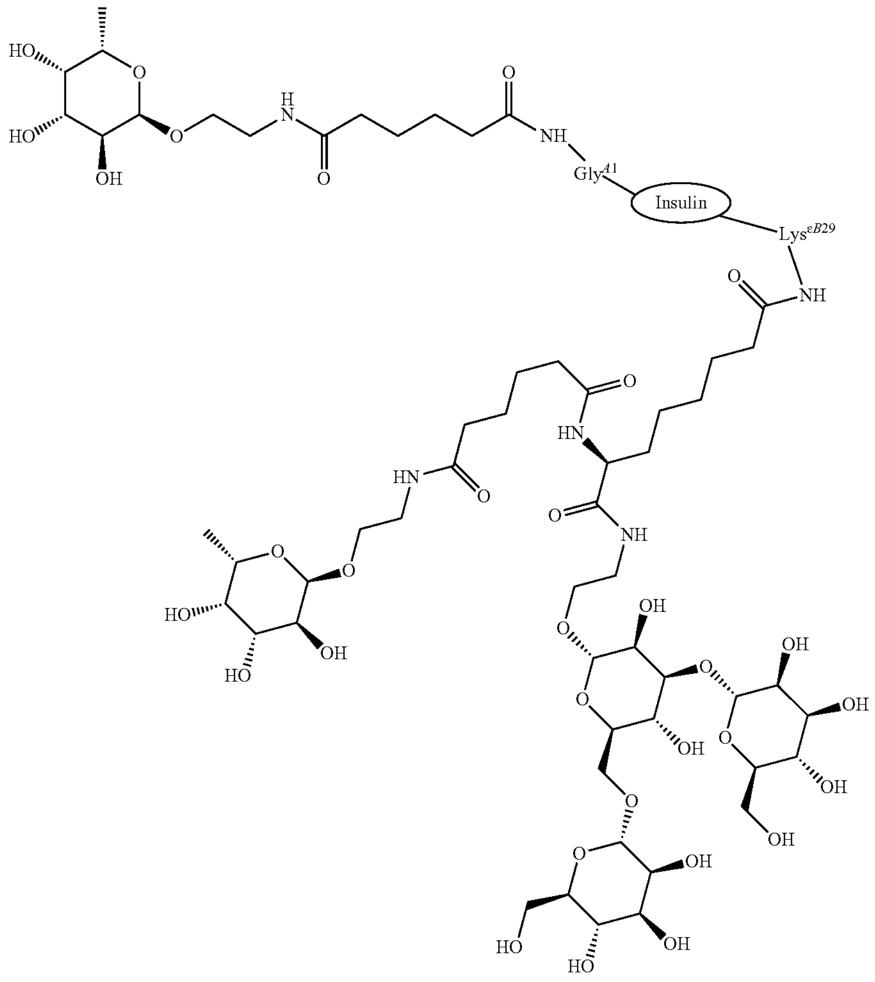

-continued
IOC-84
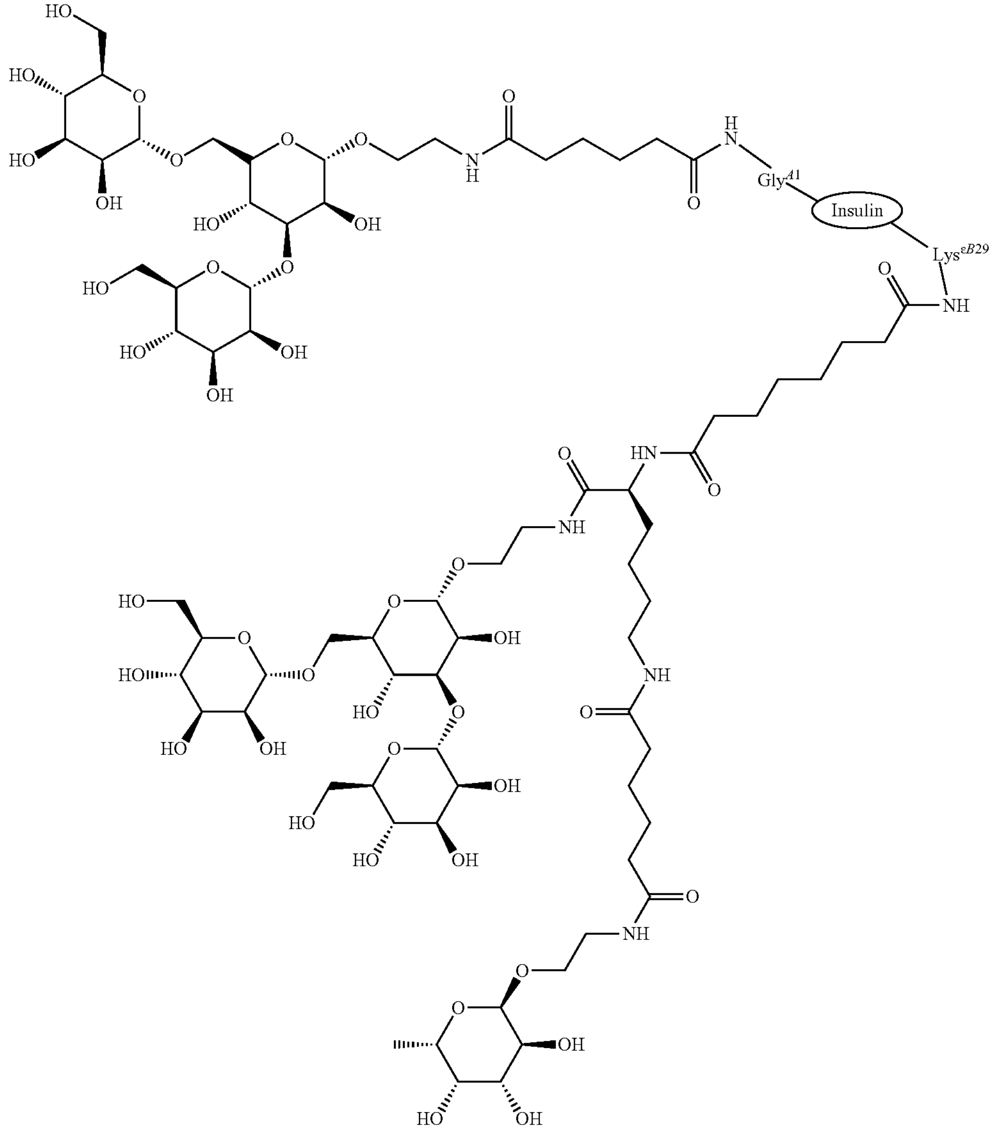

IOC-85
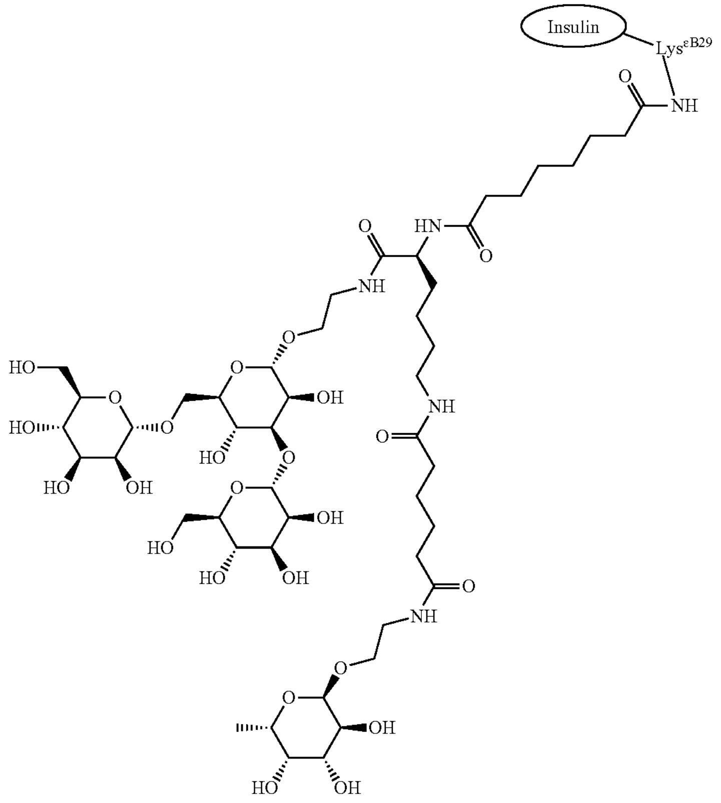
IOC-86
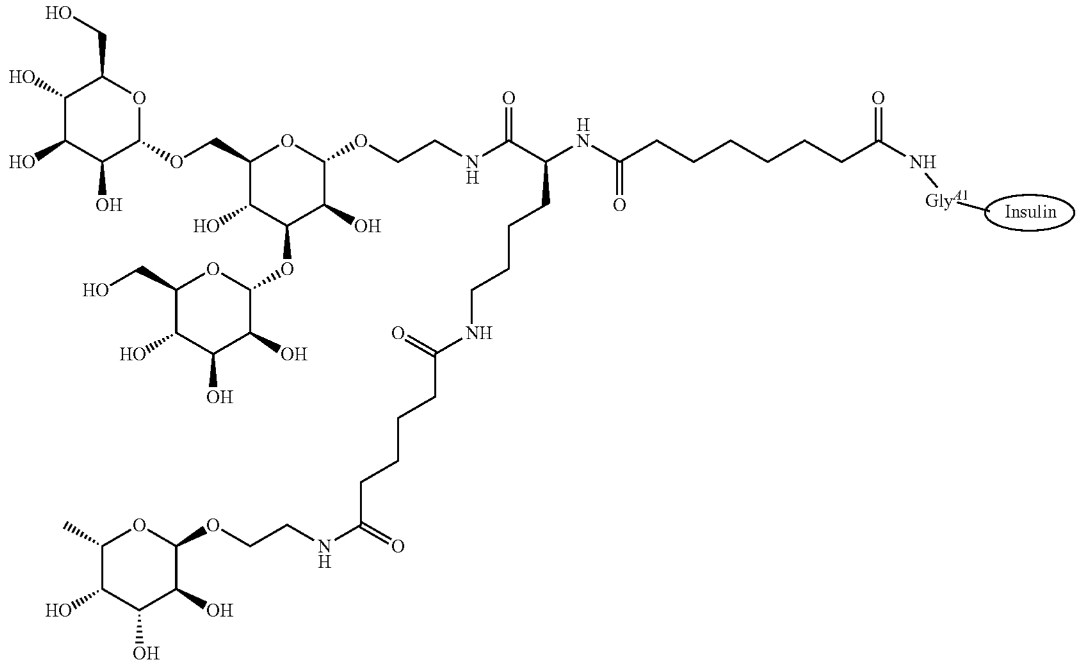

-continued
IOC-87
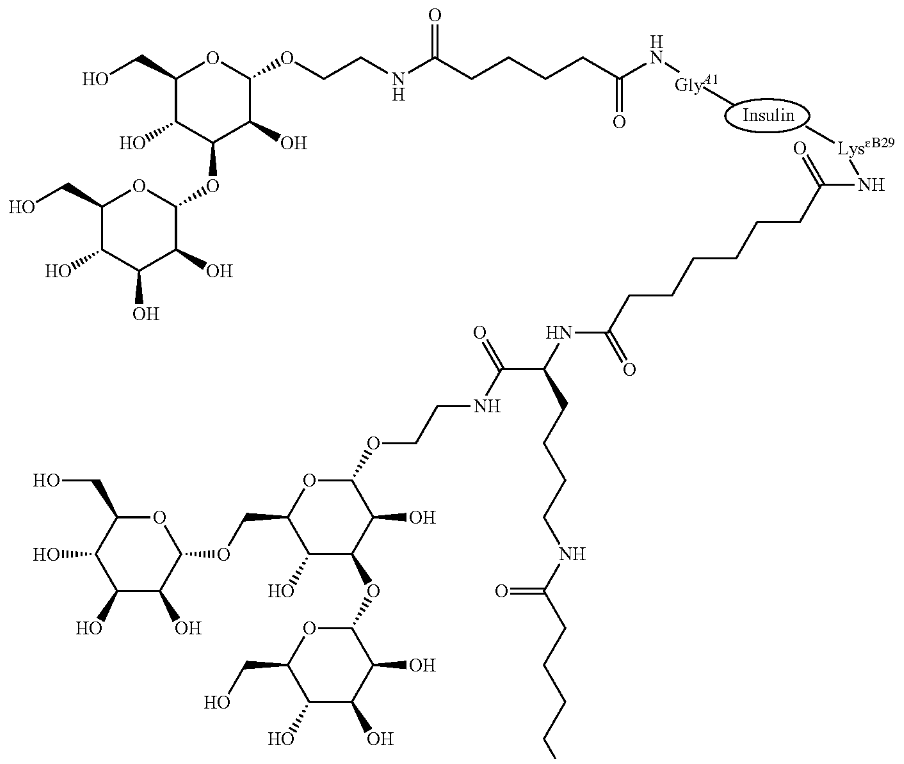
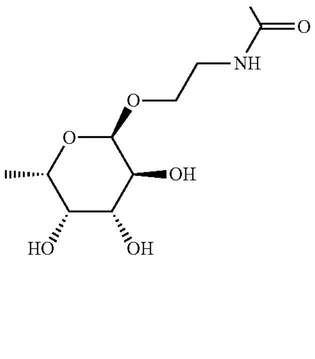

-continued
IOC-88
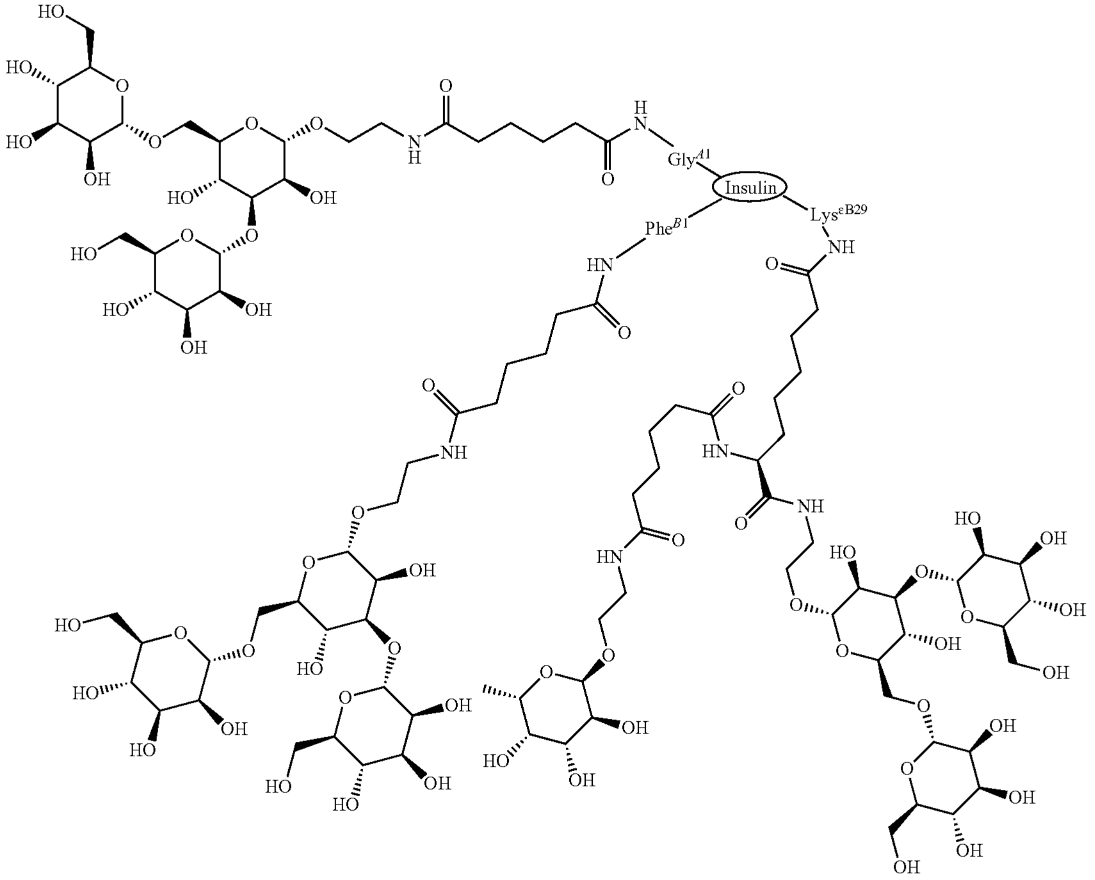
IOC-89
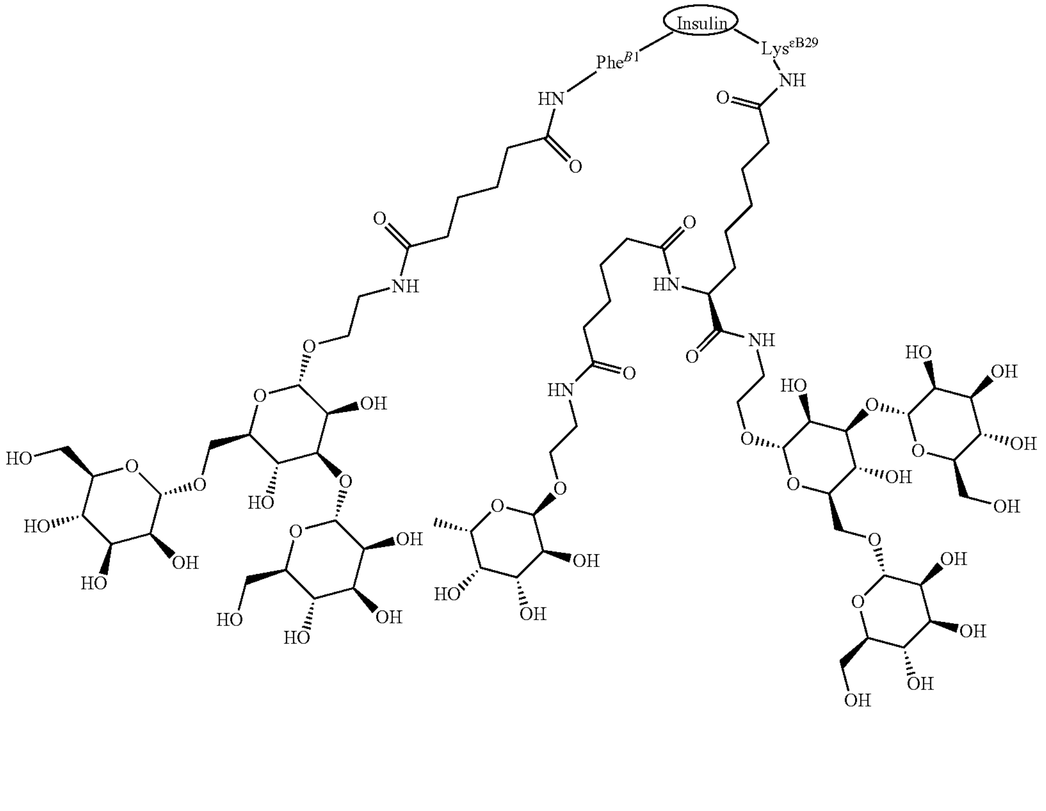

-continued
IOC-90
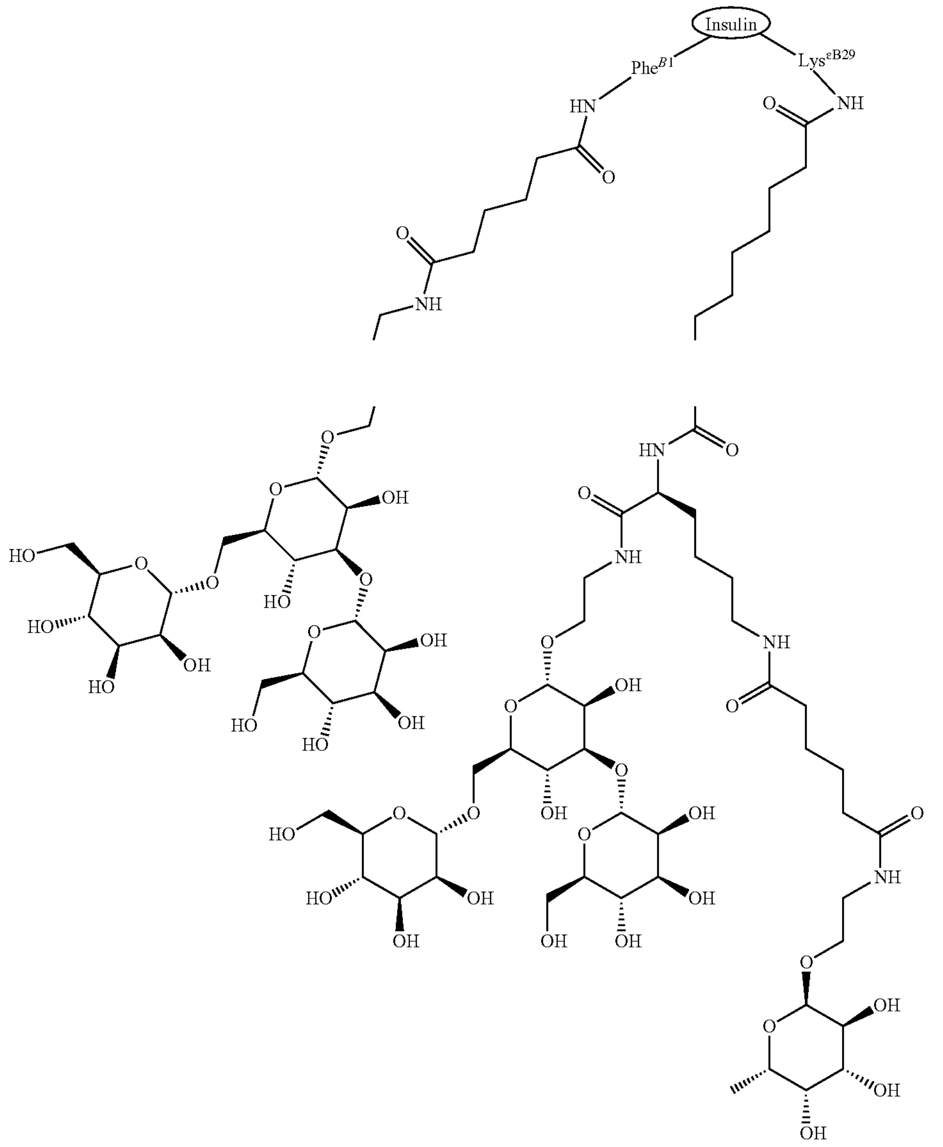
IOC-91
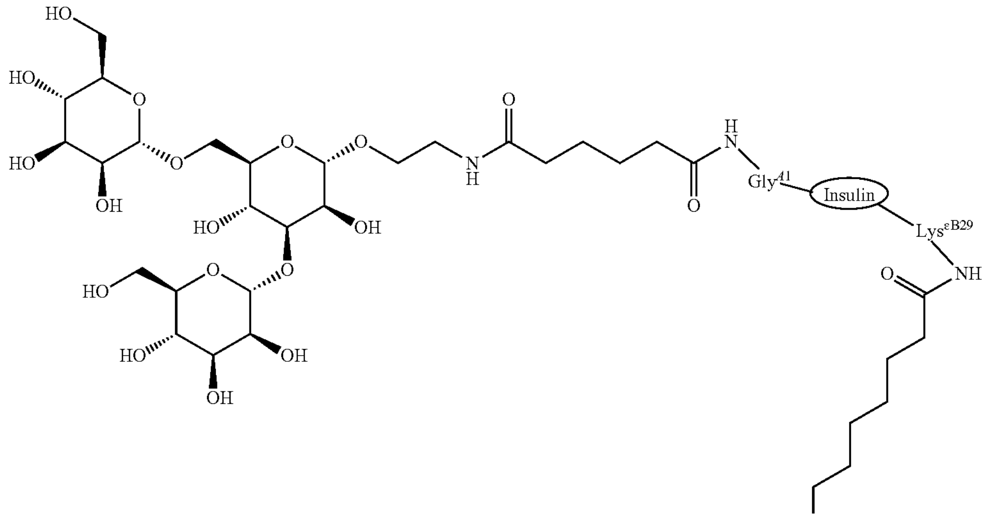

-continued
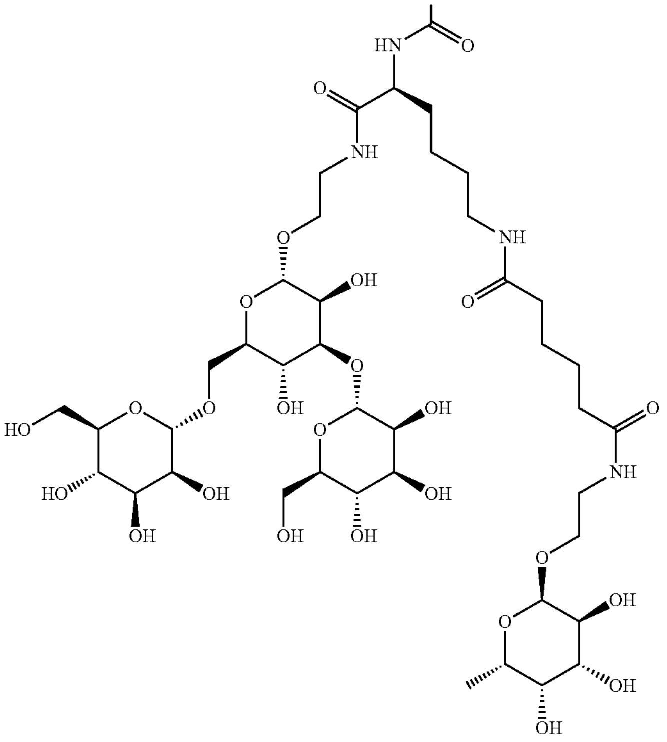
IOC-92
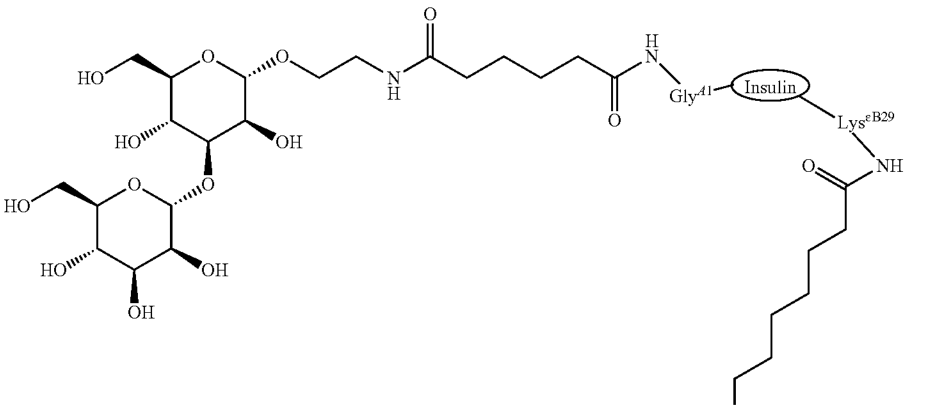

-continued
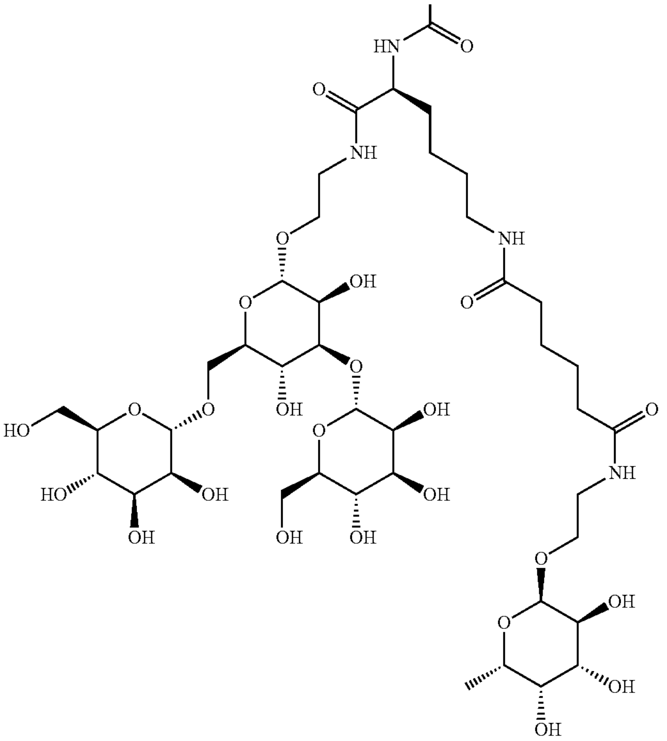
IOC-93
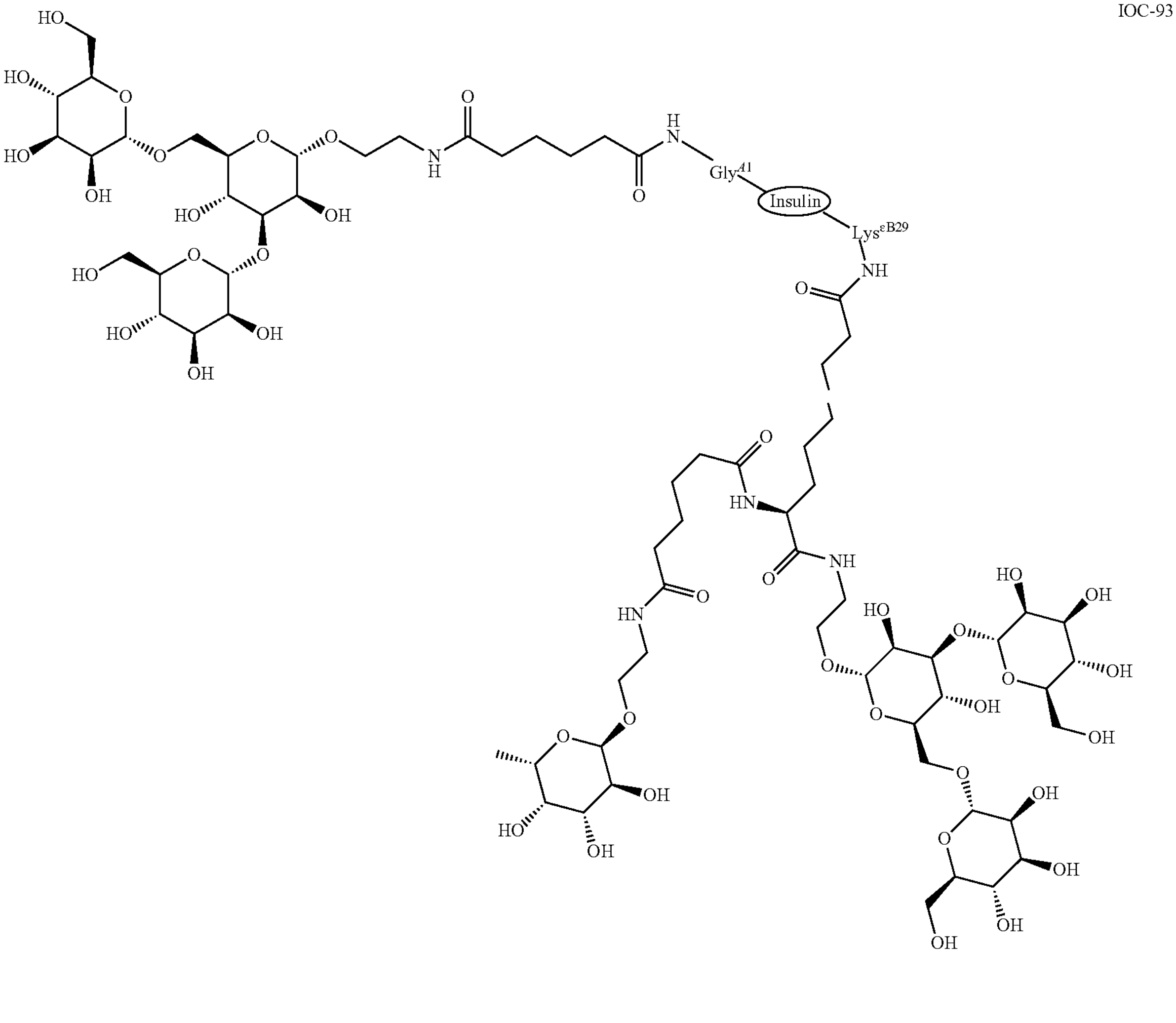

-continued
IOC-94
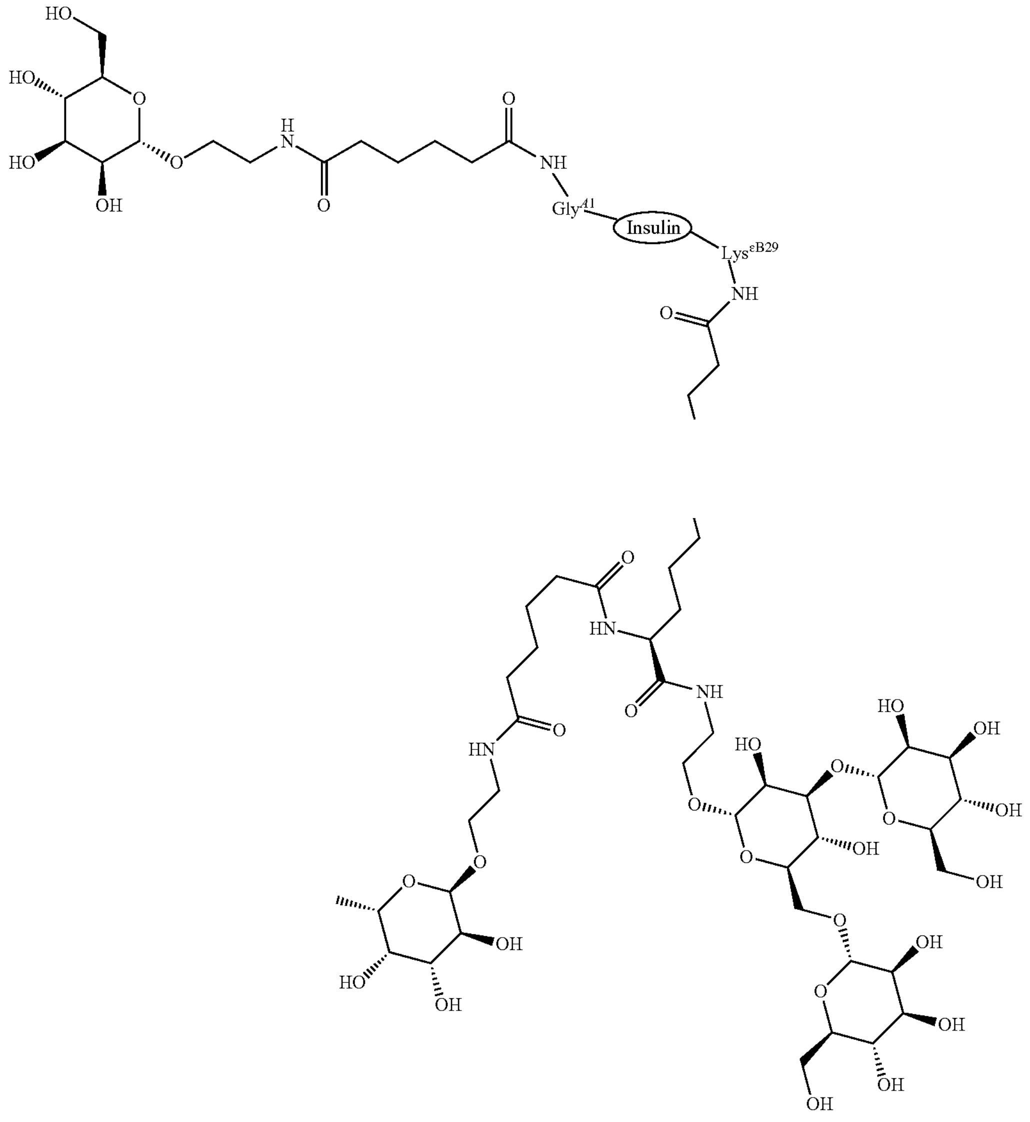
IOC-95
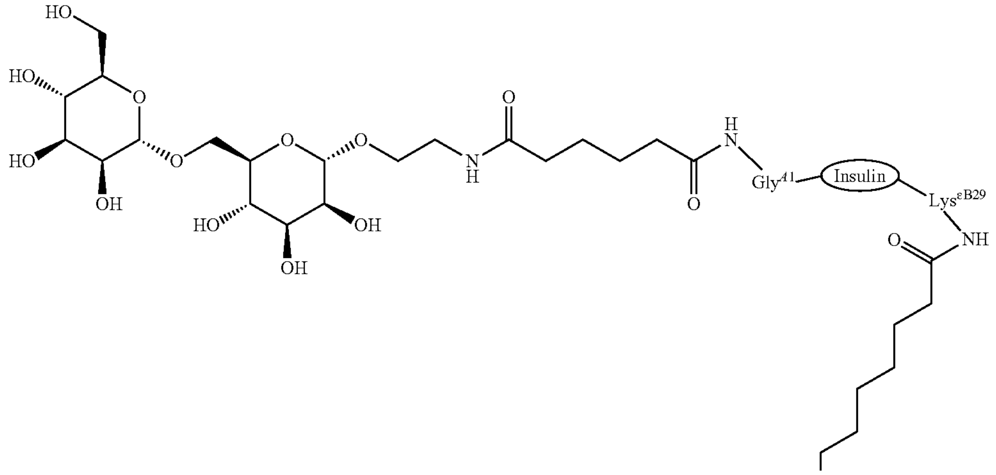

-continued
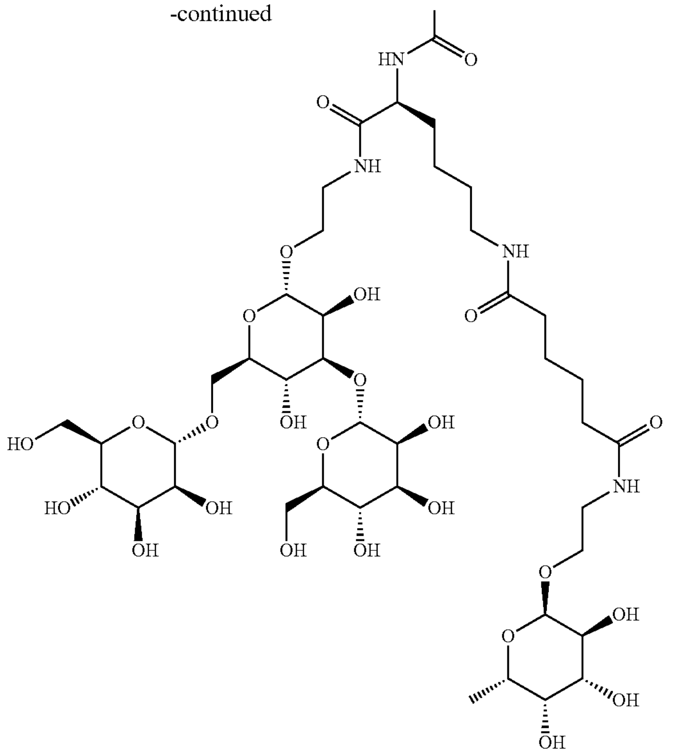
IOC-96
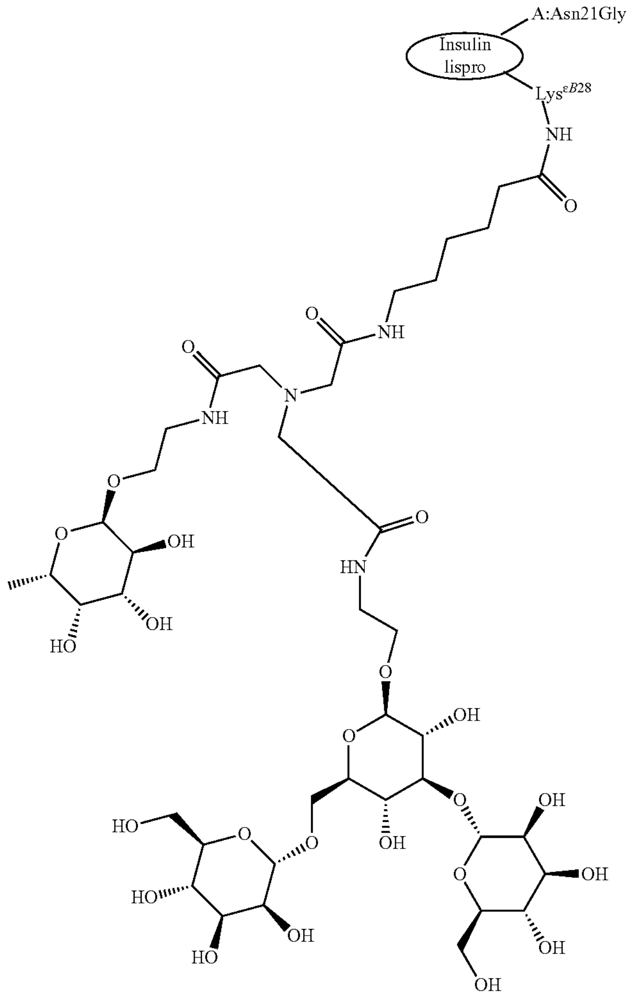

-continued
IOC-97
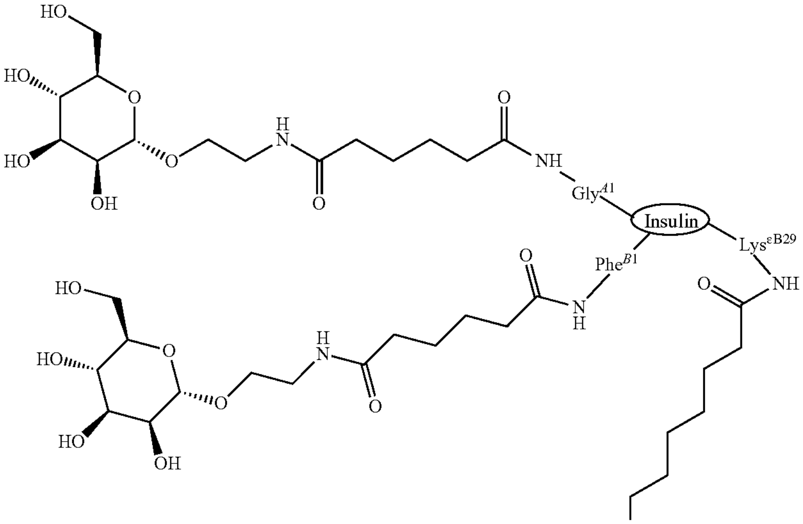
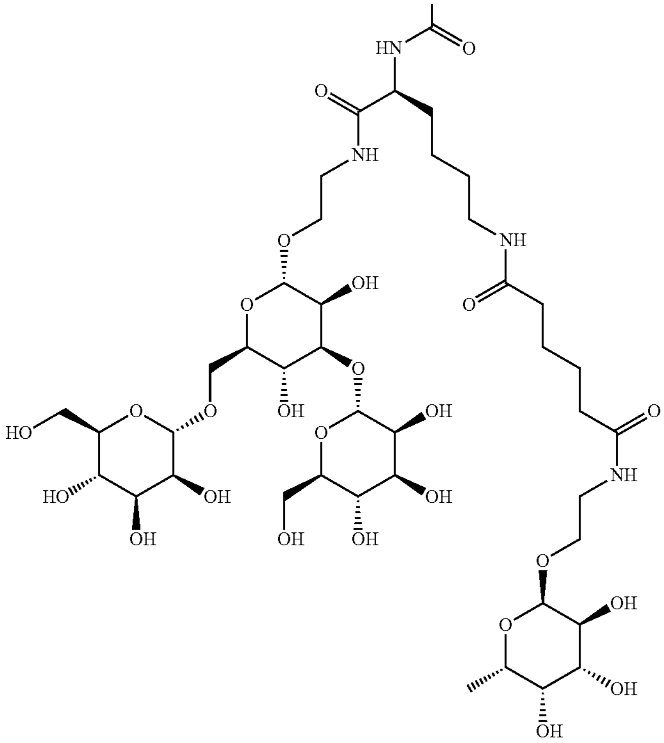

-continued
IOC-98
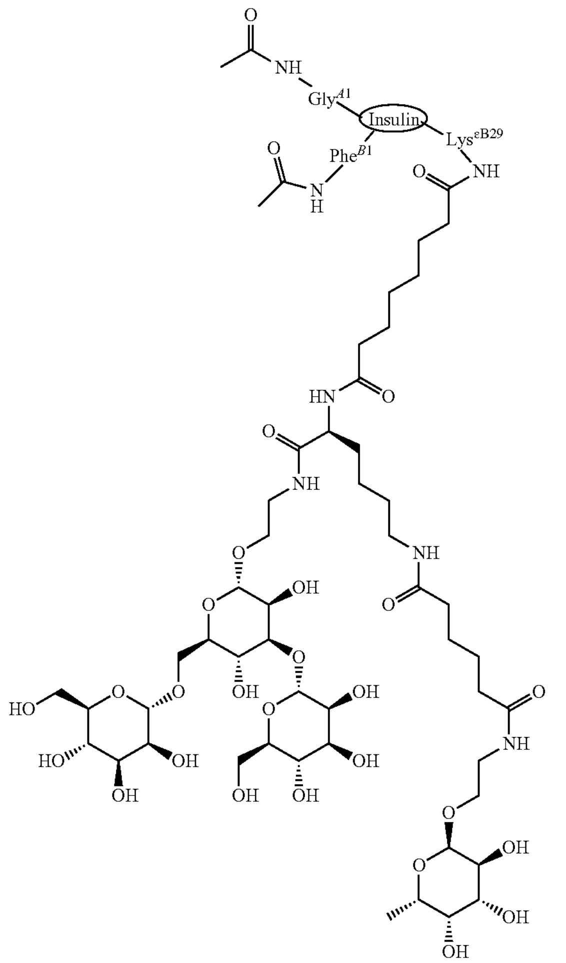
IOC-99
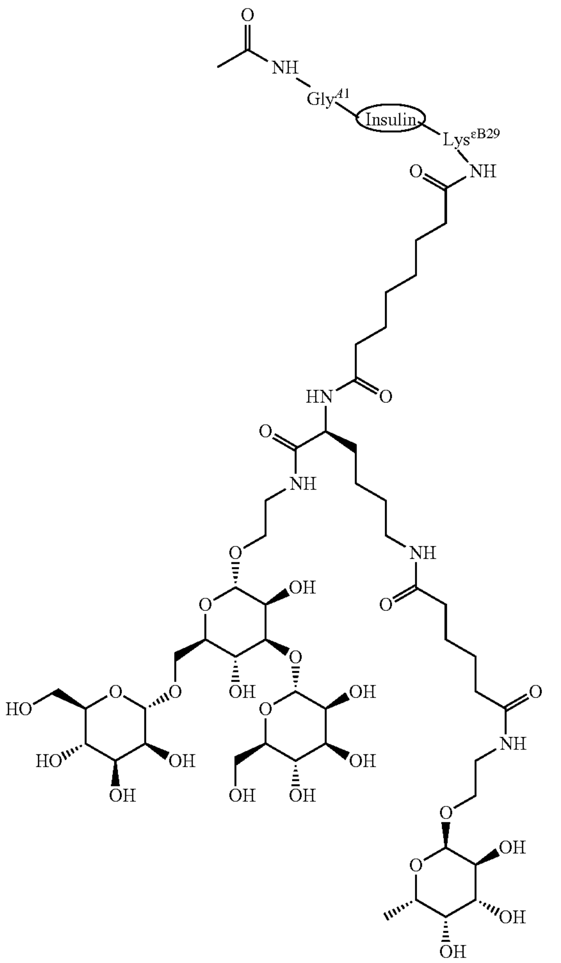
IOC-100
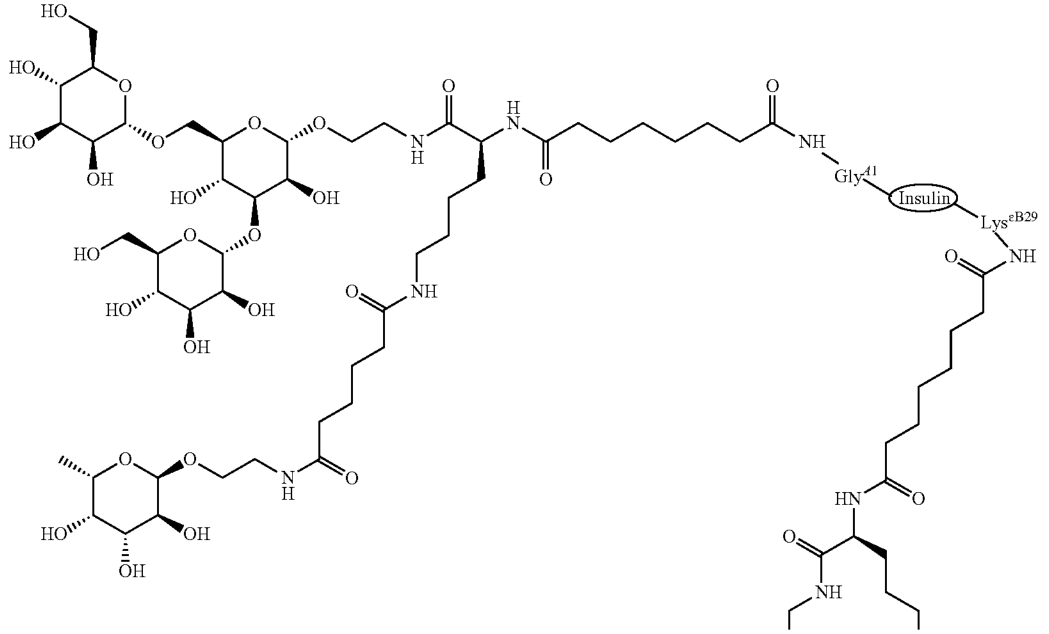

-continued
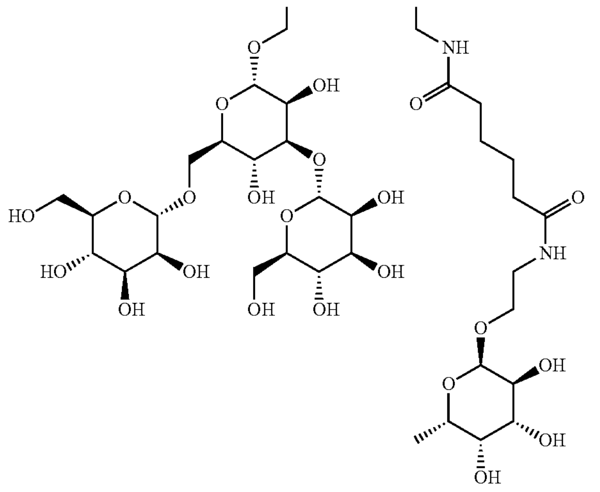
IOC-101
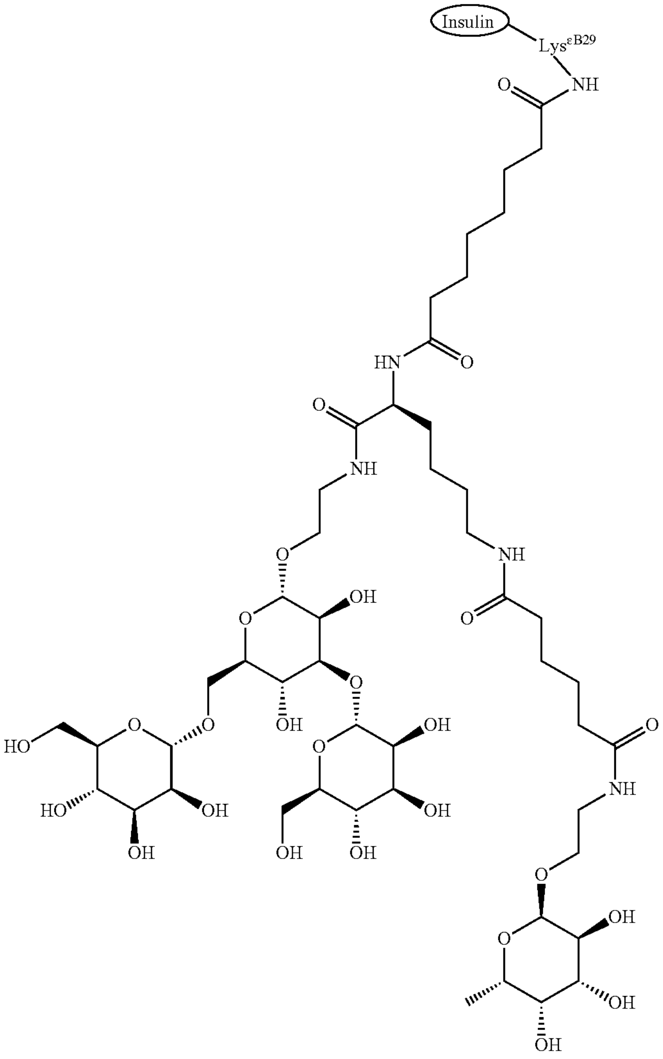

-continued
IOC-102
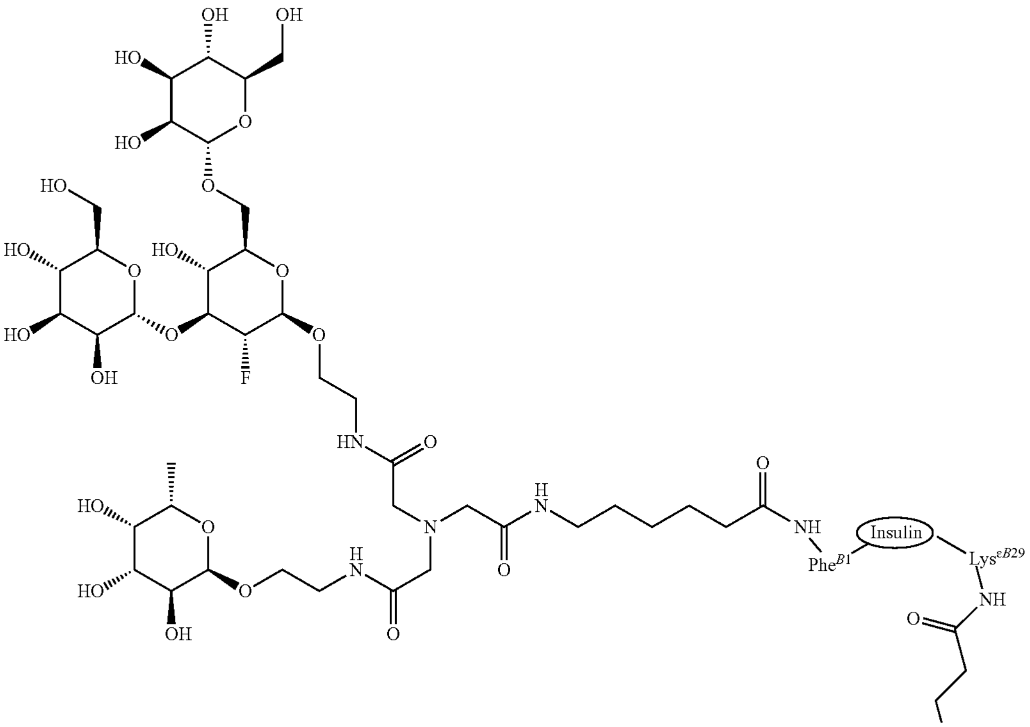
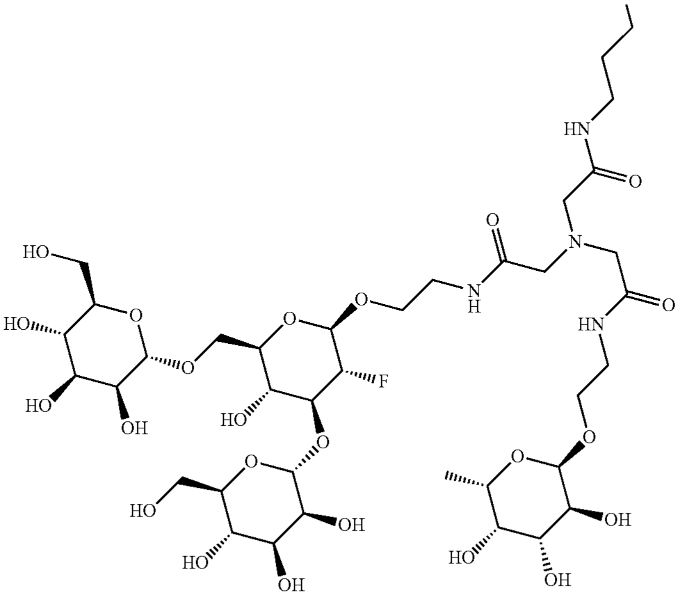

-continued
IOC-103
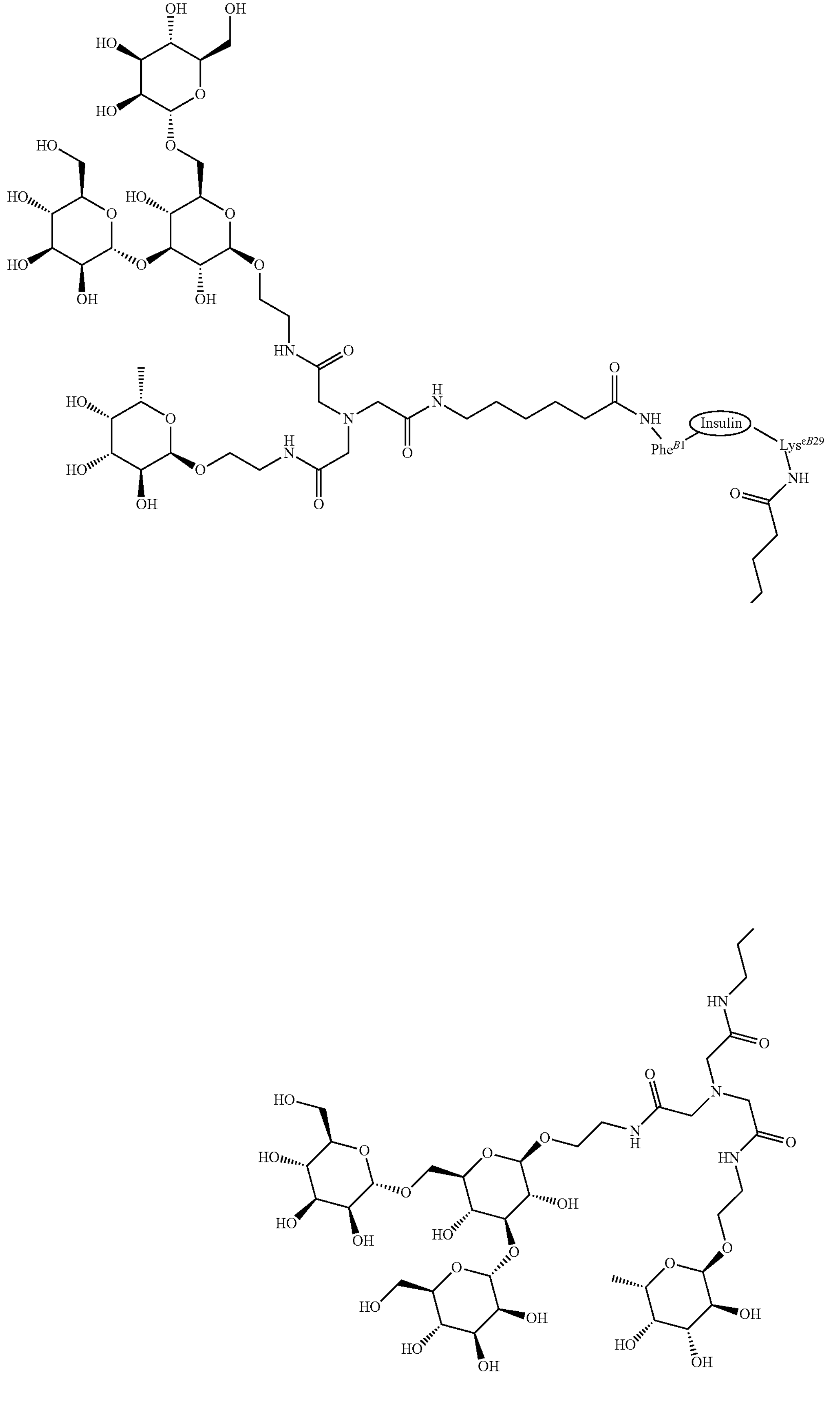

-continued
IOC-104
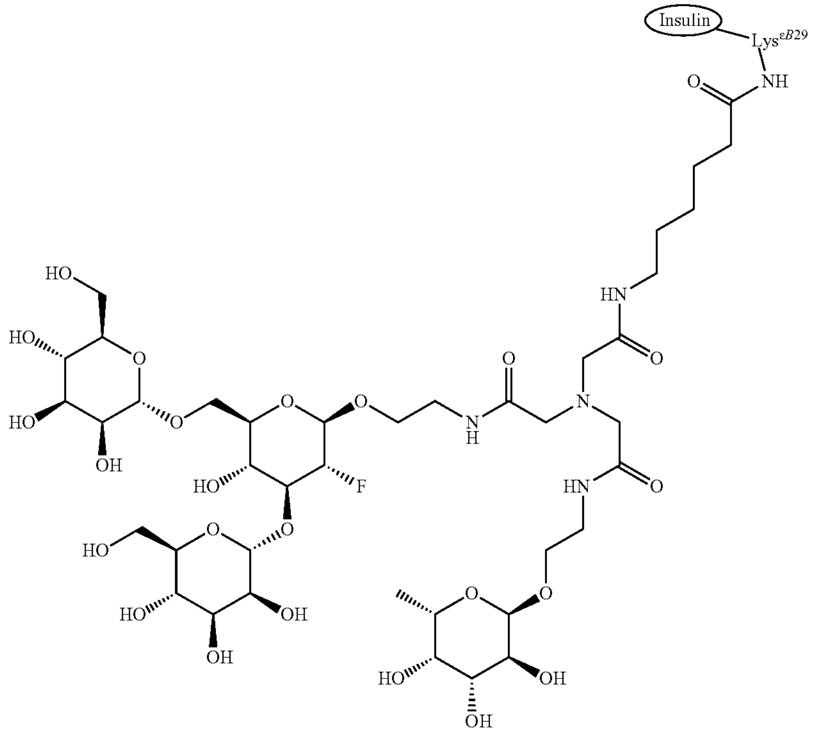
IOC-105
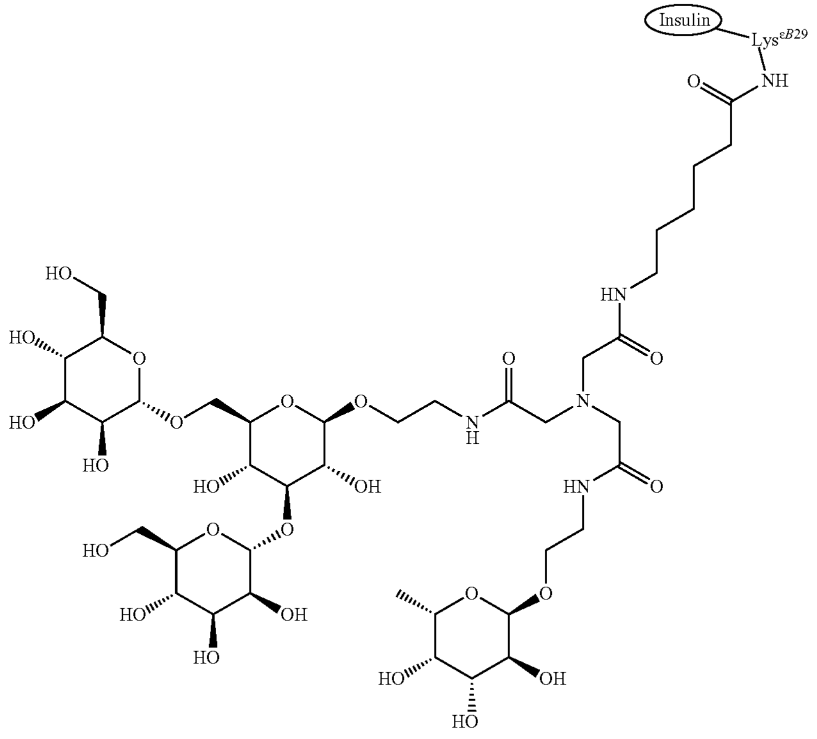

-continued
IOC-106
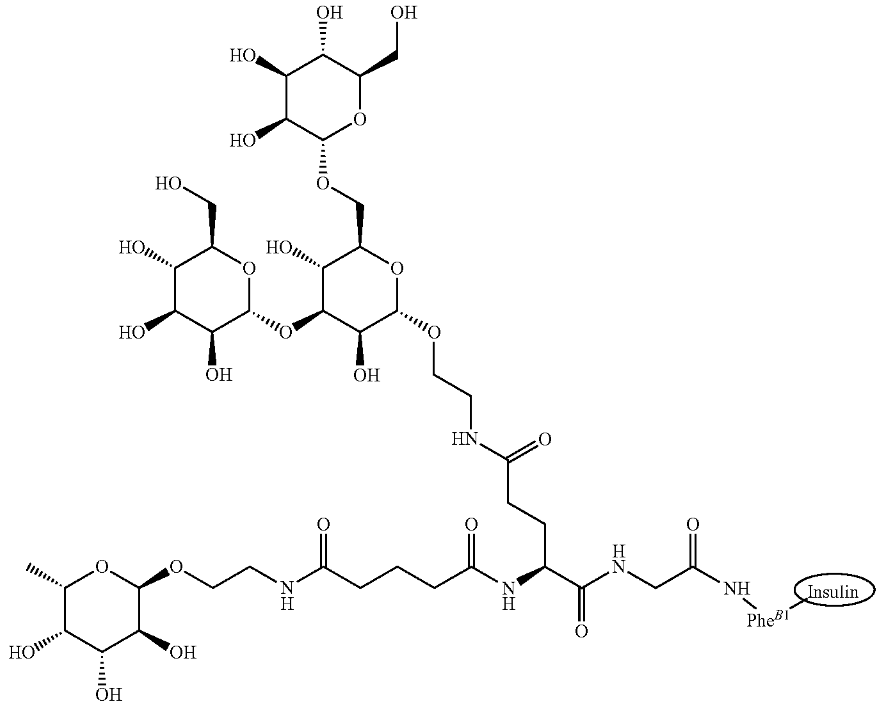
IOC-107
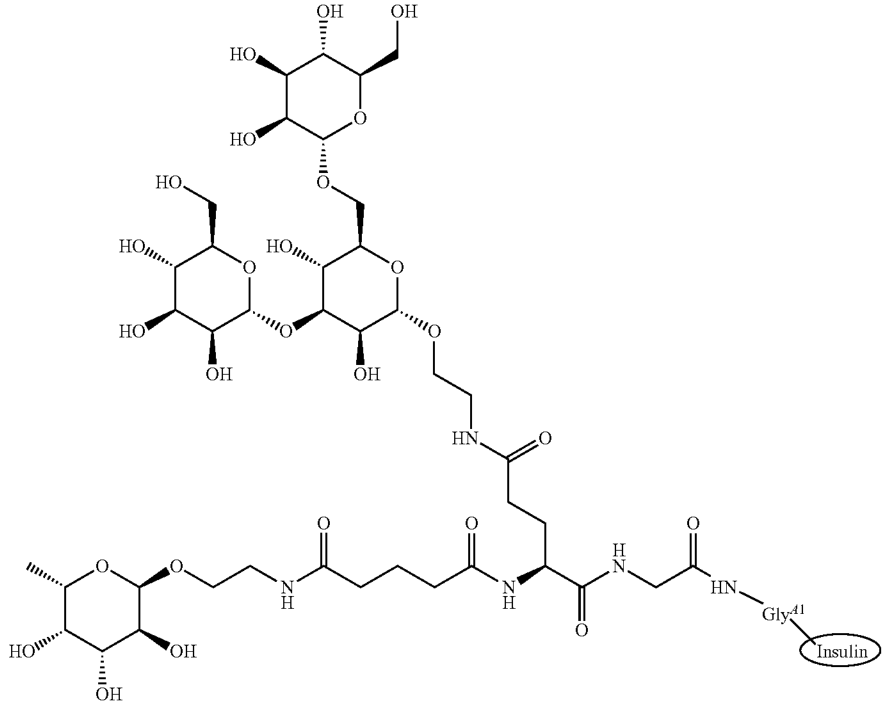

-continued
IOC-108
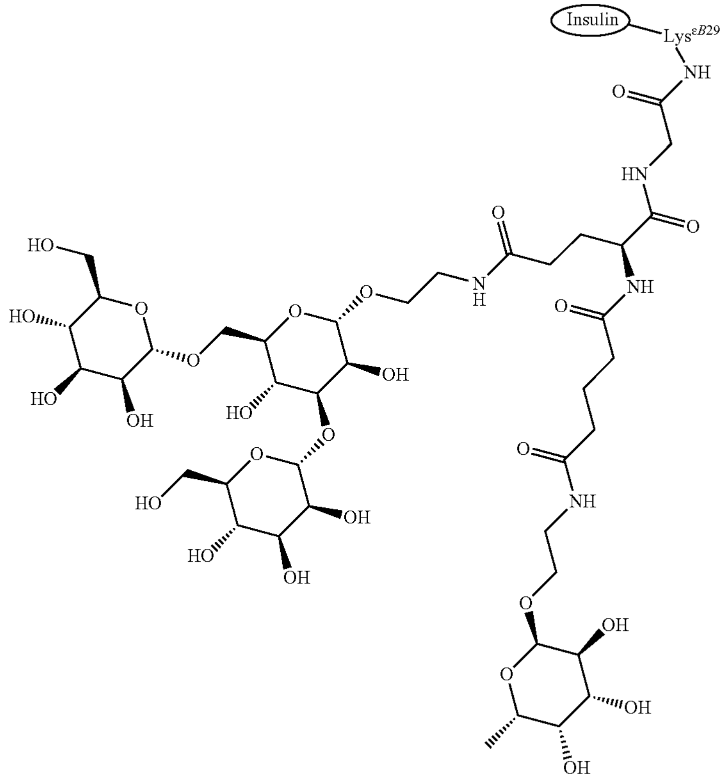
IOC-109
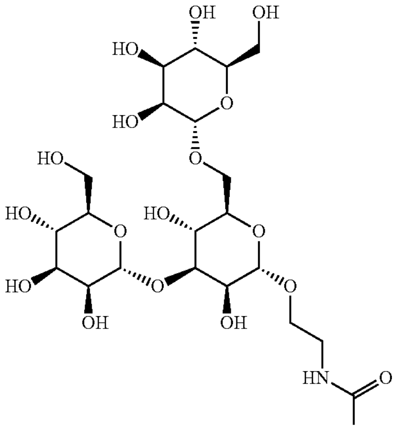

-continued
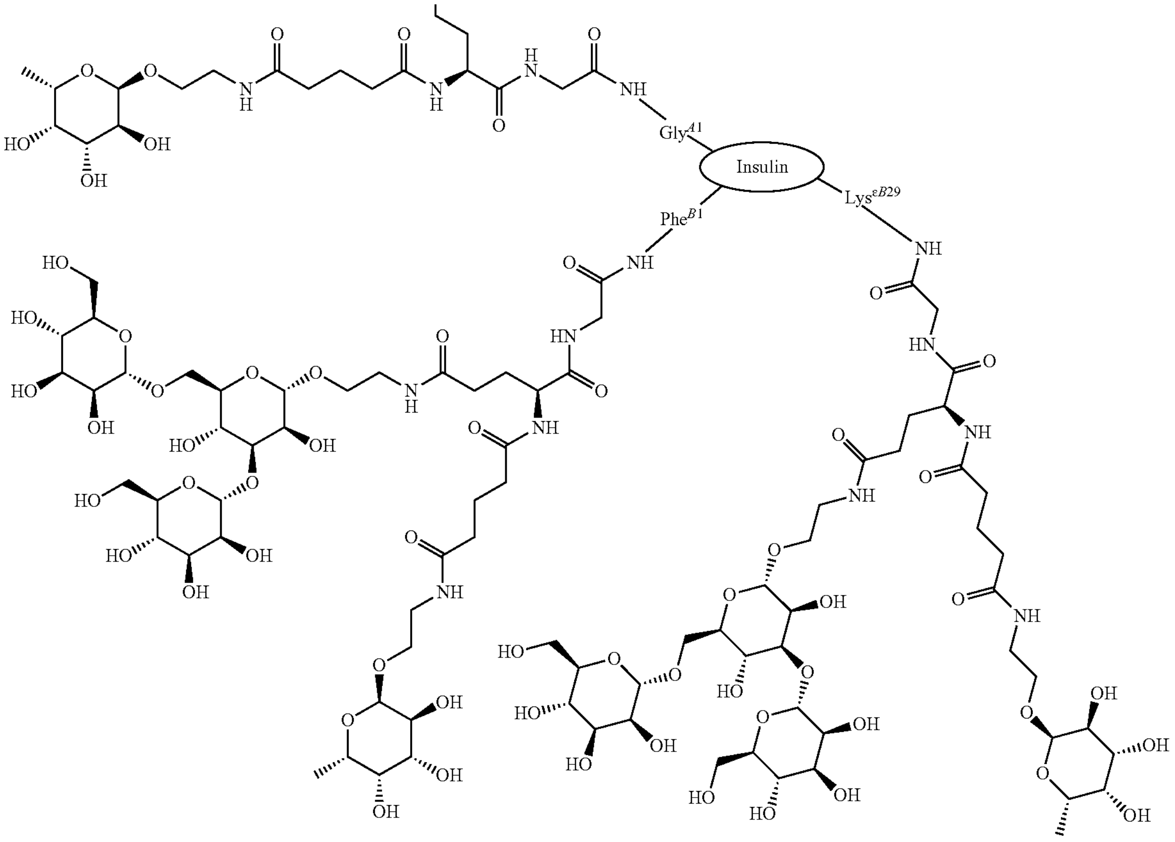
IOC-110
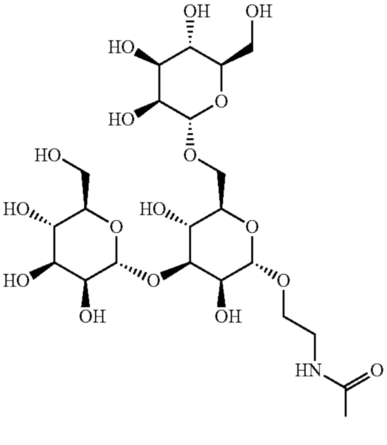

-continued
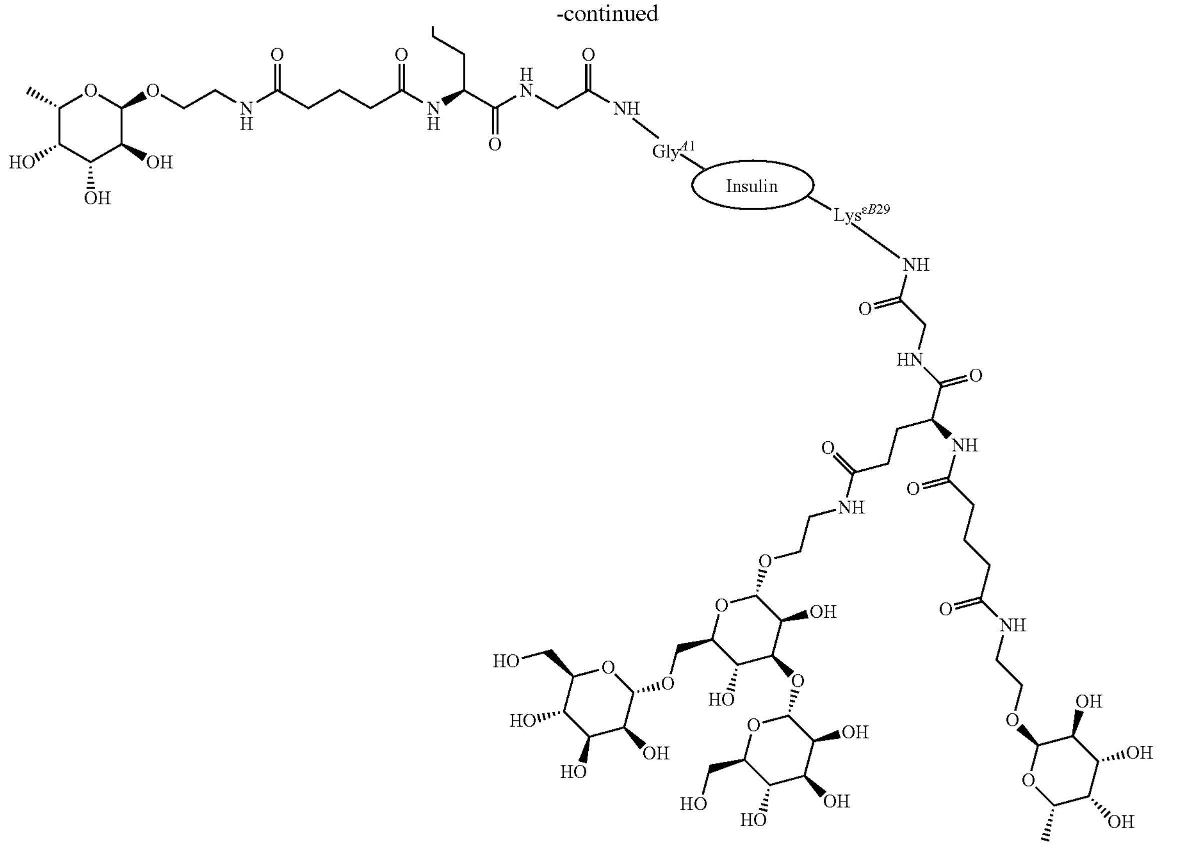
IOC-111
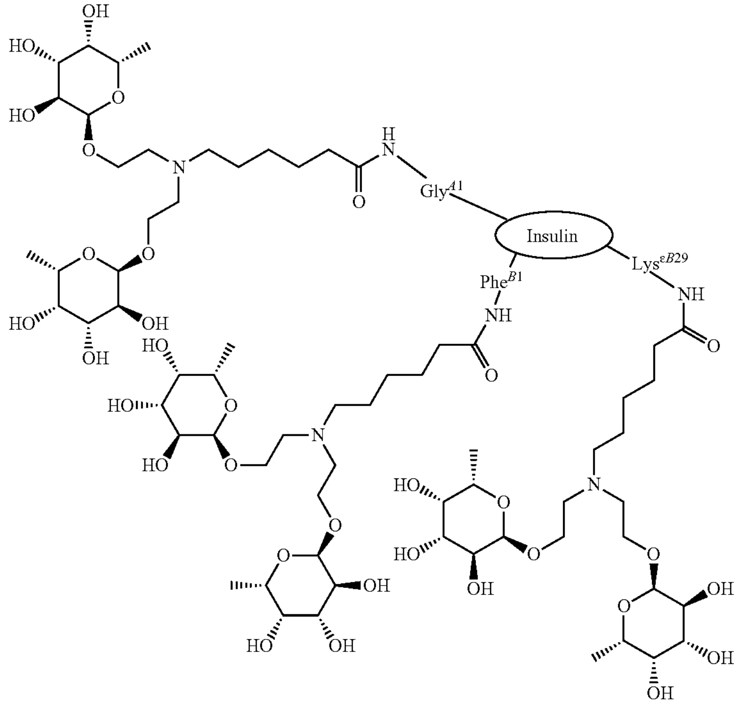

-continued
IOC-112
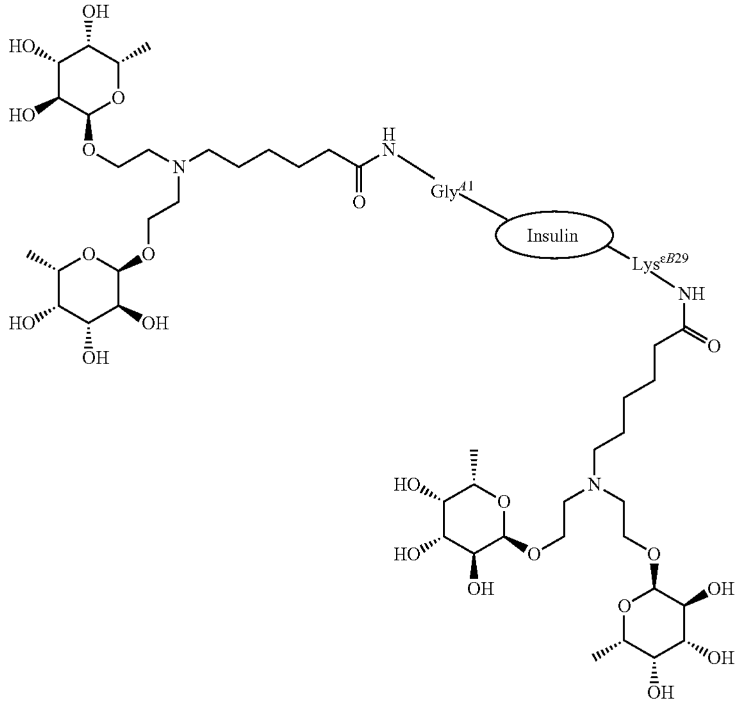
IOC-113
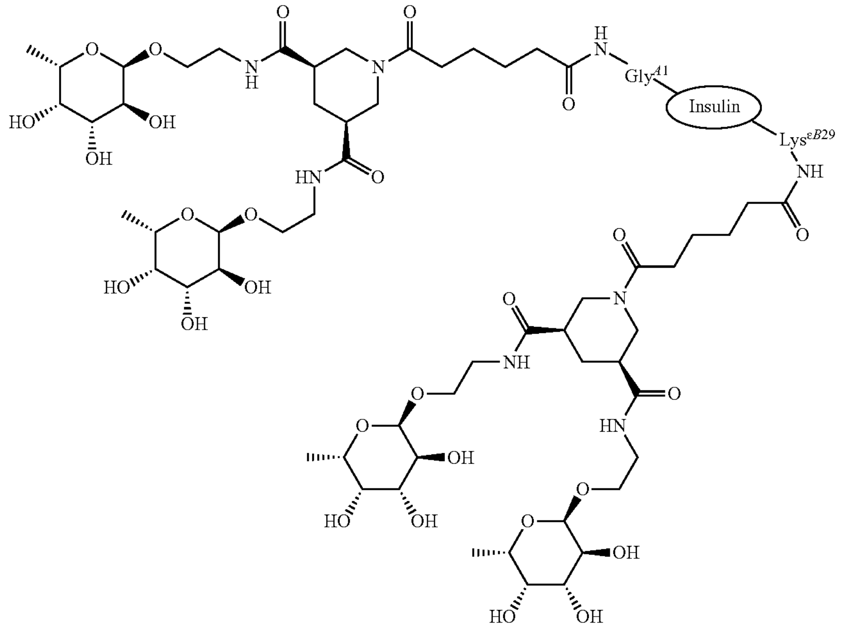

-continued
IOC-114
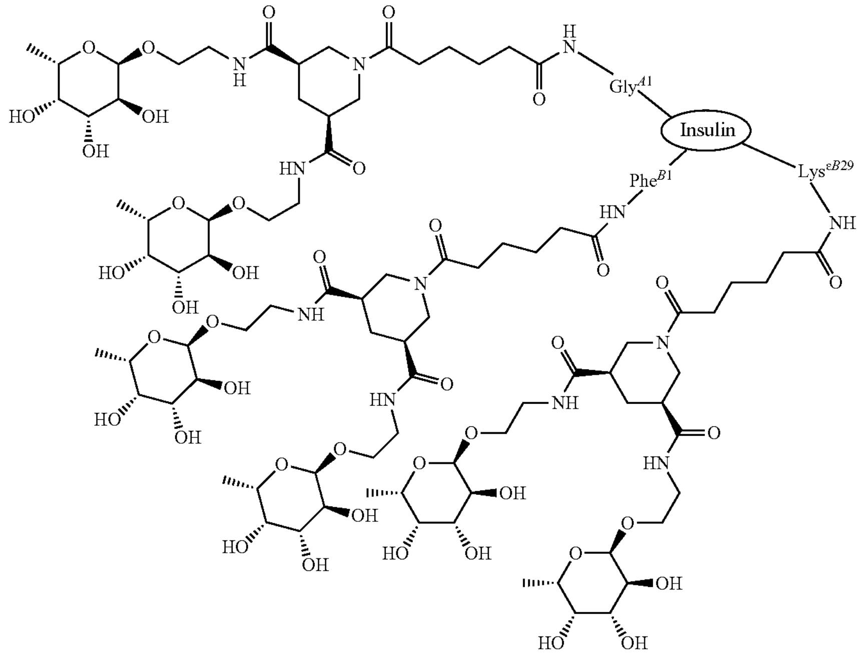
IOC-115
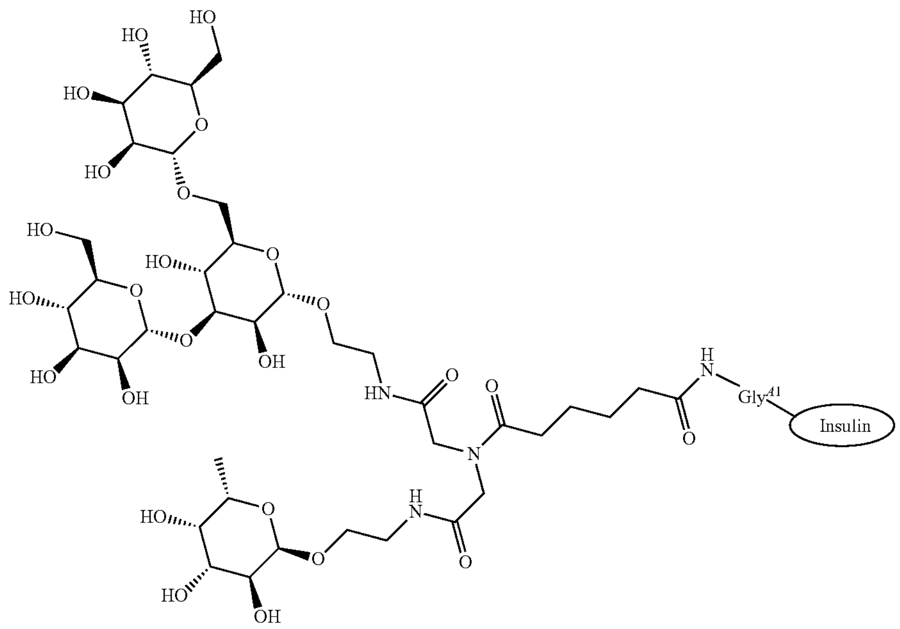

-continued
IOC-116
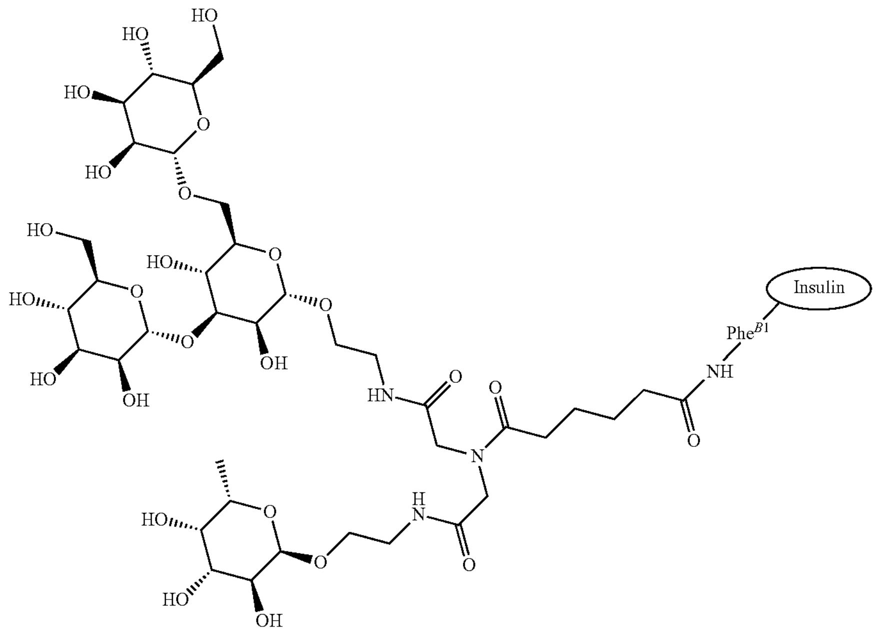
IOC-117
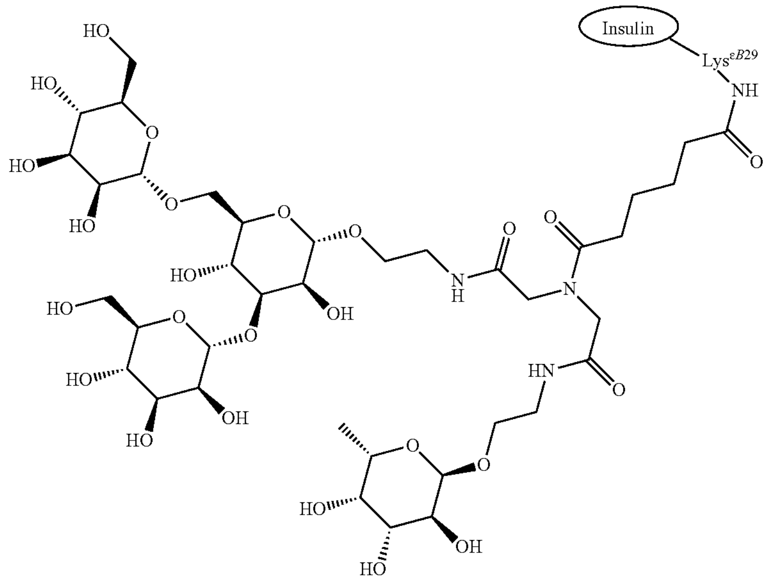

-continued
IOC-118
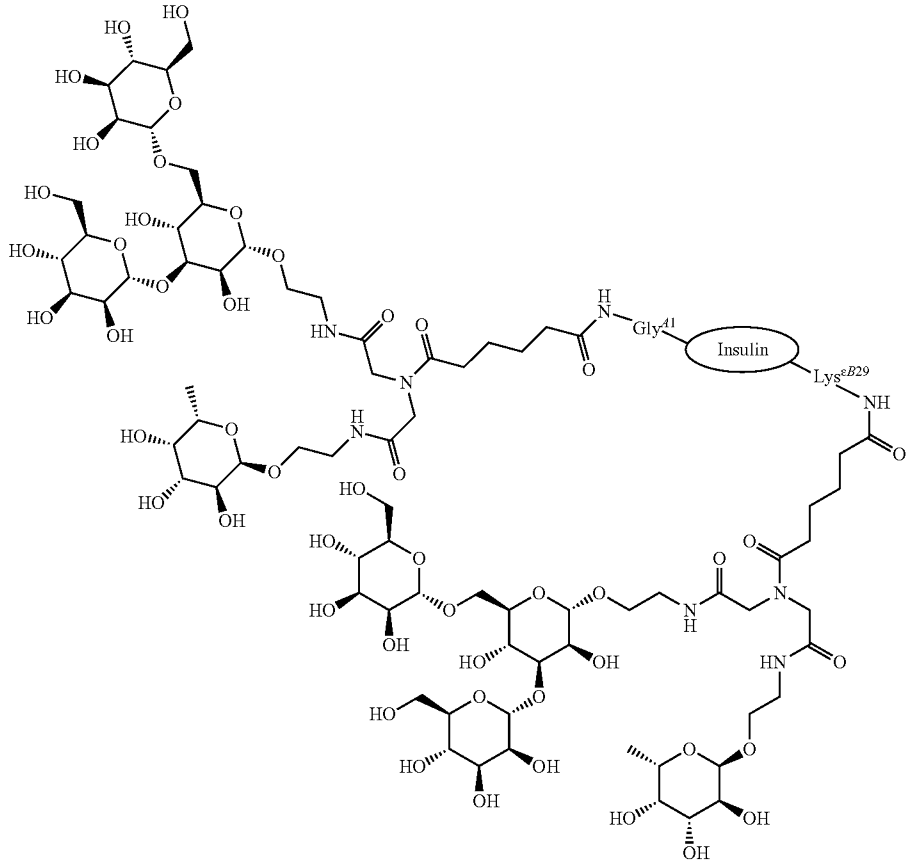
IOC-119
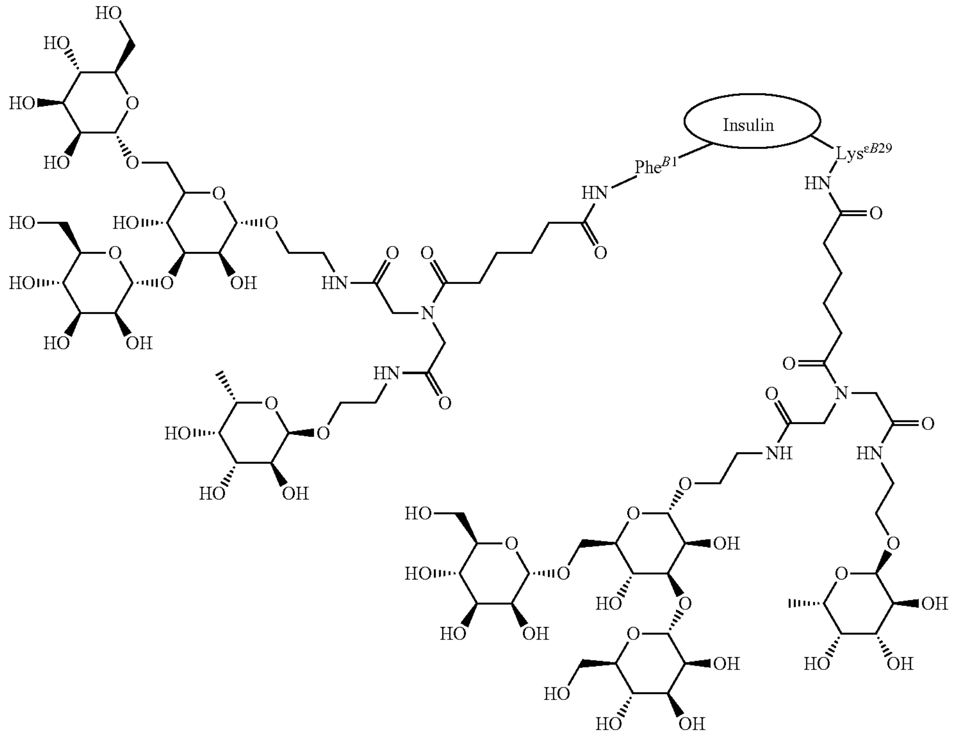

-continued
IOC-120
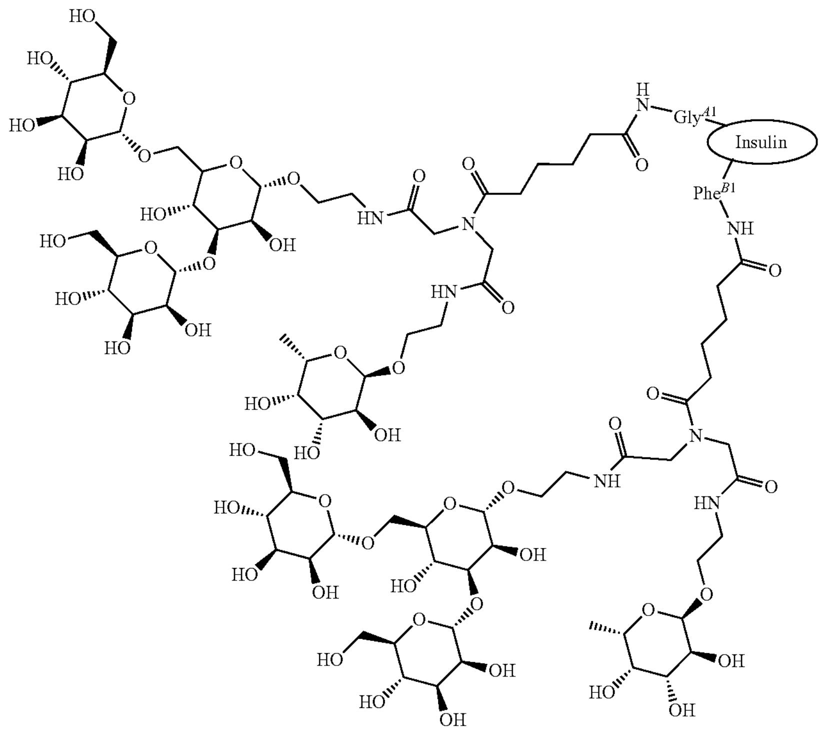
IOC-121
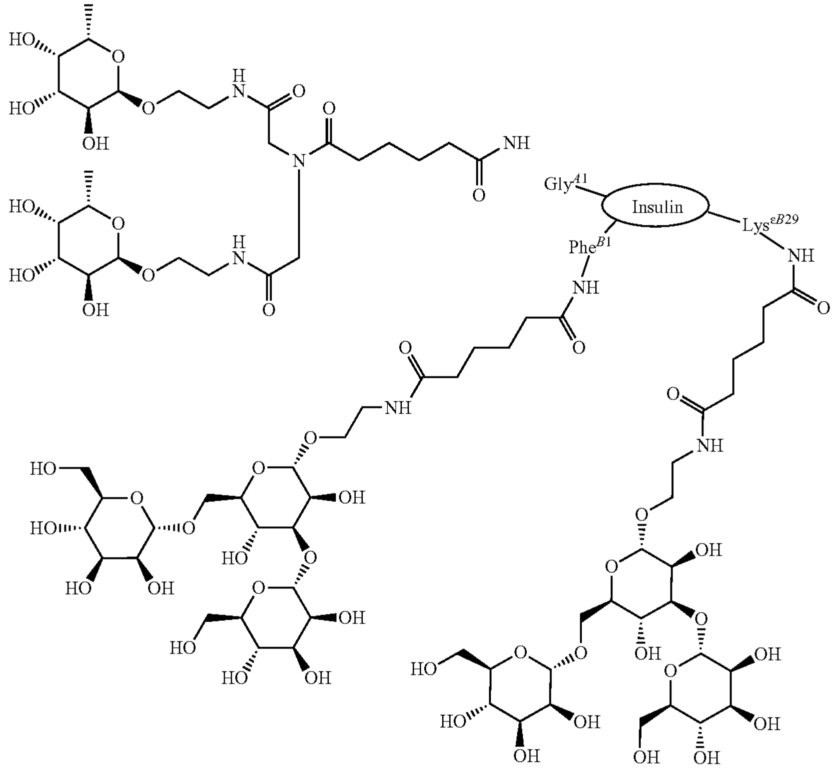

-continued
IOC-122
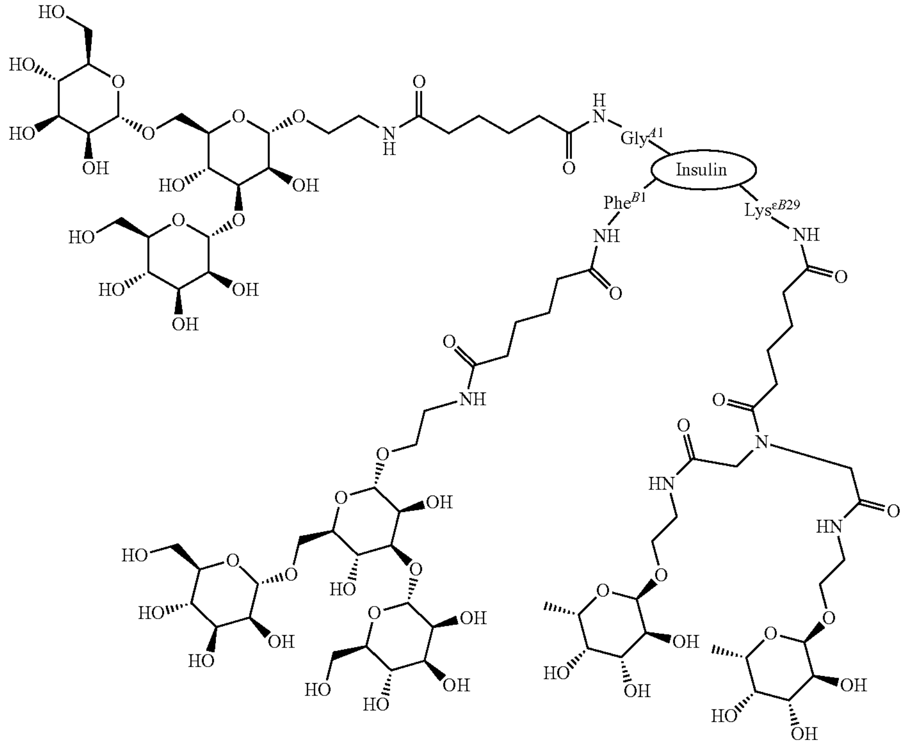
IOC-123
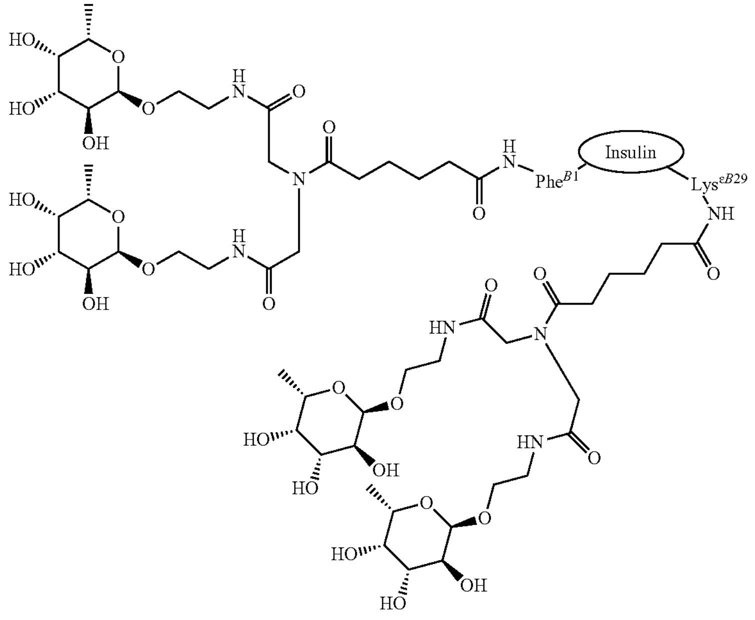

-continued
IOC-124
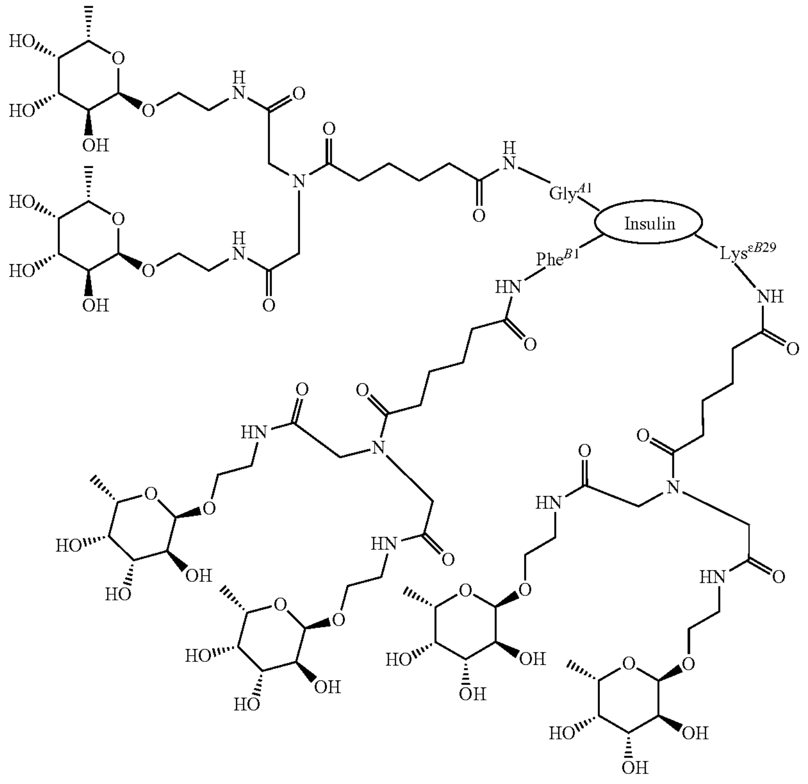
IOC-125
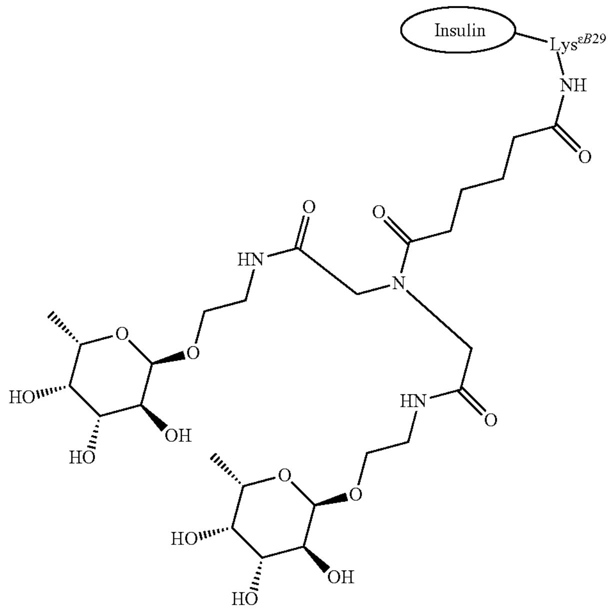

-continued
IOC-126
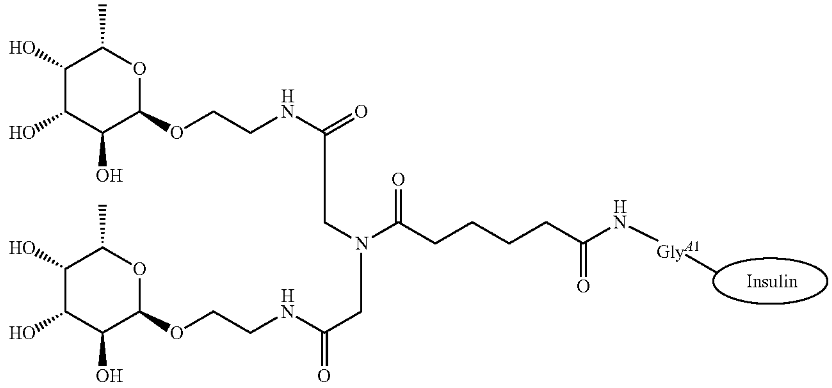
IOC-127
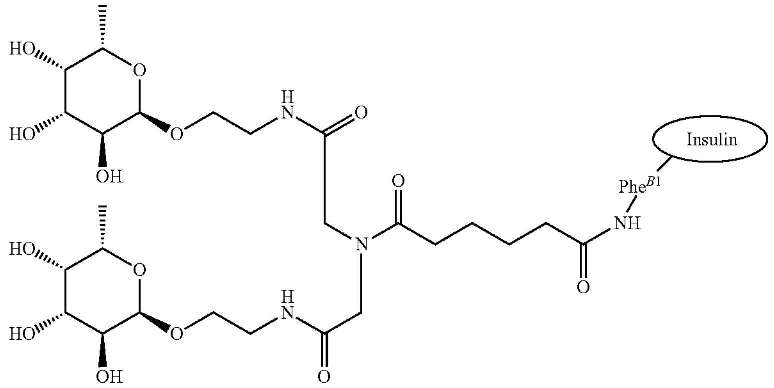
IOC-128
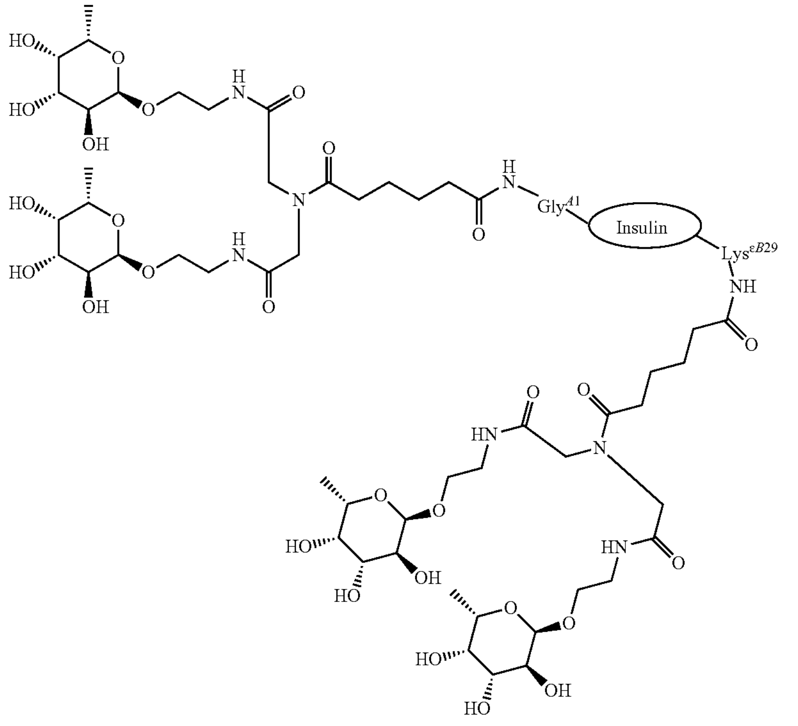

-continued
IOC-129
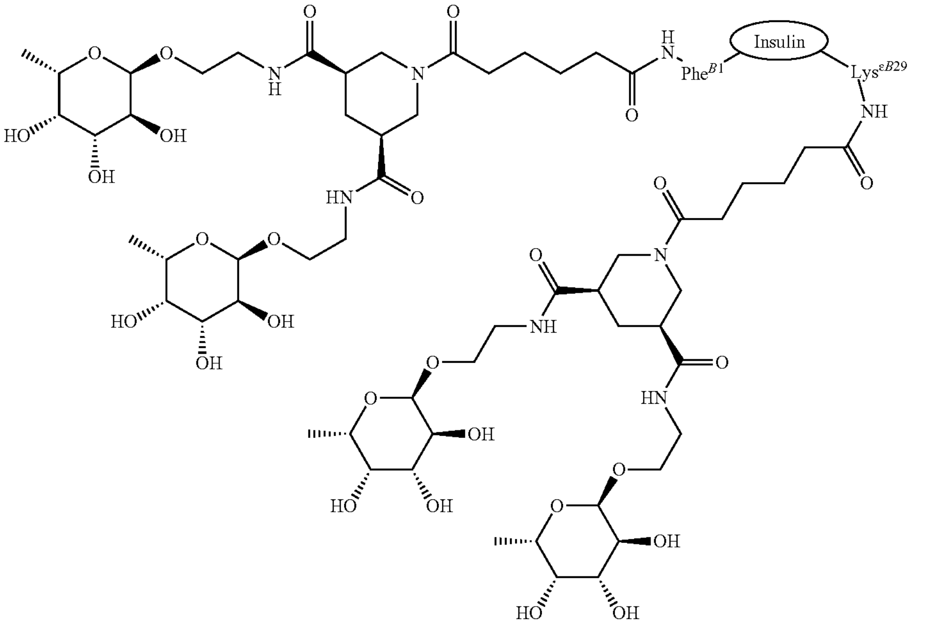
IOC-130
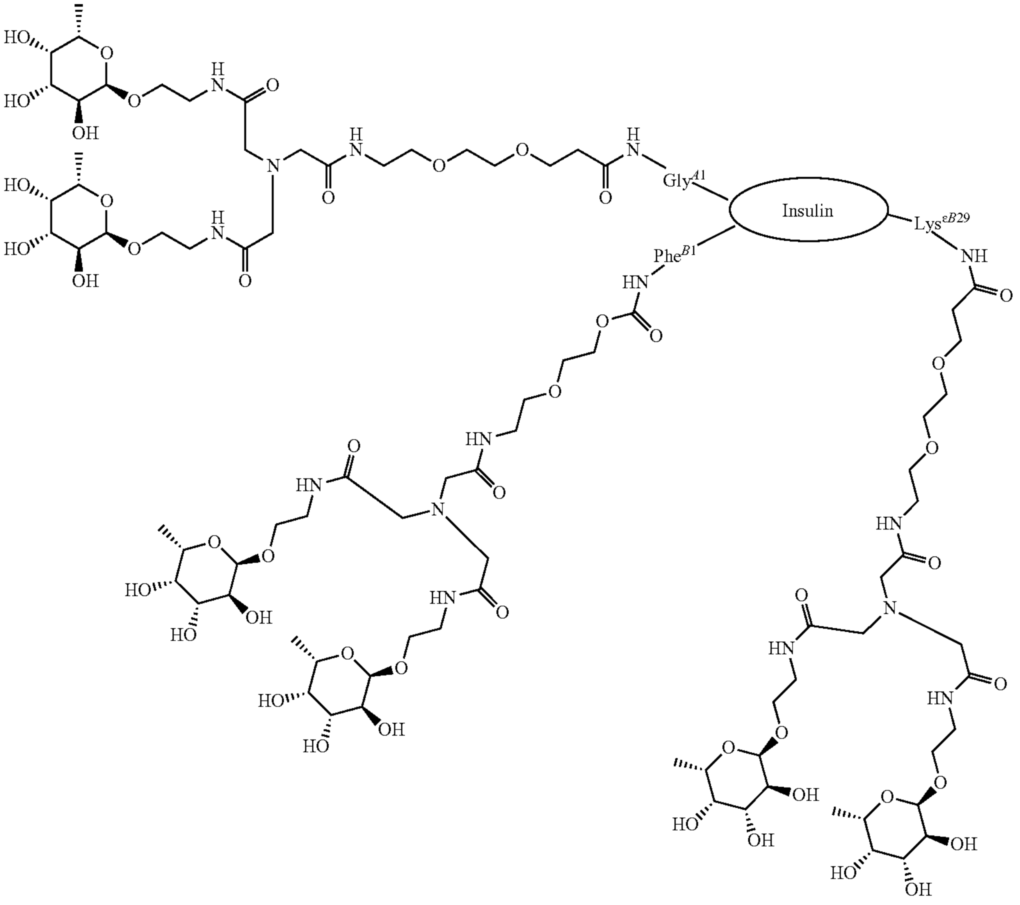

-continued
IOC-131
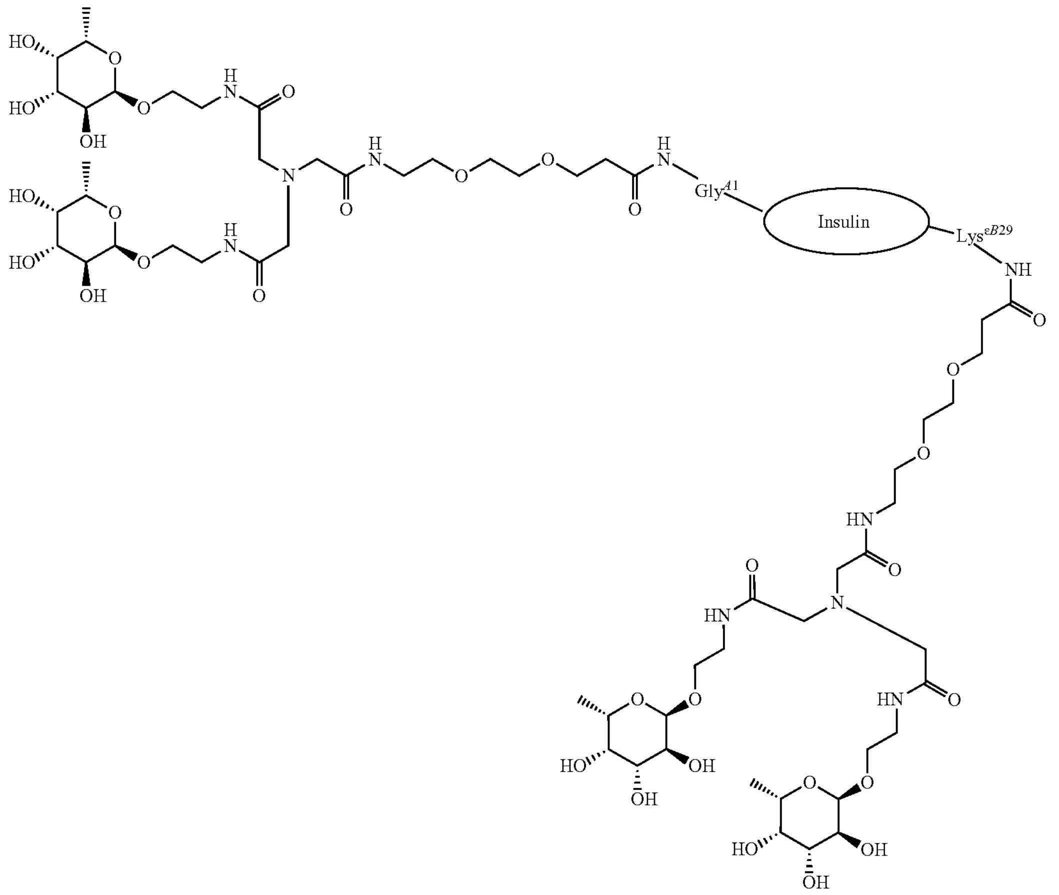
IOC-132
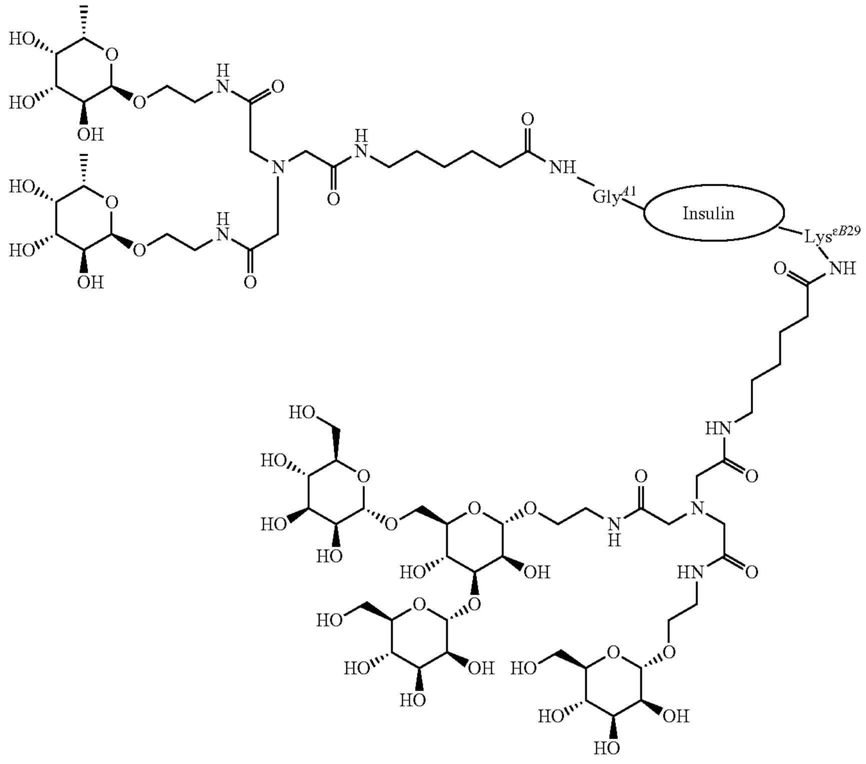

-continued
IOC-133
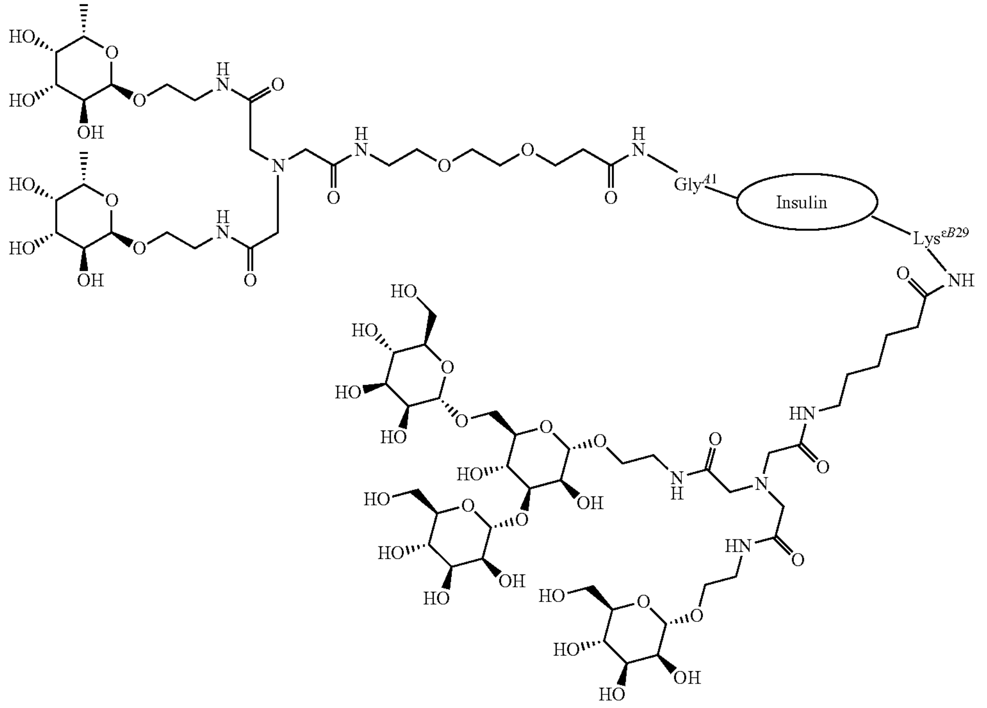
IOC-134
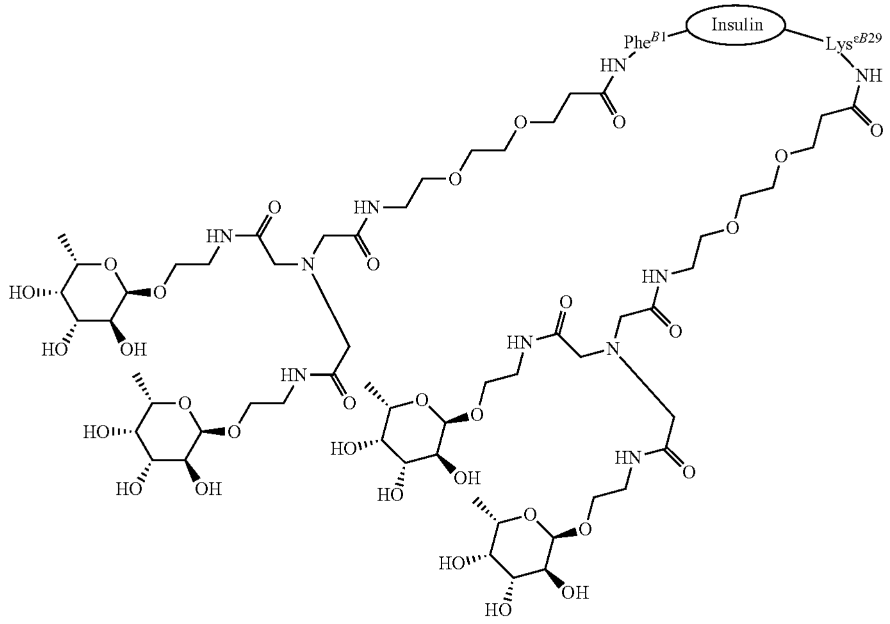

-continued
IOC-135
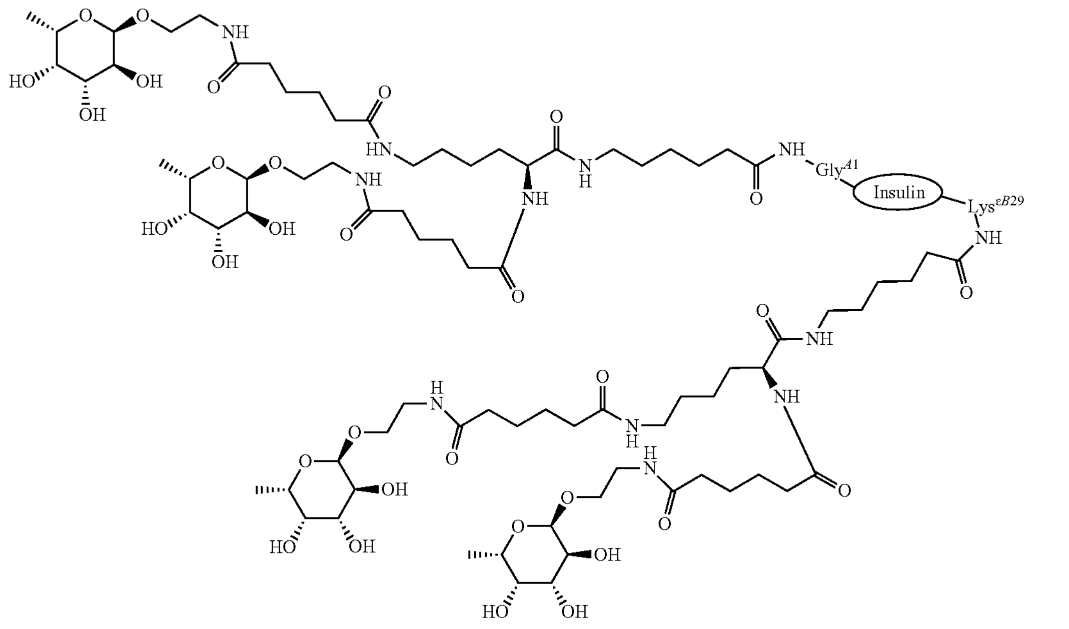
IOC-136
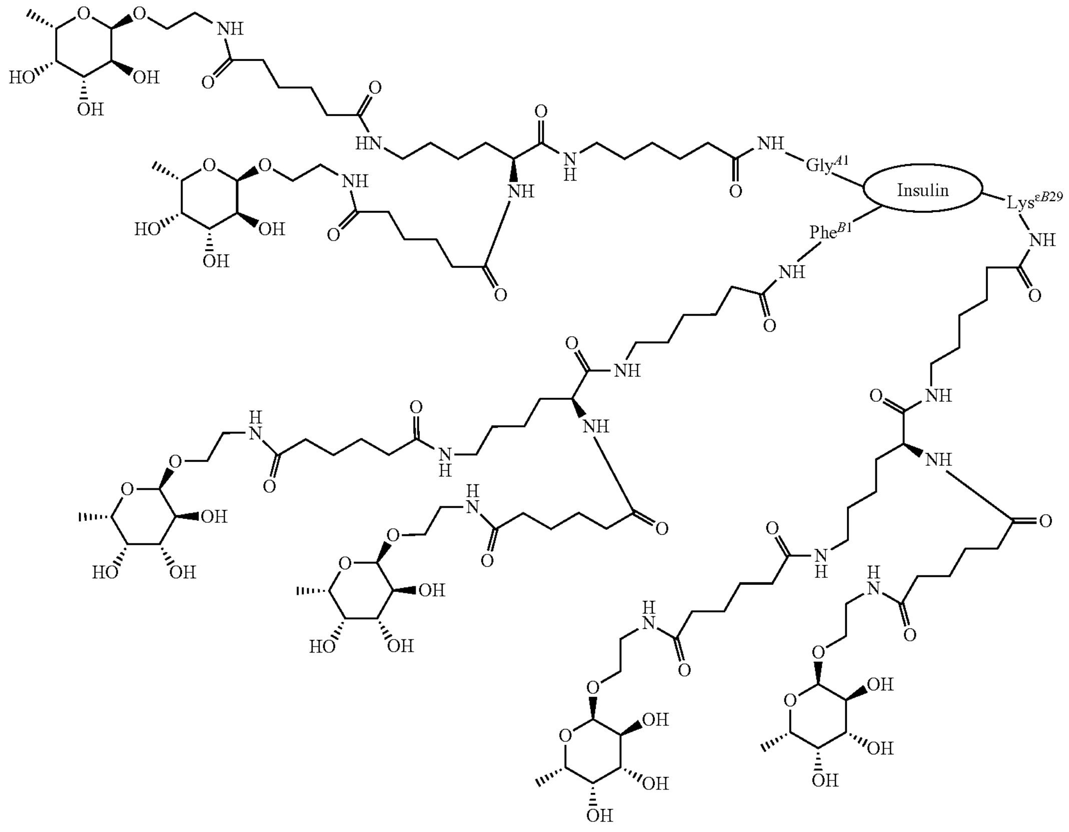

-continued
IOC-137
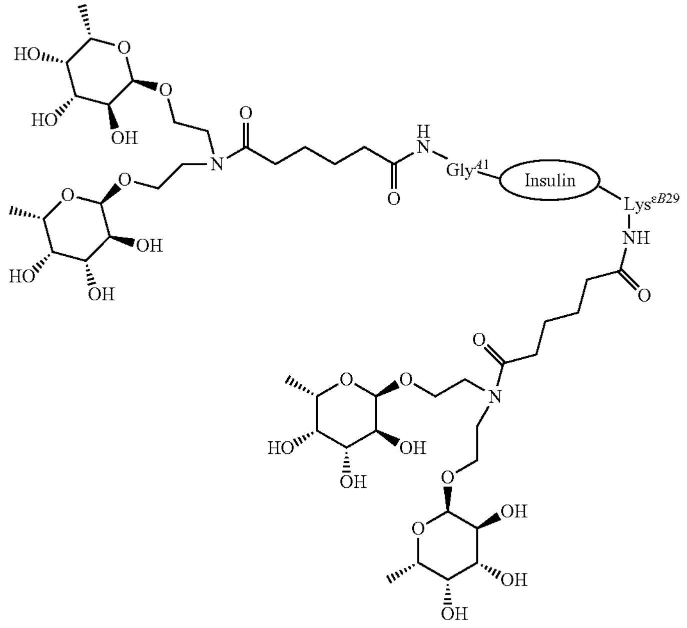
IOC-138
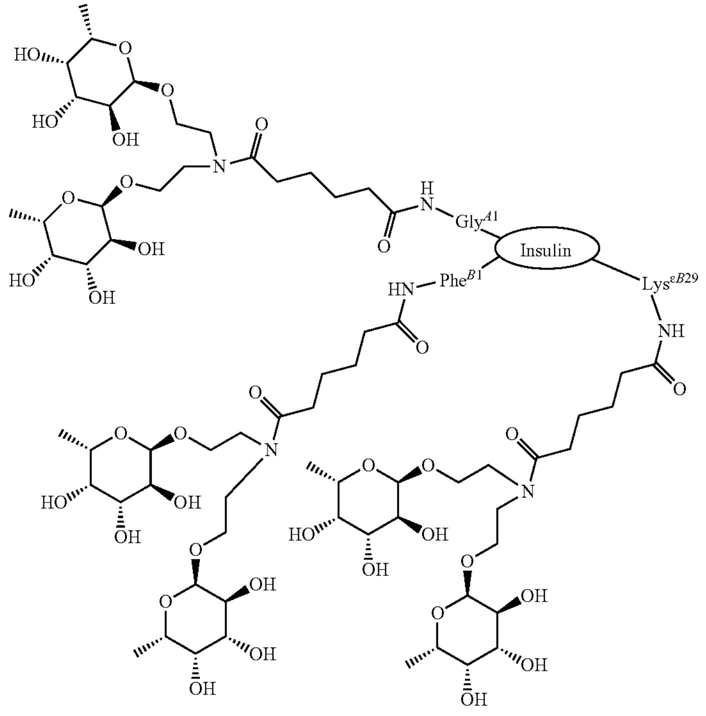

-continued
IOC-139
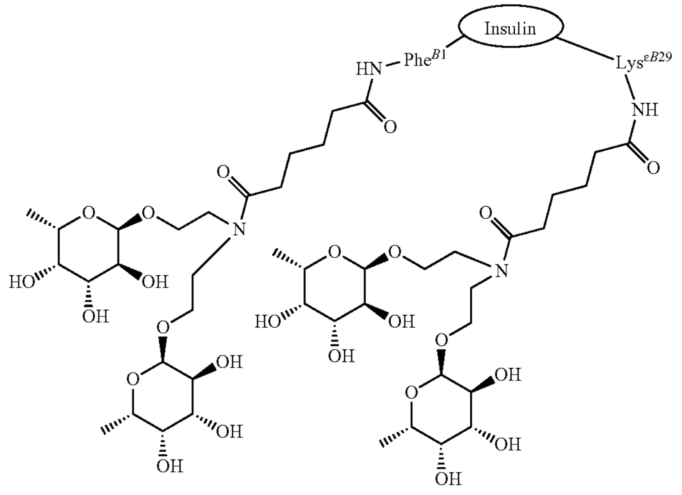
IOC-140
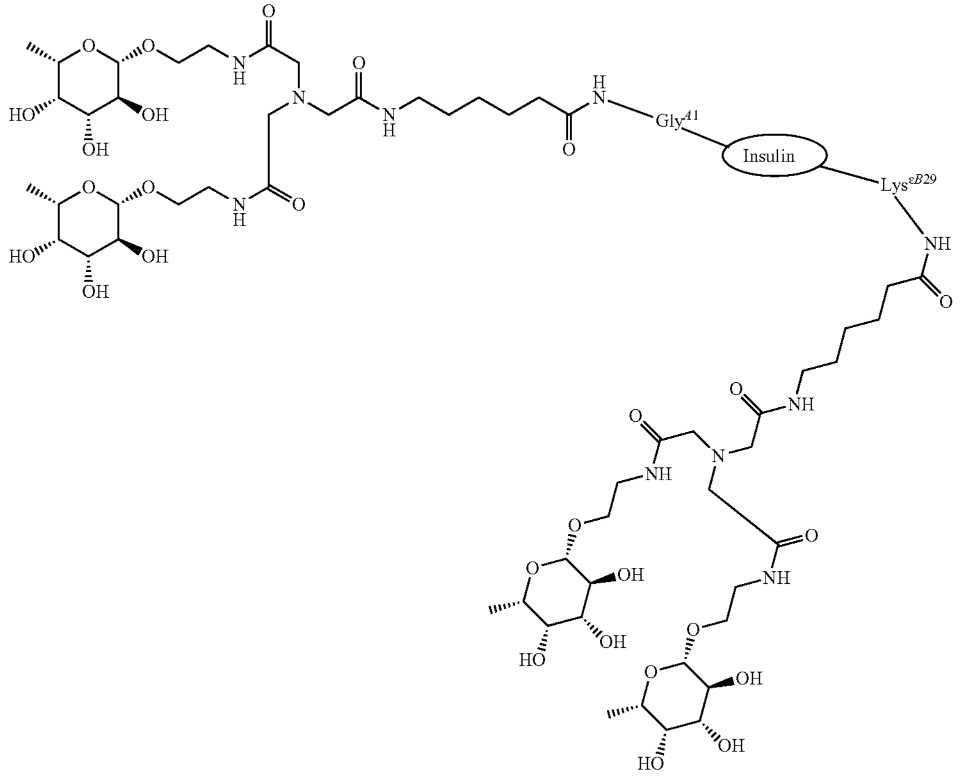

-continued
IOC-141
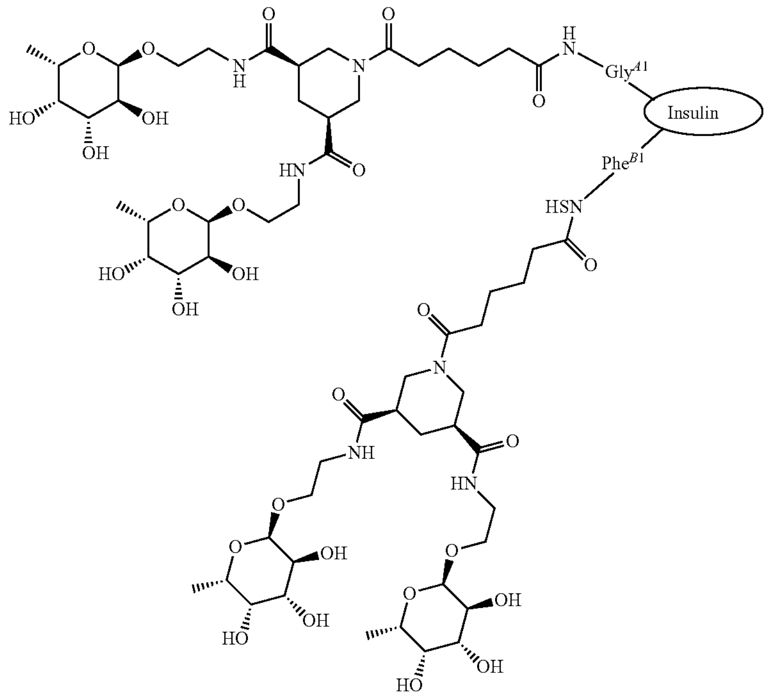
IOC-142
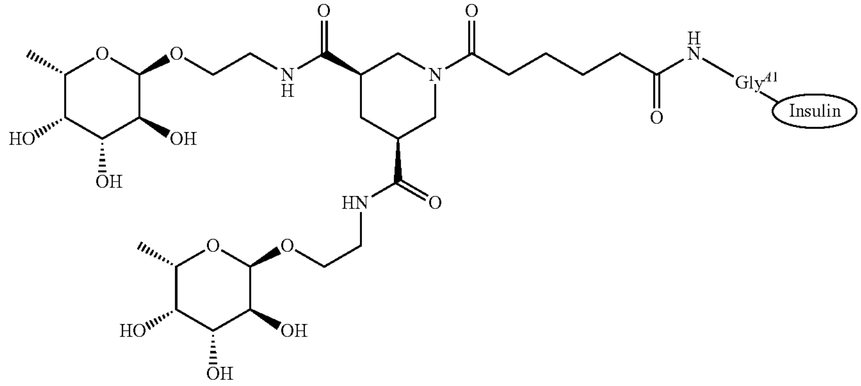

-continued
IOC-143
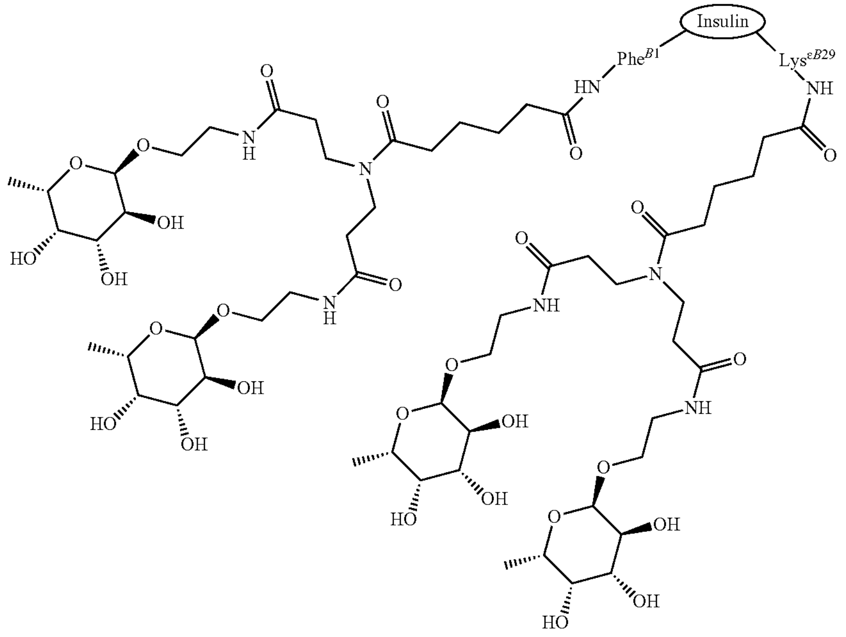
IOC-144
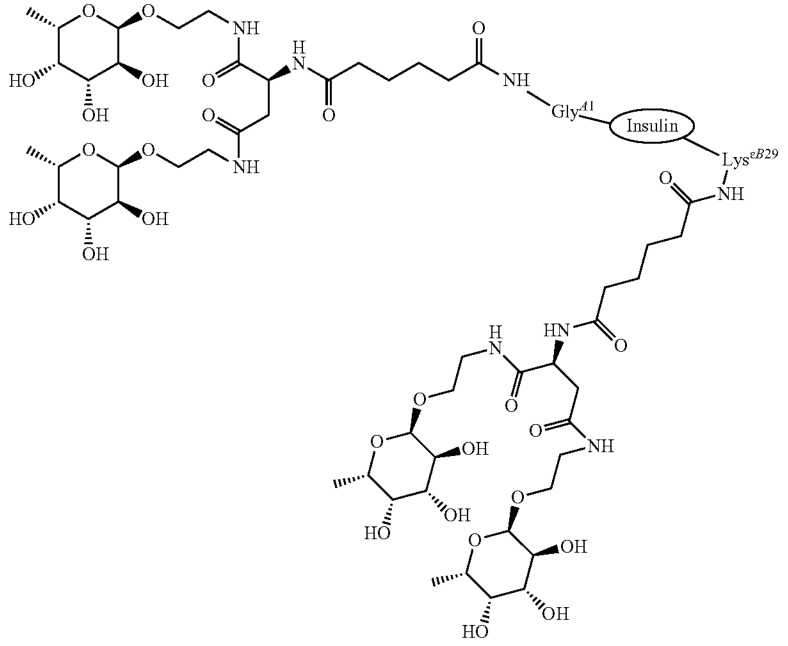

-continued
IOC-145
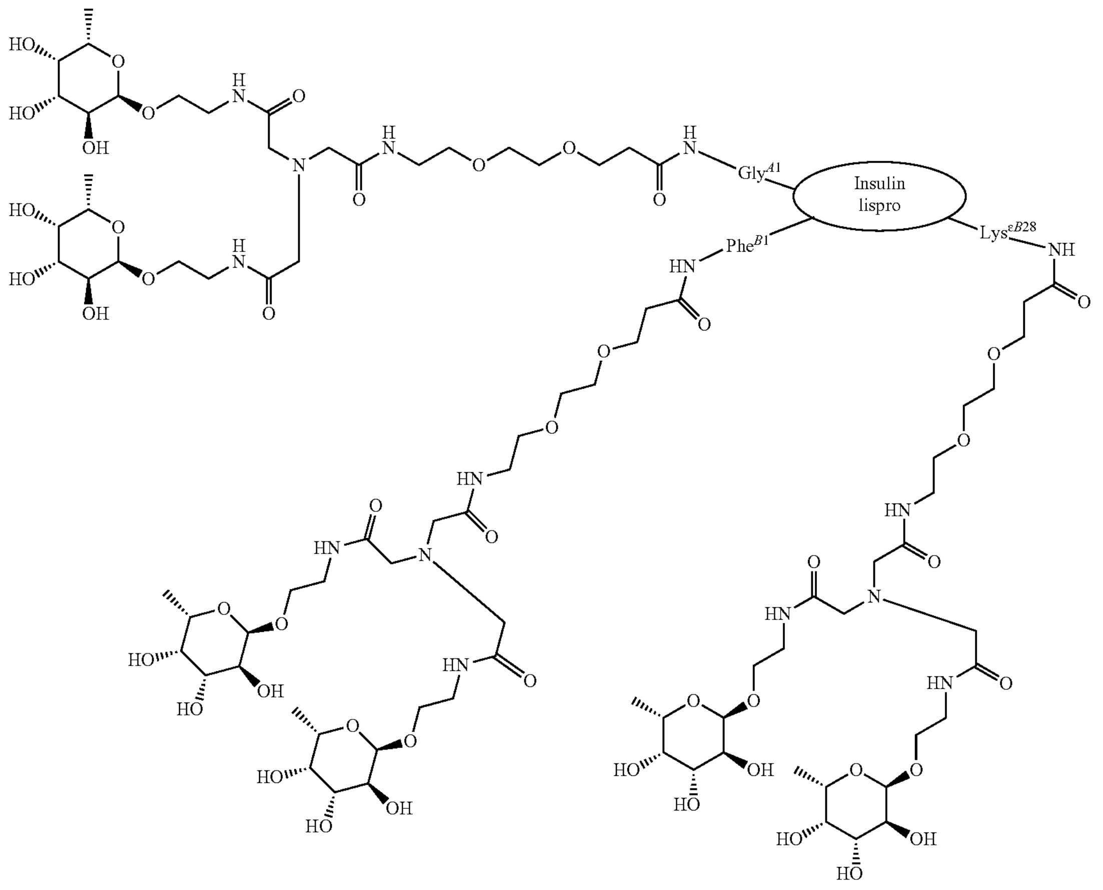

-continued
IOC-146
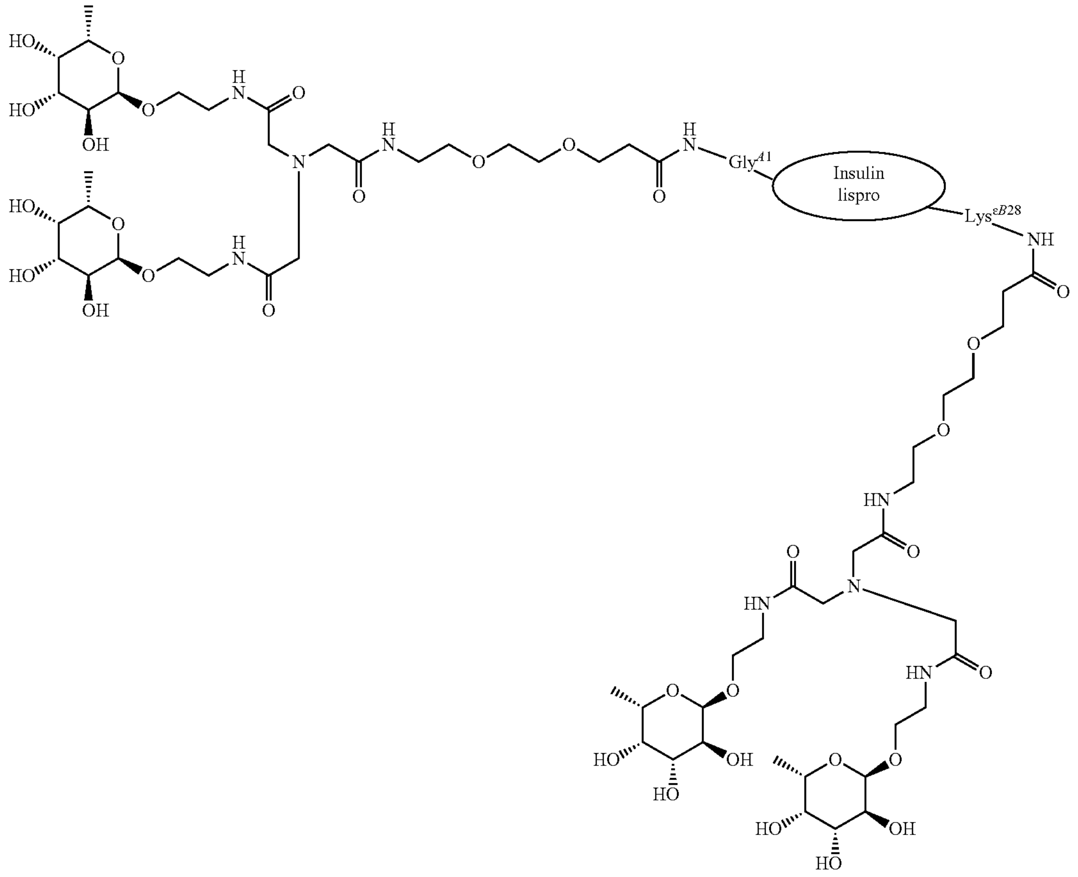

-continued
IOC-147
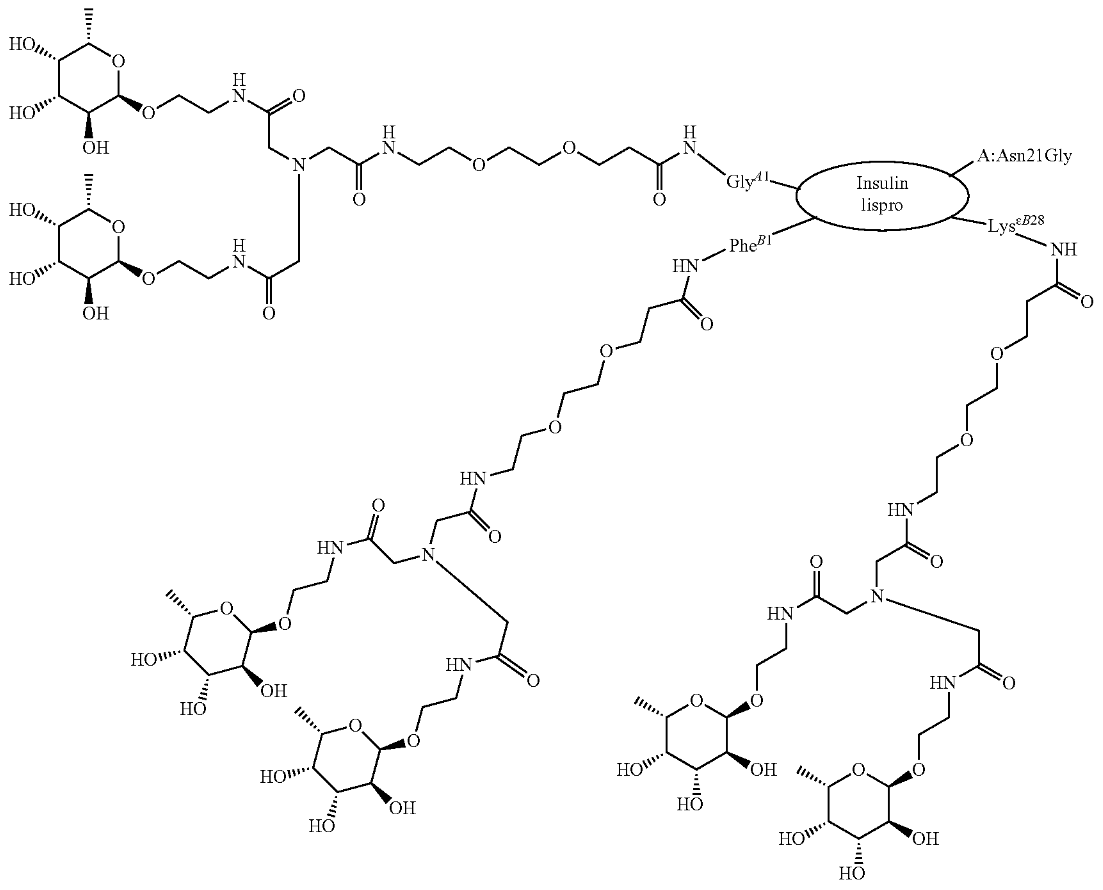

-continued
IOC-148
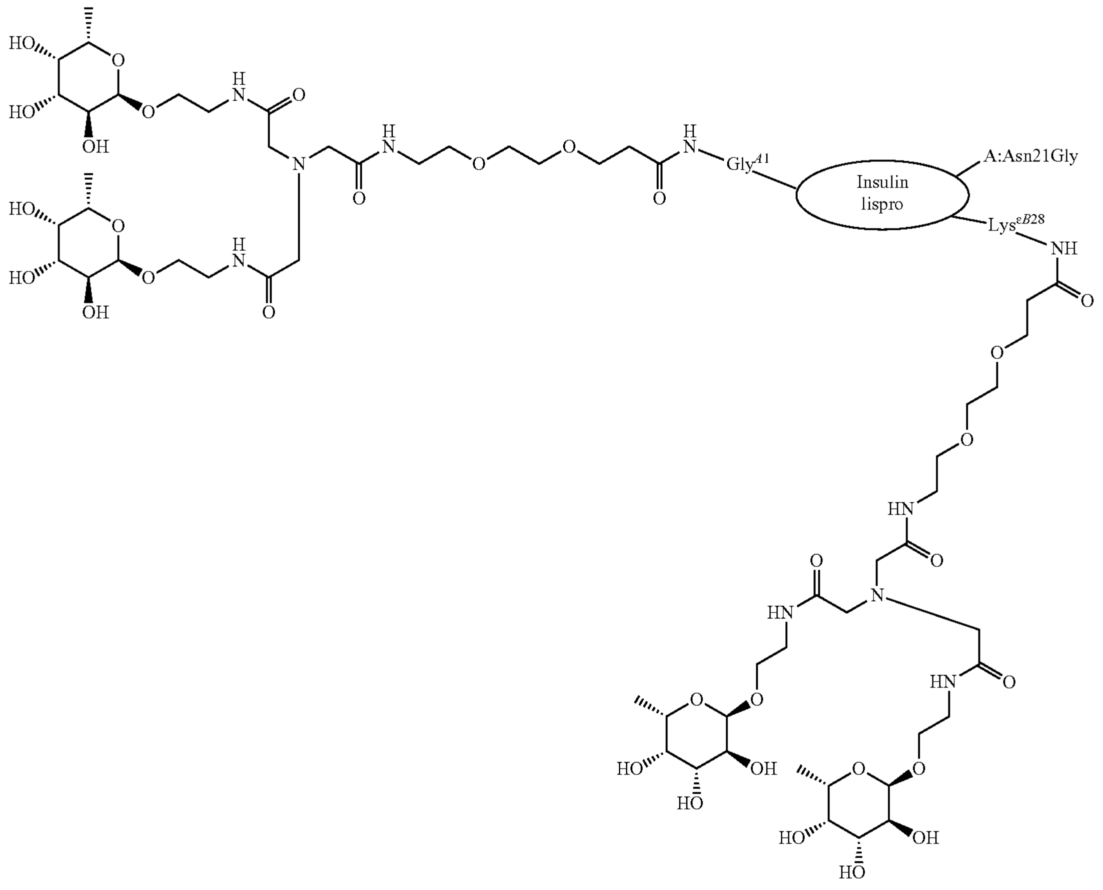

-continued
IOC-149
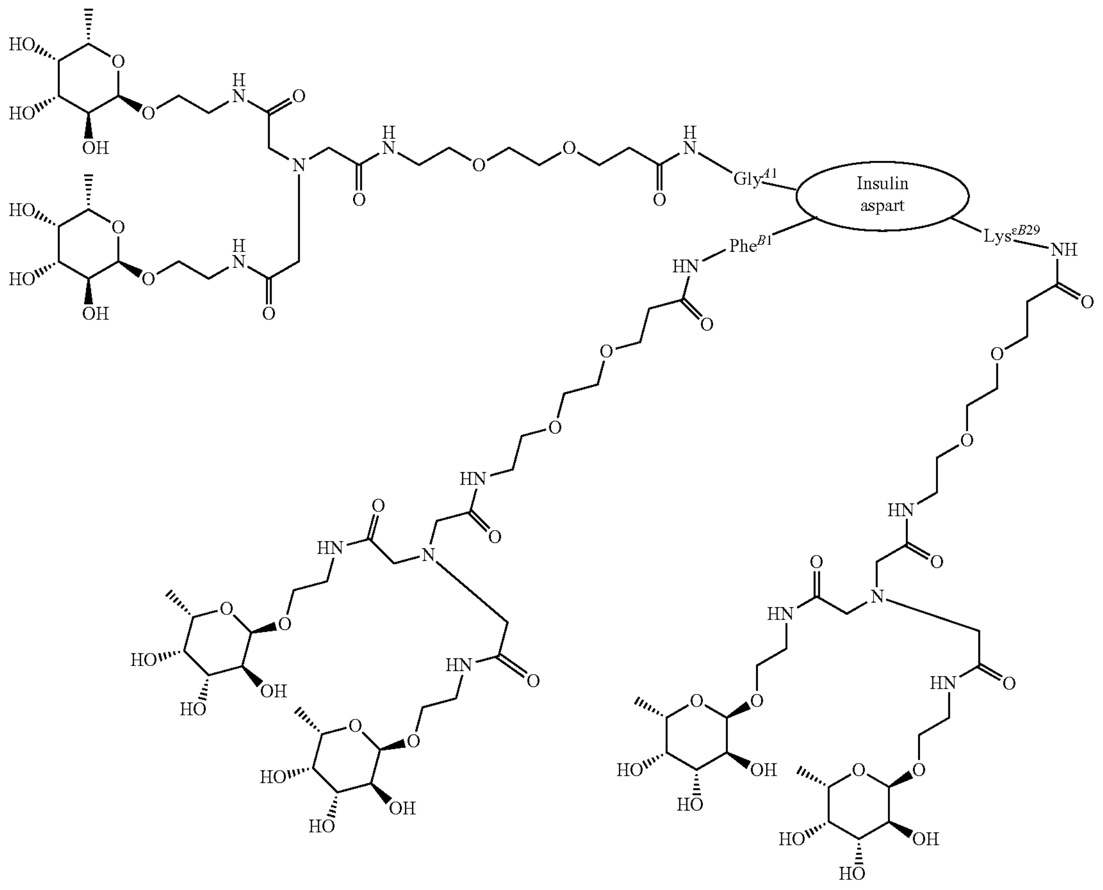

-continued
IOC-150
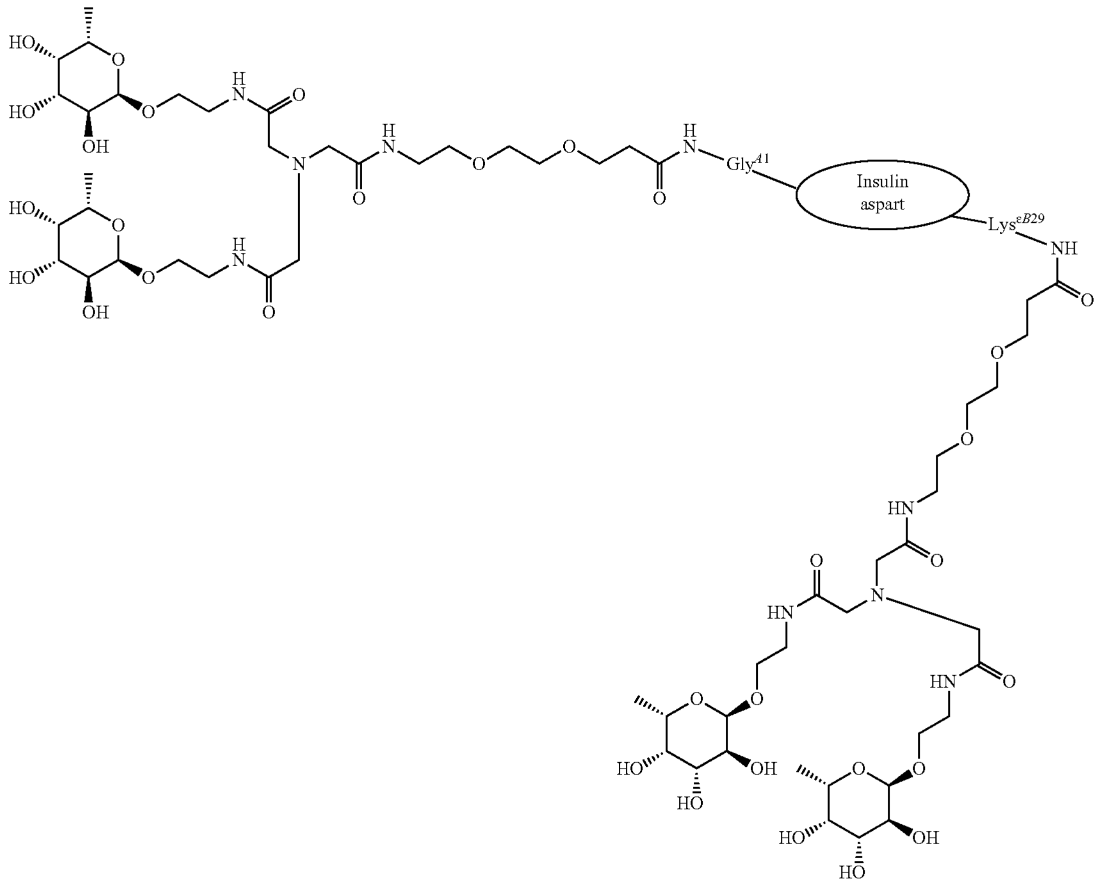

-continued
IOC-151
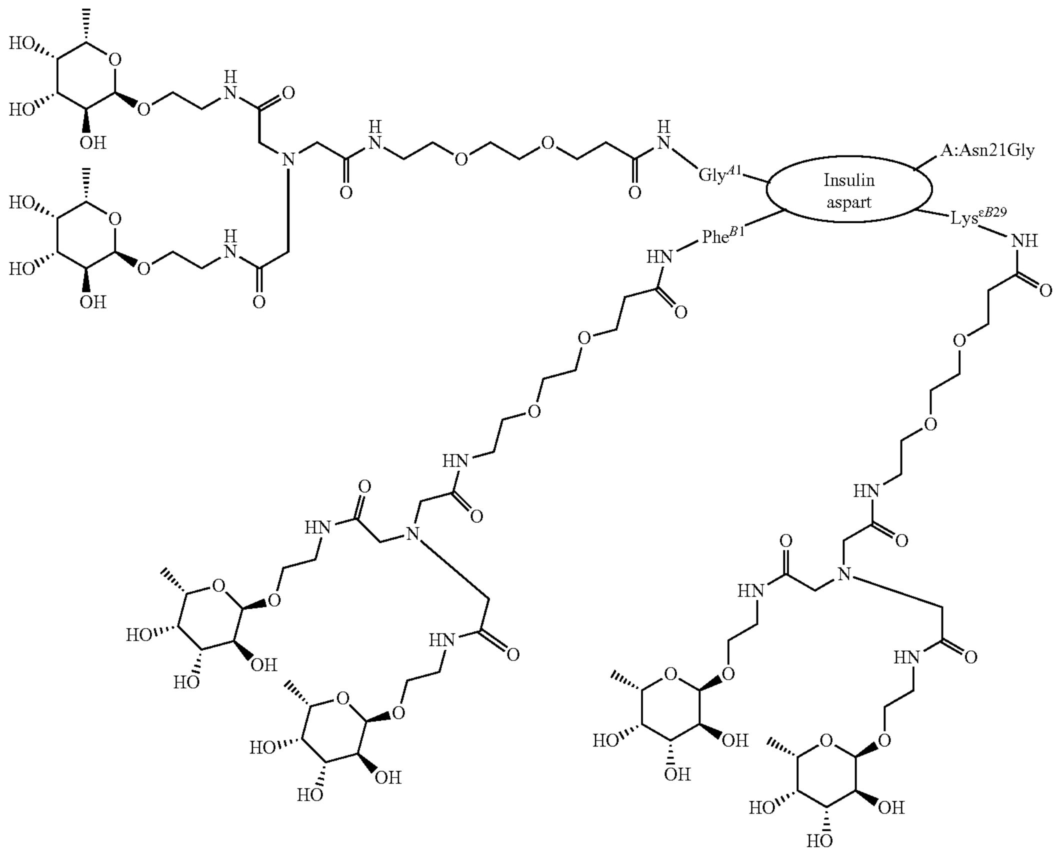

-continued
IOC-152
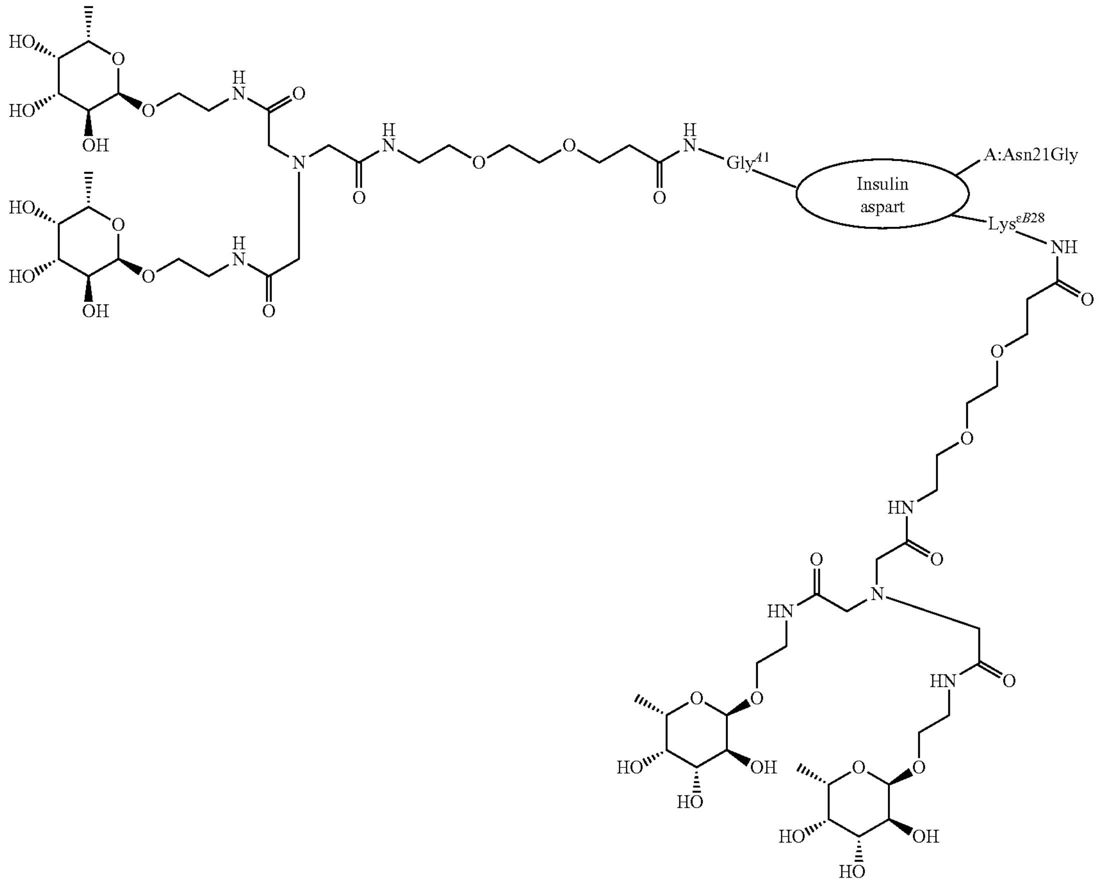
IOC-153
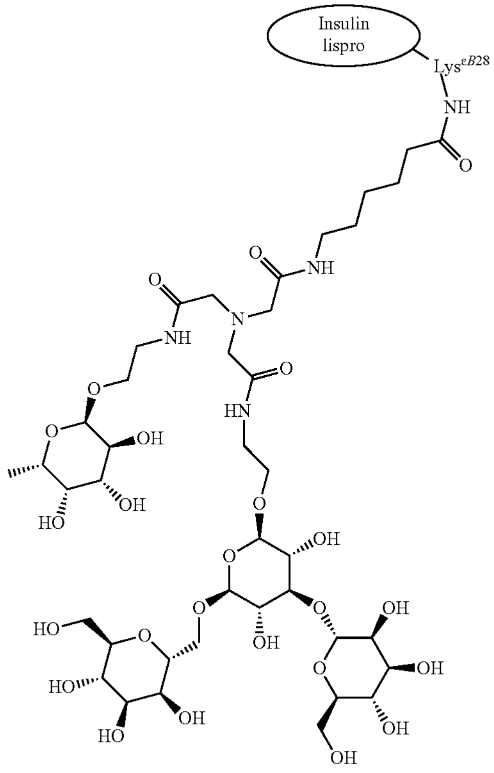

-continued
IOC-154
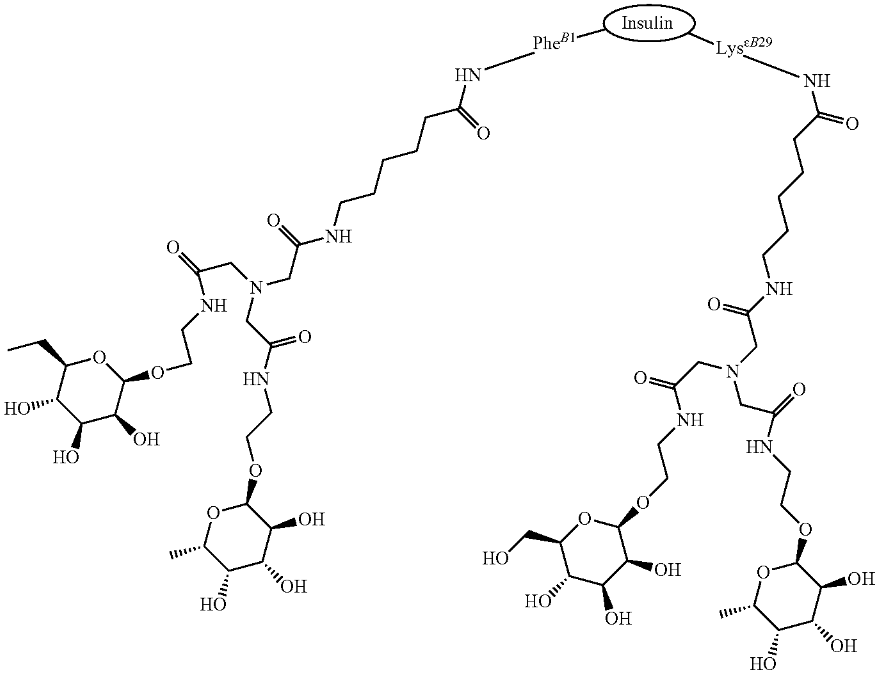
IOC-155
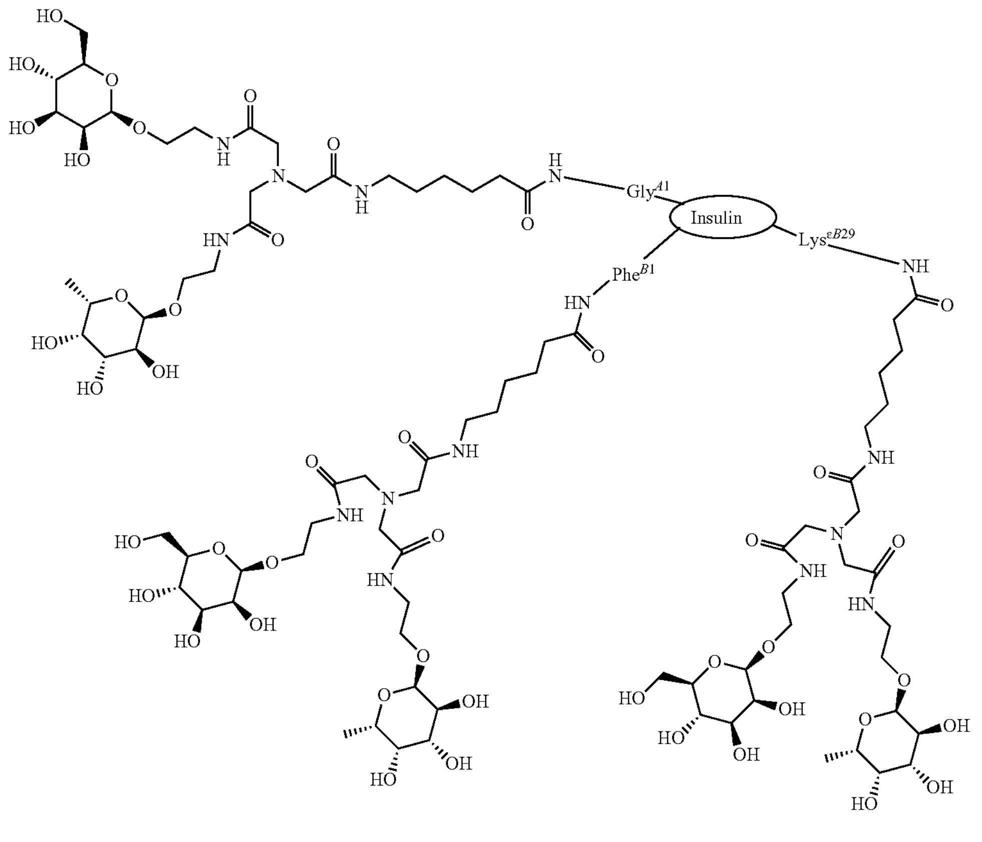

-continued
IOC-156
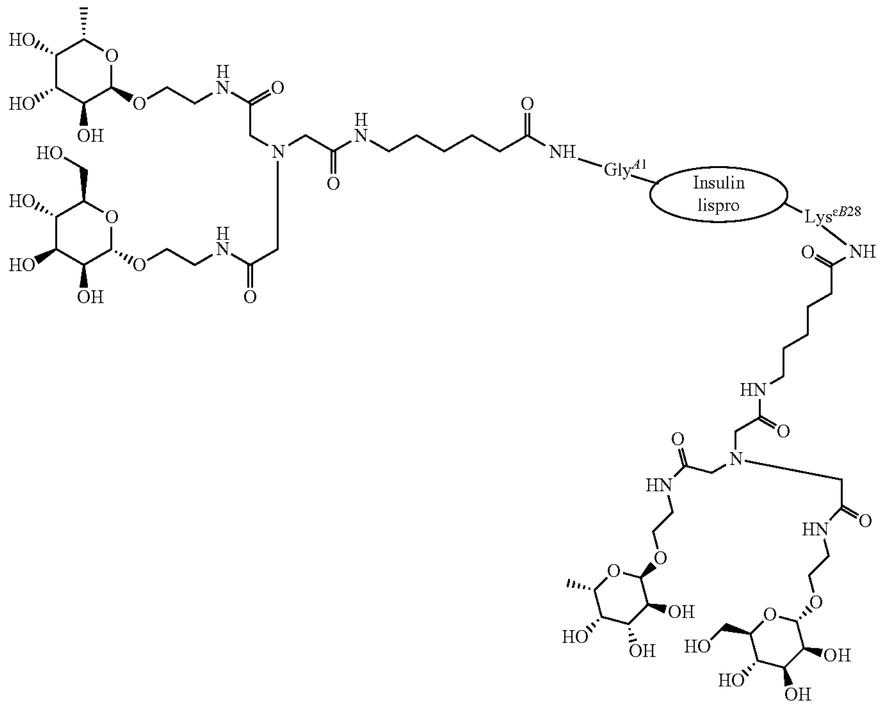
IOC-157
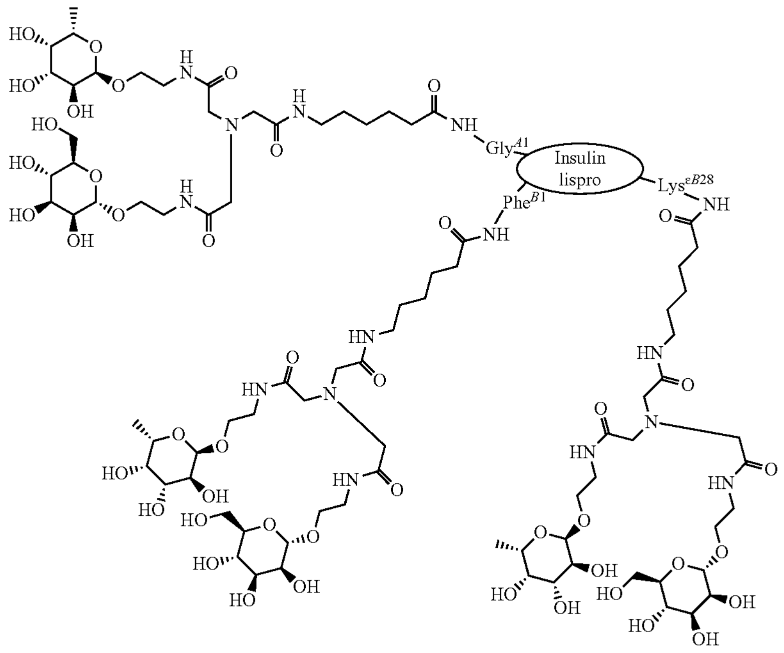

-continued
IOC-158
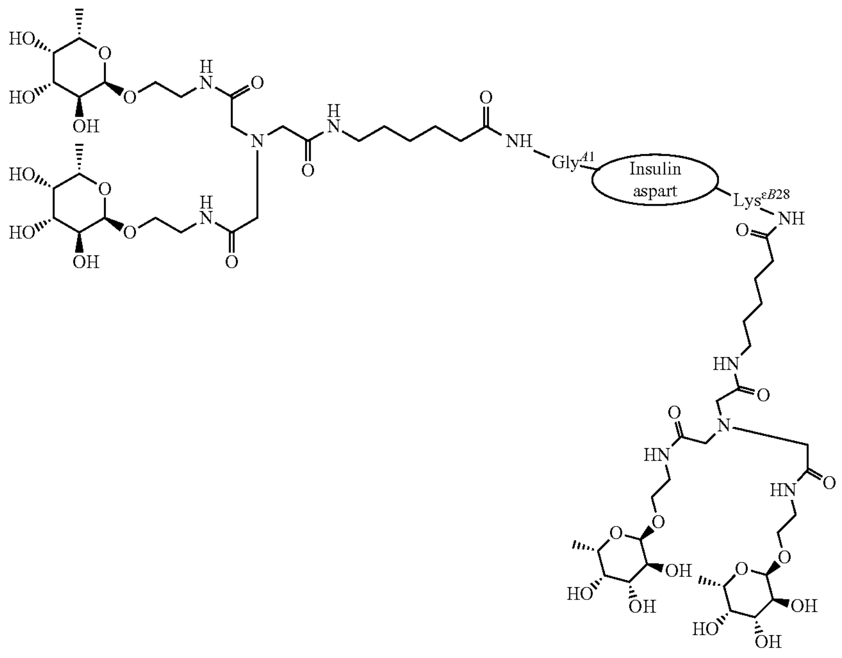
IOC-159
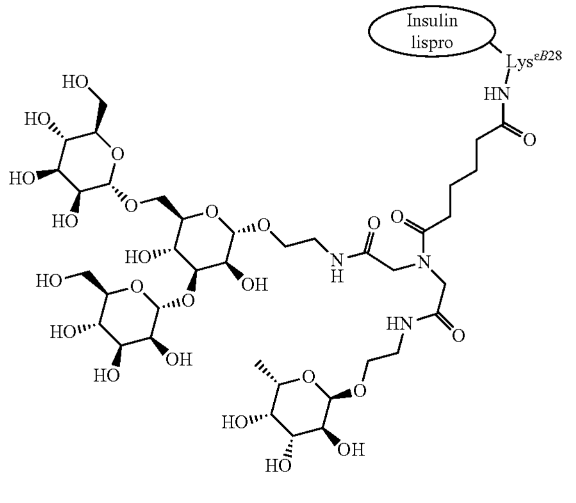
IOC-160
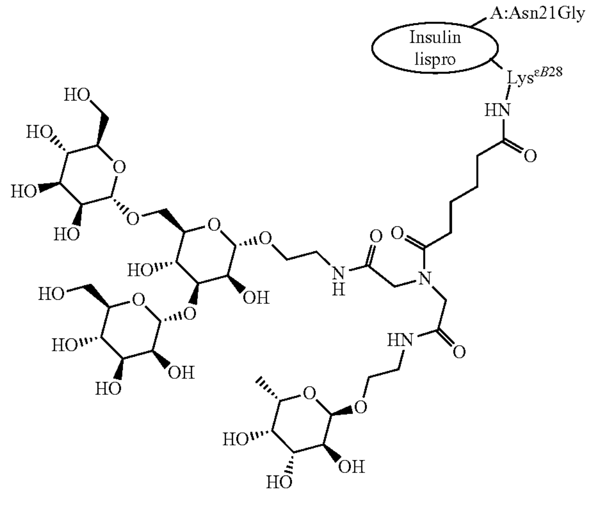

-continued
IOC-161
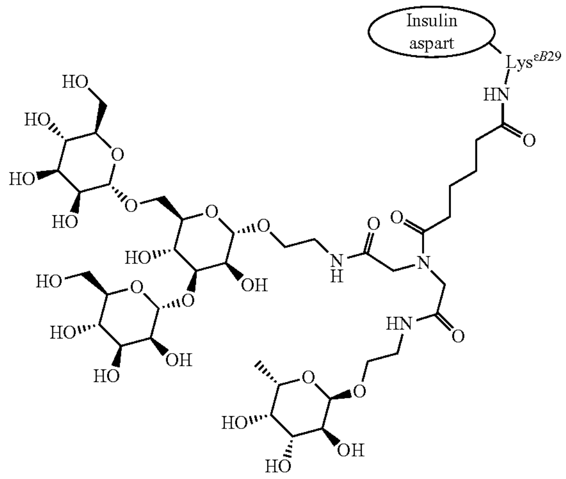
IOC-162
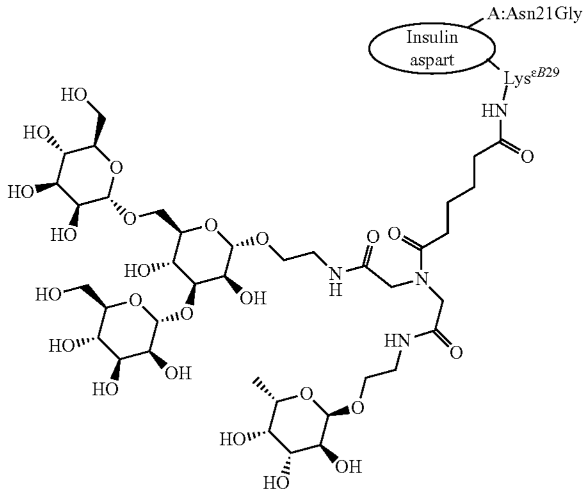
IOC-163
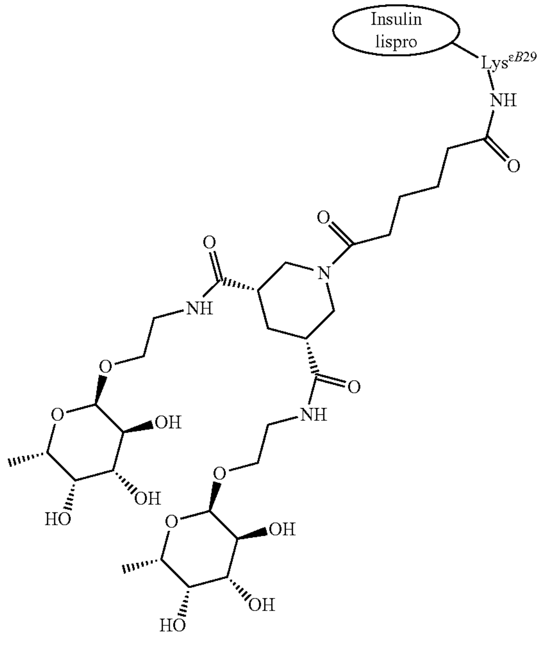

-continued
IOC-164
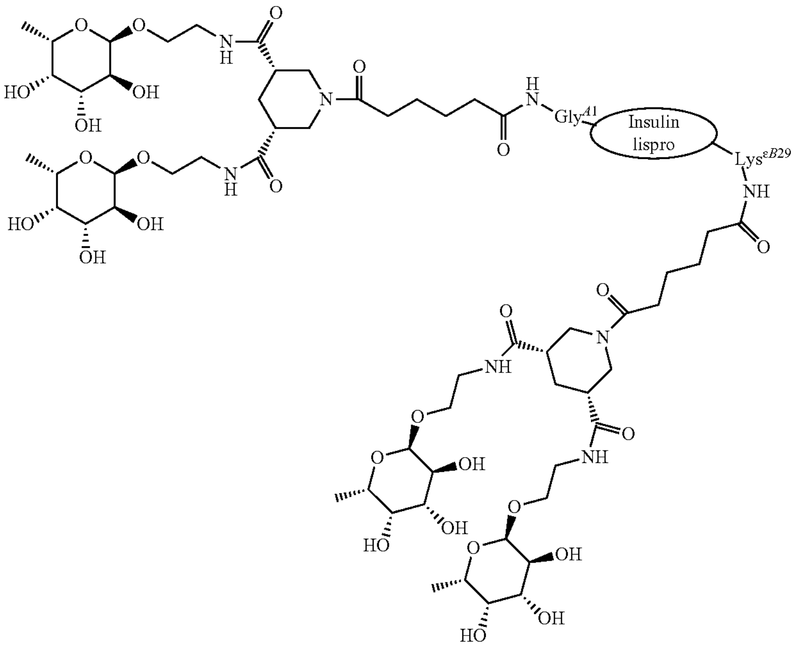
IOC-165
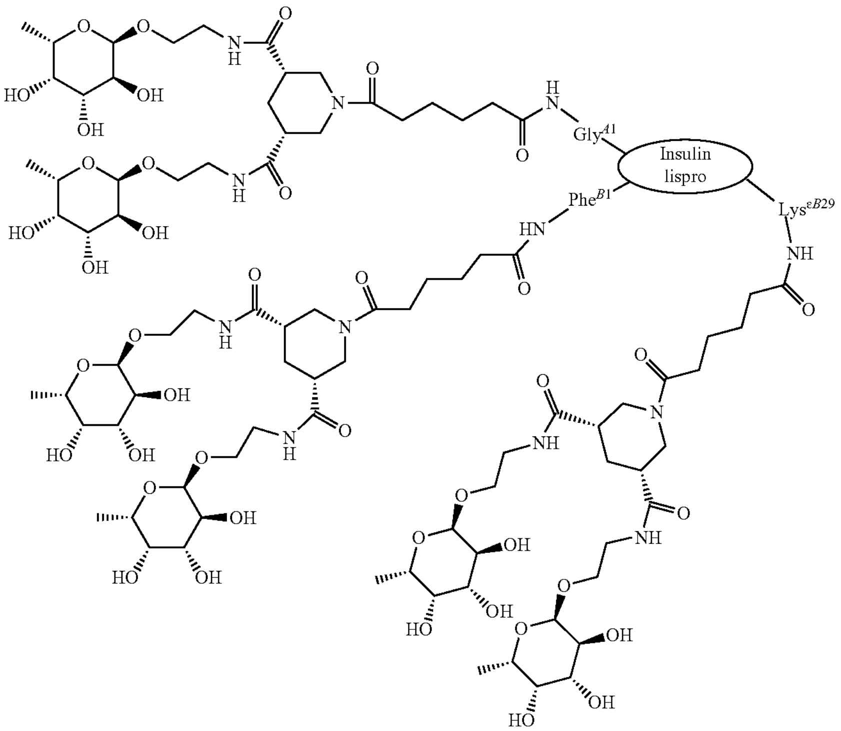

-continued
IOC-166
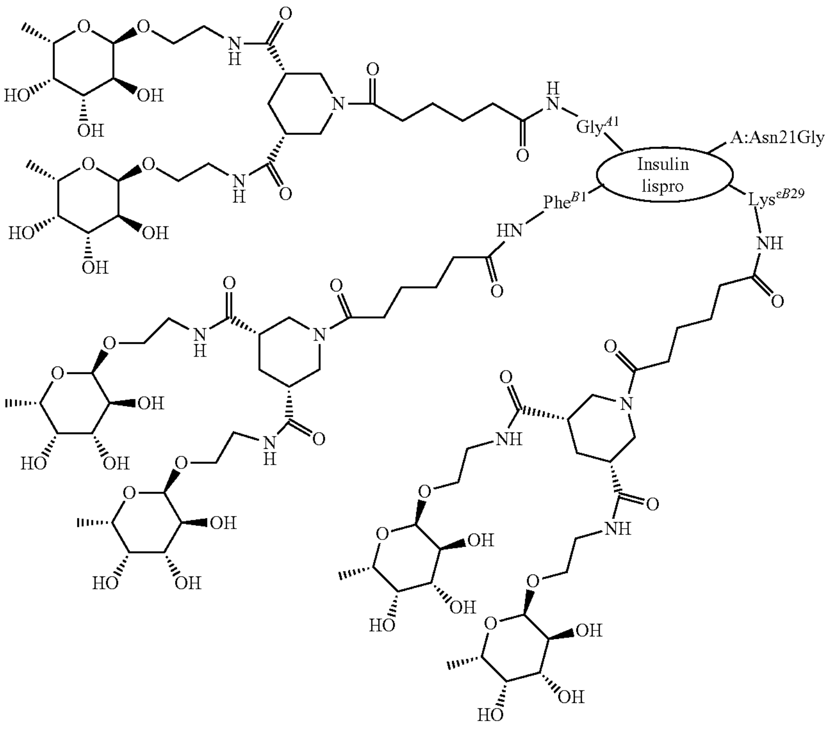
IOC-167
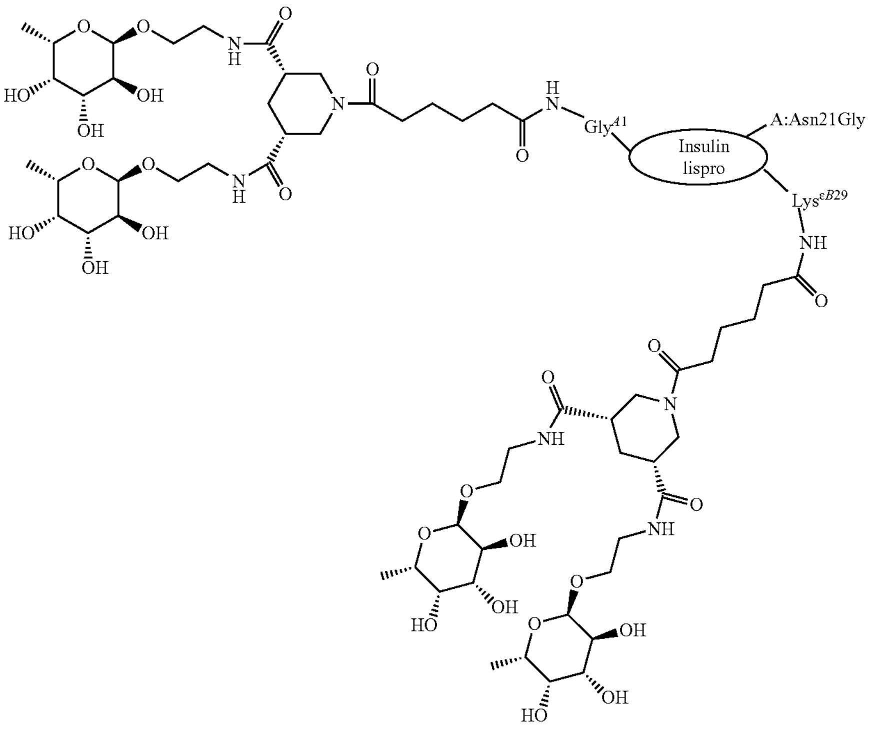

-continued
IOC-168
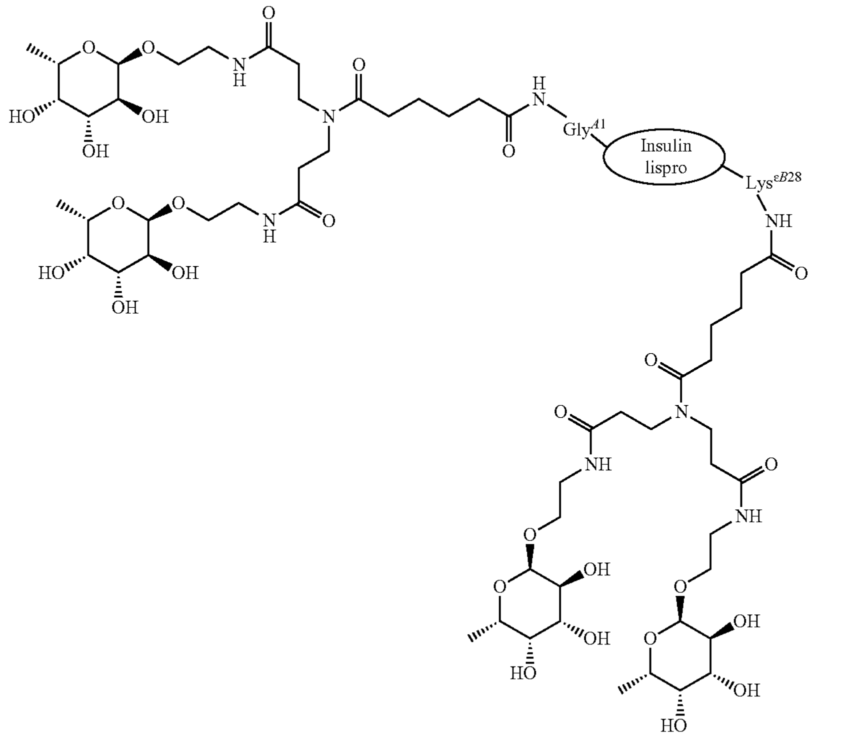
IOC-169
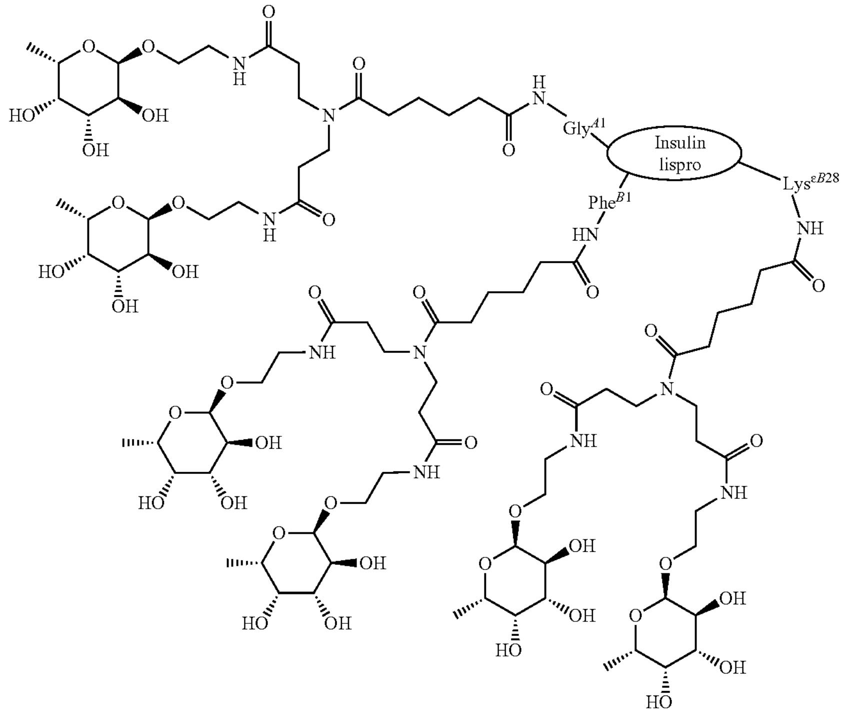

-continued
IOC-170
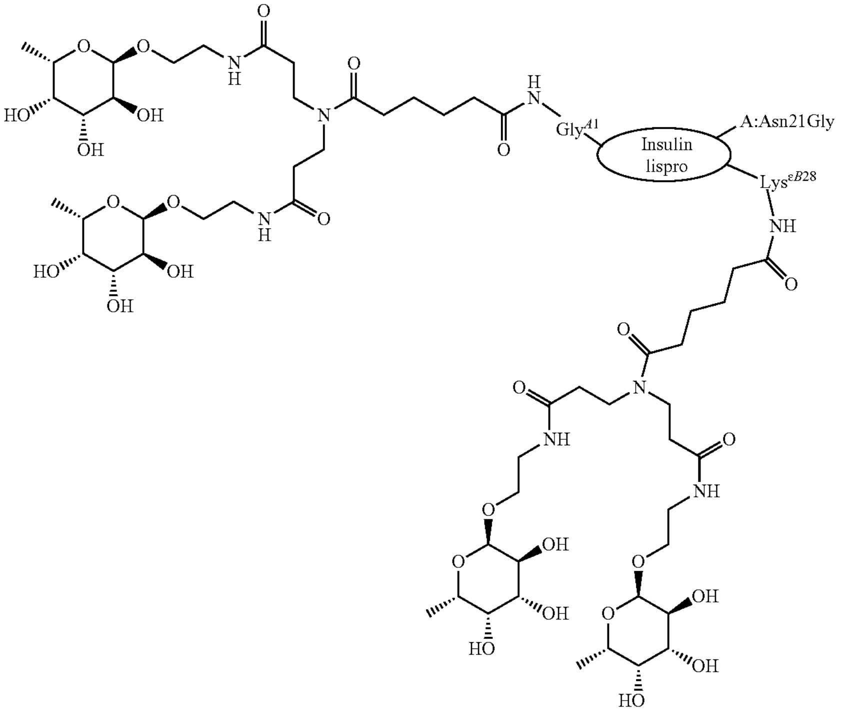
IOC-171
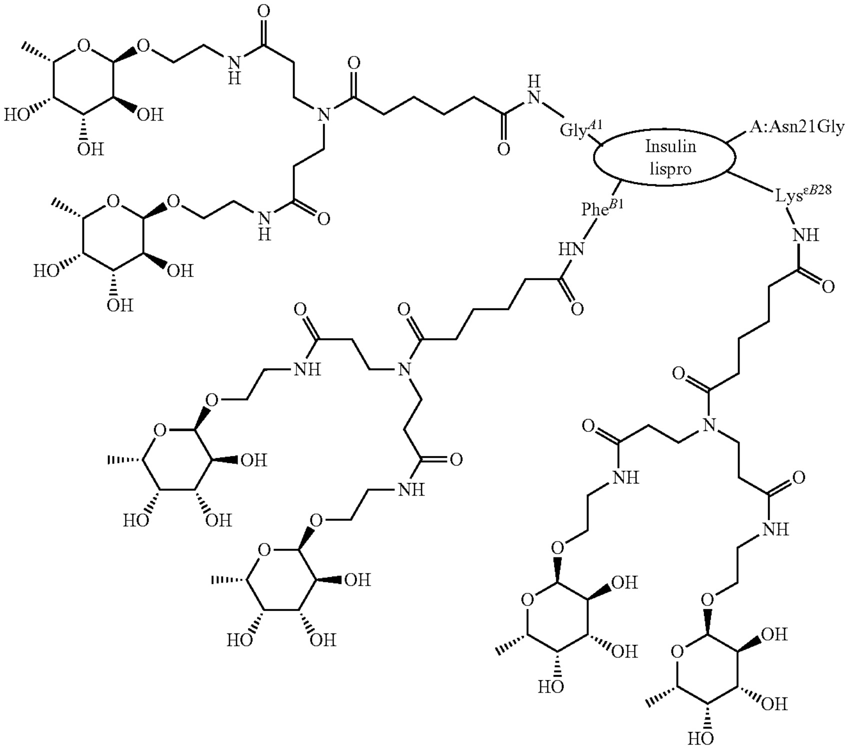

-continued
IOC-172
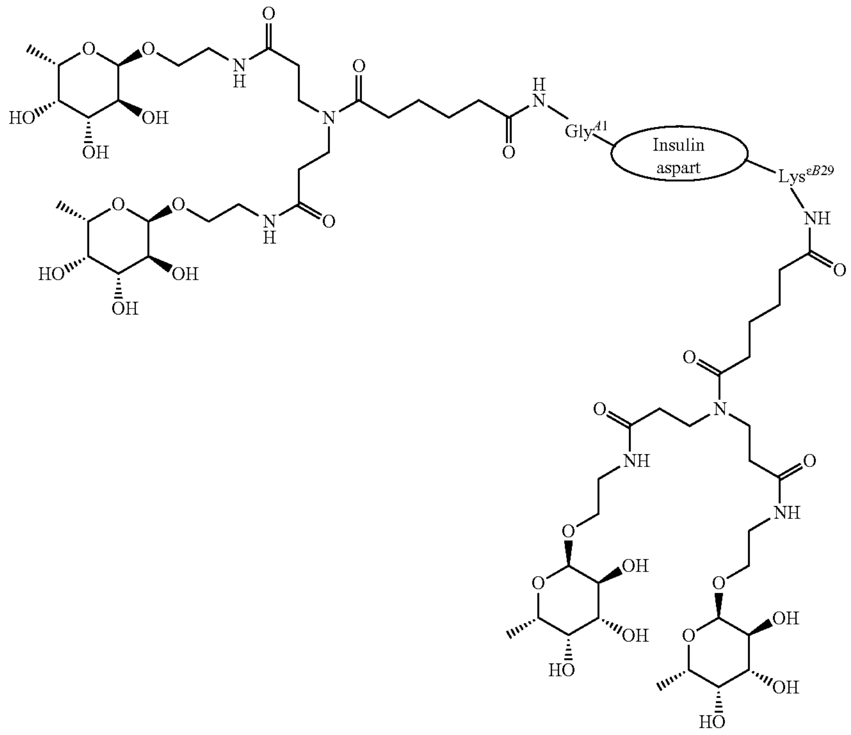
IOC-173
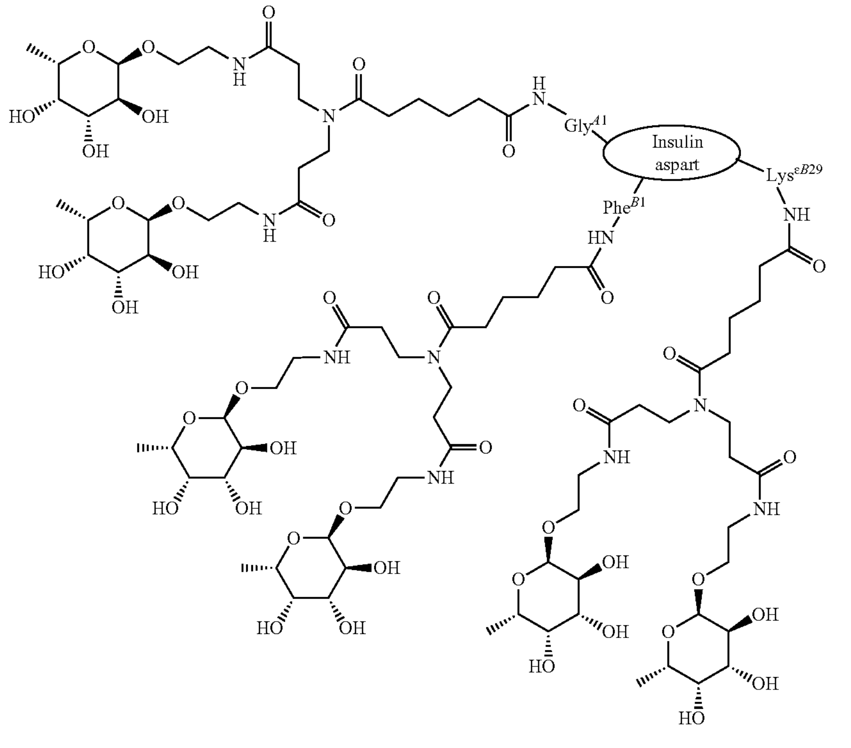

-continued
IOC-174
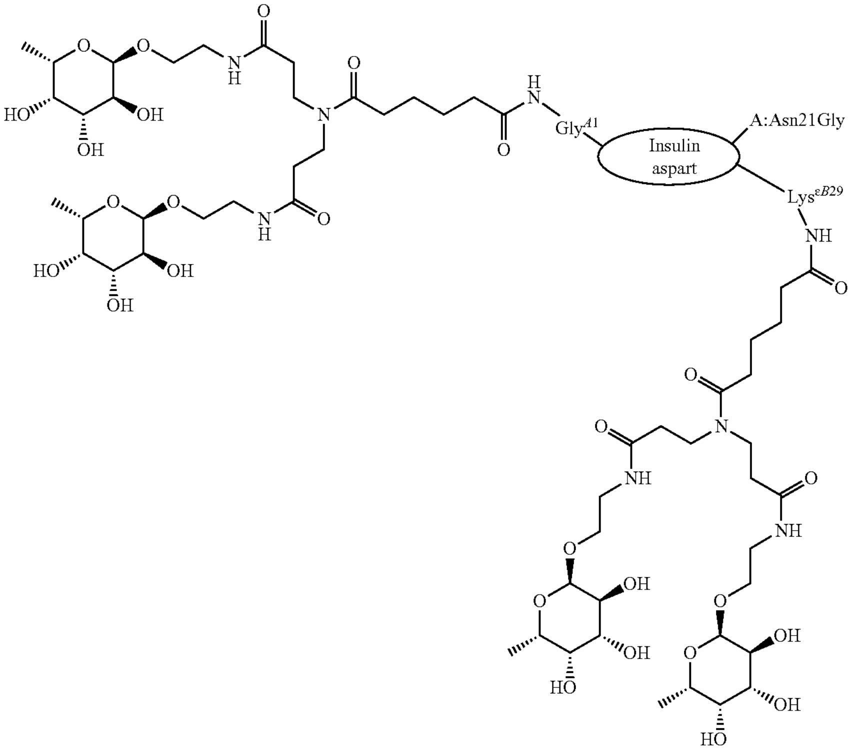
IOC-175
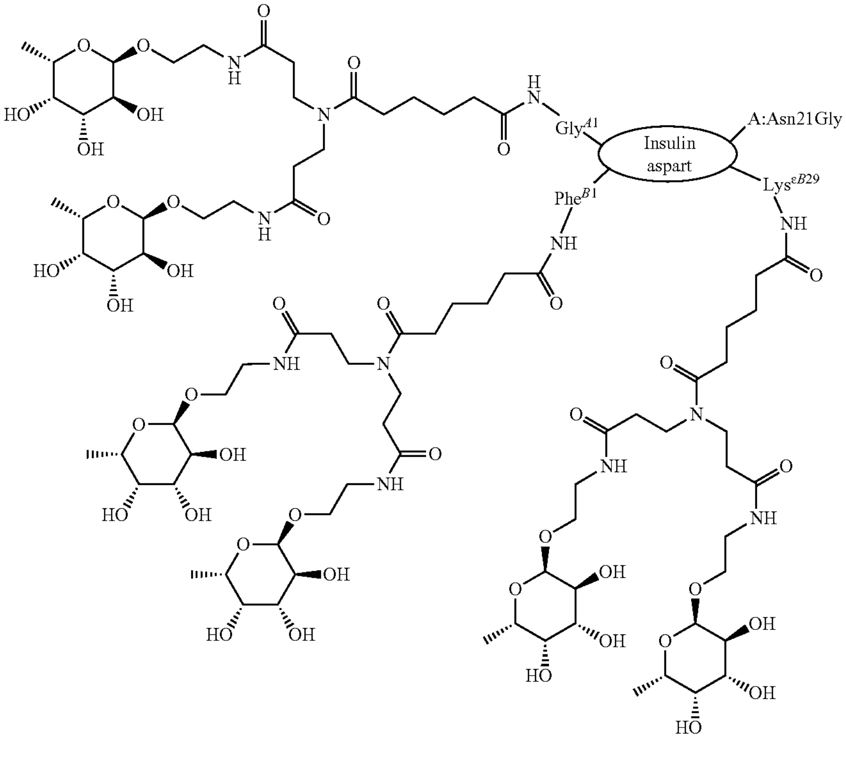

-continued
IOC-176
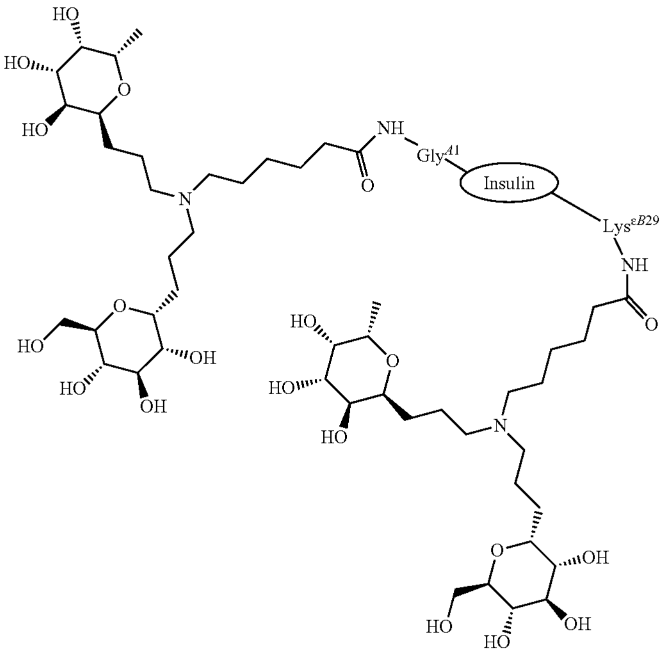
IOC-177
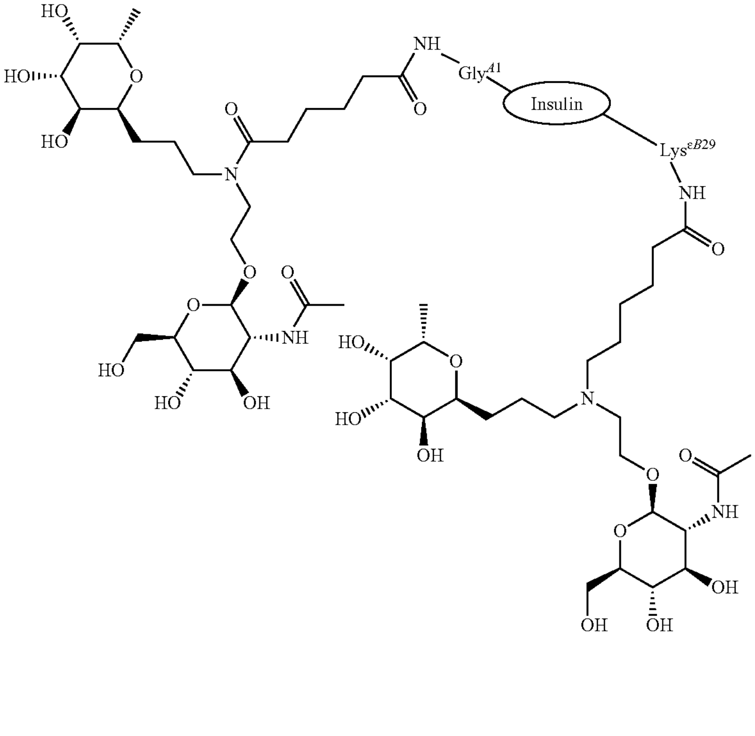

-continued
IOC-178
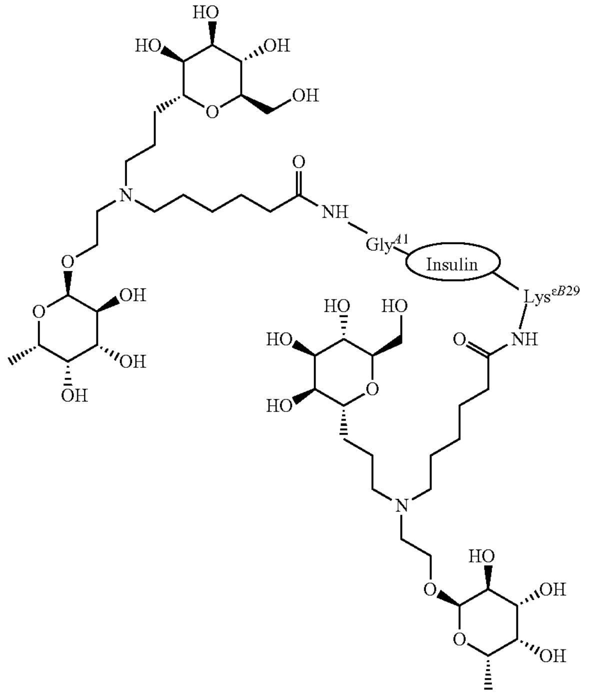
IOC-179
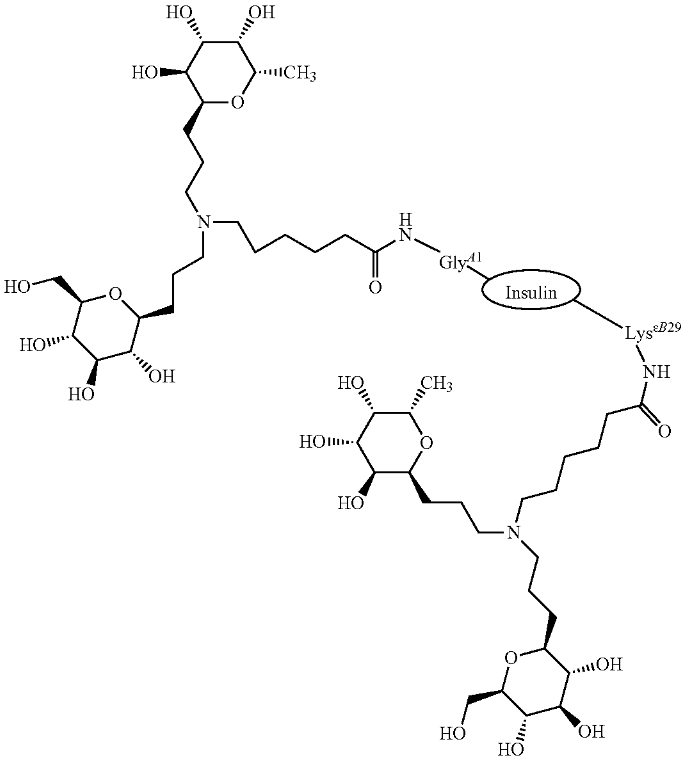

-continued
IOC-180
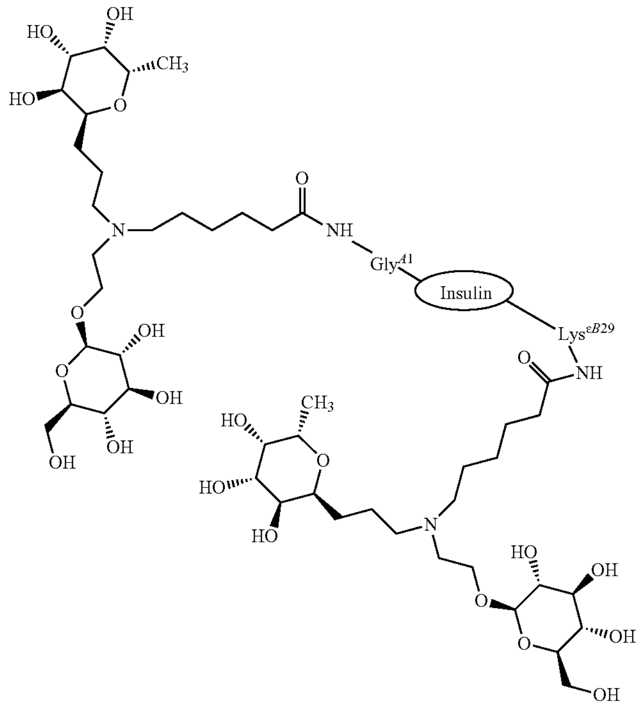
IOC-181
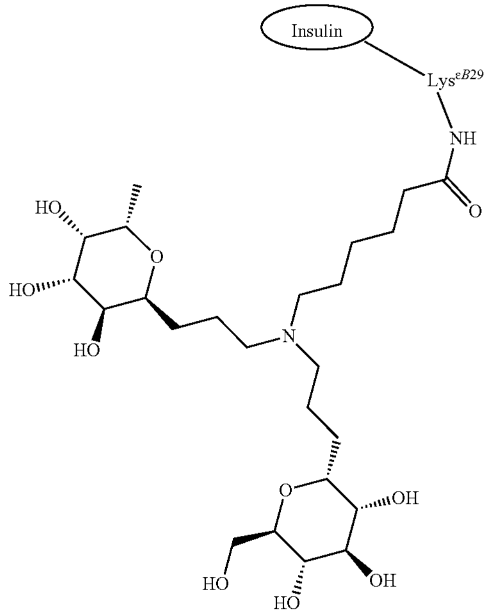

-continued
IOC-182
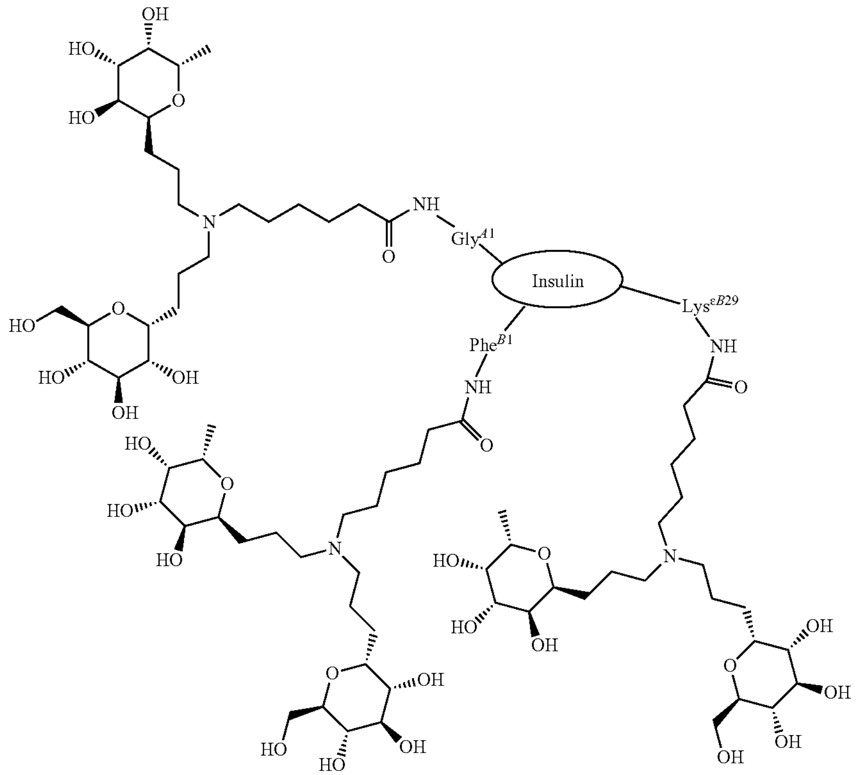
IOC-183
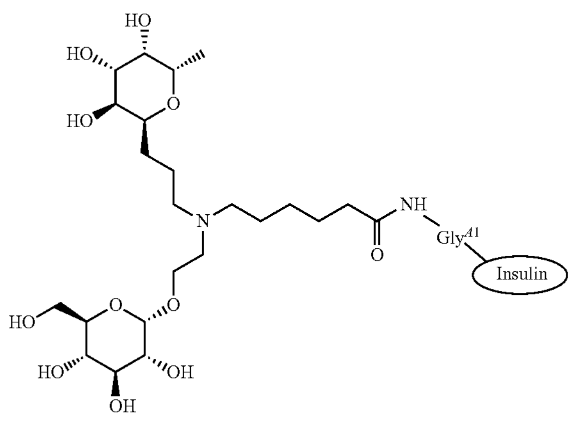
IOC-184
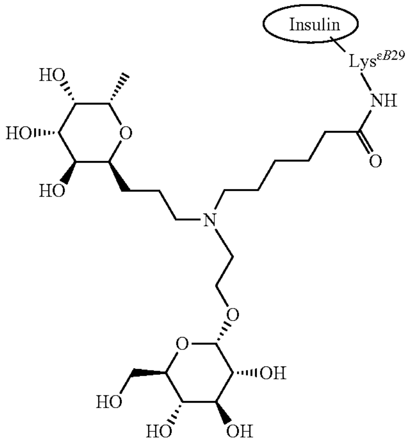

-continued
IOC-185
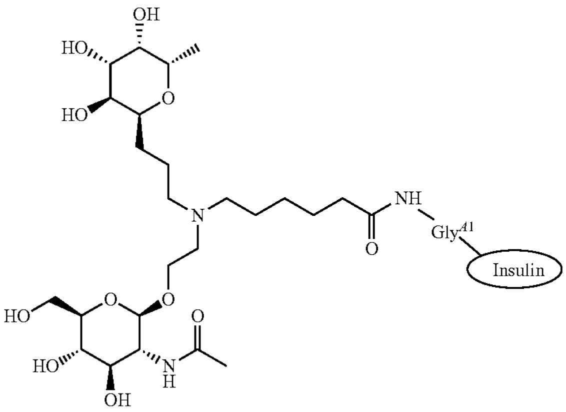
IOC-186
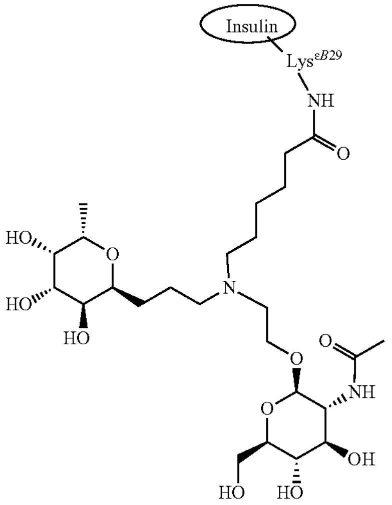
IOC-187
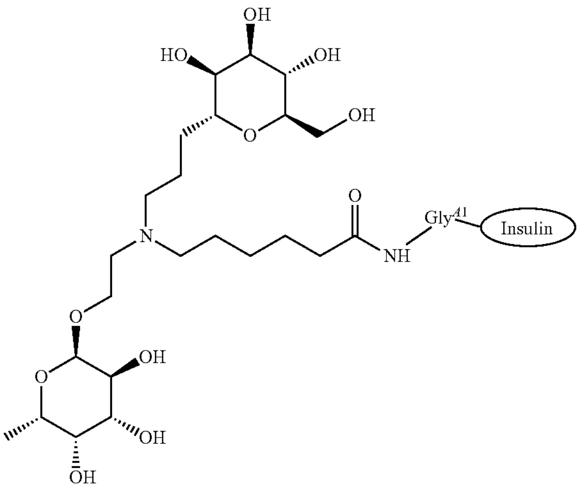
IOC-188
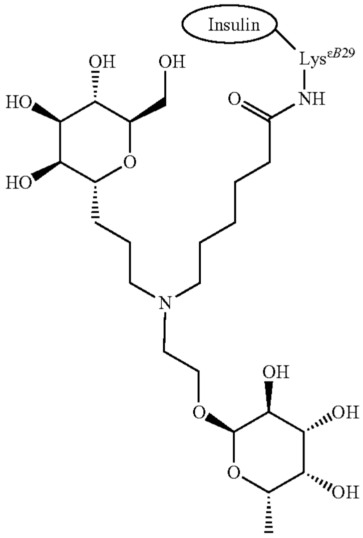

-continued
IOC-189
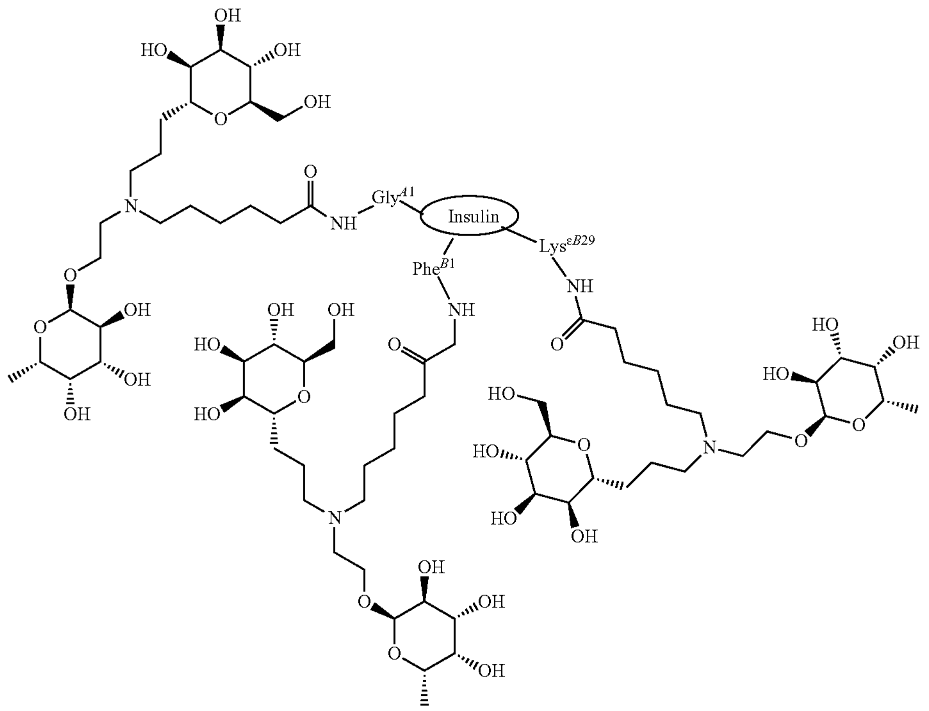
IOC-190
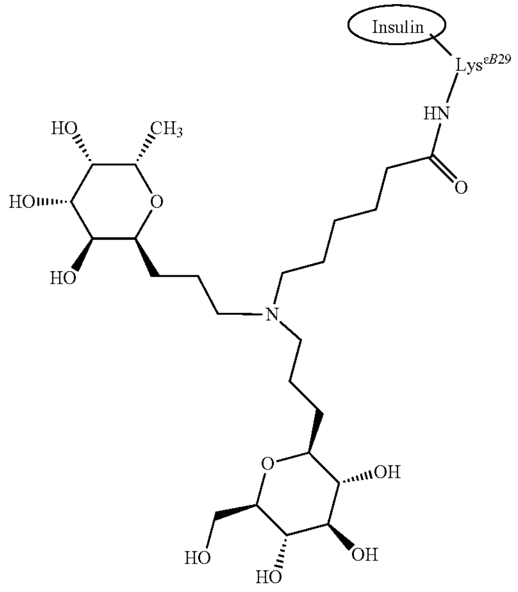

-continued
IOC-191
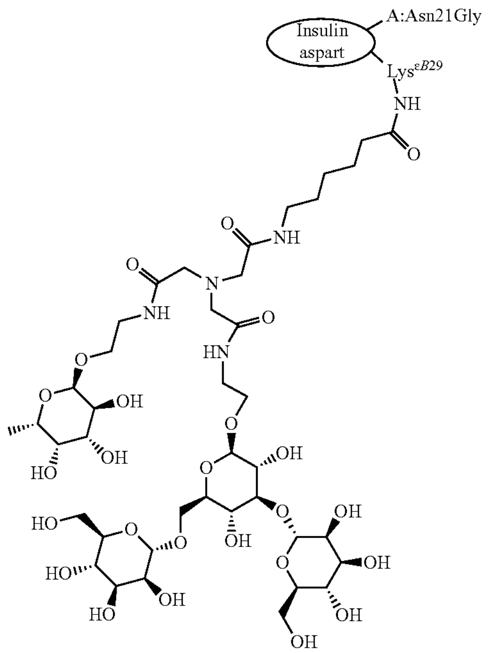
IOC-192
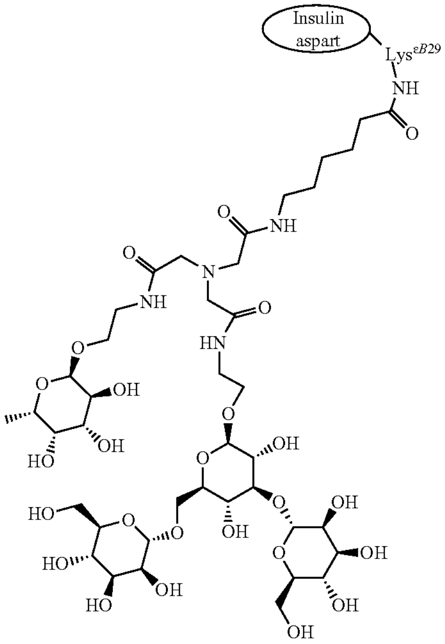
IOC-193
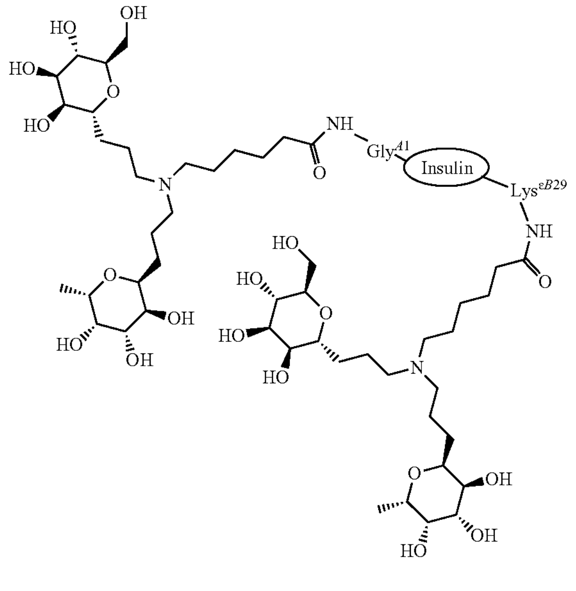
IOC-194
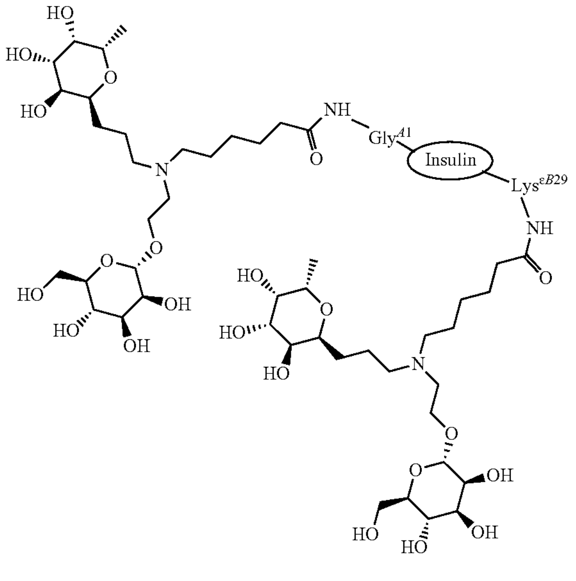

-continued
IOC-195
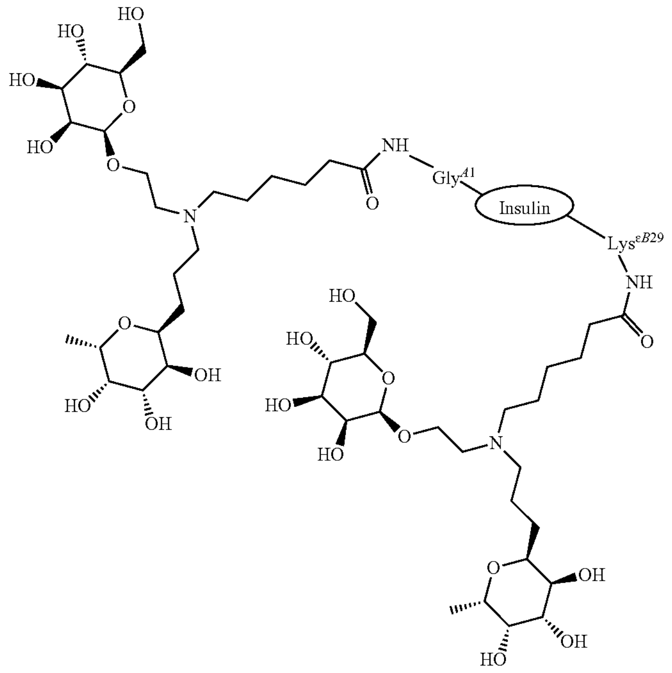
IOC-196
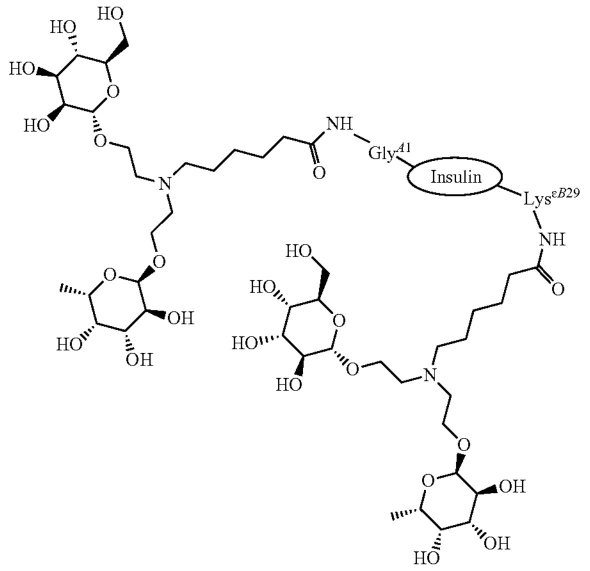
IOC-197
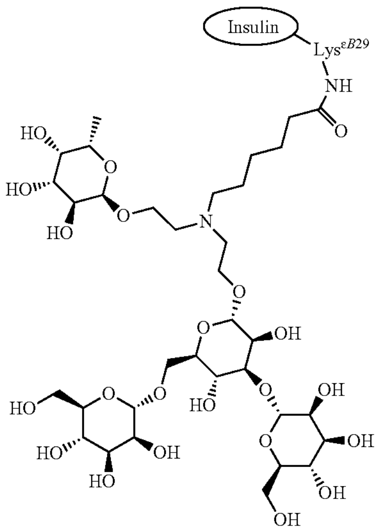

-continued
IOC-198
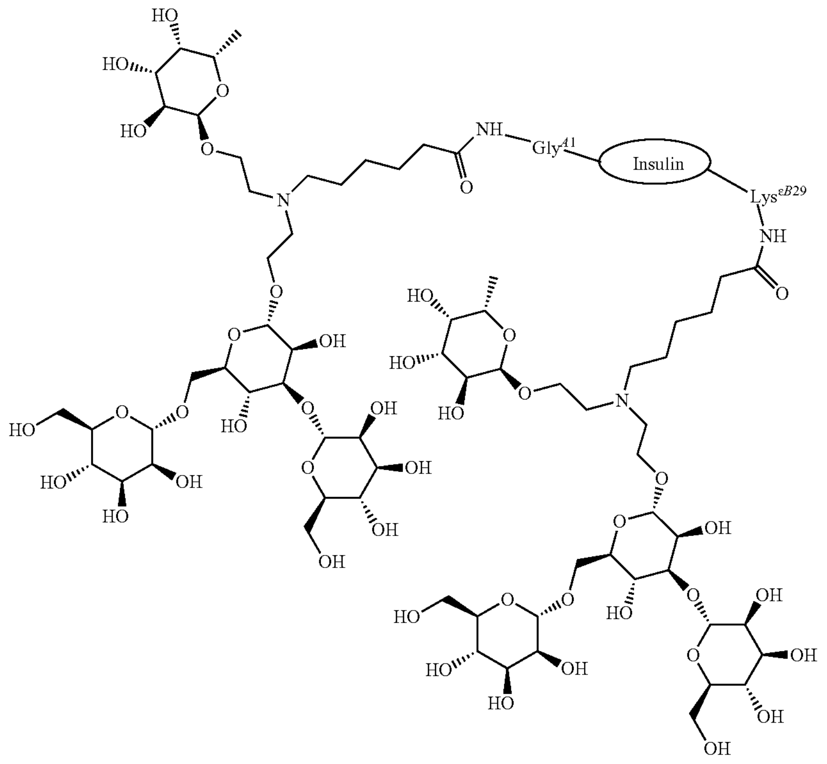
IOC-199
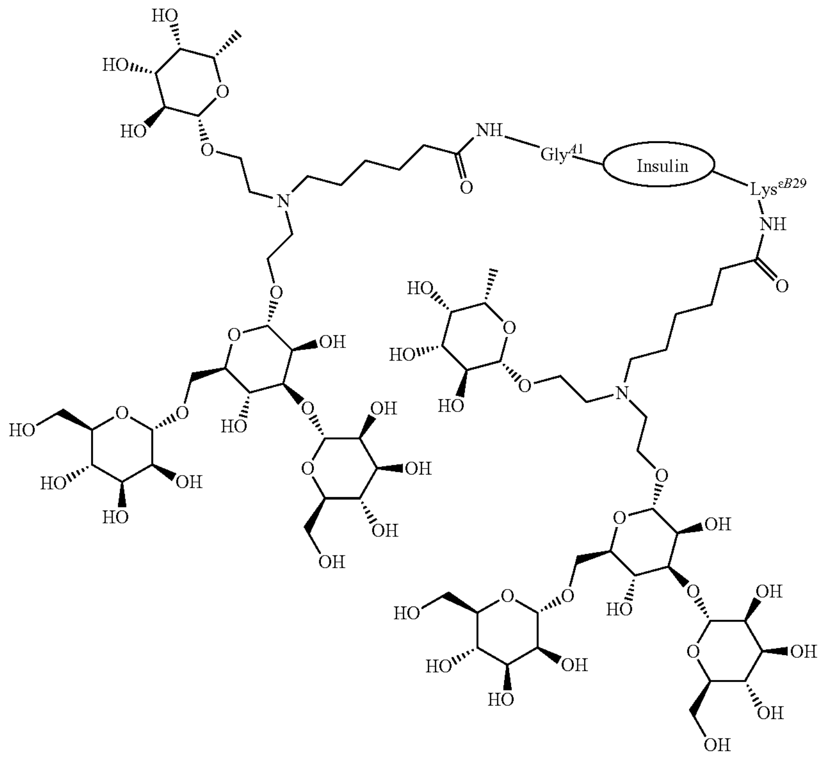

IOC-200
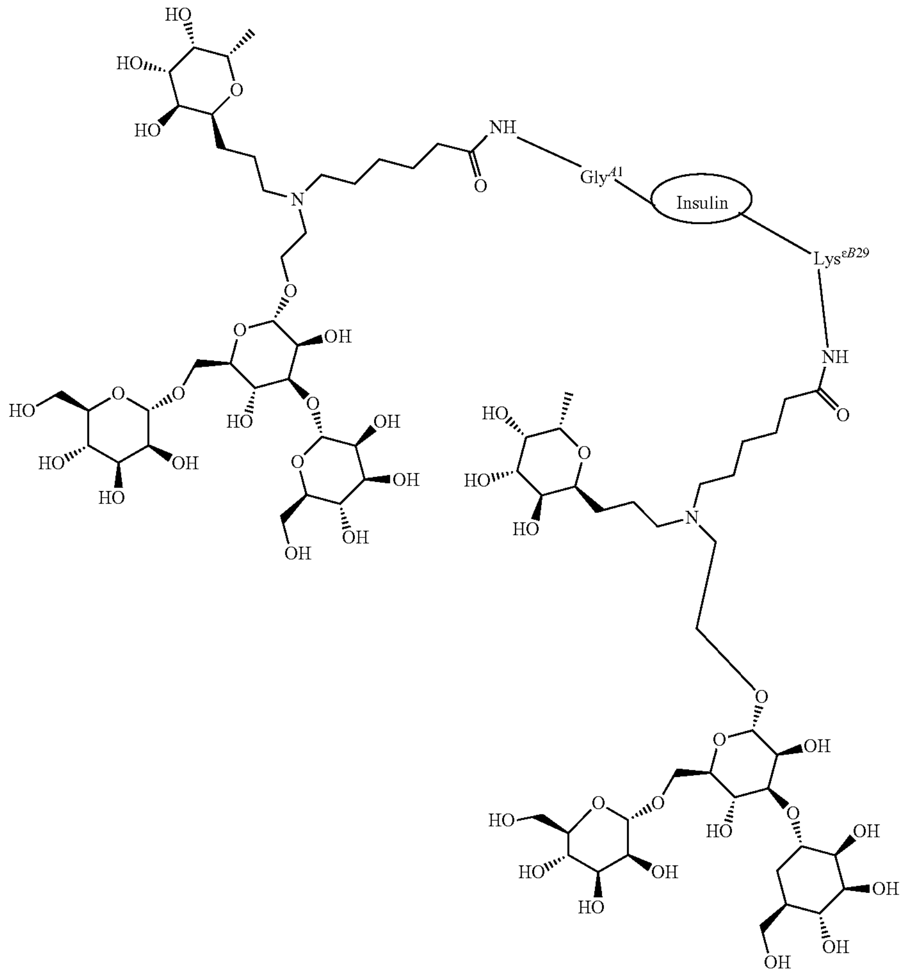
IOC-201
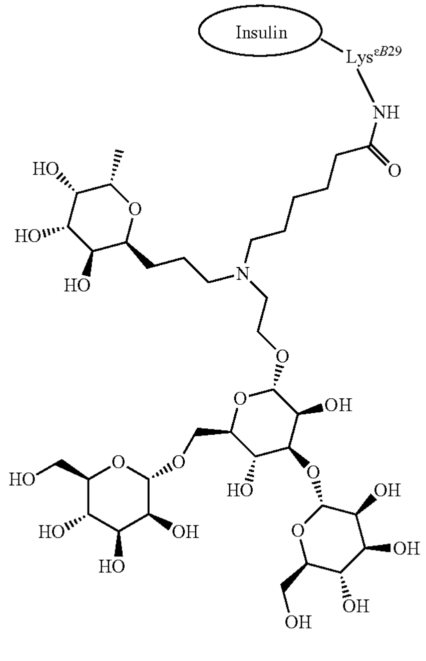

-continued
IOC-202
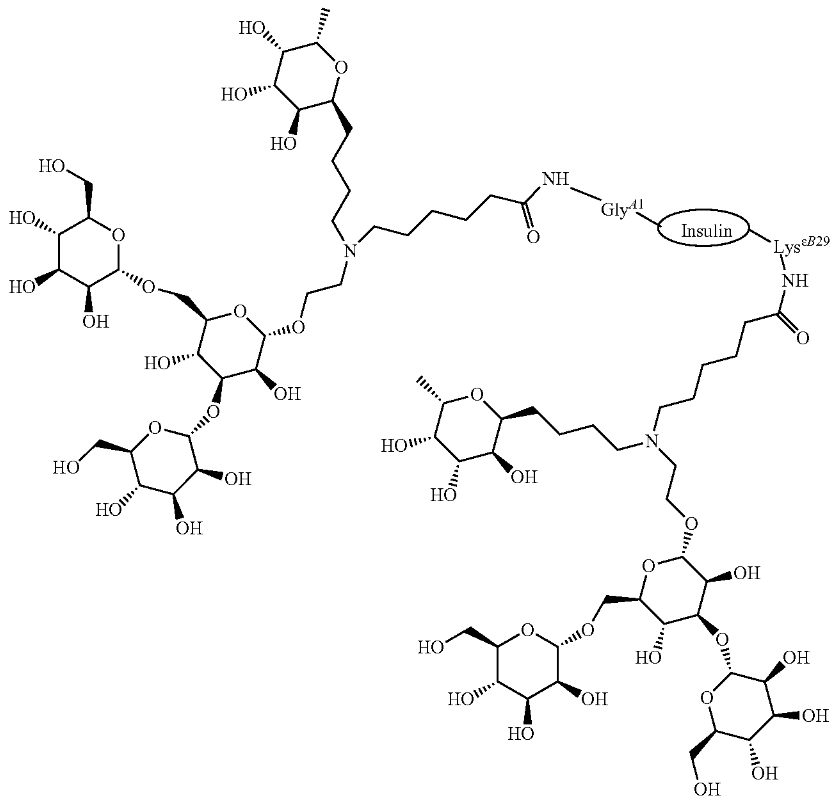
IOC-203
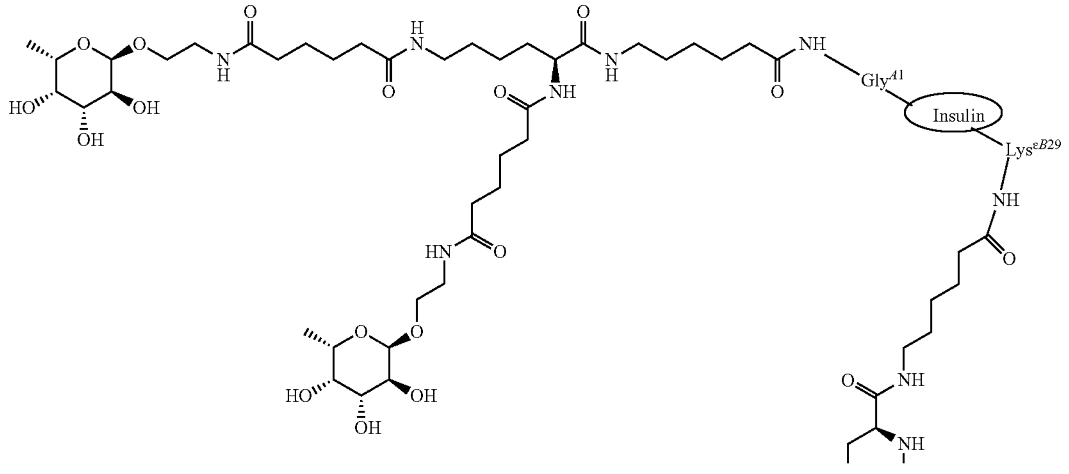

-continued
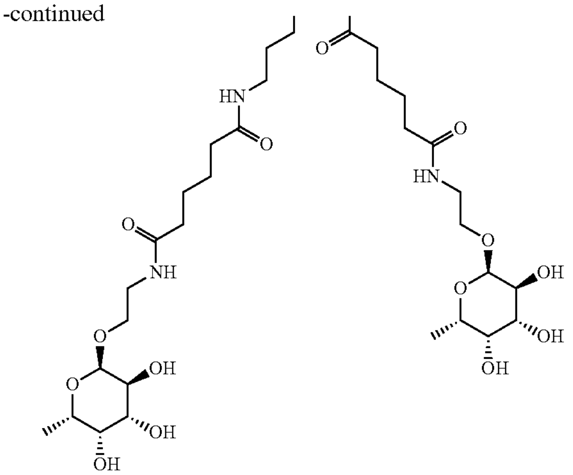
IOC-204
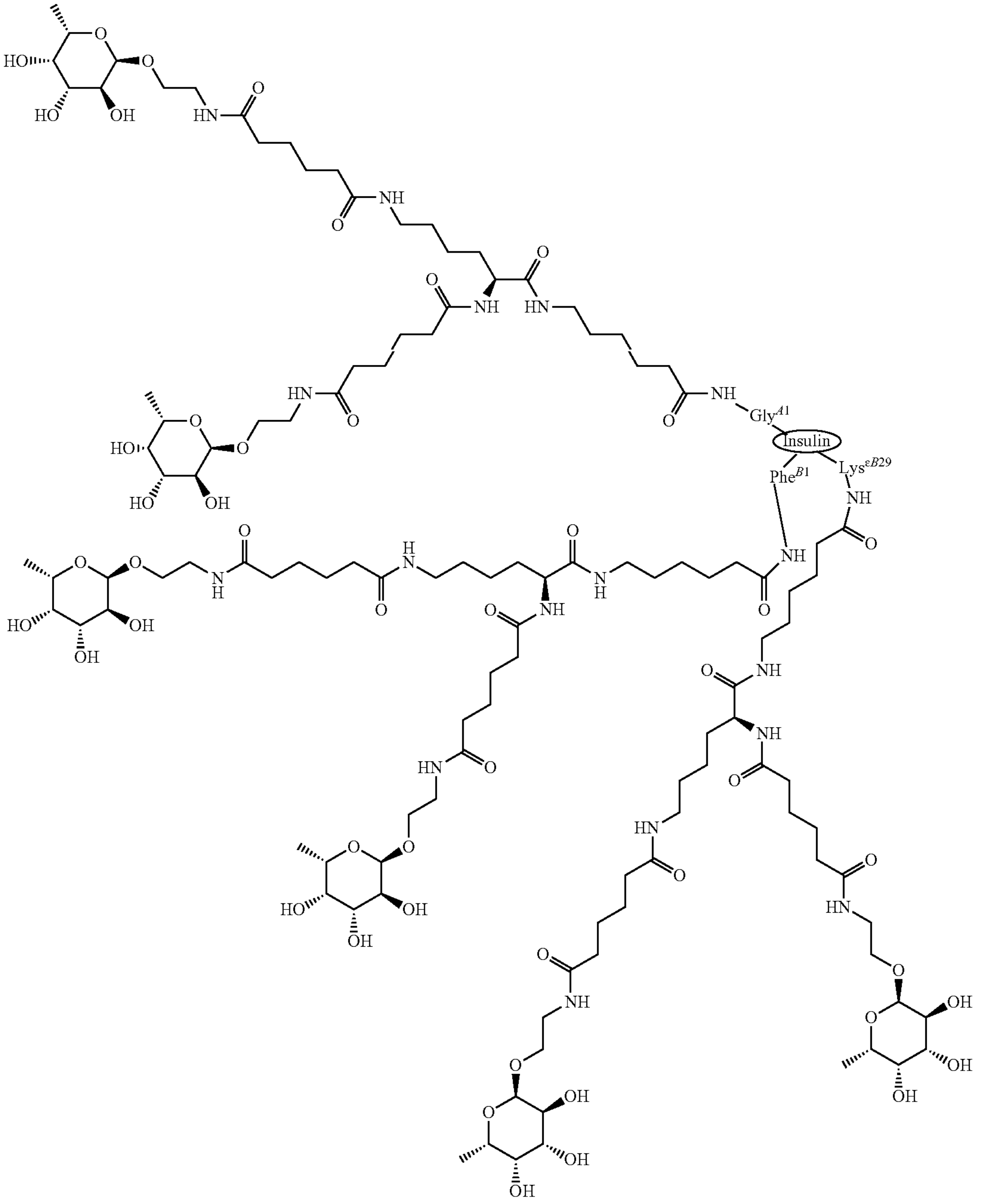

-continued
IOC-205
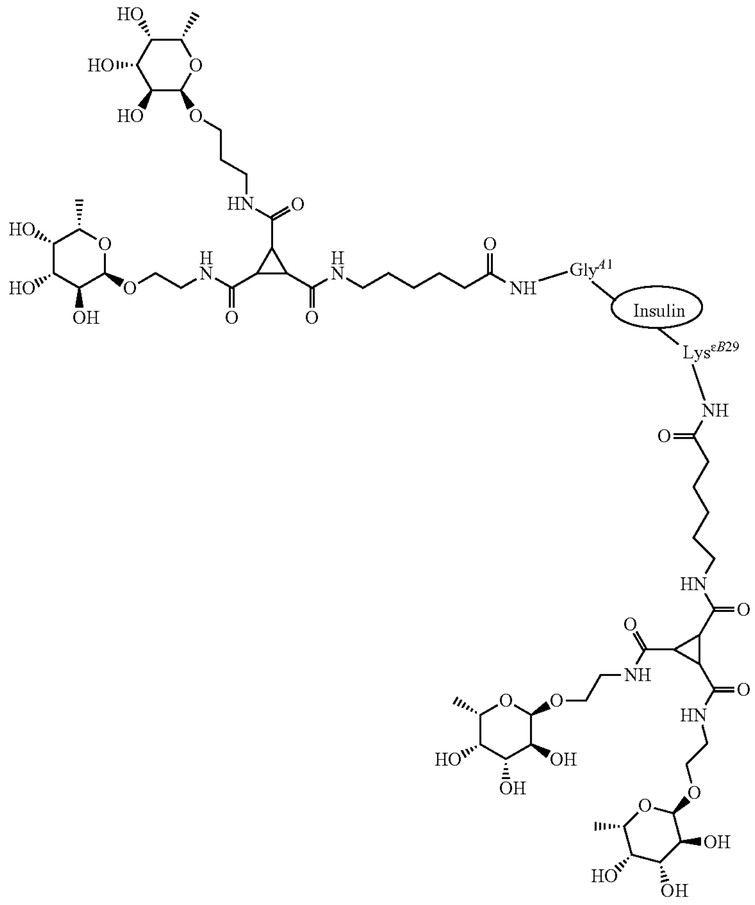

-continued
IOC-206
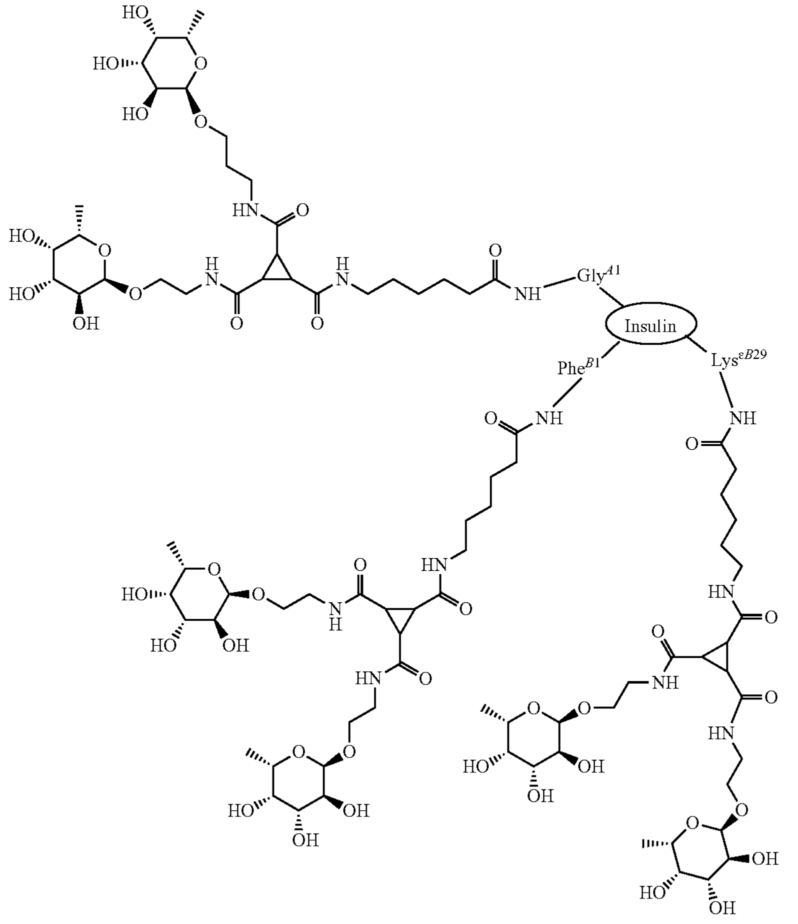
IOC-207
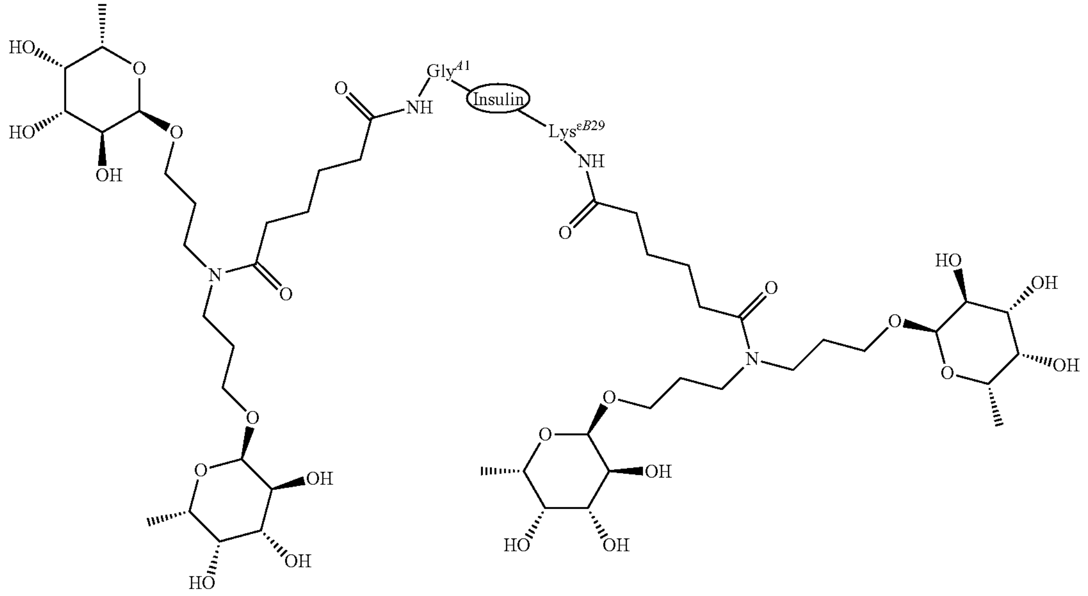

-continued
IOC-208
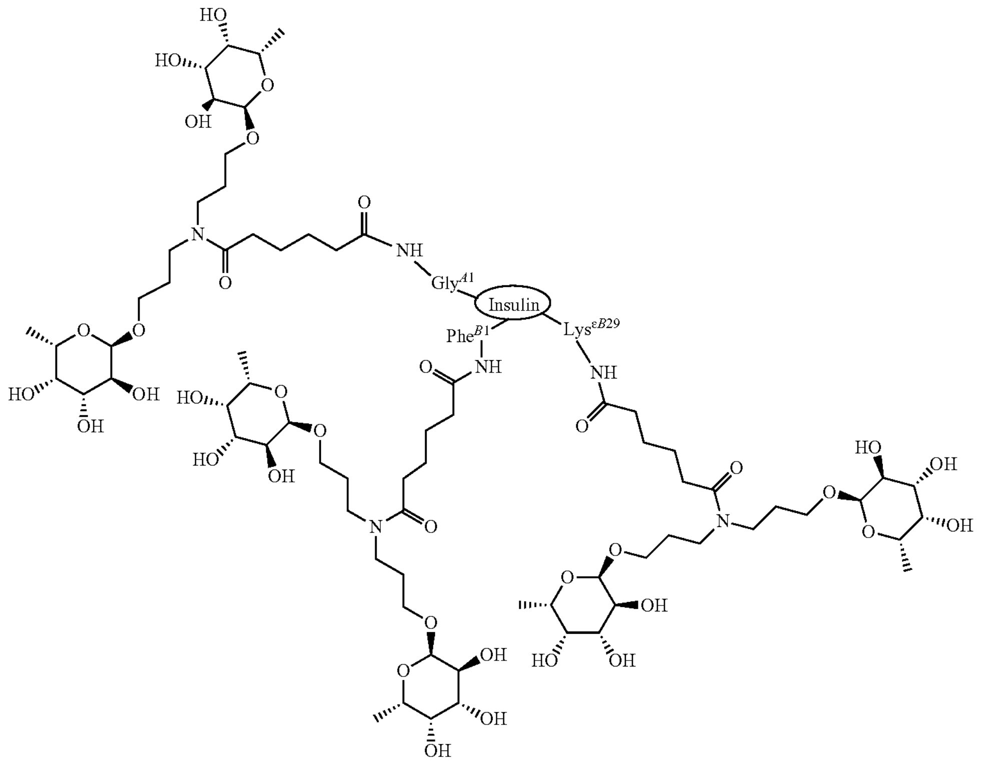
IOC-209
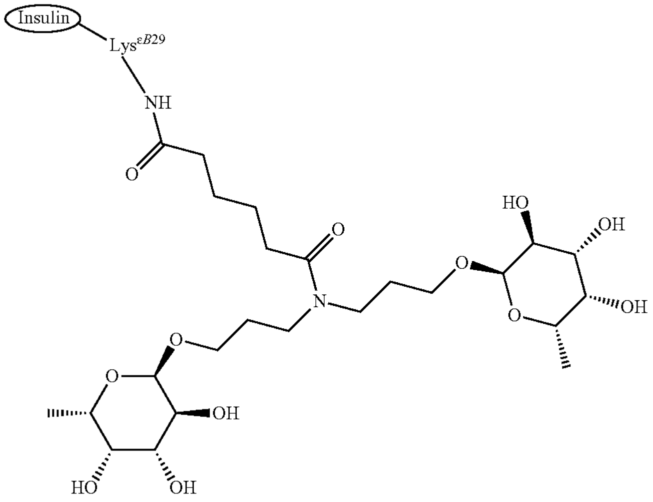

-continued
IOC-210
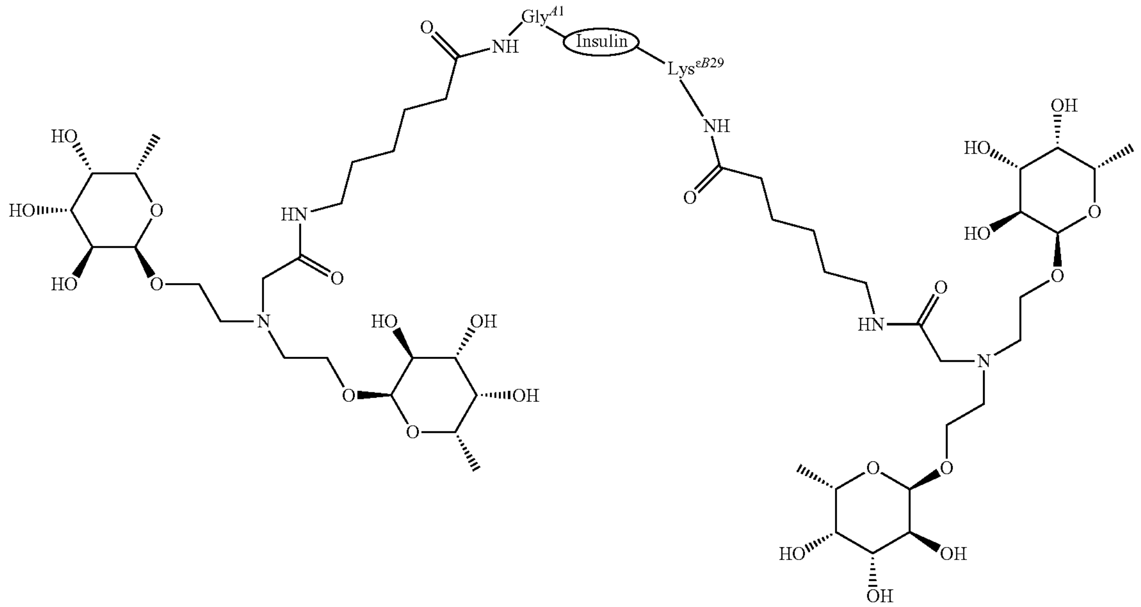
IOC-211
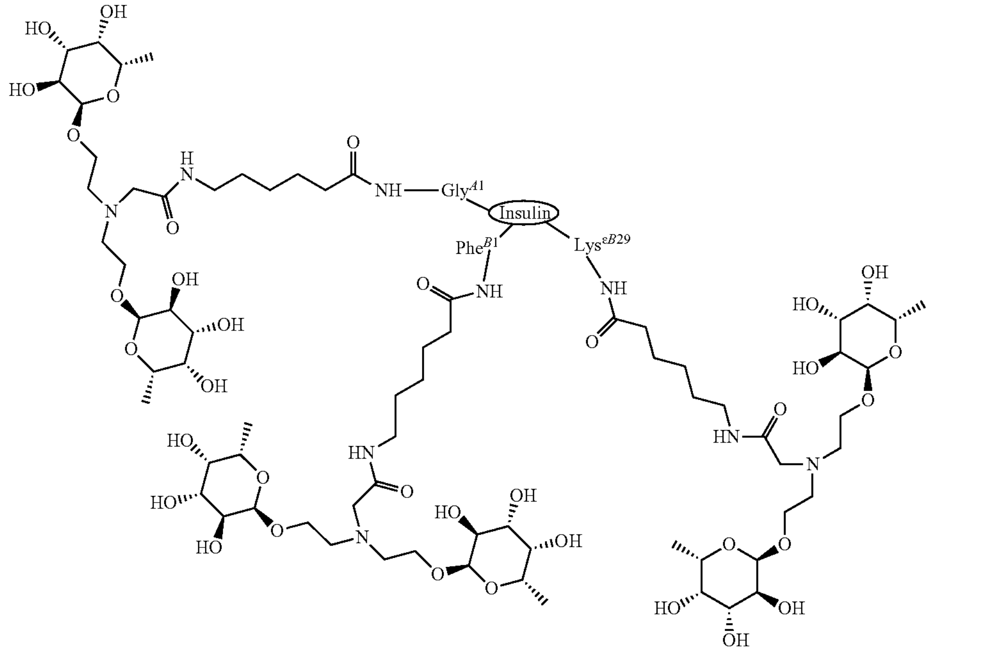

-continued
IOC-212
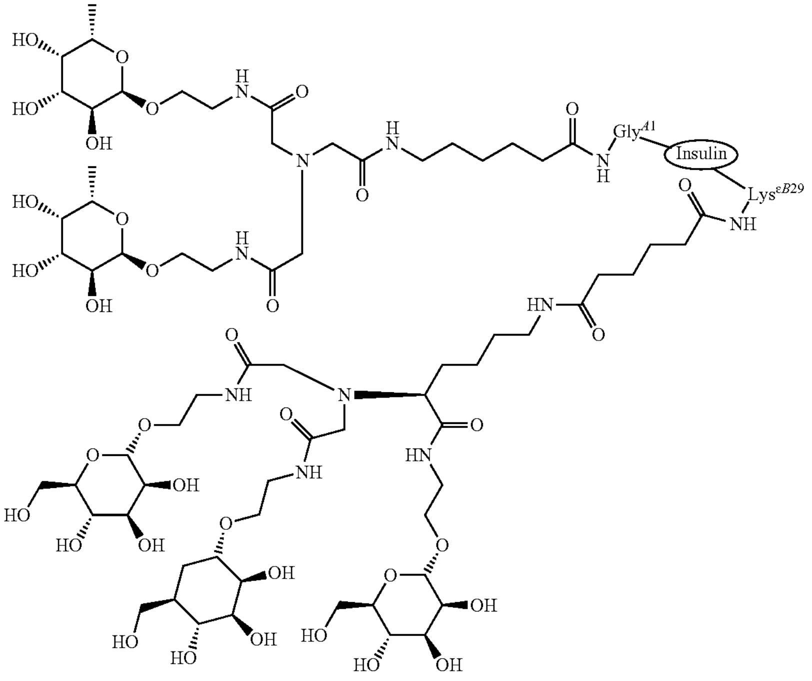
IOC-213
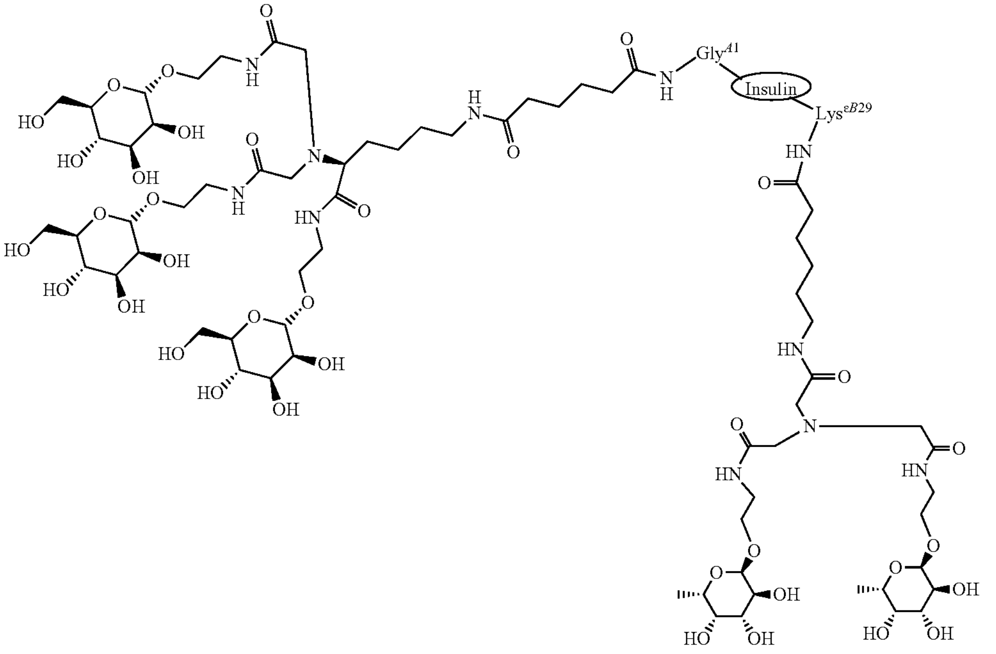

-continued
IOC-214
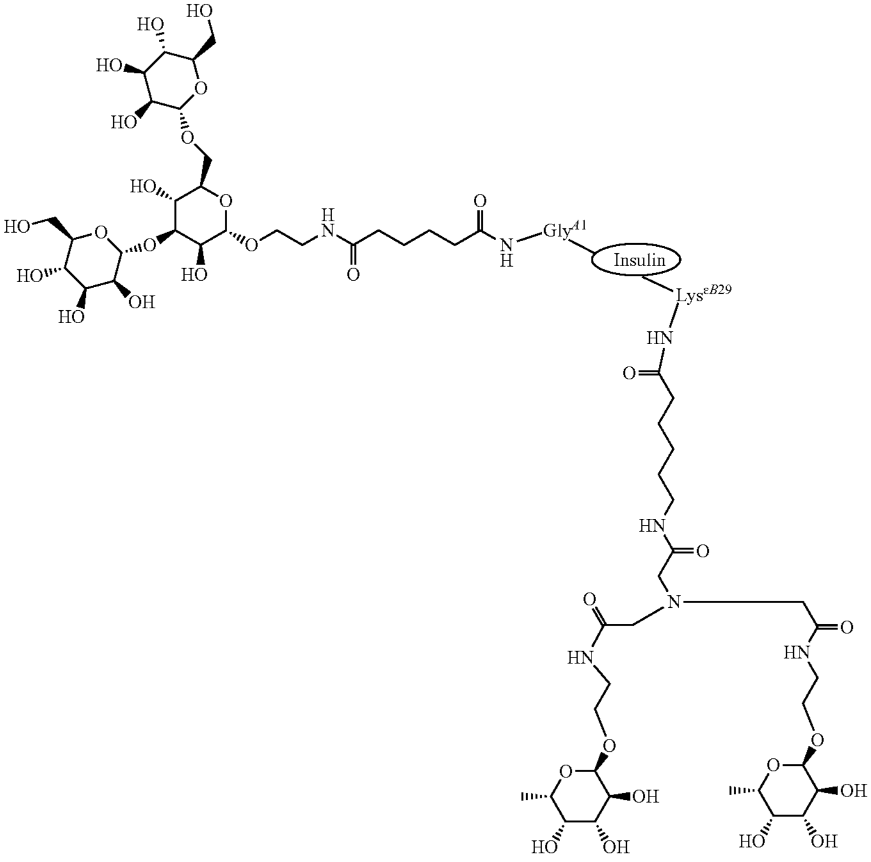
IIOC-215
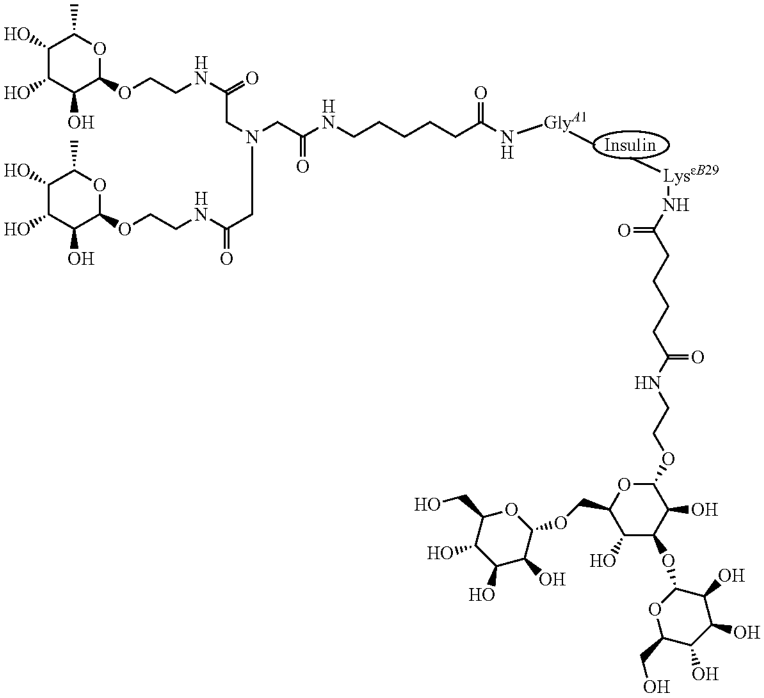

-continued
IOC-216
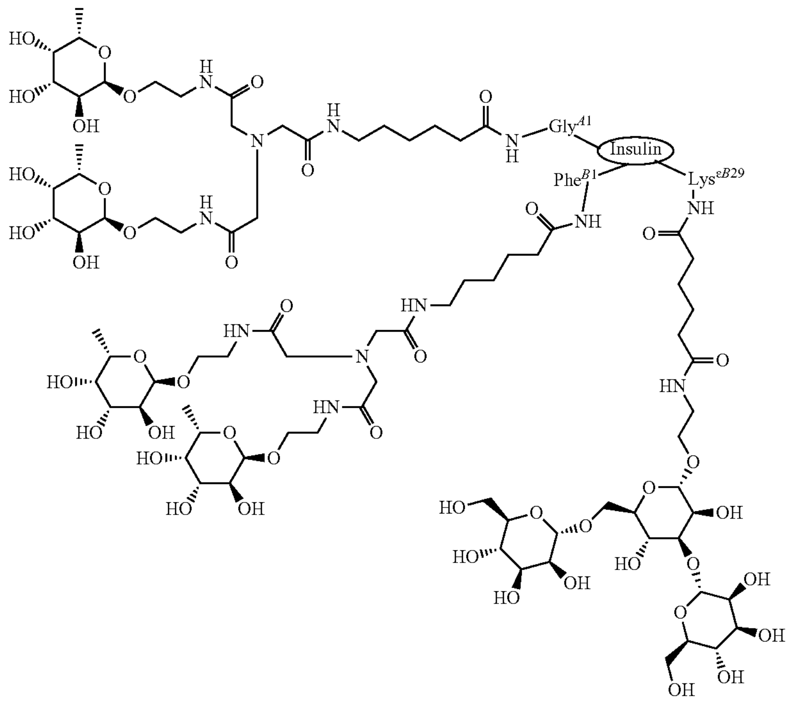
IOC-217
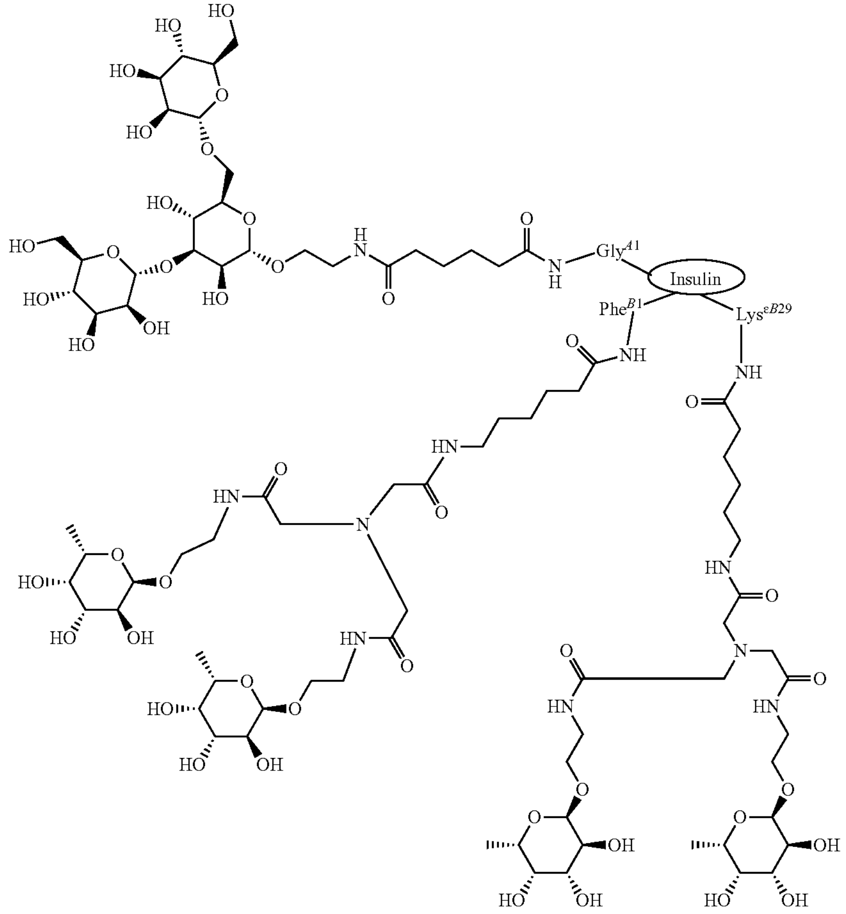

-continued
IOC-218
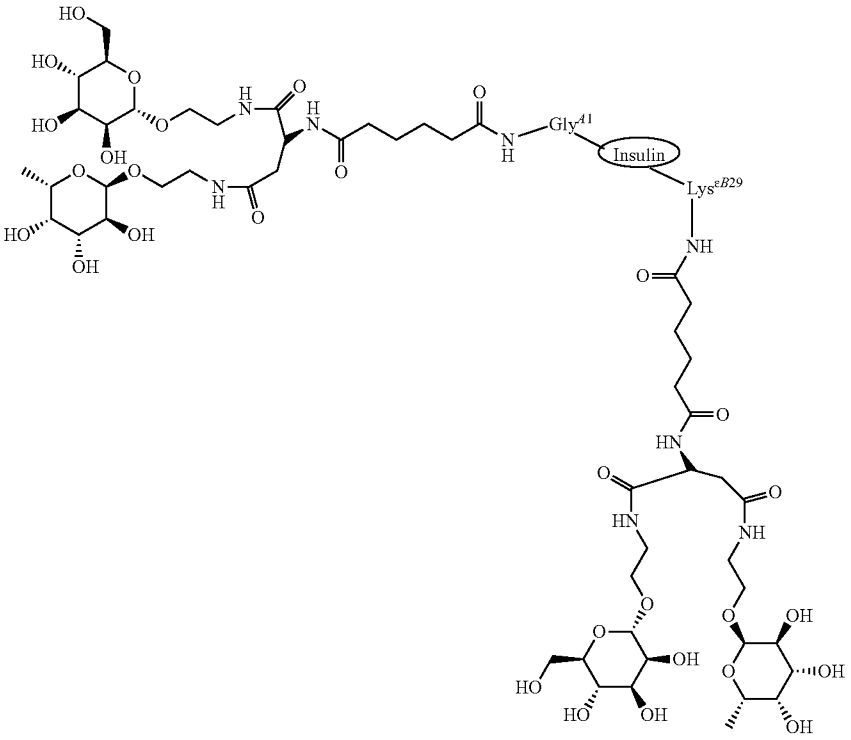
IOC-219
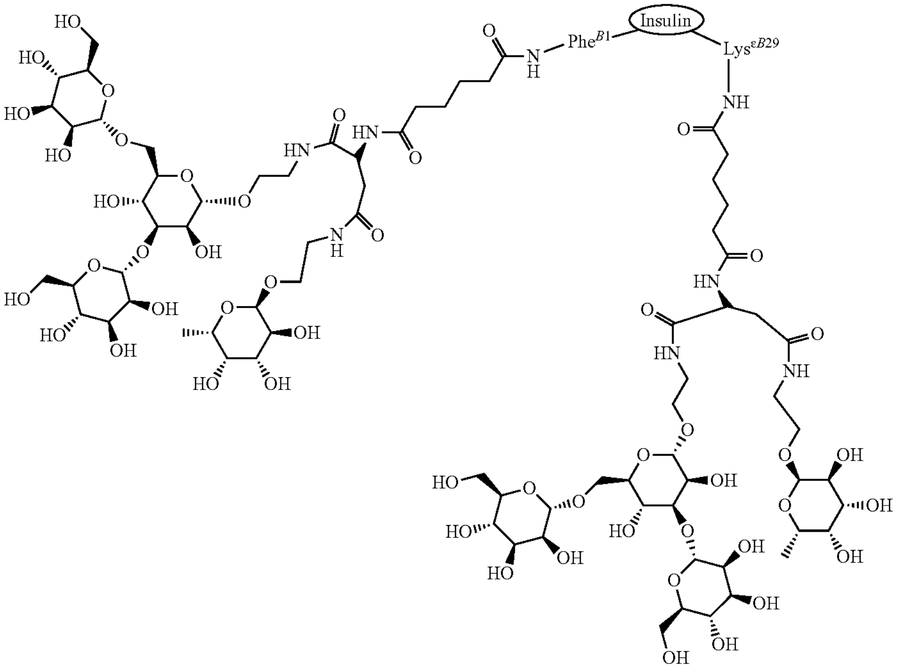

-continued
IOC-220
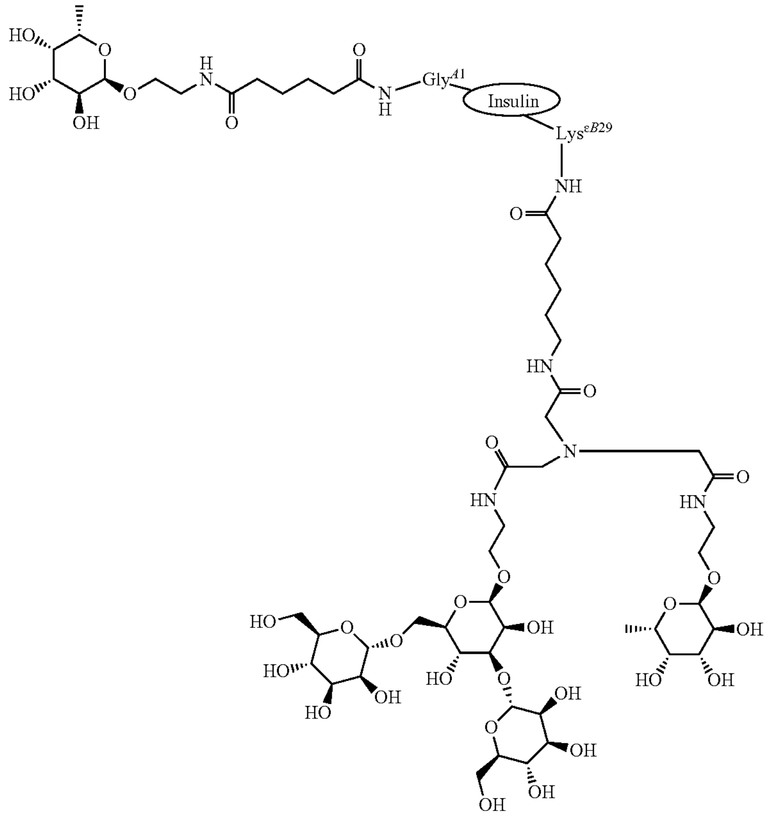
IOC-221
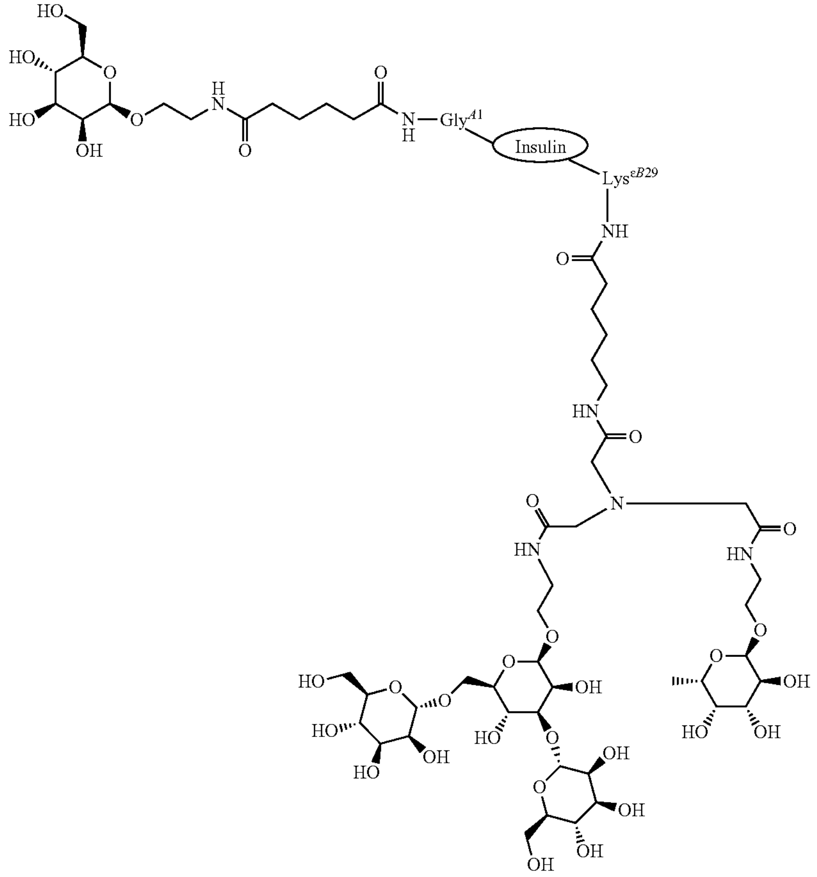

-continued
IOC-222
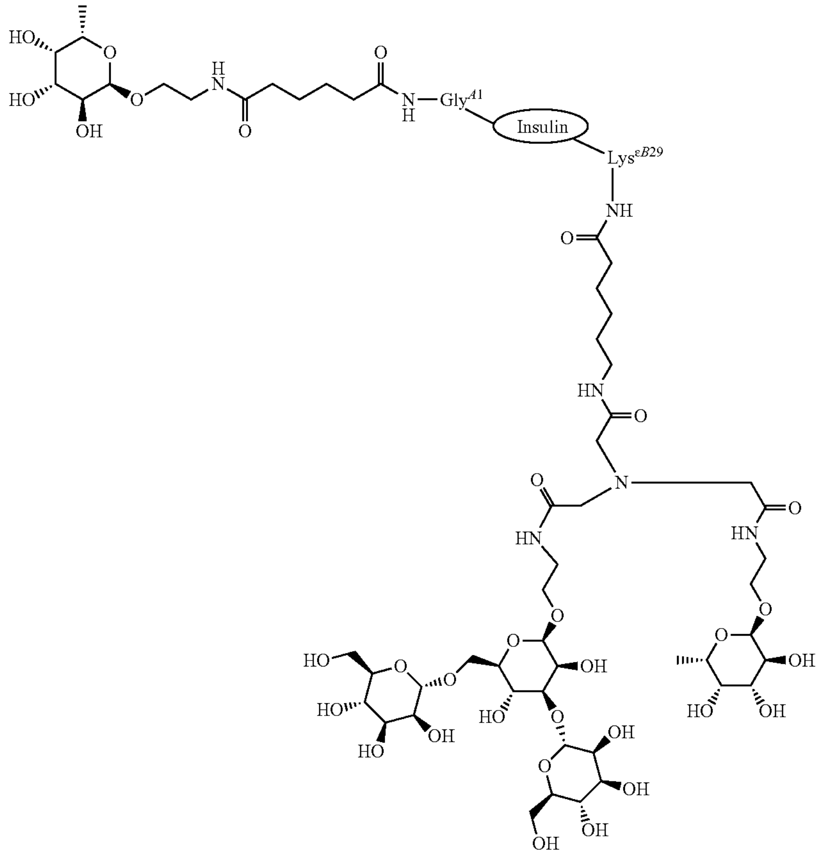

IOC-223
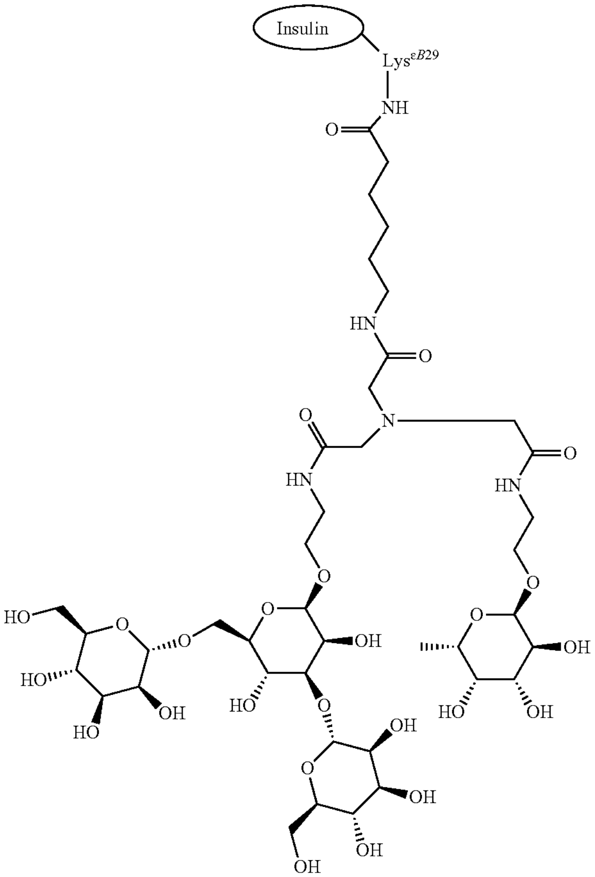
IOC-224
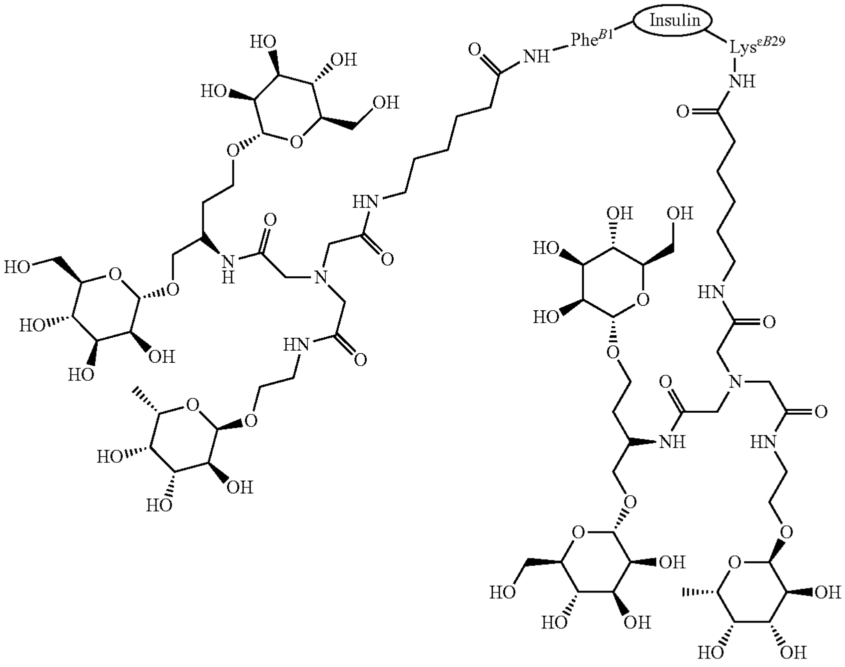

-continued
IOC-225
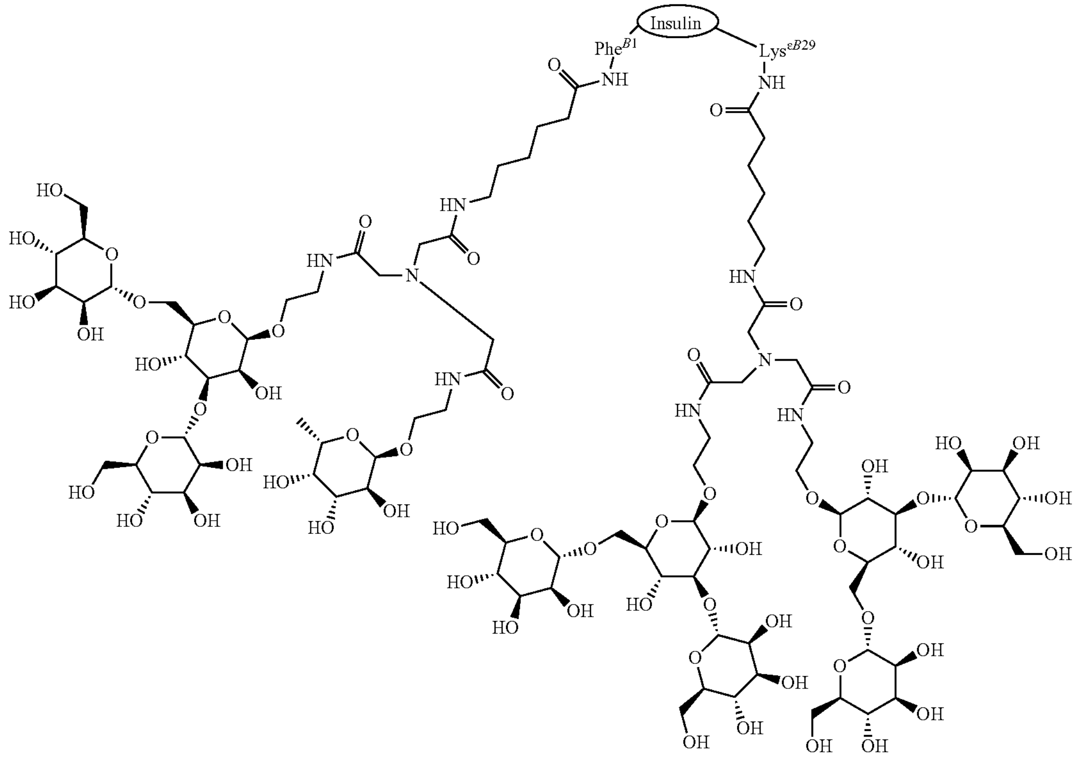
IOC-226
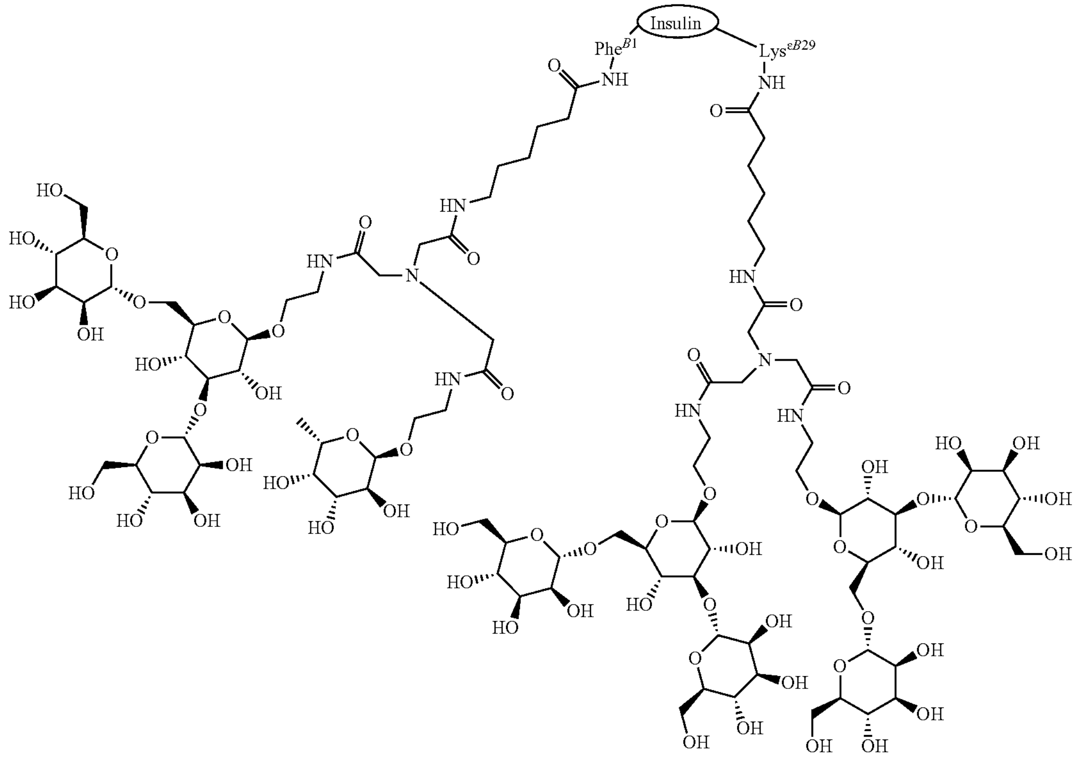

-continued
IOC-227
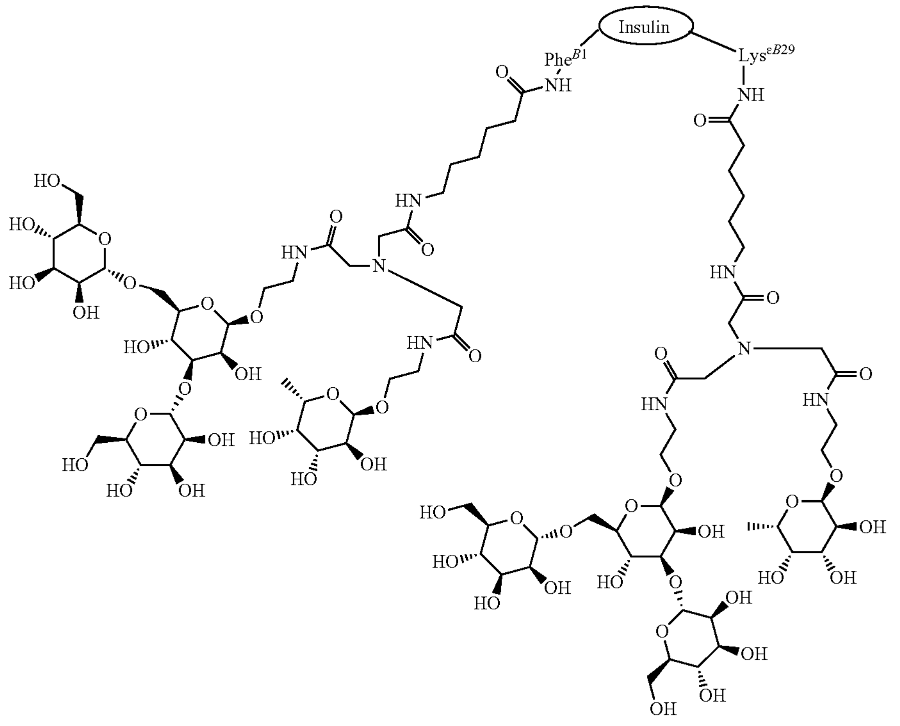
IOC-228
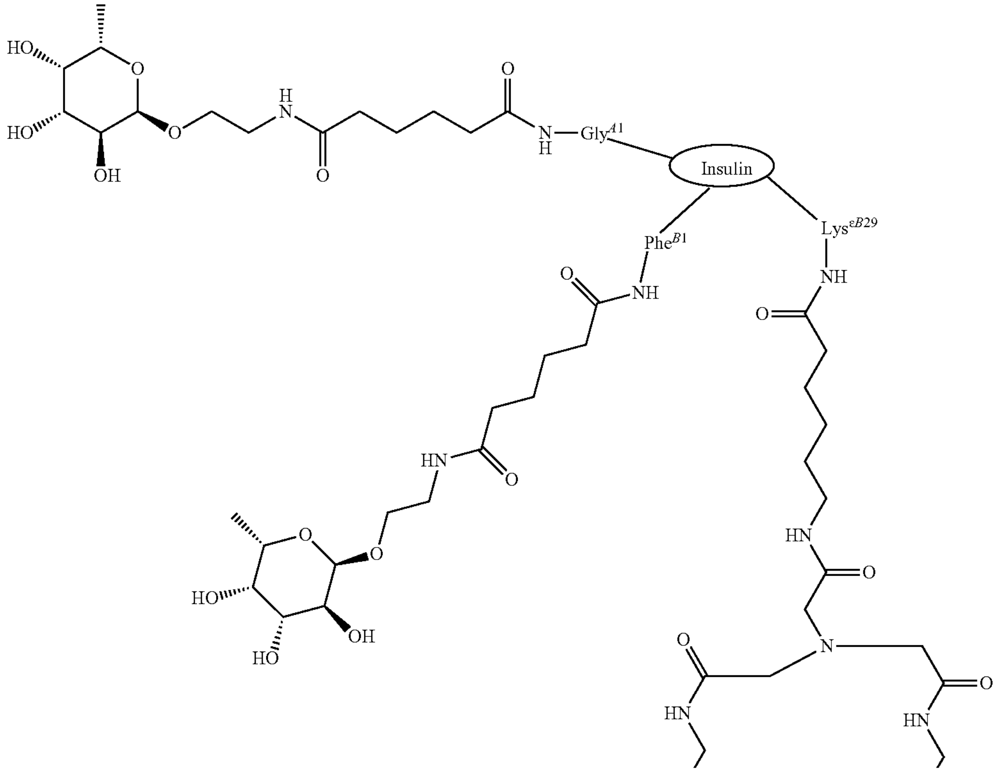

-continued
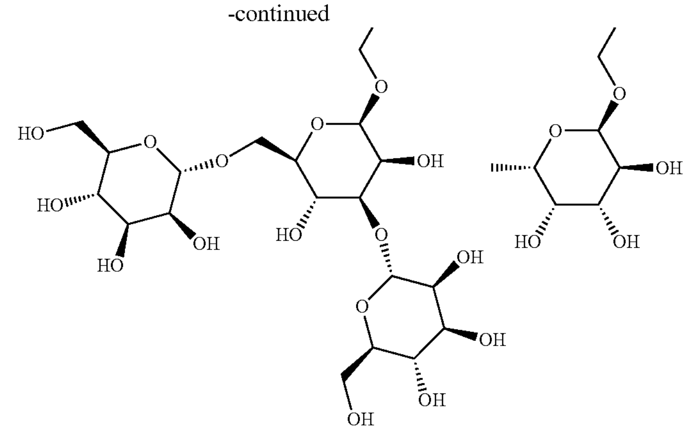
IOC-229
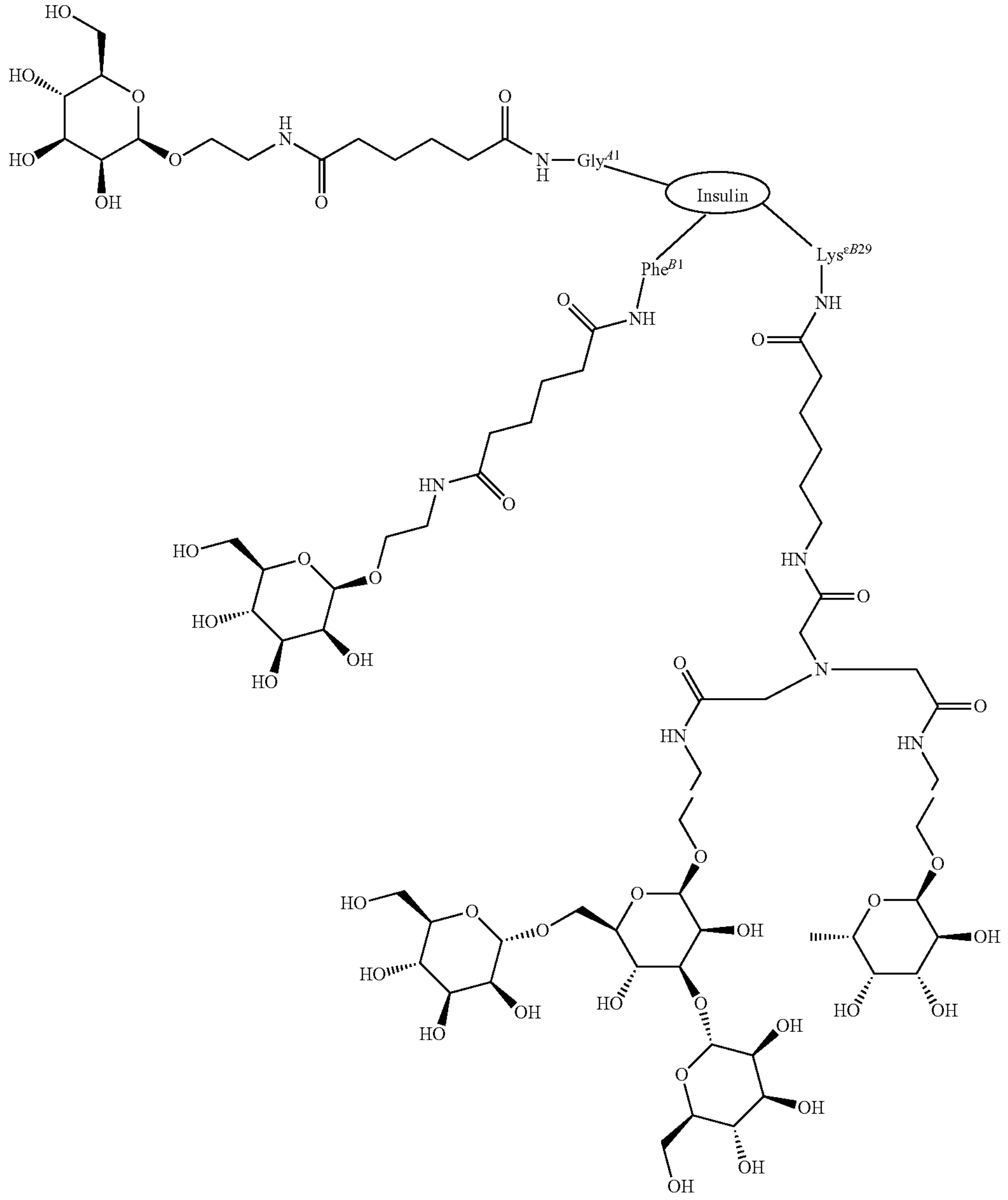

-continued
IOC-230
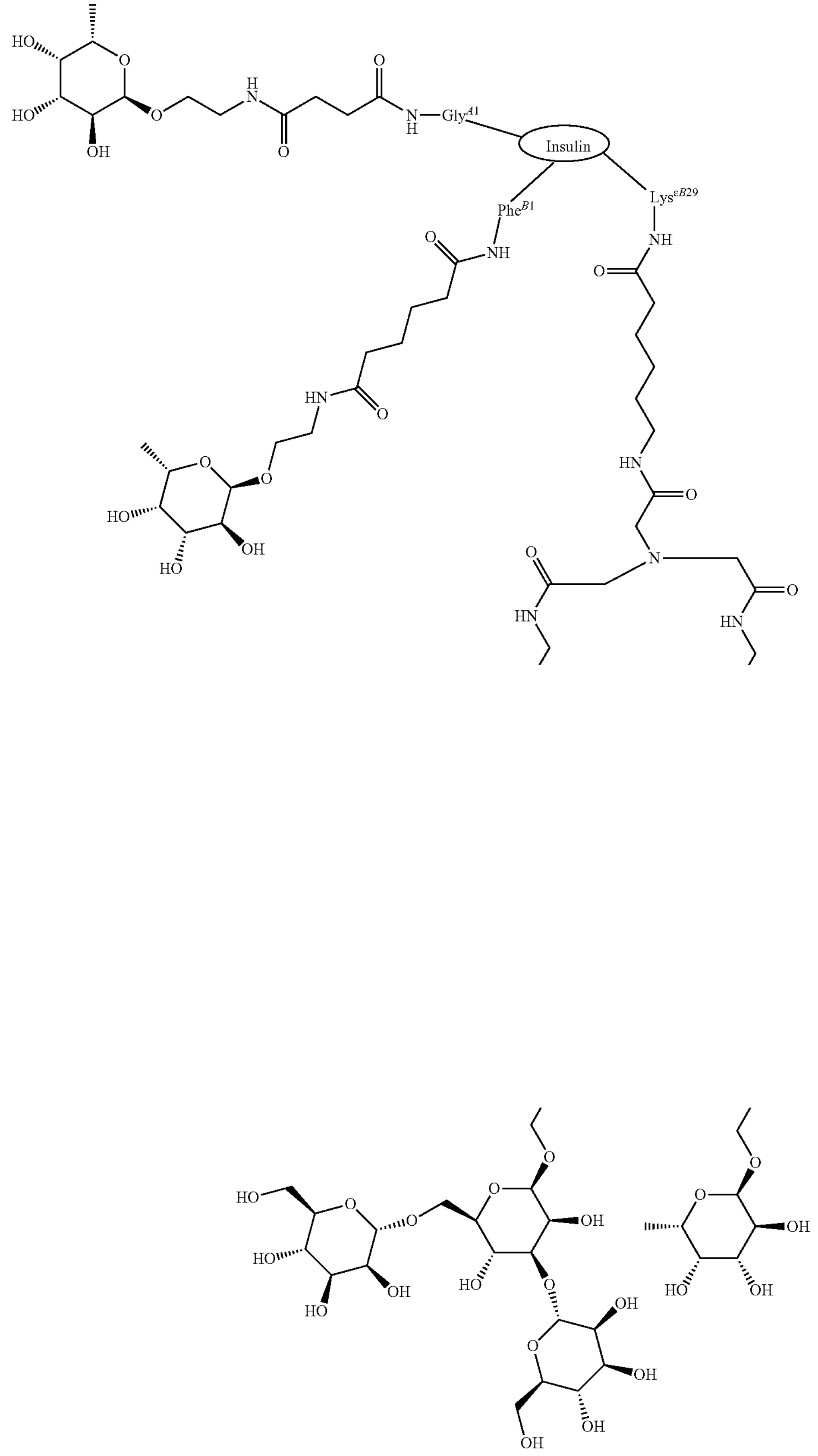

-continued
IOC-231
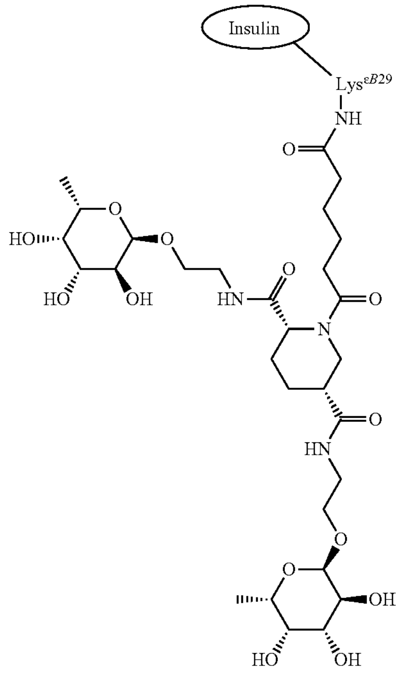
IOC-232
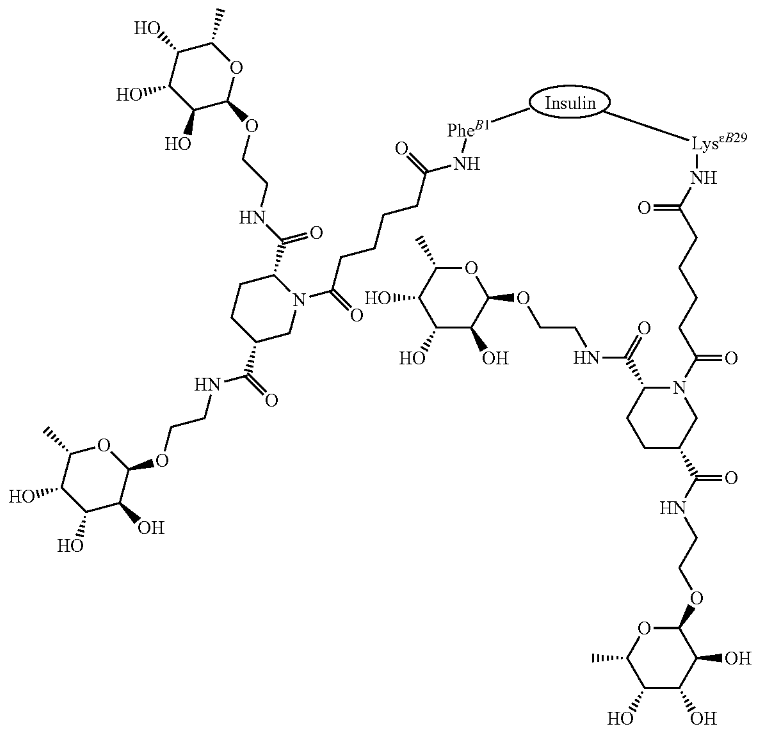

-continued
IOC-233
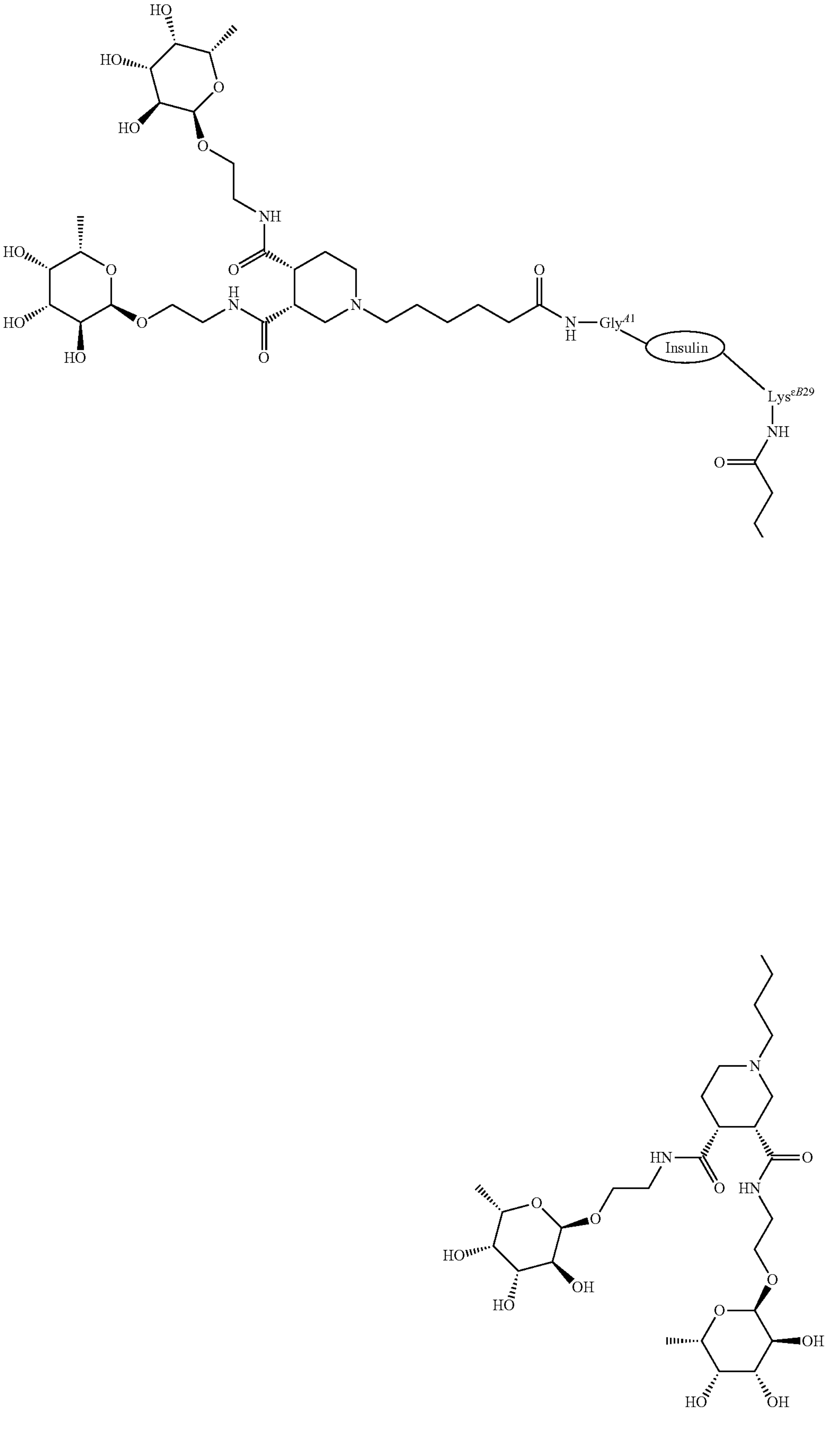

-continued
IOC-234
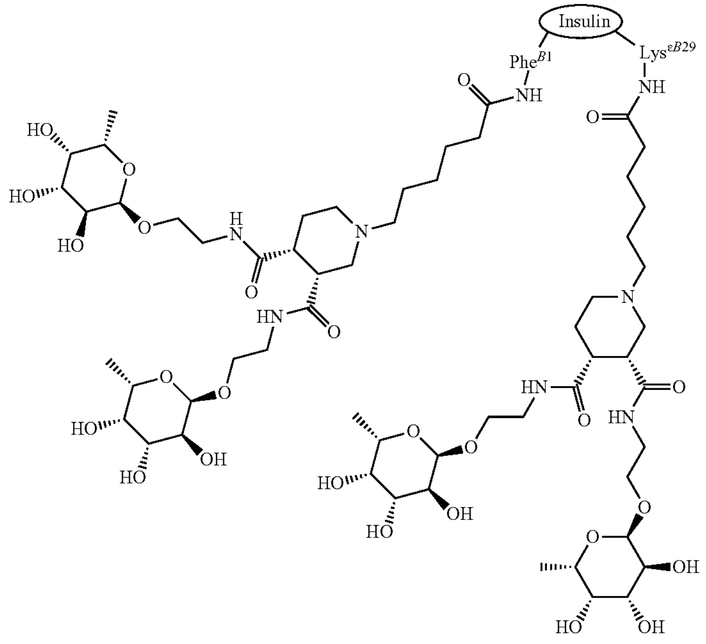
IOC-235
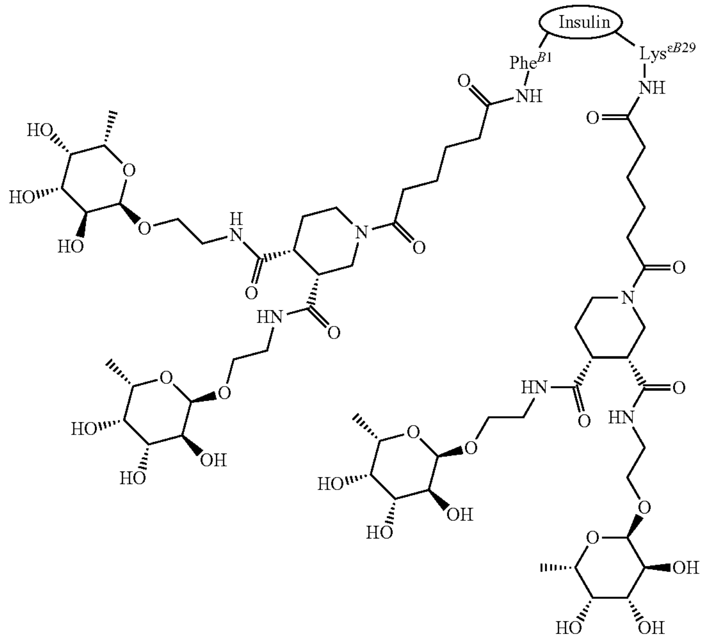

-continued
IOC-236
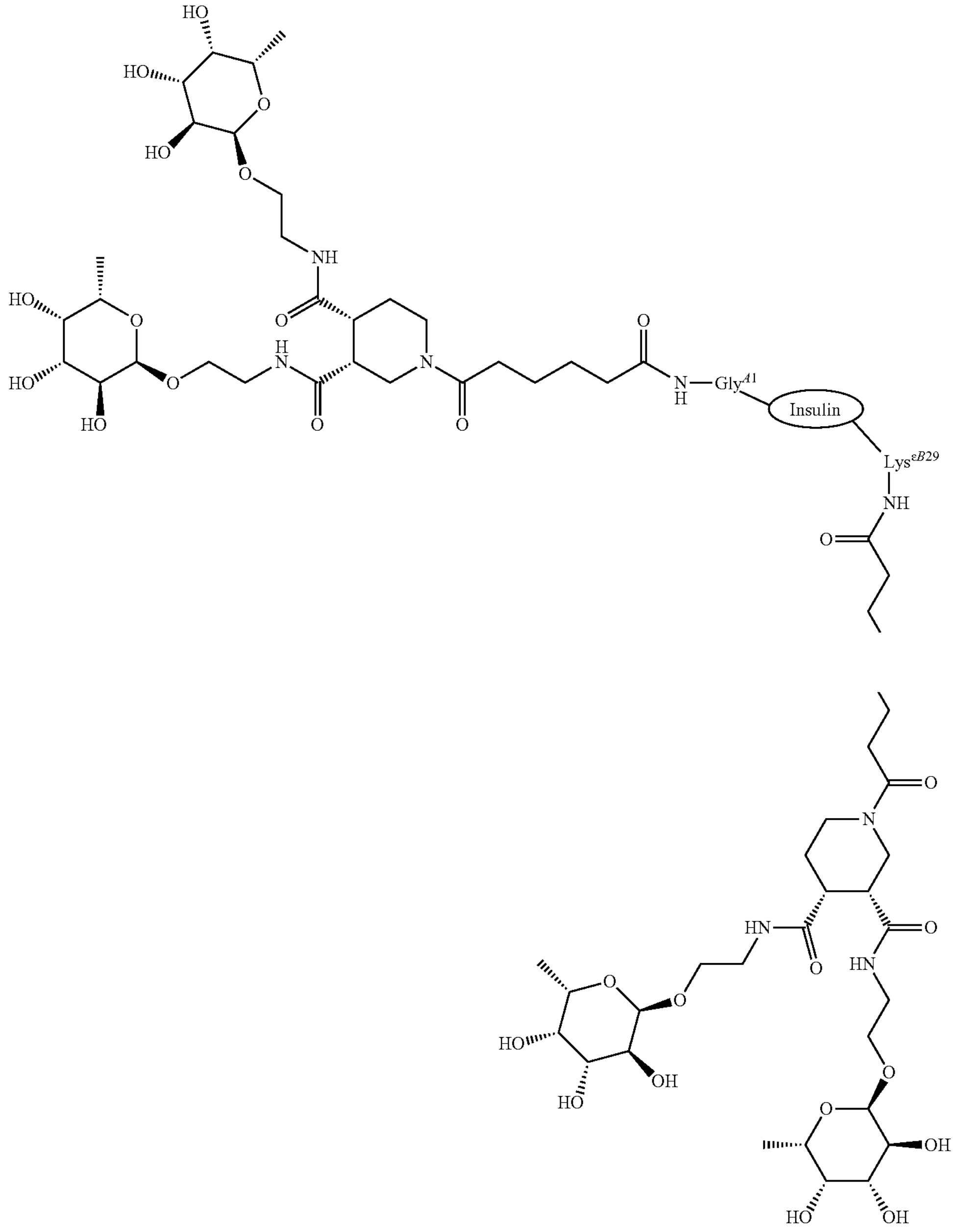
IOC-237
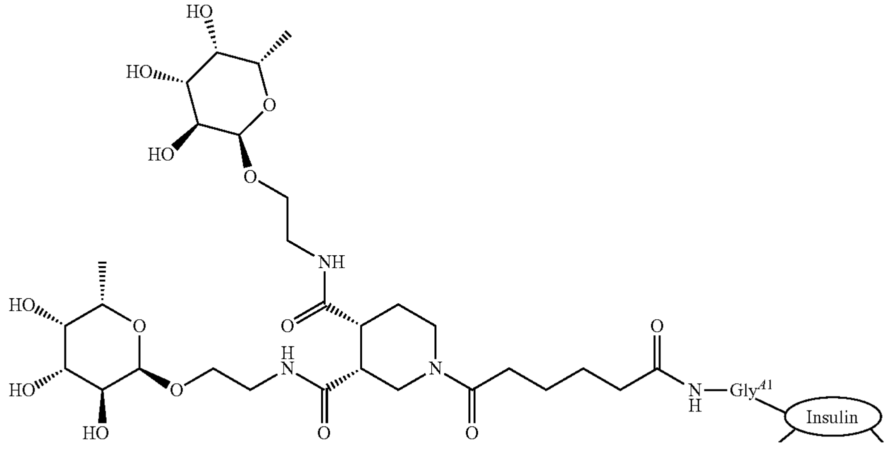

-continued
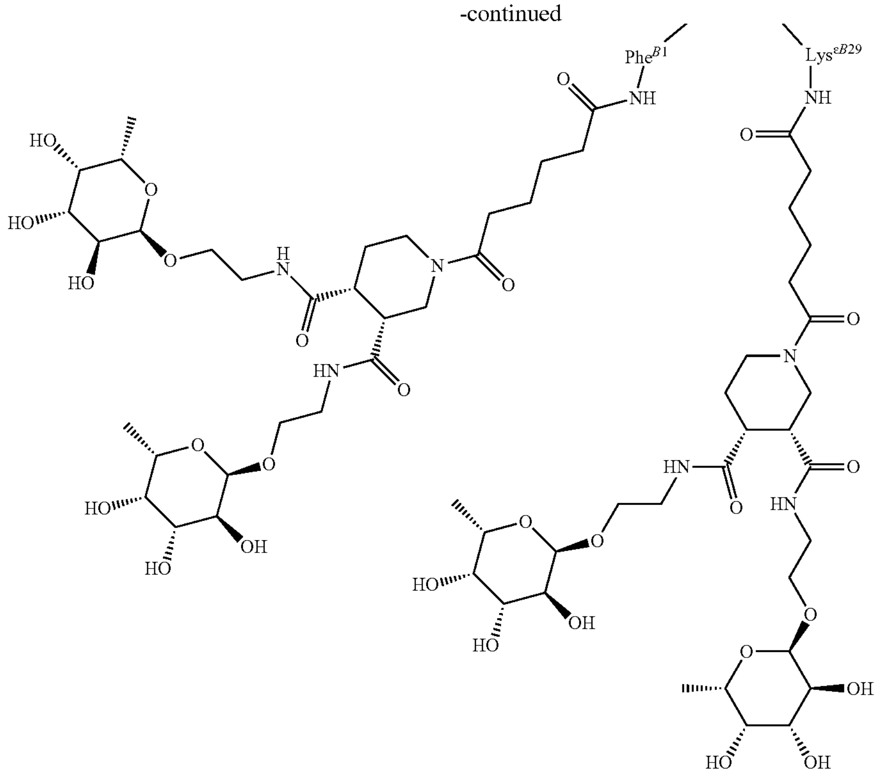
IOC-238
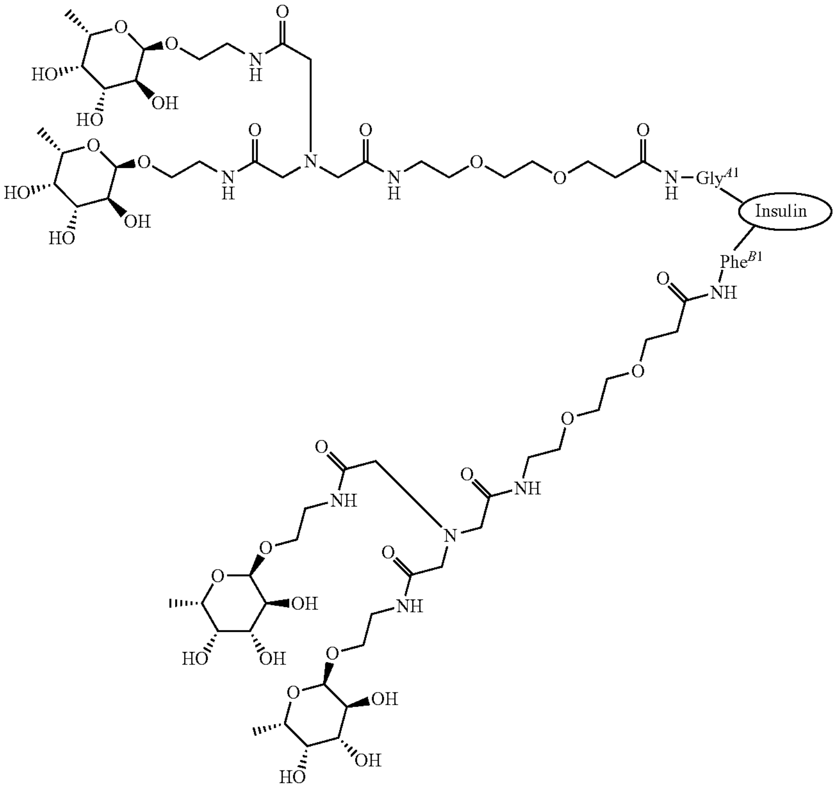

-continued
IOC-239
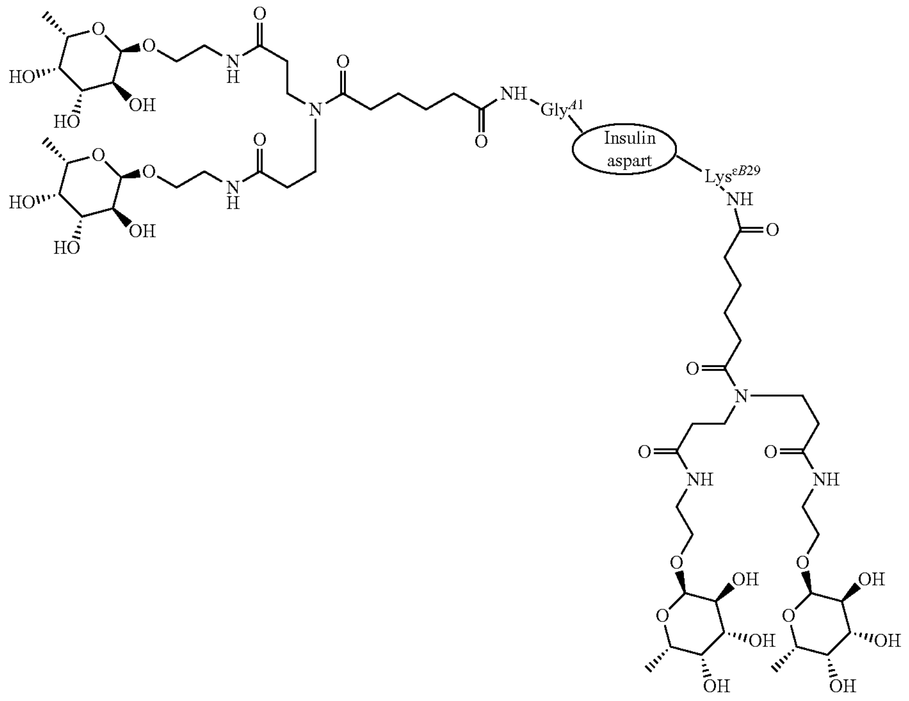
IOC-240
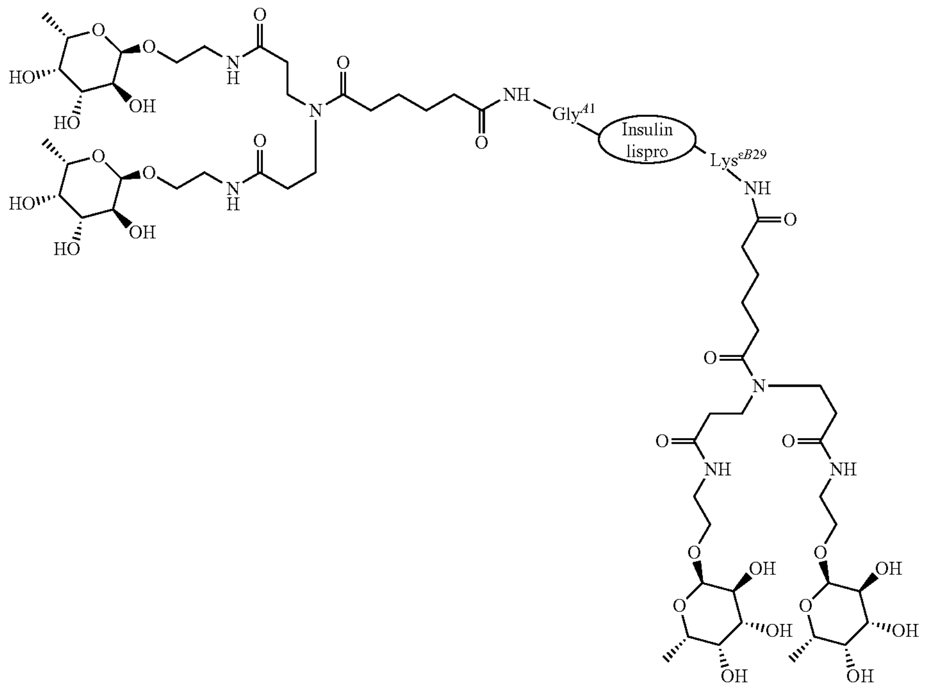

-continued
IOC-241
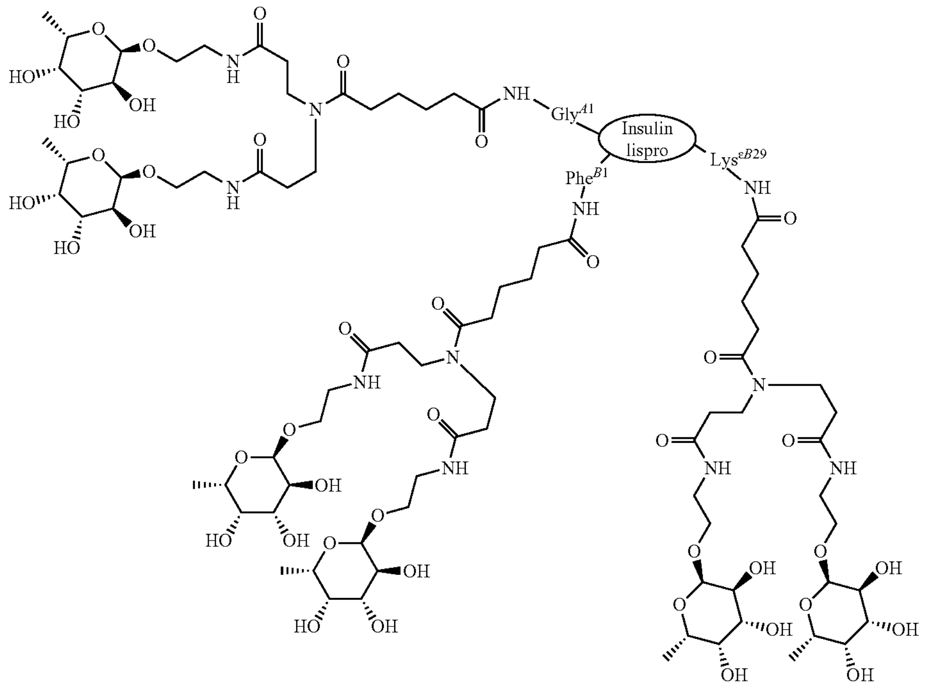
IOC-242
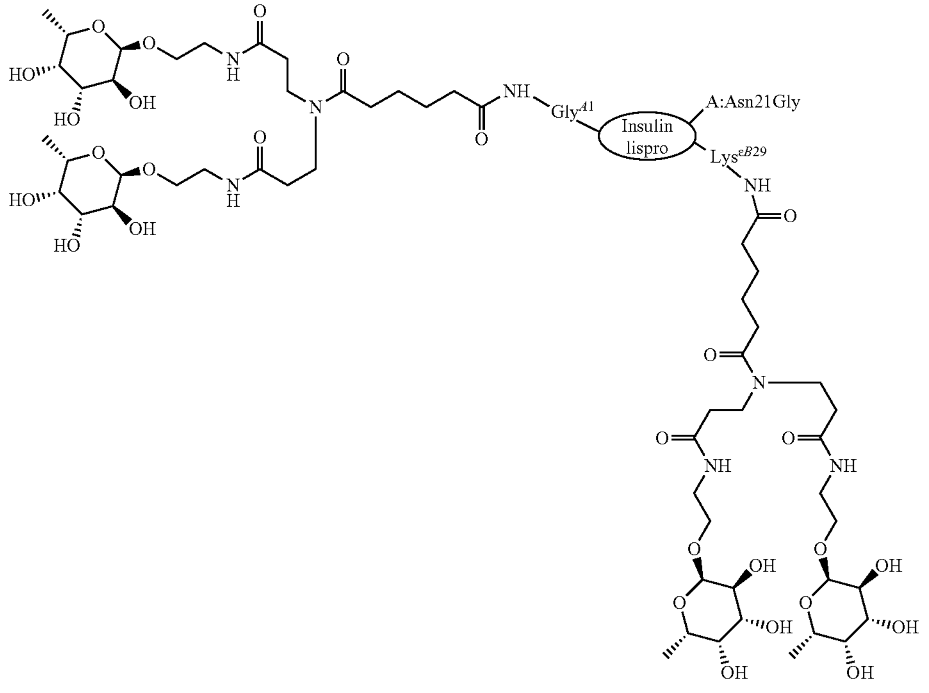

-continued
IOC-243
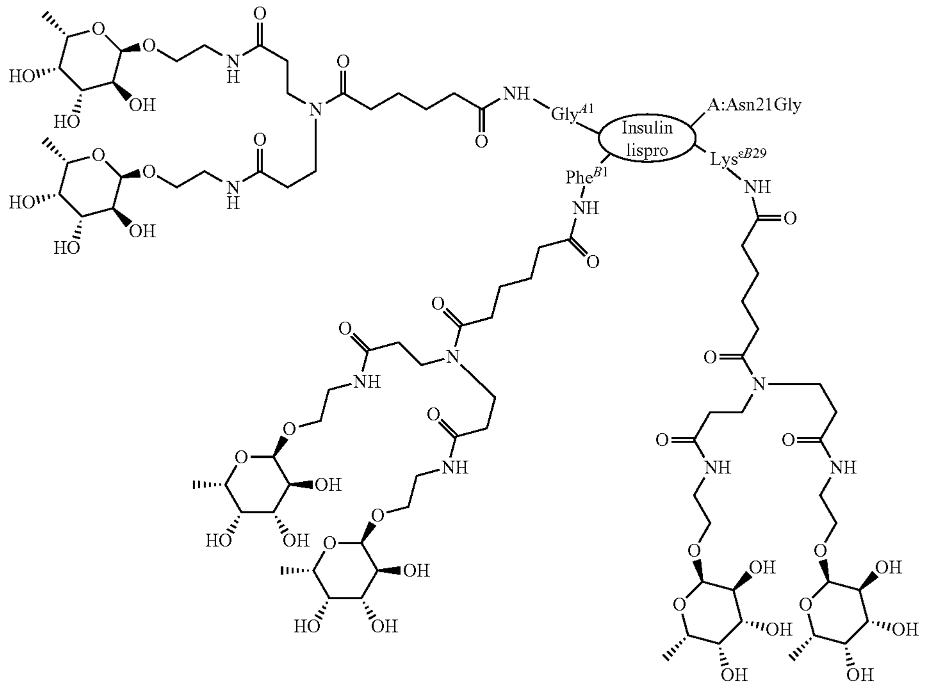
IOC-244
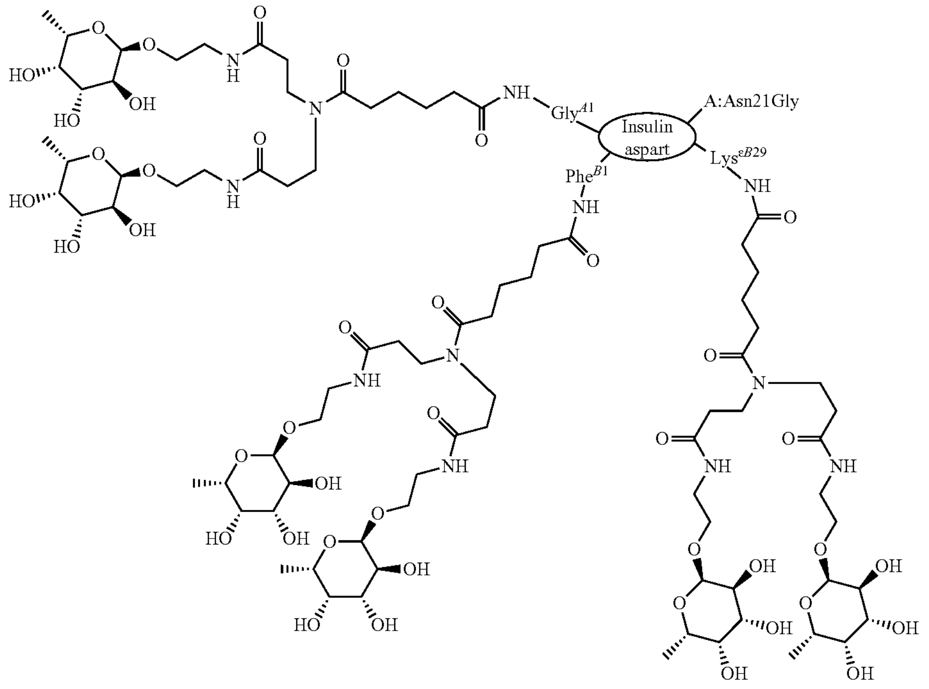

-continued
IOC-245
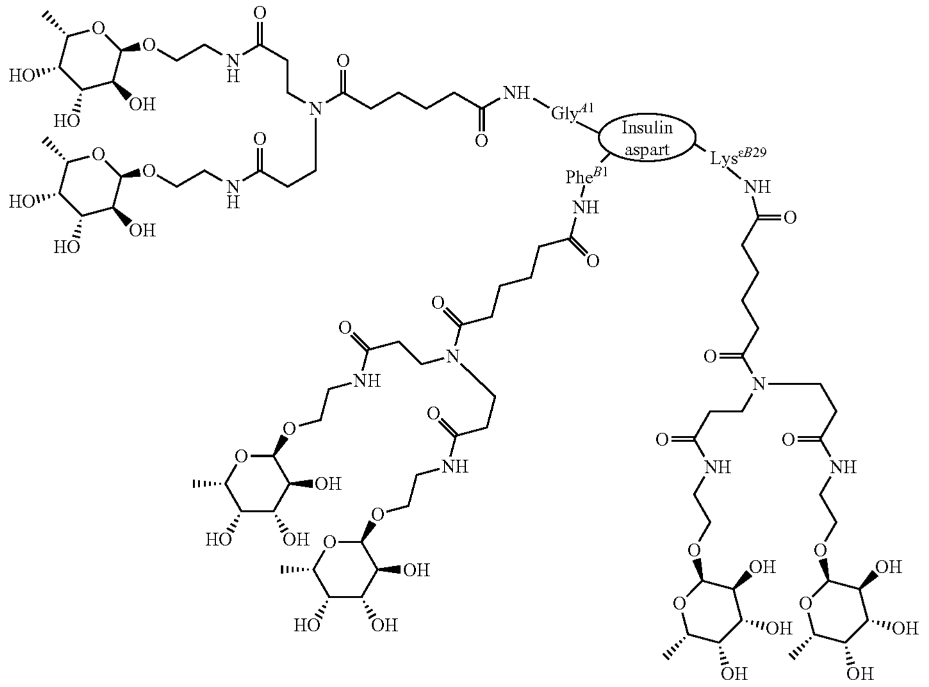
IOC-246
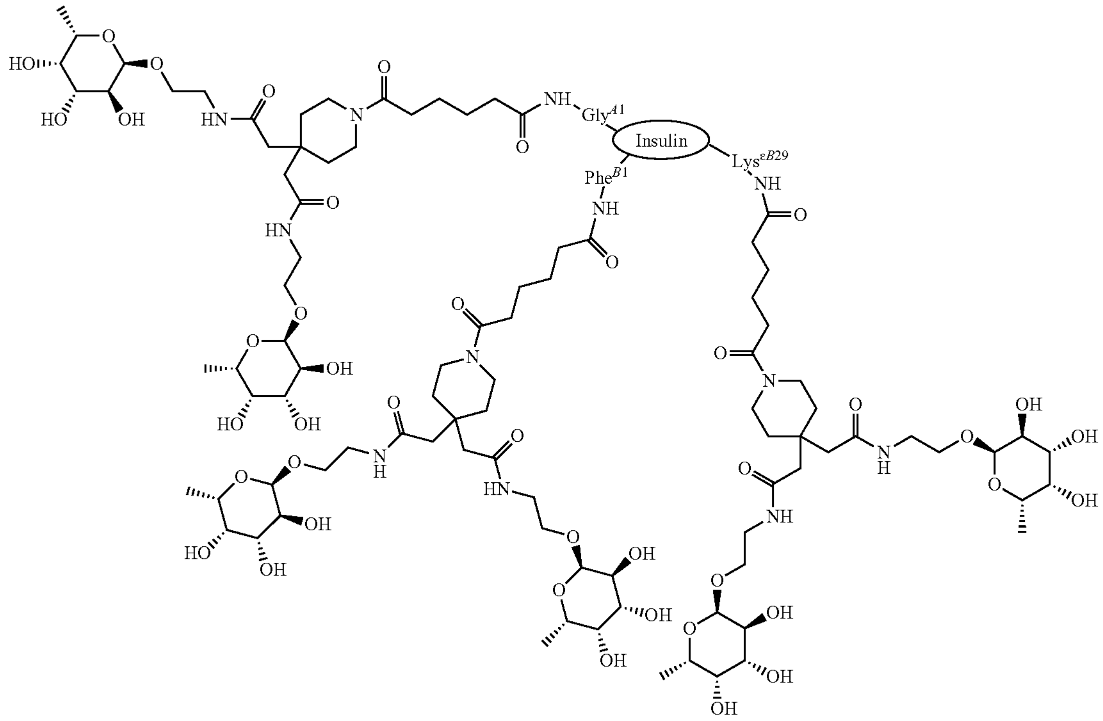

-continued
IOC-247
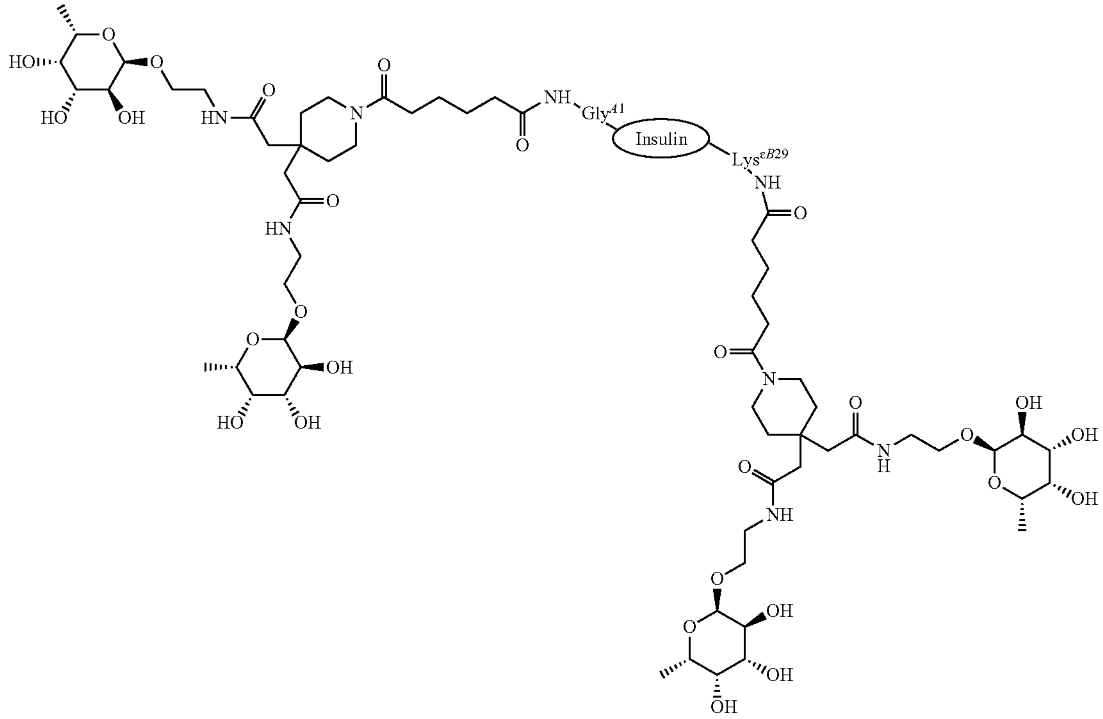
IOC-248
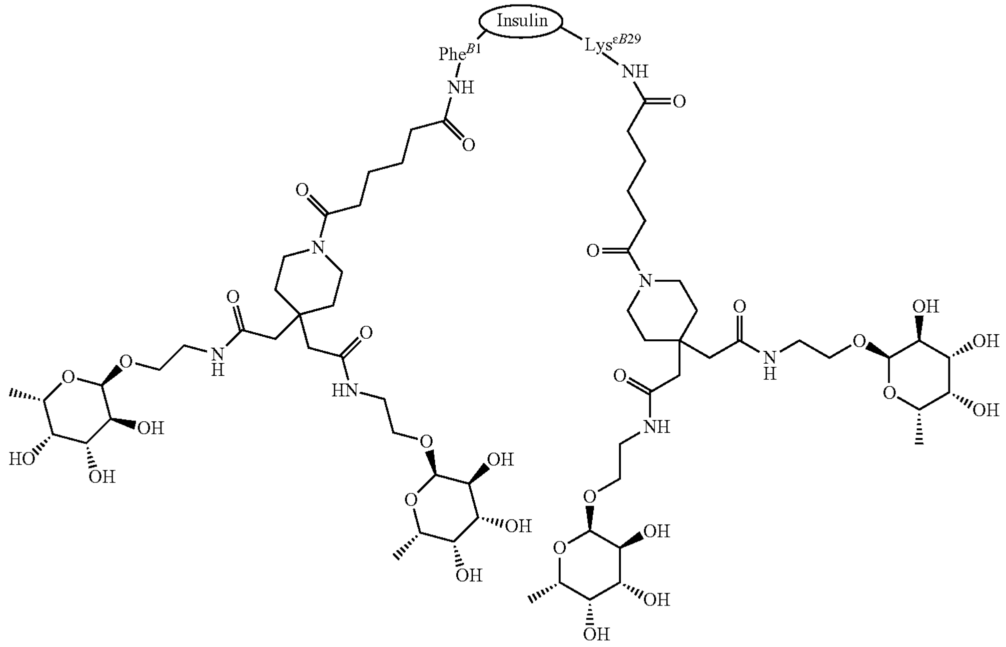

-continued
IOC-249
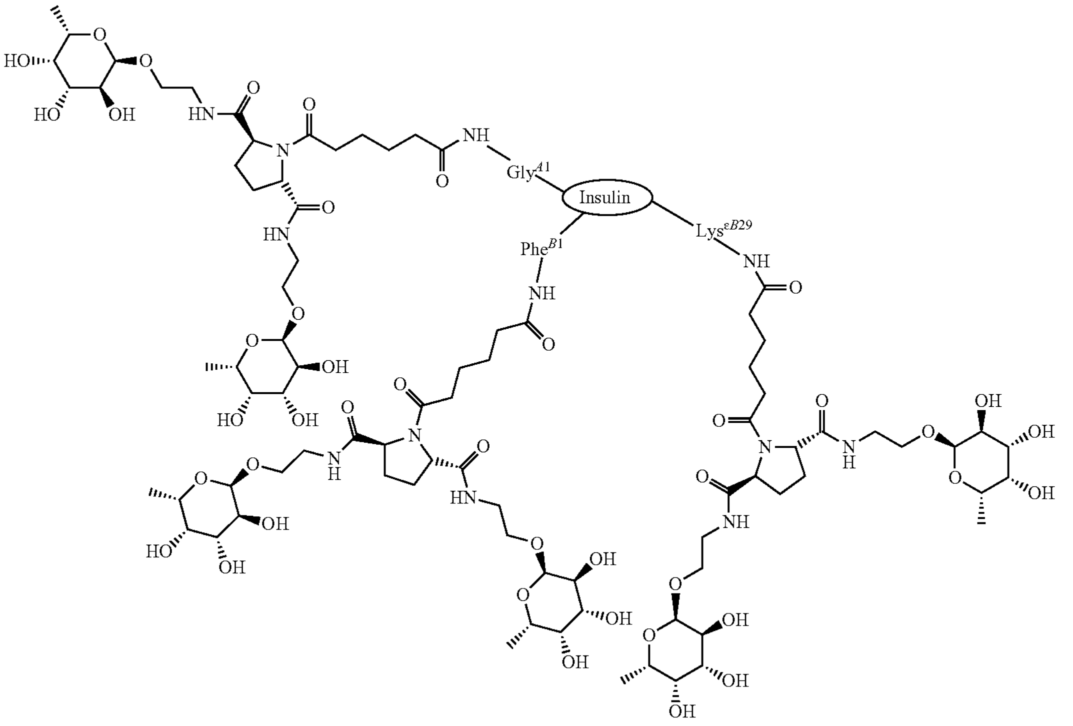
IOC-250
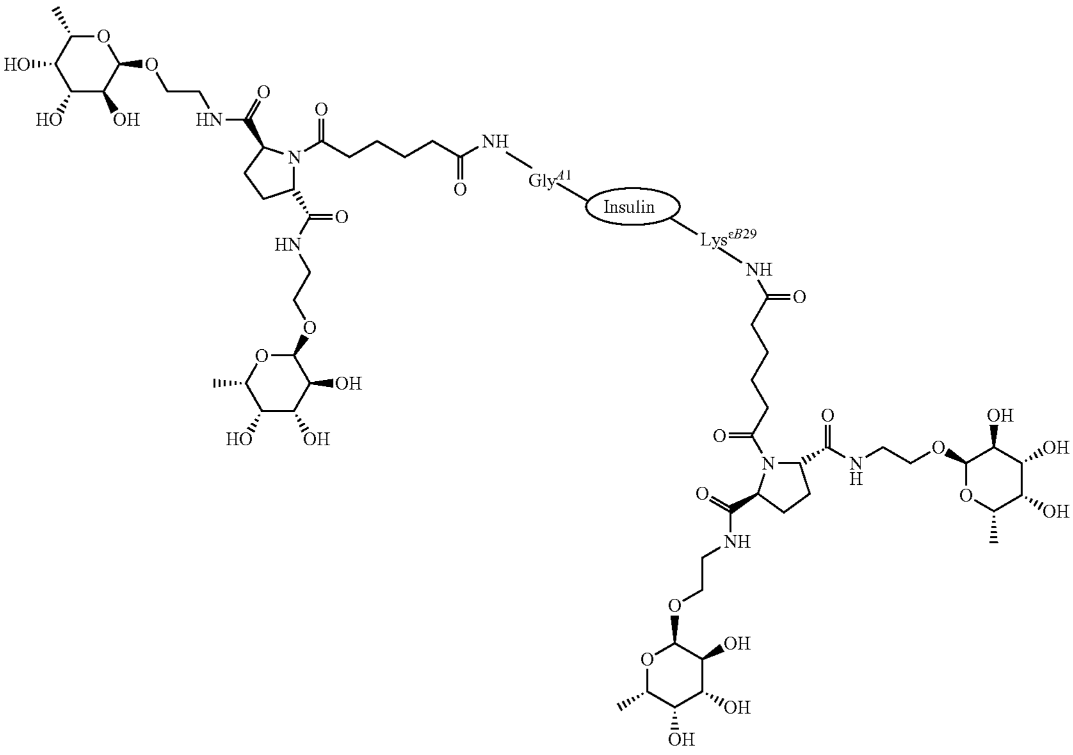

-continued
IOC-251
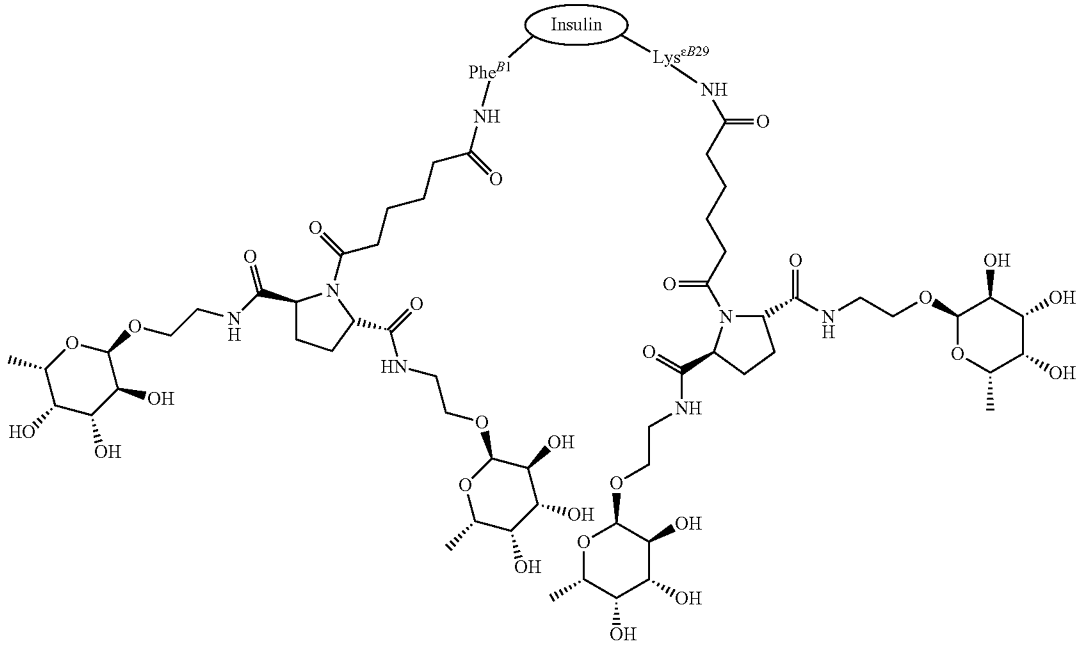
IOC-252
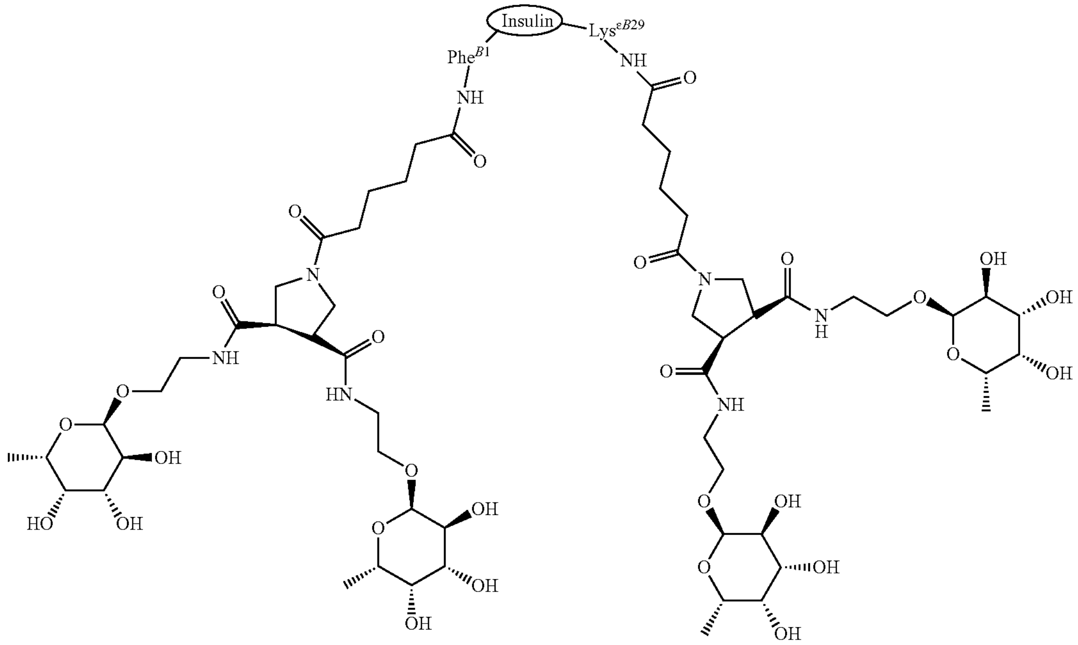

-continued
IOC-253
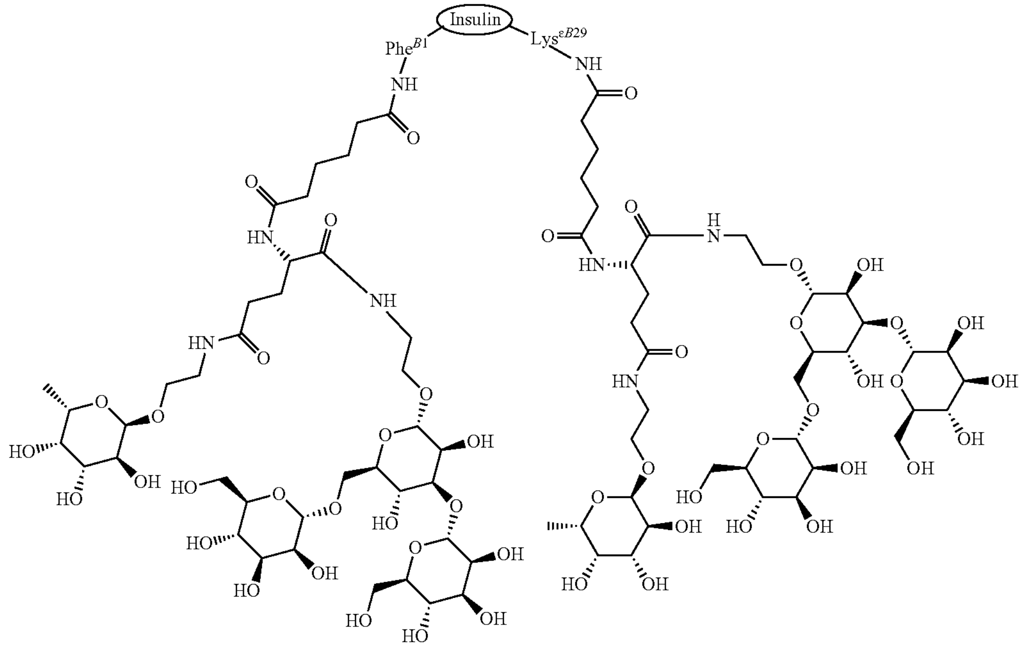
IOC-254
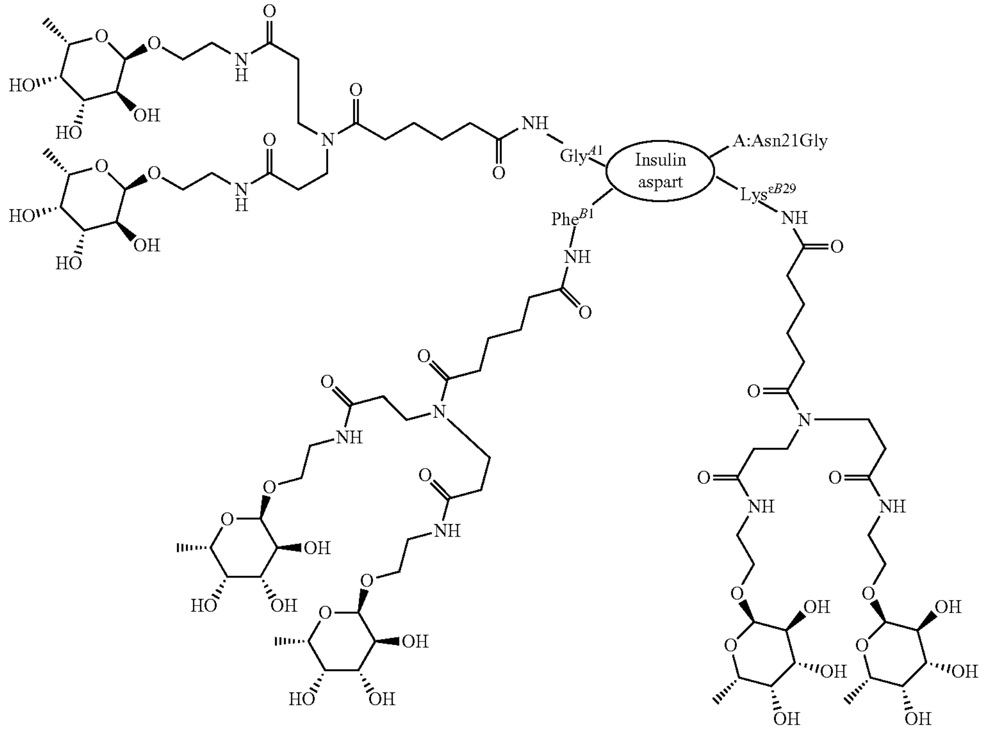

-continued
IOC-255
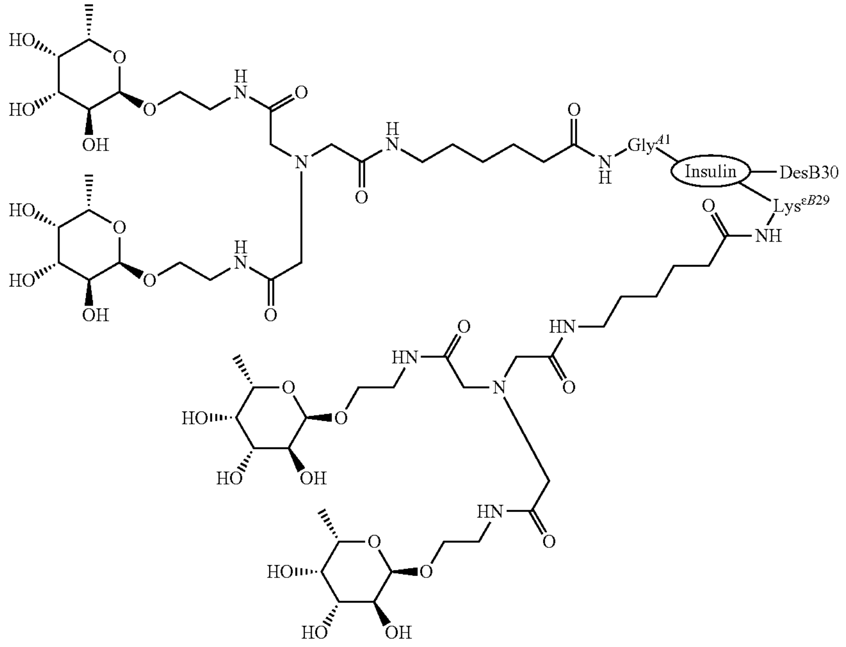
IOC-256
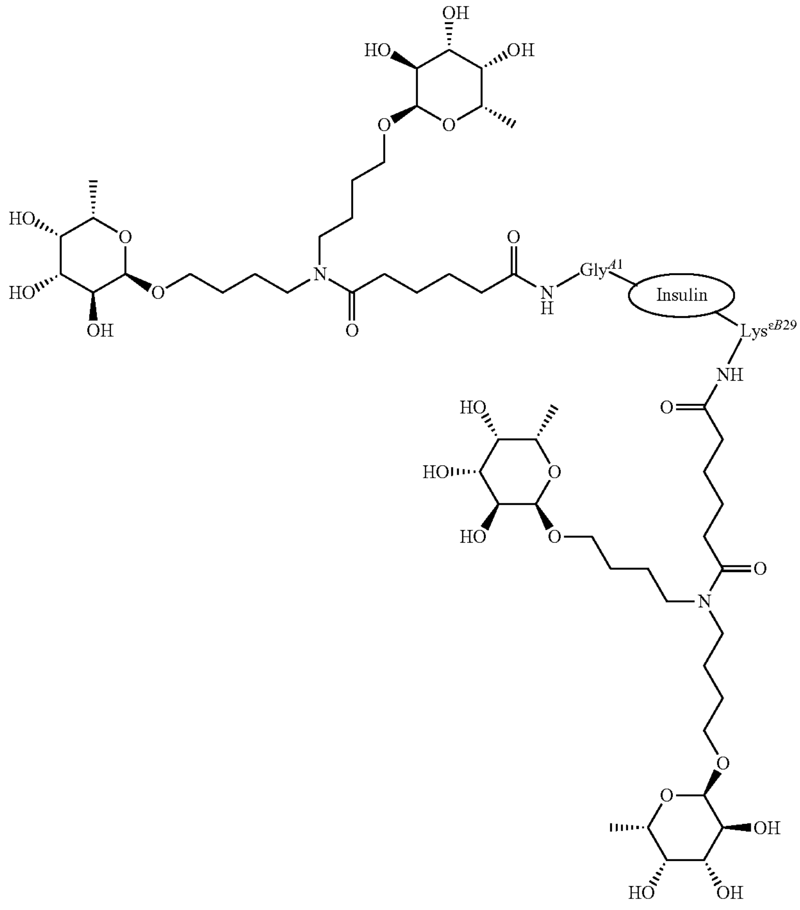

-continued
IOC-257
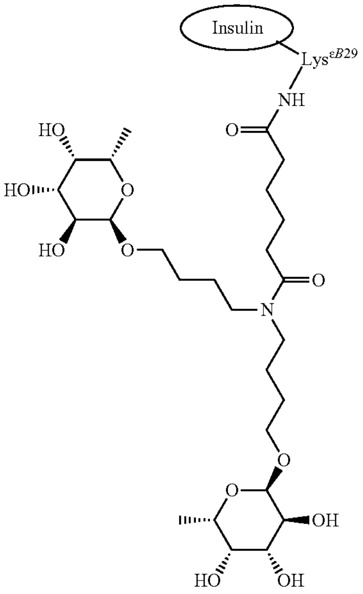
IOC-258
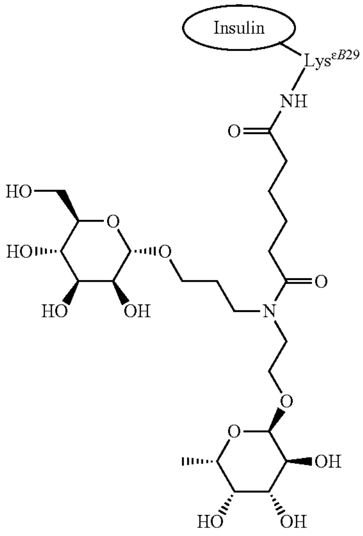
IOC-259
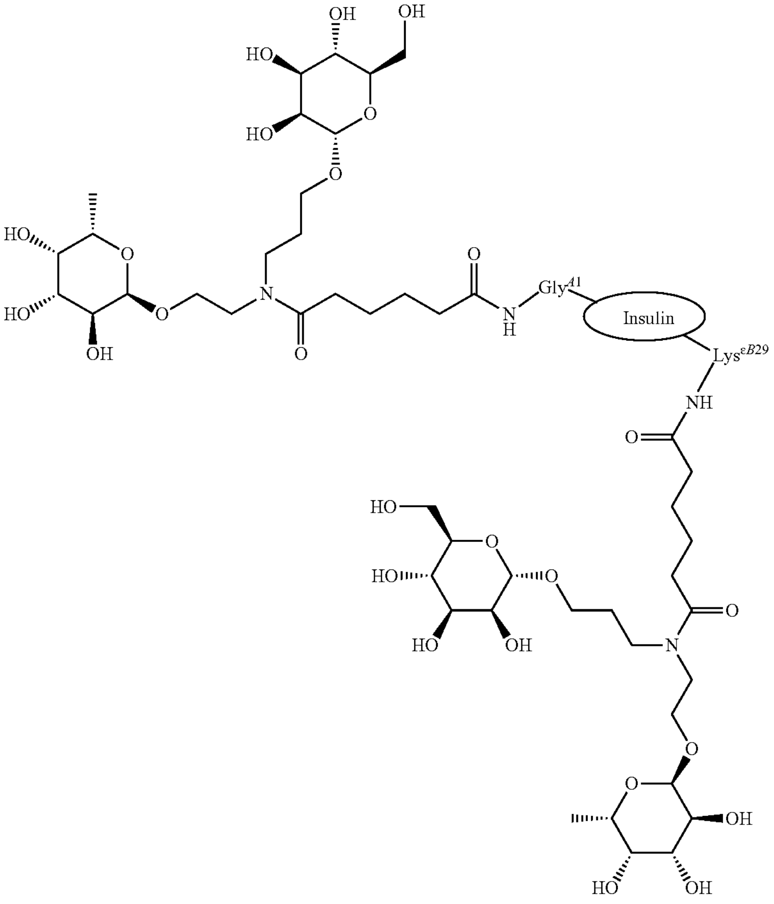

-continued
IOC-260
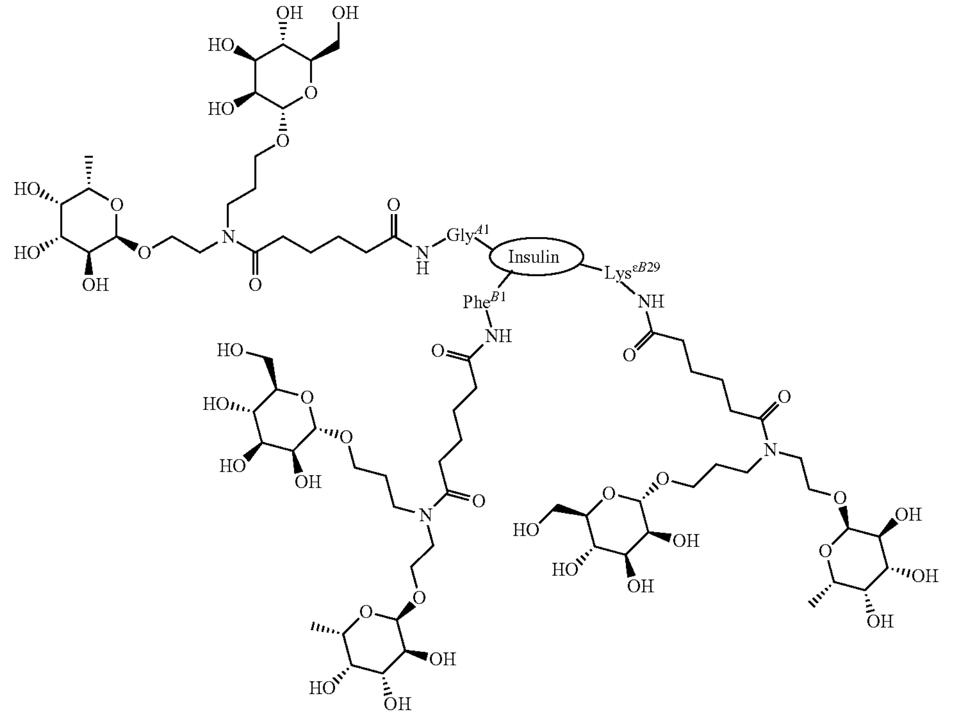
IOC-261
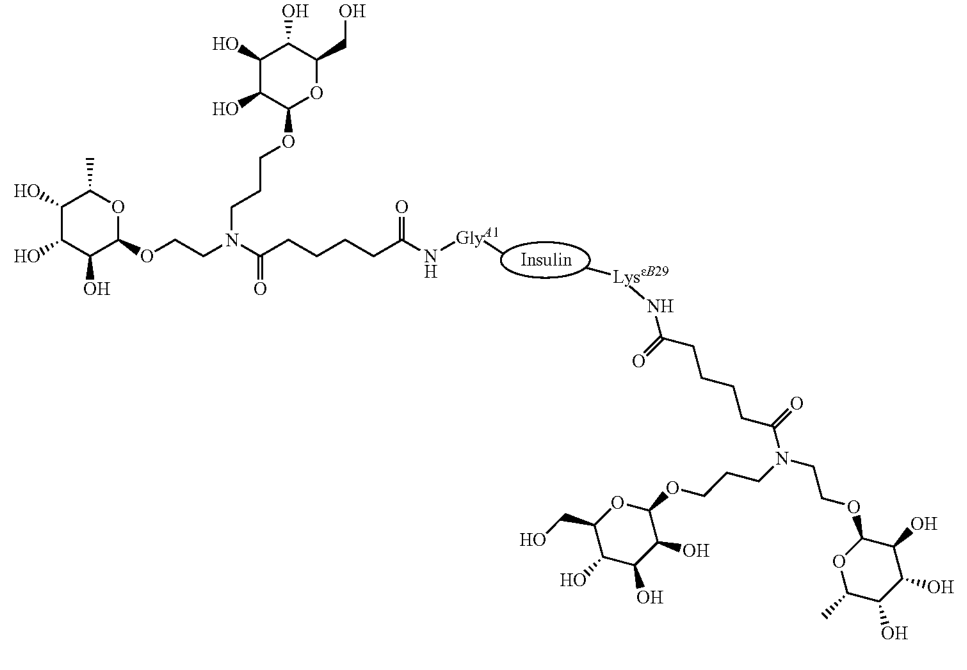

-continued
IOC-262
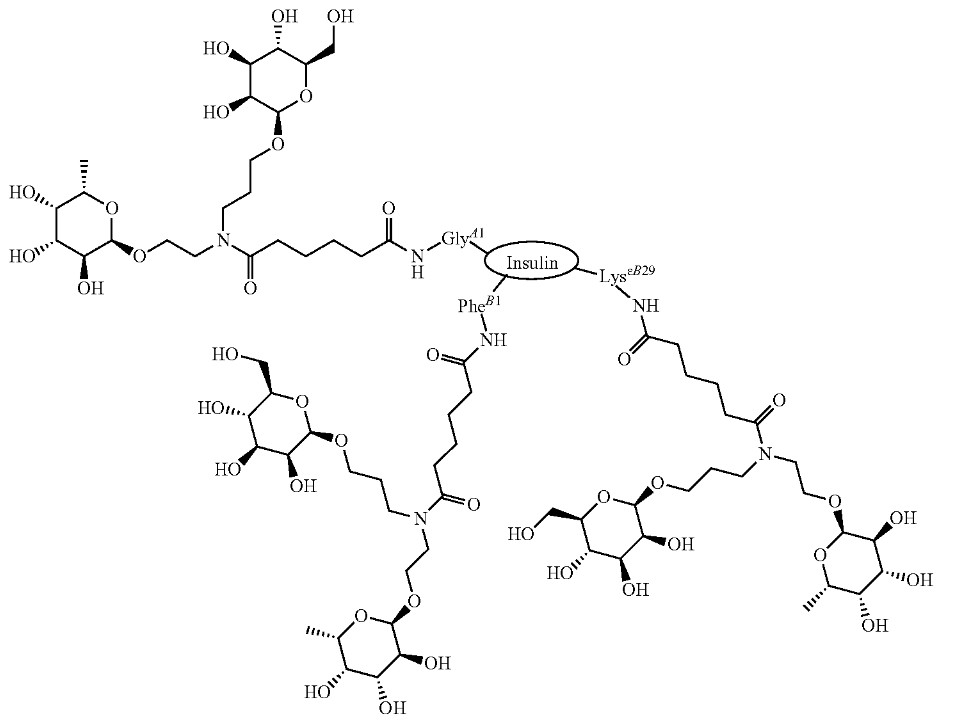
IOC-263
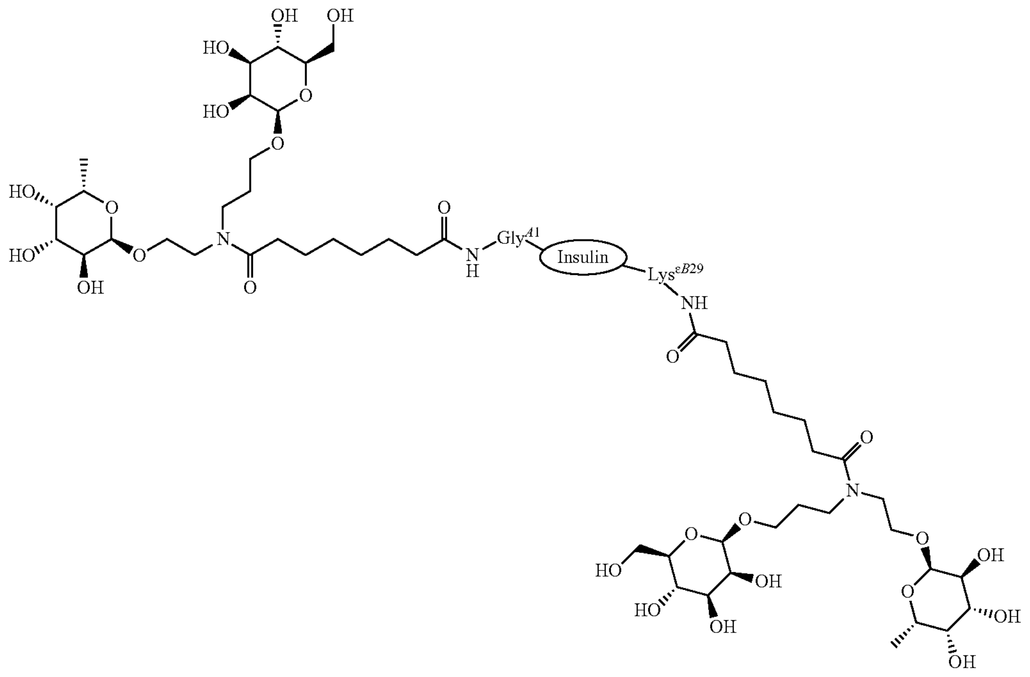

-continued
IOC-264
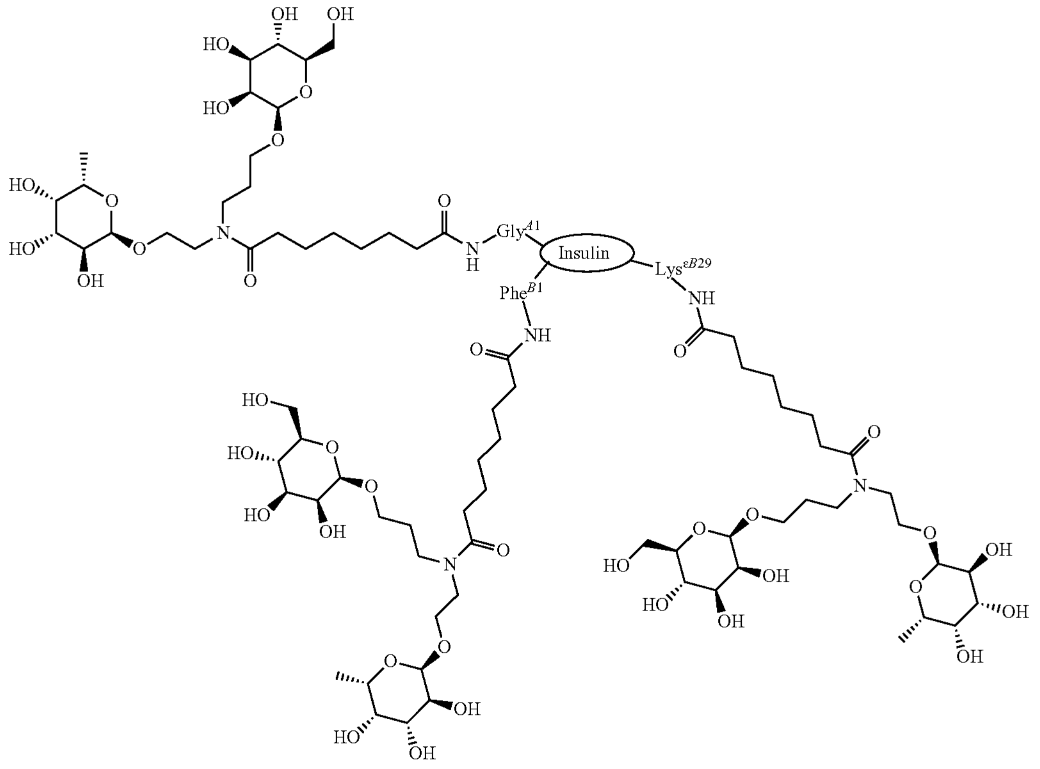
IOC-265
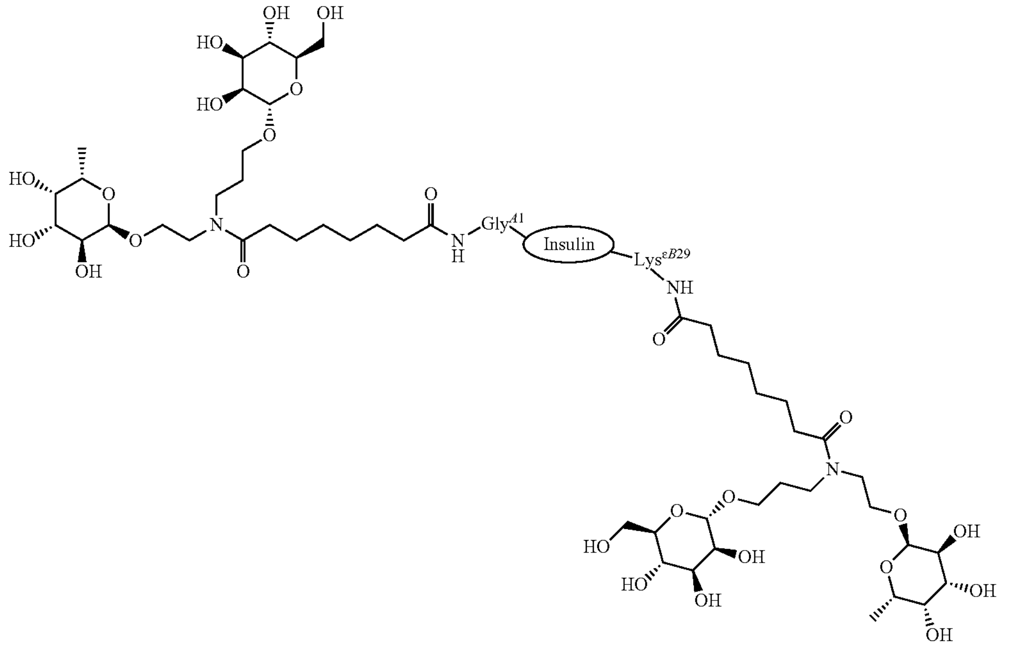

-continued
IOC-266
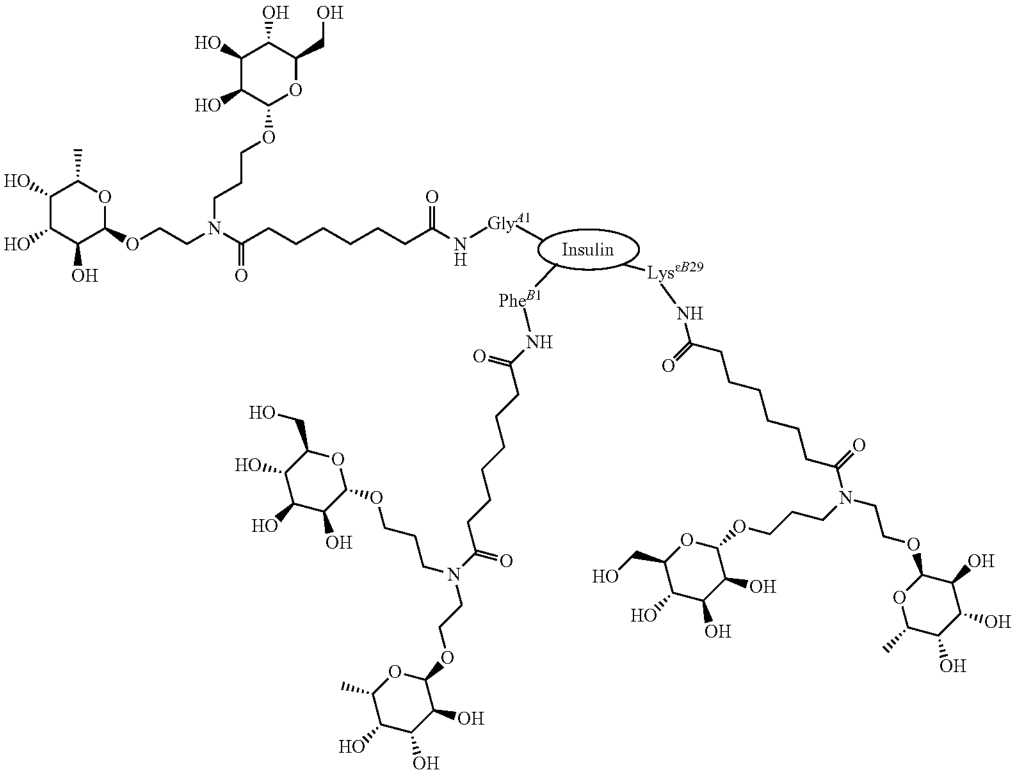
IOC-267
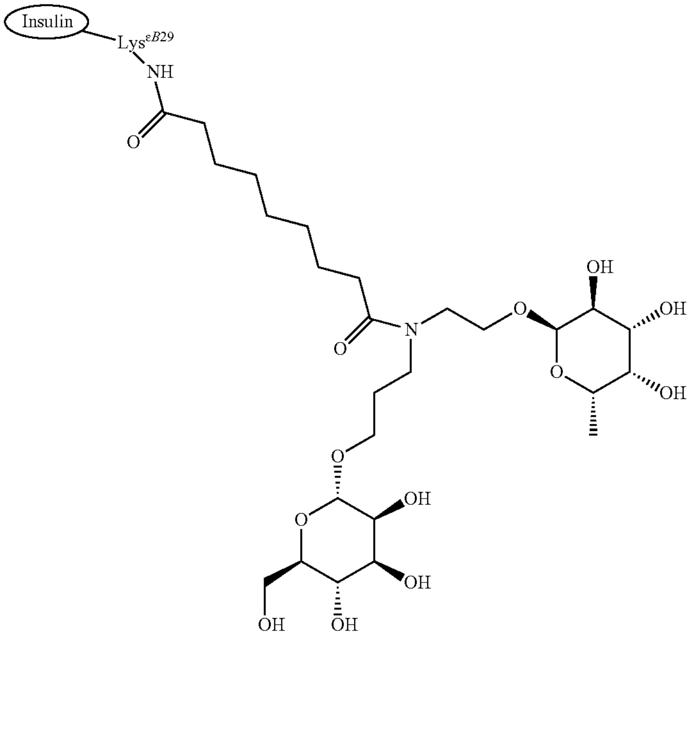

-continued
IOC-268
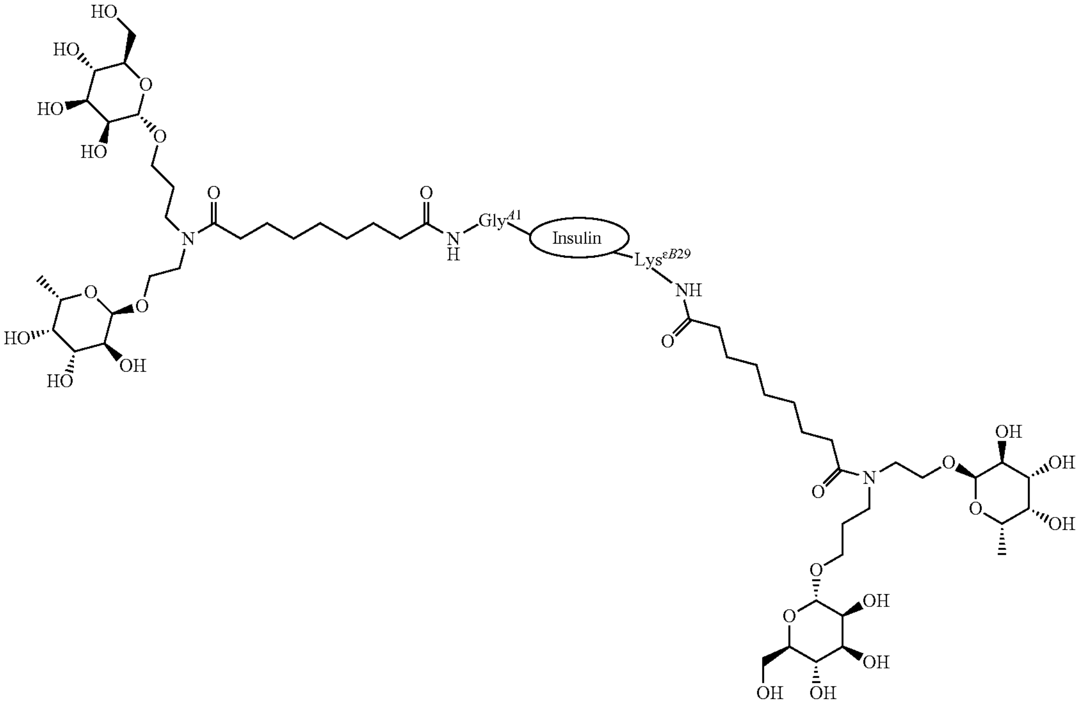
IOC-269
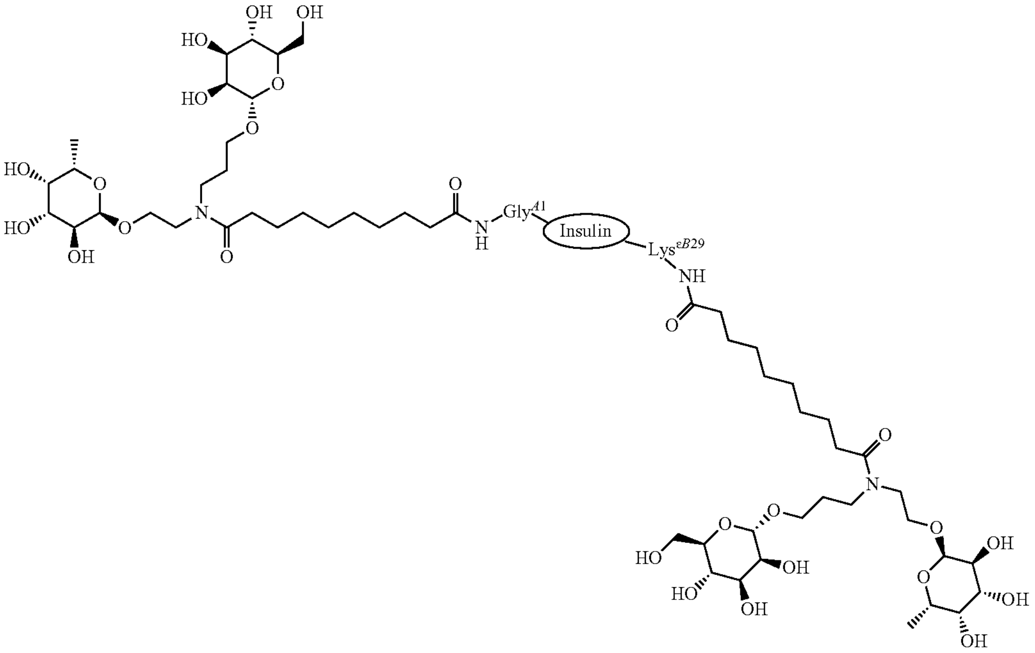

-continued
IOC-270
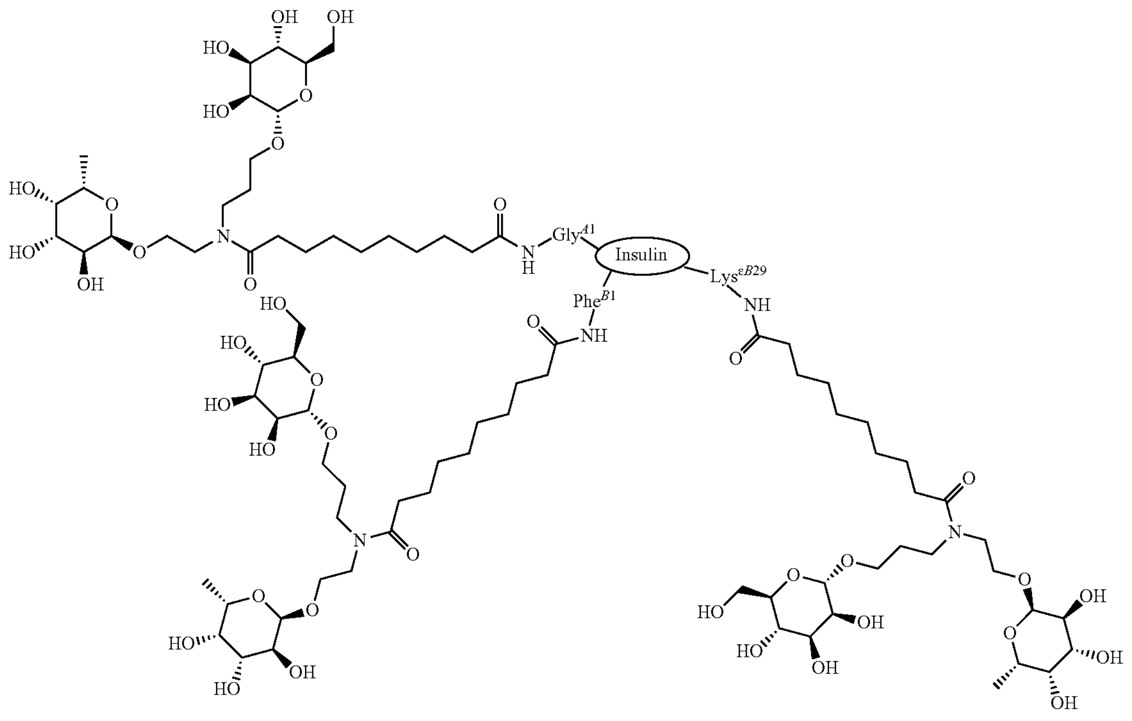
IOC-271
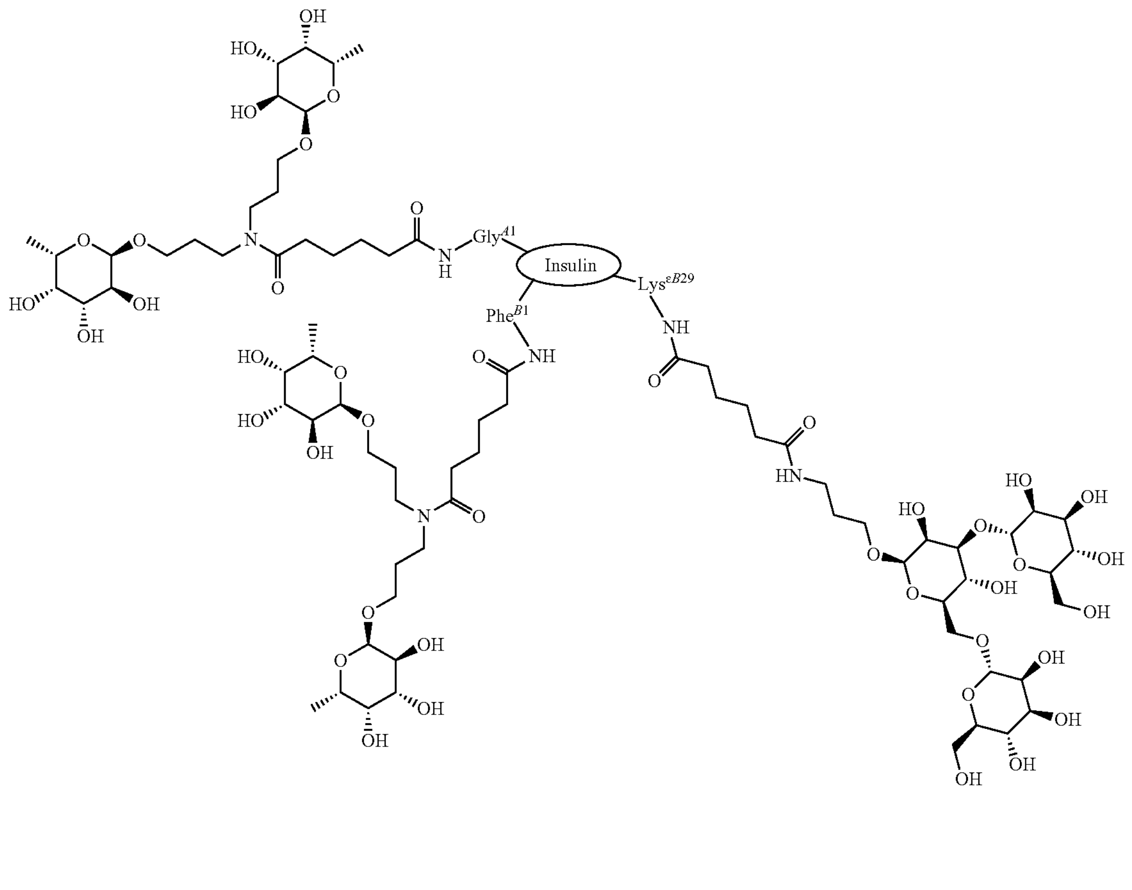

-continued

IOC-272

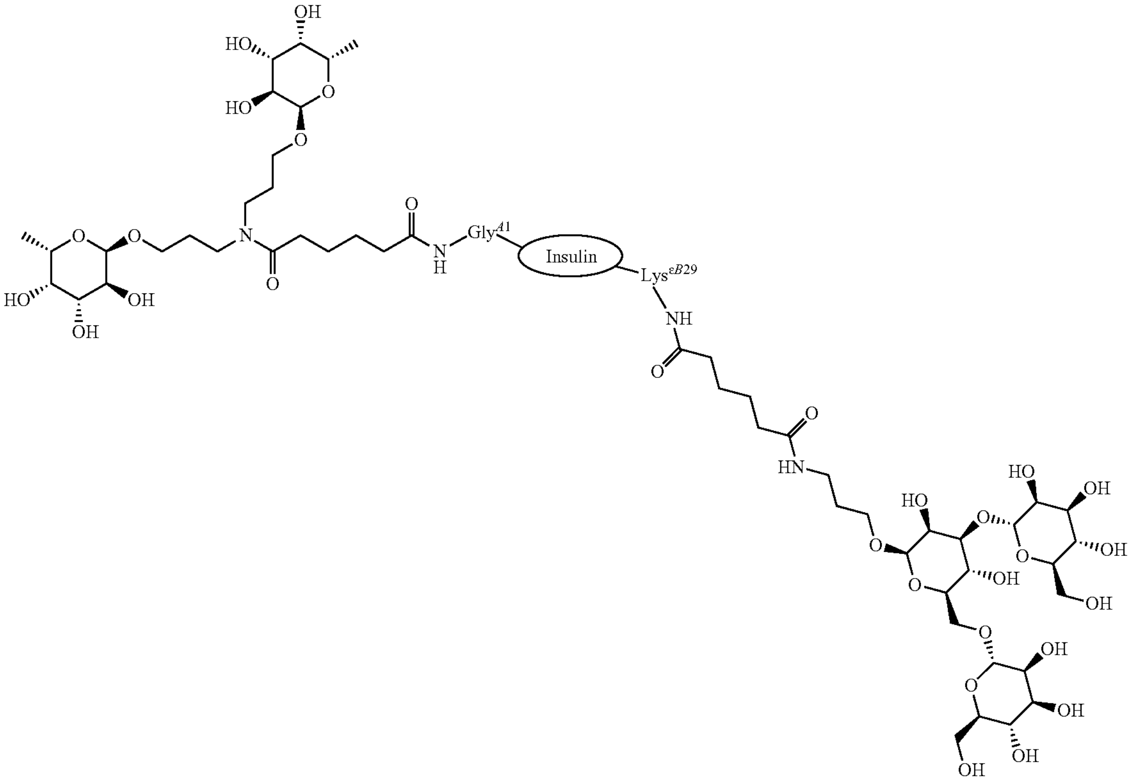

Sustained Release Formulations

In particular embodiments it may be advantageous to administer an insulin conjugate in a sustained fashion (i.e., in a form that exhibits an absorption profile that is more sustained than soluble recombinant human insulin). This will provide a sustained level of conjugate that can respond to fluctuations in glucose on a timescale that it more closely related to the typical glucose fluctuation timescale (i.e., hours rather than minutes). In particular embodiments, the sustained release formulation may exhibit a zero-order release of the conjugate when administered to a mammal under non-hyperglycemic conditions (i.e., fasted conditions).

It will be appreciated that any formulation that provides a sustained absorption profile may be used. In particular embodiments this may be achieved by combining the conjugate with other ingredients that slow its release properties into systemic circulation. For example, PZI (protamine zinc insulin) formulations may be used for this purpose. The present disclosure encompasses amorphous and crystalline forms of these PZI formulations.

Thus, in particular embodiments, a formulation of the present disclosure includes from about 0.05 to about 10 mg protamine/mg conjugate. For example, from about 0.2 to about 10 mg protamine/mg conjugate, e.g., about 1 to about 5 mg protamine/mg conjugate.

In particular embodiments, a formulation of the present disclosure includes from about 0.006 to about 0.5 mg zinc/mg conjugate. For example, from about 0.05 to about 0.5 mg zinc/mg conjugate, e.g., about 0.1 to about 0.25 mg zinc/mg conjugate.

In particular embodiments, a formulation of the present disclosure includes protamine and zinc in a ratio (w/w) in the range of about 100:1 to about 5:1, for example, from about 50:1 to about 5:1, e.g., about 40:1 to about 10:1. In particular embodiments, a PZI formulation of the present disclosure includes protamine and zinc in a ratio (w/w) in the range of about 20:1 to about 5:1, for example, about 20:1 to about 10:1, about 20:1 to about 15:1, about 15:1 to about 5:1, about 10:1 to about 5:1, about 10:1 to about 15:1.

One or more of the following components may be included in the PZI formulation: an antimicrobial preservative, an isotonic agent, and/or an unconjugated insulin molecule.

In particular embodiments a formulation of the present disclosure includes an antimicrobial preservative (e.g., m-cresol, phenol, methylparaben, or propylparaben). In particular embodiments the antimicrobial preservative is m-cresol. For example, in particular embodiments, a formulation may include from about 0.1 to about 1.0% v/v m-cresol. For example, from about 0.1 to about 0.5% v/v m-cresol, e.g., about 0.15 to about 0.35% v/v m-cresol.

In particular embodiments a formulation of the present disclosure includes a polyol as isotonic agent (e.g., mannitol, propylene glycol or glycerol). In particular embodiments the isotonic agent is glycerol. In particular embodiments, the isotonic agent is a salt, e.g., NaCl. For example, a formulation may comprise from about 0.05 to about 0.5 M NaCl, e.g., from about 0.05 to about 0.25 M NaCl or from about 0.1 to about 0.2 M NaCl.

In particular embodiments a formulation of the present disclosure includes an amount of unconjugated insulin molecule. In particular embodiments, a formulation includes a molar ratio of conjugated insulin molecule to unconjugated insulin molecule in the range of about 100:1 to 1:1, e.g., about 50:1 to 2:1 or about 25:1 to 2:1.

The present disclosure also encompasses the use of standard sustained (also called extended) release formulations that are well known in the art of small molecule formulation (e.g., see *Remington's Pharmaceutical Sciences,* 19th ed., Mack Publishing Co., Easton, Pa., 1995). The present disclosure also encompasses the use of devices that rely on pumps or hindered diffusion to deliver a conjugate on a gradual basis. In particular embodiments, a long acting formulation may (additionally or alternatively) be provided by using a modified insulin molecule. For example, one could use insulin glargine (LANTUS®) or insulin detemir (LEVEMIR®) instead of wild-type human insulin in preparing the conjugate. Insulin glargine is an exemplary long acting insulin analog in which Asn at position A21 of the A-chain has been replaced by glycine and two arginine residues are at the C-terminus of the B-chain. The effect of these changes is to shift the isoelectric point, producing an insulin that is insoluble at physiological pH but is soluble at pH 4. Insulin detemir is another long acting insulin analog in which Thr at position B30 of the B-chain has been deleted and a C14 fatty acid chain has been attached to the Lys at position B29.

Uses of Conjugates

In another aspect, the present disclosure provides methods of using the insulin conjugates. In general, the insulin conjugates can be used to controllably provide insulin to an individual in need in response to a saccharide (e.g., glucose or an exogenous saccharide such as mannose, alpha-methyl mannose, L-fucose, etc.). The disclosure encompasses treating diabetes by administering an insulin conjugate of the present disclosure. Although the insulin conjugates can be used to treat any patient (e.g., dogs, cats, cows, horses, sheep, pigs, mice, etc.), they are most preferably used in the treatment of humans. An insulin conjugate may be administered to a patient by any route. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences,* 19th ed., Mack Publishing Co., Easton, Pa., 1995. In various embodiments, the conjugate may be administered subcutaneously, e.g., by injection. The insulin conjugate may be dissolved in a carrier for ease of delivery. For example, the carrier can be an aqueous solution including, but not limited to, sterile water, saline or buffered saline.

In general, a therapeutically effective amount of the insulin conjugate will be administered. The term "therapeutically effective amount" means a sufficient amount of the insulin conjugate to treat diabetes at a reasonable benefit/risk ratio, which involves a balancing of the efficacy and toxicity of the insulin conjugate. In various embodiments, the average daily dose of insulin is in the range of 10 to 200 U, e.g., 25 to 100 U (where 1 Unit of insulin is ~0.04 mg). In particular embodiments, an amount of conjugate with these insulin doses is administered on a daily basis. In particular embodiments, an amount of conjugate with 5 to 10 times these insulin doses is administered on a weekly basis. In particular embodiments, an amount of conjugate with 10 to 20 times these insulin doses is administered on a bi-weekly basis. In particular embodiments, an amount of conjugate with 20 to 40 times these insulin doses is administered on a monthly basis.

In particular embodiments, a conjugate of the present disclosure may be used to treat hyperglycemia in a patient (e.g., a mammalian or human patient). In particular embodiments, the patient is diabetic. However, the present methods are not limited to treating diabetic patients. For example, in particular embodiments, a conjugate may be used to treat hyperglycemia in a patient with an infection associated with impaired glycemic control. In particular embodiments, a conjugate may be used to treat diabetes.

In particular embodiments, when an insulin conjugate or formulation of the present disclosure is administered to a patient (e.g., a mammalian patient) it induces less hypoglycemia than an unconjugated version of the insulin molecule. In particular embodiments, a formulation of the present disclosure induces a lower HbA1c value in a patient (e.g., a mammalian or human patient) than a formulation comprising an unconjugated version of the insulin molecule. In particular embodiments, the formulation leads to an HbA1c value that is at least 10% lower (e.g., at least 20% lower, at least 30% lower, at least 40% lower, at least 50% lower) than a formulation comprising an unconjugated version of the insulin molecule. In particular embodiments, the formulation leads to an HbA1c value of less than 7%, e.g., in the range of about 4 to about 6%. In particular embodiments, a formulation comprising an unconjugated version of the insulin molecule leads to an HbA1c value in excess of 7%, e.g., about 8 to about 12%.

Exogenous Trigger

As mentioned previously, the methods, conjugates and compositions that are described herein are not limited to glucose responsive-conjugates. As demonstrated in the Examples, several exemplary insulin conjugates were also responsive to exogenous saccharides such as alpha-methyl mannose. It will therefore be appreciated that in particular embodiments an insulin conjugate may be triggered by exogenous administration of a saccharide other than glucose such as alpha-methyl mannose or any other saccharide that can alter the PK or PD properties of the conjugate.

Once a conjugate has been administered as described above (e.g., as a sustained release formulation) it can be triggered by administration of a suitable exogenous saccharide. In a particular embodiment, a triggering amount of the exogenous saccharide is administered. As used herein, a "triggering amount" of exogenous saccharide is an amount sufficient to cause a change in at least one PK and/or PD property of the conjugate (e.g., $C_{max}$, AUC, half-life, etc. as discussed previously). It is to be understood that any of the aforementioned methods of administration for the conjugate apply equally to the exogenous saccharide. It is also be to be understood that the methods of administration for the conjugate and exogenous saccharide may be the same or different. In various embodiments, the methods of administration are different (e.g., for purposes of illustration the conjugate may be administered by subcutaneous injection on a weekly basis while the exogenous saccharide is administered orally on a daily basis). The oral administration of an exogenous saccharide is of particular value since it facilitates patient compliance. In general, it will be appreciated that the PK and PD properties of the conjugate will be related to the PK profile of the exogenous saccharide. Thus, the conjugate PK and PD properties can be tailored by controlling the PK profile of the exogenous saccharide. As is well known in the art, the PK profile of the exogenous saccharide can be tailored based on the dose, route, frequency and formulation used. For example, if a short and intense activation of the conjugate is desired then an oral immediate release formulation might be used. In contrast, if a longer less intense activation of conjugate is desired then an oral extended release formulation might be used instead. General considerations in the formulation and manufacture of immediate and extended release formulation may be found, for example, in *Remington's Pharmaceutical Sciences,* 19th ed., Mack Publishing Co., Easton, Pa., 1995.

It will also be appreciated that the relative frequency of administration of a conjugate of the present disclosure and an exogenous saccharide may be the same or different. In particular embodiments, the exogenous saccharide is administered more frequently than the conjugate. For example, in particular embodiment, the conjugate may be administered daily while the exogenous saccharide is administered more than once a day. In particular embodiment, the conjugate may be administered twice weekly, weekly, biweekly or monthly while the exogenous saccharide is administered daily. In particular embodiments, the conjugate is administered monthly and the exogenous saccharide is administered twice weekly, weekly, or biweekly. Other variations on these schemes will be recognized by those skilled in the art and will vary depending on the nature of the conjugate and formulation used.

The following examples are intended to promote a further understanding of the present invention.

EXAMPLES

General Procedures

All chemicals were purchased from commercial sources, unless otherwise noted. Reactions sensitive to moisture or air were performed under nitrogen or argon using anhydrous solvents and reagents. The progress of reactions was monitored by analytical thin layer chromatography (TLC), high performance liquid chromatography-mass spectrometry (HPLC-MS), or ultra performance liquid chromatography-mass spectrometry (UPLC-MS). TLC was performed on E. Merck TLC plates precoated with silica gel 60F-254, layer thickness 0.25 mm. The plates were visualized using 254 nm UV and/or by exposure to cerium ammonium molybdate (CAM) orp-anisaldehyde staining solutions followed by charring. High performance liquid chromatography (HPLC) was conducted on an Agilent 1100 series HPLC using Supelco Ascentis Express C18 2.7 μm 3.0×100 mm column with gradient 10:90-99:1 v/v $CH_3CN/H_2O$+v 0.05% TFA over 4.0 min then hold at 98:2 v/v $CH_3CN/H_2O$+v 0.05% TFA for 0.75 min; flow rate 1.0 mL/min, UV range 200-400 nm (LC-MS Method A). Mass analysis was performed on a Waters Micromass® ZQ™ with electrospray ionization in positive ion detection mode and the scan range of the mass-to-charge ratio was either 170-900 or 500-1500. Ultra performance liquid chromatography (UPLC) was performed on a Waters Acquity™ UPLC® system using Waters Acquity™ UPLC® BEH300 C4 1.7 μm 2.1×100 mm column with gradient 10:90-90:10 v/v $CH_3CN/H_2O$+v 0.1% TFA over 4.0 min and 90:10-95:5 v/v $CH_3CN/H_2O$+v 0.1% TFA over 0.5 min; flow rate 0.3 mL/min, UV wavelength 200-300 nm (UPLC Method A). Alternative UPLC conditions were noted as UPLC Method B (Waters Acquity™ UPLC® BEH C18 1.7 μm 2.1×100 mm column with gradient 10:90-70:30 v/v $CH_3CN/H_2O$+v 0.1% TFA over 4.0 min and 70:30-95:5 v/v $CH_3CN/H_2O$+v 0.1% TFA over 40 sec; flow rate 0.3 mL/min, UV wavelength 200-300 nm), UPLC Method C (Waters Acquity™ UPLC® BEH C18 1.7 μm 2.1×100 mm column with gradient 60:40-100:0 v/v $CH_3CN/H_2O$+v 0.1% TFA over 4.0 min and 100:0-95:5 v/v $CH_3CN/H_2O$+v 0.1% TFA over 40 sec; flow rate 0.3 mL/min, UV wavelength 200-300 nm), UPLC Method D (Waters Acquity™ UPLC® BEH300 C4 1.7 μm 2.1×100 mm column with gradient 10:90-50:50 v/v $CH_3CN/H_2O$+v 0.1% TFA over 4.3 min and 50:50-70:30 v/v $CH_3CN/H_2O$+v 0.1% TFA over 0.5 min; flow rate 0.3 mL/min, UV wavelength 200-300 nm), UPLC Method E (Waters Acquity™ UPLC® BEH C18 1.7 μm 2.1×100 mm column with gradient 10:90-60:40 v/v $CH_3CN/H_2O$+v 0.1% TFA over 4.3 min and 60:40-90:10 v/v $CH_3CN/H_2O$+v 0.1% TFA over 0.5 min; flow rate 0.3 mL/min, UV wavelength 200-300 nm), UPLC Method F (Waters Acquity™ UPLC® BEH C18 1.7 μm 2.1×100 mm column with gradient 60:40-100:0 v/v $CH_3CN/H_2O$+v 0.1% TFA over 4.0 min and 100: 0-95:5 v/v $CH_3CN/H_2O$+v 0.1% TFA over 0.4 min; flow rate 0.3 mL/min, UV wavelength 200-300 nm), and UPLC Method G (Waters Acquity™ UPLC® BEH C8 1.7 μm 2.1×100 mm column with gradient 10:90-55:45 v/v $CH_3CN/H_2O$+v 0.1% TFA over 4.2 min and 100: 0-95:5 v/v $CH_3CN/H_2O$+v 0.1% TFA over 0.4 min; flow rate 0.3 mL/min, UV wavelength 200-300 nm. Mass analysis was performed on a Waters Micromass® LCT Premier™ XE with electrospray ionization in positive ion detection mode and the scan range of the mass-to-charge ratio was 300-2000. The identification of the produced insulin conjugates was confirmed by comparing the theoretical molecular weight to the experimental value that was measured using UPLC-MS. For the determination of the position of sugar modification(s), specifically, insulin conjugates were subjected to DTT treatment (for a/b chain) or Glu-C digestion (with reduction and alkylation), and then the resulting peptides were analyzed by LC-MS. Based on the measured masses, the sugar positions were deduced.

Flash chromatography was performed using either a Biotage Flash Chromatography apparatus (Dyax Corp.) or a CombiFlash®Rf instrument (Teledyne Isco). Normal-phase chromatography was carried out on silica gel (20-70 μm, 60 Å pore size) in pre-packed cartridges of the size noted. Reverse-phase chromatography was carried out on C18-bonded silica gel (20-60 μm, 60-100 Å pore size) in pre-packed cartridges of the size noted. Preparative scale HPLC was performed on Gilson 333-334 binary system using Waters Delta Pak C4 15 μm, 300 Å, 50×250 mm column or Kromasil® C8 10 μm, 100 Å, 50×250 mm column, flow rate 85 mL/min, with gradient noted. Concentration of solutions was carried out on a rotary evaporator under reduced pressure or freeze-dried on a VirTis Freezemobile Freeze Dryer (SP Scientific).

$^1$H NMR spectra were acquired at 500 MHz (or otherwise specified) spectrometers in deuterated solvents noted. Chemical shifts were reported in parts per million (ppm). Tetramethylsilane (TMS) or residual proton peak of deutrated solvents was used as an internal reference. Coupling constant (J) were reported in hertz (Hz).

Abbreviations: acetic acid (AcOH), acetonitrile (AcCN), aqueous (aq), O-(7-azabenzotriazol-1-yl)-N,N,N',N'-tetramethyluronium hexafluorophosphate) (HATU), ethyl acetate (EtOAc), diethyl ether (ether or $Et_2O$), N,N-diisopropylethylamine or Hünig's base (DIPEA), (4-dimethylamino)pyridine (DMAP), N,N-dimethylformamide (DMF), ethyl acetate (EtOAc), N-(3-dimethylaminopropyl)-N'-ethylcarbodiimide hydrochloride (EDC), gram(s) (g), 1-hydroxybenzotriazole hydrate (HOBt), hour(s) (h or hr), mass spectrum (ms or MS), microliter(s) (μL), milligram(s) (mg), milliliter(s) (mL), millimole (mmol), minute(s) (min), pentafluorphenol-tetramethyluronium hexafluorophosphate (PFTU), petroleum ether (PE), retention time ($R_t$), room temperature (rt), saturated (sat. or sat'd), saturated aq sodium chloride solution (brine), triethylamine (TEA), trifluoroacetic acid (TFA), tetrahydrofuran (THF), and N,N,N',N'-tetramethyl-O—(N-succinimidyl)uronium tetrafluoroborate (TSTU).

Example 1

The synthesis of oligosaccharide linker 6-[(2,5-Dioxopyrrolidin-1-yl)oxy]-N-(2-{[α-D-mannopyranosyl-(1→3)-[α-D-mannopyranosyl-(1→6)]-α-D-mannopyranosyl]oxy}ethyl)-6-oxohexanamide (ML-1) having the following structure is described.

ML-1

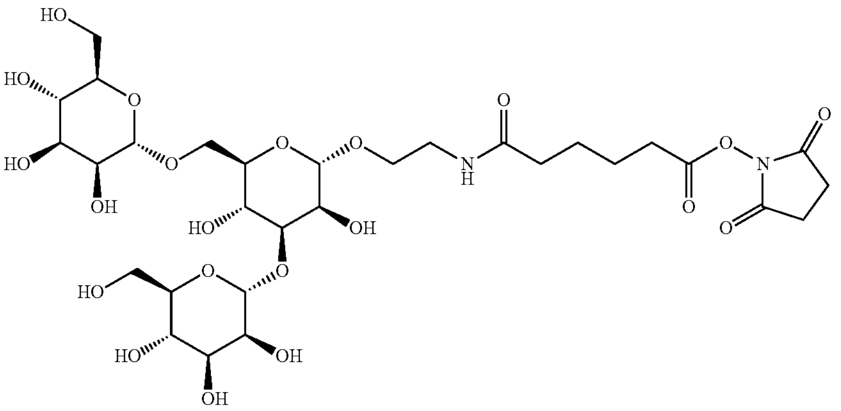

Step A: benzyl 6-[(2,5-dioxopyrrolidin-1-yl)oxy]-6-oxohexanoate

To a solution of 6-(benzyloxy)-6-oxohexanoic acid (3.3 g, 13.97 mmol) in DMF (50 mL) at 0° C. was added TSTU (4.3 g, 14.28 mmol) and DIPEA (2.5 mL, 14.31 mmol). After stirring at 0° C. for 1 hour, the reaction mixture was partitioned between $Et_2O$ and water. The organic layer was separated and the aqueous layer was further extracted with ether (2×150 mL). The combined organic phase was washed with brine, dried over $Na_2SO_4$, filtered and concentrated to afford the title compound. UPLC Method B: calculated for $C_{17}H_{19}NO_6$ 333.12, observed m/e: 334.10 [M+1]; Rt=3.75 min. $^1$H NMR ($CDCl_3$) δ 7.40-7.30 (5H, m), 5.10 (2H, s), 2.80 (4H, s), 2.62-2.58 (2H, m), 2.41-2.37 (2H, m), 1.80-1.72 (4H, m).

Step B: benzyl 6-({2-[(α-D-mannopyranosyl-(1→3)-[α-D-mannopyranosyl-(1→6)]-α-D-mannopyranosyl)oxy]ethyl}amino)-6-oxohexanoate To a solution of 2-aminoethyl α-D-mannopyranosyl-(1→3)-[α-D-mannopyranosyl-(1→6)]-α-D-mannopyranoside (1.23 g, 2.247 mmol, WO 2010/088294 A1) in DMF (20 mL) at 0° C. was added benzyl 6-[(2,5-dioxopyrrolidin-1-yl)oxy]-6-oxohexanoate (1.02 g, 3.06 mmol) and TEA (0.5 mL, 3.59 mmol). After stirring at 0° C. for 1 hour, the reaction mixture was concentrated and the residue was purified by flash chromatography on C18 reverse silica gel column (275 g), eluting with 0-40% AcCN in $H_2O$ to give the title compound. UPLC Method B: calculated for $C_{33}H_{51}NO_{19}$ 765.31, observed m/e=766.26 [M+1]; Rt=4.04 min. $^1$H NMR ($D_2O$) δ 7.43-7.37 (5H, m), 5.14 (2H, s), 5.07-5.06 (1H, m), 4.82-4.81 (1H, m), 4.77-4.76 (1H, m), 4.06-4.01 (2H, m), 3.96-3.92 (2H, m), 3.87-3.81 (5H, m), 3.79-3.77 (1H, m), 3.74-3.67 (5H, m), 3.65-3.60 (4H, m), 3.53-3.49 (1H, m), 3.37-3.35 (2H, m), 2.43-2.40 (2H, m), 2.22-2.19 (2H, m), 1.62-1.52 (4H, m).

Step C: 6-({2-[(α-D-mannopyranosyl-(1→3)-[α-D-mannopyranosyl-(1→6)]-α-D-mannopyranosyl)oxy]ethyl}amino)-6-oxohexanoic acid A mixture of benzyl 6-({2-[(α-D-mannopyranosyl-(1→3)-[α-D-mannopyranosyl-(1→6)]-α-D-mannopyranosyl)oxy]ethyl}amino)-6-oxohexanoate (1.15 g, 1.502 mmol) and Pd/C (80 mg, 0.075 mmol) in water (10 mL) was allowed to stir under a balloon of $H_2$ at room temperature for 16 hr. The catalyst was filtered off and washed with $H_2O$ (3×10 mL). The filtrate was concentrated to give the title compound. UPLC Method B: calculated for $C_{26}H_{45}NO_{19}$ 675.26, observed m/e: 676.21 [M+1]; Rt=3.50 min.

Step D: 6-[(2,5-dioxopyrrolidin-1-yl)oxy]-N-(2-{[α-D-mannopyranosyl-(1→3)-[α-D-mannopyranosyl-(1→6)]-α-D-mannopyranosyl]oxy}ethyl)-6-oxohexanamide To a solution of 6-({2-[(α-D-mannopyranosyl-(1→3)-[α-D-mannopyranosyl-(1→6)]-α-D-mannopyranosyl)oxy]ethyl}amino)-6-oxohexanoic acid (1.55 g, 2.294 mmol) in DMF (22 mL) at 0° C. was added TSTU (760 mg, 2.52 mmol) and DIPEA (0.52 mL, 2.98 mmol). After stirring at 0° C. for 1 hr, the reaction was quenched by the addition of TFA (371 μL, 4.82 mmol) and the resulting mixture was concentrated down to about 3 mL. The residue was transferred dropwise, via autopipette, to a tube containing anhydrous acetonitrile (45 mL). The white precipitate was collected through centrifugation (3000 rpm, 15 min, at 4° C.), washed with anhydrous AcCN (1 mL) and dried to yield the title compound. UPLC Method B: calculated for $C_{30}H_{48}N_2O_{21}$ 772.27, observed m/e: 773.23 [M+1]; Rt=3.65 min. $^1$H NMR ($D_2O$) δ 5.07-5.06 (1H, m), 4.84-4.83 (1H, m), 4.79-4.78 (1H, m), 4.06-4.01 (2H, m), 3.96-3.93 (2H, m), 3.87-3.83 (5H, m), 3.80-3.78 (1H, m), 3.75-3.69 (5H, m), 3.67-3.61 (4H, m), 3.57-3.52 (1H, m), 3.41-3.38 (2H, m), 2.91 (4H, s), 2.75-2.71 (2H, m), 2.29-2.25 (2H, m), 1.75-1.58 (4H, m).

Example 2

The synthesis of oligosaccharide linker 6-[(2,5-Dioxopyrrolidin-1-yl)oxy]-N-(2-{[3-O-(α-D-mannopyranosyl)-α-D-mannopyranosyl]oxy}ethyl)-6-oxohexanamide (ML-2) having the following structure is described.

ML-2

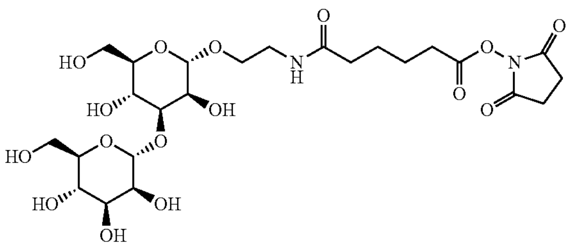

Step A: 2-azidoethyl 2,4-di-O-benzoyl-6-O-trityl-β-D-mannopyranoside

In a 250 ml round bottom flask, 2-azidoethyl 2,4-di-O-benzoyl-α-D-mannopyranoside (1.0 g, 2.186 mmol; See WO 2010/088294 A1, incorporated herein by reference) was dissolved in pyridine (50 mL). To the above solution was added DMAP (13 mg, 0.109 mmol) followed by trityl chloride (762 mg, 2.73 mmol). After stirring at 80° C. for 18 hr, the reaction mixture was concentrated. The residue was purified by flash chromatography on silica gel (40 g), eluting with 0-50% EtOAc in hexanes to give the title compound. UPLC Method C: m/e=722.2955, [M+Na]; Rt=4.50. $^1$H NMR ($CDCl_3$) δ 7.0-8.3 (m, 25H), 5.8 (t, 1H), 5.5 (m, 1H), 5.2 (s, 1H), 4.3 (m, 1H), 4.1 (m, 2H), 4.0 (m, 1H), 3.5 (m, 1H), 3.4 (m, 2H), 3.2 (dd, 1H), 2.7 (d, 1H).

Step B: 2-azidoethyl 2,4-di-O-benzoyl-3-O-(2,3,4,6-tetra-O-benzoyl-α-D-mannopyranosyl)-6-O-trityl-α-D-mannopyranoside In a 100 mL round bottom flask was added 2-azidoethyl 2,4-bis-O-benzoyl-6-O-trityl-α-D-mannopyranoside (400 mg, 0.572 mmol), 2,3,4,6-tetra-O-benzoyl-1-O-(2,2,2-trichloroethanimidoyl)-α-D-mannopyranose (508 mg, 0.686 mmol) and 4 Å molecular sieves (300 mg). To the above mixture was added $CH_2Cl_2$ (5 mL). The reaction mixture was cooled to −78° C., to which was added TMSOTf (10.33 μL, 0.057 mmol). The mixture was allowed to gradually warm to 0° C. and stirred for 30 min. The reaction was then quenched with sat'd $NaHCO_3$, and filtered through a pad of Celite. The filtrate was diluted with $CH_2Cl_2$ (20 mL), washed with brine and water. The organic phase was dried over $MgSO_4$, and concentrated. The residue was purified by flash chromatography on silica gel (80 g), eluting with 0-100% EtOAc in hexanes, to give the title product. LC-MS Method A: m/e=1278.80 [M+1]; Rt=3.14 min. $^1$H NMR ($CDCl_3$) δ 7.1-8.3 (m, 30H), 6.0 (t, 1H), 5.8 (t, 1H), 5.7 (m, 2H), 5.4 (s, 1H), 5.38 (m, 1H), 5.2 (s, 1H), 4.7 (dd, 1H), 4.6 (dd, 1H), 4.45 (m, 1H), 4.35 (dd, 1H), 3.9-4.0 (m, 2H), 3.8 (m, 2H), 3.7 (m, 1H), 3.4 (m, 2H).

Step C: 2-azidoethyl 2,4-di-O-benzoyl-3-O-(2,3,4,6-tetra-O-benzoyl-α-D-mannopyranosyl)-α-D-mannopyranoside In a 50 mL round bottom flask was added 2-azidoethyl 2,4-di-O-benzoyl-3-O-(2,3,4,6-tetra-O-benzoyl-α-D-mannopyranosyl)-6-O-trityl-α-D-mannopyranoside (450 mg, 0.352 mmol) and $CH_2Cl_2$ (3 mL). To the above solution was added TFA (3 mL, 38.9 mmol). After stirring at 25° C. for 1 hr, the reaction mixture was diluted with $CH_2Cl_2$ (10 mL), washed with water (3×15 mL) and brine (10 mL). The organic phase was dried over $MgSO_4$, filtered and concentrated. The residue was purified by flash chromatography on silica gel (40 g), eluting with 0-100% EtOAc in hexanes, to give the title product. LC-MS Method A: m/e=1053.57 [M+18]; Rt=2.73 min. $^1$H NMR ($CDCl_3$) δ 7.0-8.5 (m, 45H), 6.1 (t, 1H), 6.0 (t, 1H), 5.7 (m, 2H), 5.4 (s, 1H), 5.3 (s, 1H), 5.25 (s, 1H), 4.6 (m, 2H), 4.5 (m, 1H), 4.3 (m, 1H), 4.0-4.2 (m, 3h), 3.8 (m, 1H), 3.3-3.5 (m, 3H).

Step D: 2-azidoethyl 3-O-α-D-mannopyranosyl-α-D-mannopyranoside

In a 50 mL round bottom flask was added 2-azidoethyl 2,4-di-O-benzoyl-3-O-(2,3,4,6-tetra-O-benzoyl-α-D-mannopyranosyl)-α-D-mannopyranoside (350 mg, 0.338 mmol) and $CH_3OH$ (5 mL). To the above solution was added $NaOCH_3$ (conc) dropwise till pH>10. The reaction mixture was allowed to stir at 25° C. for 6 hr. To the above solution was added Dowex H+ (50 W×8-200) resin till pH ~7. The solid resin was filtered off and the filtrate was concentrated to give the title compound. LC-MS Method A: m/e=434.00 [M+1]; Rt=0.44 min.

Step E: 2-aminoethyl 3-O-α-D-mannopyranosyl-α-D-mannopyranoside

In a 50 mL round bottom flask, 2-azidoethyl 3-O-α-D-mannopyranosyl-α-D-mannopyranoside (139 mg, 0.338 mmol) was dissolved in water/$CH_3OH$ (v/v 1:1, 5 mL). To the above solution was added Pd/C (10%, 36 mg, 0.034 mmol). The reaction mixture was stirred at 25° C. under $H_2$ balloon for 18 hr. The mixture was filtered through a pad of Celite, and the filtrate was concentrated to give the title compound. LC-MS Method A: m/e=386.08 [M+1]; Rt=0.24 min.

Step F: 6-[(2,5-Dioxopyrrolidin-1-yl)oxy]-N-(2-{[3-O-(α-D-mannopyranosyl)-α-D-mannopyranosyl]oxy}ethyl)-6-oxohexanamide The title compound was prepared using procedures analogous to those described for ML-1 substituting 2-aminoethyl 3-O-α-D-mannopyranosyl-α-D-mannopyranoside for 2-aminoethyl α-D-mannopyranosyl-(1→3)-[α-D-mannopyranosyl-(1→6)]-α-D-mannopyranoside in Step B. UPLC Method B: m/e=611.201 [M+1]: Rt=1.82 min.

Example 3

The synthesis of oligosaccharide linker 6-[(2,5-Dioxopyrrolidin-1-yl)oxy]-N-(2-{[6-O-(α-D-mannopyranosyl)-α-D-mannopyranosyl]oxy}ethyl)-6-oxohexanamide (ML-3) having the following structure is described.

ML-3

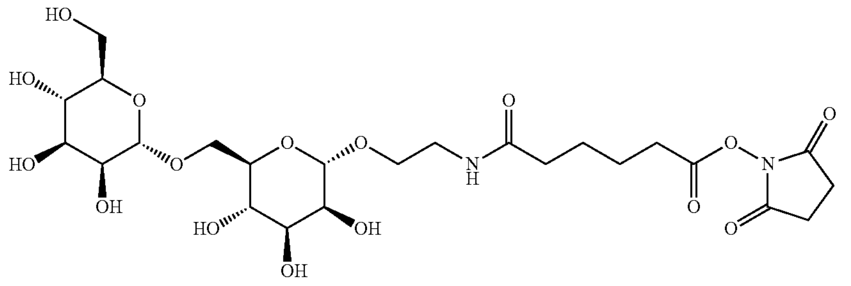

Step A: 2-azidoethyl 2,3,4-tri-O-benzoyl-6-trityl-α-D-mannopyranoside

In a 250 mL round bottom flask, 2-azidoethyl 2,4-di-O-benzoyl-α-D-mannopyranoside (1.0 g, 1.429 mmol) was dissolved in pyridine (20 mL). To the above solution at 0° C. was added benzoyl chloride (166 μL, 1.429 mmol). After stirring at rt for 18 hr, the mixture was concentrated and the residue was dissolved in EtOAc (20 mL), washed with water (10 mL) and brine (10 mL). The organic phase was dried over $MgSO_4$, filtered and concentrated. The residue was purified by flash chromatography on silica gel (40 g), eluting with 0-50% EtOAc in hexane, to to give the title compound. LC-MS Method A: m/e=804.44 [M+1]; Rt=2.88 min. $^1H$ NMR ($CDCl_3$) δ 7.0-8.2 (m, 30H), 6.1 (t, 1H), 5.8 (dd, 1H), 5.2 (d, 1H), 4.2-4.3 (m, 1H), 4.0-4.1 (m, 1H), 3.8 (m, 1H), 3.6 (m, 1H), 3.5 (m, 1H), 3.4 (dd, H), 3.3 (dd, 1H).

Step B: 2-azidoethyl 2,3,4-tri-O-benzoyl-α-D-mannopyranoside

In a 100 mL round bottom flask, 2-azidoethyl 2,3,4-tri-O-benzoyl-6-trityl-α-D-mannopyranoside (1.1 g, 1.368 mmol) was dissolved in $CH_2Cl_2$ (10 mL). To the above solution was added TFA (10 mL, 130 mmol). After stirring at 25° C. for 18 hr, the mixture was diluted with $CH_2Cl_2$ (20 mL), washed with brine (10 mL) and sat $NaHCO_3$ till pH ~7. The organic phase was dried over $MgSO_4$, filtered and concentrated. The residue was purified by flash chromatography on silica gel (40 g), eluting with 0-100% EtOAc in hexane, to give the title compound. LC-MS Method A: m/e=579.12 [M+18] and 584.10 [M+Na]; Rt=2.22 min. $^1H$ NMR ($CDCl_3$) δ 7.2-8.2 (m, 15H), 6.0 (dd, 1H), 5.9 (t, 1H), 5.7 (m, 1H), 5.2 (br-s, 1H), 4.1-4.2 (m, 2H), 3.85 (m, 1H), 3.7-3.8 (m, 2H), 3.6 (m, 1H, 3.5 (m, 1H).

Step C: 2-azidoethyl 2,3,4-tri-O-benzoyl-6-O-(2,3,4,6-tetra-O-benzoyl-α-D-mannopyranosyl)-α-D-mannopyranoside In a 100 mL round bottom flask was added 2-azidoethyl 2,3,4-tri-O-benzoyl-α-D-mannopyranoside (720 mg, 1.282 mmol), 2,3,4,6-tetra-O-benzoyl-1-O-(2,2,2-trichloroethanimidoyl)-α-D-mannopyranose (1.14 g, 1.539 mmol) and 4 Å molecular sieves (300 mg). To the above mixture was added $CH_2Cl_2$ (10 mL). The reaction mixture was cooled to −78° C. To the above mixture was added TMSOTf (23.2 μL, 0.128 mmol). The mixture was allowed to gradually warm to 0° C. and stirred for 30 min. The reaction was then quenched with sat. $NaHCO_3$, and the mixture was filtered through a pad of Celite. The filtrate was diluted with $CH_2Cl_2$ (20 mL), washed with brine and water. The organic phase was dried over $MgSO_4$, filtered and concentrated. The residue was purified by flash chromatography on silica gel (80 g), eluting with 0-100% EtOAc in hexanes, to give the title product. LC-MS Method A: m/e=1157.64 [M+18] and 1163.52 [M+Na]; Rt=3.01 min. $^1H$ NMR ($CDCl_3$) δ 7.2-8.3 (m, 25H), 6.0 (t, 1H), 5.8 (t, 1H), 5.7 (m, 2H), 5.4 (s, 1H), 5.38 (m, 1H), 5.2 (s, 1H), 4.7 (dd, 1H), 4.6 (dd, 1H), 4.45 (m, 1H), 4.35 (dd, 1H), 3.9-4.0 (m, 2H), 3.8 (m, 2H), 3.7 (m, 1H), 3.4 (m, 2H).

Step D: 6-[(2,5-dioxopyrrolidin-1-yl)oxy]-N-(2-{[6-O-(α-D-mannopyranosyl)-α-D-mannopyranosyl]oxy}ethyl)-6-oxohexanamide The title compound was prepared using procedures analogous to those described for ML-2 substituting 2-azidoethyl 2,3,4-tri-O-benzoyl-6-O-(2,3,4,6-tetra-O-benzoyl-α-D-mannopyranosyl)-α-D-mannopyranoside for 2-azidoethyl 2,4-bis-O-benzoyl-3-O-(2,3,4,6-tetra-O-benzoyl-α-D-mannopyranosyl)-α-D-mannopyranoside in Step D. UPLC Method B: m/e=611.202 [M+1]; Rt=1.88 min.

Example 4

The synthesis of oligosaccharide linker 6-[(2,5-dioxopyrrolidin-1-yl)oxy]-N-{2-[(α-L-fucopyranosyl)oxy]ethyl}-6-oxohexanamide (ML-4) having the following structure is described.

ML-4

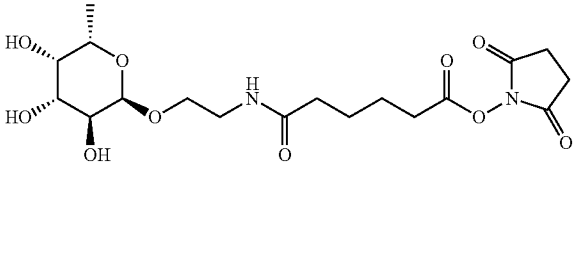

The title compound was prepared using procedures analogous to those described for ML-1 substituting 2-aminoethyl a-L-fucopyranoside (Bilstein J. Org. Chem. 2010, 6, 699-703) for 2-aminoethyl α-D-mannopyranosyl-(1→3)-[α-D-mannopyranosyl-(1→6)]-α-D-mannopyranoside in Step B. UPLC Method B: m/e=433.14 [M+1]; Rt=2.14 min.

Example 5

The synthesis of oligosaccharide linker 6-[(2,5-Dioxopyrrolidin-1-yl)oxy]-N-[2-(α-D-mannopyranosyloxy)ethyl]-6-oxohexanamide (ML-5) having the following structure is described.

ML-5

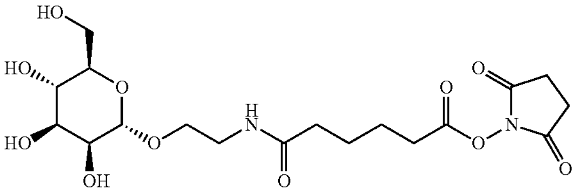

The title compound was prepared using procedures analogous to those described for ML-1 substituting 2-aminoethyl a-D-mannopyranoside (Eur. J. Org. Chem. 2002, 79-86) for 2-aminoethyl α-D-mannopyranosyl-(1→3)-[α-D-mannopyranosyl-(1→6)]-α-D-mannopyranoside in Step B. UPLC Method B: m/e=449.14 [M+1], Rt=1.90 min.

Example 6

The synthesis of oligosaccharide linker N,N-Bis[2-({2-[(α-L-fucopyranosyl)oxy]ethyl}amino)-2-oxoethyl]-6-[(2,5-dioxopyrrolidin-1-yl)oxy]-6-oxohexanamide (ML-6) having the following structure is described.

ML-6

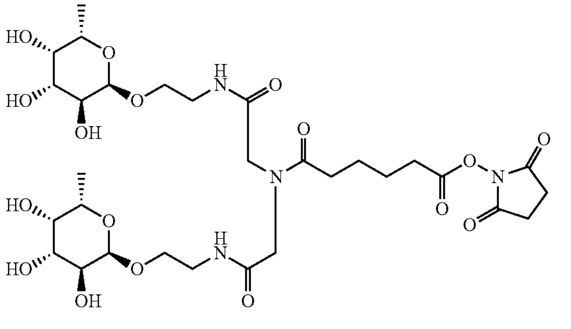

Step A: benzyl 6-[bis(2-tert-butoxy-2-oxoethyl) amino]-6-oxohexanoate

To a stirred solution of 6-(benzyloxy)-6-oxohexanoic acid (1.5 g, 6.35 mmol) in DMF (50 mL) at room temperature was added DIPEA (2.218 mL, 12.70 mmol), HOBt (1.945 g, 12.7 mmol), EDC (2.434 g, 12.7 mmol) and di-tert-butyl 2,2'-iminodiacetate (2.34 g, 9.52 mmol). After stirring at room temperature for 16 hours, the reaction mixture was diluted with $H_2O$ (30 mL) and extracted with $CH_2Cl_2$ (2×30 mL). The combined organic phase was washed with brine, dried over $Na_2SO_4$ and concentrated. The residue was purified by flash chromatography on silica gel (80 g), eluting with 0-40% EtOAc in hexane, to give the title compound. LC-MS Method A: m/e=464.04 [M+1]; Rt=2.47 min. $^1H$ NMR ($CDCl_3$) δ 7.32 (m, 5H), 5.07 (s, 2H), 4.02 (s, 2H), 3.96 (s, 2H), 2.35 (s, 2H), 2.26 (s, 2H), 1.66 (s, 4H), 1.42-1.44 (bs, 18H).

Step B: 2,2'-{[6-(benzyloxy)-6-oxohexanoyl] imino}diacetic acid

To a stirred solution of benzyl 6-[bis(2-tert-butoxy-2-oxoethyl)amino]-6-oxohexanoate (5.9 g, 12.73 mmol) in $CH_2Cl_2$ (30 mL) at room temperature was added TFA (30 mL, 12.73 mmol). After stirring at room temperature for 16 hours, the mixture was concentrated. The residue was purified by flash chromatography on C18 reverse phase silica gel to give the title compound. LC-MS Method A: m/e=486 [M+1]; Rt=2.53 min. $^1H$ NMR ($CD_3OD$) δ 7.30 (m, 5H), 5.06 (s, 2H), 4.81 (s, 4H), 4.19 (s, 2H), 4.07 (s, 2H), 2.34 (q, 4H, J=7.03).

Step C: benzyl 6-{bis[2-({2-[(α-L-fucopyranosyl) oxy]ethyl}amino)-2-oxoethyl]amino}-6-oxohexanoate To a stirred solution of 2,2'-{[6-(benzyloxy)-6-oxohexanoyl]imino}diacetic acid (800 mg, 2.277 mmol) in DMF (12 mL) at room temperature was added 2-aminoethyl a-L-fucopyranoside (1.132 g, 5.46 mmol), DMAP (834 mg, 6.83 mmol) and EDC (1.528 g, 7.97 mmol). After stirring at rt for 16 hr, the reaction mixture was concentrated and the residue was purified by flash chromatography on C18 reverse phase silica gel (120 g), eluting with 0-40% AcCN in water, to give the title compound. LC-MS Method A: m/e=730.26 [M+1]; Rt=1.42 min.

Step D: 6-{bis[2-({2-[(α-L-fucopyranosyl)oxy] ethyl}amino)-2-oxoethyl]amino}-6-oxohexanoic acid To a stirred solution of benzyl 6-{bis[2-({2-[(α-L-fucopyranosyl)oxy]ethyl}amino)-2-oxoethyl]amino}-6-oxohexanoate (900 mg, 1.233 mmol) in $H_2O$ (5 mL) at rt was added dihydroxypalladium (866 mg, 1.233 mmol). The mixture was degased and then stirred under a balloon of $H_2$. After stirring at rt under $H_2$ for 16 hr, the reaction mixture was filtered through a Celite pad and washed with $CH_3OH$ (3×10 mL). The filtrate was concentrated to give the title compound. LC-MS Method A: m/e=640.17 [M+1]; Rt=0.98 min.

Step E: N,N-bis[2-({2-[(α-L-fucopyranosyl)oxy]ethyl}amino)-2-oxoethyl]-6-[(2,5-dioxopyrrolidin-1-yl)oxy]-6-oxohexanamide To a stirred solution of 6-{bis[2-({2-[(α-L-fucopyranosyl)oxy]ethyl}amino)-2-oxoethyl]amino}-6-oxohexanoic acid (160 mg, 0.250 mmol) in DMF (3.0 mL) at 0° C. was added a solution of TSTU (94 mg, 0.313 mmol) in DMF (2 mL) and, 5 min later, DIPEA (53 μL, 0.300 mmol). After stirring for 1.5 h at 0° C., the mixture was added dropwise to $Et_2O$ (30 mL) in a centrifuge tube. After centrifuged for 30 min at 3500 rpm, the supernatant was decanted and the solid residue was dissolved in $H_2O$, which was freeze-dried to give the title product. UPLC Method B: m/e=737 [M+1]; Rt=2.19 min.

Example 7

The synthesis of oligosaccharide linker 2,2'-{[2-({6-[(2,5-Dioxopyrrolidin-1-yl)oxy]-6-oxohexyl}amino)-2-oxoethyl]imino}bis(N-{2-[(α-L-fucopyranosyl)oxy]ethyl}acetamide) (ML-7) having the following structure is described.

ML-7

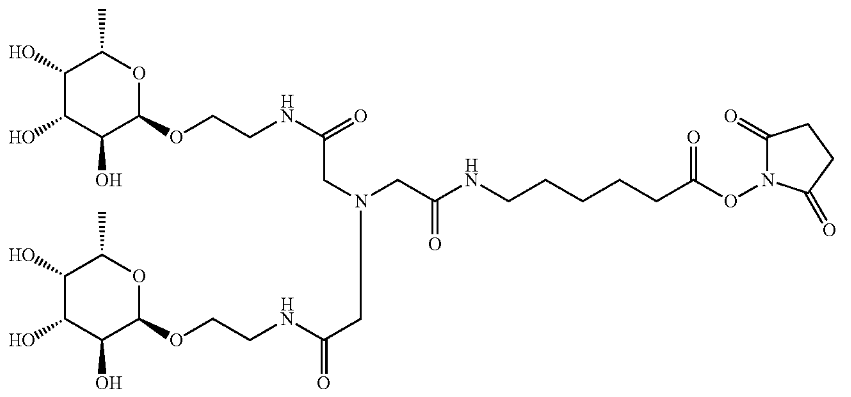

Step A: 2,2'-[(2-{[6-(benzyloxy)-6-oxohexyl]amino}-2-oxoethyl)imino]diacetic acid To a solution of 6-(benzyloxy)-6-oxohexan-1-aminium 4-methylbenzenesulfonate (2.0 g, 5.08 mmol) in DMF (10 mL) at 0° C. was added $K_2CO_3$ (738 mg, 5.34 mmol). After stirring at 0° C. for 2 hr, the supernant of the reaction mixture was added to a solution of 3-(2,6-dioxomorpholin-4-yl)propanoic acid (1.10 g, 6.35 mmol) in DMF (10 mL) at 0° C. After stirring at 0° C. for 30 min, the reaction mixture was allowed to stir at rt for 1 hr and then cooled down to 0° C. followed by the addition of water (10 mL). The resulting mixture was concentrated and the residue was suspended in water (10 mL). After stirring at 0° C. for 16 hr, the solid was collected through filtration and dried to yield the title compound. $^1H$ NMR ($CD_3OD$) δ 7.36-7.30 (m, 5H), 5.11 (s, 2H), 3.56 (s, 4H), 3.43 (s, 2H), 3.23 (t, J=6.7, 2H), 2.39 (t, J=7.3, 2H), 1.68-1.62 (m, 2H), 1.57-1.51 (m, 2H), 1.40-1.35 (m, 2H).

Step B: benzyl 6-[({bis[2-({2-[(α-L-fucopyranosyl)oxy]ethyl}amino)-2-oxoethyl]amino}acetyl)amino]hexanoate To a solution of 2-aminoethyl a-L-fucopyranoside (7.88 g, 38.04 mmol) and 2,2'-[(2-{[6-(benzyloxy)-6-oxohexyl]amino}-2-oxoethyl)imino]diacetic acid (2.5 g, 19.02 mmol) in DMF (10 mL) was added HOBt (2.43 g, 15.85 mmol) and EDC (3.04 g, 15.85 mmol). After stirring at rt for 16 hr, the reaction mixture was concentrated and the residue was purified by flash chromatography on C18 reverse phase silica gel (120 g), eluting with 0-50% AcCN in water, to give the title compound. UPLC Method B: m/e=773.292 [M+1]; Rt=3.74 min.

Step C: 2,2'-{[2-({6-[(2,5-dioxopyrrolidin-1-yl)oxy]-6-oxohexyl}amino)-2-oxoethyl]imino}bis(N-{2-[(α-L-fucopyranosyl)oxy]ethyl}acetamide)

The title compound was prepared using procedures analogous to those described for ML-6 substituting benzyl 6-[({bis[2-({2-[(α-L-fucopyranosyl)oxy]ethyl}amino)-2-oxoethyl]amino}acetyl)amino]hexanoate for benzyl 6-{bis[2-({2-[(α-L-fucopyranosyl)oxy]ethyl}amino)-2-oxoethyl]amino}-6-oxohexanoate in Step D. UPLC Method B: m/e=780.265 [M+1]; Rt=2.39 min.

Example 8

The synthesis of oligosaccharide linker 2,5-Dioxopyrrolidin-1-yl N,N-bis[2-({2-[(α-L-fucopyranosyl)oxy]ethyl}amino)-2-oxoethyl]glycyl-β-alaninate (ML-8) having the following structure is described.

ML-8

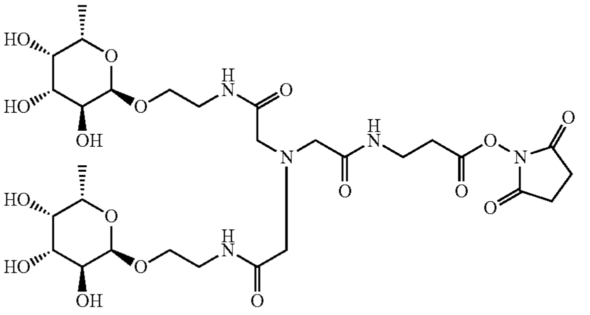

Step A: 2,2'-[(2-{[3-(benzyloxy)-3-oxopropyl]amino}-2-oxoethyl)imino]diacetic acid To an ice bath cooled solution of benzyl 3-aminopropanoate hydrochloride (4.49 g, 20.8 mmol) in DMF (30 mL) was added $K_2CO_3$ (3.02 g, 21.84 mmol) and the resulting mixture was stirred at 0° C. for 2 hr. The mixture was then filtered and the filtrate was added to an ice bath cooled solution of 2-(2,6-dioxomorpholino)acetic acid (4.47 g, 25.8 mmol) in DMF (30 mL). The resulting mixture was stirred at 0° C. for 30 min, then at rt for 2 hr. The reaction was quenched by the addition of water (30 mL) and the resulting mixture was concentrated. The residue was stirred with water (40 mL), and the resulting precipitate was collected through filtration and dried to give the title compound. $^1H$ NMR (DMSO-d6) δ 2.53 (t, J=6.8, 2H), 3.27 (s, 2H), 3.36 (q, J=6.2, 2H), 3.42 (m, m 2H), 3.49 (s, 2H), 5.09 (s, 2H), 7.28 (m, 4H), 8.16 (m, 1H), 12.45 (br s, 2H).

Step B: 2,5-Dioxopyrrolidin-1-yl N,N-bis[2-({2-[(α-L-fucopyranosyl)oxy]ethyl}amino)-2-oxoethyl]glycyl-β-alaninate The title compound was prepared using procedures analogous to those described for ML-7 substituting 2,2'-[(2-{[3-(benzyloxy)-3-oxopropyl]amino}-2-oxoethyl)imino]diacetic acid for 2,2'-[(2-{[6-(benzyloxy)-6-oxohexyl]amino}-2-oxoethyl)imino]diacetic acid in Step B. UPLC Method E: m/e=738.2149 [M+1; Rt=1.77 min.

Example 9

The synthesis of oligosaccharide linker 2,5-Dioxopyrrolidin-1-yl N,N-bis[2-({2-[(α-L-fucopyranosyl)oxy]ethyl}amino)-2-oxoethyl]glycylglycinate (ML-9) having the following structure is described.

ML-9

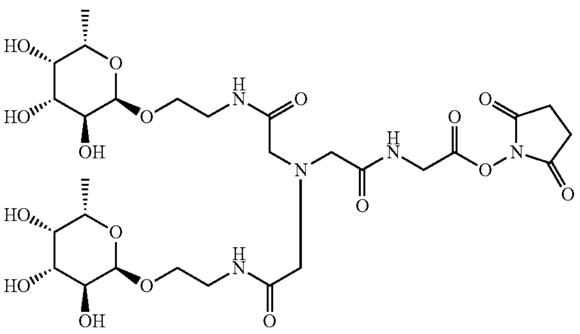

The title compound was prepared using procedures analogous to those described for ML-7 substituting benzyl glycinate for 6-(benzyloxy)-6-oxohexan-1-aminium 4-methylbenzenesulfonate in Step A. UPLC Method B: m/e=724.23 [M+1]; Rt=1.10 min.

Example 10

The synthesis of oligosaccharide linker 15-[(2,5-Dioxopyrrolidin-1-yl)oxy]-N-{2-[(α-L-fucopyranosyl)oxy]ethyl}-3-[2-({2-[(α-L-fucopyranosyl)oxy]ethyl}amino)-2-oxoethyl]-5,15-dioxo-9,12-dioxa-3,6-diazapentadecan-1-amide (ML-10) having the following structure is described.

ML-10

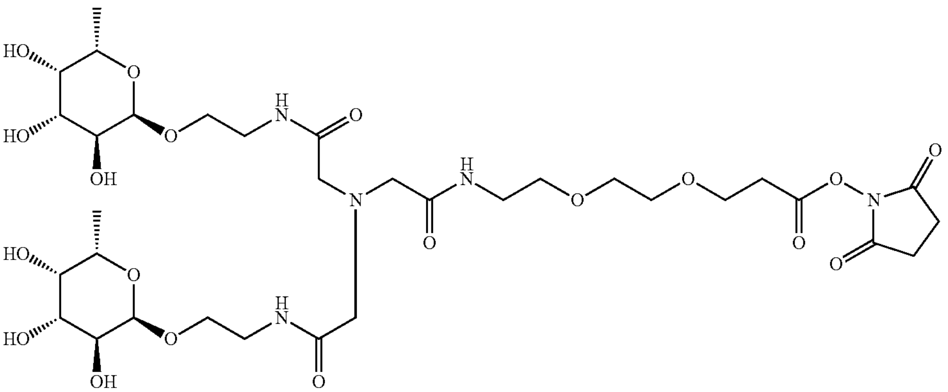

The title compound was prepared using procedures analogous to those described for ML-7 substituting benzyl 3-[2-(2-aminoethoxy)ethoxy]propanoate for 6-(benzyloxy)-6-oxohexan-1-aminium 4-methylbenzenesulfonate in Step A. UPLC Method B: m/e=825.812 [M+1]; Rt=2.17 min.

Example 11

The synthesis of oligosaccharide linker 2,5-Dioxopyrrolidin-1-yl 6-{[bis({3-oxo-3-[(α-L-fucopyranosyl)oxy]-2-oxoethyl}amino)propyl]amino}-6-oxohexanoate (ML-11) having the following structure is described.

ML-11

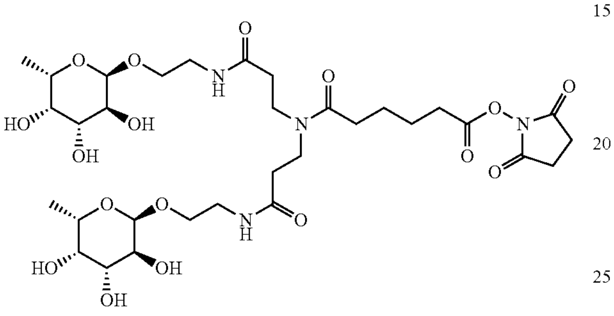

Step B: 2,5-dioxopyrrolidin-1-yl 6-{[bis({3-oxo-3-[(α-L-fucopyranosyl)oxy]-2-oxoethyl}amino)propyl]amino}-6-oxohexanoate The title compound was prepared using procedures analogous to those described for ML-6 substituting 3,3'-{[6-(benzyloxy)-6-oxohexanoyl]imino}dipropanoic acid for 2,2'-{[6-(benzyloxy)-6-oxohexanoyl]imino}diacetic acid in Step C. UPLC Method B: m/e=765.36 [M+1]; Rt=2.15 min.

Example 12

The synthesis of oligosaccharide linker 1-({6-[(2,5-Dioxopyrrolidin-1-yl)oxy]-6-oxohexyl}amino)-1-oxohexan-2-yl]-N-{2-[(α-L-fucopyranosyl)oxy]ethyl}-N'-[(2S)-6-{[6-({2-[(α-L-fucopyranosyl)oxy]ethyl}amino)-6-oxohexanoyl]amino}hexanediamide (ML-12) having the following structure is described.

ML-12

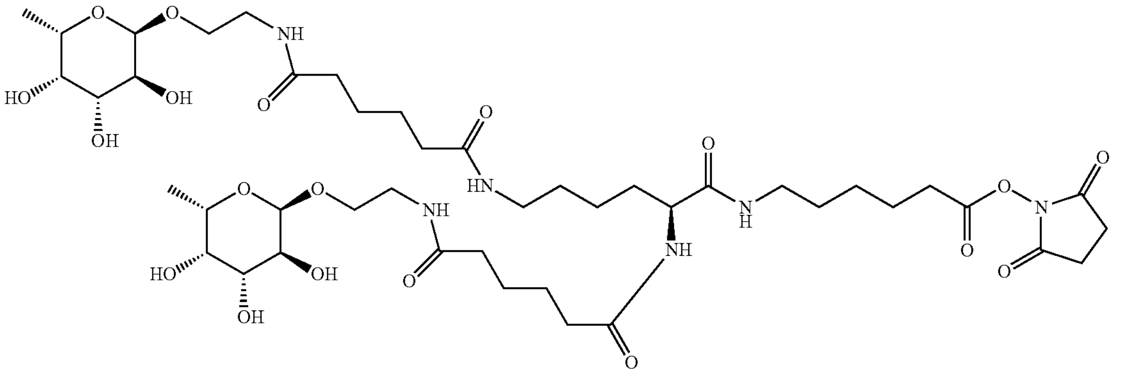

Step A: 3,3'-{[6-(benzyloxy)-6-oxohexanoyl]imino}dipropanoic acid

To a solution of 3,3'-iminodipropionic acid (2.59 g, 7.76 mmol) in DMF (20 mL) at 0° C. was added benzyl 6-[(2,5-dioxopyrrolidin-1-yl)oxy]-6-oxohenxanoate (2.59 g, 7.76 mmol) in DMF (3 mL) portionwise over a period of 15 min and then TEA (951 μL, 6.83 mmol) dropwise over a period of 10 min. The resulting suspension was stirred at rt for 16 hr. The insoluble material was removed by filtration and the filtrate was concentrated. The residue was purified by flash chromatography on C18 reverse phase silica gel (150 g), eluting with 5-50% AcCN in water, to give the title compound. UPLC Method B: m/e=380.177 [M+1]; Rt=3.46 min.

Step A: $N^2$-[(benzyloxy)carbonyl]-$N^6$-[6-({2-[(α-L-fucopyranosyl)oxy]ethyl}amino)-6-oxohexanoyl]-L-lysine In a 250 mL round bottom flask was added $N^2$-[(benzyloxy)carbonyl]-L-lysine (194 mg, 0.694 mmol) and DMF (10 mL). To the above solution was added ML-4 (300 mg, 0.694 mmol) in DMF (5 mL) dropwise, followed by the addition of DIPEA (121 μL, 0.694 mmol). After stirring at rt for 18 hr, the reaction mixture was concentrated. The residue was purified by flash chromatography on C18 reverse phase silica gel eluting with 0-40% AcCN in water to give the title product. UPLC Method B: m/e=598.2997 [M+1]; Rt=2.99 min.

Step B: $N^6$-[6-({2-[(α-L-fucopyranosyl)oxy]ethyl}amino)-6-oxohexanoyl]-L-lysine In a 100 mL flask, $N^2$-[(benzyloxy)carbonyl]-$N^6$-[6-({2-[(α-L-fucopyranosyl)oxy]ethyl}amino)-6-oxohexanoyl]-L-lysine (200 mg, 0.335 mmol) was dissolved in water (5 mL). The flask was degassed and filled with $N_2$. To the above mixture was added PdOH2 (48.7 mg, 0.069 mmol. The mixture was stirred under $H_2$ balloon for 2 hr. The mixture was filtered through a pad of Celite, and the filtrate was concentrated to give the title compound. UPLC Method B: m/e=464.2697 [M+1]; Rt=2.61 min.

Step C: benzyl 6-({$N^2$,$N^6$-bis[6-({2-[(α-L-fucopyranosyl)oxy]ethyl}amino)-6-oxohexanoyl]-L-lysyl}amino)hexanoate In a 40 mL vial was added $N^6$-[6-({2-[(α-L-fucopyranosyl)oxy]ethyl}amino)-6-oxohexanoyl]-L-lysine (150 mg, 0.324 mmol) and DMF (5 mL). The solution was cooled to 0° C. To the above solution was added ML-4 (140 mg, 0.324 mmol) in DMF (2 mL) dropwise followed by the addition of TEA (45 μL, 0.324 mmol). The reaction mixture was warmed to rt and stirred for 1 h. To the resulting mixture was added TSTU (97 mg, 0.324 mmol) followed by the addition of TEA (45 μL, 0.324 mmol). The mixture was stirred at rt for 20 min. To the resulting mixture was added a solution of 6-(benzyloxy)-6-oxohexan-1-aminium 4-methylbenzenefulfonate (127 mg, 0.324 mmol) in DMF (1.0 mL). After stirring at rt for 18 hr, the mixture was concentrated. The residue was purified by flash chromatography to give the title compound. UPLC Method B: m/e=984.5469 [M+1]; Rt=3.37 min.

Step D: 1-({6-[(2,5-dioxopyrrolidin-1-yl)oxy]-6-oxohexyl}amino)-1-oxohexan-2-yl]-N-{2-[(α-L-fucopyranosyl)oxy]ethyl}-N'-[(2S)-6-{[6-({2-[(α-L-galactopyranosyl)oxy]ethyl}amino)-6-oxohexanoyl]amino}hexanediamide The title compound was prepared using procedures analogous to those described for ML-1 substituting benzyl 6-({$N^2$,$N^6$-bis[6-({2-[(α-L-fucopyranosyl)oxy]ethyl}amino)-6-oxohexanoyl]-L-lysyl}amino)hexanoate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C. UPLC Method B: m/e=991.5182 [M+1]; Rt=2.41 min.

Example 13

The synthesis of oligosaccharide linker 2 N-{2-[(α-L-Fucopyranosyl)oxy]ethyl}-N'-[(5S)-6-{[6-({2-[(α-L-fucopyranosyl)oxy]ethyl}amino)-6-oxohexyl]amino}-5-({8-[(2,5-dioxopyrrolidin-1-yl)oxy]-8-oxooctanoyl}amino)-6-oxohexyl]hexanediamide (ML-13) having the following structure is described.

ML-13

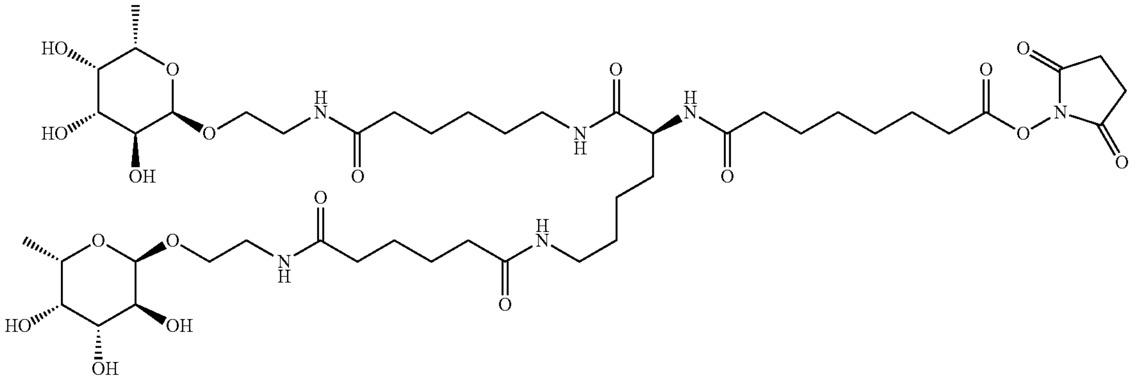

Step A: $N^2$-{8-(benzyloxy)-8-oxooctanoyl}-$N^6$-[6-({2-[(α-L-fucopyranosyl)oxy]ethyl}amino)-6-oxohexanoyl]-L-lysine To a solution of $N^6$-[6-({2-[(α-L-fucopyranosyl)oxy]ethyl}amino)-6-oxohexanoyl]-L-lysine (310 mg, 0.669 mmol) in DMF (20 mL) at 0° C. was added benzyl 8-[(2,5-dioxopyrrolidin-1-yl)oxy]-8-oxooctanoate (242 mg, 0.669 mmol), followed by the addition of DIPEA (0.117 ml, 0.669 mmol). The reaction was warmed to 25° C. and stirred at this temp for 18 hr. The reaction mixture was concentrated, and the residue was purified by flash chromatography on C18 reverse phase silica gel, eluting with 0-30% CAN in water, to give the title compound. UPLC Method B: m/e=710.423 [M+1]; Rt=4.59 min.

Step B: benzyl 8-({(12S)-1, 26-bis[(α-L-fucopyranosyl)oxy]-4,11,18,23-tetraoxo-3,10,17,24-tetraazahexacosan-12-yl}amino)-8-oxooctanoate In a 40 mL vial was added $N^2$-{8-(benzyloxy)-8-oxooctanoyl}-$N^6$-[6-({2-[(α-L-fucopyranosyl)oxy]ethyl}amino)-6-oxohexanoyl]-L-lysine (100 mg, 0.141 mmol) and DMF (5 mL). To the above solution at 0° C. was added EDC (40.5 mg, 0.211 mmol) and HOBt (23.7 mg, 0.155 mmol). The reaction was warmed to rt and stirred at rt for 20 min. To the above mixture was added 6-amino-N-{2-[(α-L-fucopyranosyl)oxy]ethyl}hexanamide (45.1 mg, 0.141 mmol). After stirring at rt for 18 hr, the mixture was concentrated. The residue was purified by flash chromatography eluting with 0-40% AcCN in water to give the title compound. UPLC Method B: m/e=1012.6348 [M+1]; Rt=3.28 min.

Step C: N-{2-[(α-L-fucopyranosyl)oxy]ethyl}-N'-[(5S)-6-{[6-({2-[(α-L-fucopyranosyl)oxy]ethyl}amino)-6-oxohexyl]amino}-5-({8-[(2,5-dioxopyrrolidin-1-yl)oxy]-8-oxooctanoyl}amino)-6-oxohexyl]hexanediamide The title compound was prepared using procedures analogous to those described for ML-1 substituting benzyl 8-

({(12S)-1,26-bis[(α-L-fucopyranosyl)oxy]-4,11,18,23-tetraoxo-3,10,17,24-tetraazahexacosan-12-yl}amino)-8-oxooctanoate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C. UPLC Method B: m/e=1019.588 [M+1]; Rt=2.38 min.

Example 14

The synthesis of oligosaccharide linker N-{(5S)-5-({8-[(2,5-Dioxopyrrolidin-1-yl)oxy]-8-oxooctanoyl}amino)-6-[(2-{[α-D-mannopyranosyl-(1→3)-[α-D-mannopyranosyl-(1→6)]-α-D-mannopyranosyl]oxy}ethyl)amino]-6-oxohexyl}-N'-{2-[(α-L-fucopyranosyl)oxy]ethyl}hexanediamide_(ML-14) having the following structure is described.

side (883 mg, 1.612 mmol) was dissolved in DMF (10 mL). To the above solution at 0° C. was added a solution of 2,5-dioxopyrrolidin-1-yl $N^2$-[(benzyloxy)carbonyl]-$N^6$-[6-({2-[(α-L-fucopyranosyl)oxy]ethyl}amino)-6-oxo-hexanoyl]-L-lysinate (700 mg, 1.008 mmol) in DMF (10 mL) dropwise. After stirring at rt for 18 hr, the mixture was concentrated. The residue was purified by HPLC (waters Delta Pak C4 300 A, 15 um, 50×250 mm column, flow rate 85 ml/min, gradient 8-30% ACN/water in 25 min) to give the title compound. UPLC Method B: m/e=1127.335 [M+1]; Rt=2.83 min.

Step C: N-{(5S)-5-amino-6-[(2-{[α-D-mannopyranosyl-(1→3)-[α-D-mannopyranosyl-(1→6)]-α-D-mannopyranosyl]oxy}ethyl)amino]-6-oxohexyl}-N'-{2-[(α-L-fucopyranosyl)oxy]ethyl}hexanediamide In a 100 mL flask, $N^2$-[(benzyloxy)carbonyl]-$N^6$-[6-({2-[(α-L-fucopyranosyl)oxy]ethyl}amino)-6-oxohexanoyl]-N-

ML-14

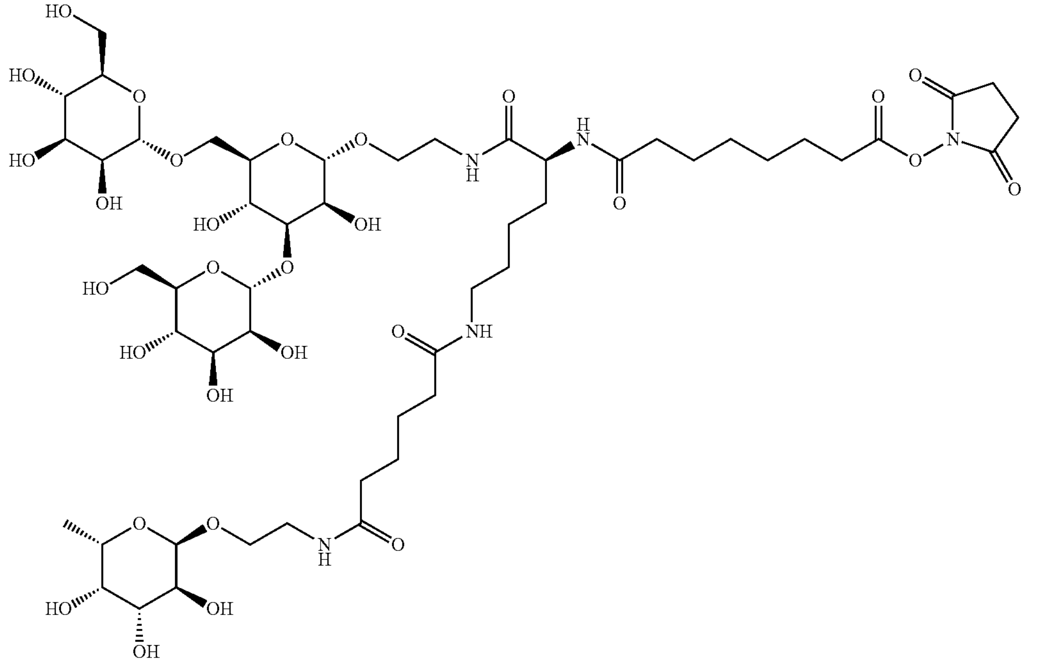

Step A: 2,5-dioxopyrrolidin-1-yl $N^2$-[(benzyloxy)carbonyl]-$N^6$-[6-({2-[(α-L-fucopyranosyl)oxy]ethyl}amino)-6-oxohexanoyl]-L-lysinate The title compound was prepared using the procedure analogous to that described for ML-1 Step A, substituting $N^2$-{8-(benzyloxy)-8-oxooctanoyl}-$N^6$-[6-({2-[(α-L-fucopyranosyl)oxy]ethyl}amino)-6-oxohexanoyl]-L-lysine for 6-(benzyloxy)-6-oxohexanoate. UPLC Method B: m/e=695.213 [M+1]; Rt=3.98 min.

Step B: $N^2$-[(benzyloxy)carbonyl]-$N^6$-[6-({2-[(α-L-fucopyranosyl)oxy]ethyl}amino)-6-oxohexanoyl]-N-(2-{[α-D-mannopyranosyl-(1→3)-[α-D-mannopyranosyl-(1→6)]-α-D-mannopyranosyl]oxy}ethyl)-L-lysinamide In a 40 mL vial, 2-aminoethyl α-D-mannopyranosyl-(1→3)-[α-D-mannopyranosyl-(1→6)]-α-D-mannopyrano- (2-{[α-D-mannopyranosyl-(1→3)-[α-D-mannopyranosyl-(1→6)]-α-D-mannopyranosyl]oxy}ethyl)-L-lysinamide (950 mg, 0.843 mmol) was dissolved in water (10 mL). The flask was degassed and filled with $N_2$. To the resulting mixture was added Pd/C (10%, 179 mg, 0.169 mmol). The mixture was stirred under $H_2$ balloon for 18 hr. The mixture was filtered through a pad of Celite, and the filtrate was concentrated to give the title compound. UPLC Method B: m/e=993.326 [M+1]; Rt=1.37 min.

Step D: N-{(5S)-5-({8-[(2,5-dioxopyrrolidin-1-yl)oxy]-8-oxooctanoyl}amino)-6-[(2-{[α-D-mannopyranosyl-(1→3)-[α-D-mannopyranosyl-(1→6)]-α-D-mannopyranosyl]oxy}ethyl)amino]-6-oxohexyl}-N'-{2-[(α-L-fucopyranosyl)oxy]ethyl}hexanediamide The title compound was prepared using procedure analogous to those described for ML-12 substituting N-{(5S)-5-amino-6-[(2-{[α-D-mannopyranosyl-(1→3)-[α-D-mannopyranosyl-(1→6)]-α-D-mannopyranosyl]oxy}ethyl) amino]-6-oxohexyl}-N'-{2-[(α-L-fucopyranosyl)oxy] ethyl}hexanediamide for $N^6$-[6-({2-[(α-L-fucopyranosyl) oxy]ethyl}amino)-6-oxohexanoyl]-L-lysine in Step C: UPLC Method B: m/e=1218.418 [M+1]; Rt=2.25 min.

Example 15

The synthesis of oligosaccharide linker 2,2'-{[2-({6-[(2,5-Dioxopyrrolidin-1-yl)oxy]-6-oxohexyl}amino)-2-oxoethyl]imino}bis[N-(2-{[α-D-mannopyranosyl-(1→3)-[α-D-mannopyranosyl-(1→6)]-α-D-mannopyranosyl] oxy}ethyl)acetamide] (ML-15) having the following structure is described.

ML-15

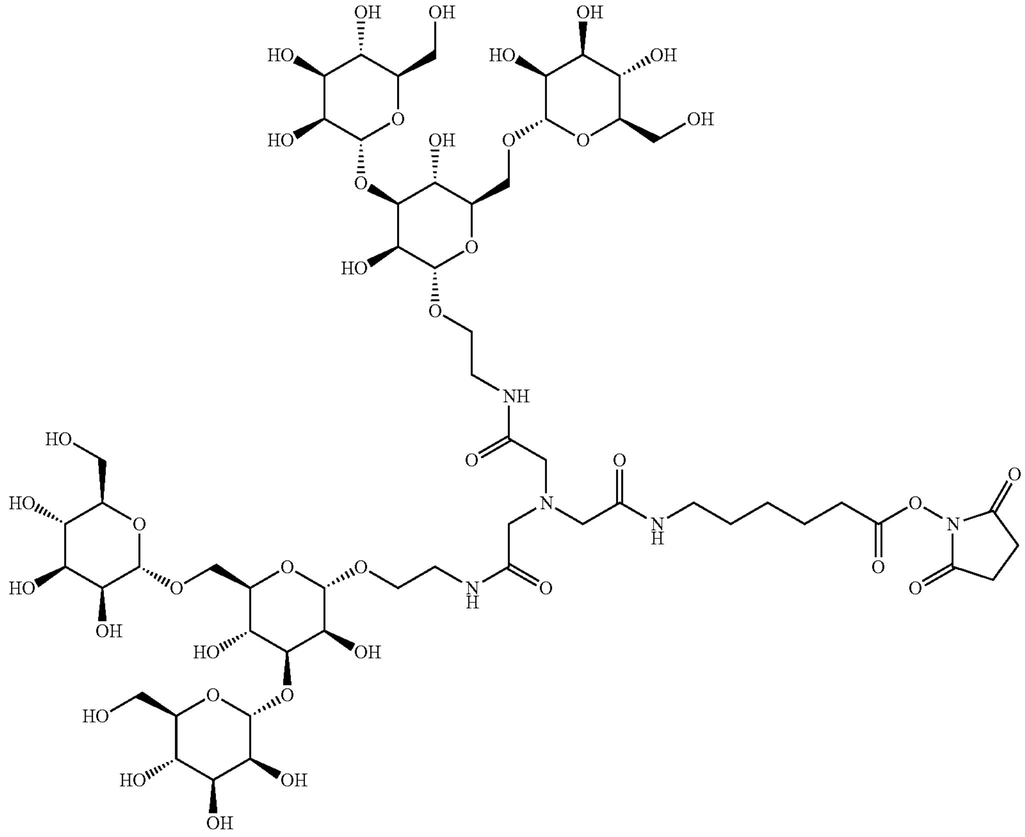

The title compound was prepared using procedures analogous to those described for ML-7 substituting 2-aminoethyl α-D-mannopyranosyl-(1→3)-[α-D-mannopyranosyl-(1→6)]-α-D-mannopyranoside for 2-aminoethyl a-L-fucopyranoside in Step B. UPLC Method B: m/e=1460.58 [M+1]; Rt=1.53 min.

Example 16

The synthesis of oligosaccharide linker N,N-Bis{2-[(α-L-fucopyranosyl)oxy]ethyl}-1-{6-[(2,5-dioxopyrrolidin-1-yl)oxy]-6-oxohexanoyl}pyrrolidine-cis-3,4-dicarboxamide (ML-16) having the following structure is described.

ML-16

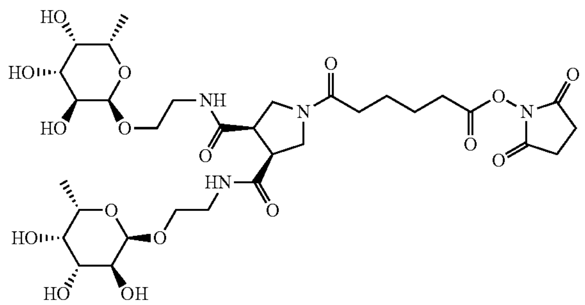

The title compound was prepared using procedures analogous to those described for ML-6 substituting pyrrolidine-cis-3,4-dicarboxylic acid for 2,2'-{[6-(benzyloxy)-6-oxohexanoyl]imino}diacetic acid in Step C. UPLC Method B: m/e=763.38 [M+1]; Rt=2.12 min.

Example 17

The synthesis of oligosaccharide linker 1-{6-[(2,5-Dioxopyrrolidin-1-yl)oxy]-6-oxohexanoyl}-N,N'-bis{2-[(α-L-fucopyranosyl)oxy]ethyl}piperidine-cis-3,5-dicarboxamide (ML-17) having the following structure is described.

ML-17

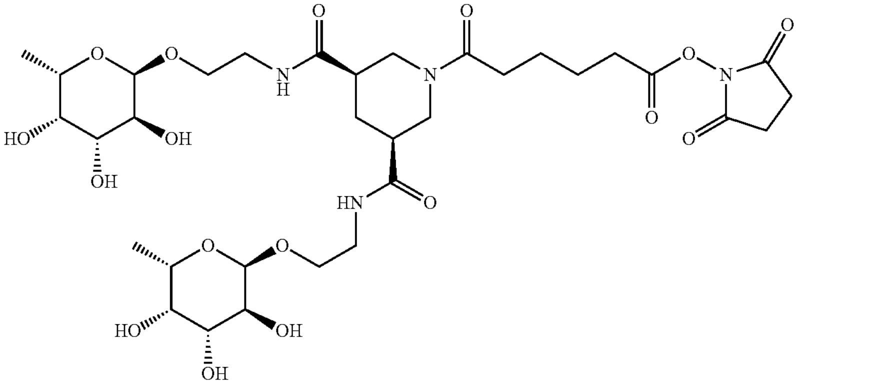

Step A: N,N'-bis{2-[(α-L-fucopyranosyl)oxy]ethyl}pyridine-3,5-dicarboxamide

To a stirred solution of 3,5-pyridinedicarboxylic acid (311 mg, 1.861 mmol) in DMF (30 mL) at room temperature was added 2-aminoethyl a-L-fucopyranoside (2.077 g, 9.30 mmol), DMAP (568 mg, 4.65 mmol), and EDC (1784 mg, 9.30 mmol). After stirring at room temperature for 16 hours, the reaction mixture was concentrated. The residue was purified by flash chromatography on C18 reverse phase silica gel (300 g), eluting with AcCN in water) to give the title compound. UPLC Method B: m/e=578.31 [M+1]; Rt=0.25 min.

Step B: N,N'-bis{2-[(α-L-fucopyranosyl)oxy]ethyl}piperidine-cis-3,5-dicarboxamide To a stirred solution of N,N'-bis{2-[(α-L-fucopyranosyl)oxy]ethyl}pyridine-3,5-dicarboxamide (550 mg, 0.952 mmol) in $H_2O$ (12 mL) at room temperature was added $PtO_2$ (64.9 mg, 0.286 mmol). The mixture was degased and then stirred under a balloon of $H_2$ at rt for 4 hr. The reaction mixture was then filtered through a Celite pad, and the filtrate was concentrated and redissolved in $CH_3OH$, centrifuged to precipitate the solid catalyst. The supernatant was concentrated to give the title compound. UPLC Method B: m/e=584.27 [M+1]; Rt=1.14 min.

Step C: benzyl 6-[cis-3,5-bis({2-[(α-L-fucopyranosyl)oxy]ethyl}carbamoyl)piperidin-1-yl]-6-oxohexanoate To a stirred solution of 6-(benzyloxy)-6-oxohexanoic acid (125 mg, 0.529 mmol) in DMF (3 mL) at room temperature was added DMAP (64.6 mg, 0.529 mmol), EDC (203 mg, 1.058 mmol) and a solution of N,N'-bis{2-[(α-L-fucopyranosyl)oxy]ethyl}piperidine-cis-3,5-dicarboxamide (438 mg, 0.794 mmol) in DMF (2 mL). After stirring at rt for overnight, the reaction mixture was concentrated and the residue was purified by flash chromatography on C18 reverse phase silica gel, eluting with 0-50% AcCN in water, to afford the title compound. UPLC Method F: m/e=770.48 [M+1]; Rt=1.38 min.

Step D: 1-{6-[(2,5-dioxopyrrolidin-1-yl)oxy]-6-oxohexanoyl}-N,N'-bis{2-[(α-L-fucopyranosyl)oxy]ethyl}piperidine-cis-3,5-dicarboxamide The title compound was prepared using procedures analogous to those described for ML-6 substituting benzyl 6-[cis-3,5-bis({2-[(α-L-fucopyranosyl)oxy]ethyl}carbamoyl)piperidin-1-yl]-6-oxohexanoate for benzyl 6-{bis[2-({2-[(α-L-fucopyranosyl)oxy]ethyl}amino)-2-oxoethyl]amino}-6-oxohexanoate in Step D. UPLC Method F: m/e=777.35 [M+1]; Rt=2.23 min.

Example 18

The synthesis of oligosaccharide linker $N^1,N^5$-Bis{2-[(α-L-fucopyranosyl)oxy]ethyl}-$N^2$-{6-[(2,5-dioxopyrrolidin-1-yl)oxy]-6-oxohexanoyl}-L-glutamamide (ML-18) having the following structure is described.

ML-18

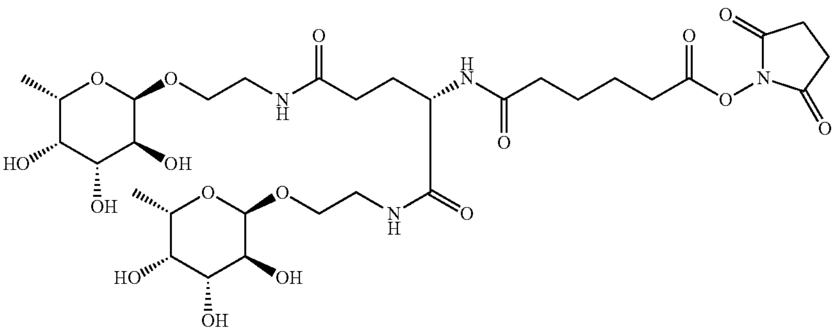

Step A: benzyl [(2S)-1,5-dioxo-1,5-bis({2-[(α-L-fucopyranosyl)oxy]ethyl}amino)pentan-2-yl]carbamate To a solution of N-[(benzyloxy)carbonyl]-L-glutamic acid (1.1 g, 3.91 mmol) and 2-aminoethyl α-L-fucopyranoside (2.026 g, 9.78 mmol) in DMF (10 mL) was added EDC (3.00 g, 15.64 mmol) and DMAP (0.048 g, 0.391 mmol). After stirring at rt for 24 hr, the reaction mixture was concentrated and the residue was purified by flash chromatography on silica gel (80 g), eluting with 100% EtOAc for 5 column volume and then isocratic EtOAc:AcCN:MeOH 6:1:1 to give the title compound. $^1$H NMR ($CD_3OD$) δ 7.38-7.29 (m, 5H), 5.13-5.05 (m, 2H), 4.76 (s, 2H), 4.09 (dd, J=5.3, 8.6, 1H), 3.95-3.91 (m, 2H), 3.74-3.65 (m, 6H), 3.53-3.25 (m, 8H), 2.30 (t, J=7.5, 2H), 2.06-2.04 (m, 1H), 1.92-1.89 (m, 1H), 1.19 (d, J=6.5, 6H).

Step B: 2-[(N-{2-[(α-L-fucopyranosyl)oxy]ethyl}-L-α-glutaminyl)amino]ethyl α-L-fucopyranoside A suspension of benzyl [(2S)-1,5-dioxo-1,5-bis({2-[(α-L-fucopyranosyl)oxy]ethyl}amino)pentan-2-yl]carbamate (940 mg, 1.425 mmol) and Pearlman's catalyst (20 mg, 0.028 mmol) in $CH_3OH$ (20 mL) was shaked under 30 Psi of $H_2$ at room temperature. After 16 hours, the catalyst was filtered off and the filtrate was concentrated to the title compound.

Step C: benzyl {[(2S)-1,5-dioxo-1,5-bis({2-[(α-L-fucopyranosyl)oxy]ethyl}amino)pentan-2-yl]amino}-6-oxohexanoate To a solution of 6-(benzyloxy)-6-oxohexanoic acid (260 mg, 1.1 mmol) in DMF (10 mL) at 0° C. was added TSTU (348 mg, 1.155 mmol) followed by DIPEA (202 μL, 1.155 mmol). After stirring at 0° C. for 1 hr, the reaction mixture was partitioned between $Et_2O$ (100 mL) and brine (100 mL). The organic phase was separated, further washed with brine (2×100 mL), dried over $MgSO_4$, and concentrated. The residue was redissolved in DMF (5 mL), added to a solution of 2-[(N-{2-[(α-L-fucopyranosyl)oxy]ethyl}-L-α-glutaminyl)amino]ethyl α-L-fucopyranoside (368 mg, 1.103 mmol) in DMF (10 mL) at 0° C. followed by adding $Et_3N$ (154 μL, 1.103 mmol). After stirring at 0° C. for 30 min, the reaction mixture was allowed to gradually warm up to rt and stir for 2 h. The reaction mixture was diluted with $CH_3OH$ (10 mL) and purified by HPLC (gradient 6-30% 0.1% TFA in water over 34 min, 50×250 mm C4 15 um, 300 A, 100 mL/min flow rate). $^1$H NMR ($CD_3OD$) δ 8.18 (m, 1H), 7.35-7.30 (m, 5H), 5.11 (s, 2H), 4.76 (d, J=3.6, 2H), 4.30 (dd, J=5.5, 8.6, 1H), 3.93 (dd, J=6.5, 13.1, 2H), 3.74-3.71 (m, 4H), 3.65 (s, 2H), 3.54-3.25 (m, 6H), 2.40 (t, J=6.7, 2H), 2.29-2.26 (m, 4H), 2.07-2.03 (m, 2H), 1.93-1.88 (m, 2H), 1.65-1.64 (m, 4H), 1.19 (d, J=6.5, 6H).

Step D: {[(2S)-1,5-dioxo-1,5-bis({2-[(α-L-fucopyranosyl)oxy]ethyl}amino)pentan-2-yl]amino}-6-oxohexanoic acid A suspension of benzyl {[(2S)-1,5-dioxo-1,5-bis({2-[(α-L-fucopyranosyl)oxy]ethyl}amino)pentan-2-yl]amino}-6-oxohexanoate (380 mg, 0.511 mmol) and Pearlman's catalyst (50 mg, 0.071 mmol) in methanol (30 mL) was agitated under 50 Psi of $H_2$ at room temperature on a Parr shaker. After 16 hours, catalyst was filtered off and the filtrate was concentrated to give the title compound. $^1$H NMR ($CD_3OD$) δ 4.76-4.75 (m, 2H), 4.32-4.29 (m, 1H), 3.96-3.91 (m, 2H), 3.76-3.66 (m, 5H), 3.55-3.27 (m, 9H), 2.34-2.27 (m, 6H), 2.09-2.04 (m, 1H), 1.99-1.88 (m, 1H), 1.67-1.61 (m, 4H), 1.20 (d, J=6.7, 6H).

Step E: $N^1$,$N^5$-bis{2-[(α-L-fucopyranosyl)oxy]ethyl}-$N^2$-{6-[(2,5-dioxopyrrolidin-1-yl)oxy]-6-oxohexanoyl}-L-glutamamide A suspension of {[(2S)-1,5-dioxo-1,5-bis({2-[(α-L-fucopyranosyl)oxy]ethyl}amino)pentan-2-yl]amino}-6-oxohexanoic acid (289 mg, 0.422 mmol) in DMF (5.0 mL) at 0° C. was added TSTU (140 mg, 0.464 mmol) followed by Hunig's base (810 μL, 0.464 mmol). After stirring for 1 hour, the mixture was concentrated to give the title product, which was used without further purification. UPLC Method B: m/e=[M+1]; Rt=1.82 min.

Example 19

The synthesis of oligosaccharide linker $N^1$,$N^4$-Bis{2-[(α-L-fucopyranosyl)oxy]ethyl}-$N^2$-{6-[(2,5-dioxopyrrolidin-1-yl)oxy]-6-oxohexanoyl}-L-aspartamide (ML-19) having the following structure is described.

ML-19

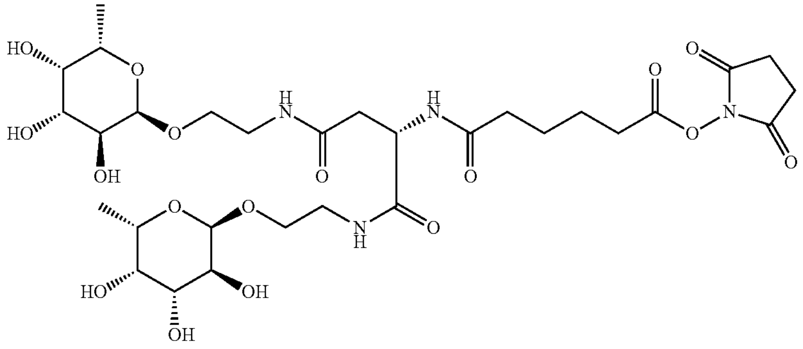

The title compound was prepared using procedures analogous to those described for ML-18 substituting N-[(benzyloxy)carbonyl]-L-aspartic acid for N-[(benzyloxy)carbonyl]-L-glutamic acid in Step A. UPLC Method B: m/e=737.3126 [M+1]; Rt=2.04 min.

Example 20

The synthesis of oligosaccharide linker $N^2$-{6-[(2,5-Dioxopyrrolidin-1-yl)oxy]-6-oxohexanoyl}-$N^5$-{2-[(α-L-fucopyranosyl)oxy]ethyl}-$N^1$-{2-[(α-D-mannopyranosyl-(1→3)-[α-D-mannopyranosyl-(1→6)]-α-D-mannopyranosyl)oxy]ethyl}-L-glutamamide (ML-20) having the following structure is described.

ML-20

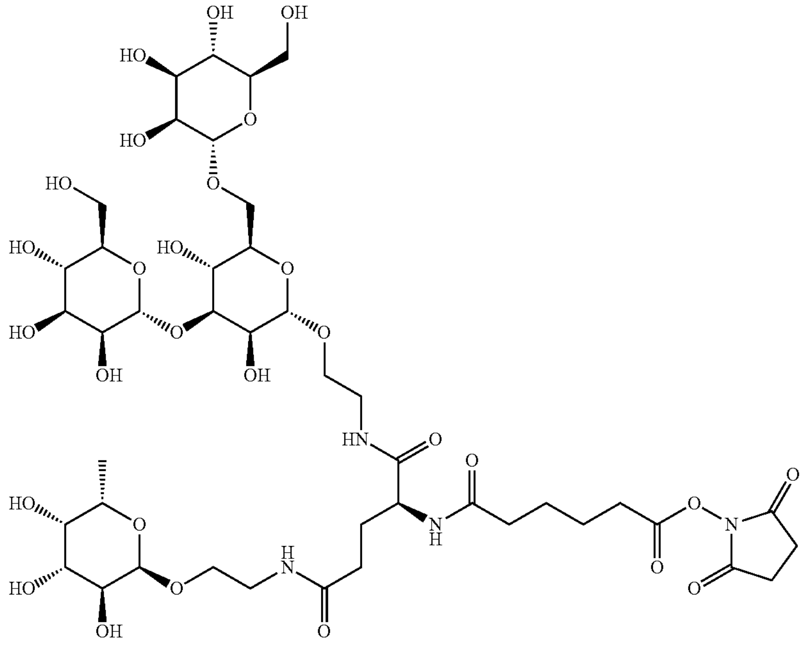

Step A: benzyl $N^2$-[(benzyloxy)carbonyl]-N-{2-[(α-D-mannopyranosyl-(1→3)-[α-D-mannopyranosyl-(1→6)]-α-D-mannopyranosyl)oxy]ethyl}-L-glutaminate To a solution of Z-Glu-γ-Bn (1.0 g, 2.69 mmol) and 2-aminoethyl α-D-mannopyranosyl-(1→3)-[α-D-mannopyranosyl-(1→6)]-α-D-mannopyranoside (2.21 g, 4.04 mmol) in DMF (10 mL) was added EDC (1.29 g, 6.73 mmol), HOBt (41 mg, 0.269 mmol), and $Et_3N$ (38 μL, 0.269 mmol). After stirring at room temperature for 16 hours, the mixture was purified by HPLC (50×250 mm, C4, flow rate 85 mL/minutes, gradient 25-35% AcCN in $H_2O$ with 0.1% TFA over 30 min) to give the title compound. $^1H$ NMR (CD3OD) δ 8.12-8.10 (m, 1H), 7.38-7.26 (m, 10H), 5.50-5.04 (m, 5H), 4.81 (s, 1H), 4.73 (s, 1H), 4.16-4.13 (m, 1H), 4.06 (s, 1H), 3.99-3.3.97 (m, 1H), 3.93-3.37 (m, 20H), 2.48 (t, J=7.6, 2H), 2.15-2.10 (m, 1H), 1.97-1.90 (m, 1H).

Step B: N-{2-[(α-D-mannopyranosyl-(1→3)-[α-D-mannopyranosyl-(1→6)]-α-D-mannopyranosyl)oxy]ethyl}-L-glutamine A mixture of benzyl $N^2$-[(benzyloxy)carbonyl]-N-{2-[(α-D-mannopyranosyl-(1→3)-[α-D-mannopyranosyl-(1→6)]-α-D-mannopyranosyl)oxy]ethyl}-L-glutaminate (1.41 g, 1.57 mmol) and Pearlman's catalyst (110 mg, 0.157 mmol) in $H_2O$ (30 mL) was agitated under 50 Psi $H_2$ on a Parr shaker at room temperature. After 16 hours, catalyst was filtered off and the filtrate was freeze-dried to give the title compound. $^1H$ NMR ($D_2O$) δ 5.07 (s, 1H), 4.87 (s, 1H), 4.81 (s, 1H), 4.08-3.55 (m, 22H), 3.41-3.36 (m, 1H), 2.32 (t, J=7.5, 2H), 2.10-2.06 (m, 2H).

Step C: $N^2$-[6-(benzyloxy)-6-oxohexanoyl]-N-{2-[(α-D-mannopyranosyl-(1→3)-[α-D-mannopyranosyl-(1→6)]-α-D-mannopyranosyl)oxy]ethyl}-L-glutamine The title compound was prepared using procedure analogous to that described for ML-18 substituting N-{2-[(α-D-mannopyranosyl-(1→3)-[α-D-mannopyranosyl-(1→6)]-α-D-mannopyranosyl)oxy]ethyl}-L-glutamine for 2-[(N-{2-[(α-L-fucopyranosyl)oxy]ethyl}-L-α-glutaminyl)amino]ethyl α-L-fucopyranoside in Step C. $^1H$ NMR ($CD_3OD$) δ 8.09-8.06 (m, 1H), 7.35-7.30 (m, 5H), 5.11 (s, 2H), 5.08 (s, 1H), 4.79 (m, 1H), 4.72 (s, 1H), 4.34-4.31 (m, 1H), 4.06-3.37 (m, 22H), 2.42-2.36 (m, 4H), 2.29-2.26 (m, 2H), 2.09-2.05 (m, 1H), 1.93-1.88 (m, 1H), 1.65-1.62 (m, 4H).

Step D: $N^2$-[6-(benzyloxy)-6-oxohexanoyl]-$N^5$-{2-[(α-L-fucopyranosyl)oxy]ethyl}-$N^1$-{2-[(α-D-mannopyranosyl-(1→3)-[α-D-mannopyranosyl-(1→6)]-α-D-mannopyranosyl)oxy]ethyl}-L-glutamamide To a solution of $N^2$-[6-(benzyloxy)-6-oxohexanoyl]-N-{2-[(α-D-mannopyranosyl-(1→3)-[α-D-mannopyranosyl-(1→6)]-α-D-mannopyranosyl)oxy]ethyl}-L-glutamine_ (500 mg, 0.559 mmol) and 2-aminoethyl a-L-fucopyranoside (116 mg, 0.559 mmol) in DMF (10 mL) was added EDC (161 mg, 0.838 mmol) and HOBt (8.56 mg, 0.056 mmol). After stirring at room temperature for 16 hours, the mixture was purified by HPLC (50×250 mm, C4, flow rate 85 mL/minutes, gradient 25-35% AcCN in $H_2O$ with 0.1% TFA over 30 min) to give the title compound. $^1H$ NMR (CD3OD) δ 8.12-8.08 (m, 1H), 7.35-7.29 (m, 5H), 5.11 (s, 2H), 5.08 (s, 1H), 4.80 (s, 1H), 4.77 (s, 1H), 4.72 (s, 1H), 4.32-4.29 (m, 1H), 4.12-3.26 (m, 30H), 2.42-2.39 (m, 2H), 2.30-2.26 (m, 4H), 2.09-2.04 (m, 1H), 1.93-1.88 (m, 1H), 1.65-1.64 (m, 4H), 1.19 (d, J=6.7, 3H).

Step E: $N^2$-{6-[(2,5-dioxopyrrolidin-1-yl)oxy]-6-oxohexanoyl}-$N^5$-{2-[(α-L-fucopyranosyl)oxy]ethyl}-$N^1$-{2-[(α-D-mannopyranosyl-(1→3)-[α-D-mannopyranosyl-(1→6)]-α-D-mannopyranosyl)oxy]ethyl}-L-glutamamide The title compound was prepared using procedures analogous to those described for ML-18 substituting $N^2$-[6-(benzyloxy)-6-oxohexanoyl]-$N^5$-{2-[(α-L-fucopyranosyl)oxy]ethyl}-$N^1$-{2-[(α-D-mannopyranosyl-(1→3)-[α-D-mannopyranosyl-(1→6)]-α-D-mannopyranosyl)oxy]ethyl}-L-glutamamide for benzyl {[(2S)-1,5-dioxo-1,5-bis({2-[(α-L-fucopyranosyl)oxy]ethyl}amino)pentan-2-yl]amino}-6-oxohexanoate in Step D. $^1H$ NMR ($CD_3OD$) δ 5.08 (s, 1H), 4.80 (s, 1H), 4.77 (s, 1H), 4.72 (s, 1H), 4.33-4.30 (m, 1H), 4.06-3.33 (m, 30H), 2.84-2.82 (m, 4H), 2.69-2.66 (m, 2H), 2.34-2.27 (m, 4H), 2.10-2.02 (m, 1H), 1.94-1.89 (m, 1H), 1.76-1.74 (m, 4H), 1.20 (d, J=6.5, 3H).

Example 21

The synthesis of oligosaccharide linker 2,5-Dioxopyrrolidin-1-yl $N^2$-[5-({2-[(α-L-fucopyranosyl)oxy]ethyl}amino)-5-oxopentanoyl]-N-(2-{[α-D-mannopyranosyl-(1→3)-[α-D-mannopyranosyl-(1→6)]-α-D-mannopyranosyl]oxy}ethyl)-L-glutaminylglycinate (ML-21) having the following structure is described.

ML-21

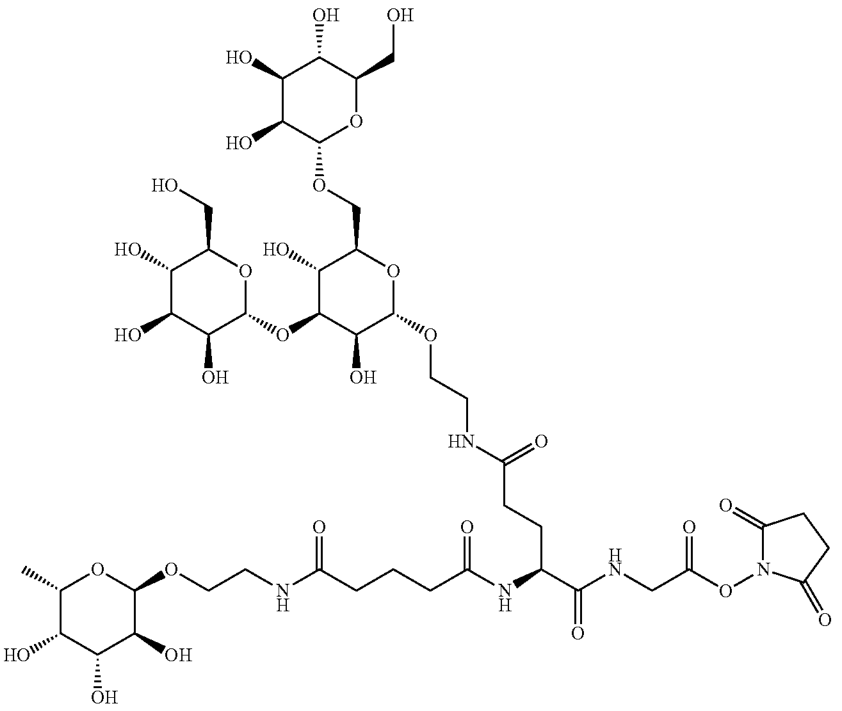

Step A: (S)-benzyl 2-{[(benzyloxy)carbonyl]amino}-5-[(2-{[α-D-mannopyranosyl-(1→3)-[α-D-mannopyranosyl-(1→6)]-α-D-mannopyranosyl]oxy}ethyl)amino]-5-oxopentanoate To a solution of 2-aminoethyl α-D-mannopyranosyl-(1→3)-[α-D-mannopyranosyl-(1→6)]-α-D-mannopyranoside (2.6 g, 4.75 mmol), and (S)-5-(benzyloxy)-4-{[(benzyloxy)carbonyl]amino}-5-oxopentanoic acid (2.0 g, 5.39 mmol) in DMF (36 mL) at 0° C. was added DMAP (580 mg, 4.75 mmol) and EDC (3.64 g, 19.00 mmol). The reaction mixture was allowed to gradually warm up to rt. After stirring for 16 hr, the reaction mixture was concentrated and the residue was purified by flash chromatography on C18 reverse phase silica gel (275 g), eluting with 10-55% AcCN in $H_2O$ to give the title compound. UPLC Method B: calculated for $C_{40}H_{56}N_2O_{21}$ 900.34, observed m/e: 901.26 [M+1]; Rt=2.46 min.

Step B: (S)-2-amino-5-((2-((α-D-mannopyranosyl-(1→3)-[α-D-mannopyranosyl-(1→6)]-α-D-mannopyranosyl)oxy)ethyl)amino)-5-oxopentanoic acid A mixture of (S)-benzyl 2-{[(benzyloxy)carbonyl]amino}-5-[(2-{[α-D-mannopyranosyl-(1→3)-[α-D-mannopyranosyl-(1→6)]-α-D-mannopyranosyl]oxy}ethyl)amino]-5-oxopentanoate (1.0 g, 1.11 mmol) and Pd/C (118 mg, 0.111 mmol) in water (10 mL) was allowed to stir under a balloon of $H_2$ at room temperature for 16 hours. The catalyst was filtered off and washed with $H_2O$ (3×10 mL). The filtrate was concentrated to give the title compound. UPLC Method B: calculated for $C_{25}H_{44}N_2O_{19}$ 676.25, observed m/e: 677.21 [M+1]; Rt=0.86 min.

Step C: 2,5-dioxopyrrolidin-1-yl 5-oxo-5-({2-[(α-L-fucopyranosyl)oxy]ethyl}amino)pentanoate The title compound was prepared using the procedure analogous to that described for ML-4 substituting benzyl 5-[(2,5-dioxopyrrolidin-1-yl)oxy]-5-oxopentanoate for benzyl 6-[(2,5-dioxopyrrolidin-1-yl)oxy]-6-oxohexanoate. UPLC Method B: calculated for $C_{17}H_{26}N_2O_{10}$ 418.16, observed m/e: 419.11 [M+1]; Rt=2.00 min.

Step D: (S)-5-[(2-{[α-D-mannopyranosyl-(1→3)-[α-D-mannopyranosyl-(1→6)]-α-D-mannopyranosyl]oxy}ethyl)amino]-5-oxo-2-[5-oxo-5-({2-[(α-L-fucopyranosyl)oxy]ethyl}amino)pentanamido]pentanoic acid To a solution of (S)-2-amino-5-[(2-{[α-D-mannopyranosyl-(1→3)-[α-D-mannopyranosyl-(1→6)]-α-D-mannopyranosyl]oxy}ethyl)amino]-5-oxopentanoic acid (350 mg, 4.75 mmol) in DMF (5 mL) at 0° C. was added 2,5-dioxopyrrolidin-1-yl 5-oxo-5-({2-[(α-L-fucopyranosyl)oxy]ethyl}amino)pentanoate (216 mg, 0.517 mmol, prepared according to Example 4, ML-4, Step A, substituting 5-(benzyloxy)-5-oxopentanoic acid for 6-(benzyloxy)-6-oxohexanoic acid and TEA (0.2 mL, 1.435 mmol). After stirring at 0° C. for 2 hr, the reaction mixture was concentrated and the residue was purified by flash chromatography on C18 silica gel (150 g), eluting with 5-40% AcCN in $H_2O$ to give the title compound. UPLC Method B: calculated for $C_{38}H_{65}N_3O_{26}$ 979.39, observed m/e: 980.31 [M+1]; Rt=0.92 min.

Step E: (S)-2,5-dioxopyrrolidin-1-yl 5-[(2-{[α-D-mannopyranosyl-(1→3)-[α-D-mannopyranosyl-(1→6)]-α-D-mannopyranosyl]oxy}ethyl)amino]-5-oxo-2-[5-oxo-5-({2-[(α-L-fucopyranosyl)oxy]ethyl}amino)pentanamido]pentanoate To a solution of (S)-5-[(2-{[α-D-mannopyranosyl-(1→3)-[α-D-mannopyranosyl-(1→6)]-α-D-mannopyranosyl]oxy}ethyl)amino]-5-oxo-2-[5-oxo-5-({2-[(α-L-fucopyranosyl)oxy]ethyl}amino)pentanamido]pentanoic acid (366 mg, 0.373 mmol) in DMF (2 mL) at 0° C. was added TSTU (115 mg, 0.381 mmol) and DIPEA (0.1 mL, 0.573 mmol). After stirring at 0° C. for 1 hour, the reaction was quenched with TFA (60 μL, 0.784 mmol). The reaction mixture was transferred dropwise, via autopipette, to a tube containing AcCN (45 mL). The resulting white suspension was centrifuged (3000 rpm, 15 minutes, at 4° C.) to generate a clear supernatant and a white pellet. The supernatant was discarded and the white pellet was washed with AcCN (1 mL) and dried to yield title compound UPLC Method B: calculated for $C_{42}H_{68}N_4O_{28}$ 1076.40, observed m/e: 1077.28 [M+1]; Rt=0.90 min.

Step F: benzyl $N^2$-[5-({2-[(α-L-fucopyranosyl)oxy]ethyl}amino)-5-oxopentanoyl]-N-(2-{[α-D-mannopyranosyl-(1→3)-[α-D-mannopyranosyl-(1→6)]-α-D-mannopyranosyl]oxy}ethyl)-L-glutaminylglycinate To a solution of (S)-2,5-dioxopyrrolidin-1-yl 5-[(2-{[α-D-mannopyranosyl-(1→3)-[α-D-mannopyranosyl-(1→6)]-α-D-mannopyranosyl]oxy}ethyl)amino]-5-oxo-2-[5-oxo-5-({2-[(α-L-fucopyranosyl)oxy]ethyl}amino)pentanamido]pentanoate (0.35 g, 0.325 mmol) in DMF (4 mL) at 0° C. was added 2-(benzyloxy)-2-oxoethanaminium chloride (77 mg, 0.382 mmol) and TEA (0.15 mL, 1.076 mmol). After stirring at rt for 24 hr, the reaction mixture was concentrated and the residue was purified by flash chromatography on C18 reverse phase silica gel (150 g), eluting with 5-40% AcCN in $H_2O$ to give the title compound. UPLC Method B: calculated for $C_{47}H_{74}N_4O_{27}$ 1126.45, observed m/e: 1127.39 [M+1]; Rt=2.84 min.

Step G: 2,5-dioxopyrrolidin-1-yl $N^2$-[5-({2-[(α-L-fucopyranosyl)oxy]ethyl}amino)-5-oxopentanoyl]-N-(2-{[α-D-mannopyranosyl-(1→3)-[α-D-mannopyranosyl-(1→6)]-α-D-mannopyranosyl]oxy}ethyl)-L-glutaminylglycinate The title compound was prepared using procedures analogous to those described for ML-1 substituting benzyl $N^2$-[5-({2-[(α-L-fucopyranosyl)oxy]ethyl}amino)-5-oxopentanoyl]-N-(2-{[α-D-mannopyranosyl-(1→3)-[α-D-mannopyranosyl-(1→6)]-α-D-mannopyranosyl]oxy}ethyl)-L-glutaminylglycinate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C. UPLC Method B: calculated for $C_{44}H_{71}N_5O_{29}$ 1133.42, observed m/e: 1134.34 [M+1]; Rt=2.17 min.

Example 22

The synthesis of oligosaccharide linker 2-{(2S)-8-[(2,5-Dioxopyrrolidin-1-yl)oxy]-1-[(2-{[α-D-mannopyranosyl-(1→3)-[α-D-mannopyranosyl-(1→6)]-α-D-mannopyranosyl]oxy}ethyl)amino]-1,8-dioxooctan-2-yl}-N'-{2-[(α-L-fucopyranosyl)oxy]ethyl}hexanediamide (ML-22) having the following structure is described.

ML-22

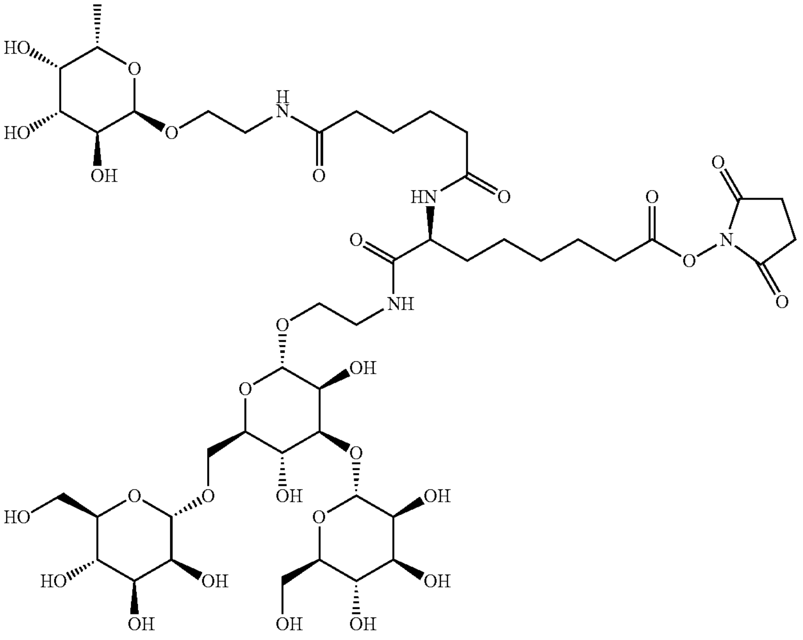

Step A: (2S)-8-(benzyloxy)-2-{[6-({2-[(α-L-fucopyranosyl)oxy]ethyl}amino)-6-oxohexanoyl]amino}-8-oxooctanoic acid To a solution of ML-4 (300 mg, 0.694 mmol) in DMF at 0° C. was added (S)-2-amino-8-(benzyloxy)-8-oxooctanoic acid (194 mg, 0.694 mmol) followed by DIPEA (121 μL, 0.694 mmol). The reaction mixture was allowed to stir at rt for 2 hr and then concentrated. The residue was purified by flash chromatography on C18 reverse phase silica gel, eluting with 5-28% AcCN in $H_2O$ to give the title compound. UPLC Method B: m/e=597.226 [M+1]; Rt=3.45 min.

Step B: N-{(2S)-8-[(2,5-Dioxopyrrolidin-1-yl)oxy]-1-[(2-{[α-D-mannopyranosyl-(1→3)-[α-D-mannopyranosyl-(1→6)]-α-D-mannopyranosyl]oxy}ethyl)amino]-1,8-dioxooctan-2-yl}-N'-{2-[(α-L-fucopyranosyl)oxy]ethyl}hexanediamide The title compound was prepared using procedures analogous to those described for ML-1 substituting (2S)-8-(benzyloxy)-2-{[6-({2-[(α-L-fucopyranosyl)oxy]ethyl}amino)-6-oxohexanoyl]amino}-8-oxooctanoic acid for benzyl 6-(benzyloxy)-6-oxohexanoic acid in Step A. UPLC Method B: m/e: 1133.312 [M+1]; Rt=2.23 min.

Example 23

The synthesis of oligosaccharide linker 2,5-Dioxopyrrolidin-1-yl 1-[(α-L-fucopyranosyl)oxy]-13-{2-[(2-{[α-D-mannopyranosyl-(1→3)-[α-D-mannopyranosyl-(1→6)]-α-D-mannopyranosyl]oxy}ethyl)amino]-2-oxoethyl}-4,11,15-trioxo-3,10,13,16-tetraazadocosan-22-oate (ML-23) having the following structure is described.

ML-23

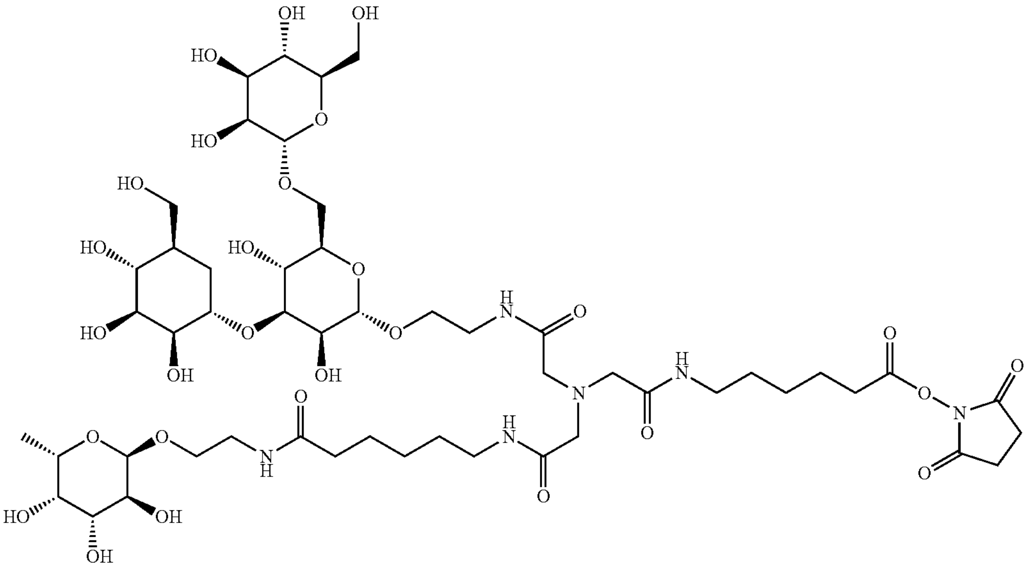

Step A: benzyl (6-{2-[(α-L-fucopyranosyl)ethyl] amino}-6-oxohexyl)carbamate

To a solution of 2-aminoethyl a-L-fucopyranoside (3.0 g, 14.48 mmol) in DMF (80 mL) at rt was added 2,5-dioxopyrrolidin-1-yl 6-{[(benzyloxy)carbonyl]amino}hexanoate (6.3 g, 17.37 mmol) and, 1 hr later, TEA (4.44 mL, 31.8 mmol). After stirring for 16 h, the reaction mixture was concentrated and the residue was purified by flash chromatography on C18 reverse phase silica gel (230 g), eluting with 5-40% AcCN in water to yield title compound. UPLC Method B: m/e=455.2568 [M+1]; Rt=2.86 min.

Step B: 6-amino-N-{2-[(α-L-fucopyranosyl)oxy] ethyl}hexanamide

To a solution of benzyl (6-{2-[(α-L-fucopyranosyl)ethyl] amino}-6-oxohexyl)carbamate (1.72 g, 3.79 mmol) in $H_2O$ (20 mL) was added Pd/C (23 mg, 0.217 mmol). The mixture was degassed and stirred under a balloon of $H_2$. After 2 h, the reaction mixture was filtered through a Celite pad and the filtrate was freeze-dried to produce the title compound. $^1$H NMR ($CD_3OD$) δ 1.21 (d, 3H), 1.40-1.38 (m, 2H), 1.62-1.60 (m, 4H), 2.23 (t, 2H), 2.76 (t, 2H), 3.28-3.27 (m, 1H), 3.44-3.43 (m, 1H), 3.54-3.52 (m, 1H), 3.66 (s, 1H), 3.75-3.74 (m, 2H), 3.94-3.93 (m, 1H), 4.76 (d, 1H). UPLC Method B: m/e=321.2323 [M+1]; Rt=3.02 min.

Step C: [(2-{[6-(benzyloxy)-6-oxohexyl]amino}-2-oxoethyl)(2-{[6-({2-[(α-L-fucopyranosyl)oxy] ethyl}amino)-6-oxohexyl]amino}-2-oxoethyl) amino]acetic acid To a suspension of 2,2'-[(2-{[6-(benzyloxy)-6-oxohexyl] amino}-2-oxoethyl)azanediyl]diacetic acid (1.0 g, 2.54 mmol) in $CH_2Cl_2$ (30 mL) at 0° C. was added trifluoroacetic anhydride (448 μL, 3.17 mmol). After stirring at 0° C. for 3 hr, the mixture was cooled to −30° C., to which a solution of $Et_3N$ (848 μL, 6.08 mmol) in DMF (20 mL) was added dropwise over 30 mins. After stirring at −30° C. for 30 min, a mixture of 6-amino-N-{2-[(α-L-fucopyranosyl)oxy] ethyl}hexanamide (812 mg, 2.54 mmol) in DMF (30 mL) was added and the resulting mixture was allowed to stir at rt. After stirring for 16 hr, the mixture was concentrated and the residue was purified by flash chromatography on C18 reverse phase silica gel (42 g), eluting with 0-40% AcCN in water to produce the title compound. UPLC Method B: m/e=697.3876 [M+1]; Rt=3.398 min. $^1$H NMR ($CD_3OD$) δ 1.23 (3H, d, J=6.59), 1.39-1.36 (4H, m), 1.56 (6H, s), 1.67 (6H, d, J=10.32), 2.23 (2H, t, J=7.50), 2.41 (2H, t, J=7.37), 3.24 (6H, m), 3.42 (4H, s), 3.49 (2H, s), 3.57-3.52 (3H, m), 3.68 (1H, s), 3.77 (3H, t, J=1.65), 3.98-3.94 (1H, m), 4.77 (1H, s), 5.14 (2H, s), 7.38 (5H, d, J=4.43).

Step D: benzyl 1-[(α-L-fucopyranosyl)oxy]-13-{2-[(2-{[α-D-mannopyranosyl-(1→3)-[α-D-mannopyranosyl-(1→6)]-α-D-mannopyranosyl]oxy}ethyl) amino]-2-oxoethyl}-4,11,15-trioxo-3,10,13,16-tetraazadocosan-22-oate To a solution of [(2-{[6-(benzyloxy)-6-oxohexyl]amino}-2-oxoethyl)(2-{[6-({2-[(α-L-fucopyranosyl)oxy] ethyl}amino)-6-oxohexyl]amino}-2-oxoethyl)amino]acetic acid (800 mg, 1.148 mmol) in DMF (15 mL) was added 2-aminoethyl α-D-mannopyranosyl-(1→3)]-[α-D-mannopyranosyl-(1→6)]-α-D-mannopyranoside (1.89 g, 3.44 mmol), HOBt (17.6 mg, 0.115 mmol), and EDC (770 mg, 4.02 mmol). After stirring for 16 h at rt, the reaction mixture was concentrated and the residue was purified by flash chromatography on C18 reverse phase silica gel (50 g), eluting with 10-40% AcCN in water to give the title compound. UPLC Method B: m/e=1226.5990 [M+1]; Rt=2.96 min. $^1$H NMR ($CD_3OD$) δ 1.23 (3H, d, J=6.58), 1.38 (6H, s), 1.56 (6H, s), 1.69-1.65 (6H, m), 2.23 (2H, t, J=7.44), 2.41 (2H, t, J=7.35), 3.27-3.23 (6H, m), 3.37 (1H, s), 3.37 (1H, s), 3.38 (1H, s), 3.45 (1H, s), 3.47 (1H, s), 3.47 (1H, s), 3.54 (3H, s), 3.60 (1H, s), 3.62 (2H, s), 3.64 (1H, s), 3.65 (1H, s), 3.67 (2H, s), 3.68 (3H, s), 3.88-3.72 (20H, m), 4.07 (1H, s), 4.76 (1H, s), 4.78 (1H, s), 4.84 (1H, d, J=1.69), 5.10 (1H, s), 5.14 (2H, s), 7.38 (5H, d, J=4.37).

Step E: 2,5-dioxopyrrolidin-1-yl 13-(2-((2-(((([α-D-mannopyranosyl-(1→3)]-[α-D-mannopyranosyl-(1→6)]-α-D-mannopyranosyl-oxy-(1-O→2))-ethyl-amino)-2-oxoethyl)-4,11,15-trioxo-1-(((2-(α-L-fucopyranosyl-oxy)-(1-O→2)))oxy)-3,10,13,16-tetraazadocosan-22-oate The title compound was prepared using procedures analogous to those described for ML-6 substituting benzyl 1-[(α-L-fucopyranosyl)oxy]-13-{2-[(2-{[α-D-mannopyranosyl-(1→3)-[α-D-mannopyranosyl-(1→6)]-α-D-mannopyranosyl]oxy}ethyl)amino]-2-oxoethyl}-4,11,15-trioxo-3,10,13,16-tetraazadocosan-22-oate for benzyl 6-{bis [2α-({2-[(α-L-fucopyranosyl)oxy]ethyl}amino)-2-oxoethyl]amino}-6-oxohexanoate in Step D. UPLC Method B: m/e=1233.6006 [M+1]; Rt=2.223 min.

Example 21

The synthesis of oligosaccharide linker 2,5-Dioxopyrrolidin-1-yl N-(2-{[6-({2-[(6-deoxy-α-L-galactopyranosyl) oxy]ethyl}amino)-6-oxohexyl]amino}-2-oxoethyl)-N-[2-({6-[(2-{[α-D-mannopyranosyl-(1→3)-[α-D-mannopyranosyl-(1→6)]-α-D-mannopyranosyl]oxy}ethyl) amino]-6-oxohexyl}amino)-2-oxoethyl]glycyl-β-alaninate (ML-21) having the following structure is described.

ML-21

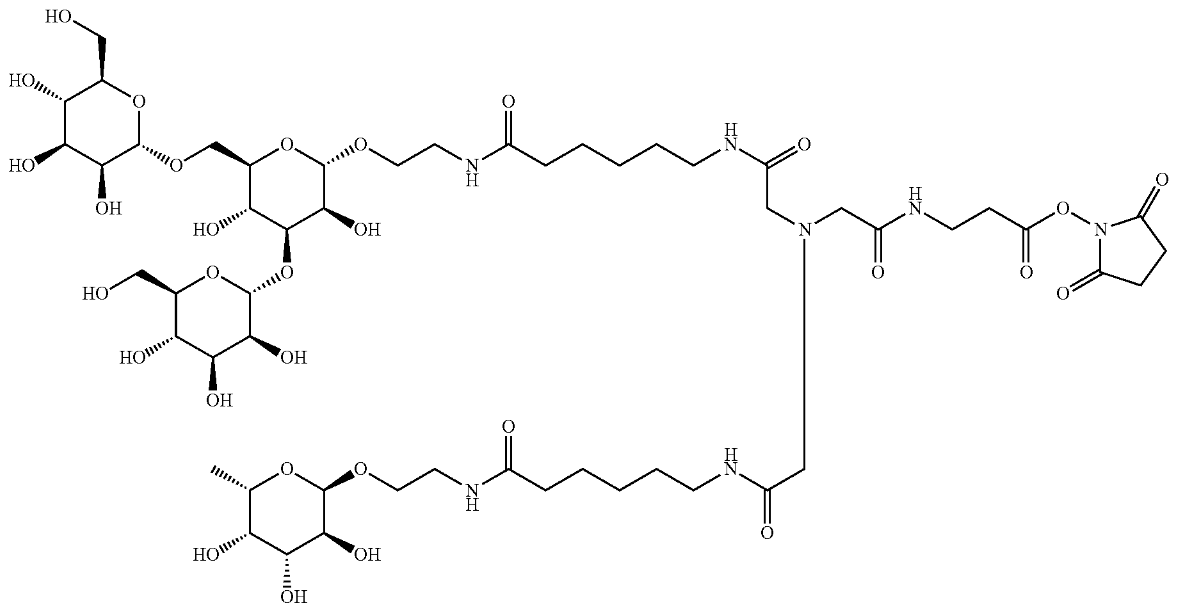

Step A: benzyl {6-[(2-{[α-D-mannopyranoyl-(1→3)-[α-D-mannopyranosyl-(1→6)]-α-D-mannopyranosyl]oxy}ethyl)amino]-6-oxohexyl}carbamate To a stirred solution of 2-aminoethyl α-D-mannopyranosyl-(1→3)-[α-D-mannopyranosyl-(1→6)]-α-D-mannopyranoside (1.8 g, 3.29 mmol) in DMF (50 mL) at 0° C. was added benzyl {6-[(2,5-dioxopyrrolidin-1-yl)oxy]-6-hexyl}carbamate (1.787 g, 4.93 mmol) and 30 minutes later $Et_3N$ (1.146 mL, 8.22 mmol). After stirring for 16 h, the reaction mixture was concentrated and the resulting residue was purified by flash chromatography on C18 reverse phase silica gel (240 g), eluting 5-40% AcCN in water to yield the title compound. $^1H$ NMR ($CD_3OD$) δ 1.35 (br s, 2H), 1.52 (br s, 2H), 1.63 (br s, 2H), 2.21 (s, 2H), 3.12 (s, 2H), 3.37 (s, 1H), 3.51-3.37 (br m, 5H), 3.81-3.69 (br m, 14H), 3.98 (s, 1H), 4.06 (s, 1H), 4.72 (s, 1H), 4.81 (s, 2H), 5.07 (s, 2H), 7.35 (s, 5H). UPLC Method B: m/e=795.303 [M+1]; Rt=2.49 min.

Step B: 6-amino-N-(2-{[α-D-mannopyranosyl-(1→3)-[α-D-mannopyranosyl-(1→6)]-α-D-mannopyranosyl]oxy}ethyl)hexanamide The title compound was prepared using procedure analogous to those described for ML-23 substituting benzyl {6-[(2-{[α-D-mannopyranoyl-(1→3)-[α-D-mannopyranosyl-(1→6)]-α-D-mannopyranosyl]oxy}ethyl)amino]-6-oxohexyl}carbamate for benzyl (6-{2-[(α-L-fucopyranosyl) ethyl]amino}-6-oxohexyl)carbamate in Step B. $^1H$ NMR ($CD_3OD$) δ 1.40 (2H, d, J=7.97), 1.63 (4H, d, J=12.78), 2.23 (2H, t, J=7.37), 2.82 (2H, q, J=8.46), 3.44-3.37 (2H, m), 3.53-3.46 (1H, m), 3.63-3.61 (4H, m), 3.72-3.70 (6H, m), 3.80 (5H, dd, J=9.96, 4.52), 3.83 (2H, s), 3.90 (1H, dd, J=11.05, 5.87), 3.97 (1H, s), 4.03 (1H, s), 4.72 (1H, s), 4.81 (1H, s), 5.06 (1H, s). UPLC Method B: m/e 661.3543 [M+1]; Rt=3.89 min.

Step C: 2,5-dioxopyrrolidin-1-yl N-(2-{[6-({2-[(6-deoxy-α-L-fucopyranosyl)oxy]ethyl}amino)-6-oxo-hexyl]amino}-2-oxoethyl)-N-[2-({6-[(2-{[α-D-mannopyranosyl-(1→3)-[α-D-mannopyranosyl-(1→6)]-α-D-mannopyranosyl]oxy}ethyl)amino]-6-oxohexyl}amino)-2-oxoethyl]glycyl-β-alaninate The title compound was prepared using procedure analogous to those described for ML-23 substituting 6-amino-N-(2-{[α-D-mannopyranosyl-(1→3)-[α-D-mannopyranosyl-(1→6)]-α-D-mannopyranosyl]oxy}ethyl)hexanamide and benzyl N,N-bis(carboxymethyl)glycyl-β-alaninate for 2-aminoethyl α-L-fucopyranoside and 2,2'-[(2-{[6-(benzyloxy)-6-oxohexyl]amino}-2-oxoethyl)imino]diacetic acid, respectively in Step C, and 6-amino-N-{2-[(6-deoxy-α-L-galactopyranosyl)oxy]ethyl}hexanamide for 6-amino-N-(2-{[α-D-mannopyranosyl-(1→3)-[α-D-mannopyranosyl-(1→6)]-α-D-mannopyranosyl]oxy}ethyl)hexanamide in Step D. UPLC Method E: m/e=1304.444 [M+1]; Rt=1.76 min.

Example 25

The synthesis of oligosaccharide linker 2,5-Dioxopyrrolidin-1-yl 1-[(α-L-fucopyranosyl)oxy]-13-[2-({6-[(2-{[α-D-mannopyranosyl-(1→3)-[α-D-mannopyranosyl-(1→6)]-α-D-mannopyranosyl]oxy}ethyl)amino]-6-oxohexyl}amino)-2-oxoethyl]-4,11,15-trioxo-3,10,13,16-tetraazadocosan-22-oate (ML-25) having the following structure is described.

ML-25

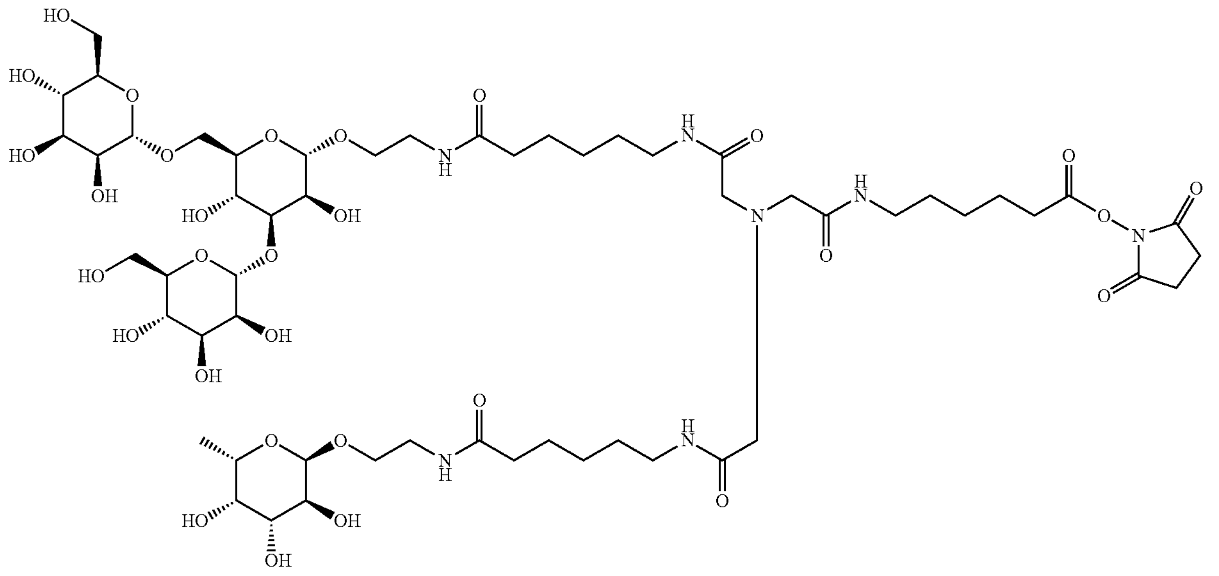

The title compound was prepared using procedure S analogous to those described for ML-23 substituting 2,2'-[(2-{[6-(benzyloxy)-6-oxohexyl]amino}-2-oxoethyl)imino] diacetic acid for benzyl N,N-bis(carboxymethyl)glycyl-β-alaninate. UPLC Method E: m/e=1346.5950 [M+1]; Rt=2.29 min.

Example 26

The synthesis of oligosaccharide linker 2,5-Dioxopyrrolidin-1-yl 1-[(α-L-fucopyranosyl)oxy]-11-[2-({4-[(2-{[α-D-mannopyranosyl-(1→3)-[α-D-mannopyranosyl-(1→6)]-α-D-mannopyranosyl]oxy}ethyl)amino]-4-oxobutyl}amino)-2-oxoethyl]-4,9,13-trioxo-3,8,11,14-tetraazaicosan-20-oate (ML-26) having the following structure is described.

ML-26

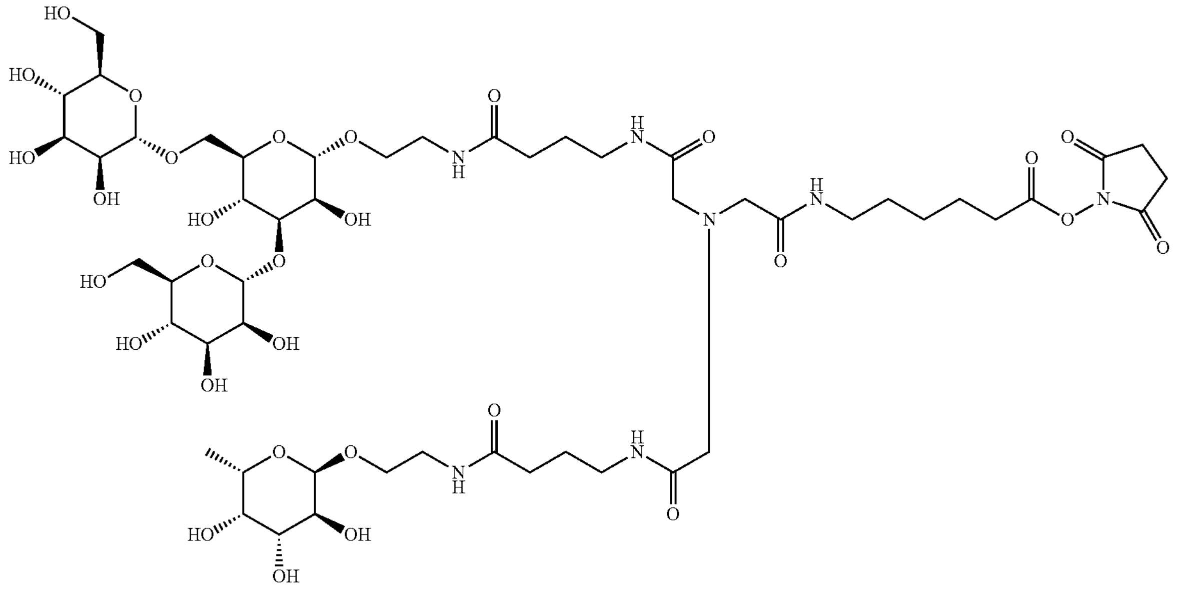

Step A: benzyl {4-[(2-{[α-D-mannopyranoyl-(1→3)-[α-D-mannopyranosyl-(1→6)]-α-D-mannopyranosyl]oxy}ethyl)amino]-4-oxobutyl}carbamate To a mixture of 2-aminoethyl α-D-mannopyranosyl-(1→3)]-[α-D-mannopyranosyl-(1→6)]-α-D-mannopyranoside (790 mg, 1.44 mmol) and 4-{[(benzyloxy)carbonyl]amino}butanoic acid (342 mg, 1.443 mmol) in DMF (5 mL) was added EDC (553 mg, 2.89 mmol) and DMAP (176 mg). After stirring at rt overnight, the reaction mixture was concentrated and the residue was purified by flash chromatography on C18 reverse phase silica gel (43 g), eluting 5-40% AcCN in water to give the title compound. UPLC Method B: m/e=767.2084 [M+1]; Rt=2.56 min.

Step B: 4-amino-N-(2-{[α-D-mannopyranosyl-(1→3)-[α-D-mannopyranosyl-(1→6)]-α-D-mannopyranosyl]oxy}ethyl)butanamide To a nitrogen flushed solution of benzyl {4-[(2-{[α-D-mannopyranoyl-(1→3)-[α-D-mannopyranosyl-(1→6)]-α-D-mannopyranosyl]oxy}ethyl)amino]-4-oxobutyl}carbamate (955 mg, 1.25 mmol) in water (6 mL) was added 10% palladium on carbon (133 mg) and the resulting mixture stirred under a balloon of $H_2$ for 4 hr. The reaction mixture was filtered through a Celite pad, and the filtrate was freeze-dried to give the title compound. UPLC Method B: m/e=633.2224 [M+1]; Rt=0.78 min.

Step C: 4-amino-N-{2-[(α-L-fucopyranosyl)oxy]ethyl}butanamide

The title compound was prepared using the procedure analogous to that described for ML-26 substituting 2-aminoethyl α-L-fucopyranoside for 2-aminoethyl α-D-mannopyranosyl-(1→3)]-[α-D-mannopyranosyl-(1→6)]-α-D-mannopyranoside in Step A. UPLC Method E: m/e=1248.365 [M+1]; Rt=1.37 min.

Step D: 11-[2-({6-[(2,5-Dioxopyrrolidin-1-yl)oxy]-1-[(α-L-fucopyranosyl)oxy]-6-oxohexyl}amino)-2-oxoethyl]-N-(2-{[α-D-mannopyranosyl-(1→3)-[α-D-mannopyranosyl-(1→6)]-α-D-mannopyranosyl]oxy}ethyl)-4,9,13-trioxo-3,8,11,14-tetraazaoctadecan-18-amide The title compound was prepared using procedures analogous to those described for ML-23 substituting 4-amino-N-{2-[(α-L-fucopyranosyl)oxy]ethyl}butanamide for 6-amino-N-{2-[(α-L-fucopyranosyl)oxy]ethyl}hexanamide in Step C, and 4-amino-N-(2-{[α-D-mannopyranosyl-(1→3)-[α-D-mannopyranosyl-(1→6)]-α-D-mannopyranosyl]oxy}ethyl)butanamide for 2-aminoethyl α-D-mannopyranosyl-(1→3)]-[α-D-mannopyranosyl-(1→6)]-α-D-mannopyranoside in Step D, respectively. UPLC Method E: m/e=1290.4012 [M+1]; Rt=2.03 min.

Example 27

The synthesis of oligosaccharide linker 2,5-Dioxopyrrolidin-1-yl N-(2-{[4-({2-[(6-deoxy-α-L-galactopyranosyl)oxy]ethyl}amino)-4-oxobutyl]amino}-2-oxoethyl)-N-[2-({4-[(2-{[α-D-mannopyranosyl-(1→3)-[α-D-mannopyranosyl-(1→6)]-α-D-mannopyranosyl]oxy}ethyl)amino]-4-oxobutyl}amino)-2-oxoethyl]glycyl-β-alaninate (ML-27) having the following structure is described.

ML-27

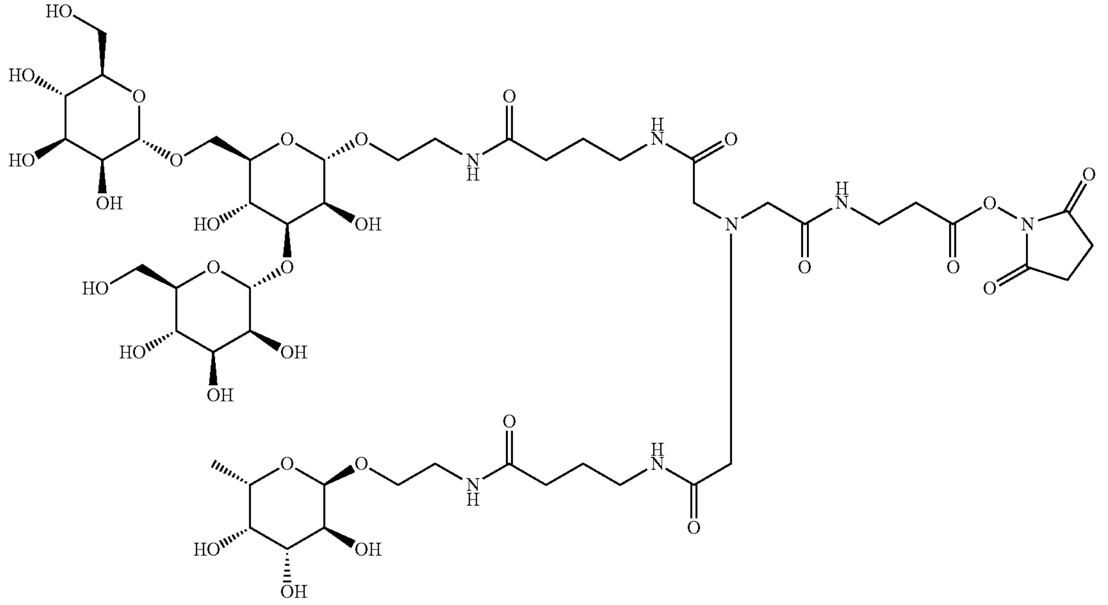

The title compound was prepared using procedures analogous to those described for ML-23 substituting benzyl {4-[(2,5-dioxopyrrolidin-1-yl)oxy]-4-oxobutyl}carbamate for benzyl {6-[(2,5-dioxopyrrolidin-1-yl)oxy]-6-oxohexyl}carbamate in step B. UPLC Method E: m/e=1248.365 [M+1]; Rt=1.37 min.

Example 28

The synthesis of oligosaccharide linker N-{2-[(α-L-Fucopyranosyl)oxy]ethyl}-11-[2-({6-[(2,5-dioxopyrrolidin-1-yl)oxy]-6-oxohexyl}amino)-2-oxoethyl]-1-{[α-D-mannopyranosyl-(1→3)-[α-D-mannopyranosyl-(1→6)]-α-D-mannopyranosyl]oxy}-4,9,13-trioxo-3,8,11,14-tetraazaicosan-20-amide (ML-28) having the following structure is described.

ML-28

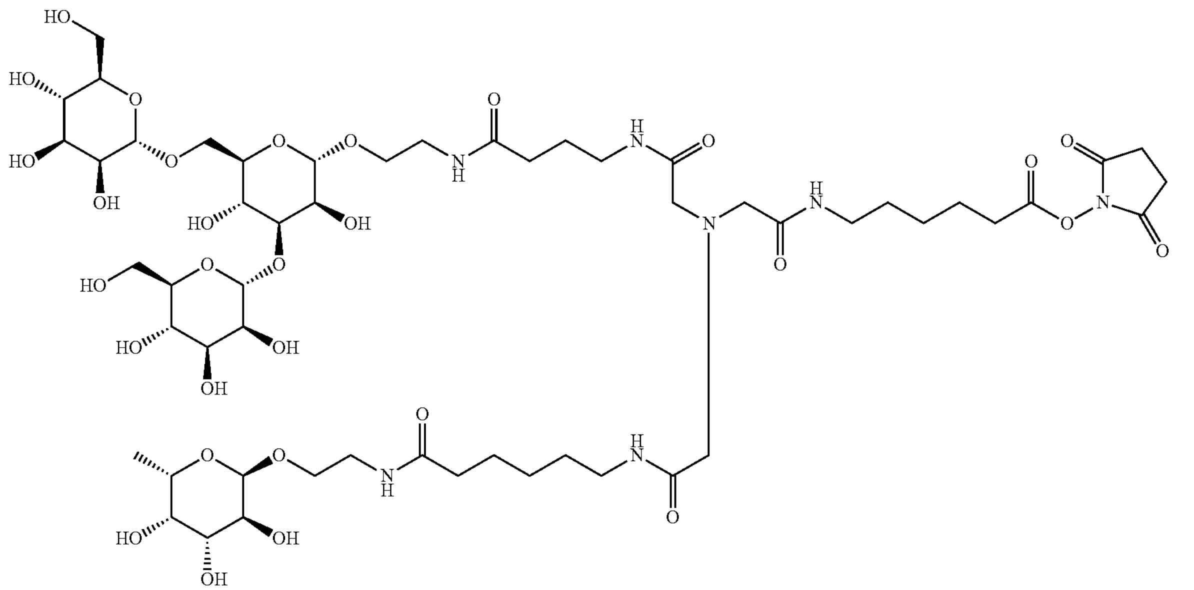

The title compound was prepared using procedures analogous to those described for ML-23 substituting 4-amino-N-(2-{[α-D-mannopyranosyl-(1→3)-[α-D-mannopyranosyl-(1→6)]-α-D-mannopyranosyl]oxy}ethyl)butanamide for 2-aminoethyl α-D-mannopyranosyl-(1→3)]-[α-D-mannopyranosyl-(1→6)]-α-D-mannopyranoside in Step D. UPLC Method E: m/e=1318.4270 [M+1]; Rt=2.19 min.

Example 29

The synthesis of oligosaccharide linker 2,5-Dioxopyrrolidin-1-yl 6-({[(2-oxo-2-{[α-D-mannopyranosyl-(1→3)-[α-D-mannopyranosyl-(1→6)]-α-D-mannopyranosyl]-2-oxyethyl}amino)({2-oxo-2-[(α-L-fucopyranosyl)oxy]-2-oxoethyl}amino)ethyl]amino}acetamido)-6-oxohexanoate (ML-29) having the following structure is described.

ML-29

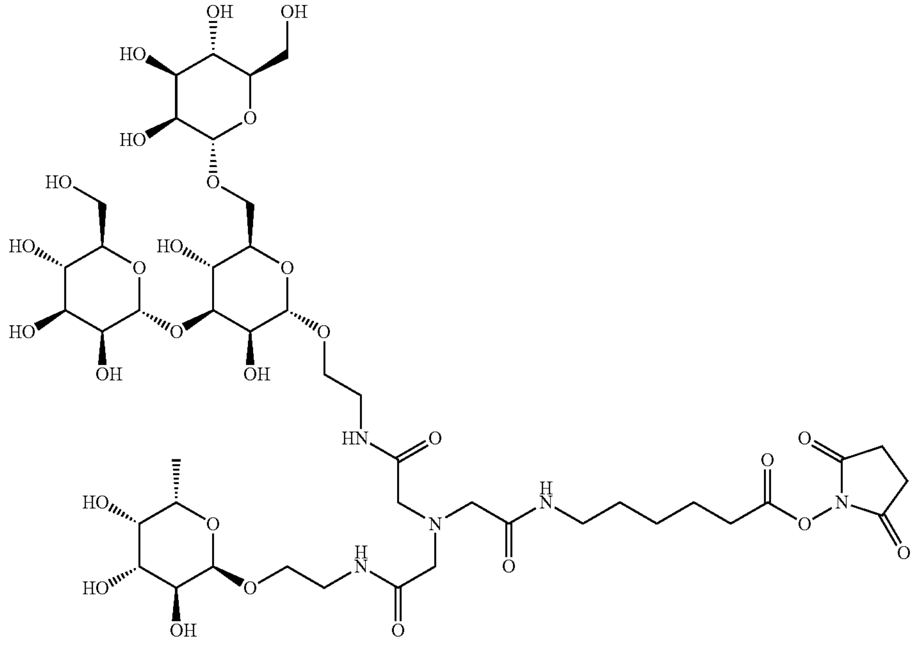

The title compound was prepared using procedures analogous to those described for ML-23 substituting 2-aminoethyl α-L-fucopyranoside for 6-amino-N-{2-[(α-L-fucopyranosyl)oxy]ethyl}hexanamide in Step C. UPLC Method A: m/e=1120.30 [M+1]; Rt=1.90 min.

Example 30

The synthesis of oligosaccharide linker 2,5-Dioxopyrrolidin-1-yl 2-({[(2-oxo-2-{[α-D-mannopyranosyl-(1→3)-[α-D-mannopyranosyl-(1→6)]-α-D-mannopyranosyl]-2-oxyethyl}amino)({2-oxo-2-[(α-L-fucopyranosyl)oxy]-2-oxoethyl}amino)ethyl]amino}acetamido)acetate (ML-30) having the following structure is described.

ML-30

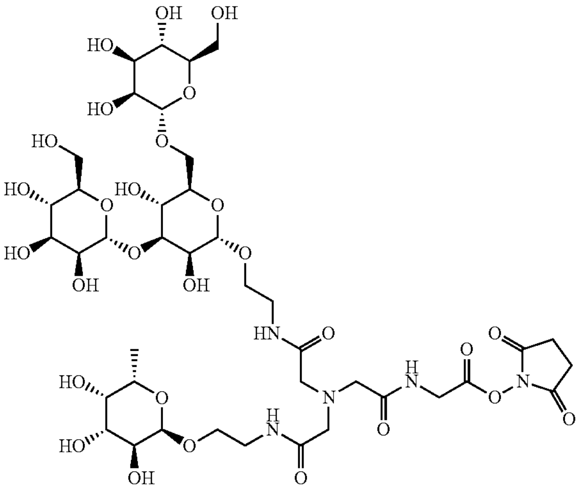

The title compound was prepared using procedures analogous to those described for ML-23 substituting benzyl N,N-bis(carboxymethyl)glycylglycinate for 2,2'-((2-((6-(benzyloxy)-6-oxohexyl)amino)-2-oxoethyl)imino)diacetic acid, and 2-aminoethyl α-L-fucopyranoside for 6-amino-N-(2-α-L-fucopyranosyl)ethyl)hexanamide in Step C, respectively. UPLC Method B: m/e=1064.25 [M+1]; Rt=2.65 min.

Example 31

The synthesis of oligosaccharide linker 2-{[2-({6-[(2,5-Dioxopyrrolidin-1-yl)oxy]-6-oxohexyl}amino)-2-oxoethyl][2-({2-[(α-L-fucopyranosyl)oxy]ethyl}amino)-2-oxoethyl]amino}-N-(2-{[α-D-mannopyranosyl-(1→3)-[α-D-mannopyranosyl-(1→6)]-β-D-glucopyranosyl]oxy}ethyl)acetamide (ML-31) having the following structure is described.

ML-31

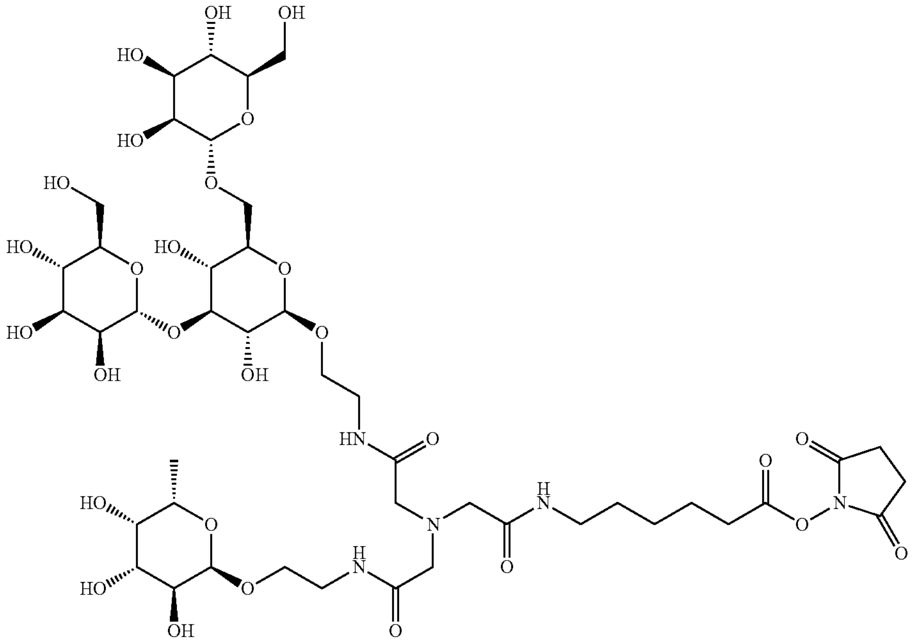

Step A: benzyl {2-[(4,6-O-benzylidene-β-D-glucopyranosyl)oxy]ethyl}carbamate

To a solution of benzyl [2-(β-D-glucopyranosyloxy)ethyl] carbamate (10 g, 28.0 mmol, Beilstein J. Org. Chem. 2010, 6, 699) in AcCN (150 mL) was added benzaldehyde dimethyl acetal (5 mL, 31.6 mmol) and p-toluenesulfonic acid monohydrate (60 mg, 0.315 mmol). After stirring for 24 hr, the reaction mixture was concentrated. The residue was purified by flash chromatography on silica gel (330 g), eluting with 0-20% $CH_3OH$ in $CH_2Cl_2$ to give the title compound. UPLC Method B: calculated for $C_{23}H_{27}NO_8$ 445.17, observed m/e: 446.06 [M+1]; Rt=3.21 min. $^1$H NMR ($CDCl_3$) δ 7.50-7.45 (2H, m), 7.35-7.25 (8H, m), 5.50 (1H, s), 5.10 (2H, s), 4.40-4.36 (1H, m), 4.31-4.26 (1H, m), 3.95-3.85 (1H, m), 3.80-3.70 (2H, m), 3.55-3.40 (4H, m), 3.40-3.30 (2H, m).

Step B: benzyl {2-[(2-O-benzoyl-4,6-O-benzylidene-β-D-glucopyranosyl)oxy]ethyl}carbamate A stirring mixture of benzyl {2-[(4,6-O-benzylidene-β-D-glucopyranosyl)oxy]ethyl}carbamate (4.5 g, 10.10 mmol) and dibutylstannanone (3 g, 12.05 mmol) in toluene (50 mL) was allowed to reflux for 5 hr. The resulting mixture was cooled down to rt and treated with benzoyl chloride (1.3 mL, 11.19 mmol). After stirring at rt for 1 hr, the mixture was concentrated. The residue was purified by flash chromatography on silica gel (330 g, eluting with 0-10% acetone in $CH_2Cl_2$) to give the title compound. UPLC Method B: calculated for $C_{30}H_{31}NO_9$ 549.20, observed m/e: 572.09 [M+Na]; Rt=3.94 min. $^1$H NMR ($CDCl_3$) δ 8.05-8.00 (2H, m), 7.55-7.45 (3H, m), 7.40-7.25 (10H, m), 5.55 (1H, s), 5.18-5.12 (1H, m), 5.04-5.00 (1H, m), 4.93-4.89 (1H, m), 4.66-4.63 (1H, m), 4.38-4.32 (1H, m), 4.05-4.00 (1H, m), 3.90-3.85 (1H, m), 3.82-3.77 (1H, m), 3.70-3.60 (2H, m), 3.55-3.45 (1H, m), 3.40-3.25 (2H, m). Regiochemistry was confirmed by 1H-1H 2D COSY experiment.

Step C: benzyl {2-[(2-O-benzoyl-4-O-benzyl-β-D-glucopyranosyl)oxy]ethyl}carbamate To a solution of benzyl {2-[(2-O-benzoyl-4,6-O-benzylidene-β-D-glucopyranosyl)oxy]ethyl}carbamate (2.58 g, 4.69 mmol) and borane tetrahydrofuran complex (40 mL, 40.0 mmol, 1.0 Min THF) at 0° C. was added a solution of dibutyl(((trifluoromethyl)sulfonyl)oxy)borane (6 mL, 6.00 mmol, 1.0 Min $CH_2Cl_2$) dropwise. After stirring at 0° C. for 2 hr, TEA (0.5 mL) was added to the reaction mixture and followed by the careful addition of $CH_3OH$ until the evolution of $H_2$ had ceased. The reaction mixture was concentrated and the residue was purified by flash chromatography on silica gel (330 g), eluting with 0-100% EtOAc in hexanes to give the title compound. TLC: silica gel, hexanes/EtOAc: 35/65, $R_f$=0.5. $^1$H NMR ($CDCl_3$) δ 8.05-8.00 (2H, m), 7.55-7.25 (13H, m), 5.05-4.98 (3H, m), 4.86-4.82 (1H, m), 4.78-4.74 (1H, m), 4.60-4.58 (1H, m), 3.95-3.90 (2H, m), 3.85-3.80 (1H, m), 3.75-3.65 (2H, m), 3.61-3.58 (1H, m), 3.45-3.40 (1H, m), 3.35-3.30 (2H, m). Regiochemistry was confirmed by $^1$H-$^1$H COSY and $^1$H-$^{13}$C one-bond correlation (HSQC) 2D NMR experiments.

Step D: benzyl (2-{[2,3,4,6-tetra-O-benzoyl-α-D-mannopyranosyl-(1→3)-[2,3,4,6-tetra-O-benzoyl-α-D-mannopyranosyl-(1→6)]-2-O-benzoyl-4-O-benzyl-β-D-glucopyranosyl]oxy}ethyl)carbamate To a mixture of benzyl {2-[(2-O-benzoyl-4-O-benzyl-β-D-glucopyranosyl)oxy]ethyl}carbamate_(1.47 g, 2.67 mmol), 2,3,4,6-tetra-O-benzoyl-D-mannopyranosyl trichloroacetimidate (4.15 g, 5.60 mmol, Organic Letters, 2003, 5, 4041) and 4 Å molecular sieves in $CH_2Cl_2$ (40 mL) at −30° C. was added trimethylsilyl trifluoromethanesulfonate (0.25 mL, 1.384 mmol) dropwise. The mixture was allowed to gradually warm up to rt. After stirring for 6 hr, the reaction was quenched with TEA (0.4 mL, 2.87 mmol). The reaction mixture was filtered and the filtrate was concentrated. The residue was purified by flash chromatography on silica gel (330 g, eluting with 0-75% EtOAc in hexanes to give the title compound. TLC: silica gel, hexanes/EtOAc 3/2, $R_f$=0.5. $^1$H NMR ($CDCl_3$) δ 8.20-7.95 (8H, m), 7.85-7.75 (8H, m), 7.65-7.60 (3H, m), 7.55-7.40 (8H, m), 7.38-7.18 (24H, m), 7.15-7.05 (4H, m), 6.00-5.95 (1H, m), 5.88-5.85 (1H, m), 5.75-5.65 (3H, m), 5.48-5.46 (1H, m), 5.35-5.25 (2H, m), 5.22-5.20 (1H, m), 5.07-5.05 (1H, m), 4.95-4.85 (2H, m), 4.78-4.75 (1H, m), 4.70-4.60 (1H, m), 4.60-4.55 (2H, m), 4.40-4.30 (2H, m), 4.27-4.23 (1H, m), 4.20-4.10 (2H, m), 3.95-3.90 (1H, m), 3.80-3.75 (1H, m), 3.75-3.70 (3H, m), 3.60-3.55 (1H, m), 3.51-3.48 (1H, m), 3.40-3.25 (2H, m).

Step E: benzyl (2-{[α-D-mannopyranosyl-(1→3)-[α-D-mannopyranosyl-(1→6)]-4-O-benzyl-β-D-glucopyranosyl]oxy}ethyl)carbamate To a solution of benzyl (2-{[2,3,4,6-tetra-O-benzoyl-α-D-mannopyranosyl-(1→3)-[2,3,4,6-tetra-O-benzoyl-α-D-mannopyranosyl-(1→6)]-2-O-benzoyl-4-O-benzyl-β-D-glucopyranosyl]oxy}ethyl)carbamate (3.39 g, 1.984 mmol) in $CH_3OH$ (30 mL) was added $NaOCH_3$ (0.4 mL, 0.2 mmol, 0.5 Min $CH_3OH$). After stirring at rt for 24 hr, amberlite IR 120 (H) ion exchange resin (pre-washed with $CH_3OH$ 3×30 mL) was added to the reaction mixture. The resulting mixture was allowed to stir for additional 15 min. The resin was filtered off and washed with $CH_3OH$ (3×5 mL). The filtrate was concentrated to give the title compound. UPLC Method B: calculated for $C_{35}H_{49}NO_{18}$ 771.29, observed m/e: 772.42 [M+1]; Rt=2.51 min.

Step F: 2-aminoethyl α-D-mannopyranosyl-(1→3)-[α-D-mannopyranosyl-(1→6)]-β-D-glucopyranoside A mixture of benzyl (2-{[α-D-mannopyranosyl-(1→3)-[α-D-mannopyranosyl-(1→6)]-4-O-benzyl-β-D-glucopyranosyl]oxy}ethyl)carbamate (0.96 g, 1.244 mmol) and Pd/C (124 mmol) in water (20 mL) was allowed to stir under a balloon of $H_2$ at rt for 16 h. The catalyst was filtered off and washed with $H_2O$ (3×10 mL). The fitrate was concentrated to give the title compound. UPLC Method B: calculated for $C_{20}H_{37}NO_{16}$ 547.21, observed m/e: 548.29 [M+1]; Rt=0.87 min. $^1$H NMR ($D_2O$) δ 5.20-5.19 (1H, m), 4.88-4.87 (1H, m), 4.51-4.49 (1H, m), 4.05 (1H, m), 4.00-3.90 (4H, m), 3.85-3.70 (9H, m), 3.70-3.60 (5H, m), 3.40-3.30 (1H, m), 3.05-3.00 (2H, m).

Step G: 2-{[2-({6-[(2,5-dioxopyrrohdin-1-yl)oxy]-6-oxohexyl}amino)-2-oxoethyl][2-({2-[(α-L-fucopyranosyl)oxy]ethyl}amino)-2-oxoethyl]amino}-N-(2-{[α-D-mannopyranosyl-(1→3)-[α-D-mannopyranosyl-(1→6)]-β-D-glucopyranosyl]oxy}ethyl)acetamide The title compound was prepared using procedure analogous to those described for ML-29 substituting 2-aminoethyl α-D-mannopyranosyl-(1→3)-[α-D-mannopyranosyl-(1→6)]-β-D-glucopyranoside for 2-aminoethyl α-D-mannopyranosyl-(1→3)-[α-D-mannopyranosyl-(1→6)]-α-D-mannopyranoside. UPLC Method B: calculated for $C_{44}H_{71}N_5O_{29}$ 1133.42, observed m/e: 1134.34 [M+1]; Rt=2.17 min.

Example 32

The synthesis of oligosaccharide linker 2-{[2-({6-[(2,5-Dioxopyrrolidin-1-yl)oxy]-6-oxohexyl}amino)-2-oxoethyl][2-({2-[(α-L-fucopyranosyl)oxy]ethyl}amino)-2-oxoethyl]amino}-N-(2-{[α-D-mannopyranosyl-(1→3)-[α-D-mannopyranosyl-(1→6)]-2-deoxy-2-fluoro-β-D-glucopyranosyl]oxy}ethyl)acetamide (ML-32) having the following structure is described.

ML-32

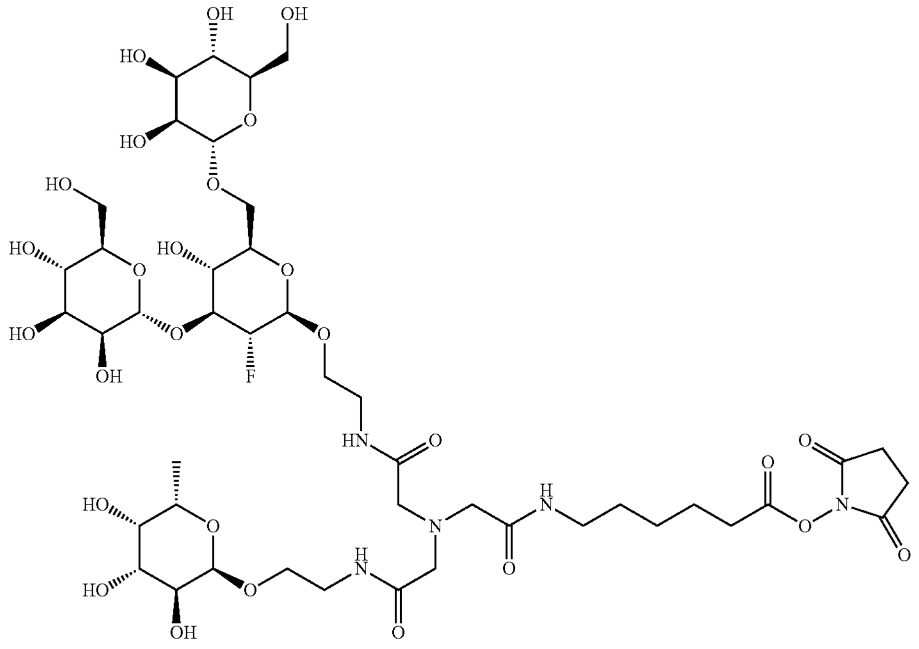

Step A: 2-chloroethyl 3,4,6-tri-O-acetyl-2-deoxy-2-fluoro-D-glucopyranoside

To a solution of 2-chloroethanol (1.0 mL, 14.92 mmol), 3,4,6-tri-O-acetyl-2-deoxy-2-fluoro-D-glucopyranosyl trichloroacetimidate (1.4 g, 3.09 mmol, Angew. Chem. Int. Ed. 2010, 49, 8724) and 4 Å molecular sieves in $CH_2Cl_2$ (50 mL) at −30° C. was added trimethylsilyl trifluoromethanesulfonate (0.25 mL, 1.384 mmol) dropwise. The mixture was allowed to gradually warm up to rt. After stirring for 2 hr, the reaction was quenched with TEA (0.13 mL, 0.933 mmol). The resulting mixture was filtered and the filtrate was concentrated. The residue was purified by flash chromatography on silica gel (80 g), eluting with 0-60% EtOAc in hexanes to give the title compound. This anomeric mixture was used directly in the next step without further purification. TLC: silica gel, hexane/EtOAc: 3/1, $R_f$=0.35.

Step B: 2-chloroethyl 2-deoxy-2-fluoro-D-glucopyranoside

To a solution of 2-chloroethyl 3,4,6-tri-O-acetyl-2-deoxy-2-fluoro-D-glucopyranoside (0.85 g, 2.293 mmol) in $CH_3OH$ (10 mL) was added $NaOCH_3$ (0.46 mL, 0.230 mmol, 0.5 Min $CH_3OH$). The resulting mixture was stirred at rt for 2 hr. Dowex 50wx2-200 (H) ion exchange resin (pre-washed with $CH_3OH$ 3×10 mL) was added to the reaction mixture. After stirring for 15 min, the resin was filtered off and the filtrate was concentrated down to give the title compound. This anomeric mixture was used directly in the next step without further purification. TLC: silica gel, hexane/EtOAc: 1/1, $R_f$=0.2.

Step C: 2-chloroethyl 4,6-O-benzylidene-2-deoxy-2-fluoro-β-D-glucopyranoside

To a solution of 2-chloroethyl 2-deoxy-2-fluoro-D-glucopyranoside (0.55 g, 2.248 mmol) in AcCN (10 mL) was added benzaldehyde dimethyl acetal (540 μL, 3.6 mmol) and p-toluenesulfonic acid monohydrate (6 mg, 0.032 mmol). After stirring for 3 hr, the reaction mixture was concentrated. The residue was purified by flash chromatography on silica gel (80 g), eluting with 0 to 60% EtOAc in hexanes to give the title compound. $^1H$ NMR ($CD_3OD$) δ 7.50-7.47 (2H, m), 7.35-7.32 (3H, m), 5.58 (1H, s), 4.76-4.72 (1H, m), 4.32-4.28 (1H, m), 4.16-4.02 (2H, m), 3.95-3.85 (2H, m), 3.80-3.74 (1H, m), 3.70-3.66 (2H, m), 3.52-3.48 (2H, m). The β anomeric stereochemistry was confirmed by $^1H$-$^{13}C$ one-bond correlation (HSQC) and $^1H$-$^1H$ NOE (NOESY) 2D NMR experiments. TLC: silica gel, hexane/EtOAc: 7/3, $R_f$=0.5.

Step D: 2-chloroethyl 4-O-benzyl-2-deoxy-2-fluoro-β-D-glucopyranoside

To a solution of 2-chloroethyl 4,6-O-benzylidene-2-deoxy-2-fluoro-3-D-glucopyranoside (422 mg, 1.268 mmol) in borane tetrahydrofuran complex (9 mL, 9.0 mmol, 1.0 M in THF) at 0° C. was added a solution of dibutyl {[(trifluoromethyl)sulfonyl]oxy}borane (1.27 mL, 1.270 mmol, 1.0 Min $CH_2Cl_2$) dropwise. After stirring at 0° C. for 2 h, TEA (0.5 mL) was added to the reaction mixture and followed by the careful addition of $CH_3OH$ until the evolution of $H_2$ had ceased. The reaction mixture was concentrated and the residue was purified by flash chromatography on silica gel (40 g), eluting with 0-60% EtOAc in hexanes to give the title compound. TLC: silica gel, hexane/EtOAc: 1/1, $R_f$=0.6. $^1H$ NMR ($CDCl_3$) δ 7.38-7.28 (5H, m), 4.84-4.71 (2H, m), 4.56-4.53 (1H, m), 4.22-4.04 (2H, m), 3.93-3.83 (3H, m), 3.77-3.71 (1H, m), 3.67-3.63 (2H, m), 3.55-3.50 (1H, m), 3.40-3.37 (1H, m). Regiochemistry was confirmed by $^1H$-$^{13}C$ one-bond correlation (HSQC); $^1H$-$^{13}C$ multiple-bond correlation (HMQC); and $^1H$-$^1H$ NOE (NOESY) 2D NMR experiments.

Step E: 2-azidoethyl 4-O-benzyl-2-deoxy-2-fluoro-β-D-glucopyranoside

To a solution of 2-chloroethyl 4-O-benzyl-2-deoxy-2-fluoro-β-D-glucopyranoside (1.53 g, 4.57 mmol) in DMF (45 mL) at rt was added sodium azide (360 mg, 5.54 mmol).

After stirring at 70° C. for 16 hr, the reaction mixture was cooled down to rt and poured onto ice water (200 mL) and extracted with $CH_2Cl_2$ (3×100 mL). The organic layers were combined and washed with brine (2×100 mL), dried over $Na_2SO_4$, filtered and concentrated. The residue was purified by flash chromatography on silica gel (120 g), eluting with 0-100% EtOAc in hexanes to give the title compound. TLC: silica gel, hexane/EtOAc: 1/1, $R_f$=0.55. $^1$H NMR ($CDCl_3$) δ 7.37-7.28 (5H, m), 4.84-4.71 (2H, m), 4.55-4.52 (1H, m), 4.22-4.07 (1H, m), 4.03-3.98 (1H, m), 3.94-3.86 (2H, m), 3.79-3.71 (2H, m), 3.56-3.51 (1H, m), 3.48-3.36 (3H, m).

Step F: 2-azidoethyl 2,3,4,6-tetra-O-benzoyl-α-D-mannopyranosyl-(1→3)-[2,3,4,6-tetra-O-benzoyl-α-D-mannopyranosyl-(1→6)]-4-O-benzyl-2-deoxy-2-fluoro-β-D-glucopyranoside To a solution of 2-azidoethyl 4-O-benzyl-2-deoxy-2-fluoro-β-D-glucopyranoside (1.23 g, 3.6 mmol), 2,3,4,6-tetra-O-benzoyl-D-mannopyranosyl trichloroacetimidate (5.35 g, 7.22 mmol, Organic Letters, 2003, 5, 4041), and 4 Å molecular sieves in $CH_2Cl_2$ (60 mL) at −30° C. was added trimethylsilyl trifluoromethanesulfonate (0.25 mL, 1.384 mmol) added dropwise. The mixture was allowed to gradually up to rt. After stirring for 6 h, the reaction was quenched with TEA (0.4 mL, 2.87 mmol). The resulting mixture was filtered and the filtrate was concentrated. The residue was purified by flash chromatography on silica gel (330 g), eluting with 0-75% EtOAc in hexanes to give the title compound. $^1$H NMR ($CDCl_3$) δ 8.20-7.70 (16H, m), 7.60-7.05 (29H, m), 6.14-5.98 (2H, m), 5.90-5.80 (2H, m), 5.79-5.77 (1H, m), 5.66-5.64 (1H, m), 5.42-5.41 (1H, m), 5.23-5.22 (1H, m), 5.03-5.02 (1H, m), 4.91-4.89 (1H, m), 4.70-4.60 (3H, m), 4.57-4.55 (1H, m), 4.50-4.48 (1H, m), 4.40-4.22 (3H, m), 4.10-4.00 (2H, m), 3.80-3.70 (3H, m), 3.55-3.45 (2H, m), 3.44-3.38 (1H, m), 3.36-3.30 (1H, m).

Step G: 2-azidoethyl α-D-mannopyranosyl-(1→3)-[α-D-mannopyranosyl-(1→6)]-4-O-benzyl-2-deoxy-2-fluoro-β-D-glucopyranoside To a solution of 2-azidoethyl 2,3,4,6-tetra-O-benzoyl-α-D-mannopyranosyl-(1→3)-[2,3,4,6-tetra-O-benzoyl-α-D-mannopyranosyl-(1→6)]-4-O-benzyl-2-deoxy-2-fluoro-β-D-glucopyranoside (5.0 g, 3.34 mmol) in $CH_3OH$ (40 mL) was added $NaOCH_3$ (1.0 mL, 0.5 mmol, 0.5 Min $CH_3OH$). After stirring at rt for 24 hr, amberlite IR 120 (H) ion exchange resin (pre-washed with $CH_3OH$ 3×30 mL) was added to the reaction mixture. After 15 min, the resin was filtered off and washed with $CH_3OH$ (3×5 mL). The filtrate was concentrated and the residue was taking into EtOAc (50 mL) and stirred for 2 hr. The solid was filtered, and washed with EtOAc (3×15 mL) and dried to give the title compound. UPLC Method B: calculated for $C_{27}H_{40}FN_3O_{15}$ 665.24, observed m/e: 666.35 [M+1]; Rt=2.03 min.

Step H: 2-aminoethyl α-D-mannopyranosyl-(1→3)-[α-D-mannopyranosyl-(1→6)]-4-O-benzyl-2-deoxy-2-fluoro-β-D-glucopyranoside A mixture of 2-azidoethyl α-D-mannopyranosyl-(1→3)-[α-D-mannopyranosyl-(1→6)]-4-O-benzyl-2-deoxy-2-fluoro-β-D-glucopyranoside (1.77 g, 2.66 mmol) and Pd/C (0.133 mmol) in water (30 mL) was allowed to stir under a balloon of $H_2$ at rt for 16 h. The catalyst was filtered off and washed with $H_2O$ (3×10 mL). The fitrate was concentrated to give the title compound. UPLC Method B: calculated for $C_{20}H_{36}FNO_{15}$ 549.21, observed m/e: 550.29 [M+1]; Rt=0.86 min. $^1$H NMR ($D_2O$) δ 5.16-5.14 (1H, m), 4.88-4.86 (1H, m), 4.80-4.76 (1H, m), 4.30-4.16 (1H, m), 4.06-4.03 (1H, m), 3.98-3.88 (4H, m), 3.86-3.72 (9H, m), 3.70-3.62 (5H, m), 2.94-2.88 (2H, m).

Step I. 2-{[2-({6-[(2,5-Dioxopyrrolidin-1-yl)oxy]-6-oxohexyl}amino)-2-oxoethyl][2-({2-[(α-L-fucopyranosyl)oxy]ethyl}amino)-2-oxoethyl]amino}-N-(2-{[α-D-mannopyranosyl-(1→3)-[α-D-mannopyranosyl-(1→6)]-2-deoxy-2-fluoro-β-D-glucopyranosyl]oxy}ethyl)acetamide The title compound was prepared using procedures analogous to those described for ML-29 substituting 2-aminoethyl α-D-mannopyranosyl-(1→3)-[α-D-mannopyranosyl-(1→6)]-4-O-benzyl-2-deoxy-2-fluoro-β-D-glucopyranoside for 2-aminoethyl α-D-mannopyranosyl-(1→3)-[α-D-mannopyranosyl-(1→6)]-α-D-mannopyranoside. UPLC Method B: calculated for C44H71N5O29 1133.42, observed m/e: 1134.34 [M+1]; Rt=2.17 min.

Example 33

The synthesis of oligosaccharide linker 2-{[2-({2-[(α-L-Fucopyranosyl)oxy]ethyl}amino)-2-oxoethyl][2-({6-[(2,5-dioxopyrrolidin-1-yl)oxy]-6-oxohexyl}amino)-2-oxoethyl]amino}-N-[2-(β-D-glucopyranosyloxy)ethyl]acetamide (ML-33) having the following structure is described.

ML-33

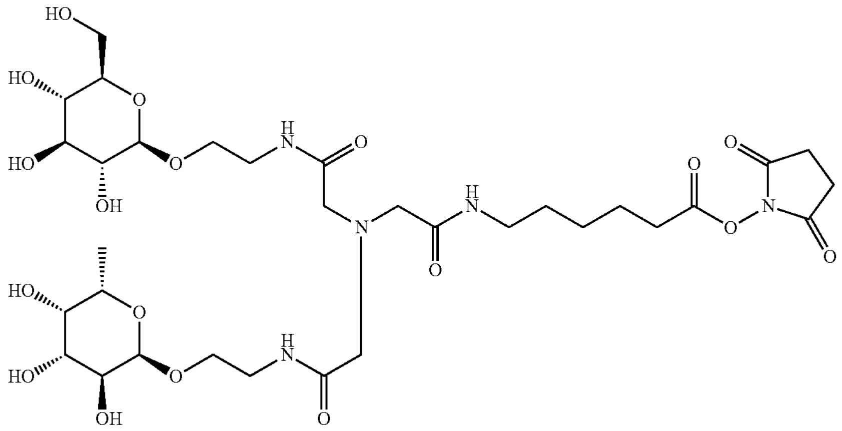

The title compound was prepared using procedures analogous to those described for ML-23 substituting 2-aminoethyl α-L-fucopyranoside for 6-amino-N-(2-α-L-fucopyranosyl)ethyl)hexanamide in Step C and 2-aminoethyl α-D-glucopyranoside for 2-aminoethyl α-D-mannopyranosyl-(1→3)-[α-D-mannopyranosyl-(1→6)]-α-D-mannopyranoside in Step D, respectively. UPLC Method B: m/e=796.38 [M+1]; Rt=1.87 min.

Example 34

The synthesis of oligosaccharide linker N,N-Bis{2-[(α-L-fucopyranosyl)oxy]ethyl}-6-[(2,5-dioxopyrrolidin-1-yl)oxy]-6-oxohexanamide_(ML-34) having the following structure is described.

ML-34

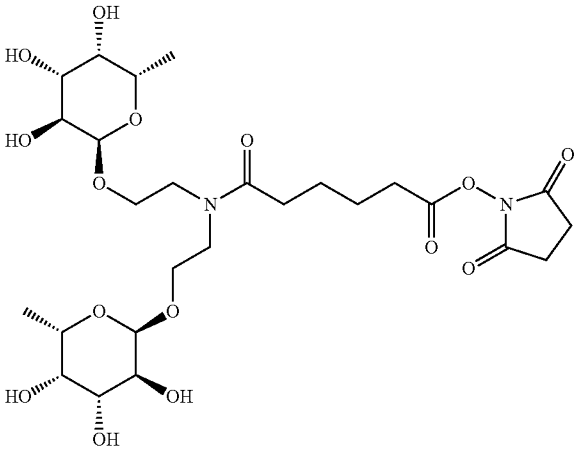

Step A: prop-2-en-1 yl 2,3,4-tri-O-benzoyl-α-L-fucopyranoside

To a stirred solution of 1,2,3,4-tetra-O-benzoyl-L-fucopyranoside (70.34 g, 121 mmol, Organic Letters 2007, 9, 1227-30) in $CH_2Cl_2$ (300 mL) at 0° C. was added allyl alcohol (12.36 mL, 182 mmol) followed by dropwise addition of boron trifluoride diethyl etherate (44.9 mL, 363 mmol) over 1 hr, while keeping the internal temperature below 20° C. After stirring at rt for 16 hr, the reaction mixture was chilled to 0° C., to which sat. $NaHCO_3$ (600 mL, 121 mmol) was added slowly. After stirring for 16 hr, the reaction mixture was extracted with $CH_2Cl_2$ (2×400 mL). The organic phase was washed with water (200 mL), sat. $NaHCO_3$ (3×100 mL), and brine (200 mL). The organic phase was separated, dried over $MgSO_4$, and filtered. The filtrate was concentrated and the residue was divided into five equal portions, which were separately purified by flash chromatography on silica gel (330 g), eluting with 0-60% EtOAc in hexanes to give the title compound. (a isomer $R_f$=0.63 30:70 EtOAc:Hexanes). $^1H$ NMR ($CDCl_3$) δ 1.32 (3H, t, J=6.77), 2.09 (1H, s), 4.15-4.14 (1H, m), 4.33-4.31 (1H, m), 4.51-4.49 (1H, m), 5.22 (1H, d, J=10.52), 5.39-5.38 (2H, m), 5.73 (1H, dd, J=10.74, 3.67), 5.82 (1H, d, J=3.30), 5.92-5.91 (1H, m), 6.04 (1H, dd, J=10.75, 3.43), 7.44 (3H, dt, J=22.64, 7.61), 7.48-7.57 (5H, m), 7.65 (1H, d, J=7.49), 7.84 (2H, d, J=7.84), 8.04 (2H, d, J=7.84), 8.15 (2H, d, J=7.79).

Step B: 2-oxoethyl 2,3,4-tri-O-benzoyl-α-L-fucopyranoside

To a solution of prop-2-en-1-yl 2,3,4-tri-O-benzoyl-α-L-fucopyranoside (6.06 g, 11.73 mmol) in acetone (94 mL) and water (23.5 mL) was added 4-methylmorpholine 4-oxide (2.75 g, 23.46 mmol) followed by the addition of 2.5% $OsO_4$ in water (5.97 g, 0.587 mmol). The mixture was allowed to stir at rt for 16 hr. To the resulting mixture was then added a solution of $NaIO_4$ (5.40 g, 23.46 mmol) in water (100 mL). After stirring for additional 6 hr, the precipitate was filtered and washed with acetone (200 mL). The volume of the filtrate was reduced to approximately ⅓ of the initial volume and then extracted with EtOAc (200 mL). The organic phase was separated, washed with sat. $NaHCO_3$ (200 mL). The aqueous phase was extracted with EtOAc (3×100 mL). The organic phases were combined and washed with brine, dried over $Na_2SO_4$, and concentrated. The residue was purified by flash chromatography on silica gel (220 g), eluting with 0-100% EtOAc in hexanes to give the title compound. $^1H$ NMR ($CDCl_3$) δ 1.33-1.29 (3H, m), 3.27 (1H, s), 3.41 (1H, s), 4.35-4.31 (1H, m), 5.51-5.45 (1H, m), 5.75-5.69 (1H, m), 5.81 (1H, dd, J=13.91, 3.57), 6.05-5.98 (1H, m), 7.42 (2H, d, J=7.76), 7.53 (5H, d, J=8.61), 7.67-7.63 (2H, m), 7.84-7.81 (2H, m), 8.01 (2H, t, J=8.82), 8.14-8.12 (2H, m), 9.77-9.77 (1H, m).

Step C: benzyl {2-[(2,3,4-tri-O-acetyl-α-L-fucopyranosyl)oxy]ethyl}carbamate

To a stirred solution of 1,2,3,4-tetra-O-acetyl-L-fucopyranose (200 g, 601.86 mmol) in AcCN (100 mL) and benzyl (2-hydroxyethyl)carbamate (140.96 g, 722.08 mmol) at 0° C. was added $BF_3.Et_2O$ (427.7 g, 3.01 mol) dropwise over 2 hr. After stirring at rt for 16 hr, the reaction mixture was cooled to 0° C. and followed by the addition of $Et_3N$ (130 mL). The resulting mixture was concentrated and the residual was dissolved in $CH_2Cl_2$ (2.0 L), which was subsequently washed with sat. $NaHCO_3$ (2×500 mL), water (2×500 mL) and brine (500 mL). The organic phase was separated, dried over $Na_2SO_4$, and concentrated. The residue was purified by flash chromatography on silica gel, eluting with EtOAc/petroleum ether (1:3) to give the title compound. $^1H$ NMR ($CDCl_3$) δ 7.33-7.37 (5H, m), 5.12-5.32 (5H, m), 4.99-5.04 (1H, m), 4.42-4.45 (1H, d), 3.87-3.94 (1H, m), 3.78-3.84 (1H, m), 3.66-3.70 (1H, m), 3.42-3.44 (2H, m), 2.19 (3H, s), 2.05-2.12 (6H, m), 1.25-1.30 (3H, d).

Step D: 2-aminoethyl 2,3,4-tri-O-acetyl-α-L-fucopyranoside

To a solution of benzyl {2-[(2,3,4-tri-O-acetyl-α-L-fucopyranosyl)oxy]ethyl}carbamate (1.0 g, 2.139 mmol) in water (10 mL) was added Pd/C (68 mg, 0.642 mmol). The resulting suspension was degassed and stirred under a balloon of $H_2$ at rt. After 1 hr, the reaction mixture was filtered through a Celite pad and the filtrate was lyophilized to yield the title compound. UPLC Method B: m/e=334.1563 [M+1]; Rt=1.43 min.

Step E: 2-(benzylamino)ethyl 2,3,4-tri-O-acetyl-α-L-fucopyranoside

To a solution of 2-aminoethyl 2,3,4-tri-O-acetyl-α-L-fucopyranoside (8.56 g, 25.7 mmol) in $CH_2Cl_2$ (100 mL) was added benzaldehyde (2.197 ml, 21.67 mmol), acetic acid (372 μL, 6.50 mmol) and $NaCNBH_3$ (3.40 g, 54.2 mmol). After stirring at rt for 16 hr, the reaction mixture was concentrated and the residue was partitioned between EtOAc (50 mL) and sat. $NaHCO_3$ (50 mL). The organic phase separated, washed with sat'd $NaHCO_3$ (2×100 mL), brine (100 mL), dried over $MgSO_4$, and concentrated. The residue was purified by flash chromatography on C18 reverse phase silica gel (130 g), eluting with 0-100% AcCN in water to give the title compound. UPLC Method B: m/e=424.2089 [M+1]; Rt=3.42 min.

Step F: 2-(benzyl{2-[(2,3,4-tri-O-benzoyl-α-L-fucopyranosyl)oxy]ethyl}amino)ethyl 2,3,4-tri-O-acetyl-α-L-fucopyranoside To a solution of 2-(benzylamino)ethyl 2,3,4-tri-O-acetyl-α-L-fucopyranoside (1.021 g, 2.411 mmol) in $CH_2Cl_2$ (50 mL) was added 2-oxoethyl 2,3,4-tri-O-benzoyl-α-L-fucopyranoside (1.25 g, 2.411 mmol), acetic acid (41 μL, 0.723 mmol) and $NaCNBH_3$ (227 mg, 3.62 mmol). After stirring at rt for 16 hr, the reaction mixture was concentrated and the residue was partitioned between EtOAc (50 mL) and sat'd $NaHCO_3$ (50 mL). The organic phase was separated, washed with saturated $NaHCO_3$ (2×100 mL) and brine (100 mL), dried over $MgSO_4$, and concentrated. The residue was purified by flash chromatography silica gel (120 g, eluting 0-100 EtOAc in hexanes). The fractions containing the title compound were combined and concentrated. The residue was further purified by flash chromatography on C18 reverse phase silica gel (130 g), eluting with 0-100% AcCN in water to give the title compound. UPLC Method B: me/e=926.3234 [M+1]; Rt=1.947 min. $^1H$ NMR ($CDCl_3$) δ 1.12 (3H, d, J=6.54), 1.27 (3H, d, J=6.57), 2.00 (6H, d, J=5.40), 2.20 (3H, s), 2.78 (2H, q, J=5.85), 2.85 (2H, t, J=5.72), 3.48-3.46 (1H, m), 3.77-3.59 (4H, m), 3.87-3.85 (1H, m), 4.09 (1H, d, J=6.63), 4.39 (1H, d, J=6.71), 5.02 (1H, d, J=3.71), 5.14 (1H, dd, J=10.82, 3.68), 5.30 (1H, d, J=3.36), 5.37-5.34 (2H, m), 5.65 (1H, dd, J=10.72, 3.66), 5.77 (1H, d, J=3.49), 5.98 (1H, dd, J=10.70, 3.47), 7.29 (6H, s), 7.36 (3H, t, J=7.74), 7.45 (1H, t, J=7.59), 7.52 (3H, t, J=7.73), 7.64 (1H, t, J=7.46), 7.81 (2H, dd, J=8.00, 1.41), 7.97 (2H, dd, J=8.07, 1.40), 8.14-8.12 (2H, m).

Step G: 2-(benzyl{2-[(α-L-fucopyranosyl)oxy]ethyl}amino)ethyl 6-α-L-fucopyranoside To a solution of 2-(benzyl{2-[(2,3,4-tri-O-benzoyl-α-L-fucopyranosyl)oxy]ethyl}amino)ethyl 2,3,4-tri-O-acetyl-α-L-fucopyranoside (432.9 mg, 0.468 mmol) in $CH_3OH$ (10 mL) was added $NaOCH_3$ (0.087 μL, 0.468 mmol, 1.0 M). After stirring for 16 hr, the reaction mixture was concentrated to give the title compound. UPLC Method B: m/e=488.2324 [M+1]; Rt=2.106 min.

Step H: 2-({2-[(α-L-fucopyranosyl)oxy]ethyl}amino)ethyl a-L-fucopyranoside

To a solution of 2-(benzyl{2-[(α-L-fucopyranosyl)oxy]ethyl}amino)ethyl 6-α-L-fucopyranoside (220 mg, 0.451 mmol) in water (10 mL) was added Pd/C (14.41 mg, 0.135 mmol). The mixture was degassed and stirred under a balloon of $H_2$. After 1 hr, the reaction mixture was filtered through a Celite pad and the filtrate was lyophilized to yield the title compound. UPLC Method: m/e=398.2161 [M+1]; Rt=1.119 min. $^1H$ NMR ($CD_3OD$) δ 1.24 (6H, d, J=6.58), 2.91-2.89 (4H, m), 3.56 (2H, ddd, J=10.66, 6.64, 4.66), 3.70-3.69 (2H, m), 3.80-3.75 (4H, m), 3.86 (2H, dt, J=10.61, 4.53), 3.98 (2H, q, J=6.63), 4.80 (2H, d, J=3.45).

Step I: benzyl 6-(bis{2-[(α-L-fucopyranosyl)oxy]ethyl}amino)-6-oxohexanoate

To a solution of 6-(benzyloxy)-6-oxohexanoic acid (40 mg, 0.169 mmol), EDC (114 mg, 0.593 mmol) and HOBt (2.59 mg, 0.017 mmol) in DMF (5 mL) at rt was added 2-({2-[(α-L-fucopyranosyl)oxy]ethyl}amino)ethyl α-L-fucopyranoside (190 mg, 0.478 mmol). After stirring for 16 hr, the reaction mixture was concentrated and the residue was purified by flash chromatography on C18 reverse phase silica gel (50 g), eluting with 5-40% AcCN in water to give the title compound. UPLC Method B: m/e=616.2923 [M+1]; Rt=3.114 min. $^1H$ NMR ($CD_3OD$) δ 1.24 (6H, d, J=6.58), 1.72-1.64 (4H, m), 2.45 (2H, t, J=7.11), 2.53 (2H, t, J=7.32), 3.91-3.55 (17H, m), 4.78-4.75 (2H, m), 5.14 (2H, s), 7.38-7.37 (5H, m).

Step J: N,N-Bis{2-[(α-L-fucopyranosyl)oxy]ethyl}-6-[(2,5-dioxopyrrolidin-1-yl)oxy]-6-oxohexanamide The title compound was prepared using procedure analogous to those described for ML-1 substituting benzyl 6-(bis{2-[(α-L-fucopyranosyl)oxy]ethyl}amino)-6-oxohexanoate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C. UPLC Method B: m/e=623.2853 [M+1]; Rt=2.155 min.

Example 35

The synthesis of oligosaccharide linker 2-({2-[(α-L-Fucopyranosyl)oxy]ethyl}{6-[(2,5-dioxopyrrolidin-1-yl)oxy]-6-oxohexyl}amino)ethyl a-L-fucopyranoside (ML-35) having the following structure is described.

ML-35

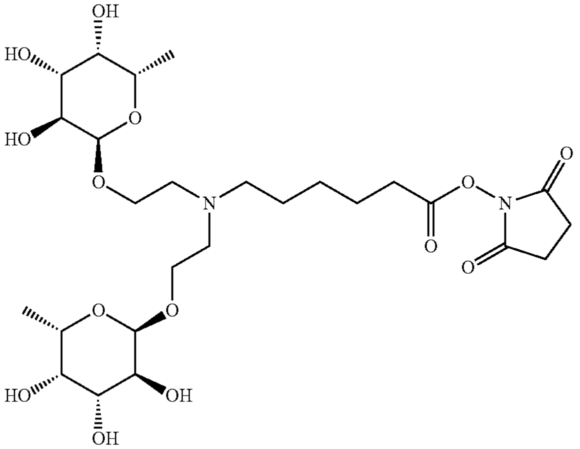

Step A: benzyl 6-(bis{2-[(2,3,4-tri-O-benzoyl-α-L-fucopyranosyl)oxy]ethyl}amino)hexanoate To a solution of 2-oxoethyl 2,3,4-tri-O-benzoyl-α-L-fucopyranoside (1.25 g, 2.411 mmol) in $CH_2Cl_2$ (50 mL) was added 6-(benzyloxy)-6-oxohexan-1-aminium 4-methylbenzenesulfonate, acetic acid (17 μL, 0.300 mmol) and $NaCNBH_3$ (189 mg, 3.00 mmol). After stirring at rt for 16 hr, the reaction mixture was concentrated and the residue was partitioned between EtOAc (50 mL) and sat'd $NaHCO_3$ (50 mL). The organic phase was separated, washed with sat'd $NaHCO_3$ (2×100 mL), brine (100 mL), dried over $MgSO_4$, and concentrated. The residue was purified by flash chromatography on silica gel (120 g), eluting with 0-100% EtOAc in hexanes. The fractions containing the title compound were combined and concentrated. The residue was further purified by flash chromatography on C18 reverse phase silica gel (50 g), eluting with 0-100% AcCN in water to give the title compound. UPLC Method B: m/e=1226.4591 [M+1]; Rt=3.310 min. $^1H$ NMR ($CDCl_3$) δ 1.29 (5H, d, J=6.62), 2.36-2.31 (2H, m), 2.75 (3H, d, J=23.31), 3.53 (2H, d, J=9.26), 3.78-3.76 (1H, m), 4.45 (1H, d, J=6.66), 5.13 (2H, s), 5.35 (1H, d, J=3.64), 5.64 (2H, dd, J=10.69, 3.63), 5.79 (2H, d, J=3.48), 5.98 (1H, dd, J=10.71, 3.44), 7.26 (4H, t, J=7.64), 7.56-7.40 (14H, m), 7.64 (2H, t, J=7.72), 7.82-7.80 (5H, m), 7.99-7.97 (5H, m), 8.19-8.12 (5H, m).

Step B: methyl 6-(bis{2-[(α-L-fucopyranosyl)oxy]ethyl}amino)hexanoate

The title compound was prepared using procedures analogous to those described for ML-34 in step G substituting benzyl 6-(bis{2-[(2,3,4-tri-O-benzoyl-α-L-fucopyranosyl)oxy]ethyl}amino)hexanoate for 2-(benzyl {2-[(2,3,4-tri-O-benzoyl-α-L-fucopyranosyl)oxy]ethyl}amino)ethyl 2,3,4-tri-O-acetyl-α-L-fucopyranoside. UPLC Method B: m/e=526.2852 [M+1]; Rt=2.112 min.

Step C: 6-(bis{2-[(α-L-fucopyranosyl)oxy]ethyl}amino)hexanoic acid

To a solution of methyl 6-(bis{2-[(α-L-fucopyranosyl)oxy]ethyl}amino)hexanoate (45 mg, 0.086 mmol) in water (10 mL) was added NaOH (0.086 μL, 0.086 mmol, 1.0 M). After stirring for 16 hours, the reaction mixture was neutralized with 0.01 M HCl and the resulting solution was lyophilized to yield the title compound. UPLC Method B: m/e=512.2866 [M+1]; Rt=1.709 min.

Step D: 2-({2-[(α-L-fucopyranosyl)oxy]ethyl}{6-[(2,5-dioxopyrrolidin-1-yl)oxy]-6-oxohexyl}amino)ethyl α-L-fucopyranoside The title compound was prepared using procedures analogous to those described for ML-1 Step D, substituting 6-(bis{2-[(α-L-fucopyranosyl)oxy]ethyl}amino)hexanoic acid for 6-({2-[(α-D-mannopyranosyl-(1→3)-[α-D-mannopyranosyl-(1→6)]-α-D-mannopyranosyl)oxy]ethyl}amino)-6-oxohexanoic acid. UPLC Method B: m/e=609.2808 [M+1]; Rt=2.088 min.

Example 36

The synthesis of oligosaccharide 2-({6-[(2,5-Dioxopyrrolidin-1-yl)oxy]-6-oxohexyl}[3-(α-L-fucopyranosyl)propyl]amino)ethyl 2-(acetylamino)-2-deoxy-β-D-glucopyranoside (ML-36) having the following structure is described.

ML-36

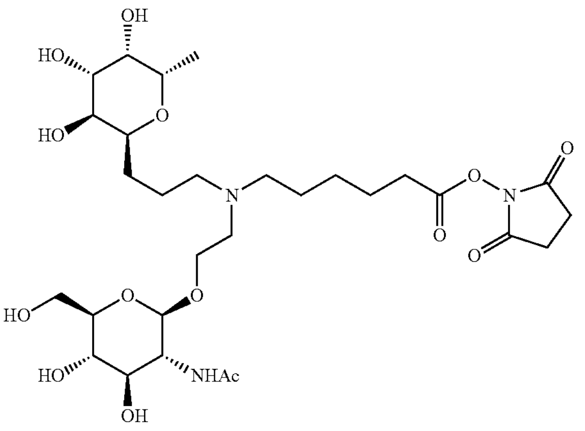

Step A: 3-(2,3,4-tri-O-acetyl-α-L-fucopyranosyl)-1-propene

To a solution of 1,2,3,4-tetra-O-acetyl-α-L-fucopyranose (12 g, 36.1 mmol) and allyltrimethyl silane (11.48 mL, 72.2 mmol) in AcCN (60 mL) at 0° C. was added TMS-OTf (3.52 mL, 19.50 mmol). The reaction mixture was stirred at 0° C. for 18 hr and then at rt for 6 hr. The resulting red solution was diluted with $CH_2Cl_2$ (250 mL) and sat'd $NaHCO_3$ (150 mL) was added carefully. The aqueous layer was separated and extracted with $CH_2Cl_2$ (2×50 mL). The combined organic layers were dried over $Na_2SO_4$, filtered and concentrated. The residue was purified by flash chromatography on silica gel (220 g), eluting with 15% EtOAc in hexanes to give the title compound. $^1H$ NMR ($CDCl_3$, 400 MHz) δ 1.16 (d, J=6.4, 3H), 2.04 (s, 3H), 2.08 (s, 3H), 2.18 (s, 3H), 2.34 (m, 1H), 2.57 (m, 1H), 4.00 (m, 1H), 4.29 (dt, J=10.4, 7.3, 1H), 5.13 (m, 2H), 5.23 (dd, J=10.0, 3.4, 1H), 5.30 (dd, J=3.4, 1.9, 1H), 5.35 (dd, J=10.0, 5.6, 1H), 5.77 (m, 1H).

Step B: 3-(α-L-fucopyranosyl)-1-propene

To a stirred solution of 3-(2,3,4-tri-O-acetyl-α-L-fucopyranosyl)-1-propene (10.65 g, 33.9 mmol) in $CH_3OH$ (50 mL) was added $NaOCH_3$ (183 mg, 3.4 mmol). After stirring at rt for 2 hr, the reaction mixture was neutralized with Amberlite IR120 (pre-washed with methanol 3×25 mL). The resin was filtered off and the filtrate was concentrated to give a white solid, which was recrystallized from EtOAc (~200 mL) to give the title compound. $^1H$ NMR ($CDCl_3$, 400 MHz) δ 1.22 (d, J=6.5, 3H), 2.41 (m, 1H), 2.47 (m, 1H), 3.73 (m, 2H), 3.85 (qd, J=6.5, 2.0, 1H), 3.90 (dd, J=8.9, 5.5, 1H), 3.99 (m, 1H), 5.07 (m, 1H), 5.15 (dq, J=17.2, 1.7, 1H), 5.85 (m, 1H).

Step C: 3-(2,3,4-tri-O-benzyl-α-L-fucopyranosyl)-1-propene

To a stirred suspension of NaH (3.91 g, 60% dispersion in oil, 98 mmol) in DMF (120 mL) at rt was added portionwise 3-(α-L-fucopyranosyl)-1-propene (4.6 g, 24.44 mmol). After 2 hr, to the resulting mixture was added tetrabutyl ammonium iodide (451 mg, 1.22 mmol) and followed by the slow addition of benzyl bromide (13.1 mL, 110 mml). After stirring at rt for 16 hr, the reaction mixture was concentrated and the residue was partitioned between water (300 mL) and $Et_2O$ (150 mL). The aqueous layer was extracted with $Et_2O$ (3×150 mL). The combined organic layers were washed with brine (100 mL), dried over $Na_2SO_4$, filtered and concentrated. The residue was purified by flash chromatography on silica gel (220 g), eluting with 0-40% EtOAc in hexanes to give the title compound. $^1H$ NMR ($CDCl_3$, 400 MHz) δ 1.34 (d, J=6.6, 3H), 2.33 (m, 1H), 2.42 (m, 1H), 3.82 (m, 3H), 3.99 (m, 1H), 4.12 (m, 1H), 4.58 (d, J=11.8, 1H), 4.64 (d, J=11.8, 2H), 4.69 (d, J=12.0, 1H), 4.76 (dd, J=12.0, 8.9, 2H), 5.05, 5.07 and 5.11 (m, 2H), 5.80 (m, 1H), 7.30-7.40 (m, 15H).

Step D: 3-(2,3,4-tri-O-benzyl-α-L-fucopyranosyl) propanol

A solution of 3-(2,3,4-tri-O-benzyl-α-L-fucopyranosyl)-1-propene (10.4 g, 22.68 mmol) in THF (100 mL) at 0° C. was added slowly 9-BBN (58.5 mL, 29.3 mmol, 0.5 Min THF). The mixture was allowed to warm up to rt, and then refluxed for 3 hr. The reaction mixture was then cooled to rt and ethanol (4.4 mL, 75 mmol) was added dropwise, followed by NaOH (11.51 ml, 46 mmol, 4.0 Min water). The resulting mixture was cooled to 0° C. and 35% hydrogen peroxide (10 mL, 115 mmol) was added. The resulting suspension was stirred at rt overnight. The reaction mixture was diluted with brine (125 mL) and ether (200 mL). The organic layer was washed with brine (2×125 mL), dried over $Na_2SO_4$, filtered and concentrated. The residue was purified by flash chromatography on silica gel (330 g), eluting with 0-100% EtOAc in hexanes to give the title compound. $^1H$ NMR ($CDCl_3$, 400 MHz) δ 1.33 (d, J=6.6, 3H), 1.67 (m, 3H), 1.70 (m, 1H), 3.65 (m, 2H), 3.80 (m, 3H), 3.98 (m, 1H), 4.02 (m, 1H), 4.56 (d, J=11.8, 1H), 4.63 (t, J=12.2, 2H), 4.69 (d, J=12.0, 1H), 4.78 (dd, J=12.1, 2.1, 2H), 7.27-7.40 (m, 15H).

Step E: 3-(2,3,4-tri-O-benzyl-α-L-fucopyranosl) propanal

To solution of 3-(2,3,4-tri-O-benzyl-α-L-fucopyranosyl) propanol (8.4 g, 17.62 mmol) in $CH_2Cl_2$ (100 mL) at 0° C. was added Dess-Martin periodinane (11.21 g, 26.4 mmol). The resulting mixture was allowed to stir at 0° C. for 1 hr and then at rt for 2 hr. TLC indicates still some starting alcohol present so further Dess-Martin periodinane (5 g, 11.8 mmol) added and the mixture was stirred at rt for additional 2 hr. The resulting mixture was washed with sat'd $NaHCO_3$ (3×150 mL), brine (50 mL), dried over $Na_2SO_4$, filtered and concentrated. The residue purified by flash chromatography on silica gel (220 g), eluting with 0-80% EtOAc in hexanes to give the title compound. $^1H$ NMR ($CDCl_3$, 400 MHz) δ 1.26 (d, J=6.6, 3H), 1.82 (m, 1H), 2.06 (m, 1H), 2.40-2.58 (m, 2H), 3.80 (m, 2H), 3.84 (m, 1H), 3.90 (m, 1H), 3.99 (dt, J=10.9, 3.8, 1H), 4.55 (d, J=11.8, 1H), 4.65 (d, J=11.8, 1H), 4.70 (t, J=12.0, 2H), 4.79 (dd, J=12.0, 9.2, 2H), 7.28-7.40 (m, 15H).

Step F: 2-{[3-(2,3,4-tri-O-benzyl-α-L-fucopyranosyl)propyl]amino}ethyl 2-(acetylamino)-2-deoxy-β-D-glucopyranoside To a mixture of 3-(2,3,4-tri-O-benzyl-α-L-fucopyranosyl) propanal (800 mg, 1.69 mmol) and 2-aminoethyl 3,4,6-tri-O-acetyl-2-(acetylamino)-2-deoxy-β-D-glucopyranoside (987 mg, 2.53 mmol) in $CH_2Cl_2$ (15 mL) was added acetic acid (29 μL, 0.506 mmol) and sodium triacetoxyborohydride (893 mg, 4.21 mmol). After stirring at rt overnight, the reaction mixture was concentrated and the residue was taken up in EtOAc (70 mL), washed with sat'd $NaHCO_3$ (2×100 mL), brine (30 mL), dried over $Na_2SO_4$, filtered and concentrated. The residue was taken up in $CH_3OH$ (8 mL), to which $NaOCH_3$ (27 mg, 0.506 mmol) was added. After stirring at rt for 2 hr, the resulting mixture was concentrated and the residue was purified by flash chromatography on C18 reverse phase silica gel (120 g), eluting with 5-100% AcCN in water to give the title compound. $^1H$ NMR ($CDCl_3$, 400 MHz) δ 1.30 (d, J=6.6, 3H), 1.50 (m, 1H), 1.60 (m, 1H), 1.68 (m, 1H), 2.02 (s, 3H), 2.64 (m, 2H), 2.81 (m, 2H), 3.39 (m, 1H), 3.57 (m, 2H), 3.69 (m, 1H), 3.78-3.85 (m, 4H), 3.92 (m, 2H), 4.00 (m, 2H), 4.45 (d, J=7.7, 1H), 4.52 (d, J=11.9, 1H), 4.62 (d, J=11.8, 1H), 4.68 (d, J=12.1, 1H), 4.79 (d, J=12.0, 2H), 7.28-7.38 (m, 15H), 7.65 (s, 1H); [M+H/e]+=723.3925.

Step G: benzyl 6-{[3-(2,3,4-tri-O-benzyl-α-L-fucopyranosyl)propyl](2-{[2-(acetylamino)-2-deoxy-β-D-glucopyranosyl]oxy}ethyl)amino}hexanoate To a mixture of benzyl 6-oxohexanoate (170 mg, 0.77 mmol) and 2-{[3-(2,3,4-tri-O-benzyloxy-α-L-fucopyranosyl)propyl]amino}ethyl 2-(acetylamino)-2-deoxy-β-D-glucopyranosid (558 mg, 0.77 mmol) in $CH_2Cl_2$ (8 mL) was added acetic acid (13 μL, 0.232 mmol) and sodium triacetoxyborohydride (327 mg, 1.54 mmol) and the resulting mixture stirred at room temperature for 2 hours. Further benzyl 6-oxohexanoate (170 mg, 0.77 mmol) added and stirring continued overnight. The mixture evaporated and the residue was partitioned between EtOAc (40 mL) and sat'd $NaHCO_3$ (60 mL); the organic layer was washed with brine (30 mL), dried over $Na_2SO_4$, filtered and concentrated. The residue was purified by flash chromatography on silica gel (40 g), eluting with 5-20% MeOH in $CH_2Cl_2$ to give the title compound. $^1H$ NMR ($CDCl_3$, 400 MHz): 1.27-1.38 (m, 5H), 1.48 (m, 1H), 1.62-1.75 (m, 4H), 1.80 (m, 1H), 2.09 (s, 3H); 2.37 (t, J=7.3, 2H), 2.90-3.02 (m, 4H), 3.04 (m, 1H), 3.13 (m, 1H), 3.42 (m, 1H), 3.59 (t, J=8.9, 1H), 3.65-3.75 (m, 3H), 3.78 (d, J=4.9, 2H), 3.86 (m, 1H), 3.87-4.05 (m, 4H), 4.15 (d, J=11.2, 1H), 4.49 (d, J=11.9, 1H), 4.62 (d, J=11.8, 1H), 4.66 (d, J=11.7, 1H), 4.69 (m, 2H), 4.74 (d, J=11.8, 1H), 4.78 (d, J=12.0, 1H), 5.12 (s, 2H), 7.25-7.38 (m, 15H), 8.36 (s, 1H); UPLC-MS [M+H/e]+=927.5049.

Step H: 2-({6-[(2,5-dioxopyrrolidin-1-yl)oxy]-6-oxohexyl}[3-(α-L-fucopyranosyl)propyl]amino) ethyl 2-(acetylamino)-2-deoxy-β-D-glucopyranoside The title compound was prepared using procedures analogous to those described for Example 1, ML-1, substituting benzyl 6-{[3-(2,3,4-tri-O-benzyl-α-L-fucopyranosyl)propyl](2-{[2-(acetylamino)-2-deoxy-β-D-glucopyranosyl]oxy}ethyl)amino}hexanoate for benzyl 6-({2-[(α-D-mannopyranosyl-(1→3)-[α-D-mannopyranosyl-(1→6)]-α-D-mannopyranosyl)oxy]ethyl}amino-6-oxohexanoate" in Step C. UPLC Method B: m/e=664.3474 [M+1]; Rt=1.08 min Example 37

The synthesis of oligosaccharide linker 2-({6-[(2,5-Dioxopyrrolidin-1-yl)oxy]-6-oxohexyl}[3-(α-L-fucopyranosyl) propyl]amino)ethyl β-D-glucopyranoside_(ML-37) having the following structure is described.

ML-37

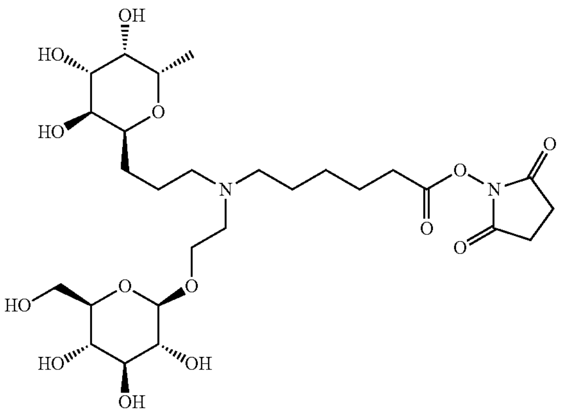

The title compound was prepared using procedures analogous to those described for ML-36 substituting 2-aminoethyl 2,3,4,6-tetra-O-acetyl-β-D-glucopyranoside for 2-aminoethyl 3,4,6-tri-O-acetyl-2-(acetylamino)-2-deoxy-β-D-glucopyranoside in Step F. UPLC Method B: m/e=623.3277 [M+1]; Rt=1.11 min.

Example 38

The synthesis of oligosaccharide linker 2-({6-[(2,5-Dioxopyrrolidin-1-yl)oxy]-6-oxohexyl}[3-(α-L-fucopyranosyl)propyl]amino)ethyl α-D-glucopyranoside_(ML-38) having the following structure is described.

ML-38

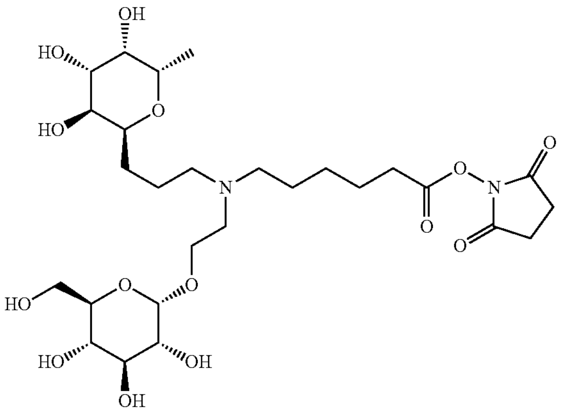

The title compound was prepared using procedures analogous to those described for ML-36 substituting 2-aminoethyl 2,3,4,6-tetra-O-acetyl-α-D-glucopyranoside for 2-aminoethyl 3,4,6-tri-O-acetyl-2-(acetylamino)-2-deoxy-β-D-glucopyranoside Step F. UPLC Method B: m/e=623.3336 [M+1]; Rt=1.11 min.

Example 39

The synthesis of oligosaccharide linker 2,5-Dioxopyrrolidin-1-yl 6-{[3-(α-L-fucopyranosyl)propyl][2-(α-D-glucopyranosyl)propyl]amino}hexanoate_(ML-39) having the following structure is described.

ML-39

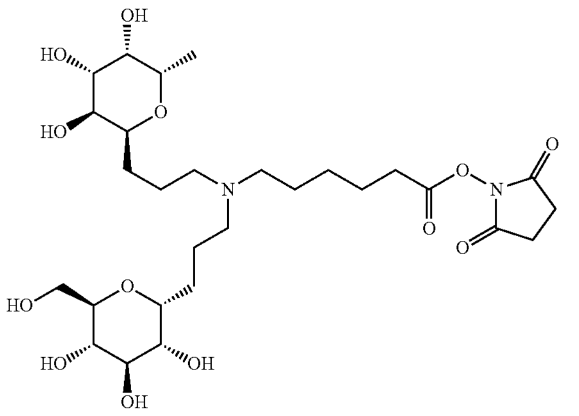

Step A: methyl 2,3,4,6-tetra-O-benzyl-α-D-glucopyranoside

To a suspension of NaH (5.19 g of a 60% dispersion in oil, 130 mmol) in DMF (150 mL) was added portionwise methyl-α-D-glucopyranoside (4.2 g, 21.6 mmol). The resulting mixture was stirred at rt for 2 hr, to which tetrabutyl ammonium bromide (800 mg, 2.16 mmol) was and followed by dropwise addition of benzyl bromide (11.58 mL, 97 mmol). After stirring at rt overnight, the mixture was concentrated and the residue was suspended in water and extracted with ether (3×150 mL). The combined ether layers were washed with brine (200 mL), dried over $Na_2SO_4$, filtered and evaporated. The residue was purified by flash chromatography on silica gel (330 g), eluting with 0-30% EtOAc in hexanes to give the title compound. $^1$H NMR ($CDCl_3$, 400 MHz) δ 3.44 (s, 3H), 3.62 (dd, J=9.6, 3.5, 1H), 3.66-3.72 (m, 2H), 3.75-3.82 (m, 2H), 4.04 (t, J=9.3, 1H), 4.51-4.55 (m, 2H), 4.66 (d, J=12.1, 1H), 4.69 (d, J=3.5, 1H), 4.72 (d, J=12.1, 1H), 4.83-4.90 (m, 3H), 5.04 (d, J=11.0, 1H), 7.19 (m, 2H), 7.30-7.43 (m, 18H).

Step B: 3-(2,3,4,6-tetra-O-benzyl-α-D-glucopyranosyl)-1-propene

The title compound was prepared using the procedure analogous to that described for ML-36 in Step A, substituting methyl 2,3,4,6-tetra-O-benzyl-α-D-glucopyranoside for 1,2,3,4-tetra-O-acetyl-α-L-fucopyranose. $^1$H NMR ($CDCl_3$) δ 2.48-2.60 (m, 2H), 3.64-3.70 (m, 3H), 3.76 (dd, J=10.5, 3.2, 1H), 3.80-3.88 (m, 2H), 4.18 (m, 1H), 4.52 (d, J=10.5, 2H), 4.68 (d, J=13.7, 2H), 4.74 (d, J=11.6, 1H), 4.86 (dd, J=10.6, 3.3, 2H), 4.98 (d, J=11.0, 1H), 5.11-5.18 (m, 2H), 5.84-5.90 (m, 1H), 7.18 (m, 2H), 7.29-7.41 (m, 18H).

Step C: 3-(2,3,4,6-tetra-O-benzyl-α-D-glucopyranosyl)propanol

The title compound was prepared using the procedure analogous to that described for ML-36 in Step D, substituting 3-(2,3,4,6-tetra-O-benzyl-α-D-glucopyranosyl)-1-propene for 3-(2,3,4-tri-O-benzyl-α-L-fucopyranosyl)-1-propene. $^1$H NMR ($CDCl_3$) δ 1.70 (m, 2H), 1.85 (m, 2H), 3.61

(m, 1H), 3.65-3.76 (m, 2H), 3.76-3.86 (m, 2H), 4.91 (m, 1H), 4.52 (d, J=10.8, 1H), 4.55 (d, J=12.3, 1H), 4.65 (d, J=12.1, 1H), 4.67 (d, J=11.8, 1H), 4.75 (d, J=11.7, 1H), 4.86 (d, J=11.3, 2H), 4.98 (d, J=11.0, 1H), 7.18 (m, 2H), 7.29-7.40 (m, 18H).

Step D: 3-(2,3,4,6-tetra-O-benzyl-α-D-glucopyranosyl)propyl methanesulfonate

To a solution of 3-(2,3,4,6-tetra-O-benzyl-α-D-glucopyranosyl)propanol (3.35 g, 5.75 mmol) in $CH_2Cl_2$ (30 mL) at 0° C. was added DIPEA (1.25 mL, 7.19 mmol) and followed by dropwise addition of methanesulfonyl chloride (538 μL, 6.9 mmol). After stirring at 0° C. for 1 hr, the reaction mixture was poured into water (50 mL). The organic layer was separated and washed with sat'd $NaHCO_3$ (50 mL), brine (30 mL), dried over $MgSO_4$, filtered and concentrated to give the title compound. $^1$H NMR ($CDCl_3$) δ 1.76-1.90 (m, 3H), 1.90-1.99 (m, 2H), 3.00 (s, 3H), 3.58-3.66 (m, 2H), 3.68-3.74 (m, 2H), 3.77-3.85 (m, 2H), 4.06 (m, 1H), 4.52 (d, J=10.7, 1H), 4.54 (d, J=12.1, 1H), 4.65 (d, J=12.1, 1H), 4.66 (d, J=11.6, 1H), 4.76 (d, J=11.6, 1H), 4.85 (d, J=10.9, 1H), 4.98 (d, J=10.9, 1H), 7.18 (m, 2H), 7.30-7.40 (m, 18H).

Step E: 3-(2,3,4,6-tetra-O-benzyl-α-D-glucopyranosyl)propyl azide

To a solution of 3-(2,3,4,6-tetra-O-benzyl-α-D-glucopyranosyl)propyl methanesulfonate (3.78 g, 5.72 mmol) in AcCN (50 mL) was added tetrabutylammonium azide (1.66 g, 5.83 mmol). The resulting mixture allowed to reflux overnight. After cooled to rt, the reaction mixture was concentrated. The residue was dissolved in ether (50 mL), which was washed with water (2×50 mL), brine (25 mL), dried over $Na_2SO_4$, filtered and concentrated. The residue was purified by flash chromatography on silica gel (120 g, eluting with 0-30% EtOAc in hexanes) to give the title compound. $^1$H NMR ($CDCl_3$) δ 1.58-1.68 (m, 2H), 1.74-1.86 (m, 2H), 3.32-3.41 (m, 2H), 3.58-3.76 (m, 4H), 3.76-3.85 (m, 2H), 4.40 (m, 1H), 4.52 (t, J=10.4, 2H), 4.65 (dd, J=11.7, 2.5, 2H), 4.75 (d, J=11.7, 1H), 4.86 (m, 2H), 4.97 (d, J=10.8, 1H), 7.16 (m, 2H), 7.28-7.40 (m, 18H).

Step F: 3-(2,3,4,6-tetra-O-benzyl-α-D-glucopyranosyl)propylamine

To a nitrogen flushed solution of 3-(2,3,4,6-tetra-O-benzyl-α-D-glucopyranosyl)propyl azide (3 g, 4.94 mmol) in $CH_3OH$ (100 mL) was added 10% Pd/C (525 mg). The resulting mixture was allowed to stir under a balloon of $H_2$ overnight. The reaction mixture was filtered through a Celite pad and the filtrate was concentrated to give the title compound. $^1$H NMR ($CDCl_3$) δ 1.48 (m, 1H), 1.59 (m, 1H), 2.23 (m, 1H), 2.30 (m, 2H), 3.66-3.76 (m, 5H), 4.00 (m, 1H), 4.09 (m, 1H), 4.38 (d, J=10.0, 1H), 4.50 (d, J=12.1, 1H), 4.61 (d, J=11.7, 1H), 4.68 (d, J=11.8, 1H), 4.70 (d, J=12.0, 1H), 4.79 (d, J=10.0, 1H), 4.86 (d, J=11.2, 1H), 5.02 (d, J=11.2, 1H), 7.00 (m, 2H), 7.25-7.40 (m, 18H), 8.06 (s, 2H).

Step G: 2,5-dioxopyrrolidin-1-yl 6-{[3-(α-L-fucopyranosyl)propyl][2-(α-D-glucopyranosyl)propyl]amino}hexanoate The title compound was prepared using procedures analogous to those described for ML-36 substituting 3-(2,3,4,6-tetra-O-benzyl-α-D-glucopyranosyl)propylamine for 2-aminoethyl 3,4,6-tri-O-acetyl-2-(acetylamino)-2-deoxy-β-D-glucopyranoside in Step F. UPLC Method B: m/e=621.3424 [M+1]; Rt=1.08 min.

Example 40

The synthesis of oligosaccharide linker 2,5-Dioxopyrrolidin-1-yl 6-{[3-(α-L-fucopyranosyl)propyl][2-(β-D-glucopyranosyl)propyl]amino}hexanoate (ML-40) having the following structure is described.

ML-40

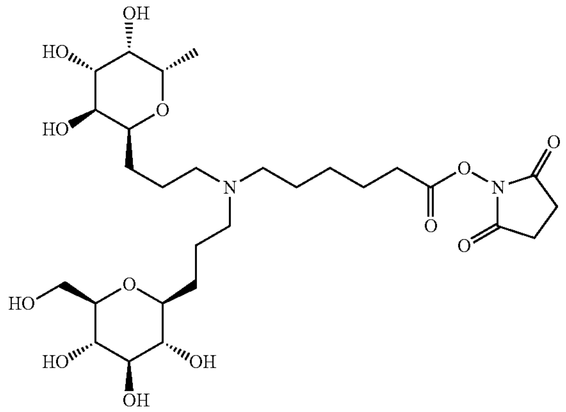

Step A: 2,3,4,6-tetra-O-acetyl-α-D-glucopyranosyl bromide

To β-D-glucose pentaacetate (5 g, 12.81 mmol) was added 33% HBr in acetic acid (30 mL, 192 mmol) at rt. After stirring for 40 min, the mixture was diluted with $CH_2Cl_2$ (150 mL) and washed with ice cold water until the washings were neutral pH. The organic layer was dried over $MgSO_4$, filtered and concentrated to give the title compound. $^1$H NMR ($CDCl_3$) δ 2.06 (s, 3H), 2.08 (s, 3H), 2.12 (s, 3H), 2.13 (s, 3H), 4.15 (d, J=11.1, 1H), 4.31-4.37 (m, 2H), 4.86 (dd, J=9.9, 4.0, 1H), 5.19 (t, J=9.8, 1H), 5.58 (t, J=9.8, 1H), 6.63 (d, J=4.0, 1H).

Step B: 3-(2,3,4,6-tetra-O-acetyl-β-D-glucopyranosyl)-1-propene

To a solution of allyl magnesium bromide (100 mL, 100 mmol, 1.0 Min ether) at 0° C. was added dropwise 2,3,4,6-tetra-O-acetyl-α-D-glucopyranosyl bromide (4.45 g, 10.82 mmol) in ether (60 mL) over a period of 1 hr. After completion of the addition, the mixture was allowed to warm up and stirred at rt overnight. To the resulting mixture was carefully added water (200 mL) and followed by the addition of acetic acid to dissolve magnesium salts. The organic layer was separated and concentrated. The residue was treated with acetic anhydride (70 mL, 740 mmol) and pyridine (100 mL). After stirring at rt overnight, the mixture was concentrated and the residue taken up in EtOAc (200 mL) and washed with sat'd $NaHCO_3$ (5×300 mL), dried over $MgSO_4$, filtered and evaporated. The residue was purified by flash chromatography on silica gel (120 g, eluting with 0-100% EtOAc in hexanes) to give the title compound. $^1$H NMR ($CDCl_3$) δ 2.00 (s, 3H), 2.03 (s, 3H), 2.04 (s, 3H), 2.09 (s, 3H), 2.26-2.37 (m, 2H), 3.51 (m, 1H), 3.65 (m, 1H), 4.10

(dd, J=12.2, 2.2, 1H), 4.24 (dd, J=12.2, 5.0, 1H), 4.93 (t, J=9.4, 1H), 5.07 (m, 2H), 5.09 (s, 1H), 5.17 (t, J=9.4, 1H), 5.83 (m, 1H).

Step C: 3-(β-D-glucopyranosyl)-1-propene

To a solution of 3-(2,3,4,6-tetra-O-acetyl-β-D-glucopyranosyl)-1-propene (4.15 g, 11.14 mmol) in $CH_3OH$ (50 mL) was added $NaOCH_3$ (0.56 mL, 2.2 mmol, 4.0 Min $CH_3OH$). After stirring at rt for 2 hr, the reaction mixture was neutralized using Dowex 50 W (acidic form). The resin was filtered off and the filtrate was concentrated to give the title compound. $^1H$ NMR (DMSO-d6) δ 2.09 (m, 1H), 2.49 (m, 1H), 2.88 (t, J=8.9, 1H), 2.98-3.07 (m, 3H), 3.11 (m, 1H), 3.39 (dd, J=11.4, 4.7, 1H), 3.60 (d, J=11.6, 1H), 4.99 (dd, J=10.3, 0.9, 1H), 5.06 (d, J=17.2, 1H), 5.90 (m, 1H).

Step D: 3-(2,3,4,6-tetra-O-benzyl-β-D-glucopyranosyl)-1-propene

The title compound was prepared using the procedure analogous to that described for ML-36 in Step C, substituting 3-(β-D-glucopyranosyl)-1-propene for 3-(α-L-fucopyranosyl)-1-propene. $^1H$ NMR ($CDCl_3$) δ 2.39 (m, 1H), 2.65 (m, 1H), 3.41 (m, 2H), 3.49 (m, 1H), 3.68 (t, J=9.5, 1H), 3.72-3.82 (m, 3H), 4.72 (dd, J=10.8, 2.1, 1H), 4.89 (d, J=10.7, 1H), 4.94-500 (m, 3H), 5.16 (m, 2H), 6.03 (m, 1H), 7.25 (m, 2H), 7.32-7.44 (m, 18H).

Step E: 3-(2,3,4,6-tetra-O-benzyl-β-D-glucopyranosyl)-1-propanol

The title compound was prepared using the procedure analogous to that described for ML-36 in Step D, substituting 3-(2,3,4,6-tetra-O-benzyl-β-D-glucopyranosyl)-1-propene for 3-(2,3,4-tri-O-benzyl-α-L-fucopyranosyl)-1-propene. $^1H$ NMR ($CDCl_3$) δ 1.60 (m, 1H), 1.76 (m, 2H), 2.04 (m, 1H), 2.36 (t, J=5.7, 1H), 3.35 (m, 2H), 3.49 (m, 1H), 3.62-3.72 (m, 4H), 3.72-3.77 (m, 2H), 4.58 (d, J=12.2, 1H), 4.60 (d, J=10.7, 1H), 4.65 (d, J=12.2, 1H), 4.70 (d, J=10.8, 1H), 4.86 (d, J=10.8, 1H), 4.95 (m, 3H), 7.21 (m, 2H), 7.31-7.41 (m, 18H).

Step F: 2,5-Dioxopyrrolidin-1-yl 6-{[3-(α-L-fucopyranosyl)propyl][2-(β-D-glucopyranosyl)propyl]amino}hexanoate The title compound was prepared using procedures analogous to those described for ML-39 substituting 3-(2,3,4,6-tetra-O-benzyl-β-D-glucopyranosyl)-1-propanol for 3-(2,3,4,6-tetra-O-benzyl-α-D-glucopyranosyl)propanol in Step D. UPLC Method B: m/e=621.3412 [M+1]; Rt=1.08 min.

Example 41

The synthesis of oligosaccharide linker 2-({6-[(2,5-Dioxopyrrolidin-1-yl)oxy]-6-oxohexyl}[3-(α-D-mannopyranosyl)propyl]amino)ethyl α-L-fucopyranoside (ML-41) having the following structure is described.

ML-41

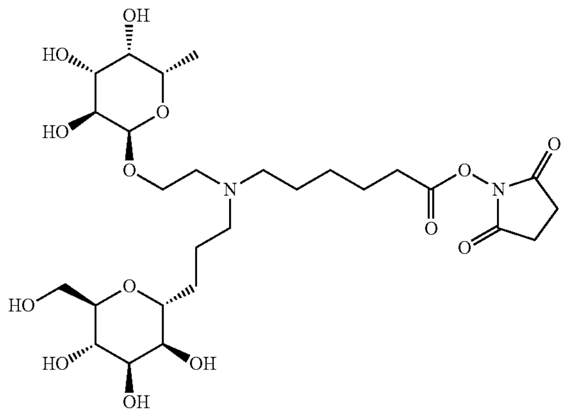

Step A: 3-(2,3,4,6-tetra-O-benzyl-α-D-mannopyranosyl)-1-propene

The title compound was prepared using the procedure analogous to that described for ML-39 in Step B, substituting methyl 2,3,4,6-tetra-O-benzyl-α-D-mannopyranoside for methyl 2,3,4,6-tetra-O-benzyl-α-D-glucopyranoside, as a mixture of α and β anomers. These anomers were separated by Chiral SFC chromatography (Column: AD-H (50×250 cm), eluting with 30% IPA (0.1% DEA)/$CO_2$, 100 bar, 200 mL/min, 220 nm; injection volume: 1.0 mL at concentration of 162 mg/mL 4:1 v/v IPA/$CH_2Cl_2$) to give the major product as the a anomer. $^1H$ NMR ($CDCl_3$) δ 2.38 (m, 2H), 3.68 (dd, J=4.6, 3.2, 1H), 3.76 (dd, J=10.4, 3.7, 1H), 3.83 (m, 2H), 3.90 (m, 2H), 4.10 (m, 1H), 4.55-4.62 (m, 4H), 4.62-4.65 (m, 3H), 4.75 (d, J=11.3, 1H), 5.06 (d, J=4.6, 1H), 5.08 (s, 1H), 5.80 (m, 1H), 7.25 (m, 2H), 7.30-7.42 (m, 18H).

Step B: 3-(2,3,4,6-tetra-O-benzyl-α-D-mannopyranosyl)-1-propanol

The title compound was prepared using the procedure analogous to that described for ML-39 in Step C, substituting 3-(2,3,4,6-tetra-O-benzyl-α-D-mannopyranosyl)-1-propene for 3-(2,3,4,6-tetra-O-benzyl-α-D-glucopyranosyl)-1-propene. $^1H$ NMR ($CDCl_3$) δ 1.85-2.00 (m, 2H), 2.53 (m, 1H), 2.60 (m, 1H), 3.62 (dd, J=6.0, 2.4, 1H), 3.73 (dd, J=10.2, 4.2, 1H), 3.78-3.87 (m, 3H), 3.90 (m, 1H), 3.98 (m, 1H), 4.54-4.62 (m, 7H), 4.67 (d, J=11.5, 1H), 7.25 (m, 2H), 7.28-7.40 (m, 18H), 9.79 (s, 1H).

Step C: 2-({6-[(2,5-dioxopyrrolidin-1-yl)oxy]-6-oxohexyl}[3-(α-D-mannopyranosyl)propyl]amino)ethyl α-L-fucopyranoside The title compound was prepared using procedures analogous to those described for ML-36, substituting 3-(2,3,4,6-tetra-O-benzyl-α-D-mannopyranosyl)-1-propanol for 3-(2,3,4-tri-O-benzyl-α-L-fucopyranosyl)propanol in Step E and 2-aminoethyl (2,3,4-tri-O-acetyl-α-L-fucopyranoside) for 2-aminoethyl (3,4,6-tri-O-acetyl-2-(acetylamino)-2-deoxy- β-D-glucopyranoside) in step F. UPLC Method B: m/e=623.3235 [M+1]; Rt=1.13 min.

Example 42

The synthesis of oligosaccharide linker 2,5-Dioxopyrrolidin-1-yl 6-{[3-(α-L-fucopyranosyl)propyl][2-(α-D-mannopyranosyl)propyl]amino}hexanoate (ML-42) having the following structure is described.

ML-42

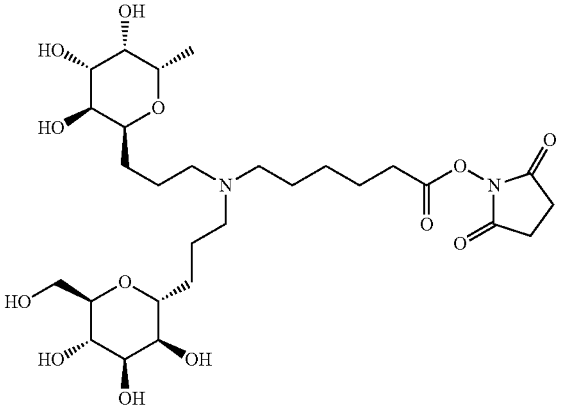

The title compound was prepared using procedures analogous to those described for ML-39, substituting 3-(2,3,4,6-tetra-O-benzyl-α-D-mannopyranosyl)-1-propanol for 3-(2,3,4,6-tetra-O-benzyl-α-D-glucopyranosyl)propanol in Step D. UPLC Method B: m/e=621.3358 [M+1]; Rt=1.11 min.

Example 43

The synthesis of oligosaccharide linker 2,5-Dioxopyrrolidin-1-yl 3-({6-[({bis[2-({2-[(α-L-fucopyranosyl)oxy]ethyl}amino)-2-oxoethyl]amino}acetyl)amino]hexyl}amino)-N-[(9H-fluoren-9-ylmethoxy)carbonyl]-D-alaninate (ML-43) having the following structure is described.

Step A: pentafluorophenyl 6-[({bis[2-({2-[(α-L-fucopyranosyl)oxy]ethyl}amino)-2-oxoethyl]amino}acetyl)amino]hexanoate To a stirred solution of 6-[({bis[2-({2-[(α-L-fucopyranosyl)oxy]ethyl}amino)-2-oxoethyl]amino}acetyl)amino]hexanoic acid (1.0 g, 1.465 mmol, in DMF (7.7 mL) at 0° C. was added PFTU (627 mg, 1.465 mmol) and, 5 min later, DIPEA (256 μL, 1.465 mmol). The mixture was allowed to warm up gradually to room temperature. After stirring for 16 hr, the reaction mixture was concentrated and the residue was purified by flash chromatography on silica gel (40 g), eluting with 300 mL of EtOAc to wash out unpolar admixtures, and then with a mix solvent (v/v EtOAc/$H_2O$/MeOH/AcCN: 6/1/1/1), =6:1:1:1) to yield the title product. LC-MS Method A: m/e=849.50 [M+1]; Rt=1.94 min.

Step B: 3-amino-N-[(9H-fluoren-9-ylmethoxy)carbonyl]-L-alanine hydrochloride

To a stirred solution of 3-[(tert-butoxycarbonyl)amino]-N-[(9H-fluoren-9-ylmethoxy)carbonyl]-D-alanine (1.0 g, 2.35 mmol) in $CH_2Cl_2$ (11.72 mL) was added HCl (4.0 M in dioxane, 11.72 mL, 46.9 mmol). After stirring for 16 hours, the reaction mixture was concentrated to give the title product, which was used without further purification. LC-MS Method A: m/e=327.19 [M+1]; Rt=1.73 min.

Step C: 3-({6-[({bis[2-oxo-2-({2-[(α-L-fucopyranosyl)oxy]ethyl}amino)ethyl]amino}acetyl)amino]hexanoyl}amino)-N-[(9H-fluoren-9-ylmethoxy)carbonyl]-L-alanine To a stirred solution of pentafluorophenyl 6-[({bis[2-({2-[(α-L-fucopyranosyl)oxy]ethyl}amino)-2-oxoethyl]amino}acetyl)amino]hexanoate (270 mg, 0.318 mmol) in DMF at 0° C. was added 3-amino-N-[(9H-fluoren-9-ylmethoxy)carbonyl]-L-alanine hydrochloride (303 mg, 0.306 mmol) and, 5 min later, DIPEA (111 μL, 0.636 mmol). After stirring at 0° C. for 2 hr, the reaction mixture was concentrated and the residue was purified by flash chromatography on silica gel (22 g), eluting first with 100 mL of EtOAc and then 0-20% of Solvent B in Solvent A (Solvent A: v/v EtOAc/MeOH/AcCN/$H_2O$: 6/1/1/1; Solvent B v/v EtOAc/

ML-43

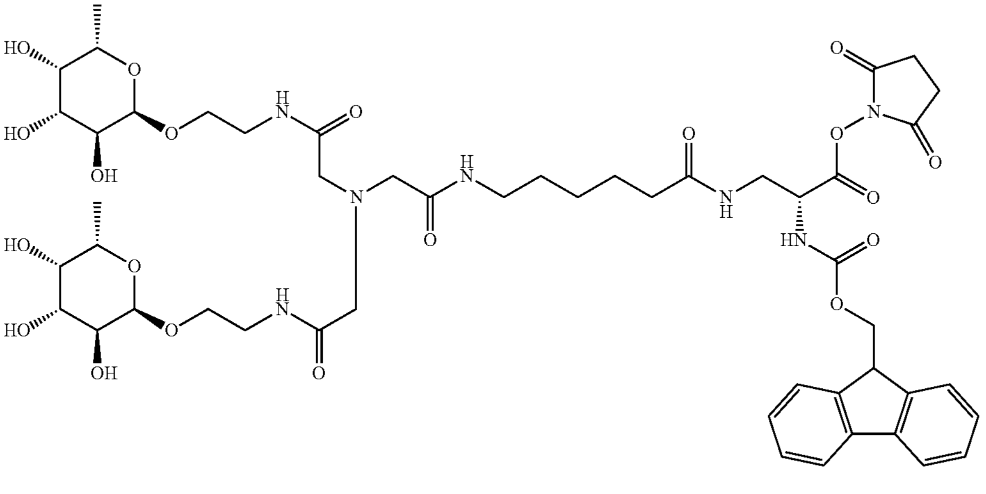

MeOH/AcCN/$H_2O$: 2/1/1/1) to afford the title compound. LC-MS Method A: m/e=991.66 [M+1]; Rt=1.84 min.

Step D: 2,5-dioxopyrrolidin-1-yl 3-({6-[({bis[2-({2-[(α-L-fucopyranosyl)oxy]ethyl}amino)-2-oxoethyl]amino}acetyl)amino]hexyl}amino)-N-[(9H-fluoren-9-ylmethoxy)carbonyl]-D-alaninate The title compound was prepared using procedures analogous to those described for ML-1 substituting 3-({6-[({bis[2-oxo-2-({2-[(α-L-fucopyranosyl)oxy]ethyl}amino)ethyl]amino}acetyl)amino]hexanoyl}amino)-N-[(9H-fluoren-9-ylmethoxy)carbonyl]-L-alanine for 6-({2-[(α-D-mannopyranosyl-(1→3)-[α-D-mannopyranosyl-(1→6)]-α-D-mannopyranosyl)oxy]ethyl}amino)-6-oxohexanoic acid in Step D. LC-MS Method A: m/e=1088.9 [M+1]; Rt=1.96 min.

Example 44

The synthesis of oligosaccharide linker 2,5-Dioxopyrrolidin-1-yl 3-({6-[({bis[2-({2-[(α-L-fucopyranosyl)oxy]ethyl}amino)-2-oxoethyl]amino}acetyl)amino]hexyl}amino)-N-[(9H-fluoren-9-ylmethoxy)carbonyl]-L-alaninate (ML-44) having the following structure is described.

ML-44

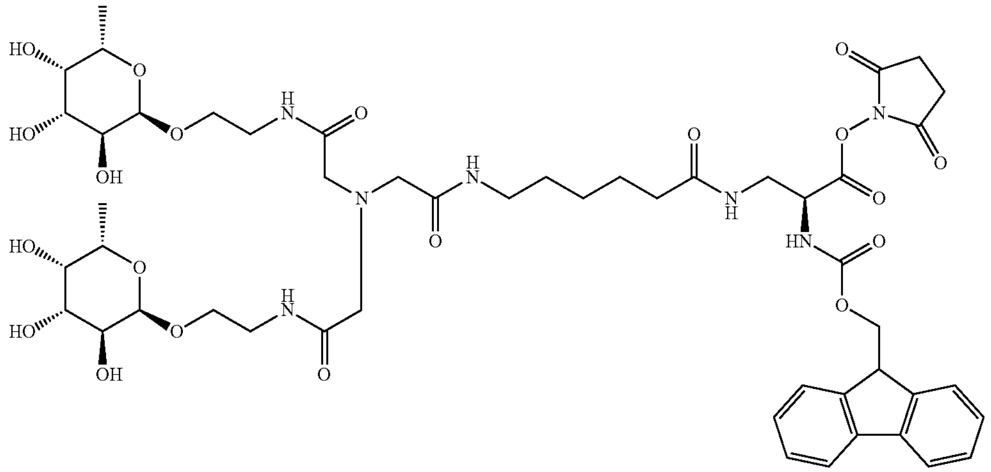

The title compound was prepared using procedures analogous to those described for ML-43 substituting 3-[(tert-butoxycarbonyl)amino]-N-[(9H-fluoren-9-ylmethoxy)carbonyl]-L-alanine for 3-[(tert-butoxycarbonyl)amino]-N-[(9H-fluoren-9-ylmethoxy)carbonyl]-D-alanine in Step B. LC-MS Method A: m/e=1088.9 [M+1]; Rt=1.96 min.

Example 45

The synthesis of oligosaccharide linker 2,2'-{[2-({6-[(2,5-Dioxopyrrolidin-1-yl)oxy]-6-oxohexyl}amino)-2-oxoethyl]imino}bis(N-{[1-(α-D-mannopyranosyl)-1H-1,2,3-triazol-4-yl]methyl}acetamide) (ML-45) having the following structure is described.

ML-45

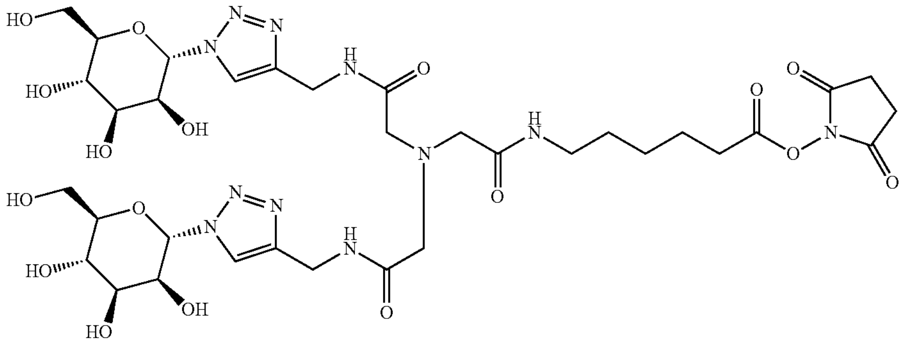

Step A: benzyl 6-[({bis[2-oxo-2-(prop-2-yn-1-ylamino)ethyl]amino}acetyl)amino]hexanoate The title compound was prepared using the procedure analogous to that described for ML-1 Step B, substituting propargylamine for 2-aminoethyl α-D-mannopyranosyl-(1→3)-[α-D-mannopyranosyl-(1→6)]-α-D-mannopyranoside. $^1$H NMR ($CDCl_3$, 400 MHz) δ 7.32 (m, 5H), 5.08 (s, 2H), 4.014 (s, 4H), 3.298 (m, 4H), 3.23 (m, 2H), 3.21 (m, 2H), 2.32 (m, 2H), 2.22 (s, 2H), 1.63 (m, 2H), 1.51 (m, 2H), 1.33 (m, 2H).

Step B: benzyl 6-[({bis[2-oxo-2-({[1-(α-D-mannopyranosyl)-1H-1,2,3-triazol-4-yl]methyl}amino)ethyl]amino}acetyl)amino]hexanoate To a stirred solution of benzyl 6-[({bis[2-oxo-2-(prop-2-yn-1-ylamino)ethyl]amino}acetyl)amino]hexanoate (546 mg, 1.165 mmol) and α-D-mannopyranosyl azide (598 mg, 2.91 mmol) in DMF (5.8 mL) was added DIPEA (1.0 mL, 5.83 mmol) and Cu(I) iodide (222 mg, 1.165 mmol). The reaction mixture was allowed to stir at 60° C. for 30 min until all CuI dissolved and then to stir at rt for 1 hr. The reaction mixture was diluted by 10× volume of $CH_3OH$. The precipitated inorganics was filtered out. The filtrate was concentrated and the residue was purified by flash chromatography on silica gel (40 g), eluting with 0-60% Solvent B in Solvent A (Solvent A: v/v EtOAc/MeOH/AcCN/$H_2O$: 6/1/1/1; Solvent B v/v EtOAc/MeOH/AcCN/$H_2O$: 2/1/1/1), to give the title compound. LC-MS Method A: m/e=879.31 [M+1]; Rt=0.98 min.

Step C: 2,2'-{[2-({6-[(2,5-dioxopyrrolidin-1-yl)oxy]-6-oxohexyl}amino)-2-oxoethyl]imino}bis(N-{[1-(α-D-mannopyranosyl)-1H-1,2,3-triazol-4-yl]methyl}acetamide)

The title compound was prepared using procedures analogous to those described for ML-1, substituting benzyl 6-[({bis[2-oxo-2-({[1-(α-D-mannopyranosyl)-1H-1,2,3-triazol-4-yl]methyl}amino)ethyl]amino}acetyl)amino]hexanoate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C. UPLC Method A: m/e=886.2 [M+1]; Rt=2.02 min.

Example 46

The synthesis of oligosaccharide linker 2,2'-{[2-({6-[(2,5-Dioxopyrrolidin-1-yl)oxy]-6-oxohexyl}amino)-2-oxoethyl]imino}bis(N-{2-[(β-L-fucopyranosyl)oxy]ethyl}acetamide) (ML-46) having the following structure is described.

ML-46

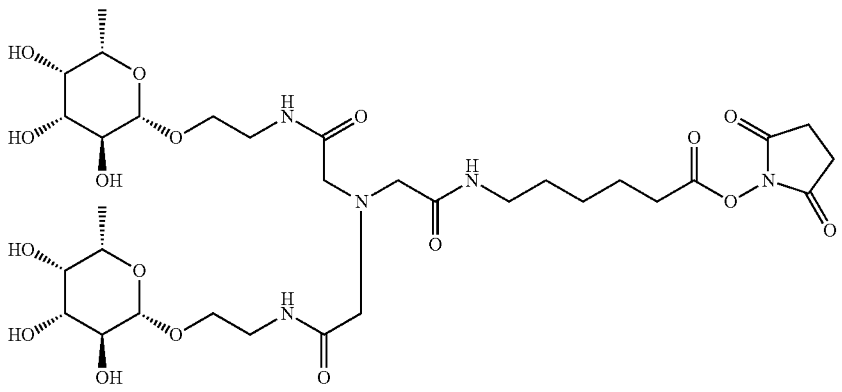

-

The title compound was prepared using procedures analogous to those described for ML-7 substituting 2-aminoethyl β-L-fucopyranoside for 2-aminoethyl a-L-fucopyranoside in Step B. UPLC Method B: m/e=780.361 [M+1]; Rt=2.09 min.

Example 47

The synthesis of oligosaccharide linker 6-[(2,5-Dioxopyrrolidin-1-yl)oxy]-N-[2-({2-[(α-L-fucopyranosyl)oxy]ethyl}amino)-2-oxoethyl]-N-{2-[(2-{[α-D-mannopyranosyl-(1→3)-[α-D-mannopyranosyl-(1→6)]-α-D-mannopyranosyl]oxy}ethyl)amino]-2-oxoethyl}-6-oxohexanamide (ML-47) having the following structure is described.

ML-47

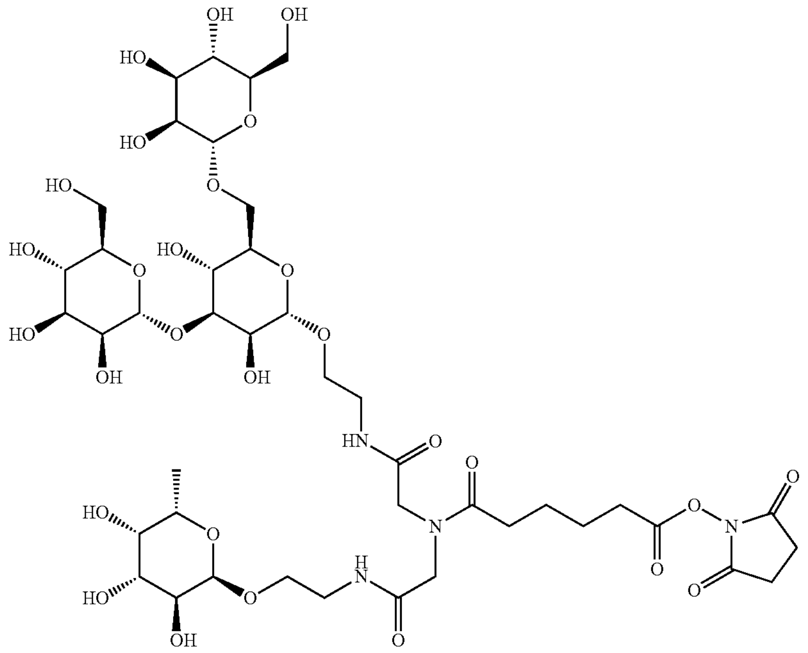

The title compound was prepared using procedure analogous to those described for ML-29 substituting 2,2'-{[6-(benzyloxy)-6-oxohexanoyl]imino}diacetic acid for 2,2'-[(2-{[6-(benzyloxy)-6-oxohexyl]amino}-2-oxoethyl)imino] diacetic acid. UPLC Method B: m/e=1070.33 [M+1]; Rt=3.08 min.

Example 48

The synthesis of oligosaccharide linker 2-{[2-({2-[(α-L-Fucopyranosyl)oxy]ethyl}amino)-2-oxoethyl][2-({6-[(2,5-dioxopyrrolidin-1-yl)oxy]-6-oxohexyl}amino)-2-oxoethyl] amino}-N-[2-(α-D-mannopyranosyloxy)ethyl]acetamide (ML-48) having the following structure is described.

ML-48

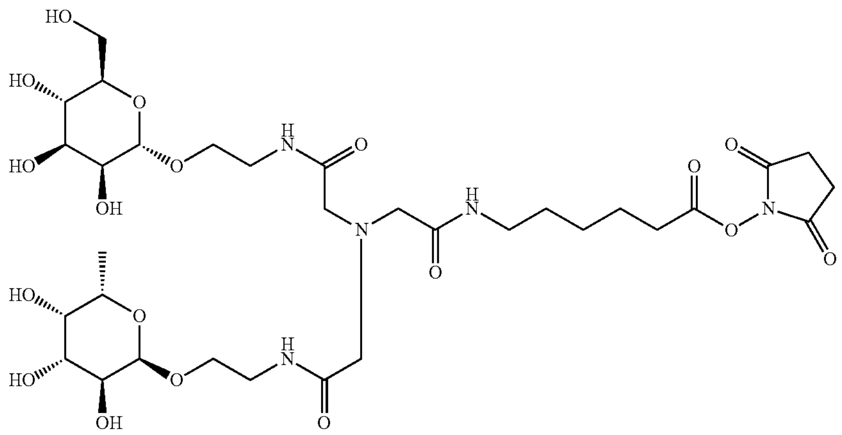

The title compound was prepared using procedures analogous to those described for ML-23 substituting 2-aminoethyl a-L-fucopyranoside for 6-amino-N-(2-α-L-fucopyranosyl)ethyl)hexanamide in Step C and 2-aminoethyl a-D-mannopyranoside for 2-aminoethyl α-D-mannopyranosyl-(1→3)-[α-D-mannopyranosyl-(1→6)]-α-D-mannopyranoside in Step D, respectively. UPLC Method B m/e=796.37 [M+1]; Rt=1.87 min.

Example 49

The synthesis of oligosaccharide linker 2-{[2-({2-[(α-L-Fucopyranosyl)oxy]ethyl}amino)-2-oxoethyl][2-({6-[(2,5-dioxopyrrolidin-1-yl)oxy]-6-oxohexyl}amino)-2-oxoethyl]amino}-N-[2-(β-D-mannopyranosyloxy)ethyl]acetamide (ML-49) having the following structure is described.

mmol) in $CH_2Cl_2$ (26 mL) at −20° C. was added pyridine (2.4 mL, 29.7 mmol) and, 5 min, triflic anhydride (1.1 mL, 6.51 mmol) dropwise. The mixture was allowed to slowly warm from −20° C. to 0° C. over 2 hr. The resulting mixture was diluted with $CH_2Cl_2$ (75 mL), which was washed with cold 1.0 M HCl (100 mL), cold sat'd $NaHCO_3$ (100 mL), cold water (100 mL), and cold brine (100 mL). The organic phase was dried over $Na_2SO_4$ and concentrated at low temperature. The residue was dissolved in AcCN (20 mL), to which a solution of tetrabutylammonium nitrite (3.0 g, 10.40 mmol) in AcCN (6 mL) was added. After stirring at 50° C. for 6 hr, the reaction mixture was concentrated and the residue was purified by flash column chromatography on silica gel (330 g), eluting with 0-75% EtOAc in hexanes, to give the title compound. TLC: silica gel, hexane/Ethylacetate: 1/1, $R_f$=0.33. UPLC Method B: calculated for

ML-49

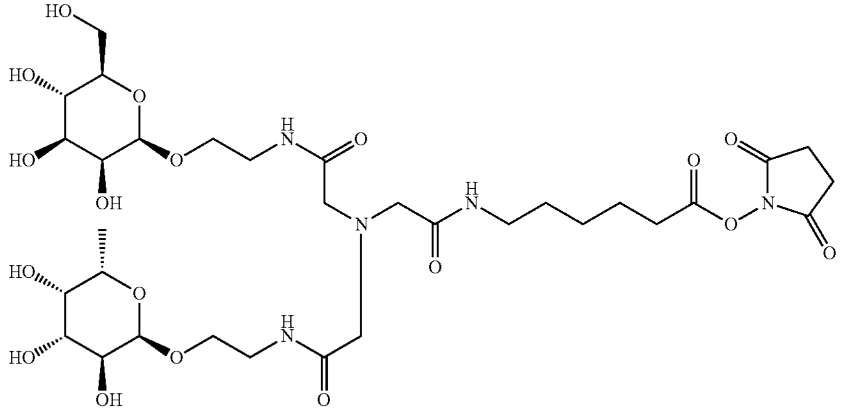

Step A: benzyl {2-[(3,6-di-O-benzyol-β-D-galactopyranosyl)oxy]ethyl}carbamate

To a solution of benzyl 2-({2-[(β-D-galactopyranosyl)oxy]ethyl}amino)carbamate (15.5 g, 43.4 mmol, Beilstein J. Org. Chem. 2010, 6, 699) and 4 Å molecular sieves in toluene (150 mL) was added dibutylstannanone (23.4 g, 94 mmol). After refluxing for 5 hr, the reaction mixture was slowly cooled down to 0° C., to which benzoyl chloride (11 mL, 95 mmol) was added dropwise. The resulting mixture was allowed gradually warm up rt. After stirring at rt for 24 hr, the reaction mixture was filtered and the filtrate was concentrated. The residue was purified by flash chromatography on silica gel (330 g), eluting with 0-75% EtOAc in hexanes, to give the title compound. TLC: silica gel, hexane/EtOAc: 1/1, $R_f$=0.35. UPLC Method B: calculated for $C_{30}H_{31}NO_{10}$ 565.19 observed m/e=566.21 [M+1]; Rt=1.87 min. $^1$H NMR ($CDCl_3$) δ 8.05-7.95 (4H, m), 7.60-7.25 (11H, m), 5.10-5.05 (1H, m), 5.02 (2H, s), 4.60-4.55 (1H, m), 4.50-4.45 (1H, m), 4.40-4.35 (1H, m), 4.20-4.15 (1H, m), 4.05-4.00 (1H, m), 3.90-3.80 (2H, m), 3.75-3.70 (1H, m), 3.45-3.30 (1H, m), 3.35-3.25 (1H, m). Regiochemistry was confirmed by $^1$H-$^{13}$C one-bond correlation (HSQC); $^1$H-$^{13}$C multiple-bond correlation (HMBC); and $^1$H-$^1$H NOE (NOESY) 2D NMR experiments.

Step B: benzyl {2-[(3,6-di-O-benoyl-β-D-mannopyranosyl)oxy]ethyl}carbamate

To a stirred solution of benzyl {2-[(3,6-di-O-benzyol-β-D-galactopyranosyl)oxy]ethyl}carbamate (1.17 g, 2.069

$C_{30}H_{31}NO_{10}$ 565.19 observed m/e=566.22 [M+1]; Rt=1.84 min. $^1$H NMR ($CDCl_3$) δ 8.10-8.00 (4H, m), 7.55-7.25 (11H, m), 5.05-5.00 (3H, m), 4.72-4.68 (1H, m), 4.64-4.58 (2H, m), 4.24-4.20 (1H, m), 4.17-4.12 (1H, m), 3.93-3.87 (1H, m), 3.77-3.72 (1H, m), 3.65-3.60 (1H, m), 3.46-3.34 (2H, m). Stereochemistry was confirmed by 1H-13C one-bond correlation (HSQC); 1H-13C multiple-bond correlation (HMBC); and 1H-1H NOE (NOESY) 2D NMR experiments.

Step C: benzyl [2-(β-D-mannopyranosyloxy)ethyl]carbamate

To a stirred solution of benzyl {2-[(3,6-di-O-benzoyl-β-D-fucopyranosyl)oxy]ethyl}carbamate (287 mg, 0.507 mmol) in $CH_3OH$ (5 mL) was added NaOCH (0.1 mL, 0.05 mmol, 0.5 Min $CH_3OH$). After 4 hr, Amberlite IR 120 (H) ion exchange resin (pre-washed with $CH_3OH$ 3×5 mL) was added to the stirred reaction mixture. After 15 min, the resin was filtered off and washed with $CH_3OH$ (3×5 mL). The filtrate was concentrated and the residue was purified by flash chromatography on (50 g) on C18 reverse phase silica gel, eluting with 5-60% AcCN in $H_2O$, to give the title compound. UPLC Method B: calculated for $C_{16}H_{23}NO_8$ 357.14 observed m/e=358.16 [M+1]; Rt=1.40 min. $^1$H NMR ($CD_3OD$) δ 7.35-7.24 (5H, m), 5.04 (2H, s), 4.50-4.48 (1H, m), 3.90-3.82 (3H, m), 3.74-3.60 (2H, m), 3.55-3.50 (1H, m), 3.42-3.37 (1H, m), 3.36-3.30 (2H, m), 3.18-3.12 (1H, m).

Step D: 2-aminoethyl fl-D-mannopyranoside

A mixture of benzyl [2-(β-D-mannopyranosyloxy)ethyl] carbamate (133 mg, 0.372 mmol), and Pd/C (20 mg, 0.019 mmol) in water (5 mL) was allowed to stir under a balloon of $H_2$ at rt for 4 hr. The catalyst was filtered off and washed with $H_2O$ (3×5 mL). The fitrate was concentrated to give the title compound. $^1$H NMR ($CD_3OD$) δ 4.53-4.52 (1H, m), 3.93-3.85 (3H, m), 3.72-3.64 (2H, m), 3.53-3.49 (1H, m), 3.44-3.42 (1H, m), 3.22-3.18 (1H, m), 2.92-2.85 (2H, m).

Step E: 2-{[2-({2-[(α-L-fucopyranosyl)oxy] ethyl}amino)-2-oxoethyl][2-({6-[(2,5-dioxopyrrolidin-1-yl)oxy]-6-oxohexyl}amino)-2-oxoethyl] amino}-N-[2-(β-D-mannopyranosyloxy)ethyl] acetamide The title compound was prepared using procedures analogous to those described for ML-48 substituting 2-aminoethyl P-D-mannopyranoside for 2-aminoethyl a-D-mannopyranoside. UPLC Method B: m/e=796.37 [M+1]; Rt=2.19 min.

Example 50

The synthesis of oligosaccharide linker 2-{[2-({6-[(2,5-dioxopyrrolidin-1-yl)oxy]-6-oxohexyl}amino)-2-oxoethyl] [2-({2-[(α-L-fucopyranosyl)oxy]ethyl}amino)-2-oxoethyl] amino}-N-(2-{1 [α-D-mannopyranosyl],4 [α-D-mannopyranosyl]-oxy}butyl)acetamide (ML-50) having the following structure is described.

ML-50

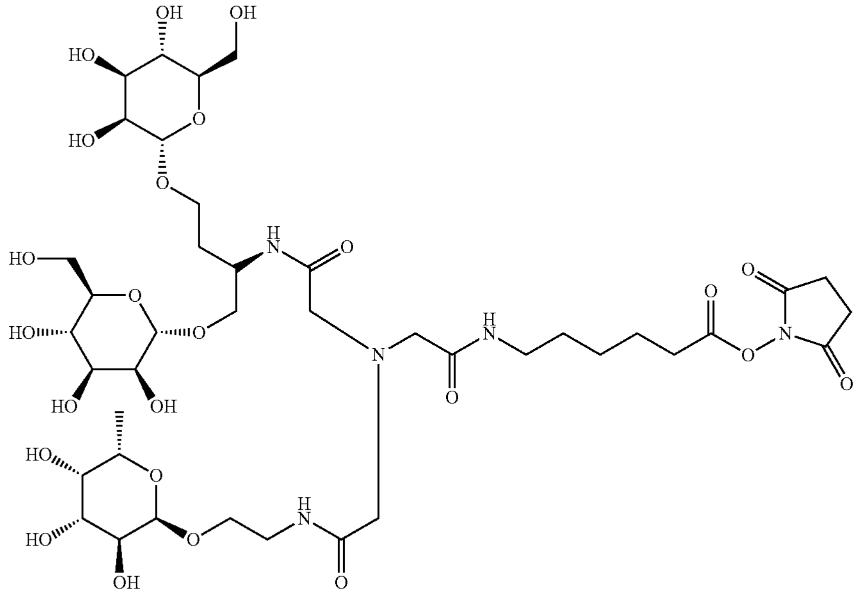

Step A: Benzyl (1[2,3,4,6-tetra-O-benzoyl-α-D-mannopyranosyl],4[2,3,4,6-tetra-O-benzoyl-α-D-mannopyranosyl]-dihydroxybutan-2-yl)carbamate To a 500 mL rb flask containing 4 Å Molecular sieves, was added a solution of (S)-benzyl (1,4-dihydroxybutan-2-yl)carbamate (2.7 g, 11.28 mmol), and 2,3,4,6-tetra-O-benzoyl-D-mannopyranosyl trichloroacetimidate (17.35 g, 23.42 mmol, prepared according to Organic Letters, 2003, vol. 5, No. 22, 4041) in anhydrous Dichloromethane (200 mL). The mixture was cooled down to −30° C. and trimethylsilyl trifluoromethanesulfonate (0.4 mL, 2.214 mmol) was added. After stirring at −30 to ambient temperature for 4 h under nitrogen, reaction mixture was quenched with TEA (3.15 mL, 22.57 mmol), filtered and concentrated under reduce pressure. The residue was purified by silica chromatography (0-60% EtOAc/hexanes) to give the title compound. (TLC: silica gel, Hexane/Ethylacetate:3/2, product $R_f$=0.4). $^1$H NMR (Chloroform-d, 500 MHz): δ 8.15-8.10 (4H, m), 8.10-8.05 (4H, m), 8.00-7.95 (4H, m), 7.80-7.75 (4H, m), 7.65-7.55 (4H, m), 7.45-7.20 (15H, m), 6.15-6.10 (2H, m), 5.95-5.85 (2H, m), 5.80-5.75 (2H, m), 5.15-5.10 (4H, m), 4.75-4.65 (2H, m), 4.55-4.40 (4H, m), 4.25-4.20 (1H, m), 4.10-4.00 (2H, m), 3.75-3.65 (2H, m), 2.15-2.05 (2H, m).

Step B: Benzyl (1[α-D-mannopyranosyl],4[α-D-mannopyranosyl]-dihydroxybutan-2-yl)carbamate To a solution of Benzyl (1[2,3,4,6-tetra-O-benzoyl-α-D-mannopyranosyl],4[2,3,4,6-tetra-O-benzoyl-α-D-mannopyranosyl]-dihydroxybutan-2-yl)carbamate (9.72 g, 6.96 mmol) in Methanol (30 mL) was added 0.5M sodium methoxide (1.5 mL, 0.750 mmol) in methanol. After stirring at room temperature for 48 hour, amberlite IR 120 (H) ion exchange resin (pre-washed with methanol 3×30 ml) was added to reaction mixture, and allowed stirring for additional 15 minutes. The ion exchange resin was filtered off and washed with methanol (2×5 mL). The filtrate was concentrated down and the residue was purified on 86 g C18 column reverse phase, eluting with 5% $CH_3CN$ in water (3 cv) then 5% to 50% $CH_3CN$ in water (20 cv) to give the title compound as a white solid. UPLC-MS: calculated for $C_{24}H_{37}NO_{14}$ 563.22 observed m/e: 564.24 (M+H)+(Rt: 2.31/5.00 min).

Step C: 1(α-D-mannopyranosyl),4(α-D-mannopyranosyl)-dihydroxybutan-2-amine

A mixture of Benzyl (1[α-D-mannopyranosyl],4[α-D-mannopyranosyl]-dihydroxybutan-2-yl)carbamate (3.73 g, 6.62 mmol), and Pd/C (0.300 g, 0.282 mmol) in water (60 mL) was allowed to stir under a balloon of $H_2$ at rt for 2 h. The catalyst was filtered off and washed with $H_2O$ (3×10 mL). The filtrate was concentrated to give the title compound. UPLC-MS: calculated for $C_{16}H_{31}NO_{12}$ 429.18 observed m/e: 430.21 (M+H)+(Rt: 1.37/5.00 min).

Step D: 2-{[2-({6-[(2,5-dioxopyrrolidin-1-yl)oxy]-6-oxohexyl}amino)-2-oxoethyl][2-({2-[(α-L-fucopyranosyl)oxy]ethyl}amino)-2-oxoethyl]amino}-N-(2-{1[α-D-mannopyranosyl],4[α-D-mannopyranosyl]-oxy}butyl)acetamide The title compound was prepared using procedure analogous to those described for ML-29 substituting 1(α-D-mannopyranosyl),4(α-D-mannopyranosyl)-dihydroxybutan-2-amine for 2-aminoethyl α-D-mannopyranosyl-(1→3)-[α-D-mannopyranosyl-(1→6)]-α-D-mannopyranoside. UPLC Method B: calculated for $C_{40}H_{67}N_5O_{24}$ 1001.42, observed m/e: 1002.48 [M+1]; Rt=2.05 min.

Example 51

The synthesis of oligosaccharide linker 2-{[2-({6-[(2,5-dioxopyrrolidin-1-yl)oxy]-6-oxohexyl}amino)-2-oxoethyl][2-({2-[(α-L-fucopyranosyl)oxy]ethyl}amino)-2-oxoethyl]amino}-N-(2-{[α-D-mannopyranosyl-(1→3)-[α-D-mannopyranosyl-(1→6)]-β-D-mannopyranosyl]oxy}ethyl)acetamide (ML-51) having the following structure is described.

Step A: (2-((3,6-O-benzoyl-β-D-galactopyranosyl)oxy)chloroethyl)

To a 500 mL Rb flask containing 4 Å Molecular sieves, 2-chloroethyl-β-D-galactopyranoside (6.58 g, 27.1 mmol, prepared according to Carbohydr. Res. 1992, 223, 303), dibutylstannanone (14.5 g, 58.2 mmol) and anhydrous Toluene (150 mL) were added. The mixture was stirred at reflux for 3 h. After 3 h, the reaction mixture were cooled down to room temperature and then to 0° C. To a cold solution of the reaction crude at 0° C., benzoyl chloride (6.7 ml, 57.7 mmol) was added, and the resulting mixture was stirred at 0° C. to ambient temperature. After 24 hours, the reaction mixture was filtered off and filtrate was concentrated under reduce pressure. The residue was purified by silica chromatography (0-75% EtOAc/hexanes) to give the title compound. UPLC-MS: calculated for $C_{22}H_{23}ClO_8$ 450.11 observed m/e: 473.11 (M+Na)+(Rt: 1.82/5.00 min). $^1$H NMR (Chloroform-d, 500 MHz): δ 8.10-8.05 (2H, m), 8.05-8.00 (2H, m), 7.60-7.55 (2H, m), 7.50-7.40 (4H, m), 5.20-5.10 (1H, m), 4.70-4.60 (1H, m), 4.55-4.50 (1H, m), 4.50-4.45 (1H, m), 4.25-4.20 (1H, m), 4.20-4.15 (1H, m), 4.12-4.08 (1H, m), 4.00-3.95 (1H, m), 3.90-3.85 (1H, m), 3.72-3.68 (2H, m). Regiochemistry was confirmed by $^1$H-$^{13}$C one-bond correlation (HSQC); $^1$H-$^{13}$C multiple-bond correlation (HMBC); and $^1$H-$^1$H NOE (NOESY) 2D NMR experiments.

Step B: (2-((3,6-O-benzoyl-β-D-mannopyranosyl)oxy)chloroethyl)

To a solution of (2-((3,6-O-benzoyl-β-D-galactopyranosyl)oxy)chloroethyl) (1 g, 2.218 mmol) in DCM (28 mL) at −20° C. was added pyridine (2.5 mL, 30.9 mmol). After stirring 5 minutes, TriflicAnhydride (1.2 mL, 7.10 mmol) was added dropwise, and the mixture was stirred while allowing to warm from −20° C. to 0° C. over 2 hours. The resulting mixture was diluted with 75 ml DCM and washed with (1×100 mL) of cold 1 M HCl; (1×100 mL) of cold

ML-51

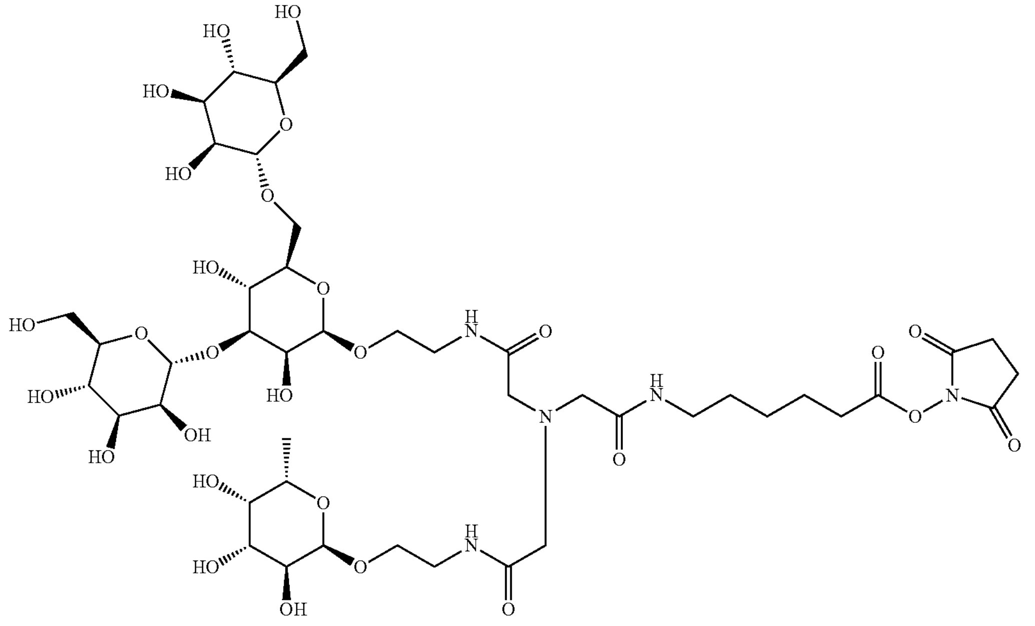

aqueous $NaHCO_3$; (1×100 mL) of cold water and 100 ml of cold brine. The organic phase was dried over $Na_2SO_4$ and concentrated in vacuo at low temperature. The residue was used directly in the next step without further purification. Solution of tetrabutylammonium nitrite (3.3 g, 11.44 mmol) in 5 ml of anhydrous acetonitrile was added to the solution of triflated intermediate in dry acetonitrile (22 mL) and then allowed to react at 50° C. for 5 hours. The resulting mixture was concentrated under reduce pressure and directly purified by silica chromatography (0-75% EtOAc/hexanes) to give the title compound. UPLC-MS: calculated for $C_{22}H_{23}ClO_8$ 450.11 observed m/e: 451.13 (M+H)+(Rt: 1.80/5.00 min). $^1H$ NMR (Chloroform-d, 500 MHz): δ 8.15-8.05 (4H, m), 7.65-7.60 (2H, m), 7.50-7.40 (4H, m), 5.12-5.08 (1H, m), 4.77-4.72 (2H, m), 4.68-4.65 (1H, m), 4.34-4.32 (1H, m), 4.24-4.14 (2H, m), 3.90-3.84 (1H, m), 3.71-3.66 (3H, m), 2.98-2.96 (1H, b), 2.41-2.39 (1H, b). Stereochemistry was confirmed by $^1H$-$^{13}C$ one-bond correlation (HSQC); $^1H$-$^{13}C$ multiple-bond correlation (HMBC); and $^1H$-$^1H$ NOE (NOESY) 2D NMR experiments.

Step C: (2-((2,4-O-benzyl,3,6-O-benzoyl-β-D-mannopyranosyl)oxy)chloroethyl)

In a 250 mL rb flask, 2-(benzyloxy)-1-methylpyridin-1-ium trifluoromethanesulfonate (5 g, 14.31 mmol), magnesium oxide (0.085 g, 2.118 mmol), trifluorotoluene (40 mL), and (2-((3,6-O-benzoyl-β-D-mannopyranosyl)oxy)chloroethyl) (1.91 g, 4.24 mmol) were added. The heterogeneous reaction mixture is then stirred at 82° C. for 48 h. Upon reaction completion, reaction mixture was filtrated and concentrated under reduce pressure. The residue was purified by silica chromatography (0 to 75% EtOAc/hexanes) to give the title compound. UPLC-MS: calculated for $C_{36}H_{35}ClO_8$ 630.20 observed m/e: 631.21 (M+H)+(Rt: 3.97/5.00 min).

Step D: (2-((2,4-O-benzyl-β-D-mannopyranosyl)oxy)chloroethyl)

To a solution of (2-((2,4-O-benzyl,3,6-O-benzoyl-β-D-mannopyranosyl)oxy)chloroethyl), (1.6 g, 2.54 mmol) in methanol (25 mL) and DCM (5 mL) was added 0.5M sodium methoxide (0.5 mL, 0.25 mmol) in methanol. After stirring at room temperature for 4 hour, amberlite IR 120 (H) ion exchange resin (pre-washed with methanol 3×5 mL) was added to reaction mixture, and allowed stirring for additional 15 minutes. The ion exchange resin was filtered off and washed with methanol (3×5 mL). The filtrate was concentrated under reduce pressure and the residue was purified by silica chromatography (0-75% EtOAc/hexanes) to give the title compound. UPLC-MS: calculated for $C_{22}H_{27}ClO_6$ 422.15 observed m/e: 423.14 (M+H)+(Rt: 1.90/5.00 min).

Step E: (2-((2,4-O-benzyl-β-D-mannopyranosyl)oxy)azidoethyl)

To a solution of (2-((2,4-O-benzyl-β-D-mannopyranosyl)oxy)chloroethyl) (800 mg, 1.892 mmol) in anhydrous DMF (25 mL) was added sodium azide (140 mg, 2.154 mmol) at room temperature. The reaction mixture was then heated to 70° C. and stirred for 16 h under nitrogen. Upon reaction completion, crude reaction mixture was cooled down to room temperature and poured onto ice water (200 mL) and extracted with ether (3×100 mL). The organic layers were combined and washed with brine (2×100 mL), dried over $Na_2SO_4$, filtered and concentrated under reduce pressure. The residue was purified by silica chromatography (0-100% EtOAc/hexanes) to give the title compound. UPLC-MS: calculated for $C_{22}H_{27}N_3O_6$ 429.19 observed m/e: 430.19 (M+H)+(Rt: 1.87/5.00 min).

Step F: (2-((2,3,4,6-tetra-O-benzoyl-α-D-mannopyranosyl-(1→3)-[2,3,4,6-tetra-O-benzoyl-α-D-mannopyranosyl-(1→6)]-(2,4-O-benzyl-β-D-mannopyranosyl)oxy)azidoethyl)

To a 250 mL Rb flask containing 4 Å Molecular sieves was added a solution of (2-((2,4-O-benzyl-β-D-mannopyranosyl)oxy)azidoethyl) (710 mg, 1.653 mmol) and 2,3,4,6-tetra-O-benzoyl-D-mannopyranosyl trichloroacetimidate (2.6 g, 3.51 mmol, prepared according to Organic Letters, 2003, vol. 5, No. 22, 4041) in anhydrous Dichloromethane (30 mL). The mixture was cooled down to −30° C. and trimethylsilyl trifluoromethanesulfonate (0.03 mL, 0.166 mmol) was added. After stirring at −30 to ambient temperature for 4 h under nitrogen, reaction mixture was quenched with TEA (0.1 mL, 0.717 mmol), filtered and concentrated under reduce pressure. The residue was purified by silica chromatography (0-75% EtOAc/hexanes) to give the title compound. (TLC: silica gel, Hexane/Ethylacetate:3/2, product $R_f$=0.6). $^1H$ NMR (Chloroform-d, 500 MHz): δ 8.15-7.80 (16H, m), 7.62-7.49 (8H, m), 7.47-7.32 (20H, m), 7.30-7.15 (6H, m), 6.13-6.05 (2H, m), 6.01-5.91 (2H, m), 5.87-5.85 (1H, m), 5.71-5.69 (1H, m), 5.43-5.42 (1H, m), 5.26-5.23 (1H, m), 5.13-5.12 (1H, m), 5.03-5.00 (1H, m), 4.84-4.81 (1H, m), 4.68-4.63 (2H, m), 4.60-4.55 (2H, m), 4.54-4.48 (2H, m), 4.31-4.25 (2H, m), 4.20-4.15 (1H, m), 4.08-4.07 (1H, m), 3.98-3.88 (3H, m), 3.84-3.80 (1H, m), 3.78-3.73 (1H, m), 3.62-3.54 (2H, m), 3.38-3.33 (1H, m).

Step G: (2-((α-D-mannopyranosyl-(1→3)-[α-D-mannopyranosyl-(1→6)]-(2,4-O-benzyl, β-D-mannopyranosyl)oxy)azidoethyl)

To a solution of 2-((2,3,4,6-tetra-O-benzoyl-α-D-mannopyranosyl-(1→3)-[2,3,4,6-tetra-O-benzoyl-α-D-mannopyranosyl-(1→6)]-(2,4-O-benzyl-β-D-mannopyranosyl)oxy) azidoethyl (2.52 g, 1.588 mmol) in Methanol (20 mL) and DCM (4 mL) was added 0.5M sodium methoxide (0.32 mL, 0.16 mmol) in methanol. After stirring at room temperature for 24 hour, amberlite IR 120 (H) ion exchange resin (pre-washed with methanol 3×30 mL) was added to reaction mixture, and allowed stirring for additional 15 minutes. The ion exchange resin was filtered off and washed with methanol (3×5 mL). The filtrate was concentrated under reduce pressure and the residue was purified by reverse phase chromatography (C18 column) (ACN/$H_2O$ with no modifier) to afford the title product. UPLC-MS: calculated for $C_{34}H_{47}N_3O_{16}$ 753.30 observed m/e: 754.29 (M+H)+(Rt: 2.93/5.00 min).

Step H: 2-aminoethyl α-D-mannopyranosyl-(1→3)-[α-D-mannopyranosyl-(1→6)]-β-D-mannopyranoside A mixture of 2-((α-D-mannopyranosyl-(1→3)-[α-D-mannopyranosyl-(1→6)]-(2,4-O-benzyl, β-D-mannopyranosyl)oxy)azidoethyl (1.05 g, 1.393 mmol), and Pd/C (0.148 g, 0.139 mmol) in water (25 mL) was allowed to stir under a balloon of $H_2$ at rt for 16 h. The catalyst was filtered off and washed with $H_2O$ (3×5 mL). The filtrate was concentrated under reduce pressure to give the title compound. UPLC-MS: calculated for $C_{20}H_{37}NO_{16}$ 547.21 observed m/e: 548.23 (M+H)+(Rt: 1.07/5.00 min). $^1H$ NMR ($D_2O$, 500 MHz): δ 5.06-5.05 (1H, m), 4.86-4.85 (1H, m), 4.655-4.65 (1H, m), 4.13-4.12 (1H, m), 4.02-4.01 (1H, m), 3.95-3.82 (6H, m), 3.80-3.67 (8H, m), 3.66-3.57 (3H, m), 3.53-3.49 (1H, m), 2.90-2.85 (2H, m).

Step I. 2-{[2-({6-[(2,5-dioxopyrrolidin-1-yl)oxy]-6-oxohexyl}amino)-2-oxoethyl][2-({2-[(α-L-fucopyranosyl)oxy]ethyl}amino)-2-oxoethyl]amino}-N-(2-{[α-D-mannopyranosyl-(1→3)-[α-D-mannopyranosyl-(1→6)]-β-D-mannopyranosyl]oxy}ethyl)acetamide The title compound was prepared using procedure analogous to those described for ML-29 substituting 2-aminoethyl α-D-mannopyranosyl-(1→3)-[α-D-mannopyranosyl-(1→6)]-β-D-mannopyranoside for 2-aminoethyl α-D-mannopyranosyl-(1→3)-[α-D-mannopyranosyl-(1→6)]-α-D-mannopyranoside. UPLC Method B: calculated for $C_{44}H_{73}N_5O_{28}$ 1119.44, observed m/e: 1120.46 [M+1]; Rt=2.09 min.

Example 52

The synthesis of oligosaccharide linker 6-[(2,5-dioxopyrrolidin-1-yl)oxy]-N-{2-[(β-D-mannopyranosyl)oxy]ethyl}-6-oxohexanamide (ML-52) having the following structure is described.

ML-52

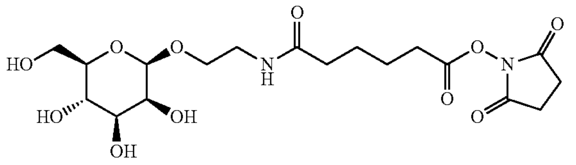

The title compound was prepared using procedures analogous to those described for ML-1 substituting 2-aminoethyl β-D-mannopyranoside for 2-aminoethyl α-D-mannopyranosyl-(1→3)-[α-D-mannopyranosyl-(1→6)]-α-D-mannopyranoside in step B. UPLC-MS: calculated for $C_{18}H_{28}N_2O_{11}$ 448.17 observed m/e: 449.19 (M+H)+(Rt: 1.96/5.00 min).

Example 53

The synthesis of oligosaccharide linker 4-[(2,5-dioxopyrrolidin-1-yl)oxy]-N-{2-[(α-L-fucopyranosyl)oxy]ethyl}4-oxobutanamide (ML-53) having the following structure is described.

ML-53

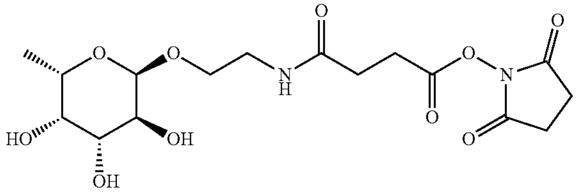

The title compound was prepared using procedures analogous to those described for ML-4 substituting 4-(benzyloxy)-4-oxobutanoic acid for 6-(benzyloxy)-6-oxohexanoic acid in Step A. UPLC-MS: calculated for $C_{16}H_{24}N_2O_{10}$ 404.14 observed m/e: 405.14 (M+H)+(Rt: 1.87/5.00 min).

Example 54

The synthesis of oligosaccharide linker 2,2'-{[2-({6-[(2,5-Dioxopyrrolidin-1-yl)oxy]-6-oxohexyl}amino)-2-oxoethyl]imino}bis[N-(2-{[α-D-mannopyranosyl-(1→3)-[α-D-mannopyranosyl-(1→6)]-β-D-glucopyranosyl]oxy}ethyl)acetamide] (ML-54) having the following structure is described.

ML-54

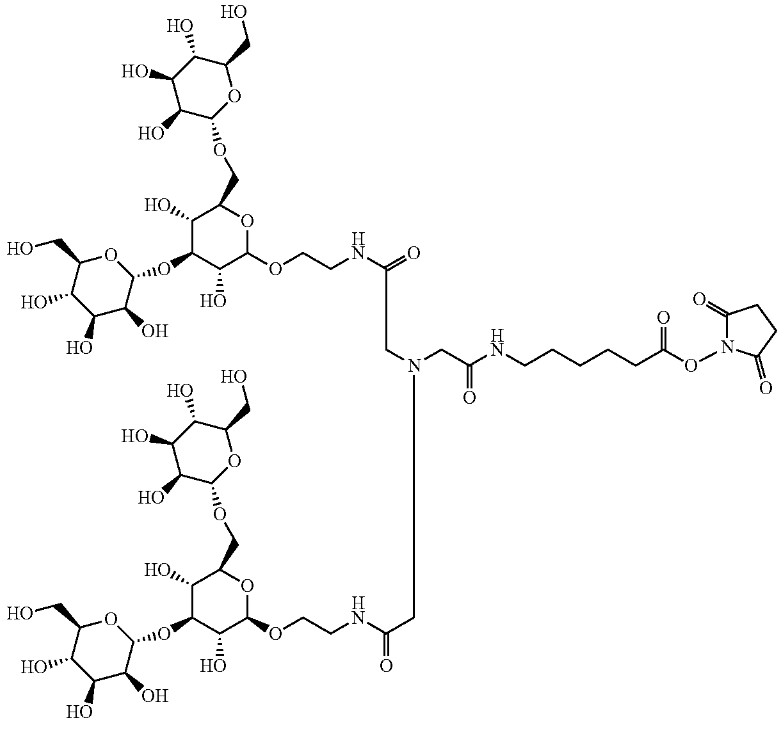

The title compound was prepared using procedures analogous to those described for ML-15 substituting 2-aminoethyl α-D-mannopyranosyl-(1→3)-[α-D-mannopyranosyl-(1→6)]-β-D-glucopyranoside for 2-aminoethyl α-D-mannopyranosyl-(1→3)-[α-D-mannopyranosyl-(1→6)]-α-D-mannopyranoside in Step B. UPLC Method B: calculated for $C_{56}H_{93}N_5O_{39}$ 1459.54, observed m/e: m/e=1460.62 [M+1]; Rt=0.92 min.

Example 55

The synthesis of oligosaccharide linker 2-(2-{([α-D-mannopyranosyl-(1→3)-[α-D-mannopyranosyl-(1→6)]-α-D-mannopyranosyl]oxy)ethyl}{6-[(2,5-dioxopyrrolidin-1-yl)oxy]-6-oxohexyl}amino)ethyl α-L-fucopyranoside (ML-55) having the following structure is described.

Step B: benzyl 6-(2-{2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranosyl]-2-oxyethyl}amino) hexanoate To a solution of 2-aminoethyl 2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranoside (18 g, 11.35 mmol) and benzyl 6-oxohexanoate (1 g, 4.54 mmol) in DCM (150 mL) was added acetic acid (0.26 mL, 4.54 mmol) and sodium triacetoxyborohydride (2.41 g, 11.35 mmol) and the resulting mixture stirred at room temperature overnight. Mixture evaporated and the residue dissolved in EtOAc (300 mL) and washed with sat. $NaHCO_3$ (2×300 mL), sat. NaCl (200 mL), dried over $Na_2SO_4$, filtered and evaporated. The residue was purified by silica gel column chromatography (Teledyne Isco: 2×330 g) eluent: gradient 2-5% MeOH in DCM over 8CV to

ML-55

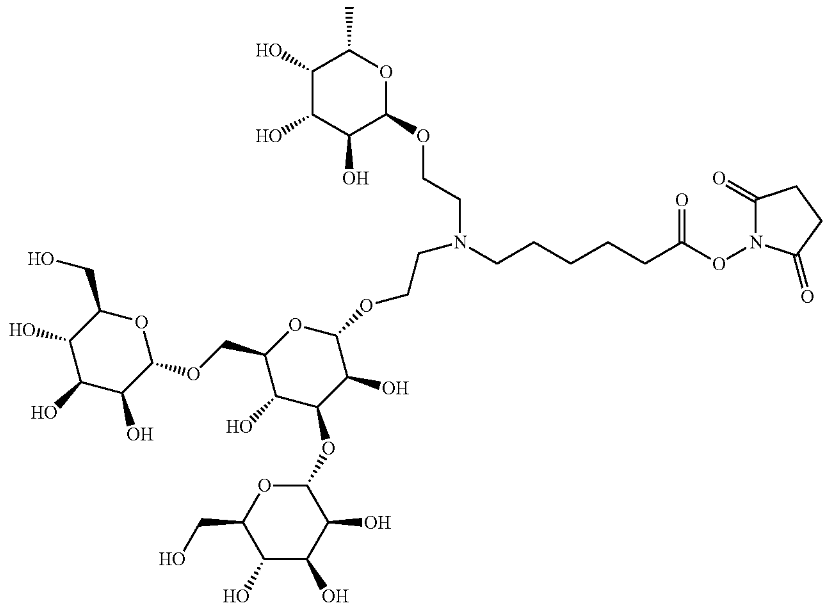

Step A: 2-aminoethyl 2,3,4,6-penta-benzoyl-α-D-mannopyranosyl-(1→3)-[2,3,4,6-penta-benzoyl-α-D-mannopyranosyl-(1→6)]-2,4-dibenzoyl-α-D-mannopyranoside To a nitrogen flushed solution of 2-azidoethyl 2,3,4,6-penta-O-benzoyl-α-D-mannopyranosyl-(1→3)-[2,3,4,6-O-penta-benzoyl-α-D-mannopyranosyl-(1→6)]-2,4-di-O-benzoyl-α-D-mannopyranoside (25 g, 15.5 mmol WO 2010/088294 A1) in EtOAc (300 mL) was added 10% Palladium on Carbon (1.65 g) and the resulting mixture stirred at room temperature under a balloon of hydrogen overnight. Mixture filtered through Celite and the filtrate evaporated, the residue was purified by silica gel column chromatography (Teledyne Isco: 330 g) eluent: gradient 2-5% MeOH in DCM over 8CV to give the title compound (18 g, 73%) as an off-white foam. UPLC Method C: calculated for $C_{90}H_{77}NO_{26}$ 1587.47, observed m/e: 1588.6636 [M+1]; Rt=4.17 min.

give the title compound (4.8 g, 59%) as a white foam. $^1H$ NMR ($CDCl_3$) δ 8.33 (2H, m), 8.18 (2H, m), 8.13 (2H, dd, J=8.0 and 1.4 Hz), 8.10 (2H, dd, J=8.0 and 1.4 Hz), 8.06 (2H, m), 8.05 (2H, dd, J 4.8 and 1.6 Hz), 7.84 (4H, m), 7.78 (2H, dd, J=8.0 and 1.4 Hz), 7.74 (2H, dd, J=8.0 and 1.4 Hz), 7.67-7.48 (8H, m), 7.47-7.30 (23H, m), 7.25 (2H, t, J=7.8 Hz), 6.14 (1H, t, J=10.1 Hz), 6.10 (1H, t, J=10.0 Hz), 6.03 (1H, dd, J=10.1 and 3.3 Hz), 5.93 (1H, t, J=10.0 Hz), 5.80 (2H, m), 5.75 (1H, dd, J=10.1 and 3.3 Hz), 5.42 (1H, d, J=1.9 Hz), 5.38 (1H, dd, J=3.3 and 1.9 Hz), 5.20 (1H, s), 5.18 (1H, d, J=1.8 Hz), 5.11 (2H, s), 4.69 (1H, dd, J=9.7 and 3.5 Hz), 4.67 (1H, dd, J=12.4 and 2.6 Hz), 4.62 (1H, dd, J=12.2 and 2.4 Hz), 4.57 (1H, m), 4.48 (1H, dt, J=10.1 and 2.8 Hz), 4.42-4.31 (3H, m), 4.22 (1H, dd, J=10.8 and 6.3 Hz), 4.09 (1H, dt, J=10.0 and 5.4 Hz), 3.83 (1H, d, J=10.6 Hz), 3.78 (1H, m), 3.02 (2H, m), 2.73 (2H, t, J=7.3 Hz), 2.37 (2H, t, J=7.6 Hz), 1.71 (2H, m), 1.59 (2H, m), 1.40 (2H, m).

Step C: 2-oxoethyl 2,3,4-tri-O-acetyl-α-L-fucopyranoside

To a solution of prop-2-en-1-yl 2,3,4-tri-O-acetyl-α-L-fucopyranoside (1.34 g, 4.06 mmol) in acetone (30 mL) and water (7.5 mL) was added 4-methylmorpholine 4-oxide (950 mg, 8.11 mmol) followed by the addition of 2.5% $OsO_4$ in tert-butanol (2.04 mL, 0.162 mmol). The mixture was allowed to stir at rt for 16 hr. To the resulting mixture was then added a solution of $NaIO_4$ (1.74 g, 8.11 mmol) in water (15 mL). After stirring for additional 4 hr, the precipitate was filtered and washed with acetone (50 mL). The volume of the filtrate was reduced to approximately ⅓ of the initial volume and then diluted with sat. $NaHCO_3$ (100 mL). The mixture was extracted with EtOAc (3×50 mL). The organic phases were combined and washed with brine, dried over $Na_2SO_4$, and concentrated. The residue was purified by silica gel column chromatography (Teledyne Isco: 120 g), eluting with 0-80% EtOAc in hexanes to give the title compound (660 mg, 49%). $^1H$ NMR ($CDCl_3$) δ 9.72 (1H, s), 5.44 (1H, dd, J=10.9 and 3.3 Hz), 5.35 (1H, dd, J=3.4 and 1.8 Hz), 5.19 (1H, dd, J=10.9 and 3.8 Hz), 5.13 (1H, d, J=3.8 Hz), 4.26 (3H, m), 2.19 (3H, s), 2.15 (3H, s), 2.02 (3H, s), 1.17 (3H, d, J=6.6 Hz).

Step D: benzyl 6-{[{2-(2,3,4-tri-O-acetyl-α-L-fucopyranosyl)-oxy}ethyl](2-{(2-{2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranosyl]-oxy}ethyl)amino}hexanoate To a solution of benzyl 6-(2-{2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranosyl]-2-oxyethyl}amino) hexanoate (1.3 g, 0.725 mmol) and 2-oxoethyl 2,3,4-tri-O-acetyl-α-L-fucopyranoside (651 mg, 1.96 mmol) in DCM (20 mL) was added acetic acid (0.042 mL, 0.725 mmol) and sodium triacetoxy borohydride (307 mg, 1.45 mmol) and the resulting mixture stirred at room temperature overnight. Mixture evaporated and the residue partitioned between EtOAc (60 mL) and sat. $NaHCO_3$ (80 mL); organic layer washed with a further portion of sat. $NaHCO_3$ (80 mL), sat. NaCl (50 mL), dried over $Na_2SO_4$, filtered and evaporated. The residue purified by silica gel column chromatography (Teledyne Isco: 80 g) eluent: gradient 20-100% EtOAc in Hexanes over 10CV to give the title compound (1.5 g, 99%) as a white foam. $^1H$ NMR ($CDCl_3$) δ 8.34 (2H, dd, J 6.7 and 3.2 Hz), 8.15 (2H, m), 8.10 (4H, m), 8.07 (2H, dd, J=8.0 and 1.4 Hz), 8.05 (2H, dd, J 8.1 and 1.5 Hz), 7.88 (4H, m), 7.78 (2H, dd, J=8.0 and 1.4 Hz), 7.72 (2H, dd, J=7.8 and 1.5 Hz), 7.62-7.55 (6H, m), 7.54-7.36 (14H, m), 7.34-7.29 (11H, m), 7.25 (2H, t, J=7.7 Hz), 6.14 (1H, t, J=10.0 Hz), 6.07 (1H, m), 6.03 (2H, m), 5.83 (1H, dd, J=3.3 and 1.8 Hz), 5.75 (2H, m), 5.41 (1H, m), 5.39 (2H, m), 5.35 (1H, d, J=3.8 Hz), 5.33 (2H, m), 5.59 (1H, d, J=3.7 Hz), 5.18 (3H, m), 5.16 (1H, d, J=3.8 Hz), 5.13 (1H, t, J=4.2 Hz), 5.10 (1H, d, J=3.7 Hz), 5.06 (2H, s), 4.62 (2H, m), 4.54 (1H, m), 4.50 (2H, m), 4.57 (1H, m), 4.33 (3H, m), 4.25 (2H, m), 4.19 (2H, m), 3.80 (2H, m), 2.82 (2H, m), 2.60 (1H, t, J=7.3 Hz), 2.32 (2H, t, J=7.5 Hz), 2.20 (3H, s) 2.11 (3H, s) 2.02 (3H, s), 1.63 (2H, m), 1.51 (1H, m) 1.34 (1H, m) 1.18 (3H, d, J=6.6 Hz).

Step E: methyl 6-{[{2-(-α-L-fucopyranosyl)-oxy}ethyl](2-{(2-{-α-D-mannopyranosyl-(1→3)-[-α-D-mannopyranosyl-(1→6)]-α-D-mannopyranosyl]-oxy}ethyl)amino}hexanoate To a solution of benzyl 6-{[{2-(2,3,4-tri-O-acetyl-α-L-fucopyranosyl)-oxy}ethyl](2-{(2-{2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranosyl]-oxy}ethyl)amino}hexanoate (1.5 g, 0.71 mmol) in a mixture of DCM (5 mL) and MeOH (15 mL) was added sodium methoxide (0.284 mL of a 0.5M soln in MeOH, 0.142 mmol) and the mixture stirred at room temperature for 4 days. Mixture evaporated to a volume of ~4 mL and added dropwise to stirred acetonitrile (80 mL) to give a white precipitate. Mixture centrifuged at 3500 rpm for 20 mins, supernatant decanted and solids re-suspended in acetonitrile (80 mL) and centrifuged at 3500 rpm for a further 20 mins, supernatant decanted and solids dried under a stream of dry nitrogen to give the title compound (580 mg, 94%) as a white solid. UPLC Method B: calculated for $C_{35}H_{63}NO_{23}$ 865.38, observed m/e: 866.48 [M+1]; Rt=1.71 min.

Step F: 6-{[{2-(-α-L-fucopyranosyl)-oxy}ethyl][2-{(2-{-α-D-mannopyranosyl-(1→3)-[-α-D-mannopyranosyl-(1→6)]-α-D-mannopyranosyl]-oxy}ethyl)amino}hexanoic acid To a solution of methyl 6-{[{2-(-α-L-fucopyranosyl)-oxy}ethyl][2-{(2-{-α-D-mannopyranosyl-(1→3)-[-α-D-mannopyranosyl-(1→6)]-α-D-mannopyranosyl]-oxy}ethyl)amino}hexanoate (580 mg, 0.67 mL) in water (3 mL) was added 5N NaOH (0.161 mL, 0.804 mmol) and the resulting mixture stirred at room temperature for 6 hours. Acetic acid (0.039 mL, 0.683 mmol) added and mixture lyophilized to give the title compound (620 mg, 100%). UPLC Method B: calculated for $C_{34}H_{61}NO_{23}$ 851.36, observed m/e: 852.48 [M+1]; Rt=1.74 min.

Step G: 2-(2-{([α-D-mannopyranosyl-(1→3)-[α-D-mannopyranosyl-(1→6)]-α-D-mannopyranosyl]oxy)ethyl}{6-[(2,5-dioxopyrrolidin-1-yl)oxy]-6-oxohexyl}amino)ethyl α-L-fucopyranoside To a suspension of 6-{[{2-(-α-L-fucopyranosyl)-oxy}ethyl](2-{(2-{-α-D-mannopyranosyl-(1→3)-[-α-D-mannopyranosyl-(1→6)]-α-D-mannopyranosyl]-oxy}ethyl)amino}hexanoic acid (100 mg, 0.117 mmol) in anhydrous DMF (2 mL) was added Hunig's base (0.082 mL, 0.47 mmol) and 1-(((2,5-dioxopyrrolidin-1-yl)oxy)(pyrrolidin-1-yl)methylene)pyrrolidin-1-ium hexafluorophosphate(V) (58 mg, 0.141 mmol) and the resulting mixture stirred at room temperature for 30 mins. TFA (0.036 mL, 0.47 mmol) added and the resulting mixture added dropwise to anhydrous acetonitrile (40 mL) to form a white precipitate. Mixture centrifuged at 3500 rpm for 20 mins, solvent decanted and solid re-suspended in acetonitrile (40 mL) and centrifuged at 3500 rpm for 20 mins. Solvent decanted and solid dried under a stream of dry nitrogen to give the title compound (84 mg, 75%). UPLC Method B: calculated for $C_{38}H_{64}N_2O_{25}$ 948.38, observed m/e: 949.48 [M+1]; Rt=3.64 min.

Example 56

The synthesis of oligosaccharide linker 2-(2-{([α-D-mannopyranosyl-(1→3)-[α-D-mannopyranosyl-(1→6)]-α-D-mannopyranosyl]oxy)ethyl}{6-[(2,5-dioxopyrrolidin-1-yl)oxy]-6-oxohexyl}amino)ethyl β-L-fucopyranoside (ML-56) having the following structure is described.

ML-56

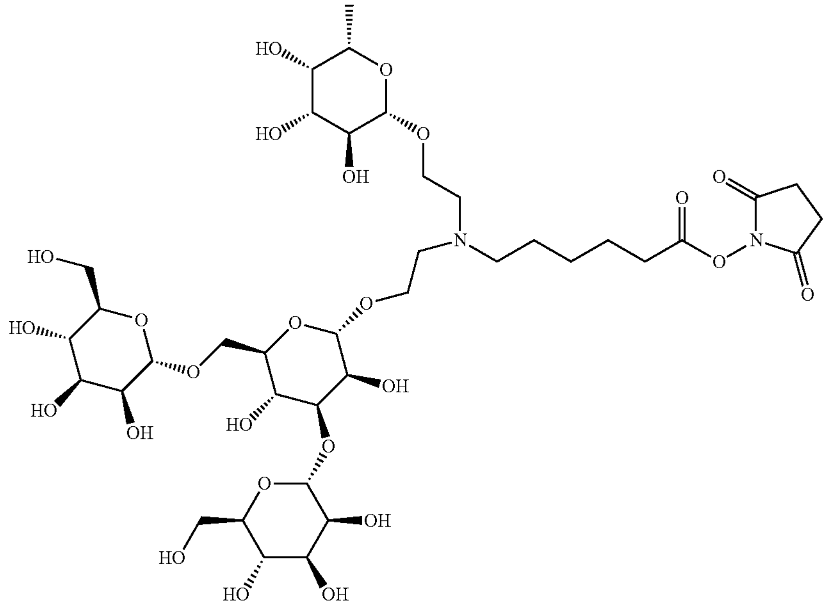

The title compound was prepared using procedures analogous to those described for ML-55 substituting prop-2-en-1-yl 2,3,4-tri-O-acetyl-β-L-fucopyranoside for prop-2-en-1-yl 2,3,4-tri-O-acetyl-α-L-fucopyranoside in Step C. UPLC Method B: m/e=949.48 [M+1]; Rt=3.70 min.

Example 57

The synthesis of oligosaccharide linker 3-(2-{([α-D-mannopyranosyl-(1→3)-[α-D-mannopyranosyl-(1→6)]-α-D-mannopyranosyl]oxy)ethyl}{6-(2,5-dioxopyrrolidin-1-yl)-6-oxohexyl}amino)propyl a-L-fucopyranoside (ML-57) having the following structure is described.

ML-57

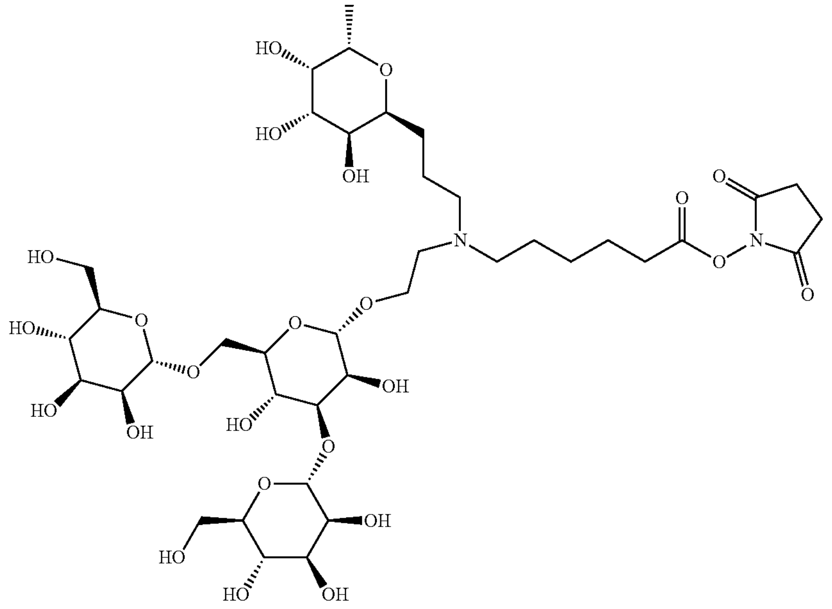

Step A: benzyl 6-{[3-(2,3,4-tri-O-benzyl-α-L-fucopyranosyl)propyl](2-[2-{2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranosyl}-oxy]ethyl)amino}hexanoate Prepared from benzyl 6-(2-{2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranosyl]-2-oxyethyl}amino) hexanoate [ML-XX step B] and 3-(2,3,4-tri-O-benzyl-α-L-fucopyranosyl)propanal [ML-36 Step E] according to the procedure outlined for ML-XX Step D. $^1$H NMR ($CDCl_3$) δ 8.35 (2H, dd, J=6.4 and 2.9 Hz), 8.17 (2H, d, J=7.7 Hz), 8.10 (4H, m), 8.06 (2H, dd, J=7.1 and 1.5 Hz), 8.04 (2H, dd, J=7.7 and 1.5 Hz), 7.89 (2H, m), 7.87 (2H, m), 7.80 (2H, dd, J=7.9 and 1.4 Hz), 7.74 (2H, m), 7.61 (2H, m), 7.59-7.55 (4H, m), 7.49 (2H, d, J=7.2 Hz), 7.45-7.35 (12H, m), 7.35-7.27 (26H, m), 7.23 (2H, m), 6.18 (1H, t, J=9.9 Hz), 6.11-6.02 (3H, m), 5.85 (1H, dd, J=3.3 and 1.8 Hz), 5.75 (2H, m), 5.37 (2H, m), 5.17 (2H, m), 5.06 (2H, s), 4.77 (1H, d, J=12.0 Hz), 4.70 (2H, d, J=8.3 Hz), 4.67-4.60 (5H, m), 4.56 (2H, d, J=8.6 Hz), 4.55-4.47 (4H, m), 4.33 (3H, m), 4.19 (1H, dd, J=11.0 and 4.8 Hz), 4.01 (1H, dd, J=10.5 and 4.7 Hz), 3.86 (1H, m), 3.79 (1H, d, J=11.2 Hz), 3.75 (2H, m), 3.62 (1H, m), 2.79 (2H, t, J=6.5 Hz), 2.52 (4H, m), 2.32 (2H, t, J=7.6 Hz), 1.65 (4H, m), 1.48 (2H, m), 1.30 (3H, m), 1.25 (3H, d, J=6.6 Hz).

Step B: methyl 6-{[3-(2,3,4-tri-O-benzyl-α-L-fucopyranosyl)propyl](2-[2-{-α-D-mannopyranosyl-(1→3)+α-D-mannopyranosyl-(1→6)]-α-D-mannopyranosyl}-oxy ethyl)amino}hexanoate To a solution of benzyl 6-{[3-(2,3,4-tri-O-benzyl-α-L-fucopyranosyl)propyl](2-[2-{2,3,4,6-penta-O-benzoyl-α-D-mannopyranosyl-(1→3)-[2,3,4,6-penta-O-benzoyl-α-D-mannopyranosyl-(1→6)]-2,4-di-O-benzoyl-α-D-mannopyranosyl}-oxy]ethyl)amino}hexanoate (1.3 g, 0.577 mmol) in a mixture of anhydrous DCM (5 mL) and anhydrous MeOH (15 mL) was added sodium methoxide (1.16 mL of a 0.5M soln in MeOH, 0.577 mmol) and the resulting mixture stirred at room temperature for 3 days. Mixture evaporated to a volume of ~5 mL and added dropwise to stirring anhydrous acetonitrile (80 mL). Mixture centrifuged at 3500 rpm for 30 mins, decanted the solvent and solid re-suspended in acetonitrile (80 mL). Mixture centrifuged at 3500 rpm for 30 mins, decanted the solvent and solid air dried under a stream of dry nitrogen to give the title compound (650 mg, 100%). UPLC Method B: calculated for $C_{57}H_{83}NO_{22}$ 1133.54, observed m/e: 1134.64 [M+1]; Rt=2.08 min.

Step C: methyl 6-{[3-(-α-L-fucopyranosyl)propyl](2-[2-{-α-D-mannopyranosyl-(1→3)-[-α-D-mannopyranosyl-(1→6)]-α-D-mannopyranosyl}-oxy]ethyl)amino}hexanoate hydrochloride To a solution of methyl 6-{[3-(2,3,4-tri-O-benzyl-α-L-fucopyranosyl)propyl](2-[2-{-α-D-mannopyranosyl-(1→3)-[-α-D-mannopyranosyl-(1→6)]-α-D-mannopyranosyl}-oxy]ethyl)amino}hexanoate (650 mg, 0.577 mmol) in methanol (5 mL) was added conc. HCl (0.142 mL, 1.73 mmol), flushed with nitrogen and 10% palladium on carbon (61 mg) added and stirred under a balloon of hydrogen for 3 hours. Filtered through a 0.4 micron syringe tip filter and the filtrate evaporated. The residue was dissolved in water (4 mL) and lyophilized to give the title compound (531 mg, 100%). UPLC Method B: calculated for $C_{39}H_{66}N_2O_{24}$ 863.40, observed m/e: 864.43 [M+1]; Rt=1.64 min.

Step D: 3-(2-{([α-D-mannopyranosyl-(1→3)-[α-D-mannopyranosyl-(1→6)]-α-D-mannopyranosyl]oxy)ethyl}{6-(2,5-dioxopyrrolidin-1-yl)-6-oxohexyl}amino)propyl α-L-fucopyranoside Prepared from methyl 6-{[3-(-α-L-fucopyranosyl)propyl](2-[2-{-α-D-mannopyranosyl-(1→3)-[-α-D-mannopyranosyl-(1→6)]-α-D-mannopyranosyl}-oxy]ethyl)amino}hexanoate hydrochloride according to the procedures outlined for ML-XX steps F and G. UPLC Method B: calculated for $C_{39}H_{66}N_2O_{24}$ 946.40, observed m/e: 947.51 [M+1]; Rt=3.55 min.

Example 58

The synthesis of oligosaccharide linker 4-(2-{([α-D-mannopyranosyl-(1→3)-[α-D-mannopyranosyl-(1→6)]-α-D-mannopyranosyl]oxy)ethyl}{6-(2,5-dioxopyrrolidin-1-yl)-6-oxohexyl}amino)butyl a-L-fucopyranoside (ML-58) having the following structure is described.

ML-58

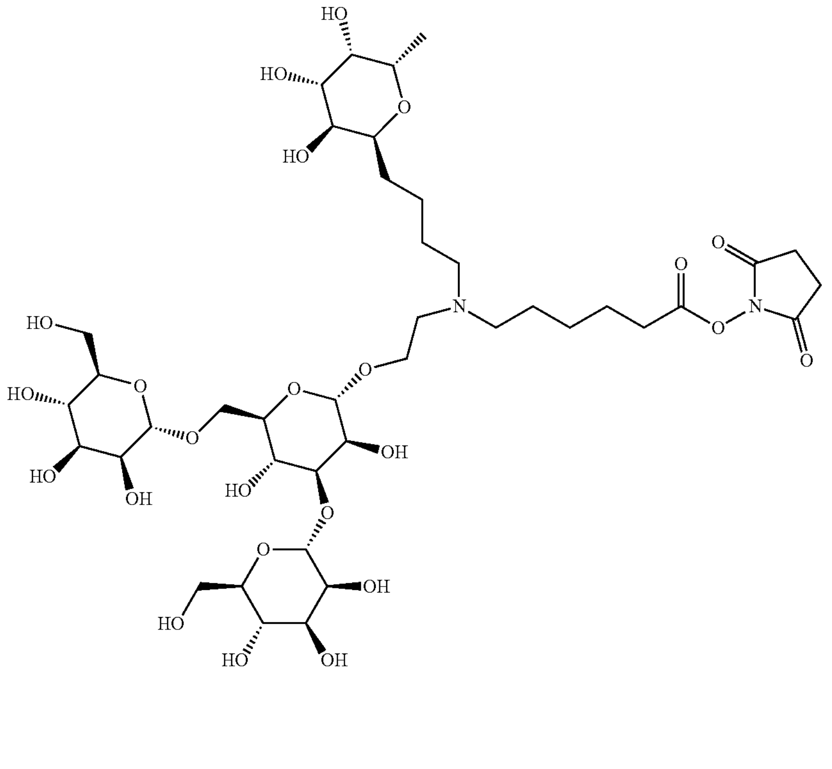

Step A: 3-(2,3,4-tri-O-benzyl-α-L-fucopyranosyl)propyl methanesulfonate

To a solution of 3-(2,3,4-tri-O-benzyl-α-L-fucopyranosyl)propanol [ML-36 step D] (10.6 g, 22.2 mmol) and Hunig's Base (4.66 mL, 26.7 mmol) in anhydrous DCM (100 mL) cooled in an ice bath was added dropwise methanesulfonyl chloride (1.9 mL, 24.5 mmol). After complete addition the mixture was stirred at ice bath temperature for 1 hour. Mixture washed with water (100 mL), sat. NaCl (50 mL); dried over $Na_2SO_4$, filtered and evaporated to give the title compound (12.6 g, 100%). $^1$H NMR ($CDCl_3$) δ 7.37 (15H, m), 4.80 (2H, m), 4.68 (2H, m), 4.63 (1H, d, J=11.8 Hz), 4.53 (1H, J=11.8 Hz), 4.22 (2H, m), 4.00 (1H, d, J=9.8 Hz), 3.94 (1H, m), 2.99 (3H, s), 1.88 (1H, m), 1.75 (2H, m), 1.62 (1H, m), 1.31 (3H, d, J=6.6 Hz).

Step B: 3-(2,3,4-tri-O-benzyl-α-L-fucopyranosyl) butanenitrile

To a solution of 3-(2,3,4-tri-O-benzyl-α-L-fucopyranosyl)propyl methanesulfonate (3 g, 5.4 mmol) in anhydrous DMF (30 mL) was added sodium azide (422 mg, 6.49 mmol) and the resulting mixture heated at 60° C. overnight. Mixture cooled and diluted with water (100 mL) and extracted with $Et_2O$ (3×30 mL); combined $Et_2O$ layers washed with sat. NaCl (30 mL); dried over $Na_2SO_4$, filtered and evaporated. The residue was purified by silica gel column chromatography (Teledyne Isco; 120 g) eluent: gradient 0-70% EtOAc in Hexanes to give the title compound (6 g, 76%). $^1$H NMR ($CDCl_3$) δ 7.29 (15H, m), 4.80 (2H, m), 4.71 (1H, d, J=11.8 Hz), 4.69 (1H, d, J=11.8 Hz), 4.65 (1H, d, J=11.8 Hz), 4.54 (1H, d, J=11.8 Hz), 3.95 (2H, m), 3.79 (3H, m), 2.37 (2H, m), 1.80 (2H, m), 1.62 (2H, m), 1.31 (3H, d, J=6.6 Hz).

Step C: 3-(2,3,4-tri-O-benzyl-α-L-fucopyranosyl) butanoic acid

A mixture of 3-(2,3,4-tri-O-benzyl-α-L-fucopyranosyl) butanenitrile (6 g, 12.36 mmol) in ethanol (100 mL) was treated with water (100 mL) and 5N NaOH (25 mL, 124 mmol) and the resulting mixture heated at reflux for 3 days. Mixture cooled and ethanol removed by evaporation, the remaining aqueous was acidified by the addition of conc. HCl and extracted with EtOAc (3×100 mL); combined EtOAc layers washed with sat. NaCl (100 mL), dried over $Na_2SO_4$, filtered and evaporated to give the title compound (5.2 g, 83%) as a light yellow oil. $^1$H NMR ($CDCl_3$) δ 7.40-7.30 (15H, m), 4.79 (2H, m), 4.71 (1H, d, J=12.0 Hz), 4.65 (2H, m), 4.53 (1H, d, J=11.8 Hz), 4.01 (1H, m), 3.92 (1H, m), 3.83 (1H, m), 3.78 (2H, m), 2.39 (2H, m), 1.75 (2H, m), 1.59 (2H, m), 1.30 (3H, d, J=6.6 Hz).

Step D: 4-(2,3,4-tri-O-benzyl-α-L-fucopyranosyl) butan-1-ol

To an ice bath cooled solution of 3-(2,3,4-tri-O-benzyl-α-L-fucopyranosyl)butanoic acid (5.2 g, 10.3 mmol) in anhydrous THF (100 mL) was added slowly borane-tetrahydrofuran complex (12.3 mL of a 1M soln in THF, 12.3 mmol) and the resulting mixture allowed to warm to room temperature and stirred for 3 days. Mixture quenched by the addition of methanol (5 mL) and diluted with sat. NaCl (200 mL) and extracted with EtOAc (2×150 mL); combined EtOAc layers dried over $Na_2SO_4$, filtered and evaporated. Residue purified by silica gel column chromatography (Teledyne Isco: 120 g) eluent: gradient 0-100% EtOAc in Hexanes to give the title compound (1.73 g, 34%) as a clear oil. $^1$H NMR ($CDCl_3$) δ 7.40-7.28 (15H, m), 4.79 (2H, m), 4.71 (1H, d, J=12.1 Hz), 4.66 (2H, m), 4.54 (1H, d, J=11.9 Hz), 3.99 (1H, m), 3.93 (1H, m), 3.80 (3H, m), 3.65 (2H, t, J=6.5 Hz), 1.67 (2H, m), 1.60-1.41 (4H, m), 1.30 (3H, d, J=6.6 Hz).

Step E: 4-(2,3,4-tri-O-benzyl-α-L-fucopyranosyl) butanal

To a solution of 4-(2,3,4-tri-O-benzyl-α-L-fucopyranosyl)butan-1-ol (1.73 g, 3.53 mmol) in DCM (50 mL) was added Dess-Martin reagent (2.24 g, 5.29 mmol) and the resulting mixture stirred at room temperature for 3 hours. Mixture washed with sat. $NaHCO_3$ (100 mL); dried over $Na_2SO_4$, filtered and evaporated. The residue was purified by silica gel column chromatography (Teledyne Isco: 80 g) eluent: gradient 0-80% EtOAc in Hexanes to give the title compound (1.24 g, 72%). $^1$H NMR ($CDCl_3$) δ 9.77 (1H, s), 7.40-7.28 (15H, m), 4.80 (1H, d, J=12.0 Hz), 4.78 (1H, J=12.0 Hz), 4.71 (1H, d, J=12.0 Hz), 4.66 (2H, m), 4.54 (1H, d, J=11.8 Hz), 3.98 (1H, m), 3.92 (1H, m), 3.83-3.76 (3H, m), 2.43 (2H, m), 1.80-1.63 (2H, m), 1.62-1.48 (2H, m), 1.30 (3H, d, J=6.6 Hz).

Step F: 4-(2-{([α-D-mannopyranosyl-(1→3)-[α-D-mannopyranosyl-(1→6)]-α-D-mannopyranosyl]oxy) ethyl}{6-(2,5-dioxopyrrolidin-1-yl)-6-oxohexyl}amino)butyl α-L-fucopyranoside Prepared from 4-(2,3,4-tri-O-benzyl-α-L-fucopyranosyl) butanal according to the procedures outlined for ML-57. UPLC Method B: calculated for $C_{40}H_{68}N_2O_{24}$ 960.42, observed m/e: 961.48 [M+1]; Rt=3.46 min.

Example 59

The synthesis of oligosaccharide linker 2-({6-[(2,5-Dioxopyrrolidin-1-yl)oxy]-6-oxohexyl}[3-(α-L-fucopyranosyl) propyl]amino)ethyl a-D-mannopyranoside (ML-59) having the following structure is described.

ML-59

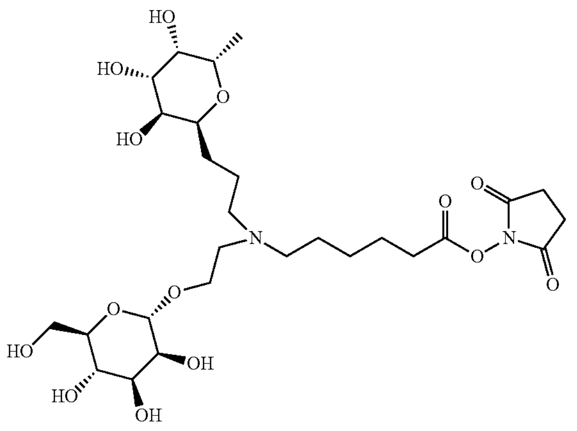

The title compound was prepared using procedures analogous to those described for ML-36 substituting 2-aminoethyl 2,3,4,6-tetra-O-acetyl-α-D-mannopyranoside for 2-aminoethyl 3,4,6-tri-O-acetyl-2-(acetylamino)-2-deoxy-β-D-glucopyranoside in Step F. UPLC Method B: calculated for $C_{27}H_{46}N_2O_{14}$ 622.29, observed m/e=623.3231 [M+1]; Rt=1.16 min.

Example 60

The synthesis of oligosaccharide linker 2-({6-[(2,5-Dioxopyrrolidin-1-yl)oxy]-6-oxohexyl}[3-(α-L-fucopyranosyl)propyl]amino)ethyl β-D-mannopyranoside (ML-60) having the following structure is described.

ML-60

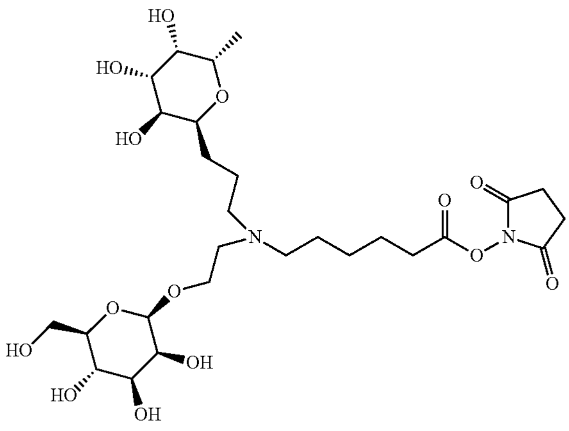

Step A: benzyl (2-((4,6-di-O-benzoyl-β-D galactopyranosyl)oxy)ethyl)carbamate To benzyl (2-((4,6-di-O-benzoyl-β-D galactopyranosyl) oxy)ethyl)carbamate (9.4 g, 26.3 mmol) was added 3 g of 4 A° powdered molecular sieves and mixture suspended in anhydrous toluene (100 mL). To this mixture was added dibutyltin (IV) oxide (14.21 g, 57.1 mmol) and the resulting mixture heated at 95° C. for 5 hours. The mixture was allowed to cool to room temperature then cooled in an ice bath and benzoyl chloride (6.66 mL, 57.3 mmol) added dropwise. Fine white precipitate formed, anhydrous acetonitrile (15 mL) added and stirred at room temperature for 48 hrs. Mixture evaporated and the residue was purified by column chromatography on silica gel (Teledyne Isco: 330 g), eluent: 0 to 50% EtOAc in Hexanes (8cv); and 50% EtOAc in Hexanes (10cv) to give the title compound (11.56 g, 78%) as a white solid.

$^1$H NMR ($CDCl_3$) δ 8.11 (2H, d, J=7.7 Hz), 8.04 (2H, dd, J=7.9 and 1.4 Hz), 7.58 (2H, m), 7.45 (4H, m), 7.36-7.29 (5H, m), 5.53 (1H, m), 5.14 (1H, dd, J=10.1 and 3.3 Hz), 5.06 (2H, s), 4.64 (1H, dd, J=11.5 and 6.3 Hz), 4.55 (1H, dd, J=11.5 and 6.6 Hz), 4.4 (1H, d, J=7.7 Hz), 4.24 (1H, t, J=4.2 Hz), 4.08 (1H, t, J=8.8 Hz), 3.93 (2H, m), 3.76 (1H, m), 3.48 (1H, m), 3.37 (1H, m), 3.28 (1H, d, J=3.3 Hz), 2.80 (1H, d, J=5.3 Hz).

Step B: benzyl (2-((((3,5-bis(trifluoromethyl)sulfonyl)oxy)-4,6-di-O-benzoyl-β-D galactopyranosyl) oxy)ethyl)carbamate To a solution of benzyl (2-((4,6-di-O-benzoyl-β-D galactopyranosyl)oxy)ethyl)carbamate (11.56 g, 20.44 mmol) dissolved in DCM (200 mL) cooled to −15° C. was added pyridine (21.5 mL, 266 mmol) followed by slow addition of triflic anhydride (10.36 mL, 61.3 mmol) and the resulting mixture allowed to warm to 0° C. over 3 hours. Mixture diluted with further DCM (200 mL) and washed with ice cold 1N HCl (500 mL), ice cold sat. $NaHCO_3$ (500 mL) and ice cold sat. NaCl (500 mL); dried over $Na_2SO_4$, filtered and evaporated to give the title compound (16.9 g, 100%) as a yellow foam. $^1$H NMR ($CDCl_3$) δ 8.16 (2H, dd, J=8.0 and 1.4 Hz), 8.04 (2H, dd, J=8.1 and 1.4 Hz), 7.65 (2H, m),7.52 (2H, m), 7.50 (2H, m), 7.39 (4H, m), 7.33 (1H, m), 5.55 (1H, dd, J=10.4 and 3.1 Hz), 5.50 (1H, d, J=3.1 Hz), 5.35 (1H, t, J=6.4 Hz), 5.14 (2H, s), 5.12 (1H, m), 4.77 (1H, d, J=7.9 Hz), 4.73 (1H, m), 4.28 (2H, m), 4.06 (1H, m), 3.80 (1H, m), 3.55 (1H, m), 3.47 (1H, m).

Step C: benzyl (2-((3,5-di-O-acetyl-4,6-di-O-benzoyl-β-D mannopyranosyl)oxy)ethyl)carbamate To a solution of benzyl (2-((((3,5-bis(trifluoromethyl) sulfonyl)oxy)-4,6-di-O-benzoyl-β-D galactopyranosyl)oxy) ethyl)carbamate (16.9 g, 20.37 mmol) in anhydrous toluene (100 mL), was added a solution of tetra butylammonium acetate (25 g, 82.9 mmol) in a mixture of toluene (150 mL) and DMF (4 mL) was added and the resulting mixture stirred at room temperature overnight. Diluted with of $CH_2Cl_2$ (30 mL) and washed with sat. NaCl (2×100 mL), dried over $MgSO_4$, filtered and evaporated. The residue was purified by silica gel column chromatography (Teledyne Isco: 330 g) eluent: 0-50% EtOAc/Hexane (10cv) then 50% EtOAc/Hexane (5cv) to give the title compound (8 g, 60.5%). $^1$H NMR ($CDCl_3$) δ 8.10 (2H, m), 7.98 (2H, dd, J=8.1 and 1.4 Hz), 7.61 (2H, m), 7.48 (2H, t, J=7.8 Hz), 7.46 (2H, t, J=7.7 Hz), 7.37 (4H, m), 7.33 (1H, m), 5.70 (1H, d, J=3.3 Hz), 5.61 (1H, t, J=10.0 Hz), 5.29 (1H, dd, J=10.0 and 3.3 Hz), 5.26 (1H, m), 5.10 (2H, s), 4.79 (1H, s), 4.64 (1H, dd, J=12.1 and 2.7 Hz), 4.47 (1H, dd, J=12.1 and 5.8 Hz), 3.94 (2H, m), 3.74 (1H, m), 3.48 (1H, m), 3.37 (1H, m), 2.15 (3H, s), 2.00 (3H, s).

Step D: 2-aminoethyl 3,5-di-O-acetyl-4,6-di-O-benzoyl-β-D mannopyranoside

To a nitrogen flushed solution of benzyl (2-((3,5-di-O-acetyl-4,6-di-O-benzoyl-b-D mannopyranosyl)oxy)ethyl) carbamate (8 g, 12.31 mmol) in EtOAc (100 ml) was added 10% palladium on carbon (1.31 g) and the resulting mixture stirred under a balloon of hydrogen overnight. The mixture was filtered through Celite and the filtrate evaporated to give the title compound (6.3 g, 99%) as a light yellow foam. $^1$H NMR ($CDCl_3$) δ 8.11 (2H, m), 7.90 (2H, m), 7.60 (2H, m), 7.47 (4H, m), 5.72 (1H, ddd, J=9.2, 3.2 and 1.1 Hz), 5.59 (1H, t, J=9.7 Hz), 5.33 (1H, ddd, J=10.1, 4.8 and 3.3 Hz), 4.85 (1H, dd, J 16.0 and 1.1 Hz), 4.65 (1H, m), 4.45 (1H, ddd, J=12.1, 5.7 and 2.0 Hz), 3.95 (2H, m), 3.73 (1H, m), 3.09 (2H, bs), 2.90 (1H, m), 2.15 (3H, s), 1.99 (3H, s).

Step E: 2-({6-[(2,5-Dioxopyrrolidin-1-yl)oxy]-6-oxohexyl}[3-(α-L-fucopyranosyl)propyl]amino) ethyl α-D-mannopyranoside The title compound was prepared using procedures analogous to those described for ML-36 substituting 2-aminoethyl 3,5-di-O-acetyl-4,6-di-O-benzoyl-β-D mannopyranoside for 2-aminoethyl 3,4,6-tri-O-acetyl-2-(acetylamino)-2-deoxy-β-D-glucopyranoside in Step F. UPLC Method B: calculated for $C_{27}H_{46}N_2O_{14}$ 622.29, observed m/e=623.3536 [M+1]; Rt=1.13 min.

Example 61

The synthesis of oligosaccharide linker 2-({6-[(2,5-Dioxopyrrolidin-1-yl)oxy]-6-oxohexyl}-2-[(α-L-fucopyranosyl)

oxy]ethyl)-α-D-mannopyranoside (ML-61) having the following structure is described.

ML-61

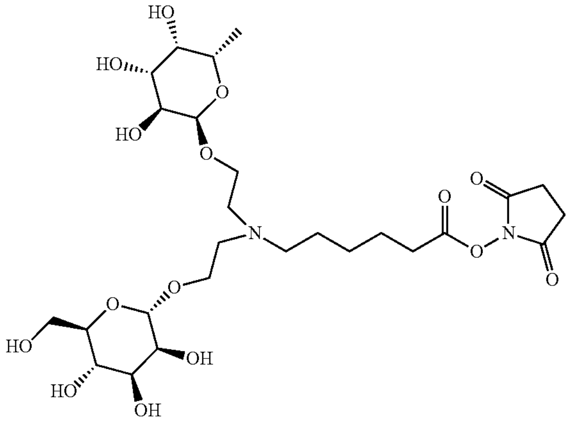

Step A: 2-{[2-(2,3,4-tri-O-acetyl-α-L-fucopyranosyl)ethyl]amino}ethyl-2,3,4,6-tetra-O-acetyl-α-D-mannoopyranoside To a mixture of 2-oxoethyl 2,3,4,6 tetra-O-acetyl-α-D-mannopyranoside (1.3 g, 3.33 mmol) and 2-aminoethyl 2,3,4-tri-O-acetyl-α-L-fucopyranoside (2.22 g, 6.7 mmol) in anhydrous DCM (20 mL) was added TFA (0.257 mL, 3.3 mmol) and mixture stirred at room temperature for 10 mins then sodium triacetoxyborohydride (1.41 g, 6.66 mmol) added and mixture stirred at room temperature overnight. Mixture evaporated and the residue partitioned between EtOAc (50 mL) and sat. $NaHCO_3$ (100 mL); organic layer washed with sat. NaCl (50 mL); dried over $Na_2SO_4$; filtered and evaporated. The residue purified by reverse phase silica gel column chromatography (Teledyne Isco: C18 275 g) eluent: gradient 10-100% $CH_3CN$ in water to give the title compound (667 mg, 28%). $^1H$ NMR ($CDCl_3$) δ 5.37 (1H, dd, J=10.0 and 3.5 Hz), 5.32 (1H, d, J=9.8 Hz), 5.29 (1H, dd, J=3.4 and 1.9 Hz), 5.26 (1H, dd, J=3.5 and 1.1 Hz), 5.20 (1H, dd J=10.5 and 7.9 Hz), 5.04 (1H, dd, J 10.5 and 3.4 Hz), 4.87 (1H, d, J=1.8 Hz), 4.50 (1H, d, J=7.9 Hz), 4.32 (1H, dd, J=12.3 and 2.5 Hz), 4.13 (1H, dd, J=12.2 and 2.5 Hz), 4.04 (1H, m), 4.00 (1H, m), 3.86-3.79 (2H, m), 3.69 (1H, m), 3.59 (1H, m), 2.91-2.85 (4H, m), 2.19 (3H, s), 2.18 (3H, s), 2.13 (3H, s), 2.09 (3H, s), 2.07 (3H, s), 2.02 (3H, s), 2.01 (3H, s), 1.25 (3H, d, J=6.4 Hz).

Step B: benzyl 6-{[2-(2,3,4-tri-O-acetyl-α-L-fucopyranosyl)ethyl](2-{[2,3,4,6-tetra-O-acetyl-α-D-mannoopyran]oxy}ethyl)amino}hexanoate To a solution of 2-{[2-(2,3,4-tri-O-acetyl-α-L-fucopyranosyl)ethyl]amino}ethyl-2,3,4,6-tetra-O-acetyl-a-D-mannoopyranoside (667 mg, 0.943 mmol) and benzyl 6-oxohexanoate (311 mg, 1.41 mmol) in DCM (6 mL) was added acetic acid (0.054 mL, 0.943 mmol) mixture stirred at room temperature for 10 mins then sodium triacetoxyborohydride (400 mg, 1.89 mmol) added and mixture stirred at room temperature overnight. UPLC-MS shows complete conversion. Mixture evaporated and the residue partitioned between EtOAc (30 mL) and sat. $NaHCO_3$ (40 mL); organic layer washed with sat. NaCl (20 mL); dried over $Na_2SO_4$, filtered and evaporated. The residue was purified by reverse phase silica gel column chromatography (Teledyne Isco: C18 40 g) eluent: gradient 5-100% $CH_3CN$ in water to give the title compound (434 mg, 50%). $^1H$ NMR ($CDCl_3$) δ 7.37 (5H, m), 5.35 (1H, dd, J=9.9 and 3.1 Hz), 5.32 (1H, d, J=9.2 Hz), 5.25 (2H, dd, J=3.2 and 1.7 Hz), 5.19 (1H, dd, J=10.5 and 7.9 Hz), 5.14 (2H, s), 5.04 (1H, dd, J=10.4 and 3.5 Hz), 4.85 (1H, d, J=1.7 Hz), 4.51 (1H, d, J=7.9 Hz), 4.32 (1H, dd, J=12.2 and 5.1 Hz), 4.12 (1H, dd, J=12.2 and 2.5 Hz), 4.04 (1H, m), 3.93 (1H, dt, J=9.9 and 5.9 Hz), 3.85 (1H, m), 3.72 (1H, dt, J=10.1 and 6.0 Hz), 3.59 (1H, dt, J=9.9 and 6.6 Hz), 3.51 (1H, m), 2.74-2.71 (4H, m), 2.50 (2H, t, J=7.4 Hz), 2.39 (2H, t, J=7.5 Hz), 2.19 (3H, s), 2.18 (3H, s), 2.13 (3H, s), 2.07 (3H, s), 2.06 (3H, s), 2.01 (3H, s), 2.00 (3H, s), 1.70-1.66 (4H, m), 1.44 (2H, m), 1.32 (2H, m), 1.24 (3H, d, J=6.4 Hz).

Step C: 2-({6-[(2,5-Dioxopyrrolidin-1-yl)oxy]-6-oxohexyl}-2-[(α-L-fucopyranosyl)oxy]ethyl)-α-D-mannopyranoside The title compound was prepared using procedures analogous to those described for ML-35 in step B substituting benzyl 6-{[2-(2,3,4-tri-O-acetyl-α-L-fucopyranosyl)ethyl](2-{[-2,3,4,6-tetra-O-acetyl-a-D-mannoopyran]oxy}ethyl)amino}hexanoate for benzyl 6-(bis{2-[(2,3,4-tri-O-benzoyl-α-L-fucopyranosyl)oxy]ethyl}amino)hexanoate. UPLC Method B: calculated for $C_{26}H_{44}N_2O_{15}$ 624.27, observed m/e=625.2990 [M+1]; Rt=1.12.

Example 62

The synthesis of oligosaccharide linker N,N'-Bis{2-[(α-L-fucopyranosyl)oxy]ethyl}-1-{6-[(2,5-dioxopyrrolidin-1-yl)oxy]-6-oxohexanoyl}pyrrolidine-(2R,5R)-2,5-dicarboxamide (ML-62) having the following structure is described.

ML-62

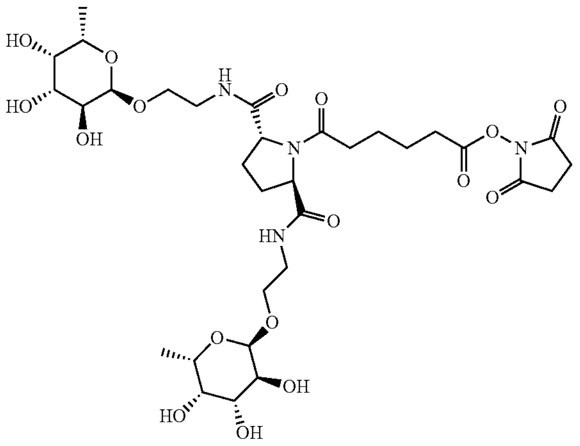

The title compound was prepared using procedures analogous to those described for ML-6 substituting (2R,5R)-pyrrolidine-2,5-dicarboxylic acid for 2,2'-{[6-(benzyloxy)-6-oxohexanoyl]imino}diacetic acid in Step C. UPLC Method B: m/e=736.36 [M+1]; Rt=2.22 min.

Example 63

The synthesis of oligosaccharide linker N,N'-Bis{2-[(α-L-fucopyranosyl)oxy]ethyl}-1-{6-[(2,5-dioxopyrrolidin-1-yl)oxy]-6-oxohexanoyl}(piperidine-4,4-diyl)diacetamide (ML-63) having the following structure is described.

ML-63

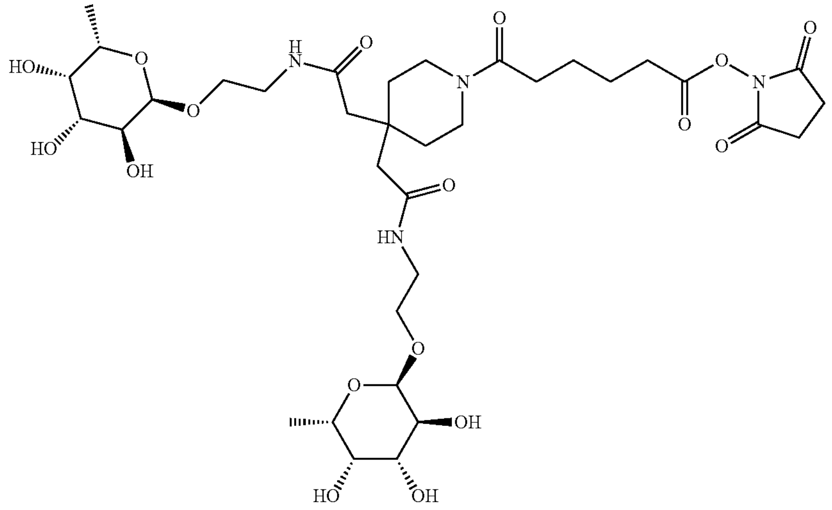

The title compound was prepared using procedures analogous to those described for ML-6 substituting 2,2'-(piperidine-4,4-diyl)diacetic acid for 2,2'-{[6-(benzyloxy)-6-oxohexanoyl]imino}diacetic acid in Step C. UPLC Method B: m/e=805.38 [M+1]; Rt=2.35 min.

Example 64

The synthesis of oligosaccharide linker 1-{6-[(2,5-Dioxopyrrolidin-1-yl)oxy]-6-oxohexanoyl}-N,N'-bis{2-[(α-L-fucopyranosyl)oxy]ethyl}piperidine-cis-3,4-dicarboxamide (ML-64) having the following structure is described.

ML-64

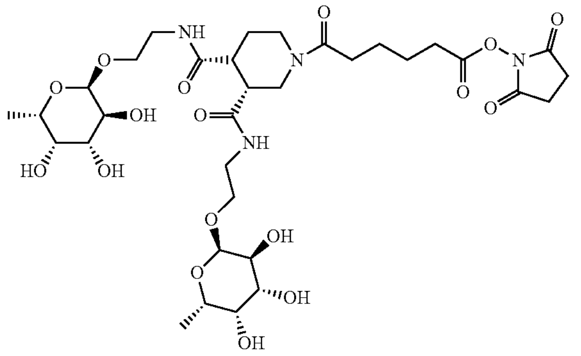

The title compound was prepared using procedures analogous to those described for ML-17 substituting 3,4-pyridinedicarboxylic acid for 3,5-pyridinedicarboxylic acid as the starting material in step A. UPLC Method F: m/e=777.3660 [M+1]; Rt=2.15 min.

Example 65

The synthesis of oligosaccharide linker 2,5-dioxopyrrolidin-1-yl 6-((3R,4R)-3,4-bis((2-(((2R,3S,4R,5S,6S)-3,4,5-trihydroxy-6-methyltetrahydro-2H-pyran-2-yl)oxy)ethyl)carbamoyl)piperidin-1-yl)hexanoate (ML-65) having the following structure is described.

ML-65

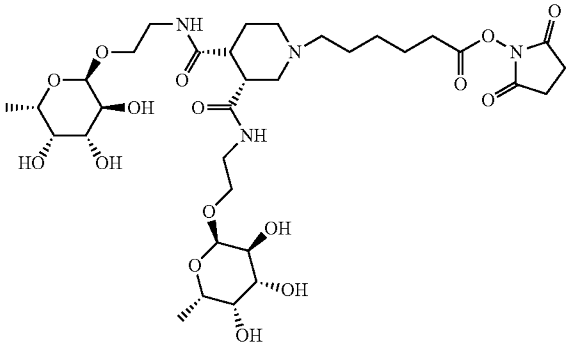

Step A: (3R,4R)—N3,N4-bis(2-(((2R,3S,4R,5S,6S)-3,4,5-trihydroxy-6-methyltetrahydro-2H-pyran-2-yl)oxy)ethyl)piperidine-3,4-dicarboxamide The title compound was prepared using the procedure analogous to that described for ML-17 Steps A and B, substituting 3,4-pyridinedicarboxylic acid for 3,5-pyridinedicarboxylic acid as the starting material in step A. UPLC Method F: m/e=552.2733 [M+1]; Rt=1.37 min

Step B: benzyl 6-((3R,4R)-3,4-bis((2-(((2R,3S,4R,5S,6S)-3,4,5-trihydroxy-6-methyltetrahydro-2H-pyran-2-yl)oxy)ethyl)carbamoyl)piperidin-1-yl)hexanoate (3R,4R)—N3,N4-bis(2-(((2R,3S,4R,5S,6S)-3,4,5-trihydroxy-6-methyltetrahydro-2H-pyran-2-yl)oxy)ethyl)piperidine-3,4-dicarboxamide (118 mg, 0.214 mmol) was dissolved in THF (2 mL), to which benzyl 6-oxohexanoate (70.7 mg, 0.321 mmol) in THF (0.5 mL) was added, followed by sodium triacetoxyborohydride (136 mg, 0.642 mmol) and acetic acid (3.67 μL, 0.064 mmol) were added, and the mixture was stirred at room temperature for 3 h. The product was isolated by preparative reverse-phase chromatography on C-18 column, using a gradient of 0-30% of AcN in water. UPLC Method F: m/e=756.4241 [M+1]; Rt=3.05 min

Step C: The synthesis of oligosaccharide linker 2,5-dioxopyrrolidin-1-yl 6-((3R,4R)-3,4-bis((2-(((2R,3S,4R,5S,6S)-3,4,5-trihydroxy-6-methyltetrahydro-2H-pyran-2-yl)oxy)ethyl)carbamoyl)piperidin-1-yl)hexanoate The title compound was prepared using procedure analogous to those described for ML-1 Steps C and D substituting benzyl 6-((3R,4R)-3,4-bis((2-(((2R,3S,4R,5S,6S)-3,4,5-trihydroxy-6-methyltetrahydro-2H-pyran-2-yl)oxy)ethyl)carbamoyl)piperidin-1-yl)hexanoate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C and substituting 6-((3R,4R)-3,4-bis((2-(((2R,3S,4R,5S,6S)-3,4,5-trihydroxy-6-methyltetrahydro-2H-pyran-2-yl)oxy)ethyl)carbamoyl)piperidin-1-yl)hexanoic acid for 6-({2-[(α-D-mannopyranosyl-(1→3)-[α-D-mannopyranosyl-(1→6)]-α-D-mannopyranosyl)oxy]ethyl}amino)-6-oxohexanoic acid in Step D: UPLC Method F: m/e=763.7796 [M+1]; Rt=2.15 min.

Example 66

The synthesis of oligosaccharide linker 2,5-dioxopyrrolidin-1-yl 6-((2R,5R)-2,5-bis((2-(((2R,3S,4R,5S,6S)-3,4,5-trihydroxy-6-methyltetrahydro-2H-pyran-2-yl)oxy)ethyl)carbamoyl)piperidin-1-yl)-6-oxohexanoate (ML-66) having the following structure is described.

ML-66

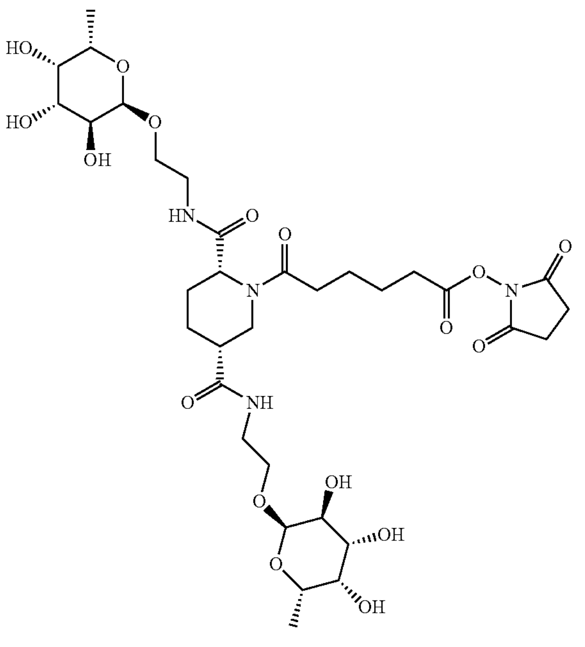

The title compound was prepared using procedures analogous to those described for ML-17 substituting 2,5-pyridinedicarboxylic acid for 3,5-pyridinedicarboxylic acid as the starting material in step A. UPLC Method A: UPLC m/e=777.0 [M+1]; Rt=0.5 min.

Example 67

The synthesis of oligosaccharide linker 2,5-dioxopyrrolidin-1-yl 6-(((R)-1,4-dioxo-1-((2-(((2S,3S,4S,5S,6R)-3,4,5-trihydroxy-6-(hydroxymethyl)tetrahydro-2H-pyran-2-yl)oxy)ethyl)amino)-4-((2-(((2R,3S,4R,5S,6S)-3,4,5-trihydroxy-6-methyltetrahydro-2H-pyran-2-yl)oxy)ethyl)amino)butan-2-yl)amino)-6-oxohexanoate (ML-67) having he following structure is described.

ML-67

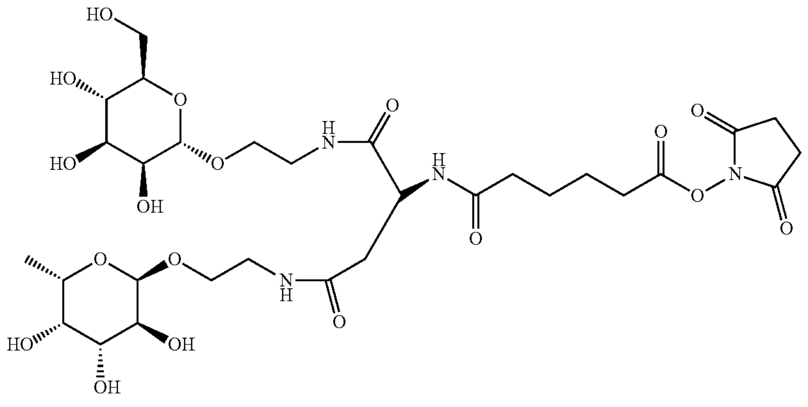

The title compound was prepared using procedures analogous to those described for ML-20 substituting Z-Glu-γ-Bn for Z-ASP(OBZL)-OH and substituting 2-aminoethyl α-D-mannopyranosyl-(1→3)-[α-D-mannopyranosyl-(1→6)]-α-D-mannopyranoside for 2-aminoethyl α-D-mannopyranoside in Step A. UPLC Method B: m/e=753.26 [M+1]; Rt=1.59 min.

Example 68

The synthesis of oligosaccharide linker (ML-68) having the following structure is described.

Step A: 1,2,3,4-tetrakis(oxy)tetrakis(trimethylsilane) L-Fucose

To a solution of L-Fucose (4.0 g, 24.37 mmol, 1.0 eq) in DMF (25 mL) at 0° C. was added TEA (17.32 mL, 124 mmol, 5.1 eq). To above mixture was added TMS-Cl (15.88 mL, 125 mmol, 5.1 eq) dropwise. The reaction was then warmed to r.t. and stirred at r.t. for 4 hr. The reaction mixture was poured to ice and hexance mixture (100 mL, 1:1). The mixture was extracted with hexane (100 mL×3). The organic was washed with water (10 ml×3), dried over MgSO4, filtered. The filtrated was concentrated and dried over high vacuum pump to give the titled compound as colorless oil (8.7 g, 19.2 mmol, 79%). 13C NMR (CDCl3, 125 MHz) δ 94.5 (1C), 70.6 (1C), 69.6 (1C), 66.6 (1C), 39.6 (4C), 16.7 (Me), 0.67 (3Me), 0.43 (3Me), 0.29 (3Me), 0.16 (3Me); $^{1}$H NMR (CDCl3, 500 MHz) δ 5.0 (s, 1H), 4.0 (m, 1H), 3.8 (1H), 3.6 (1H), 1.0 (d, 3H), 0-0.2 (m, 36H).

ML-68

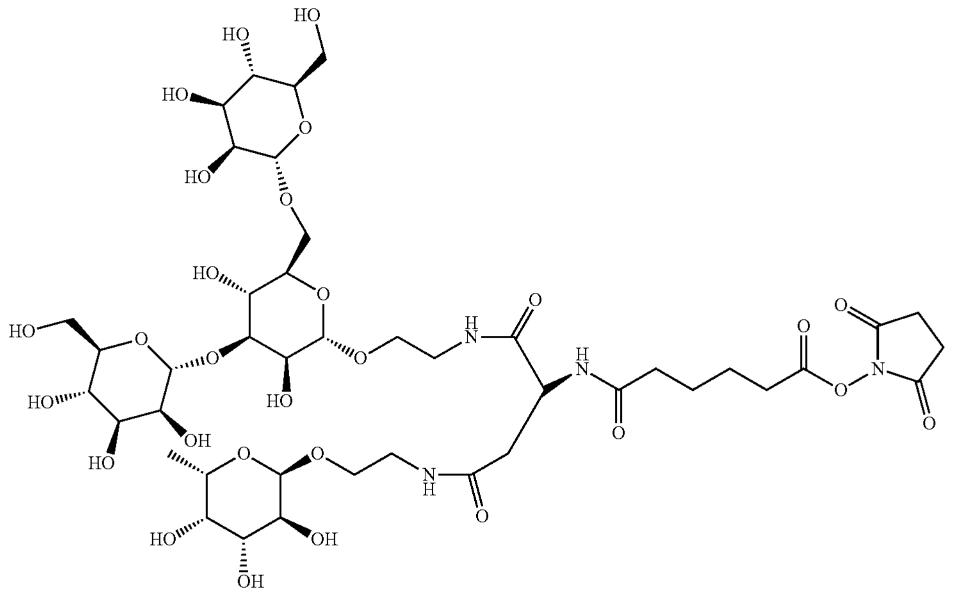

The title compound was prepared using procedures analogous to those described for ML-20 substituting Z-Glu-γ-Bn for Z-ASP(OBZL)-OH in Step A. UPLC Method B: m/e=1077.52 [M+1]; Rt=2.93 min.

Example 69

The synthesis of oligosaccharide linker 2,5-dioxopyrrolidin-1-yl 6-(2-(bis(-[(α-L-fucopyranosyl)oxy)ethyl)amino)acetamido)hexanoate (ML-69) having the following structure is described.

ML-69

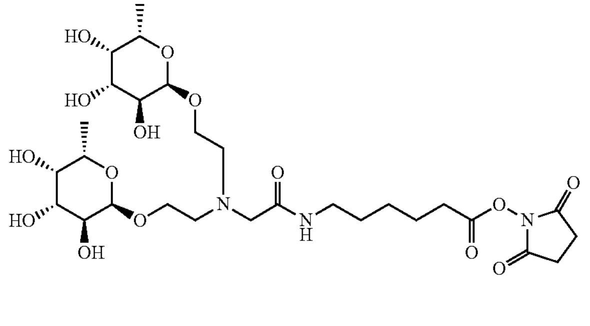

Step B: benzyl 6-(2-(bis(2-hydroxyethyl)amino)acetamido)hexanoate

To a solution of 2-(bis(2-hydroxyethyl)amino)acetic acid (500 mg, 3.06 mmol, 1.0 eq) in DMF (10 mL) at zero degree, was added TSTU (1107 mg, 3.68 mmol, 1.2 eq) followed by TEA (0.512 mL, 3.68 mmol, 1.2 eq). The reaction was warmed to rt and stirred at that temperature for 2 h. To above mixture was added L-000503048-001W001 (1447 mg, 3.68 mmol, 1.2 eq) pre-mixed with TEA (0.512 ml, 3.66 mmol). The reaction was stirred at rt for 18 hr. UPLC indicated formation of desired product. DMF was removed under reduced pressure. The crude was purified by C18 Reverse phase chromatography (eluted with 0-30% ACN/water in 16 CV). Fractions containing desired product were combined, concentrated and lyo to give the titled compound as colorless syrup. UPLC Method B: m/e=367.2356 [M+1]; Rt=3.54 min.

Step C: benzyl 6-(2-(bis(2-[(α-L-fucopyranosyl)oxy)ethyl)amino)acetamido)hexanoate To a solution of benzyl 6-(2-(bis(2-hydroxyethyl)amino)acetamido)hexanoate (210 mg, 0.573 mmo, 1.0 eq) in DCM (10 mL) at zero degree, was added TBAI (1820 mg, 4.93 mmol, 8.6 eq), DIPEA (0.500 ml, 2.87 mmol, 5.0 eq). The mixture was warmed to rt and stirred at rt for 30 min. To above solution was added 1,2,3,4-tetrakis(oxy)tetrakis(trimethylsilane) L-Fucose (1557 mg, 3.44 mmol, 6.0 eq) with iodotrimethylsilane (0.390 ml, 2.87 mmol, 5.0 eq) in DCM (10 ml) dropwise. The mixture was stirred at rt for 18 hr. UPLC indicated formation of desired product. Remove DCM and added MeOH (10 ml) and Dowex H+ resin till pH ~2. Stirred at rt for 1 h. filtered through a pad of celite. The filtrated was concentrated and purified by C18 Reverse phase chromatography (eluted with 0-30% ACN/water in 16 CV). Fractions containing desired product were combined, concentrated and lyo to give the titled compound as colorless syrup (40 mg, 0.061 mmol, 10.6%). UPLC Method B: m/e=659.3745 [M+1]; Rt=3.36 min.

Step D: 6-(2-(bis(2-[(α-L-fucopyranosyl)oxy)ethyl)amino)acetamido)hexanoic acid

To a solution of benzyl 6-(2-(bis(2-[(α-L-fucopyranosyl)oxy)ethyl)amino)acetamido)hexanoate (40 mg, 0.061 mmol) in water (5 ml), was added Pd/C (30.5 mg, 0.029 mmol). The reaction was stirred under H2 balloon for 18 hr. UPLC indicated formation of desired product. The above solution was diluted with MeOH (5 mL), filtered through a pad of celite, concentrated and lyo to give the titled compound as colorless syrup (20 mg, 6.1%). UPLC Method B: m/e=569.3191 [M+1]; Rt=1.93 min.

Step E: 2,5-dioxopyrrolidin-1-yl 6-(2-(bis(-[(α-L-fucopyranosyl)oxy)ethyl)amino) acetamido) hexanoate To a solution of 6-(2-(bis(2-[(α-L-fucopyranosyl)oxy)ethyl)amino)acetamido)hexanoic acid (20 mg, 0.037 mmol, 1.0 eq) in DMF (1 mL) was added TSTU (16.68 mg, 0.055 mmol, 1.5 eq) followed by Hunig's Base (7.74 μl, 0.044 mmol, 1.2 eq). The reaction was stirred at rt for 1 h. TLC (4/1/1/1 EtOAc/MeOH/ACN/water) indicated no starting material left. UPLC indicated formation of pdt. Remove DMF under reduced pressure. The crude product was used without purification. UPLC Method B: m/e=666.3351 [M+1]; Rt=2.28 min.

Example 70

The synthesis of oligosaccharide linker 2,5-dioxopyrrolidin-1-yl 6-(2-(bis(-[(α-L-fucopyranosyl)oxy)propyl)amino)acetamido)hexanoate (ML-70) having the following structure is described.

ML-70

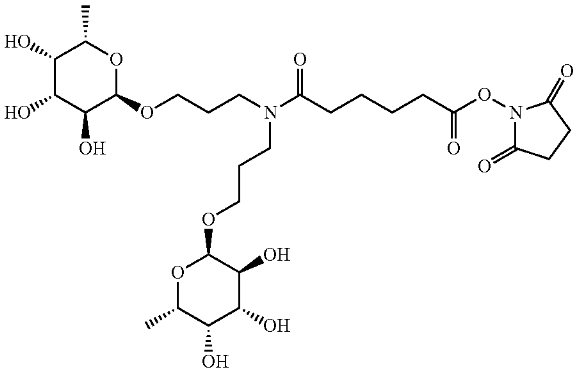

Step A: benzyl 6-(bis(3-hydroxypropyl)amino)-6-oxohexanoate

To a solution of 3,3'-azanediylbis(propan-1-ol) (1000 mg, 7.51 mmol, 1.0 eq) was in DMF (10 ml), was added benzyl (2,5-dioxopyrrolidin-1-yl) adipate (2503 mg, 7.51 mmol, 1.0 eq) followed by TEA (1.046 ml, 7.51 mmol, 1.0 eq). The reaction was stirred at 25 deg for 18 hr. UPLC indicated formation of desired product. DMF was removed under reduced pressure. The crude was purified by C18 Reverse phase chromatograph (eluted with 0-40% ACN/water in 16 CV). Fractions containing desired product were combined and concentrated to give the titled compound as colorless oil (1.55 g, 4.41 mmol, 58.7%). UPLC Method B: m/e=352.2171 [M+1]; Rt=3.47 min. $^1$H NMR (CDCl3, 500 MHz) δ 7.3-7.5 (m, 5H), 5.15 (m, 2H), 3.65 (m, 2H), 3.40 (m, 5H), 2.66 (s, 3H), 2.45 (m, 3H), 2.29 (s, 1H), 1.84 (s, 1H), 1.70 (m, 7H).

Step B: benzyl 6-(2-(bis(2-[(α-L-fucopyranosyl)oxy)propyl)amino)acetamido)hexanoate The title compound was prepared using procedures analogous to those described for ML-YZ-1 substituting benzyl 6-(bis(3-hydroxypropyl)amino)-6-oxohexanoate for benzyl 6-(2-(bis(2-hydroxyethyl)amino)acetamido)hexanoate in Step C. UPLC Method B: m/e=644.3454 [M+1]; Rt=3.28 min.

Step C: 6-(2-(bis(2-[(α-L-fucopyranosyl)oxy)propyl)amino)acetamido)hexanoic acid The title compound was prepared using procedures analogous to those described for ML-YZ-1 substituting benzyl 6-(2-(bis(2-[(α-L-fucopyranosyl)oxy)propyl)amino)acetamido)hexanoate for benzyl 6-(2-(bis(2-[(α-L-fucopyranosyl)oxy)ethyl)amino)acetamido)hexanoate in Step D. UPLC Method B: m/e=554.3076 [M+1]; Rt=2.13 min.

Step E: 2,5-dioxopyrrolidin-1-yl 6-(2-(bis(-[(α-L-fucopyranosyl)oxy)propyl)amino)acetamido)hexanoate The title compound was prepared using procedures analogous to those described for ML-YZ-1 substituting 6-(2-(bis (2-[(α-L-fucopyranosyl)oxy)propyl)amino)acetamido) hexanoic acid for 6-(2-(bis(2-[(α-L-fucopyranosyl)oxy) ethyl)amino)acetamido)hexanoic acid in Step E. UPLC Method B: m/e=651.3166 [M+1]; Rt=2.41 min.

Example 71

The synthesis of oligosaccharide linker benzyl 6-(2-(bis (2-[(α-L-fucopyranosyl)oxy)butyl)amino)acetamido) hexanoate (ML-71) having the following structure is described.

ML-71

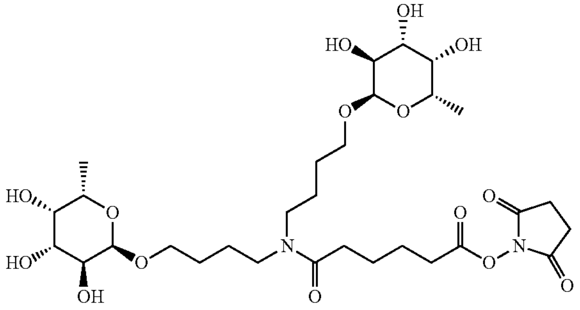

Step A: 4-(benzyoxy)-N-(4-(benzyloxy)butyl)butanamide

To a solution 4-(benzyloxy)butanoic acid (1 g, 5.15 mmol, 1.0 eq) in DMF (5 ml) at zero deg, was added TSTU (1.627 g, 5.41 mmol, 1.05 eq) followed by TEA (0.718 ml, 5.15 mmol, 1.0 eq). The reaction was warmed to rt and stirred at rt for 2 hr. To above reaction was added 4-(benzyloxy)butan-1-amine (0.969 g, 5.41 mmol, 1.05 eq) followed by TEA (0.718 ml, 5.15 mmol, 1.0 eq). The reaction was stirred at rt for 18 hr. LC-MS showed formation of desired product. DMF was removed under reduced pressure. The crude was purified by silica gel column (120 g, eluted with 0-15% MeOH/DCM in 16 CV). Fractions containing desired product were combined and concentrated to give the titled compound (1.65 g, 4.64 mmol, 90% yield). LC-MS Method A: m/e=356.70 [M+1]; Rt=1.22 min. $^1$H NMR (CDCl3, 500 MHz) δ 7.2-7.4 (m, 10H), 5.98 (s, 1H), 4.51 (m, 4H), 3.53 (m, 4H), 3.24 (m, 2H), 2.28 (m, 2H), 1.96 (m, 2H), 1.5-1.7 (m, 4H).

Step B: bis(4-(benzyloxy)butyl)amine

In a 200 mL round bottom flask, to a solution of 4-(benzyoxy)-N-(4-(benzyloxy)butyl)butanamide (1.65 g, 4.64 mmol) in THF (5 ml) at zero deg, was added BH3.THF (13.93 ml, 13.93 mmol) dropwise. The reaction was warmed to rt and stirred at rt for 18 hr. TLC showed formation of pdt and disappear of starting material. The reaction was quenched with aqueous saturated NH4Cl. The mixture was concentrated, dilute with EtOAc, shake with 1 N HCl, also wash with bicarbonate, brine and water. The organic layer was dried over MgSO4, filtered and concentrated. The crude was used to next step without purification. LC-MS Method A: m/e=341.00 [M+1]; Rt=1.06 min.

Step C: 4,4'-azanediylbis(butan-1-ol)

To a solution of bis(4-(benzyloxy)butyl)amine (300 mg, 0.879 mmol) was in a mixed solvent of Dioxane (5 ml)/Water (5 mL), was added PdOH2 (30.8 mg, 0.044 mmol). The reaction was stirred under H2 at 40 PSI for 18 h. LC-MS showed no starting material and formation of desired product. The mixture was filtered through a pad of celite, washed with dioxane/water (10 mL, 1/1). The filtrate was concentrated and dried over high vacuum pump to give the titled compound (130 mg, 0.806 mmol, 92% yield). LC-MS Method A: m/e=162.01 [M+1]; Rt=0.18 min.

Step D: benzyl 6-(2-(bis(2-[(α-L-fucopyranosyl) oxy)butyl)amino)acetamido)hexanoate The title compound was prepared using procedures analogous to those described for ML-69 substituting benzyl 6-(bis(3-hydroxybutyl)amino)-6-oxohexanoate for benzyl 6-(2-(bis(2-hydroxyethyl)amino)acetamido)hexanoate in Step C. UPLC Method B: m/e=644.3454 [M+1]; Rt=3.28 min.

Step E: 6-(2-(bis(2-[(α-L-fucopyranosyl)oxy)propyl)amino)acetamido)hexanoic acid The title compound was prepared using procedures analogous to those described for ML-69 substituting benzyl 6-(2-(bis(2-[(α-L-fucopyranosyl)oxy)butyl)amino)acetamido)hexanoate for benzyl 6-(2-(bis(2-[(α-L-fucopyranosyl)oxy)ethyl)amino)acetamido)hexanoate in Step D. UPLC Method B: m/e=554.3076 [M+1]; Rt=2.13 min.

Step F: 2,5-dioxopyrrolidin-1-yl 6-(2-(bis(-[(α-L-fucopyranosyl)oxy)butyl)amino)acetamido)hexanoate The title compound was prepared using procedures analogous to those described for ML-69 substituting 6-(2-(bis(2-[α-L-fucopyranosyl)oxy)butyl)amino)acetamido)hexanoic acid for 6-(2-(bis(2-[(α-L-fucopyranosyl)oxy)ethyl)amino) acetamido)hexanoic acid in Step E. UPLC Method B: m/e=651.3166 [M+1]; Rt=2.41 min.

Step G: benzyl 6-(2-(bis(2-[(α-L-fucopyranosyl) oxy)butyl)amino)acetamido)hexanoate The title compound was prepared using procedures analogous to those described for ML-69 substituting benzyl 6-(bis(3-hydroxybutyl)amino)-6-oxohexanoate for benzyl 6-(2-(bis(2-hydroxyethyl)amino)acetamido)hexanoate in Step C. UPLC Method B: m/e=644.3454 [M+1]; Rt=3.28 min.

Example 72

The synthesis of oligosaccharide linker 2,5-dioxopyrrolidin-1-yl 6-(2,3-bis-2[2-(α-L-fucopyranosyl)oxyethyl)carbamoyl)cyclopropanecarboxylic)amino)acetamido)) hexanoate (ML-72) having the following structure is described.

ML-72

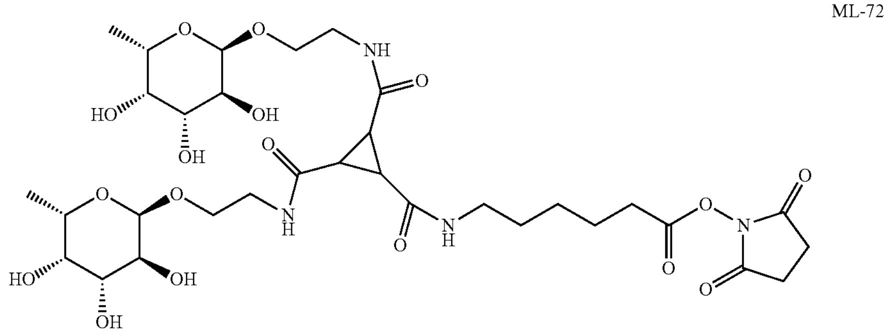 [SMILES: C[C@@H]1O[C@@H](OCCNC(=O)C2C(C(=O)NCCCCCC(=O)ON3C(=O)CCC3=O)C2C(=O)NCCO[C@@H]2O[C@@H](C)[C@@H](O)[C@@H](O)[C@@H]2O)[C@@H](O)[C@H](O)[C@@H]1O]

Step A: 2,3-bis-2[2-(α-L-fucopyranosyl)oxyethyl) carbamoyl)cyclopropanecarboxylic acid To a solution L-000719504-000X003 (353 mg, 2.027 mmol) in DMF (10 ml), was added EDC (816 mg, 4.26 mmol) and HOBT (93 mg, 0.608 mmol). The mixture was stirred at 25 deg for 30 min. To above mixture was added AEF (882 mg, 4.26 mmol). The mixture was stirred at 25 for 18 hr. UPLC indicated formation of desired product. DMF was removed under reduced pressure. The crude was purified by C18 reverse phase chromatograph (eluted with 0-30% ACN/water with 0.05% TFA in 37 min). Fractions containing desired product were combined and lyo to give the titled compound (80 mg, 0.145 mmol, 7.14% yield). UPLC Method B: m/e=553.2539 [M+1]; Rt=2.63 min.

Step B: benzyl 6-(2,3-bis-2[2-(α-L-fucopyranosyl) oxyethyl)carbamoyl)cyclopropanecarboxylic)amino) acetamido)hexanoate The title compound was prepared using procedures analogous to those described for ML-69 substituting 2,3-bis-2[2-(α-L-fucopyranosyl)oxyethyl)carbamoyl)cyclopropanecarboxylic acid for 2-(bis(2-hydroxyethyl)amino)acetic acid in Step B. UPLC Method B: m/e=756.3689 [M+1]; Rt=3.15 min.

Step C: 6-(2,3-bis-2[2-(α-L-fucopyranosyl)oxyethyl)carbamoyl)cyclopropanecarboxylic)amino) acetamido)hexanoic acid The title compound was prepared using procedures analogous to those described for ML-69 substituting for benzyl 6-(2-(bis(2-[(α-L-fucopyranosyl)oxy)ethyl)amino)acetamido)hexanoate for benzyl 6-(2-(bis(2-[(α-L-fucopyranosyl)oxy)ethyl)amino)acetamido)hexanoate in Step D. UPLC Method B: m/e=666.3151 [M+1]; Rt=1.23 min.

Step D: 2,5-dioxopyrrolidin-1-yl 6-(2,3-bis-2[2-(α-L-fucopyranosyl)oxyethyl)carbamoyl)cyclopropanecarboxylic)amino)acetamido))hexanoate The title compound was prepared using procedures analogous to those described for ML-69 substituting 6-(2,3-bis-2[2-(α-L-fucopyranosyl)oxyethyl)carbamoyl)cyclopropanecarboxylic)amino)acetamido)hexanoic acid for 6-(2-(bis(2-[(α-L-fucopyranosyl)oxy)ethyl)amino)acetamido)hexanoic acid in Step E. UPLC Method B: m/e=763.3411 [M+1]; Rt=1.99 min.

Example 73

The synthesis of oligosaccharide linker 2,5-dioxopyrrolidin-1-yl 16-oxo-(6-((3-alpha-D-mannopyranosyl)propyl-α-L-fucopyranosyl)ethyl]amino)hexanoate (ML-73) having the following structure is described.

ML-73

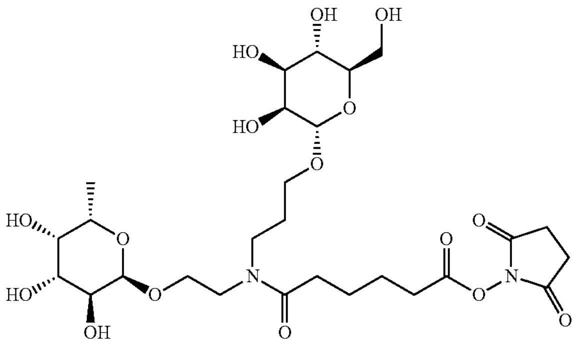

Step A: per-TMS D-Mannose

The titled compound was prepared using procedures analogous to those described for ML-69 substituting D-Mannose for L-Fucose in Step A. $^1$H NMR (CDCl3, 500 MHz) δ 4.9 (s, 1H), 3.5-3.9 (m, 6H), 0-0.3 (m, 45H).

Step B: 2,3,4,6-tetra-O-trimethylsilane D-mannopyranosyl

To the solution of per-TMS D-Mannose (5.4 g, 9.98 mmol) in DCM (25 ml) at zero degress, was added iodotrimethylsilane (1.426 ml, 10.48 mmol). The reaction was warmed to rt and stirred at rt for 1 hr. Remove DCM by reduced pressure. The intermediate was used next step without purification.

Step C: 3-Iodopropoxyl alpha-D-Mannopyranoside and 3-Iodopropoxyl beta-D-Mannopyranoside To the solution of 2,3,4,6-tetrakis(trimethylsilane) D-mannopyranosyl (2.89 g, 4.99 mmol) in DCM (10 ml) at zero deg, was added oxetane (0.488 ml, 7.49 mmol). The reaction was warmed to rt and stirred at rt for 5 hr. DCM was removed by rotavap. The mixture was dissolved in MeOH (10 mL). To above solution was added Dowex H+ resin till pH ~2. The mixture was stirred at rt for 1 hr. LC-MS indicated formation of desired product. The mixture was filtered through through a pad of celite, concentrated and purified by C8 reverse phase chromatography (eluted with 5-25% ACN/water with 0.05% TFA in 25 min). Fractions containing desired product were collected and lyo to give 3-iodopropoxyl alpha-D-mannopyranoside (710 mg, 2.04 mmol, 40.8%) and 3-iodopropoxyl beta-D-mannopyranoside (420 mg, 1.21 mmol, 24.2%). LC-MS Method A: m/e=696.96 [M+1]; Rt=0.46 min and Rt=0.53 min. $^1$H NMR (CD3OD, 500 MHz) 3-iodopropoxyl beta-D-mannopyranoside: δ 4.54 (d, J=0.95 Hz, 1H), 3.95 (m, 1H), 3.88-3.92 (m, 2H), 3.75 (m, 1H), 3.65 (m, 1H), 3.50 (m, 1H), 3.45 (m, 1H), 3.3-3.4 (m, 2H), 3.23 (m, 1H), 2.1 (m, 2H). $^1$H NMR (CD3OD, 500 MHz) 3-iodopropoxyl alpha-D-mannopyranoside: δ 4.81 (m, 1H), 3.8-3.9 (m, 3H), 3.6-3.8 (m, 3H), 3.5-3.6 (m, 2H), 3.3-3.4 (m, 2H), 2.1 (m, 2H).

Step D: α-L-fucopyranosyl)ethyl]amino}propyl alpha-D-Mannopyranoside

To the solution of 3-iodopropoxyl alpha-D-mannopyranoside (220 mg, 0.632 mmol) in DMF (5 mL), was added AEF (131 mg, 0.632 mmol) and LiOH (15.13 mg, 0.632 mmol). The mixture was stirred at rt for 24 hr. UPLC indicated formation of pdt. DMF was removed under reduced pressure. The crude was carried to next step without purification. UPLC Method B: m/e=428.2252 [M+1]; Rt=1.02 min.

Step E: benzyl 6-oxo-(6-((3-alpha-D-mannopyranosyl)propyl-α-L-fucopyranosyl)ethyl]amino)hexanoate The titled compound was prepared using procedures analogous to those described for ML-69 substituting α-L-fucopyranosyl)ethyl]amino}propyl alpha-D-Mannopyranoside for α-L-fucopyranosyl)ethyl]amino}propyl alpha-D-Mannopyranoside in Step A. UPLC Method B: m/e=646.3233 [M+1]; Rt=3.13 min.

Step F: 6-oxo-(6-((3-alpha-D-mannopyranosyl)propyl-α-L-fucopyranosyl)ethyl]amino) hexanoic acid The titled compound was prepared using procedures analogous to those described for ML-69 substituting benzyl 6-oxo-(6-((3-alpha-D-mannopyranosyl)propyl-α-L-fucopyranosyl)ethyl]amino)hexanoate for benzyl 6-(2-(bis(2-[(α-L-fucopyranosyl)oxy)ethyl)amino)acetamido)hexanoate in Step D. UPLC Method B: m/e=556.2731 [M+1]; Rt=1.77 min.

Step G: 2,5-dioxopyrrolidin-1-yl 6-oxo-(6-((3-alpha-D-mannopyranosyl)propyl-α-L-fucopyranosyl) ethyl]amino)hexanoate The title compound was prepared using procedures analogous to those described for ML-69 substituting 6-oxo-(6-((3-alpha-D-mannopyranosyl)propyl-α-L-fucopyranosyl) ethyl]amino) hexanoic acid for 6-(2-(bis(2-[(α-L-fucopyranosyl)oxy)ethyl)amino)acetamido)hexanoic acid in Step E. UPLC Method B: m/e=653.3008 [M+1]; Rt=2.09 min.

Example 74

The synthesis of oligosaccharide linker 2,5-dioxopyrrolidin-1-yl 6-oxo-(6-((3-beta-D-mannopyranosyl)propyl-α-L-fucopyranosyl)ethyl]amino)hexanoate (ML-74) having the following structure is described.

ML-74

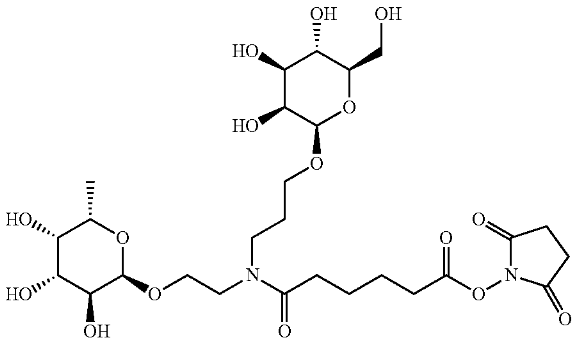

The title compound was prepared using procedures analogous to those described for ML-73 substituting beta-D-mannopyranose for alpha-D-mannose in Step A-F. UPLC Method B: m/e=653.3167 [M+1]; Rt=2.07 min.

Example 75

The synthesis of oligosaccharide linker 2,5-dioxopyrrolidin-1-yl 8-oxo-(6-((3-beta-D-mannopyranosyl)propyl-α-L-fucopyranosyl)ethyl]amino)octanediate (ML-75) having the following structure is described.

ML-75

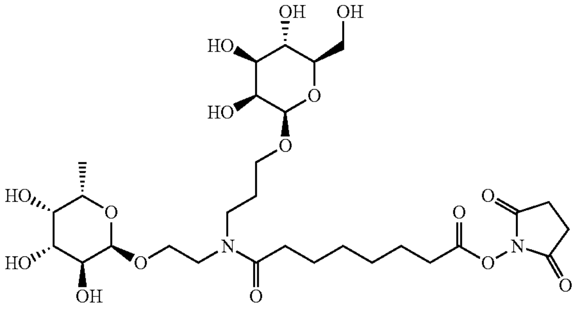

The title compound was prepared using procedures analogous to those described for ML-73 substituting beta-D-mannopyranose for alpha-D-mannose in Step A-F and substituting benzyl 8-(2,5-dioxopyrrolidin-1-yl) octanediate for benzyl (2,5-dioxopyrrolidin-1-yl) adipate. UPLC Method B: m/e=681.3568 [M+1]; Rt=2.44 min.

Example 76

The synthesis of oligosaccharide linker 2,5-dioxopyrrolidin-1-yl 8-oxo-(6-((3-alpha-D-mannopyranosyl)propyl-α-L-fucopyranosyl)ethyl]amino)octanediate (ML-76) having the following structure is described.

ML-76

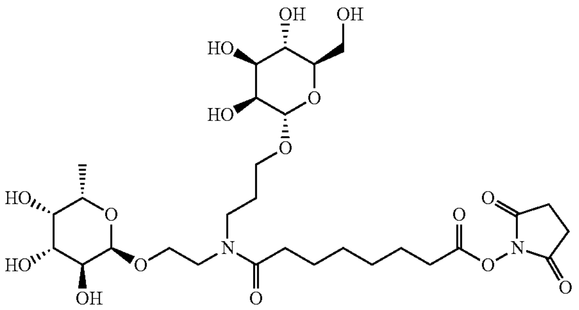

The title compound was prepared using procedures analogous to those described for ML-73 substituting benzyl 8-(2,5-dioxopyrrolidin-1-yl) octanediate for benzyl (2,5-dioxopyrrolidin-1-yl) adipate. UPLC Method B: m/e=681.3456 [M+1]; Rt=2.21 min.

Example 77

The synthesis of oligosaccharide linker 2,5-dioxopyrrolidin-1-yl 9-oxo-(6-((3-alpha-D-mannopyranosyl)propyl-α-L-fucopyranosyl)ethyl]amino)nonanedioate (ML-77) having the following structure is described.

ML-77

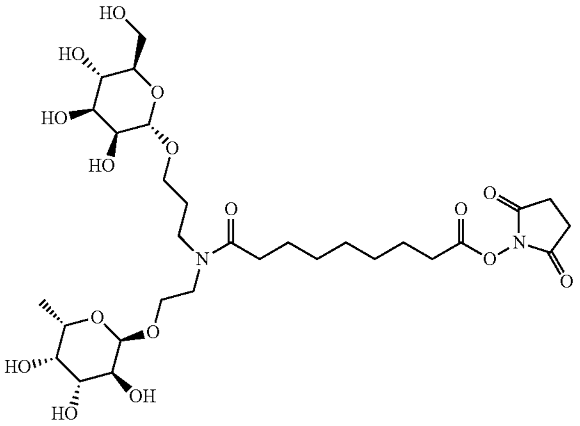

The title compound was prepared using procedures analogous to those described for ML-73 substituting benzyl 9-(2,5-dioxopyrrolidin-1-yl) nonanedioate for benzyl (2,5-dioxopyrrolidin-1-yl) adipate. UPLC Method B: m/e=695.3532 [M+1]; Rt=2.55 min.

Example 78

The synthesis of oligosaccharide linker 2,5-dioxopyrrolidin-1-yl 10-oxo-(6-((3-alpha-D-mannopyranosyl)propyl-α-L-fucopyranosyl)ethyl]amino) decanedioate (ML-78) having the following structure is described.

ML-78

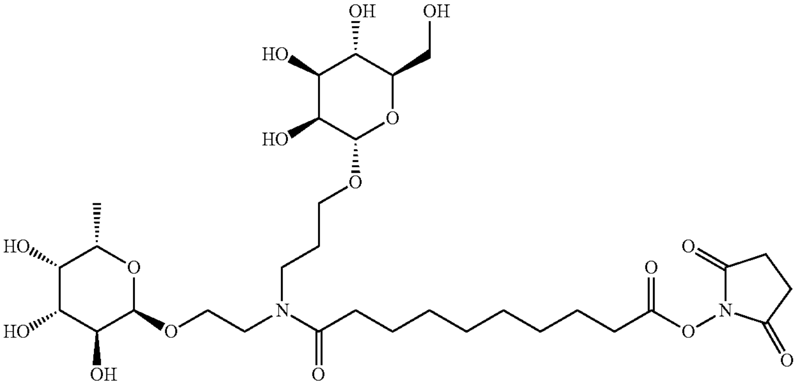

The title compound was prepared using procedures analogous to those described for ML-73 substituting benzyl 10-(2,5-dioxopyrrolidin-1-yl) decanedioate for benzyl (2,5-dioxopyrrolidin-1-yl) adipate. UPLC Method B: m/e=709.3766 [M+1]; Rt=2.79 min.

Example 79

The synthesis of oligosaccharide linker 6-[(2,5-dioxopyrrolidin-1-yl)oxy]-N-(2-{[α-D-mannopyranosyl-(1→3)-[α-D-mannopyranosyl-(1→6)]-β-D-mannopyranosyl] oxy}propyl)-6-oxohexanamide (ML-79) having the following structure is described.

ML-79

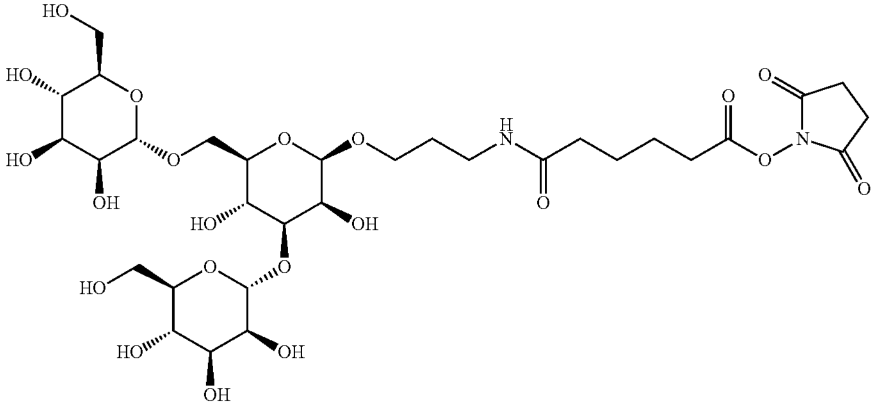

Step A: 3-azidopropoxyl β-D-mannopyranoside

To the solution of 3-iodopropoxyl β-D-mannopyranoside (2.0 g, 5.74 mmol) in DMF (10 ml), was added sodium azide (448 mg, 0.448 mmol). The reaction was warmed up to 60 degrees and stirred at this temperature for 12 hr under N2. LC-MS indicated formation of desired product. DMF was removed under reduced pressure. The crude was purified by C18 reverse phase chromatography (eluted with 0-20% ACN/water in 16 CV, then 100% ACN in 2 CV, 0% ACN 2CV). Fractions containing desired pdt were combined and lyo to give the titled compound (1.27 g, 4.82 mmol, 84% yield). LC-MS Method A: m/e=264.16 [M+1]; Rt=0.21. $^1$H NMR (CD3OD, 500 MHz): δ 4.53 (m, 1H), 4.02 (m, 1H), 3.97 (m, 2H), 3.65 (m, 2H), 3.56 (m, 1H), 3.48 (m, 3H), 3.22 (m, 1H), 1.92 (m, 2H).

Step B: 2.4-benzoyl 3-azidopropoxyl β-D-mannopyranoside

To the solution 3-azidopropoxyl β-D-mannopyranoside (1030 mg, 3.91 mmol) in acetonitrile (15 ml) was added triethyl orthobenzoate (2.352 ml, 10.17 mmol) followed by TFA (0.030 ml, 0.391 mmol) and in ACN (0.5 mL). The mixture was allowed to stir at room temperature for 1 hour. Rotavap to remove ACN. TFA (10% in water) (4.28 ml, 5.55 mmol) was added. The mixture was stirred at rt for 2 hours. The residue was purified by column chromatography on silica gel eluting with Ether/$CH_2Cl_2$ to give above product as a white solid. $^1$H NMR (CDCl3, 500 MHz): δ 7.0-8.2 (m, 10H), 5.72 (dd, 1H, J=3.4 Hz, J=1.1 Hz), 5.44 (t, 1H, J=9.6 Hz), 4.79 (d, 1H, J=1.1 Hz), 4.16 (dd, 1H, J=3.4 Hz, J=1.1 Hz), 4.00 (m, 1H), 3.88 (m, 1H), 3.82 (m, 1H), 3.66 (m, 2H), 3.31 (m, 2H), 1.82 (m, 2H).

Step C: 2-azidopropoxyl 2,4-di-O-benzoyl-3,6-O-(2,3,4,6-tetra-O-benzoyl-α-D-mannopyranosyl)-β-D-mannopyranoside The title compound was prepared using procedures analogous to those described for ML-2 substituting 2.4-benzoyl 3-azidopropoxyl β-D-mannopyranoside for 2-azidoethyl 2,4-bis-O-benzoyl-6-O-trityl-α-D-mannopyranoside in Step B. $^1$H NMR (CDCl3, 500 MHz): δ 7.0-8.3 (m, 50H), 6.2 (m, 2H), 5.95 (m, 2H), 5.85 (m, 2H), 5.70 (m, 1H), 5.35 (m, 2H), 5.22 (s, 1H), 3.0-5.0 (m, 15H), 1.90 (m, 2H).

Step D: 6-[(2,5-dioxopyrrolidin-1-yl)oxy]-N-(2-{[α-D-mannopyranosyl-(1→3)-[α-D-mannopyranosyl-(1→6)]-β-D-mannopyranosyl]oxy}propyl)-6-oxo-hexanamide The title compound was prepared using procedures analogous to those described for ML-2 in Step D-F. UPLC Method B: m/e=787.3816 [M+1]; Rt=3.39 min.

Example 80

Synthesis of A1 protected insulin is described.

In an appropriate sized container, insulin is suspended at rt in an organic solvent, e.g., DMSO, in the presence of a base, e.g., TEA. The mixture is allowed to stir gently until insulin completely dissolved. To the resulting solution was added protecting reagent, e.g., ethyl trifluoroacetate or 9-fluorenylmethyl pentafluorophenyl carbonate, neat or in solution of organic solvents, such as DMSO or DMF. After UPLC chromatogram shows that a substantial portion of the reaction mixture has converted into A1-protected insulin, the reaction mixture may be subjected directly for reverse phase HPLC purification (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN), or the reaction may be quenched by careful dilution with cold acidic $H_2O$ (20×, pH about 3.0) at 0° C. and its pH is adjusted to a final pH of 2.5 using 1 N HCl (and 0.1 N NaOH if needed). The solution may first be concentrated by ultrafiltration, either through a tangential flow filtration (TFF) system or using Amicorn Ultra-15 Centrifugal Units, with 1K, 3K or 10K MWCO membrane. The concentrated solution is then subjected to reverse phase HPLC purification (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicorn Ultra-15 to give the $N^{A1}$ protected insulin.

Example 81

The synthesis of $N^{A1}$-Trifluoroacetyl insulin is described.

In a 100 round bottom flask is charged with insulin (300 mg, 0.052 mmol), to which was added 8 mL DMSO, then TEA (43.4 mg, 0.429 mmol). The mixture is gently stirred at rt for about 30 minute until a clear solution is obtained. To the resulting solution is added ethyl trifluroacetate (35.2 mg, 0.248 mml). After stirring at rt for 4 hr, the mixture is diluted carefully with $H_2O$ (100 mL, pH=3.00). After its volume is reduced to 20 mL using 10 MWCO Amicon Ultra-15 Centrifugal tubes, the resulting solution is purified by HPLC (Kromasil® C8 10 μm, 100 Å, 50×250 mm column at 210 nm, flow rate at 85 mL/min, 0.05% TFA in AcCN/$H_2O$, 26% AcCN to 37% AcCN in $H_2O$, 20 min ramp). Desired fractions were combined and freeze-dried to give the $N^{A1}$-Trifluoroacetyl insulin. UPLC Method A: m/e=1476.55 [(M+4)/4]; Rt=3.62 min.

Example 82

This example shows the synthesis of IOC-143.

To a solution of $N^{A1}$-Trifluoroacetyl Human Insulin (77.7 mg, 0.013 mmol) in DMSO (1.2 mL) at rt was added TEA (18 μL, 0.132 mmol) and a solution of ML-11 (30.2 mg, 0.039 mmol) in DMSO (300 μL). After stirring at rt for 4 hours, the mixture was added to AcCN (40 mL). Precipitate was collected through centrifugation. The collected solid was dissolved in water (5 mL, pH=3.00) and the mixture was cooled down to 0° C., to which a solution of $NH_4OH$ (5 mL, 28% in water) was added. The mixture was stirred at 0° C. for 2 hr and then diluted with water (20 mL, pH=3.00). The volume of the resulting solution was reduced to 5 mL using 10K MWCO Amicon Ultra-15 Centrifugal Filter Units, and was further diafiltrated with water (100 mL, pH=3.00) to final volume about 7.5 mL, which was purified by HPLC to give the IOC-143. UPLC Method A: Rt=3.58 min; m/e=1801.906.

Example 83

The synthesis of $N^{A1}$-[(9H-Fluoren-9-ylmethoxy)carbonyl] Human Insulin ($N^1$-Fmoc Insulin) is described.

Insulin (1.5 g, 0.258 mmol) was dissolved in DMSO (6 mL) in a 20 ml scintillation vial. To the insulin solution was added 9-fluorenylmethyl pentafluorophenyl carbonate (0.105 g, 0.258 mmol) in DMSO (1 mL). The mixture was stirred for 15 minutes.

Product was purified by Gilson HPLC chromatography on a C-4 Reverse Phase column. The desired fractions (the first-eluting monomer) were collected and lyophilized to give the desired $N^{\alpha A1}$-Fmoc Insulin product. UPLC MS (C4, 5 minutes): 1508.37 (M+4/4) at 4.47 minutes.

Example 84

Synthesis of A1, B29 protected insulin or A1,B28 protected insulin lispro is described.

In an appropriate sized container, insulin is suspended at rt in an organic solvent or mixed aq/organic solvents, e.g., DMSO, in the presence of a base, e.g., TEA. The mixture is allowed to stir gently until insulin completely dissolved. To the resulting solution is added protecting reagent, e.g., ethyl trifluoroacetate or 9-fluorenylmethyl pentafluorophenyl carbonate, neat or in solution of organic solvents, such as DMSO or DMF. After UPLC chromatogram shows that a substantial portion of the reaction mixture has converted into A1,B29-protected insulin (A1,B28-protected insulin lispro). The reaction mixture may be subjected directly to reverse phase HPLC purification (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN), or the reaction may be quenched by careful dilution with cold acidic $H_2O$ (20×, pH ~3.0) at 0° C. and its pH is adjusted to a final pH of 2.5 using 1 N HCl (and 0.1 N NaOH if needed). The solution may first be concentrated by ultrafiltration, either through a tangential flow filtration (TFF) system or using Amicon Ultra-15 Centrifugal Units, with 1K, 3K or 10K MWCO membrane. The concentrated solution is then subjected to reverse phase HPLC purification (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 85

Synthesis of $N^{A1}$, $N^{\epsilon B29}$-Bis(trifluoroacetyl) Human Insulin is described.

In a 100 round bottom flask was charged with human insulin (300 mg, 0.052 mmol), to which was added AcCN (6.0 mL), water (6.0 mL), and DIPEA (1.5 mL, 8.59 mmol). To the resulting mixture at 0° C. was added ethyl trifluroacetate (0.9 mL, 7.54 mml). After stirring at 0° C. for 2 hr, the mixture was purified by HPLC (Kromasil® C8 10 μm, 100 Å, 50×250 mm column at 210 nm, flow rate at 85 mL/min, 0.05% TFA in AcCN/$H_2O$, 27% AcCN to 37% AcCN in $H_2O$, 20 min ramp). Desired fractions were combined and freeze-dried to give the $N^{A1}$, $N^{\epsilon B29}$-Bis(trifluoroacetyl) Human Insulin. UPLC Method A: m/e=1500.677 [(M+4)/4]; Rt=3.87 min.

Example 86

Synthesis of $N^{A1}$, $N_{\epsilon B29}$-Bis[(9H-Fluoren-9-ylmethoxy) carbonyl]Human Insulin is described.

In a 20 mL scintillation vial, human insulin (1.19 g, 0.205 mmol) and TEA (257 μL, 1.844 mmol) was dissolved in DMSO (10 mL). To this insulin solution was added 1-{[(9H-fluoren-9-ylmethoxy)carbonyl]oxy}pyrrolidine-2,5-dione (207 mg, 0.615 mmol) in DMSO (2 mL). After stirring at rt for 30 min, the reaction was quenched by the addition of HCl (1.84 mL, 1.844 mmol, 1.0 M). The resulting mixture was purified by reverse phase HPLC chromatography. The desired fractions were collected and lyophilized to give the $N^{A1}$, $N^{\epsilon B29}$-Bis[(9H-Fluoren-9-ylmethoxy)carbonyl]Human Insulin. UPLC Method A: m/e=1564.04 [(M+4/4)]; Rt=4.41 min.

Example 87

Synthesis of Conjugates with Same Linker-Oligosaccharides on $N^{A1}$ and $N^{\epsilon B29}$ of Insulin In an appropriate sized container, insulin is suspended at rt in an organic solvent, e.g., DMSO, in the presence of a base, e.g., TEA. The mixture is allowed to stir gently until insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified insulin has reacted and that a substantial portion of the reaction mixture has converted into A1,B29-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 m, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing A1,B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 88

Synthesis of Conjugates with Linker-Oligosaccharide on $N^{A1}$ of Insulin

In an appropriate sized container, insulin is suspended at rt in an organic solvent, e.g., DMSO, in the presence of a base, e.g., TEA. The mixture is allowed to stir gently until insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that most of the unmodified insulin has reacted and that a substantial portion of the reaction mixture has converted into A1-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing A1-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 89

Synthesis of Conjugates with Linker-Oligosaccharide on $N^{B1}$ of Insulin $N_{B1}$ insulin conjugate may be prepared according to Example 50. Or it may be prepared using protected insulin as substrate:

In an appropriate sized container, protected insulin, e.g., $N^{A1}$, $N^{\epsilon B29}$-bis[(9H-fluoren-9-ylmethoxy)carbonyl]- or $N^{A1}$, $N^{\epsilon B29}$-bis(trifluoroacetyl) human insulin is suspended at rt in an organic solvent, e.g., DMSO, in the presence of a base, e.g., TEA. The mixture is allowed to stir gently until protected insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified insulin has reacted and that a substantial portion of the reaction mixture has converted into B1-conjugated protected insulin. The reaction is quenched at low temperature by the addition of excess amount of an amine nucleophile, e.g., 2-aminoethanol or ammonia. The reaction solution is stirred at low temperature until UPLC chromatogram indicated complete removal of the protecting group. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B1-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 90

Synthesis of Conjugates with Linker-Oligosaccharide on $N^{\epsilon B29}$ of Insulin In an appropriate sized container, insulin is dissolved, with gentle stirring, at rt in a mixed solvent: 2:3 v/v 0.1 $MNa_2CO^3$:AcCN. After the mixture cleared, the pH is adjusted to the value of 10.5-10.8 using alkaline solution, e.g., 0.1 N NaOH. In a separate vial, an activated ester intermediate is dissolved in an organic solvent, e.g., DMSO, at rt. Aliquots of the solution of the activated ester is added over a period of time to the solution containing insulin until UPLC chromatogram shows that most of the unmodified insulin has reacted and that a substantial portion of the reaction mixture has converted into B29-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column;

Buffer A: 0.05-0.1% TFA in water; Buffer B: 0.05-0.1% TFA in AcCN). Fractions containing the title conjugate are combined and freeze-dried or buffer exchanged using TFF system and/or Amicon Ultra-15 to give the title product.

Example 91

Synthesis of Conjugates with Same Linker-Oligosaccharides on $N^{B1}$ and $N^{\epsilon B29}$ of Insulin In an appropriate sized container, protected insulin, e.g., $N^{A1}$-(9H-fluoren-9-ylmethoxy)carbonyl- or $N^{A1}$-(trifluoroacetyl) human insulin is suspended at rt in an organic solvent, e.g., DMSO, in the presence of a base, e.g., TEA. The mixture is allowed to stir gently until protected insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified protected insulin has reacted and that a substantial portion of the reaction mixture has converted into B1,B29-conjugated protected insulin. The reaction is quenched at low temperature by the addition of excess amount of an amine nucleophile, e.g., 2-aminoethanol or ammonia. The reaction solution is stirred at low temperature until UPLC chromatogram indicated complete removal of the protecting group. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B1,B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 92

Synthesis of Conjugates with Same Linker-Oligosaccharides on $N^{A1}$, $N^{B1}$, and $N^{\epsilon B29}$ of Insulin In an appropriate sized container, insulin is suspended at rt in an organic solvent, e.g., DMSO, in the presence of a base, e.g., TEA. The mixture is allowed to stir gently until insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified insulin has reacted and that a substantial portion of the reaction mixture has converted into A1-, B1-, and B29-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl).

Fractions containing A1, B1, B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 93

Synthesis of Conjugates with Different Linker-Oligosaccharides on $N^{A1}$ and $N^{\epsilon B29}$ of Insulin In an appropriate sized container, $N^{\epsilon B29}$-conjugated insulin is suspended at rt in an organic solvent, e.g., DMSO, in the presence of a base, e.g., TEA. The mixture is allowed to stir gently until insulin completely dissolved. In a separate vial, an activated ester intermediate was dissolved in an organic solvent, e.g., DMSO, at rt. Aliquots of the solution of the activated ester are added over a period of time to the solution containing insulin until UPLC chromatogram shows that all of the unmodified insulin had been reacted and that a substantial portion of the reaction mixture had been converted into A1,B29-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH was adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution may be first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing A1,B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 94

Synthesis of Conjugates with Same Linker-Oligosaccharides on $N^{B1}$ and $N^{\epsilon B29}$ of Insulin In an appropriate sized container, protected insulin, e.g., $N^{\epsilon B29}$-(9H-fluoren-9-ylmethoxy)carbonyl- or $N^{A1}$-(trifluoroacetyl) human insulin is suspended at rt in an organic solvent, e.g., DMSO, in the presence of a base, e.g., TEA. The mixture is allowed to stir gently until protected insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified protected insulin has reacted and that a substantial portion of the reaction mixture has converted into A1,B1-conjugated protected insulin. The reaction is quenched at low temperature by the addition of excess amount of an amine nucleophile, e.g., 2-aminoethanol or ammonia. The reaction solution is stirred at low temperature until UPLC chromatogram indicated complete removal of the protecting group. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B1,B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 95

Synthesis of $N^{\epsilon B29}$-(trifluoroacetyl) Human Insulin is described.

In a 100 round bottom flask was charged with human insulin (200 mg, 0.034 mmol), to which was added AcCN (4.0 mL), water (4.0 mL), and TEA (0.5 mL, 3.44 mmol). To the resulting mixture at 0° C. was added ethyl trifluroacetate (0.41 mL, 3.44 mml). After stirring at 0° C. for 30 min, the mixture was diluted with water (20 mL, pH ~3.0). After acidify the resulting solution until pH ~2.5 carefully, the mixture was purified by HPLC (Delta Pak C4 15 μm, 300 Å, 50×250 mm column at 210 nm, flow rate at 85 mL/min, 0.05% TFA in AcCN/H2O, 27% AcCN to 37% AcCN in H2O, 20 min ramp). Desired fractions were combined and freeze-dried to give the title compound. UPLC Method A: m/e=1476.5012 [(M+4)/4]; Rt=3.71 min.

Example 96

Synthesis of IOC-3, human insulin conjugated at B1 and B29 to linker ML-7.

$N^{\alpha A1}$-Tfa-Insulin (60 mg, 0.01 mmol) was dissolved in 1 ml DMSO at rt, to this solution was added triethylamine (10.3 mg, 0.102 mmol), ML-7 (18.2 mg, 0.023 mmol) was dissolved in 100 uL DMSO and added to the reaction mixture. After stirring at rt for 4 hours, the mixture was added to 40 ml AcCN. Precipitate was formed and collected by centrifugation. The collected solid was dissolved in 5 mL PH=3.00 DI water and cooled down to 0° C., then 5 mL $NH_4OH$ (28% in water) was added to the water solution, the mixture was stirred at 0° C. for 2 hours and then diluted with 20 mL DI water PH=3.00. The mixtures was concentrated down to 5 mL with a 10K membrane Amicon centrifuge tube, and was further diafiltrated with 100 mL PH=3.00 DI water to a final volume about 7.5 mL and purified by prep HPLC. HPLC conditions were as follow: Kromasil® C8 10 μm, 100 Å, 50×250 mm column at 210 nm, flow rate at 85 mL/min, 0.05% TFA in AcCN/$H_2O$, 26% AcCN to 32% AcCN in H2O, 25 min ramp, collected the fractions and lyophilized to powder. (38.8 mg, yield 52.4%) 1784.76[M+4]/4, $t_R$=3.435

Example 97

This example shows the preparation of an insulin oligosaccharide conjugate (IOC-123) in which oligosaccharide linker ML-11 is linked to the $NH_2$ group at positions B1 and B29 of human insulin.

$N^{\alpha A1}$-Fmoc insulin (80 mg, 0.014 mmol) and linker ML-11 (100 mg, 0.068 mmol) were warmed up to room temperature for 30 minutes. To the $N^{\alpha A1}$-Fmoc insulin (80 mg, 0.014 mmol) in DMSO (1.00 mL) in a 20 mL vial was added triethylamine (18.95 μL, 0.136 mmol). ML-11 (100 mg, 0.068 mmol) in DMSO (0.90 mL) was added in to the reaction vial in three equal portions and 50 minutes interval. The reaction was quenched by adding 2-aminoethanol (103 μL, 1.700 mmol) and stir the mixture at room temperature for 20 min. The mixture was diluted into $H_2O$ (10 mL) at 0° C. The pH of the reaction mixture is adjusted to be about 2.5 using 1 N HCl.

The crude product was first purified by ion exchange Chromatography. The desired fractions were concentrated using Amicon Ultra Centrifugel Filters or lyophilized overnight and then further purified by reverse phase prepare HPLC (Gilson C-4 column). The combined desired fractions were lyophilized to produce a solid. Then the solid was dissolved in water and the pH adjusted to 7 using 0.1N NaOH solution to provide a solution of IOC-123.

Example 98

This example illustrates the synthesis of IOC-113 ($N^{A1}$, $N^{\beta B29}$-Bis{6-[cis-3,5-bis({2-[(α-L-fucopyranosyl)oxy] ethyl}carbamoyl)piperidin-1-yl]-6-oxohexanoyl}human insulin) in which the A1 and B1 positions of human insulin are conjugated to ML-17.

To a 20 mL scintillation vial containing human insulin (105 mg, 0.018 mmol) at room temperature was added DMSO (1 mL) and DIPEA (35.1 mg, 0.271 mmol). The mixture was allowed to stir gently until insulin dissolved. In a separate vial, linker ML-17 (35.1 mg, 0.045 mmol) was dissolved in DMSO (0.9 mL) at room temperature. To the solution containing human insulin was added the solution of ML-17 in three equal portions in 50 minute intervals. The reaction was quenched by adding 2-aminoethanol (34 μL, 0.42 mmol). After stirring at room temperature for 20 minutes, the resulting mixture was carefully diluted with cold $H_2O$ (4 mL) at 0° C. The pH of the resulting mixture was adjusted to a final pH of 2.5 using 1 N HCl (or 0.1 N NaOH). The mixture was first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing the title conjugate as major product were combined and concentrated using Amicon-15 MWCO 3 k or 10 k Ultra Centrifugel Filters or freeze-dried after being neutralized to a pH of about 7.0. The resulting solution or reconstituted conjugate solution was then further purified by reverse phase prepare HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing >95% title conjugate were combined and freeze-dried to give the title product. UPLCMS (C4, 5 minutes): 1948.66 (M+4/4) at 3.48 min.

Example 99

This example shows the construction of IOC-52 ($N^{A1}$-6-oxo-6-((2-(α-L-fucopyranosyloxy)ethyl)amino)hexanoyl-$N^{\epsilon B29}$-6-((((2-oxo-2-((α-D-mannopyranosyl-(1→3)-[α-D-mannopyranosyl-(1→6)]-α-D-mannopyranosyl)-2-oxyethyl)amino)(2-oxo-2-((α-L-fucopyranosyloxy)-2-oxoethyl)amino)ethyl)amino)acetamido)-6-oxohexanoyl Human Insulin) in which the A1 and B1 residues of human insulin are conjugated to linkers ML-4 and ML-29, respectively.

Synthesis of $N^{\epsilon B29}$-6-((((2-oxo-2-((α-D-mannopyranosyl-(1→3)-[α-D-mannopyranosyl-(1→6)]-α-D-mannopyranosyl)-2-oxyethyl)amino)(2-oxo-2-((α-L-fucopyranosyloxy)-2-oxoethyl)amino)ethyl)amino) acetamido)-6-oxohexanoyl Human Insulin (IOC-58)

Human insulin (1000 mg, 0.172 mmol) was dissolved in aqueous $Na_2CO_3$ (8.6 mL, 0.1 M) and AcCN (5.7 mL). The pH of the resulting solution was adjusted to 10.5, to which a solution of ML-29 (2,5-Dioxopyrrolidin-1-yl 6-((((2-oxo-2-((α-D-mannopyranosyl-(1→3)-[α-D-mannopyranosyl-(1→6)]-α-D-mannopyranosyl)-2-oxyethyl)amino)(2-oxo-2-((α-L-fucopyranosyloxy)-2-oxoethyl)amino)ethyl)amino) acetamido)-6-oxohexanoate) (289 mg, 0.258 mmol) in DMF (2.9 mL) was added in portion. The reaction progress was monitored by UPLC-MS and the reaction was quenched by adding ethanolamine (52.1 μL, 0.861 mmol). The reaction mixture was diluted with $H_2O$ (15 mL) and pH was adjusted to about 2.5 using 1.0 N HCl solution. The resulting mixture was purified by HPLC (ION Chromatography, PolySULFOEthyl A, 9.4×250 mm, gradient 10-45%) (Mobile Phase A: 0.1% (v/v) $H_3PO_4$/25% Acetonitrile in water, Mobile Phase B: 0.1% (v/v) $H_3PO_4$/25% Acetonitrile/0.5M NaCl in water) over 30 minutes, flow rate 15 mL/minutes). The desired fractions were combined, concentrated using 6 Amicon Ultra Centrifugel Filters with Utracel 10K at 3500 RPM at 4° C., and freeze-dried to give the title compound (600 mg, 51% yield) as white powder. UPLC Method A: $t_R$=3.58 minutes. $[M+4H/4]^+$=1703.99.

Synthesis of $N^{A1}$-6-oxo-6-((2-(α-L-fucopyranosyloxy)ethyl)amino)hexanoyl-$N^{\epsilon B29}$-6-((((2-oxo-2-((α-D-mannopyranosyl-(1→3)-[α-D-mannopyranosyl-(1→6)]-α-D-mannopyranosyl)-2-oxyethyl)amino)(2-oxo-2-((α-L-fucopyranosyloxy)-2-oxoethyl)amino) ethyl)amino)acetamido)-6-oxohexanoyl Human Insulin To a solution of $N^{\epsilon B29}$-6-((((2-oxo-2-((α-D-mannopyranosyl-(1→3)-[α-D-mannopyranosyl-(1→6)]-α-D-mannopyranosyl)-2-oxyethyl)amino)(2-oxo-2-((α-L-fucopyranosyloxy)-2-oxoethyl)amino)ethyl)amino)acetamido)-6-oxohexanoyl Human Insulin (150 mg, 0.022 mmol) and TEA (30.7 μL, 0.22 mmol) in DMSO (1.5 mL) at room temperature was added a solution of 2,5-Dioxopyrrolidin-1-yl 6-oxo-6-((2-(α-L-fucopyranosyloxy)ethyl)amino) hexanoate (17 mg, 0.040 mmol) (ML-4) in DMSO (1.0 mL) in portion. The reaction was quenched by adding ethanolamine (13.32 μL, 0.22 mmol). After stirring at room temperature for 15 minutes, the reaction mixture was diluted with $H_2O$ (15 mL) and pH was adjusted to about 2.5 using 1.0 N HCl solution. The resulting mixture was purified by HPLC (ION Chromatography, PolySULFOEthyl A, 9.4×250 mm, gradient 10-40%) (Mobile Phase A: 0.1% (v/v) $H_3PO_4$/25% Acetonitrile in water, Mobile Phase B: 0.1% (v/v) $H_3PO_4$/25% Acetonitrile/0.5MNaCl in water) over 30 minutes, flow rate 15 mL/minutes). The desired fractions were combined, concentrated using 2 Amicon Ultra Centrifugel Filters with Utracel 10K at 3500 RPM at 4° C. The resulting mixture was purified on HPLC (C4, 50×250 mm, gradient 25-30% AcCN in $H_2O$ with 0.1% TFA over 30 minutes, flow rate 85 mL/minutes). The desired fractions were combined and freeze-dried to give the title compound (31 mg, 19% yield) as white powder. UPLC Method A: $t_R$=3.79 min. $[M+4H/4]^+$=1783.3.

Example 100

Synthesis of IOC-10, human insulin conjugated at B1 and B29 to linker ML-6.

A1 Fmoc insulin (80 mg, 0.014 mmol) and linker ML-6 (100 mg, 0.068 mmol) were warmed up to room temperature for 30 minutes; To A1 Fmoc insulin (80 mg, 0.014 mmol) in DMSO (1.00 mL) in a 20 mL vial was added triethylamine (18.95 μL, 0.136 mmol). Linker ML-6 (100 mg, 0.068 mmol) in DMSO (0.90 ml) was added in to the reaction vial in three equal portions and 50 minutes interval. The reaction was quenched by adding 2-aminoethanol (103 μl, 1.700 mmol) and stir the mixture at room temperature for 20 minutes. The mixture was diluted into $H_2O$ (10 mL) at 0° C. The pH of the reaction mixture is adjusted to be about 2.5 using 1 N HCl.

The crude product was first purified by ion exchange Chromatography. The desired fractions were concentrated using Amicon Ultra Centrifugel Filters or lyophilized overnight and then further purified by reverse phase prepare HPLC (Gilson C-4 column). The combined desire fractions were lyophilized. Then the solid was dissolved in water and the pH adjusted to 7 using 0.1N NaOH solution. The concentration of the sample was measured by Lambda Bio+UV\Vis Spectrometer at λ276. UPLCMS (C4, 5 minutes): 1763.3 (M+4/4) at 3.72 minutes.

Example 101

Synthesis of IOC-226, human insulin conjugated at B1 and B29 to Linker ML-31 and ML-54, respectively.

$N^{\alpha A1}$-Tfa-Insulin (40 mg, 0.0067 mmol) was dissolved in 1 ml DMSO at rt, to this solution was added DIPEA (0.038 ml, 0.215 mmol), ML-54 (11.5 mg, 0.0078 mmol) was dissolved in 115 uL DMSO and added to the reaction mixture. The reaction mixture was stirred at rt for 2 h or until UPLC chromatogram shows a substantial portion of the reaction mixture had been converted into B29-conjugated insulin. Then, second activated ester, ML-31 (16 mg, 0.014 mmol) was dissolved in 160 uL DMSO and added to the reaction mixture. The reaction mixture was stirred at rt for 16 h or until UPLC chromatogram shows an extensive portion of the reaction mixture had been converted into B1, B29-conjugated insulin. The mixture was added to 40 ml AcCN. Precipitate was formed and collected by centrifugation. The collected solid was dissolved in 5 mL PH=3.00 DI water and cooled down to 0° C., then 5 mL $NH_4OH$ (28% in water) was added to the water solution, the mixture was stirred at 0° C. for 2 hours and then diluted with 20 mL DI water PH=3.00. The mixtures was concentrated down to 3 mL with a 10K membrane Amicon centrifuge tube, and was further diafiltrated with 60 mL PH=3.00 DI water to a final volume about 5 ml. The crude product was first purified by ion exchange Chromatography. The desired fractions were concentrated using Amicon Ultra Centrifugel Filters and then further purified by reverse phase prep HPLC. HPLC conditions were as follow: Kromasil® C8 10 μm, 100 Å, 50×250 mm column at 210 nm, flow rate at 85 mL/min, 0.05% TFA in AcCN/$H_2O$, 27% AcCN to 33% AcCN in H2O, 25 min ramp, collected the fractions and lyophilized to powder. Then the solid was dissolved in water and the pH adjusted to 7 using 0.1N NaOH solution. The concentration of the sample was measured by Lambda Bio+UV\Vis Spectrometer at λ276. (16.53 mg, yield 29.2%) 1632.54[M+5]/5, $t_R$=3.35

Example 101

Insulin Receptor Binding Assays were performed as follows.

Two competition binding assays were utilized to determine IOC affinity for the human insulin receptor type B (IR(B)) against the endogenous ligand, insulin, labeled with $^{125}$[I].

Method E: IR binding assay was a whole cell binding method using CHO cells overexpressing human IR(B). The cells were grown in F12 media containing 10% FBS and antibiotics (G418, Penicillin/Strepavidin), plated at 40,000 cells/well in a 96-well tissue culture plate for at least 8 hrs. The cells were then serum starved by switching to DMEM media containing 1% BSA (insulin-free) overnight. The cells were washed twice with chilled DMEM media containing 1% BSA (insulin-free) followed by the addition of IOC molecules at appropriate concentration in 90 μL of the same media. The cells were incubated on ice for 60 min. The $^{125}$[I]-insulin (10 μL) was added at 0.015 nM final concentration and incubated on ice for 4 hrs. The cells were gently washed three times with chilled media and lysed with 30 μL of Cell Signaling lysis buffer (cat #9803) with shaking for 10 min at room temperature. The lysate was added to scintillation liquid and counted to determine $^{125}$[I]-insulin binding to IR and the titration effects of IOC molecules on this interaction.

Method D: IR binding assay was run in a scintillation proximity assay (SPA) in 384-well format using cell membranes prepared from CHO cells overexpressing human IR(B) grown in F12 media containing 10% FBS and antibiotics (G418, Penicillin/Strepavidin). Cell membranes were prepared in 50 mM Tris buffer, pH 7.8 containing 5 mM $MgCl_2$. The assay buffer contained 50 mM Tris buffer, pH 7.5, 150 mM NaCl, 1 mM $CaCl_2$, 5 mM $MgCl_2$, 0.1% BSA and protease inhibitors (Complete-Mini-Roche). Cell membranes were added to WGA PVT PEI SPA beads (5 mg/ml final concentration) followed by addition of IOC molecules at appropriate concentrations. After 5-15 min incubation at room temperature, $^{125}$[I]-insulin was added at 0.015 nM final concentration for a final total volume of 50 μL. The mixture was incubated with shaking at room temperature for 1 to 12 hours followed by scintillation counting to determine $^{125}$[I]-insulin binding to IR and the titration effects of IOC molecules on this interaction.

Example 102

Insulin Receptor Phosphorylation Assays were performed as follows.

The insulin receptor phosphorylation assays were performed using the commercially available Meso Scale Discovery (MSD) pIR assay (See Meso Scale Discovery, 9238 Gaithers Road, Gaitherburg, Md.). CHO cells stably expressing human IR(B) were in grown in F12 cell media containing 10% FBS and antibiotics (G418, Penicillin/Strepavidin) for at least 8 hours and then serum starved by switching to F12 media containing 0.5% BSA (insulin-free) in place of FBS for overnight growth. Cells were harvested and frozen in aliquots for use in the MSD pIR assay. Briefly, the frozen cells were plated in either 96-well (40,000 cells/well, Methods A and B) or 384-well (10,000 cells/well, Method C) clear tissue culture plates and allowed to recover. IOC molecules at the appropriate concentrations were added and the cells incubated for 8 min at 37° C. The media was aspirated and chilled MSD cell lysis buffer was added as per MSD kit instructions. The cells were lysed on ice for 40 min and the lysate then mixed for 10 minutes at room temperature. The lysate was transferred to the MSD kit pIR detection plates. The remainder of the assay was carried out following the MSD kit recommended protocol.

Example 103

Human macrophage mannose receptor 1 (MRC1) Binding Assays were performed as follows.

The competition binding assay for MRC1 utilized a ligand, mannosylated-BSA labeled with the DELFIA Eu-N1-ITC reagent, as reported in the literature. Anti-MRC1 antibody (25 μl at 2 ng/μl) was added to a Protein G plate that had been washed three times with 100 μl of 50 mM Tris buffer, pH 7.5 containing 100 mM NaCl, 5 mM $CaCl_2$, 1 mM $MgCl_2$ and 0.1% Tween-20 (wash buffer). The antibody was incubated in the plate for 1 hr at room temperature with shaking. The plate was washed with wash buffer 3-5 times followed by addition of MRC1 (2 ng/μl final concentration) in 25 μl PBS containing 1% stabilizer BSA. The plate was incubated at room temperature with gentle shaking for 1 hr. The plate was washed three times with wash buffer. The IOC molecules in 12.5 μl of buffer at appropriate concentrations were added followed by 12.5 μl of Eu-mannosylated-BSA (0.1 nM final concentration) in 50 mM Tris, pH 7.5 containing 100 mM NaCl, 5 mM $CaCl_2$, 1 mM $MgCl_2$ and 0.2% stabilizer BSA. The plate was incubated for 2 hrs at room temperature with shaking followed by washing three times with wash buffer. Perkin Elmer Eu-inducer reagent (25 μl) was added and incubated for 30 min at room temperature prior to detection of the Eu signal (Excitation=340 nm: Emission=615 nm). Assay was performed in a 96-well plate with a manual liquid dispense (Method F) or using an automated liquid dispense (Method G) or in a 384-well plate with an automated dispense (Method H).

Example 104

The following table lists conjugates that were prepared using appropriate intermediates following one of the General Methods described above. These conjugates were characterized using UPLC Method A or UPLC Method D noted by an asterisk, or UPLC Method G noted by a #, exhibiting either four charged, i.e. [(M+4)/4], (or five charged, i.e. [(M+5)/5]) species of parent compound at certain retention time (Rt). Their in vitro biological activities towards insulin receptor (IR) were measured by either ligand competition assays or functional phosphorylation assays, as described above, labeled as following: Method A: IR phosphorylation assay based on 96-well with manual liquid dispense; Method B: IR phosphorylation assay based on 96-well with automated liquid dispense; Method C: IR phosphorylation assay based on 384-well with automated liquid dispense; Method D: IR binding assay method D; Method E: IR binding assay method E; Method F: MRC1 assay was performed in a 96-well plate with a manual liquid dispense; Method G:

MRC1 assay was performed in a 96-well plate with an automated liquid dispense; Method H: MRC1 assay was performed in a 384-well plate with an automated dispense. The results are shown in Table 1.

TABLE 1

| | | Mass [(m + 4)/4 or | IR Activation | | IR Binding | | MRC1 Binding | |
|---|---|---|---|---|---|---|---|---|
| IOC # | RT (min) | (m + 5)/5] | IP† (nM) | Method | IP‡ (nM) | Method | IP‡ (nM) | Method |
| IOC-1 | 3.46 | 1793.16 | 2.04 | B | 4.84 | D | 7.64 | H |
| IOC-2 | 4.49 | 1951.04 | 1.83 | A | 4.92 | E | 3.64 | F |
| IOC-3 | 3.47 | 1784.12 | 0.99 | A | 2.52 | D | 7.28 | F |
| IOC-4 | 3.50 | 1784.80 | 1.83 | C | 3.99 | D | 10.11 | G |
| IOC-5 | 3.37 | 1618.99 | 6.80 | A | 0.89 | E | 98.17 | F |
| IOC-6 | 3.37 | 1618.99 | 0.27 | C | 1.82 | E | 123.70 | G |
| IOC-7 | 3.37 | 1618.99 | 1.40 | A | 0.81 | E | 139.10 | F |
| IOC-8 | 3.11 | 1793.22 | 3.71 | B | 5.16 | E | 24.17 | G |
| IOC-9 | 3.10 | 1792.96 | 2.17 | B | 5.19 | E | 698.00 | G |
| IOC-10 | 3.72 | 1763.30 | 0.38 | A | 0.31 | E | 9.60 | F |
| IOC-11 | 3.63 | 1918.78 | 12.78 | A | 3.37 | E | 5.82 | F |
| IOC-12 | 3.50 | 1608.55 | 1.46 | A | 0.42 | E | 92.46 | F |
| IOC-13 | 3.47 | 1607.55 | 4.22 | A | 1.60 | E | 106.60 | F |
| IOC-14 | 3.54 | 1608.08 | 3.21 | A | 0.67 | E | 8.33 | F |
| IOC-15 | 3.49 | 1763.12 | 16.47 | A | 2.49 | E | 39.22 | F |
| IOC-16 | 4.66 | 1785.46 | 27.47 | B | 3.58 | E | 25.29 | G |
| IOC-17 | 3.31 | 1770.70 | 3.91 | C | 15.33 | D | 25.05 | G |
| IOC-18 | 3.33 | 1762.05 | 754.60 | C | 400.20 | D | 28.32 | G |
| IOC-19 | 3.26 | 1789.60 | 2.41 | C | 3.27 | D | 26.62 | G |
| IOC-20 | 3.30 | 1774.90 | 2.51 | C | 8.05 | D | 15.83 | G |
| IOC-21 | 3.43 | 1848.64 | 2.60 | C | NA | NA | 11.65 | G |
| IOC-22 | 3.62 | 1763.67 | 18.93 | A | 1.24 | E | 18.19 | F |
| IOC-23 | 3.49 | 1757.00 | 20.34 | A | 11.67 | D | 25.05 | F |
| IOC-24 | 3.43 | 1940.00 | 2.02 | C | 1.33 | D | 2.47 | H |
| IOC-25 | 3.47 | 1777.52 | 2.90 | C | 3.30 | D | 10.23 | H |
| IOC-26 | 3.47 | 1776.66 | 3.03 | C | 2.33 | D | 46.40 | H |
| IOC-27 | 3.71 | 1918.29 | 32.43 | A | 7.37 | E | 1.92 | F |
| IOC-28 | 3.73 | 1929.29 | 75.67 | A | 39.46 | E | 4.36 | F |
| IOC-29 | 3.76 | 1770.22 | 41.71 | A | 5.11 | E | 14.87 | F |
| IOC-30 | 3.70 | 1940.61 | 1.83 | A | 0.59 | E | 0.44 | F |
| IOC-31 | 3.70 | 1861.27 | 13.14 | A | 1.18 | E | 4.31 | F |
| IOC-32 | 3.61 | 1748.08 | 29.02 | A | 5.11 | E | 0.47 | F |
| IOC-33 | 3.69 | 1940.21 | 24.37 | A | 4.30 | E | 0.53 | F |
| IOC-34 | 3.78 | 1696.43 | 0.76 | A | 0.23 | E | 32.92 | F |
| IOC-35 | 3.60 | 1777.42 | 1.41 | C | 3.15 | D | 108.70 | G |
| IOC-36 | 3.56 | 1926.78 | 22.33 | B | 5.66 | E | 0.54 | G |
| IOC-37 | 3.63 | 1689.86 | 3.49 | B | 1.80 | E | 16.92 | G |
| IOC-38 | 3.63 | 1689.86 | 11.79 | B | 1.43 | E | 23.23 | G |
| IOC-39 | 3.46 | 1909.10 | 14.24 | A | 1.61 | E | 6.90 | F |
| IOC-41 | 3.52 | 1604.94 | 6.11 | A | 0.88 | E | 113.50 | F |
| IOC-42 | 3.66 | 1782.89 | 2.83 | B | 0.43 | E | 13.13 | G |
| IOC-43 | 3.53 | 1955.10 | 10.98 | A | 2.00 | E | NA | NA |
| IOC-44 | 3.64 | 1955.10 | 56.62 | A | 2.93 | E | 0.16 | F |
| IOC-45 | 3.72 | 1704.00 | 4.30 | A | 0.76 | E | 11.54 | F |
| IOC-46 | 3.72* | 1703.60* | 1.45 | A | 1.50 | E | 0.18 | F |
| IOC-47 | 3.57 | 1725.10 | 16.53 | A | 1.42 | E | 20.41 | F |
| IOC-48 | 3.47 | 1714.00 | 12.75 | A | 1.88 | E | 17.79 | F |
| IOC-49 | 3.37 | 1868.30 | 15.37 | A | 1.51 | E | 1.14 | F |
| IOC-50 | 3.67* | 1869.90* | 37.08 | A | 6.11 | E | 0.49 | F |
| IOC-51 | 3.67* | 1703.90* | 31.45 | A | 7.79 | E | 0.37 | F |
| IOC-52 | 3.75 | 1783.30 | 16.75 | A | 5.69 | D | 9.80 | F |
| IOC-53 | 3.41 | 1697.70 | 11.31 | A | 1.09 | E | 45.46 | F |
| IOC-54 | 3.40 | 1787.30 | 14.34 | A | 2.33 | E | 18.84 | F |
| IOC-55 | 3.40 | 1870.50 | 15.95 | A | 1.76 | E | 17.32 | F |
| IOC-56 | 3.68* | 1954.90* | 34.99 | A | 4.83 | E | 1.41 | F |
| IOC-57 | 3.63* | 1697.30* | 49.88 | A | 8.66 | E | 1.01 | F |
| IOC-58 | 3.72* | 1703.60* | 1.44 | A | 0.41 | E | 7.95 | F |
| IOC-59 | 3.75 | 1735.50 | 1.96 | A | 1.15 | E | 20.60 | F |
| IOC-60 | 3.29 | 1785.21 | 39.32 | A | 8.49 | D | 10.32 | F |
| IOC-61 | 3.65 | 1615.55 | 99.94 | A | 9.48 | E | NA | NA |
| IOC-62 | 3.51 | 1637.87 | 57.38 | A | 11.53 | E | NA | NA |
| IOC-63 | 3.70 | 1750.00 | 1.90 | A | 0.91 | E | 29.26 | F |
| IOC-64 | 3.35 | 1609.35 | 51.08 | A | 6.14 | E | 0.46 | F |
| IOC-65 | 3.42 | 1731.60 | 2.87 | A | 0.68 | E | 21.61 | F |
| IOC-66 | 3.38 | 1926.98 | 41.29 | A | 6.88 | E | 3.62 | F |
| IOC-67 | 3.43 | 1918.85 | 34.42 | A | 6.65 | E | 44.95 | F |
| IOC-68 | 3.47 | 1839.78 | 28.79 | A | 4.33 | E | 44.61 | F |
| IOC-69 | 3.50 | 1866.88 | 62.09 | A | 14.64 | E | NA | NA |
| IOC-70 | 3.64 | 1632.15 | 77.13 | A | 9.62 | E | NA | NA |
| IOC-71 | 3.74 | 1746.08 | 2.41 | A | 1.37 | E | 21.47 | F |
| IOC-72 | 3.50 | 1884.29 | 43.52 | A | 26.02 | E | NA | NA |
| IOC-73 | 3.57 | 1643.44 | 70.50 | A | 5.44 | E | NA | NA |

TABLE 1-continued

| IOC # | RT (min) | Mass [(m + 4)/4 or (m + 5)/5] | IR Activation IP† (nM) | IR Activation Method | IR Binding IP‡ (nM) | IR Binding Method | MRC1 Binding IP‡ (nM) | MRC1 Binding Method |
|---|---|---|---|---|---|---|---|---|
| IOC-74 | 3.75 | 1753.44 | 3.27 | A | 0.59 | E | 27.37 | F |
| IOC-75 | 3.65 | 1654.71 | 41.39 | A | 4.90 | E | 0.58 | F |
| IOC-76 | 3.76 | 1760.52 | 4.28 | A | 0.49 | E | 27.14 | F |
| IOC-77 | 3.68 | 1827.80 | 57.29 | B | 6.45 | E | 20.43 | G |
| IOC-78 | 3.79 | 1827.70 | 25.84 | B | 18.09 | E | 12.74 | G |
| IOC-79 | 3.73 | 1811.57 | 13.48 | A | 1.73 | E | 49.26 | F |
| IOC-80 | 3.47 | 1704.88 | 5.30 | C | NA | NA | 2.83 | G |
| IOC-81 | 3.48 | 1904.44 | 4.35 | C | NA | NA | 27.13 | G |
| IOC-82 | 4.52 | 1866.14 | 2.75 | C | 2.39 | E | 16.61 | G |
| IOC-83 | 4.67 | 1786.54 | 5.96 | C | 2.62 | E | 69.77 | G |
| IOC-84 | 3.63 | 1899.84 | 22.99 | B | 3.82 | E | 4.24 | G |
| IOC-85 | 4.11 | 1735.17 | 4.01 | B | 0.84 | E | 31.42 | G |
| IOC-86 | 4.42 | 1735.24 | 13.41 | B | 0.71 | E | 84.94 | G |
| IOC-87 | 4.34 | 1859.16 | 23.47 | B | 1.43 | E | 67.94 | G |
| IOC-88 | 3.87 | 1628.73 | 15.06 | B | 6.39 | E | 1.08 | G |
| IOC-89 | 4.10 | 1871.51 | 4.15 | B | 2.28 | E | 2.06 | G |
| IOC-90 | 3.52 | 1892.85 | 2.92 | B | 1.13 | E | 2.63 | G |
| IOC-91 | 3.47 | 1892.93 | 32.77 | B | 8.96 | E | 4.67 | G |
| IOC-92 | 3.51 | 1852.31 | 4.83 | B | 4.20 | E | 5.69 | G |
| IOC-93 | 3.80 | 1871.12 | 10.75 | B | 1.68 | E | 4.65 | G |
| IOC-94 | 3.52 | 1790.30 | 13.21 | B | 2.37 | E | 61.05 | G |
| IOC-95 | 3.78 | 1853.48 | 12.02 | B | 1.87 | E | 47.13 | G |
| IOC-96 | 3.49 | 1690.29 | 0.76 | B | 0.66 | D | 71.49 | H |
| IOC-97 | 3.60 | 1894.87 | 25.71 | B | 2.07 | E | 56.62 | G |
| IOC-98 | 3.61 | 1749.43 | 28.44 | B | 1.11 | E | 128.10 | G |
| IOC-99 | 3.84 | 1738.89 | 16.31 | A | 1.29 | E | NA | NA |
| IOC-100 | 3.64 | 1603.19 | 53.03 | A | 6.55 | E | NA | NA |
| IOC-101 | 3.62 | 1728.12 | 0.75 | A | 0.34 | E | 78.00 | F |
| IOC-102 | 3.46 | 1956.55 | 0.88 | C | 0.92 | D | 1.49 | H |
| IOC-103 | 3.38 | 1955.25 | 0.92 | C | 0.68 | D | 1.31 | H |
| IOC-104 | 3.43 | 1704.57 | 0.31 | C | NA | NA | 42.85 | G |
| IOC-105 | 3.42 | 1703.58 | 0.41 | C | NA | NA | 34.47 | G |
| IOC-106 | 4.56 | 1706.54 | 1.22 | B | 0.79 | E | 31.90 | G |
| IOC-107 | 4.45 | 1706.89 | 21.47 | B | 0.61 | E | 75.41 | G |
| IOC-108 | 4.57 | 1706.90 | 8.62 | B | 0.83 | E | 53.19 | G |
| IOC-109 | 3.64 | 1739.29 | 136.70 | B | 9.01 | E | 0.60 | G |
| IOC-110 | 3.62 | 1933.29 | 242.20 | B | 13.73 | E | 2.63 | G |
| IOC-111 | 3.64 | 1821.80 | 5.66 | A | 1.11 | E | 464.30 | F |
| IOC-112 | 3.71 | 1698.50 | 6.27 | A | 1.52 | E | 335.30 | F |
| IOC-113 | 3.51 | 1783.55 | 2.89 | C | 1.77 | D | 20.73 | H |
| IOC-114 | 3.48 | 1949.31 | 2.17 | C | 2.19 | D | 3.83 | H |
| IOC-115 | 3.62 | 1693.27 | 17.80 | B | 0.68 | E | 30.92 | G |
| IOC-116 | 3.63 | 1692.81 | 2.65 | B | 0.52 | E | 13.28 | G |
| IOC-117 | 4.28 | 1693.09 | 5.47 | B | 0.46 | E | 24.12 | G |
| IOC-118 | 4.11 | 1933.41 | 60.22 | B | 3.77 | E | 0.63 | G |
| IOC-119 | 4.01 | 1933.72 | 4.39 | B | 0.60 | E | 0.40 | G |
| IOC-120 | 3.96 | 1933.70 | 14.72 | B | 1.31 | E | 0.43 | G |
| IOC-121 | 3.58 | 1772.28 | 16.43 | B | 1.05 | E | 1.77 | G |
| IOC-122 | 3.89 | 1871.38 | 11.12 | A | 3.36 | E | NA | NA |
| IOC-129 | 3.54 | 1783.64 | 0.37 | C | 0.41 | D | 22.86 | H |
| IOC-130 | 4.00 | 1588.44 | 965.90 | B | 6.46 | E | 3.51 | G |
| IOC-131 | 4.08 | 1808.21 | 23.39 | B | 3.23 | E | 15.36 | G |
| IOC-132 | 4.19 | 1498.92 | 43.05 | B | 3.55 | E | 5.09 | G |
| IOC-133 | 4.28 | 1508.40 | 66.81 | B | 3.95 | E | 5.22 | G |
| IOC-134 | 4.47 | 1807.76 | 5.50 | B | 1.30 | E | 11.38 | G |
| IOC-135 | 3.31 | 1890.75 | 3.29 | C | 4.24 | D | 30.59 | H |
| IOC-136 | 3.28 | 1688.38 | 7.83 | C | 4.25 | D | 12.71 | H |
| IOC-137 | 3.50 | 1706.80 | 0.99 | C | 1.13 | D | 475.50 | H |
| IOC-138 | 3.34 | 1833.60 | 3.35 | C | 2.25 | D | 279.60 | H |
| IOC-139 | 3.52 | 1706.03 | 0.30 | C | 0.30 | D | 785.30 | H |
| IOC-140 | 3.24 | 1784.78 | 2.12 | C | 3.19 | D | 235.60 | H |
| IOC-141 | 3.48 | 1949.31 | 0.82 | C | 0.91 | D | 44.34 | H |
| IOC-142 | 3.51 | 1783.55 | 0.87 | C | 1.00 | D | 182.80 | H |
| IOC-143 | 3.58 | 1777.59 | 0.51 | C | 0.38 | D | 7.17 | H |
| IOC-144 | 3.50 | 1763.92 | 6.63 | C | 9.24 | D | 30.46 | H |
| IOC-145 | 3.49 | 1985.78 | 6.75 | C | 15.05 | D | 2.69 | H |
| IOC-146 | 3.55 | 1808.57 | 6.04 | C | 9.65 | D | 15.63 | H |
| IOC-147 | 3.53 | 1971.72 | 3.12 | B | 20.33 | D | 5.42 | H |
| IOC-148 | 3.60 | 1793.57 | 3.09 | B | 15.76 | D | 21.67 | H |
| IOC-149 | 3.47 | 1990.59 | 3.47 | B | 2.32 | D | 2.62 | H |
| IOC-150 | 3.54 | 1811.75 | 2.82 | B | 2.10 | D | 18.08 | H |
| IOC-151 | 3.53 | 1975.17 | 1.48 | B | 6.59 | D | 3.33 | H |
| IOC-152 | 3.59 | 1798.10 | 2.36 | B | 3.12 | D | 9.50 | H |
| IOC-153 | 3.41 | 1703.52 | 0.40 | B | 0.20 | D | 1121.00 | H |
| IOC-154 | 3.34 | 1792.79 | 0.76 | B | 0.52 | D | 5.32 | H |

TABLE 1-continued

| IOC # | RT (min) | Mass [(m + 4)/4 or (m + 5)/5] | IR Activation IP† (nM) | IR Activation Method | IR Binding IP‡ (nM) | IR Binding Method | MRC1 Binding IP‡ (nM) | MRC1 Binding Method |
|---|---|---|---|---|---|---|---|---|
| IOC-155 | 3.40 | 1963.07 | 2.82 | B | 4.82 | D | 3.34 | H |
| IOC-156 | 3.48 | 1793.12 | 1.26 | B | 2.86 | D | 16.32 | H |
| IOC-157 | 3.41 | 1964.48 | 3.22 | B | 2.85 | D | 4.98 | H |
| IOC-158 | 3.52 | 1797.41 | 0.50 | B | 0.66 | D | 11.57 | H |
| IOC-159 | 3.50 | 1692.99 | 0.54 | B | 0.45 | D | 56.84 | H |
| IOC-160 | 3.54 | 1678.14 | 0.59 | B | 0.80 | D | 48.55 | H |
| IOC-161 | 3.50 | 1697.68 | 0.78 | C | 0.61 | D | 39.81 | H |
| IOC-162 | 3.55 | 1683.65 | 0.41 | B | 0.18 | D | 21.28 | H |
| IOC-163 | 3.56 | 1617.96 | 0.70 | C | 1.26 | D | 95.98 | H |
| IOC-164 | 3.50 | 1784.06 | 1.57 | B | 7.09 | D | 24.35 | H |
| IOC-165 | 3.49 | 1948.95 | 1.29 | B | 3.51 | D | 3.22 | H |
| IOC-166 | 3.53 | 1935.09 | 5.36 | C | 15.14 | D | 3.85 | H |
| IOC-167 | 3.54 | 1768.64 | 1.73 | B | 3.25 | D | 25.61 | H |
| IOC-168 | 3.43 | 1778.13 | 1.20 | B | 2.76 | D | 6.28 | H |
| IOC-169 | 3.43 | 1940.02 | 0.93 | B | 1.94 | D | 1.40 | H |
| IOC-170 | 3.49 | 1763.28 | 1.10 | B | 2.87 | D | 7.06 | H |
| IOC-171 | 3.49 | 1925.61 | 1.27 | B | 1.98 | D | 1.49 | H |
| IOC-172 | 3.43 | 1782.34 | 1.49 | C | 7.18 | D | 8.66 | H |
| IOC-173 | 3.43 | 1944.07 | 0.59 | B | 1.13 | D | 1.22 | H |
| IOC-174 | 3.48 | 1767.66 | 0.74 | B | 1.61 | D | 4.05 | H |
| IOC-175 | 3.43 | 1930.01 | 0.89 | B | 1.95 | D | 0.58 | H |
| IOC-176 | 3.45 | 1705.38 | 0.54 | B | 0.80 | D | 21.01 | H |
| IOC-177 | 3.45 | 1727.38 | 0.88 | B | 0.84 | D | 27.85 | H |
| IOC-178 | 3.47 | 1706.39 | 0.59 | B | 1.06 | D | 17.65 | H |
| IOC-179 | 3.47 | 1705.71 | 0.60 | B | 0.88 | D | 28.44 | H |
| IOC-180 | 3.48 | 1706.43 | 0.66 | B | 0.36 | D | 22.91 | H |
| IOC-181 | 3.53 | 1578.92 | 0.37 | B | 0.12 | D | 40.56 | H |
| IOC-182 | 3.41 | 1831.90 | 1.09 | B | 1.81 | D | 27.78 | H |
| IOC-183 | 3.54 | 1579.64 | 0.65 | B | 0.63 | D | 132.80 | H |
| IOC-184 | 3.54 | 1579.85 | 0.59 | B | 0.12 | D | 78.63 | H |
| IOC-185 | 3.51 | 1589.51 | 0.49 | B | 0.73 | D | 61.87 | H |
| IOC-186 | 3.51 | 1589.98 | 0.53 | C | 0.47 | D | 38.06 | H |
| IOC-187 | 3.53 | 1579.56 | 0.48 | B | 0.52 | D | 42.02 | H |
| IOC-188 | 3.53 | 1579.74 | 0.37 | B | 0.11 | D | 42.77 | H |
| IOC-189 | 3.44 | 1833.23 | 0.68 | B | 0.32 | D | 8.18 | H |
| IOC-190 | 3.54 | 1579.12 | 0.20 | B | 0.17 | D | 36.60 | H |
| IOC-191 | 3.48 | 1693.64 | 0.54 | B | 0.55 | D | 32.11 | H |
| IOC-192 | 3.43 | 1708.06 | 0.45 | B | 0.27 | D | 61.62 | H |
| IOC-193 | 3.29 | 1705.27 | 2.15 | C | 4.68 | D | 1.06 | H |
| IOC-194 | 3.57 | 1706.16 | 2.26 | C | 4.14 | D | 4.62 | H |
| IOC-195 | 3.19 | 1707.01 | 2.10 | C | 2.37 | D | 14.94 | H |
| IOC-196 | 3.15# | 1707.84 | 2.50 | C | 3.35 | D | 148.80 | H |
| IOC-197 | 4.09# | 1661.24 | 1.60 | C | 1.95 | D | 15.77 | H |
| IOC-198 | 4.05# | 1870.09 | 12.81 | C | 20.57 | D | 1.88 | H |
| IOC-199 | 4.06# | 1870.08 | 9.18 | C | 15.12 | D | 4.35 | H |
| IOC-200 | 3.96# | 1869.10 | 9.67 | C | 19.76 | D | 0.48 | H |
| IOC-201 | 4.08# | 1664.55 | 2.23 | C | 4.64 | D | 7.98 | H |
| IOC-202 | 4.07# | 1875.95 | 8.67 | C | 11.91 | D | 0.58 | H |
| IOC-205 | 3.62# | 1776.62 | 5.14 | C | 18.67 | D | 35.88 | H |
| IOC-206 | 3.49# | 1938.42 | 5.05 | C | 7.27 | D | 5.97 | H |
| IOC-207 | 3.56# | 1720.43 | 6.71 | C | 19.67 | D | 292.20 | H |
| IOC-208 | 3.56# | 1854.45 | 2.08 | C | 6.94 | D | 43.47 | H |
| IOC-209 | 3.59# | 1586.34 | 1.25 | C | 1.14 | D | 709.60 | H |
| IOC-210 | 3.35# | 1727.73 | 6.71 | C | 15.29 | D | 1047.00 | H |
| IOC-211 | 3.32# | 1865.23 | 8.64 | C | 34.34 | D | 645.00 | H |
| IOC-212 | 3.31# | 1492.67 | 31.40 | A | 11.41 | D | 8.96 | F |
| IOC-213 | 3.33# | 1492.86 | 16.89 | C | 9.49 | D | 53.73 | H |
| IOC-214 | 3.34# | 1783.20 | 7.12 | C | 4.11 | D | 45.82 | H |
| IOC-215 | 3.33# | 1782.94 | 7.94 | C | 4.45 | D | 65.78 | H |
| IOC-216 | 3.37# | 1559.84 | 24.41 | C | 24.60 | D | 25.79 | H |
| IOC-217 | 3.35 | 1559.62 | 5.17 | C | 5.52 | D | 19.99 | H |
| IOC-218 | 3.49 | 1771.33 | 0.84 | C | 1.40 | D | 61.81 | H |
| IOC-219 | 3.73# | 1933.61 | 0.97 | C | 0.93 | D | 0.73 | H |
| IOC-220 | 3.41# | 1783.30 | 3.83 | C | 5.60 | D | 43.99 | H |
| IOC-221 | 3.4# | 1787.17 | 5.78 | C | 6.62 | D | 52.43 | H |
| IOC-222 | 3.41# | 1776.39 | 4.52 | C | 5.23 | D | 40.61 | H |
| IOC-223 | 3.41# | 1703.87 | 0.95 | C | 0.77 | D | 33.04 | H |
| IOC-224 | 3.43# | 1896.33 | 1.31 | C | 0.94 | D | 2.28 | H |
| IOC-225 | 3.29# | 1632.63 | 1.29 | C | 1.42 | D | 2.45 | H |
| IOC-226 | 3.35# | 1632.54 | 1.22 | C | 0.85 | D | 2.04 | H |
| IOC-227 | 3.38# | 1955.37 | 1.92 | C | 0.71 | D | 0.93 | H |
| IOC-228 | 3.43# | 1862.43 | 10.22 | C | 7.57 | D | 64.93 | H |
| IOC-229 | 3.42# | 1870.65 | 5.09 | C | 8.08 | D | 43.66 | H |
| IOC-230 | 3.47 | 1848.22 | 9.84 | C | 7.46 | D | 46.40 | H |
| IOC-231 | 3.57 | 1618.65 | 2.06 | C | 1.53 | D | 231.20 | H |

TABLE 1-continued

| IOC # | RT (min) | Mass [(m + 4)/4 or (m + 5)/5] | IR Activation IP† (nM) | Method | IR Binding IP‡ (nM) | Method | MRC1 Binding IP‡ (nM) | Method |
|---|---|---|---|---|---|---|---|---|
| IOC-232 | 3.48 | 1783.50 | 4.12 | C | 4.05 | D | 21.24 | H |
| IOC-233 | 3.40 | 1776.58 | 1.65 | C | 7.07 | D | 33.12 | H |
| IOC-234 | 3.51 | 1777.03 | 0.73 | C | 1.36 | D | 23.11 | H |
| IOC-235 | 3.43 | 1783.00 | 0.60 | C | 0.56 | D | 9.01 | H |
| IOC-236 | 3.51 | 1783.70 | 3.54 | C | 8.27 | D | 27.34 | H |
| IOC-237 | 3.49# | 1948.88 | 2.75 | C | 6.34 | D | 3.70 | H |
| IOC-238 | 4.02 | 1807.35 | 3.54 | C | 4.02 | D | 21.88 | H |
| IOC-246 | 3.52 | 1970.09 | 7.74 | C | 10.05 | D | 2.08 | H |
| IOC-247 | 3.57 | 1797.76 | 2.59 | C | 9.18 | D | 21.59 | H |
| IOC-248 | 3.55 | 1797.82 | 0.94 | C | 0.93 | D | 11.36 | H |
| IOC-249 | 3.51 | 1938.30 | 2.96 | C | 6.29 | D | 2.69 | H |
| IOC-250 | 3.52 | 1776.47 | 6.77 | C | 10.52 | D | 37.92 | H |
| IOC-251 | 3.58 | 1776.50 | 1.05 | C | 2.17 | D | 52.27 | H |
| IOC-252 | 3.47 | 1776.55 | 1.61 | C | 1.21 | D | 40.68 | H |
| IOC-253 | 3.65 | 1552.35 | 0.53 | C | 0.73 | D | 1.52 | H |
| IOC-255 | 3.46 | 1760.10 | 11.20 | C | 7.24 | D | 41.82 | H |
| IOC-256 | 3.36 | 1734.75 | 3.98 | C | 3.20 | D | 52.56 | H |
| IOC-257 | 3.59 | 1593.57 | 0.76 | C | 0.79 | D | 440.40 | H |
| IOC-258 | 3.36 | 1587.43 | 1.29 | C | 0.72 | D | 234.10 | H |
| IOC-259 | 3.35 | 1721.28 | 3.93 | C | 4.53 | D | 76.67 | H |
| IOC-260 | 3.36 | 1855.61 | 4.40 | C | 4.97 | D | 18.08 | H |
| IOC-261 | 3.32 | 1721.46 | 4.47 | C | 2.62 | D | 280.90 | H |
| IOC-262 | 3.34 | 1856.36 | 4.08 | C | 3.07 | D | 102.30 | H |
| IOC-263 | 3.23 | 1735.74 | 5.54 | C | 4.77 | D | 132.40 | H |
| IOC-264 | 3.25 | 1876.85 | 6.01 | C | 9.15 | D | 34.11 | H |
| IOC-265 | 3.23 | 1735.38 | 2.18 | C | 2.32 | D | 55.74 | H |
| IOC-266 | 3.24 | 1876.68 | 2.14 | C | 4.70 | D | 9.72 | H |
| IOC-267 | 3.50 | 1597.63 | 1.28 | C | 1.46 | D | 217.20 | H |
| IOC-268 | 3.74 | 1742.53 | 4.86 | C | 4.28 | D | 76.89 | H |
| IOC-269 | 3.87 | 1749.83 | 4.74 | C | 3.36 | D | 167.60 | H |
| IOC-270 | 3.88 | 1898.28 | 1.81 | C | 2.84 | D | 9.74 | H |
| IOC-271 | 4.37 | 1888.65 | 1.02 | C | 9.38 | D | 7.01 | H |
| IOC-272 | 4.35 | 1754.71 | 0.90 | C | 5.38 | D | 17.11 | H |

†IP is inflection point and corresponds to $EC_{50}$.
‡IP is inflection point and corresponds to $IC_{50}$.

Example 105

Effect of Methyl α-D-Mannopyranoside (aMM) on PK and PD of IOCs in Non-Diabetic Minipigs was evaluated.

Male Yucatan miniature pigs, non-diabetic, instrumented with two Jugular vein vascular access ports (VAP), are used in these studies. Animals are fasted overnight prior to the study. On the day of the study, animals are restrained in slings, and VAPs accessed for infusion and sampling. At t=−60 minutes, a constant infusion of PBS (n=3) or 21.2% α-methyl mannose (aMM) (n=3) is started, at a rate of 2.67 mL/kg/hr. This infusion will be maintained for the duration of the study. At t=0 min, and after collecting a baseline blood sample for plasma glucose measurement, animals are administered IOC as a single bolus IV. Sampling continues for 90 minutes, with final readouts of plasma glucose and compound levels.

IOCs are formulated at 17-69 nmol/mL in sodium chloride (87 mM), phenol (21 mM), dibasic sodium phosphate (26.5 mM), Osmolality=275 mOsm, pH=7.4; QS with Water for Injection.

Time points for sample collection: −60 min, 0 min, 1 min, 2 min, 4 min, 6 min, 8 min, 10 min, 15 min, 20 min, 25 min, 30 min, 35 min, 45 min, 60 min, and 90 min.

Blood is collected in K3-EDTA tubes, supplemented with 10 μg/ml Aprotinin, and kept on an ice bath until processing, within 30 minutes of collection. After centrifugation at 3000 rpm, 4° C., for 8 min, plasma is collected and aliquoted for glucose measurement using a Beckman Coulter AU480 Chemistry analyzer and for compound levels measurement by LC-MS.

Glucose results are expressed as % changes over baseline values at t=0 minutes and are shown for IOC-2, IOC-3, IOC-8, IOC-9, IOC-16, IOC-22, IOC-23, IOC-46, IOC-48, IOC-52, IOC-56, IOC-60, IOC-75, IOC-75, and IOC-76 in FIGS. 1-14, respectively.

FIG. 1 shows plots of serum concentrations of IOC-2 following a 0.69 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 2:
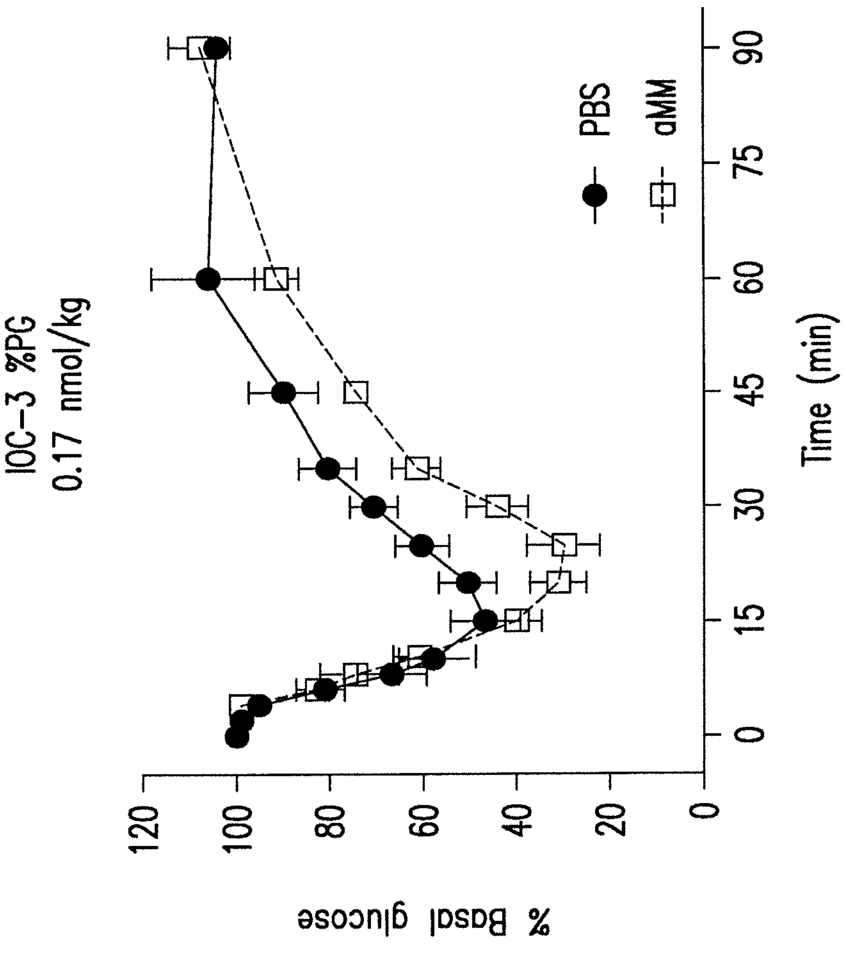
FIG. 2: Plots of serum concentrations of IOC-3 following a 0.17 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 2 shows plots of serum concentrations of IOC-3 following a 0.17 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 3:
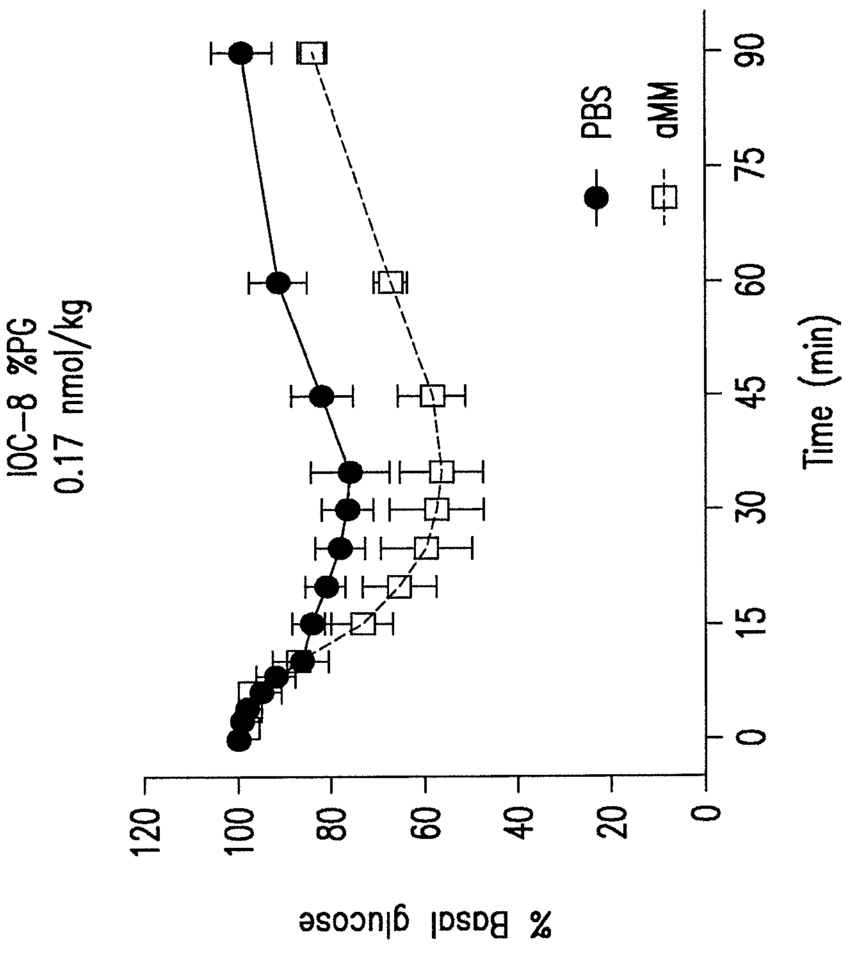
FIG. 3: Plots of serum concentrations of IOC-8 following a 0.17 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 3 shows plots of serum concentrations of IOC-8 following a 0.17 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 4:
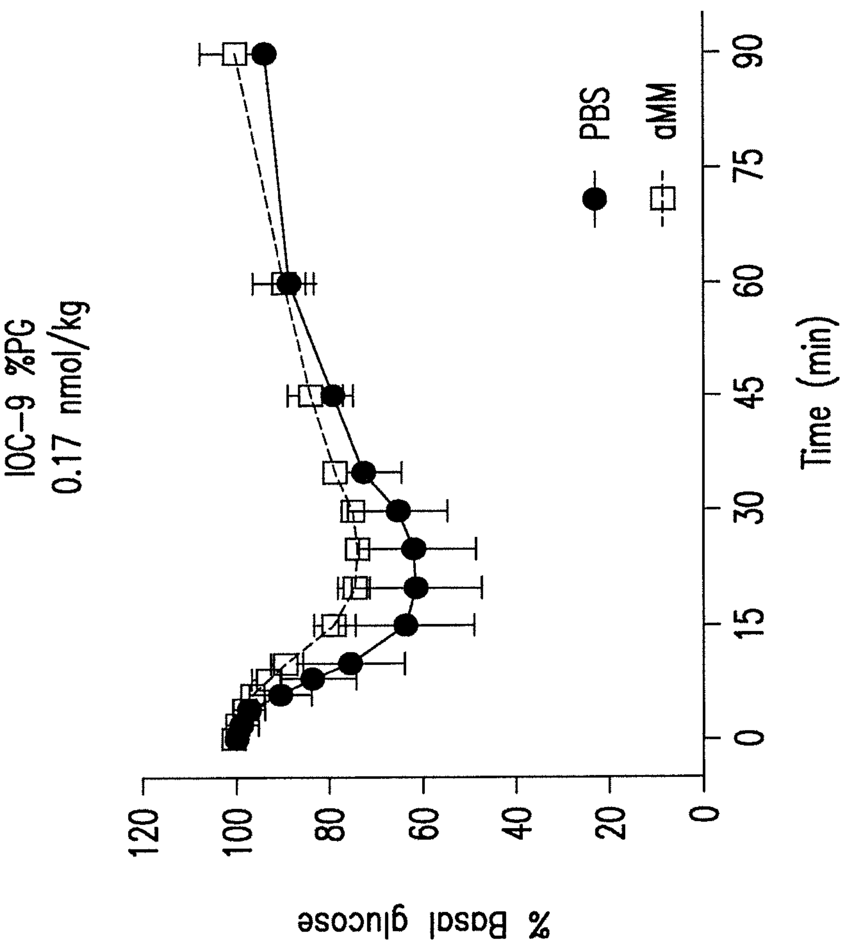
FIG. 4: Plots of serum concentrations of IOC-9 following a 0.17 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 4 shows plots of serum concentrations of IOC-9 following a 0.17 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 5:
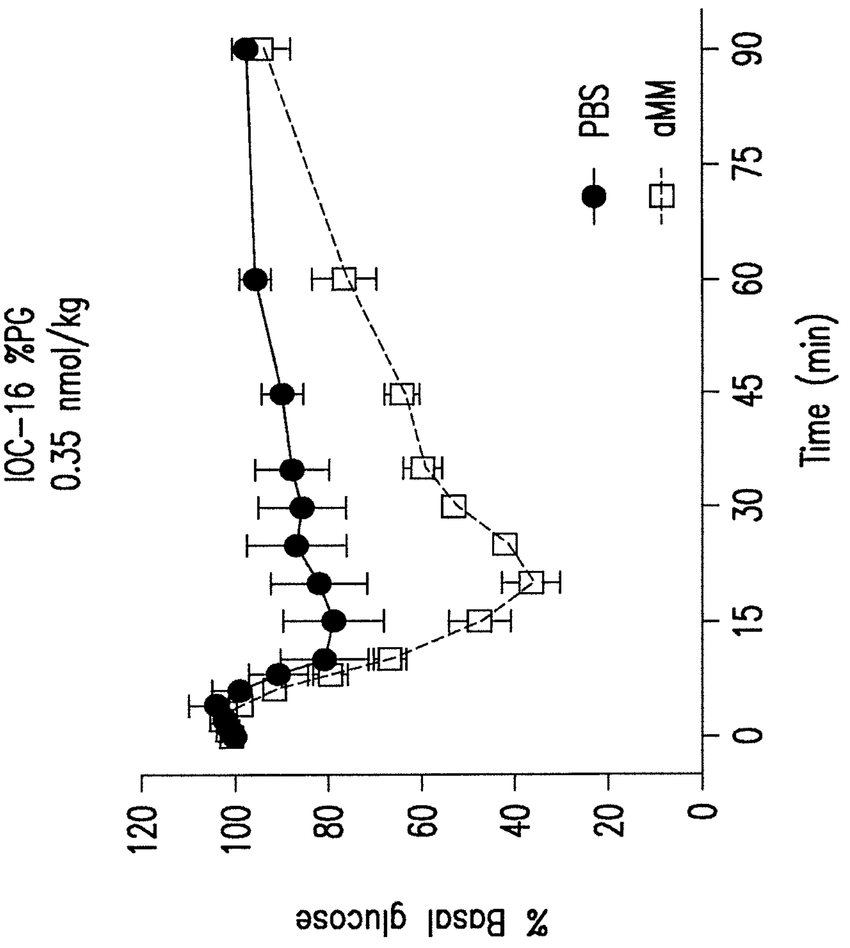
FIG. 5: Plots of serum concentrations of IOC-16 following a 0.35 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 5 shows plots of serum concentrations of IOC-16 following a 0.35 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 6:
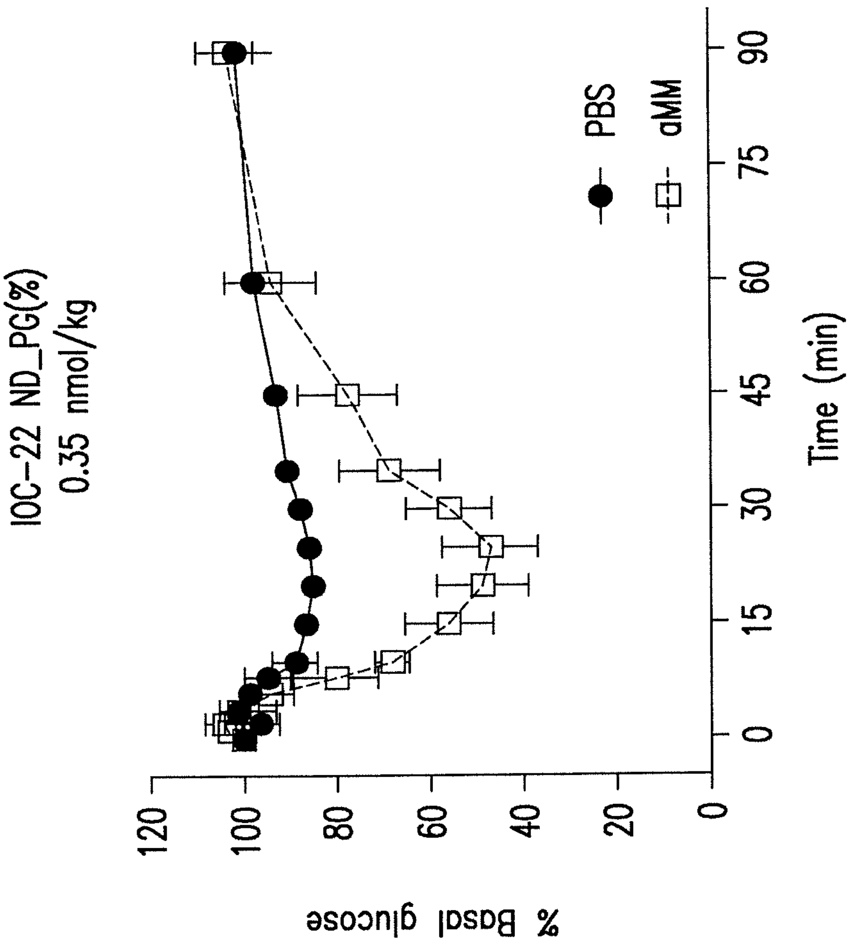
FIG. 6: Plots of serum concentrations of IOC-22 following a 0.35 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 6 shows plots of serum concentrations of IOC-22 following a 0.35 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 7:
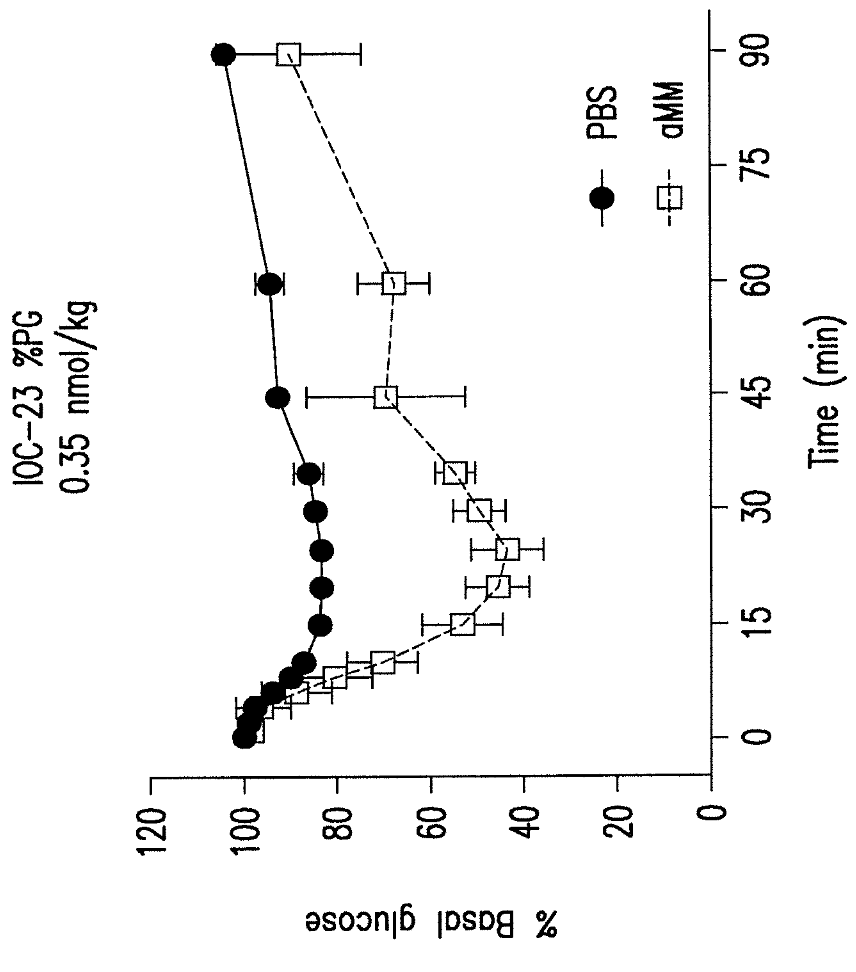
FIG. 7: Plots of serum concentrations of IOC-23 following a 0.35 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 7 shows plots of serum concentrations of IOC-23 following a 0.35 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 8:
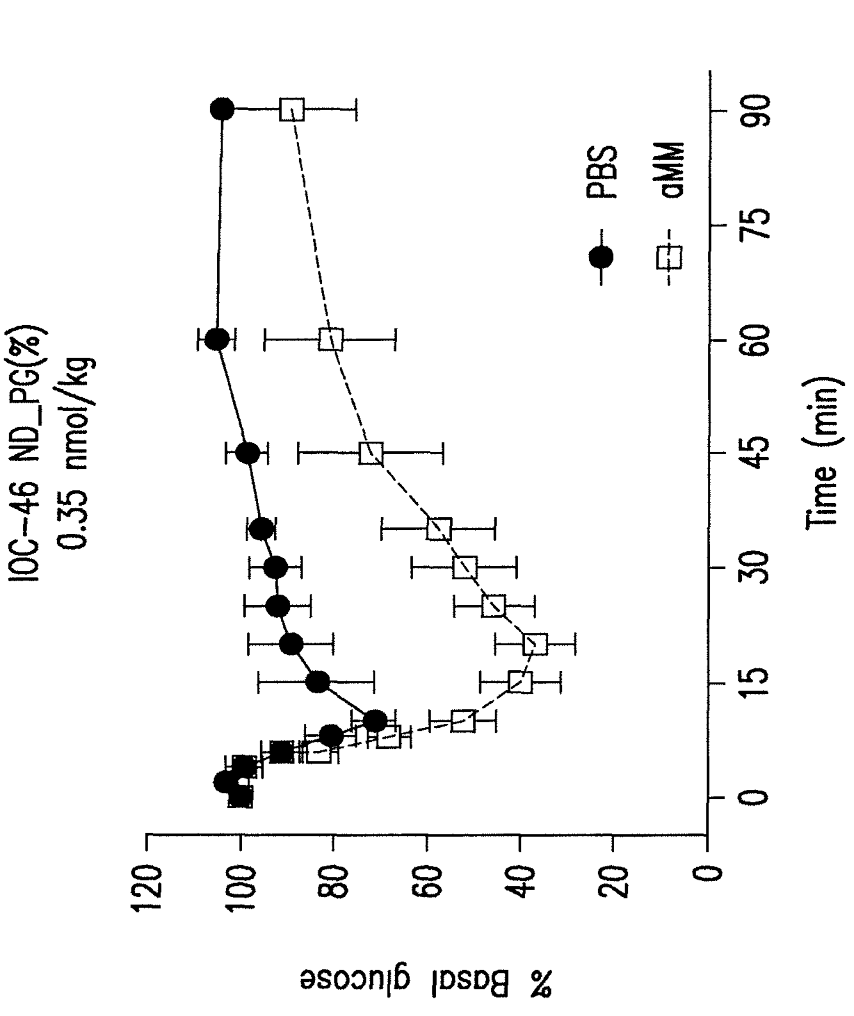
FIG. 8: Plots of serum concentrations of IOC-46 following a 0.35 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 8 shows plots of serum concentrations of IOC-46 following a 0.35 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 9:
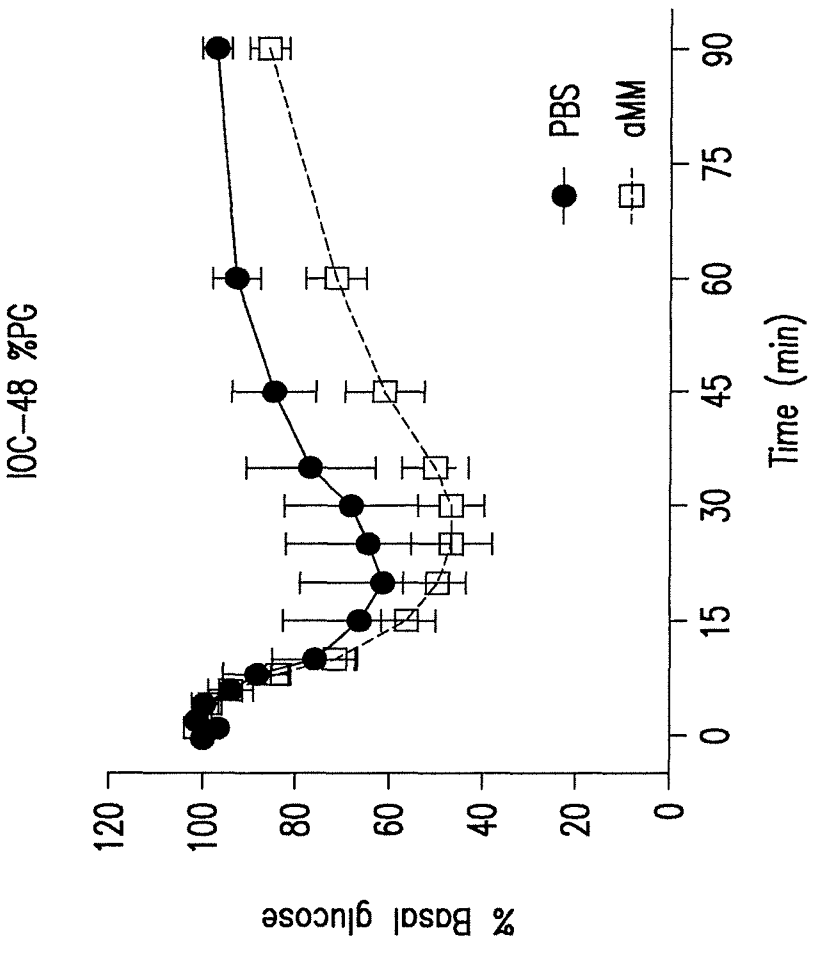
FIG. 9: Plots of serum concentrations of IOC-48 following a 0.35 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 9 shows plots of serum concentrations of IOC-48 following a 0.35 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 10:
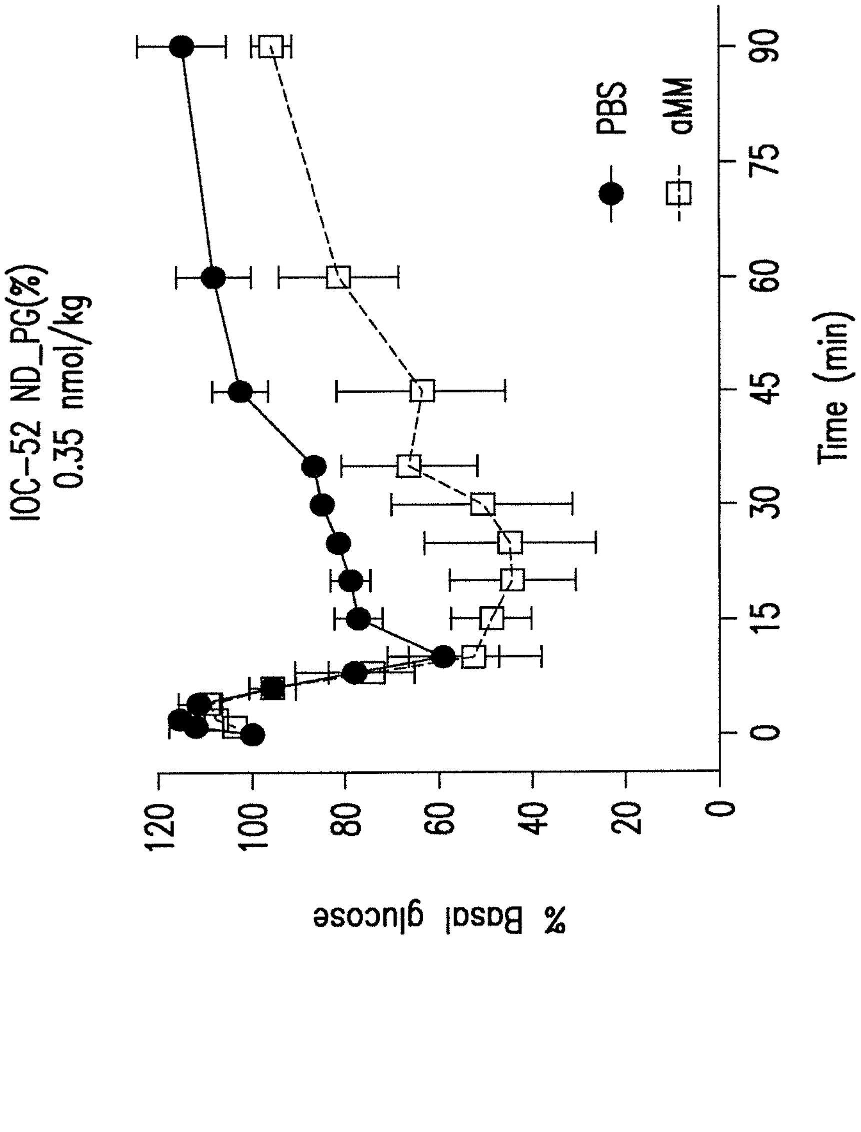
FIG. 10: Plots of serum concentrations of IOC-52 following a 0.35 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 10 shows plots of serum concentrations of IOC-52 following a 0.35 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 11:
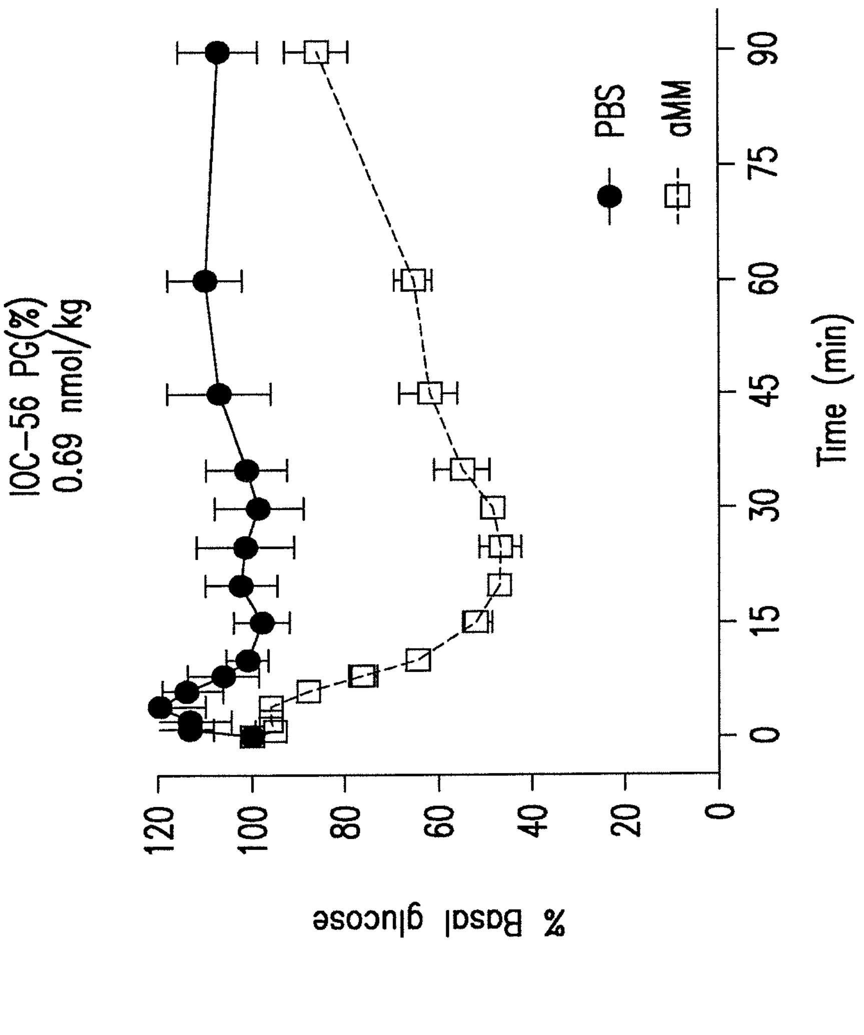
FIG. 11: Plots of serum concentrations of IOC-56 following a 0.69 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 11 shows plots of serum concentrations of IOC-56 following a 0.69 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 12:
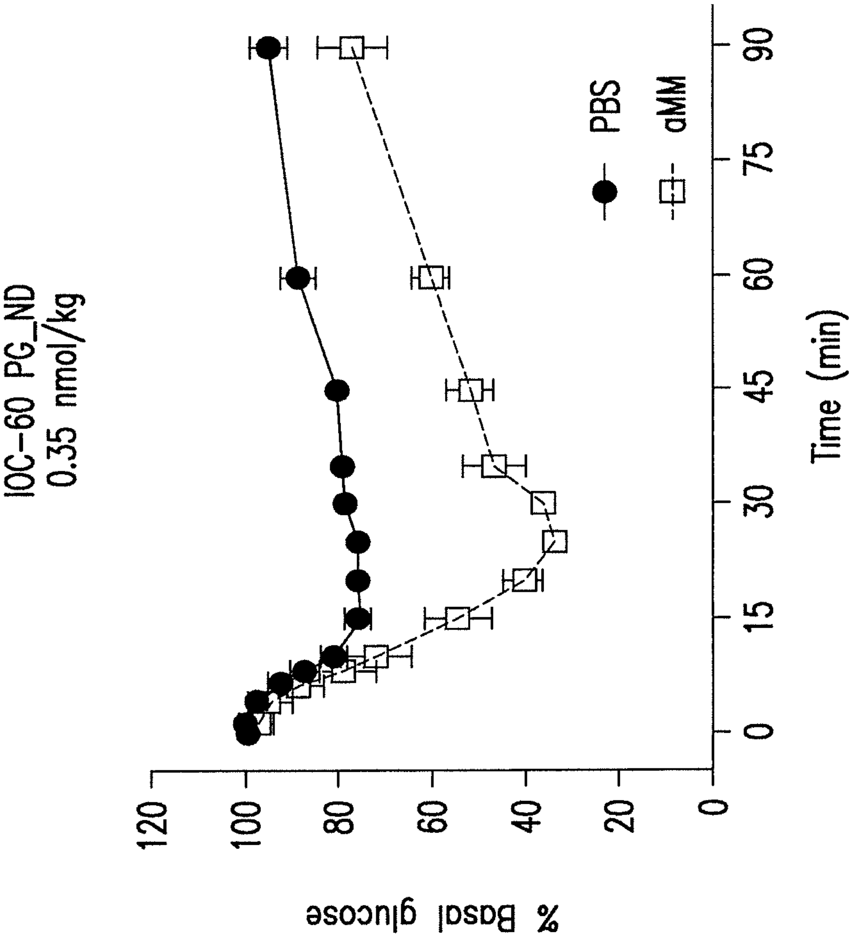
FIG. 12: Plots of serum concentrations of IOC-60 following a 0.35 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 12 shows plots of serum concentrations of IOC-60 following a 0.35 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 13:
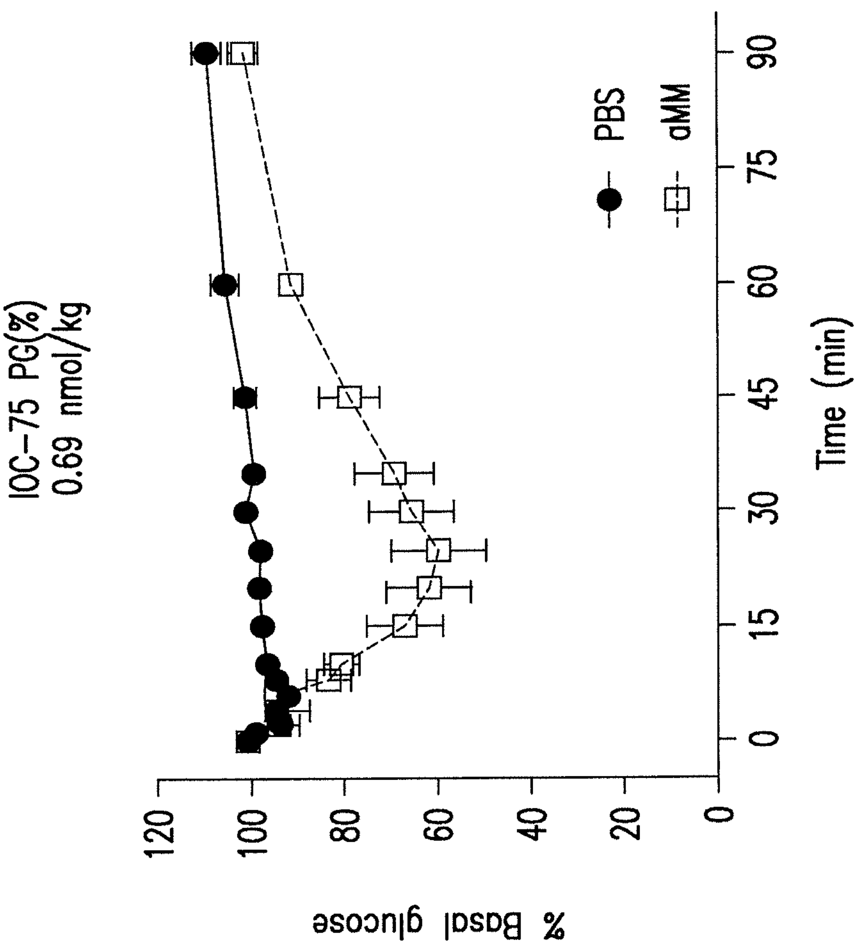
FIG. 13: Plots of serum concentrations of IOC-75 following a 0.69 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 13 shows plots of serum concentrations of IOC-75 following a 0.69 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

Figure 14:
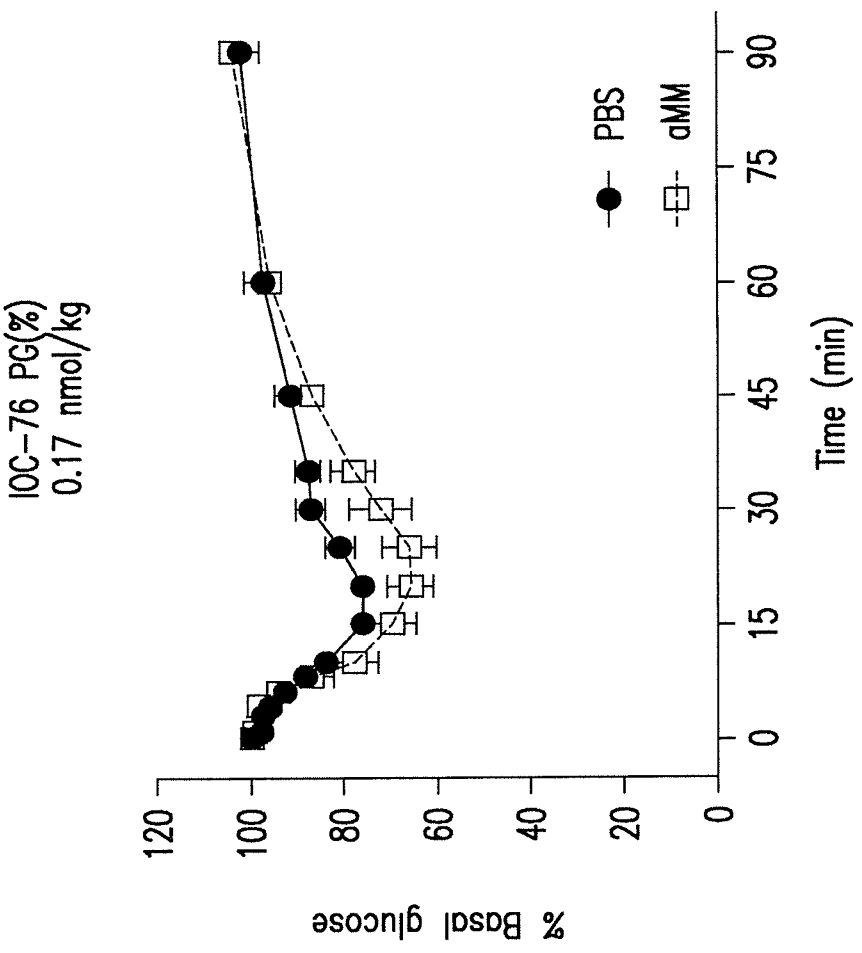
FIG. 14: Plots of serum concentrations of IOC-76 following a 0.17 nmol/kg intravenous (i.v.) injection into non-diabetic male Yucatan minipigs equipped with dual vascular access ports (n=3 per study). In each experiment, the animals were infused with (□) i.v. alpha methyl mannose (aMM) solution (21.2% w/v infused at constant rate of 2.67 mL/kg/hr) or (●) PBS. Data are plotted as the average values fit with a curve derived from the two-compartment, bi-exponential model.

FIG. 14 shows plots of serum concentrations of IOC-76 following a 0.17 nmol/kg intravenous (i.v.) injection into non-diabetic male Yucatan minipigs equipped with dual vascular access ports (n=3 per study) infused with i.v. alpha methyl mannose (aMM) solution (21.2% w/v infused at constant rate of 2.67 mL/kg/hr) or PBS.

PK results for IOC-2, IOC-3, IOC-16, IOC-22, IOC-23, IOC-52, IOC-56, and IOC-60 are shown in FIGS. 15-22, respectively.

Figure 15:
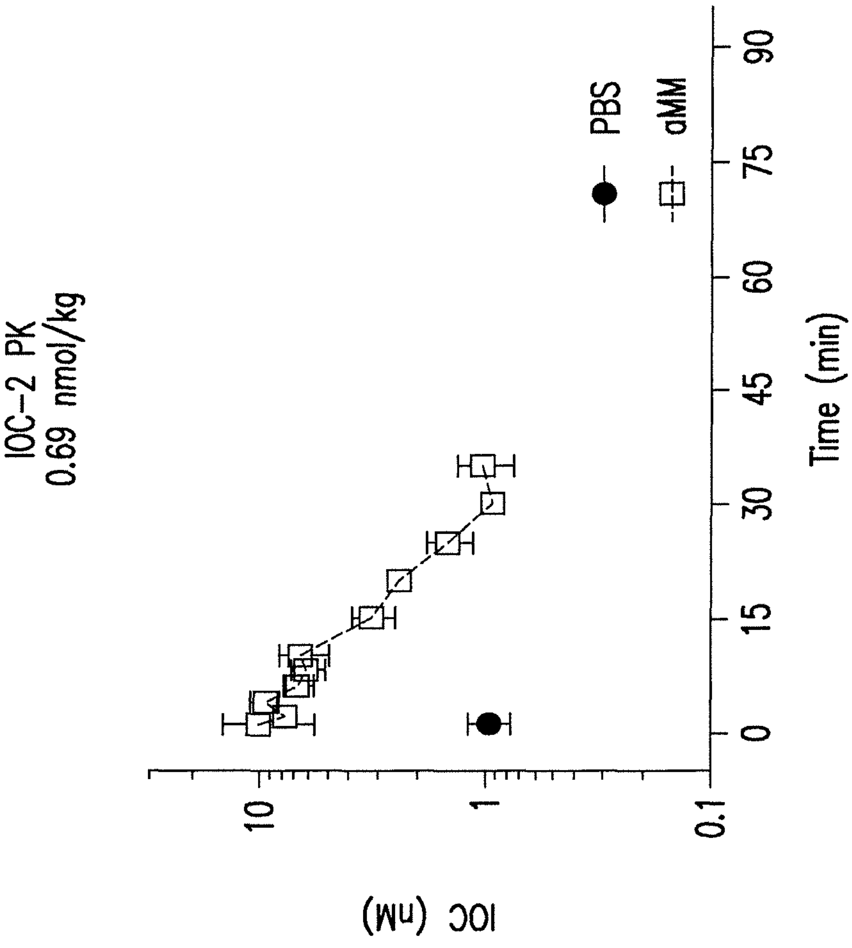
FIG. 15: Blood glucose depression curves in non-diabetic male Yucatan minipigs equipped with dual vascular access ports (n=3 per study) following i.v. injection of conjugate IOC-2 at 0.69 nmol/kg under conditions of (●) PBS infusion or (□) i.v. alpha methyl mannose (aMM) infusion (21.2% w/v infused at constant rate of 2.67 mL/kg/hr).

FIG. 15 shows blood glucose depression curves in non-diabetic male Yucatan minipigs equipped with dual vascular access ports (n=3 per study) following i.v. injection of conjugate IOC-2 at 0.69 nmol/kg under conditions of PBS infusion or i.v. alpha methyl mannose (aMM) infusion.

Figure 16:
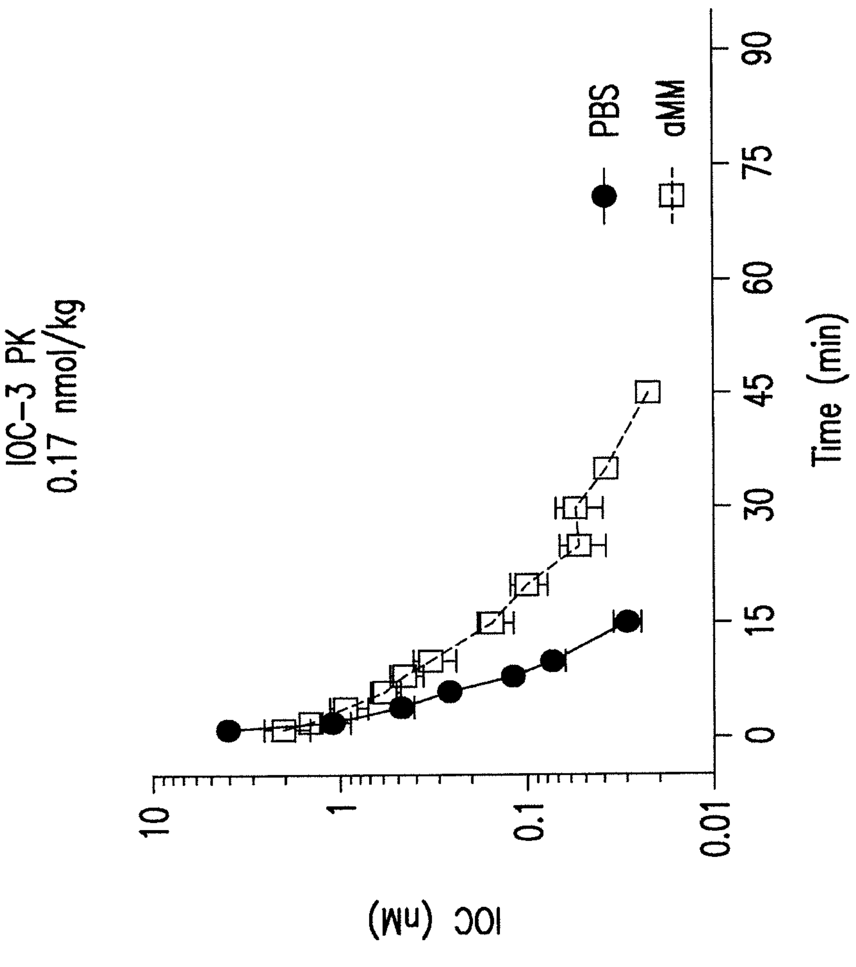
FIG. 16: Blood glucose depression curves in non-diabetic male Yucatan minipigs equipped with dual vascular access ports (n=3 per study) following i.v. injection of conjugate IOC-3 at 0.17 nmol/kg under conditions of (●) PBS infusion or (□) i.v. alpha methyl mannose (aMM) infusion (21.2% w/v infused at constant rate of 2.67 mL/kg/hr).

FIG. 16 shows blood glucose depression curves in non-diabetic male Yucatan minipigs equipped with dual vascular access ports (n=3 per study) following i.v. injection of conjugate IOC-3 at 0.17 nmol/kg under conditions of PBS infusion or i.v. alpha methyl mannose (aMM) infusion.

Figure 17:
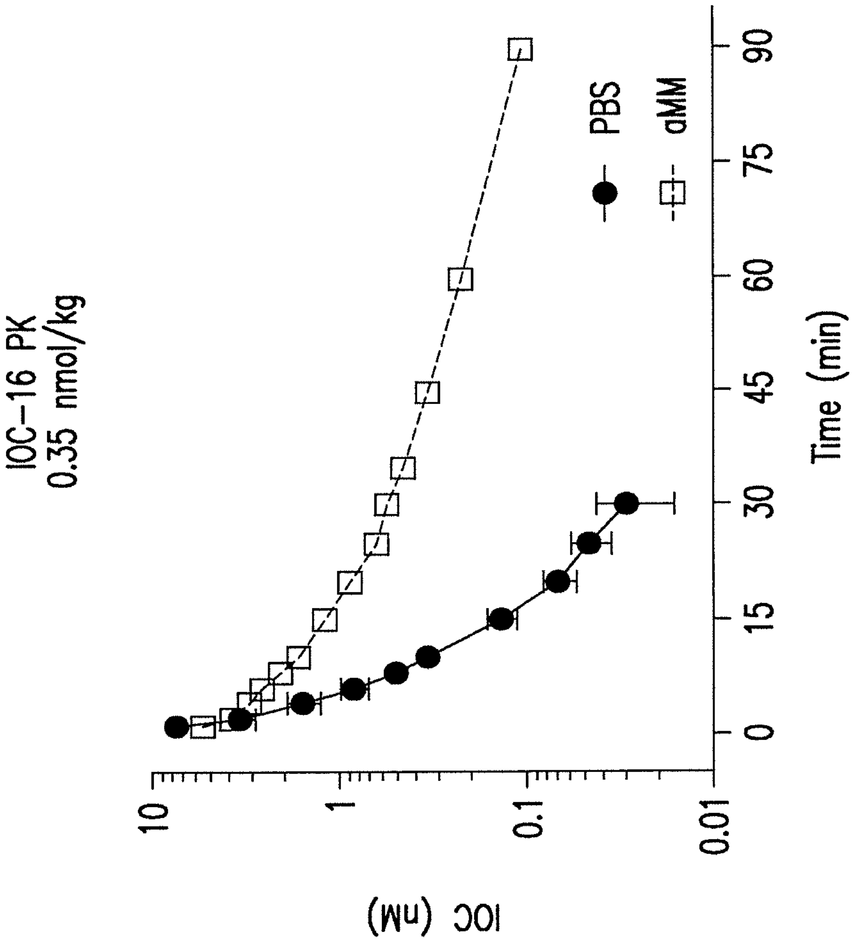
FIG. 17: Blood glucose depression curves in non-diabetic male Yucatan minipigs equipped with dual vascular access ports (n=3 per study) following i.v. injection of conjugate IOC-16 at 0.35 nmol/kg under conditions of (●) PBS infusion or (□) i.v. alpha methyl mannose (aMM) infusion (21.2% w/v infused at constant rate of 2.67 mL/kg/hr).

FIG. 17 shows blood glucose depression curves in non-diabetic male Yucatan minipigs equipped with dual vascular access ports (n=3 per study) following i.v. injection of conjugate IOC-16 at 0.35 nmol/kg under conditions of PBS infusion or i.v. alpha methyl mannose (aMM) infusion.

Figure 18:
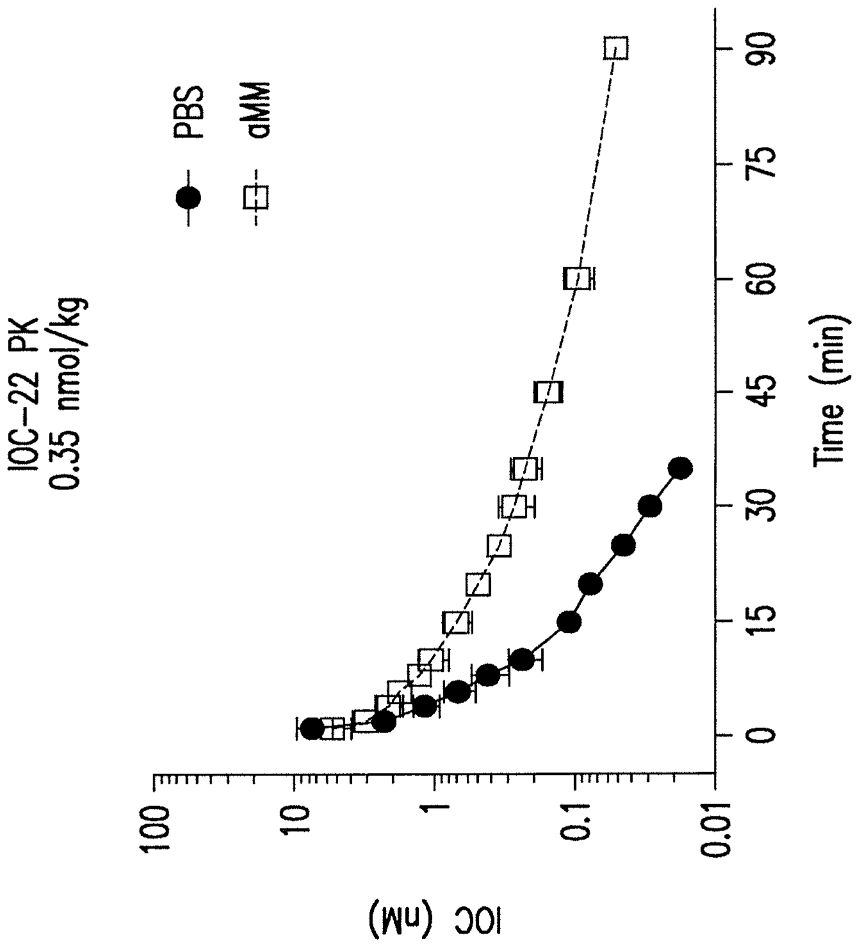
FIG. 18: Blood glucose depression curves in non-diabetic male Yucatan minipigs equipped with dual vascular access ports (n=3 per study) following i.v. injection of conjugate IOC-22 at 0.35 nmol/kg under conditions of (●) PBS infusion or (□) i.v. alpha methyl mannose (aMM) infusion (21.2% w/v infused at constant rate of 2.67 mL/kg/hr).

FIG. 18 shows blood glucose depression curves in non-diabetic male Yucatan minipigs equipped with dual vascular access ports (n=3 per study) following i.v. injection of conjugate IOC-22 at 0.35 nmol/kg under conditions of PBS infusion or i.v. alpha methyl mannose (aMM) infusion.

Figure 19:
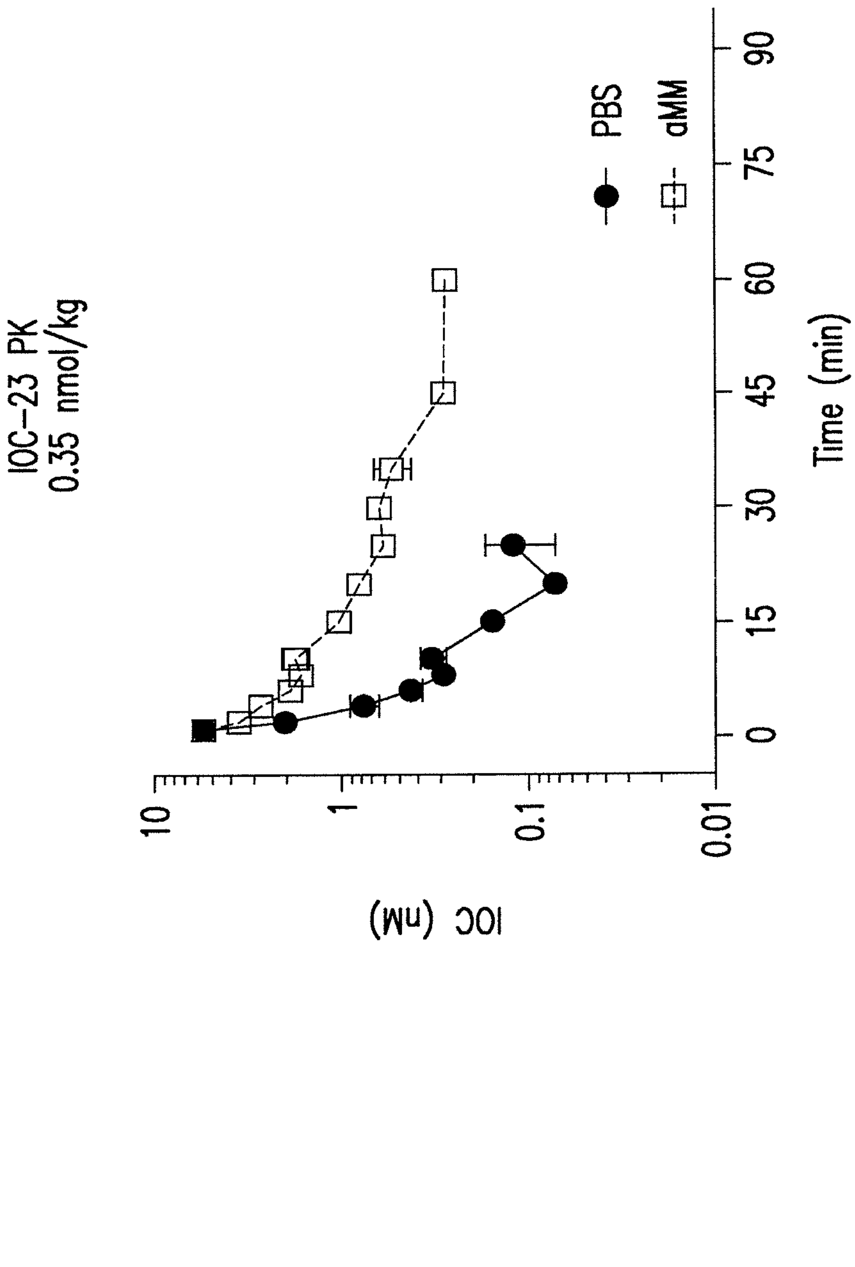
FIG. 19: Blood glucose depression curves in non-diabetic male Yucatan minipigs equipped with dual vascular access ports (n=3 per study) following i.v. injection of conjugate IOC-23 at 0.35 nmol/kg under conditions of (●) PBS infusion or (□) i.v. alpha methyl mannose (aMM) infusion (21.2% w/v infused at constant rate of 2.67 mL/kg/hr).

FIG. 19 shows blood glucose depression curves in non-diabetic male Yucatan minipigs equipped with dual vascular access ports (n=3 per study) following i.v. injection of conjugate IOC-23 at 0.35 nmol/kg under conditions of PBS infusion or i.v. alpha methyl mannose (aMM) infusion.

Figure 20:
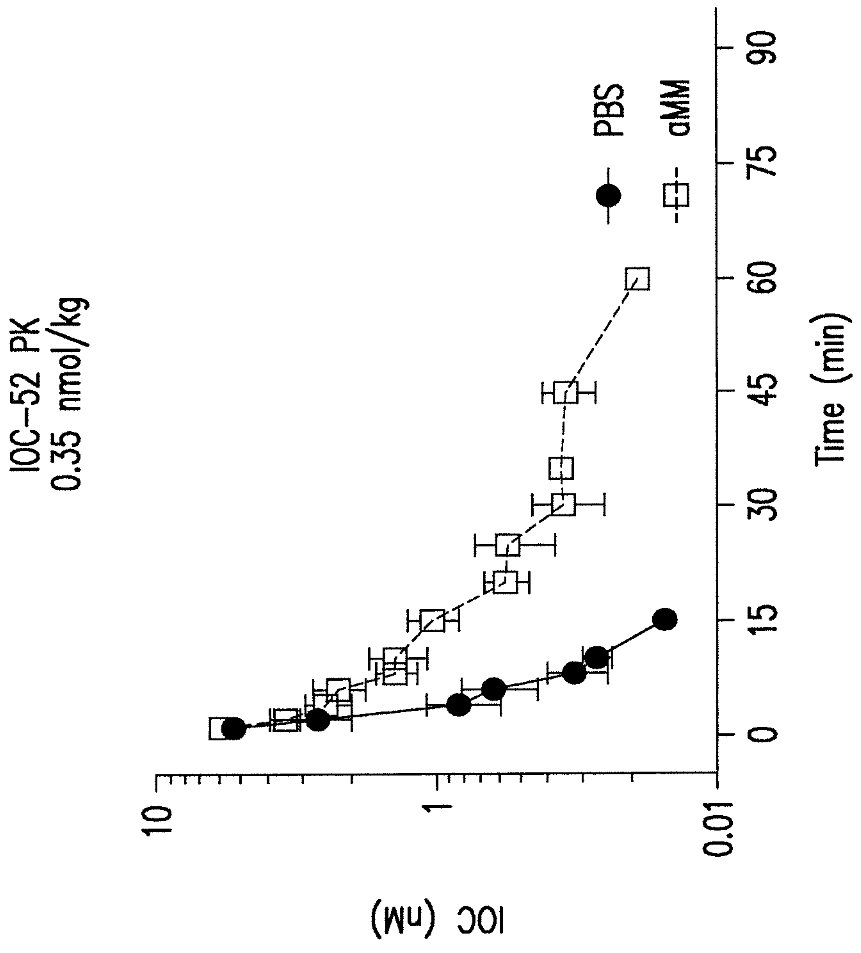
FIG. 20: Blood glucose depression curves in non-diabetic male Yucatan minipigs equipped with dual vascular access ports (n=3 per study) following i.v. injection of conjugate IOC-52 at 0.35 nmol/kg under conditions of (●) PBS infusion or (□) i.v. alpha methyl mannose (aMM) infusion (21.2% w/v infused at constant rate of 2.67 mL/kg/hr).

FIG. 20 shows blood glucose depression curves in non-diabetic male Yucatan minipigs equipped with dual vascular access ports (n=3 per study) following i.v. injection of conjugate IOC-52 at 0.35 nmol/kg under conditions of PBS infusion or i.v. alpha methyl mannose (aMM) infusion.

Figure 21:
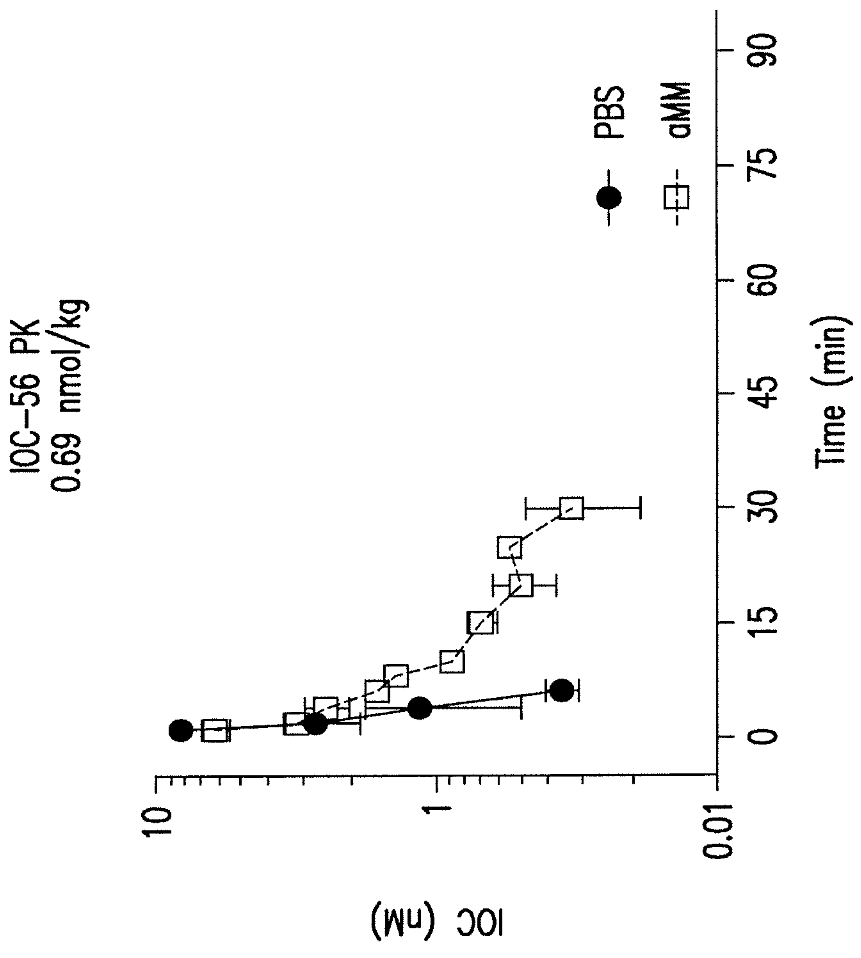
FIG. 21: Blood glucose depression curves in non-diabetic male Yucatan minipigs equipped with dual vascular access ports (n=3 per study) following i.v. injection of conjugate IOC-56 at 0.69 nmol/kg under conditions of (●) PBS infusion or (□) i.v. alpha methyl mannose (aMM) infusion (21.2% w/v infused at constant rate of 2.67 mL/kg/hr).

FIG. 21 shows blood glucose depression curves in non-diabetic male Yucatan minipigs equipped with dual vascular access ports (n=3 per study) following i.v. injection of conjugate IOC-56 at 0.69 nmol/kg under conditions of PBS infusion or i.v. alpha methyl mannose (aMM) infusion.

Figure 22:
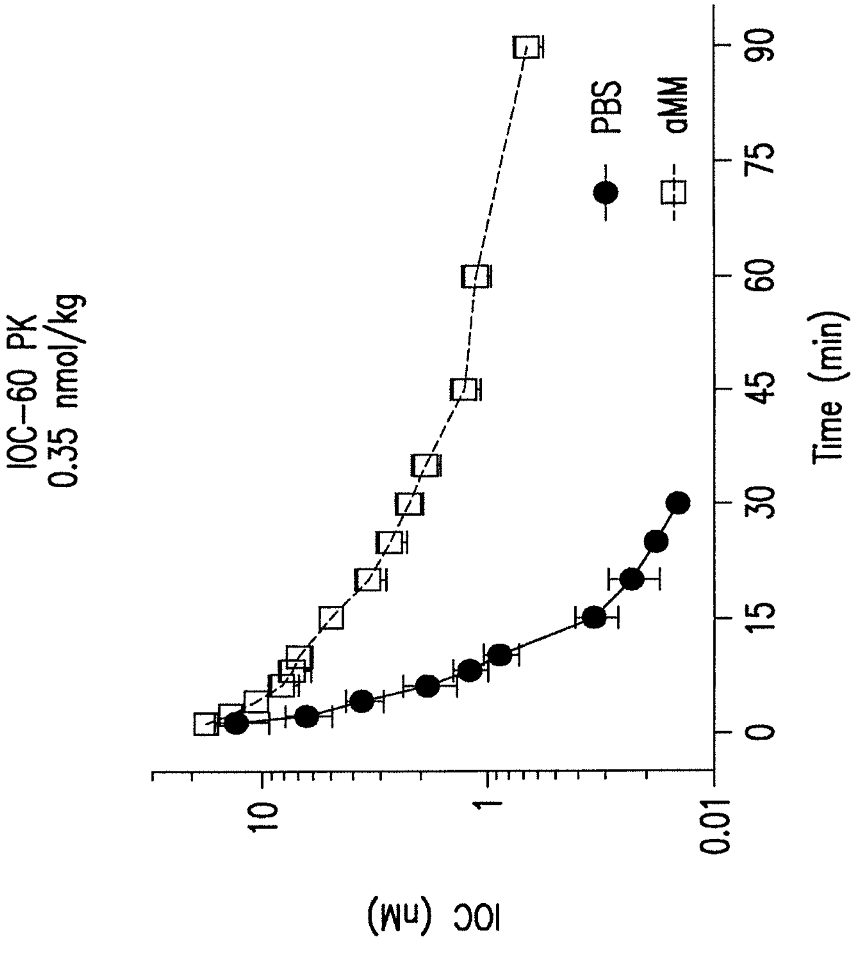
FIG. 22: Blood glucose depression curves in non-diabetic male Yucatan minipigs equipped with dual vascular access ports (n=3 per study) following i.v. injection of conjugate IOC-60 at 0.35 nmol/kg under conditions of (●) PBS infusion or (□) i.v. alpha methyl mannose (aMM) infusion (21.2% w/v infused at constant rate of 2.67 mL/kg/hr).

FIG. 22 shows blood glucose depression curves in non-diabetic male Yucatan minipigs equipped with dual vascular access ports (n=3 per study) following i.v. injection of conjugate IOC-60 at 0.35 nmol/kg under conditions of PBS infusion or i.v. alpha methyl mannose (aMM) infusion.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A conjugate having the formula

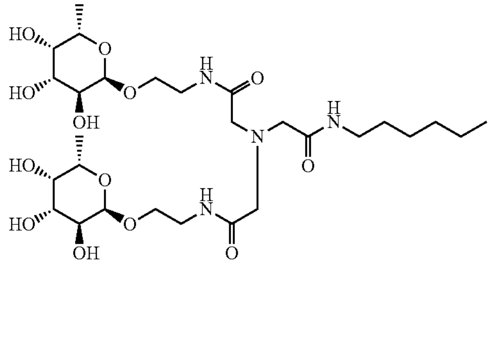

IOC-60

-continued

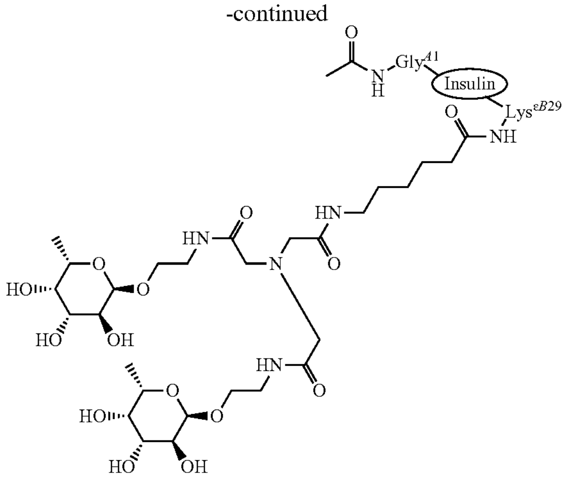

wherein the insulin is human recombinant insulin.

2. A composition comprising:
a conjugate having the formula
IOC-60
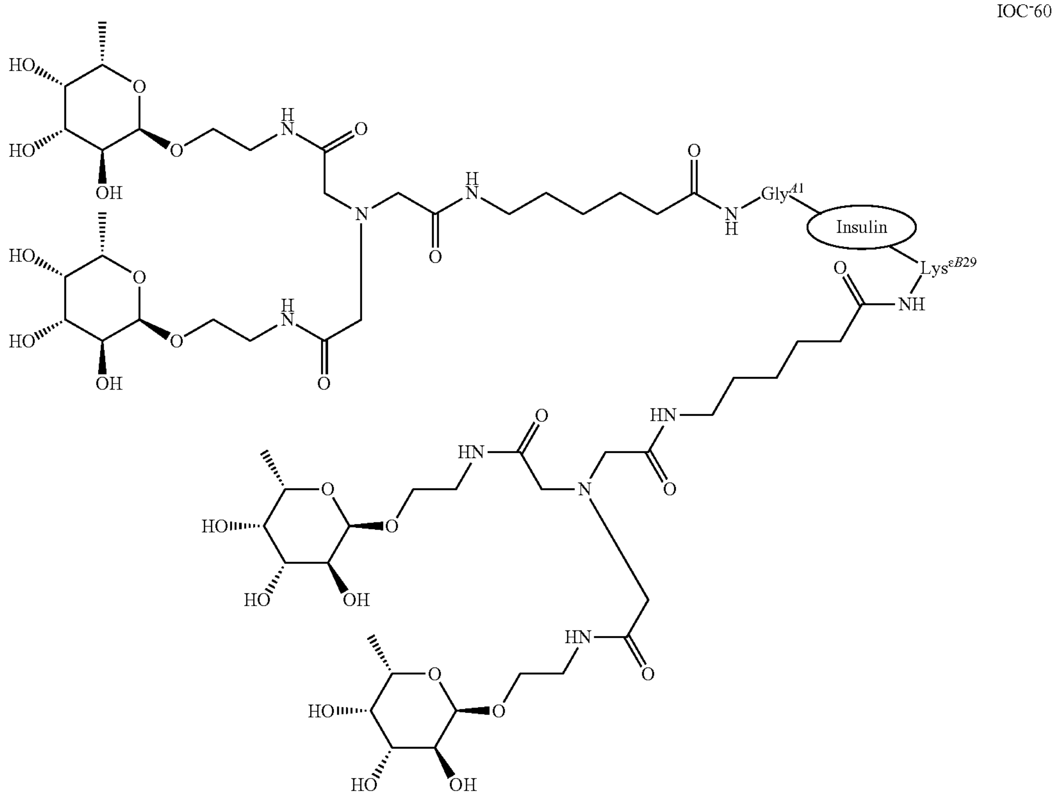
and wherein the insulin is human recombinant insulin, and a pharmaceutically acceptable carrier.
* * * * *

SEQUENCE LISTING

```
<160> NUMBER OF SEQ ID NOS: 10

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 2
<211> LENGTH: 30
<212> TYPE: PRT
<213> ORGANISM: Homo sapiens

<400> SEQUENCE: 2

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 3
<211> LENGTH: 30
<212> TYPE: PRT
<213> ORGANISM: artificial sequence
<220> FEATURE:
<223> OTHER INFORMATION: Insulin lispro B-chain

<400> SEQUENCE: 3

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30
```

<210> SEQ ID NO 4
<211> LENGTH: 30
<212> TYPE: PRT
<213> ORGANISM: artificial sequence
<220> FEATURE:
<223> OTHER INFORMATION: Insulin aspart B-chain

<400> SEQUENCE: 4

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

<210> SEQ ID NO 5
<211> LENGTH: 30
<212> TYPE: PRT
<213> ORGANISM: artificial sequence
<220> FEATURE:
<223> OTHER INFORMATION: Insulin glulisine B-chain

<400> SEQUENCE: 5

```
Phe Val Lys Gln His Leu Cys Gly Ser His Leu Val Glu Ala Leu Tyr
1               5                   10                  15

Leu Val Cys Gly Glu Arg Gly Phe Phe Tyr Thr Asn Lys Thr
            20                  25                  30
```

<210> SEQ ID NO 6
<211> LENGTH: 21
<212> TYPE: PRT
<213> ORGANISM: artificial sequence
<220> FEATURE:
<223> OTHER INFORMATION: Insulin glargine A-chain

<400> SEQUENCE: 6

```
Gly Ile Val Glu Gln Cys Cys Thr Ser Ile Cys Ser Leu Tyr Gln Leu
1               5                   10                  15
```

```
Glu Asn Tyr Cys Gly
            20


<210> SEQ ID NO 7
<211> LENGTH: 32
<212> TYPE: PRT
<213> ORGANISM: artificial sequence
<220> FEATURE:
<223> OTHER INFORMATION: Insulin glargine B-chain

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 8
<211> LENGTH: 21
<212> TYPE: PRT
<213> ORGANISM: artificial sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine or histidine
<220> FEATURE:
<221> NAME/KEY: MISC_FEATURE
<222> LOCATION: (21)..(21)
<223> OTHER INFORMATION: Xaa at position 21 is asparagine, glycine,
      alanine, glutamine, glutamate, threonine, or serine
<220> FEATURE:
<221> NAME/KEY: MISC_FEATURE
<222> LOCATION: (21)..(21)
<223> OTHER INFORMATION: Xaa is asparagine, glycine, alanine, glutamine,
      glutamate, threonine, or serine

<400> SEQUENCE: 8

Gly Ile Val Glu Gln Cys Cys Xaa Ser Ile Cys Ser Leu Tyr Gln Leu
1               5                   10                  15

Glu Asn Tyr Cys Xaa
            20


<210> SEQ ID NO 9
<211> LENGTH: 21
<212> TYPE: PRT
<213> ORGANISM: artificial sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (6)..(6)
<223> OTHER INFORMATION: Xaa is histidine, aspartic acid, glutamic acid,
      homocysteic acid or cysteic acid

<400> SEQUENCE: 9

Xaa Leu Cys Gly Xaa Xaa Leu Val Glu Ala Leu Tyr Leu Val Cys Gly
```

-continued

```
1               5                   10                  15

Glu Arg Gly Phe Phe
            20


<210> SEQ ID NO 10
<211> LENGTH: 32
<212> TYPE: PRT
<213> ORGANISM: artificial sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine or
      desamino-phenylalanine
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa is histidine, aspartic acid, glutamic acid,
      homocysteic acid or cysteic acid
<220> FEATURE:
<221> NAME/KEY: MISC_FEATURE
<222> LOCATION: (28)..(29)
<223> OTHER INFORMATION: Xaa for position 28 and Xaa for position 29 are
      selected from aspartate-lysine, lysine-proline, and a
      proline-lysine, respectively
<220> FEATURE:
<221> NAME/KEY: MISC_FEATURE
<222> LOCATION: (30)..(30)
<223> OTHER INFORMATION: Xaa is threonine or alanine
<220> FEATURE:
<221> NAME/KEY: MISC_FEATURE
<222> LOCATION: (31)..(32)
<223> OTHER INFORMATION: Xaa at positions 31-32 are either each arginine
      or each absent when position 30 is threonine

<400> SEQUENCE: 10

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Xaa Xaa Xaa Xaa Xaa
            20                  25                  30
```